(12) United States Patent (10) Patent No.: US 8,227,236 B2
Picataggio et al. (45) Date of Patent: Jul. 24, 2012

(54) ENGINEERED MICROORGANISMS WITH ENHANCED FERMENTATION ACTIVITY

(75) Inventors: Stephen Picataggio, Carlsbad, CA (US); Kirsty Anne Lily Salmon, Carlsbad, CA (US); Jose Miguel LaPlaza, Carlsbad, CA (US)

(73) Assignee: Verdezyne, Inc., Carlsbad, CA (US)

( * ) Notice: Subject to any disclaimer, the term of this patent is extended or adjusted under 35 U.S.C. 154(b) by 0 days.

(21) Appl. No.: 13/045,855

(22) Filed: Mar. 11, 2011

(65) Prior Publication Data

US 2011/0165661 A1 Jul. 7, 2011

Related U.S. Application Data

(63) Continuation of application No. PCT/US2010/041607, filed on Jul. 9, 2010.

(60) Provisional application No. 61/224,430, filed on Jul. 9, 2009, provisional application No. 61/316,780, filed on Mar. 23, 2010, provisional application No. 61/334,097, filed on May 12, 2010.

(51) Int. Cl.
*C12N 1/00* (2006.01)
(52) U.S. Cl. .............................. 435/254.21; 435/254.11
(58) Field of Classification Search ............. 435/254.21, 435/254.11
See application file for complete search history.

(56) References Cited

U.S. PATENT DOCUMENTS

| | | | |
|---|---|---|---|
| 4,490,468 A | 12/1984 | Gong et al. |
| 4,683,195 A | 7/1987 | Mullis et al. |
| 4,683,202 A | 7/1987 | Mullis |
| 4,965,188 A | 10/1990 | Mullis et al. |
| 5,232,841 A | 8/1993 | Hashimoto et al. |
| 5,268,273 A | 12/1993 | Buckholz |
| 5,389,529 A | 2/1995 | Panayotatos et al. |
| 5,470,719 A | 11/1995 | Meng et al. |
| 5,595,899 A | 1/1997 | Sato |
| 5,656,493 A | 8/1997 | Mullis et al. |
| 5,712,114 A | 1/1998 | Mankovich et al. |
| 5,766,891 A | 6/1998 | Shuman |
| 5,786,186 A | 7/1998 | Lancashire et al. |
| 5,789,210 A | 8/1998 | Ho et al. |
| 5,798,237 A | 8/1998 | Picataggio et al. |
| 5,843,760 A | 12/1998 | Zhang et al. |
| 5,846,818 A | 12/1998 | Robinson et al. |
| 5,888,732 A | 3/1999 | Hartley et al. |
| 5,932,474 A | 8/1999 | Tsien et al. |
| 5,935,837 A | 8/1999 | Rasmussen |
| 6,008,378 A | 12/1999 | Tsien et al. |
| 6,054,271 A | 4/2000 | Tsien et al. |
| 6,143,557 A | 11/2000 | Hartley et al. |
| 6,171,861 B1 | 1/2001 | Hartley et al. |
| 6,270,969 B1 | 8/2001 | Hartley et al. |
| 6,277,608 B1 | 8/2001 | Hartley et al. |
| 6,288,302 B1 | 9/2001 | Yu et al. |
| 6,333,181 B1 | 12/2001 | Ingram et al. |
| 6,451,569 B1 | 9/2002 | Tsien et al. |
| 6,475,768 B1 | 11/2002 | Otero et al. |
| 6,566,107 B1 | 5/2003 | Zhang |
| 6,720,140 B1 | 4/2004 | Hartley et al. |
| 7,198,933 B2 | 4/2007 | Zeikus et al. |
| 7,226,735 B2 | 6/2007 | Jeffries et al. |
| 7,285,403 B2 | 10/2007 | Jeffries et al. |
| 7,432,085 B2 | 10/2008 | Hara et al. |
| 7,514,247 B2 | 4/2009 | Rush |
| 7,527,927 B1 | 5/2009 | Ho et al. |
| 7,622,284 B2 | 11/2009 | Op Den Camp et al. |
| 7,670,823 B1 | 3/2010 | Hartley et al. |
| 2002/0007051 A1 | 1/2002 | Cheo et al. |
| 2003/0083373 A1 | 5/2003 | Tsien et al. |
| 2004/0142435 A1 | 7/2004 | Yoshiya et al. |
| 2004/0142456 A1 | 7/2004 | Jeffries et al. |
| 2005/0112590 A1 | 5/2005 | Van Den Boom et al. |
| 2005/0287592 A1 | 12/2005 | Kless |
| 2006/0115878 A1 | 6/2006 | Yoshihiko et al. |
| 2006/0216804 A1 | 9/2006 | Karhumaa |
| 2006/0228789 A1 | 10/2006 | Jeffries et al. |
| 2006/0234364 A1 | 10/2006 | Rajgarhia et al. |
| 2006/0281908 A1 | 12/2006 | Callen et al. |
| 2007/0082386 A1 | 4/2007 | Gorwa-Grauslund |
| 2007/0141690 A1 | 6/2007 | Karhumaa et al. |
| 2008/0014620 A1 | 1/2008 | Op Den Camp et al. |
| 2008/0085341 A1 | 4/2008 | Dai et al. |
| 2008/0187973 A1 | 8/2008 | Viitanen et al. |
| 2008/0261287 A1 | 10/2008 | Winkler et al. |
| 2009/0221078 A1 | 9/2009 | Caimi et al. |
| 2009/0246857 A1 | 10/2009 | Ho et al. |
| 2009/0311771 A1 | 12/2009 | Boles et al. |
| 2010/0028975 A1 | 2/2010 | Gorwa-Grauslund |
| 2010/0035306 A1 | 2/2010 | Op Den Camp et al. |
| 2010/0120105 A1 | 5/2010 | Anthony |

(Continued)

FOREIGN PATENT DOCUMENTS

EP 1468093 10/2004

(Continued)

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*

(Continued)

*Primary Examiner* — Ganapathirama Raghu
(74) *Attorney, Agent, or Firm* — Grant Anderson LLP

(57) ABSTRACT

Provided herein are genetically modified microorganisms that have enhanced fermentation activity, and methods for making and using such microorganisms.

16 Claims, 28 Drawing Sheets

U.S. PATENT DOCUMENTS

| | | |
|---|---|---|
| 2010/0146842 A1 | 6/2010 | Dumenil |
| 2010/0146843 A1 | 6/2010 | Dumenil |
| 2011/0165660 A1 | 7/2011 | Picataggio et al. |
| 2011/0229959 A1 | 9/2011 | Picataggio et al. |

FOREIGN PATENT DOCUMENTS

| | | |
|---|---|---|
| KR | 10-0697551 | 3/2007 |
| WO | WO 95/13362 | 5/1995 |
| WO | WO 95/25799 | 9/1995 |
| WO | WO 96/19497 | 6/1996 |
| WO | WO 97/42307 | 11/1997 |
| WO | WO 98/56943 | 12/1998 |
| WO | WO 99/21013 | 4/1999 |
| WO | WO 03/062430 | 7/2003 |
| WO | WO 2004/099381 | 11/2004 |
| WO | WO 2005/023998 | 3/2005 |
| WO | WO 2005/091733 | 10/2005 |
| WO | WO 2006/096130 | 9/2006 |
| WO | WO 2007/028811 | 3/2007 |
| WO | WO 2009/109630 | 9/2009 |
| WO | WO 2009/109631 | 9/2009 |
| WO | WO 2009/109633 | 9/2009 |
| WO | WO 2009/109634 | 9/2009 |
| WO | WO 2010/074677 | 7/2010 |
| WO | WO 2010/079065 | 7/2010 |
| WO | WO 2010/079067 | 7/2010 |
| WO | WO 2011/006126 | 1/2011 |
| WO | WO 2011/006136 | 1/2011 |

OTHER PUBLICATIONS

Sauna et al., Silent polymorhisms speak: How they affect pharmacogenomics and the treatment of cancer. Cancer Res., 2007, vol. 67(20): 9609-9612.*

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Wishart et al., A single mutation converts a novel phosphotyrosine binding domain into a dual-specificity phosphatase. J. Biol. Chem., 1995, vol. 270(45): 26782-26785.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

U.S. Appl. No. 60/587,583, filed Jul. 14, 2004, Wieslaw.

Akbergenov et al., "ARC-1, a sequence element complementary to an internal 18S rRNA segment, enhances translation efficiency in plants when present in the leader or intercistronic region of mRNAs," Nucleic Acids Research 32: 239-247 (2004).

Alani et al., "A method for gene disruption that allows repeated use of URA3 selection in the construction of multiply disrupted yeast strains", Genetics 116(4):541-545 Aug. 1987.

Alper et al., "Engineering yeast transcription machinery for improved ethanol tolerance and production," Science, American Association for the Advancement of Science, Washington, DC, US, vol. 314, No. 5805, Dec. 8, 2006, pp. 1565-1568.

Brat et al, Functional Expression of a Bacterial Xylose Isomerase in *Saccharomyces cerevisiae* (Applied and Evnironmental Microbiol., Apr. 2009; p. 2304-2311; vol. 75, No. 8).

Capone et al., Amber, ochre and opal suppressor tRNA genes derived from a human serine tRNA gene. EMBO J. 4:213, 1985.

Cheriyan et al., "Mutagenesis of the phosphate-binding pocket of KDPG aldolase enhances selectivity for hydrophobic substrates," Protein Science 16:2368-2377, 2007.

Coppella et al., "A Detailed Analysis of *Saccharomyces cerevkiae* Growth Kinetics in Batch, Fed-batch, and Hollow-fiber Bioreactors," The Chemical Engineering Journal, 41 (1989) B27-B35.

Current Protocols in Molecular Biology, John Wiley & Sons, N.Y., 6.3.1-6.3.6 (1989).

De Graaf Albert A et al., "Metabolic state of *Zymomonas mobilis* in glucose-, fructose-, and xylose-fed continuous cultures as analyzed by 13C- and 31P-NMR spectroscopy" Archives of Microbiology, Springer, DE, vol. 171. No. 6, May 1, 1999, pp. 371-385.

Deshpande, Mukund V., "Ethanol production from cellulose by coupled saccharification/fermentation using *Saccharomyces cerevisiae* and cellulase complex from *Sclerotium rolfsii* UV-8 mutant.," Appl. Biochem. Biotechnol., 36:227-234 (1992).

Ding et al., "Identification, expression, and characterization of the highly conserved d-xylose isomerase in animals," Acta Biochim Biophys Sin (2009) 41 (2): 116-122.

Eggertsson, et al., "Transfer ribonucleic acid-mediated suppression of termination codons in *Escherichia coli*." (1988) Microbiological Review 52(3):354-374.

Fong et al., "Directed evolution of D-2-keto-3-deoxy-6-phosphogluconate adolase to new variants fot the efficient synthesis of D- and L-sugars," Chemistry & Biochemistry, 2000, vol. 7, No. 11, pp. 873-883.

Fuhrman et al., :Rapid accumulation of intracellular 2-keto-3-deoxy-6-phosphogluconate in an Entner-Doudoroff aldolase mutant results in bacteriostasis. FEMS Microbiology Letters 1998, vol. 159, Issue 2, pp. 261-266.

Gallie et al., "The 5'-leader sequence of tobacco mosaic virus RNA enhances the expression of foreign gene transcripts in vitro and in vivo," Nucleic Acids Research 15: 3257-3273 (1987).

Gallie, "The 5'-leader of tobacco mosaic virus promotes translation through enhanced recruitment of eIF4F," Nucleic Acids Research 30: 3401-3411 (2002).

Hitchman et al., "Hexanoate Synthase, a Specialized Type I Fatty Acid Synthase in Aflatoxin B1 Biosynthesis," Bioorganic Chemistry 29, 293-307 (2001).

Hill, Craig, "Automating nucleic acid amplification tests" IVD Technology Magazine, published Nov./Dec. 2000, downloaded from: http://www.devicelink.com/ivdt/archive/00/11/007.

Innis et al., eds, (1990) PCR Protocols: A Guide to Methods and Applications (Table of Contents).

International Search Report and Written Opinion mailed: Mar. 11, 2011 in International Application No. PCT/US2010/041618 filed on: Jul. 9, 2010 and published as: WO/2011/006136 on: Jan. 13, 2011.

International Search Report and Written Opinion mailed: Jun. 3, 2011 in International Application No. PCT/US2010/041607 filed on: Jul. 9, 2010 and published as: WO/2011/006126 on: Jan. 13, 2011.

Jeffries, Thomas W., "Engineering yeasts for xylose metabolism," Current Opinion in Biotechnology 2006, 17:320-326.

Kuyper et al., "High-level functional expression of a fungal xylose isomerase: the key to efficient ethanolic fermentation of xylose by *Saccharomyces cerevisiae*?" FEMS Yeast Res., 4:69-78 [2003].

Landy, "Mechanistic and structural complexity in the site-specific recombination pathways of Int and FLP," Curr. Opin. Biotech. 3:699-707 (1993).

Larkin, et al., "Clustal W and Clustal X version 2.0," Bioinformatics 2007 23(21): 2947-2948.

Larsen et al., "Computationally Optimized DNA Assembly of synthetic genes," Int. J. Bioinform. Res. Appl; 2008:4[3]; 324-336.

Madhavan et al., "Xylose isomerase from polycentric fungus *Orpinomyces*: gene sequencing, cloning, and expression in *Saccharomyces cerevisiae* for bioconversion of xylose to ethanol," Appl Microbiol Biotechnol (2009) 82:1067-1078.

Meyers & Miller, "Optimal alignments in linear space," CABIOS 4: 11-17 (1989).

Mignone et al., "Untranslated regions of mRNAs," Genome Biology 3(3): reviews0004.1-0001.10 (2002).

Mignone et al., "UTRdb and UTRsite: a collection of sequences and regulatory motifs of the untranslated regions of eukaryotic mRNAs," Nucleic Acids Research 33: D141-D146 (2005).

Mumberg D, et al., "Regulatable promoters of *Saccharomyces cerevisiae*: comparison of transcriptional activity and their use for heterologous expression," Nucleic Acids Res. 22: 5767-5768, 1994.

Mumberg et al., "Yeast vectors for the controlled expression of heterologous proteins in different genetic backgrounds," 1995, Gene 156: 119-122.

Needleman & Wunsch,"A general method applicable to the search for similarities in the Amino Acid Sequence of two proteins." J. Mol. Biol. 48: 443-453 (1970).

Nelson et al., "Simultaneous detection of multiple nucleic acid targets in a homogeneous format," Biochemistry Jun. 25, 1996;35(25):8429-8438.

Ost et al., "Rational re-design of the substrate binding site of £avocytochrome P450 BM3," FEBS Letters 486(2000) 173-177.

Paulous et al., "Comparison of the capacity of different viral internal ribosome entry segments to direct translation initiation in poly(A)-dependent reticulocyte lysates," Nucleic Acids Research 31: 722-733 (2003).

Sambrook et al., (1989) Revised ed. of: "Molecular cloning, a Laboratory Manual," 1982 by Maniatis, Fritsch, Sambrook, Maniatis, "Molecular Cloning: a Laboratory Manual; Cold Spring Harbor Laboratory, Cold Spring Harbor, N.Y." Table of contents.

Sauer, B., "Site-specific recombination: developments and applications," Curr. Opin. Biotech. 5:521-527 (1994).

Sekiguchi and Shuman, "Requirements for noncovalent binding of vaccinia topoisomerase I to duplex DNA," Nucl. Acids Res. 22:5360-5365, 1994.

Shaloiko et al., "Effective non-viral leader for cap-independent translation in a eukaryotic cell-free system," Biotechnology and Bioengineeringvol. 88, Issue 6, pp. 730-739, 2004.

Shuman, "Site-specific interaction of vaccinia virus topoisomerase I with duplex DNA. Minimal DNA substrate for strand cleavage in vitro," J. Biol. Chem. 266:11372-11379, 1991.

Sikorski RS, Boeke JD., "In vitro mutagenesis and plasmid shuffling: From cloned gene to mutant yeast," Methods Enzymol. 194: 302-318, 1991.

Tjalsma et al., "Signal peptide-dependent protein transport in *Bacillus subtilis*: a genome-based survey of the secretome," Microbiol. Molec. Biol. Rev. 64: 515-547 (2000).

Vincent et al., "Helicase-dependent isothermal DNA amplification". EMBO reports 5 (8): 795-800 (2004).

Winzeler EA, et al. "Functional characterization of the *S. cerevisiae* genome by gene deletion and parallel analysis," Science 285: 901-906, 1999.

Office Action mailed on: Sep. 19, 2011 in U.S. Appl. No. 13/045,841, filed Sep. 12, 2011, and published as: 2011-0229959 on Sep. 22, 2011.

Score Search Results for U.S. Appl. No. 13/045,847 cited in Office Action dated: Sep. 19, 2011 as Temple et al., J. Bacteriol, 1994 vol. 176, 4700-4709; Accession # P31961; Q9HZ45.

Score Search Results for U.S. Appl. No. 13/045,847 cited in Office Action dated Sep. 19, 2011 as DeSouza et al, Accession # U17155 and GI 577838 (1994).

Score Search Results of U.S. Appl. No. 13/045,847 cited in Office Action dated: Sep. 19, 2011 as Borneman et al., FEMS Yeast Res, 2008, vol. 8: 1185-1195; Accession # B5VK90.

Score Search Results of U.S. Appl. No. 13/045,847 cited in Office Action dated: Sep. 19, 2011 as Nogae et al., Gene, 1990, vol. 96: 161-169; Cited as Accession # P11412; D6W0V2.

Aurilia, V., et al., "Organization and variable incidence of genes concerned with the utilization of xylans in the rumen celluolytic bacterium *Ruminococcus flavefaciens*," Anerobe, vol. 6, No. 6, pp. 333-340, 2000.

Office Action mailed on: Oct. 18, 2011 in U.S. Appl. No. 13/045,829, filed Mar. 12, 2011, and published as: 2011-0224416 on Sep. 15, 2011.

Thurston, B., et al., "Pentose utilization by the ruminal bacteria *Ruminococcus albus*," Applied and Environmental Microbiology, vol. 60, No. 4, pp. 1087-1092 (1994).

* cited by examiner

DNA Sequence Alignment for ZM4 Native, ZM4 Matched, ZM4 HR and E.coli Eda

```
ZM4_NATIVE      ATGCGTGAT-----ATCGATTCCGTAATGCGTT-TGGCA------CCGGT
ZM4_MATCHED     ATGAGGGAT-----ATTGATAGTGTGATGAGGT-TAGCC------CCTGT
ZM4_HR          ATGAGAGAC-----ATTGATTCTGTTATGAGAT-TGGCT------CCAGT
ECOLI_NATIVE    ATGAAAAACTGGAAAACAAGTGCAGAATCAATCCTGACCACCGGCCCGGT
                ***       *    *   *     **      *  *        ** **

ZM4_NATIVE      TATGCCGGTCCTCGTCATTGAAGATATTGCTGATGCAAAACCTATCGCAG
ZM4_MATCHED     TATGCCTGTTCTCGTTATTGAAGATATTGCAGATGCCAAACCTATTGCCG
ZM4_HR          TATGCCAGTCTTGGTTATAGAAGATATAGCTGATGCTAAGCCAATTGCTG
ECOLI_NATIVE    TGTACCGGTTATCGTGGTAAAAAAACTGGAACACGCGGTGCCGATGGCAA
                *  ** ** **  * **  * ** *  *  *  **     ** ** ** **

ZM4_NATIVE      AAGCTTTGGTTGCTGGTGGTCTGAACGTTCTTGAAGTAACGCTTCGCACC
ZM4_MATCHED     AAGCACTCGTTGCAGGTGGTCTAAACGTTCTAGAAGTGACACTAAGGACT
ZM4_HR          AGGCTTTGGTTGCTGGTGGTTTAAATGTTTTGGAAGTTACATTGAGAACT
ECOLI_NATIVE    AAGCGTTGGTTGCTGGTGGGGTGCGCGTTCTGGAAGTGACTCTGCGTACC
                * **   * ***** *****   *   *** * ***** **  *  * **

ZM4_NATIVE      CCTTGTGCTCTTGAAGCCATCAAGATCATG---AAAGAAGTTCCGGGTGC
ZM4_MATCHED     CCTTGTGCACTAGAAGCTATTAAGATTATG---AAGGAAGTTCCTGGTGC
ZM4_HR          CCATGTGCTTTGGAAGCTATTAAAATTATG---AAGGAAGTTCCAGGTGC
ECOLI_NATIVE    GAGTGTGCAGTTGACGCTATCCGTGCTATCGCCAAAGAAGTGCCTGAAGC
                   ***** *  ** **   **  *        ** ***** ** * **

ZM4_NATIVE      CGTTGTTGGTGCCGGTACGGTTCTGAACGCAAAAATGCTCGACCAAGCTC
ZM4_MATCHED     TGTTGTTGGTGCTGGTACAGTTCTAAACGCCAAAATGCTCGACCAGGCAC
ZM4_HR          TGTTGTTGGTGCTGGTACTGTTTTAAACGCTAAAATGTTGGATCAAGCTC
ECOLI_NATIVE    GATTGTGGGTGCCGGTACGGTGCTGAATCCACAGCAGCTGGCAGAAGTCA
                 *** ***** ** ***** ** **   *  * *  * * * *** *  *

ZM4_NATIVE      AGGAAGCTGGTTGCG-AATTTTTCGTTAGCCCCGGGTCTGACCG--CTGAC
ZM4_MATCHED     AAGAAGCAGGTTGCG-AATTTTTCGTTTCACCTGGTCTAACTG--CCGAC
ZM4_HR          AAGAAGCTGGTTGTG-AGTTCTTTGTATCACCAGGTTTGACTG--CTGAT
ECOLI_NATIVE    CTGAAGCGGGT-GCACAGTTCGCAATTAGCCCGGGTCTGACCGAGCCG-C
                  ***** ***       *  *  *      ** ***  **  *  *

ZM4_NATIVE      CTCGGCAAGCATGCTGTTGCCCAGAAAGCAGCTTTGCTT---CCAGGTGT
ZM4_MATCHED     CTCGGAAAGCACGCAGTTGCTCAAAAAGCCGCATTACTA---CCCGGTGT
ZM4_HR          TTGGGAAAACATGCTGTTGCTCAAAAAGCGGCTCTTCTA---CCAGGGGT
ECOLI_NATIVE    TGCTGAAA----GCTGCTACCGAAGGGACTATTCCTCTGATTCCGGGGAT
                   **      **  **     *      *      **    ** **  *

ZM4_NATIVE      TGCTAATGCTGCTGATGTGATGCTTGGTCTTGACCTTGGTCTTGATCGCT
ZM4_MATCHED     TGCAAATGCAGCAGATGTGATGCTAGGTCTAGACCTAGGTCTAGATAGGT
ZM4_HR          TGCTAATGCTGCTGATGTTATGTTGGGATTGGATTTGGGTTTGGATAGAT
ECOLI_NATIVE    CAGCACTGTTTCCGAACTGATGCTGGGTATGGACTACGGTTTGAAAGAGT
                    * **  ** *   * **   * ** *  **  * *** * *  *

ZM4_NATIVE      TCAAATTCTTCCCGGCTGAAAATATCGGTGGTTTACCTGCCCTGAAGTCC
ZM4_MATCHED     TCAAGTTCTTCCCTGCCGAAAACATTGGTGGTCTACCTGCTCTAAAGAGT
ZM4_HR          TTAAATTCTTCCCAGCTGAAAATATAGGTGGTTTGCCAGCTTTAAAATCT
```

FIG. 6A

```
ECOLI_NATIVE       TCAAATTCTTCCCGGCTGAAGCTAACGGCGGCGTGAAAGCCCTGCAGGCG
                   *  **  ********  **  ***      *    **   **     *       **    *    *

ZM4_NATIVE         ATGGCT--TCTGTTTTCCGTCAGGTTCGTTTCTGCCCGACCGGCGGTATC
ZM4_MATCHED        ATGGCA--TCAGTTTTCAGGCAAGTTAGGTTCTGCCCTACTGGAGGTATA
ZM4_HR             ATGGCT--TCTGTTTTTAGACAAGTTAGATTTTGTCCAACTGGAGGAATT
ECOLI_NATIVE       ATCGCGGGTCCGTTCTCC--CAGGTCCGTTTCTGCCCGACGGGTGGTATT
                   **  **        **  ***   *        **  **    *  **  **  **  **  **  **  **

ZM4_NATIVE         ACCCCGACGTCAGCTCCTAAATATCTTG-----AAAACCCGTCCATTCTT
ZM4_MATCHED        ACTCCTACAAGTGCACCTAAATATCTAG-----AAAACCCTAGTATTCTA
ZM4_HR             ACTCCCACTTCTGCTCCAAAATATTTGG-----AAAATCCATCTATTTTG
ECOLI_NATIVE       TCTCCGGCTAACTACCGTGACTACCTGGCGCTGAAAAGC-----GTGCTG
                   *   **    *           *       *   **      *   *       ****  *           *   *

ZM4_NATIVE         TGCGTCGGTGGTAGCTGGGTTGTTCCGGCTGGCAAACCAGATGTCG-CAA
ZM4_MATCHED        TGCGTTGGTGGTTCATGGGTTGTTCCTGCCGGAAAACCCGATGTTG-CCA
ZM4_HR             TGTGTTGGTGGTTCTTGGGTTGTTCCAGCGGGTAAACCAGATGTTG-CGA
ECOLI_NATIVE       TGCATCGGTGGTTCCTGGCTGGTTCCGGCAGATGCGCTGGAAGCGGGCGA
                   **   *  ******     ***  *  ***** **  *      *   **  *    *  **

ZM4_NATIVE         AAATCACGGCACTCGCTAAAGAAGCTTCTG---CTTTCAAGCGCGCTGCT
ZM4_MATCHED        AAATTACAGCCCTCGCAAAAGAAGCAAGTG---CATTCAAGAGGGCAGCA
ZM4_HR             AAATTACTGCTTTGGCTAAAGAGGCTTCAG---CTTTTAAAGAGCTGCT
ECOLI_NATIVE       TTACGACCGCATT-ACTAAGCTGGCGCGTGAAGCTGTAGAAGGCGCTA-A
                   *    **  **     *      *    **         **       *      *      *       *    **

ZM4_NATIVE         GTTGCC
ZM4_MATCHED        GTTGCT
ZM4_HR             GTGGCG
ECOLI_NATIVE       GCTG--
                   *   *
```

FIG. 6A (Cont.)

Protein Sequence Alignment for ZM4 Native, ZM4 Matched, ZM4 HR and *E.coli* Eda

```
ZM4_NATIVE      MR----DIDSVMRLAPVMPVLVIEDIADAKPIAEALVAGGLNVLEVTLRTPCALEAIK-I
ZM4_MATCHED     MR----DIDSVMRLAPVMPVLVIEDIADAKPIAEALVAGGLNVLEVTLRTPCALEAIK-I
ZM4_HR          MR----DIDSVMRLAPVMPVLVIEDIADAKPIAEALVAGGLNVLEVTLRTPCALEAIK-I
ECOLI_NATIVE    MKNWKTSAESILTTGPVVPVIVVKKLEHAVPMAKALVAGGVRVLEVTLRTECAVDAIRAI
                *:    . :*:: .**:**:*::.: .* *:*:******:.******** **::**: *

ZM4_NATIVE      MKEVPGAVVGAGTVLNAKMLDQAQEAGCEFFVSPGLTADLGKHAVAQKAALLPGVANAAD
ZM4_MATCHED     MKEVPGAVVGAGTVLNAKMLDQAQEAGCEFFVSPGLTADLGKHAVAQKAALLPGVANAAD
ZM4_HR          MKEVPGAVVGAGTVLNAKMLDQAQEAGCEFFVSPGLTADLGKHAVAQKAALLPGVANAAD
ECOLI_NATIVE    AKEVPEAIVGAGTVLNPQQLAEVTEAGAQFAISPGLTEPLLKAATEGTIPLIPGISTVSE
                **** *:********.: * :. ***.:* :***** * * *. . . .*:**::..::

ZM4_NATIVE      VMLGLDLGLDRFKFFPAENIGGLPALKSMASVFRQVRFCPTGGITPTSAPKYLENPSILC
ZM4_MATCHED     VMLGLDLGLDRFKFFPAENIGGLPALKSMASVFRQVRFCPTGGITPTSAPKYLENPSILC
ZM4_HR          VMLGLDLGLDRFKFFPAENIGGLPALKSMASVFRQVRFCPTGGITPTSAPKYLENPSILC
ECOLI_NATIVE    LMLGMDYGLKEFKFFPAEANGGVKALQAIAGPFSQVRFCPTGGISPANYRDYLALKSVLC
                :***:* **..******* **: **:::.*. * **********:*:.. .** *:**

ZM4_NATIVE      VGGSWVVPAG--KP-DVAKITALAKEASAFKRAAVA
ZM4_MATCHED     VGGSWVVPAG--KP-DVAKITALAKEASAFKRAAVA
ZM4_HR          VGGSWVVPAG--KP-DVAKITALAKEASAFKRAAVA
ECOLI_NATIVE    IGGSWLVPADALEAGDYDRITKLAREA--VEGAKL-
                :***:***. :. * :** **:** .: * :
```

FIG. 6B

DNA Sequence Alignment for ZM4 Native, ZM4 Matched, ZM4 HR and E.coli Edd

```
ZM4_NATIVE      ATGACTGATCTGCATTCAACGGTAGAAAAGGTTACCGCGCGCGTTATTGAACGCTCGCGG
ZM4_MATCHED     ATGACGGATCTACATAGTACAGTGGAGAAGGTTACTGCCAGGGTTATTGAAAGGAGTAGG
ZM4_HR          ATGACGGATTTGCATTCAACTGTTGAGAAAGTAACTGCTAGAGTAATTGAAAGATCAAGG
ECOLI_NATIVE    ATGA---ATCCACA----ATTGTTACGC--GTAACAAATCGAATCATTGAACGTTCGCGC
                ****    **    **   *  **       ** **     *  * ******  *    *

ZM4_NATIVE      GAAACCCGTAAGGCTTATCTGGATTTGATCCAGTATGAGCGGGAAAA----AGGCGTAGA
ZM4_MATCHED     GAAACTAGGAAGGCATATCTAGATTTAATTCAATATGAGAGGGAAAA----AGGAGTGGA
ZM4_HR          GAAACTAGAAAGGCTTATTTGGATTTGATACAATATGAGAGGGAAAA----AGGTGTTGA
ECOLI_NATIVE    GAGACTCGCTCTGCTTATCTCGCCCGGATAGAACA----AGCGAAAACTTCGACCGTTCA
                ** **   *    ** *** * *         **   *   *  * *****       ** *

ZM4_NATIVE      CCGTCCAAACCTGTCCTGTAGTAACCTTGCTCATGGCTTTGCGGC-TATGAAT--GGTGA
ZM4_MATCHED     CAGGCCCAACCTAAGTTGTAGCAACCTAGCACATGGATTCGCCGC-AATGAAT--GGTGA
ZM4_HR          TAGACCAAATTTGTCTTGTTCTAATTTGGCTCATGGTTTTGCTGC-TATGAAT--GGTGA
ECOLI_NATIVE    TCGTTCGCAGTTGGCATGCGGTAACCTGGCACACGGTTTCGCTGCCTGCCAGCCAGAAGA
                  *   *    *  *    **    **    *  ** ** ** **  *      *    **

ZM4_NATIVE      CAAGCCAGCTTTGCGCGACTTCAACCGCATGA--ATATCGGCGTCGTGACTTCCTACAAC
ZM4_MATCHED     CAAGCCCGCATTAAGGGACTTCAACAGCATGA--ATATTGGAGTTGTGACGAGTTACAAC
ZM4_HR          TAAACCAGCTTTGAGAGATTTTAATAGAATGA--ATATAGGTGTAGTTACTTCTTATAAT
ECOLI_NATIVE    CAAAGCCTCTTTGAAAAGCAT--GTTGCGTAACAATATCGCCATCATCACCTCCTATAAC
                 **  *   * **   *  *    *    ** *  ****  *    *    *  ** **

ZM4_NATIVE      GATATGTTGTCGGCTCATGAACCATATTATCGCTATCCGGAG--CAGATGAAAGTATTTG
ZM4_MATCHED     GATATGTTAAGTGCACATGAACCCTATTATAGGTATCCTGAG--CAAATGAAGGTGTTTG
ZM4_HR          GATATGTTGTCTGCTCATGAACCATATTATAGATATCCAGAA--CAAATGAAGGTTTTTG
ECOLI_NATIVE    GACATGCTCTCCGCGCACCAGCCTTATGAACACTATCCAGAAATCATTCGTAAAGCCCTG
                ** ***  *    ** **   **  **  *     ***** **    **    *    **

ZM4_NATIVE      CTCGCGAAGTTGCCGCAACGGTTCAGGTCGCCCGTGGCGTGCCTGCTATGTGCGATGGTG
ZM4_MATCHED     CAAGGGAAGTTGGAGCCACAGTTCAAGTTGCTGGTGGAGTGCCTGCAATGTGCGATGGTG
ZM4_HR          CTCGTGAAGTTGGTGCTACAGTTCAAGTTGCTGGTGGTGTTCCTGCAATGTGTGATGGTG
ECOLI_NATIVE    C--ATGAAGCGAATGCGGTTGGTCAGGTTGCGGGCGGTGTTCCGGCGATGTGTGATGGTG
                *    ****       **   * *** ** **  ** ** ** **  ***** ** *******

ZM4_NATIVE      TGACCCAAGGTCAGCCGGGCATGGAAGAATCCCTGTTTAGCCGCGATGTTATCGCTTTGG
ZM4_MATCHED     TGACTCAGGGTCAACCTGGAATGGAAGAATCCCTATTTTCAAGGGATGTTATTGCATTAG
ZM4_HR          TTACTCAAGGTCAACCAGGTATGGAAGAATCTTTGTTTTCCAGAGATGTAATTGCTTTGG
ECOLI_NATIVE    TCACCCAGGGGCAGGATGGAATGGAATTGTCGCTGCTAAGCCGCGAAGTGATAGCGATGT
                * ** **  **  **    * ******    *   *   **   **  *  **  * * *

ZM4_NATIVE      CTACCAGCGTTTCTTTGTCTCATGGTATGTTTGAAGGGGCTGCCCTTCTCGGTATCTGTG
ZM4_MATCHED     CAACTTCAGTTTCATTATCACATGGTATGTTTGAAGGGGCAGCTCTACTCGGTATATGTG
ZM4_HR          CTACATCTGTTTCATTGTCTCACGGAATGTTTGAAGGTGCTGCATTGTTGGGAATTTGTG
ECOLI_NATIVE    CTGCGGCGGTGGGGCTGTCCCATAACATGTTTGATGGTGCTCTGTTCCTCGGTGTGTGCG
                * *    **        *    * ** * ********  **         * ** * * *

ZM4_NATIVE      ACAAGATTGTCCCTGGTCTGTTGATGGGCGCTCTGCGCTTTGGTCACCTGCCGACCATTC
ZM4_MATCHED     ACAAGATTGTTCCTGGTCTACTAATGGGAGCACTAAGGTTTGGTCACCTACCTACTATTC
ZM4_HR          ATAAAATTGTTCCAGGTTTGTTGATGGGTGCTTTGAGGTTCGGTCATTTGCCAACTATTT
ECOLI_NATIVE    ACAAGATTGTCCCGGGTCTGACGATGGCAGCCCTGTCGTTTGGTCATTTGCCTGCGGTGT
                * ** ***** **  **     ****   **     *    ****** **  *   *  *
```

FIG. 6C

```
ZM4_NATIVE    TGGTCCCATCAGGCCCGATGACGACTGGTATCCCGAACAAAGAAAAAATCCGTATCCGTC
ZM4_MATCHED   TAGTTCCCAGTGGACCTATGACAACGGGTATACCTAACAAAGAAAAAATTAGGATTAGGC
ZM4_HR        TGGTTCCATCTGGTCCAATGACTACTGGAATCCCAAATAAAGAAAAGATTAGAATTAGAC
ECOLI_NATIVE  TTGTGCCGTCTGGACCGATGGCAAGCGGTTTGCCAAATAAAGAAAAAGTGCGTATTCGCC
                * **  **     ** ** ***  *  **   * ** ** ********   *   * **    * *

ZM4_NATIVE    AGCTCTATGCTCAGGGTAAAATCGGCCAGAAAGAACTTCTGGATATGGAAGCGGCTTGCT
ZM4_MATCHED   AACTCTATGCACAAGGTAAAATTGGACAAAAAGAACTACTACATATGGAAGCCGCATGCT
ZM4_HR        AATTGTATGCTCAAGGAAAAATTGGTCAAAAGGAATTGTTGCATATGGAAGCTGCCTGTT
ECOLI_NATIVE  AGCTTTATGCCGAAGGTAAAGTGGACCGCATGGCCTTACTGGAGTCAGAAGCCGCGTCTT
                *  * *****    *  ** ***     *     *   *    * **    *****  **  *    *

ZM4_NATIVE    ACCATGCTGAAGGTACCTGCACCTTCTATGGTACGGCAAACACCAACCAGATGGTTATGG
ZM4_MATCHED   ACCATGCAGAAGGTACTTGCACTTTCTATGGTACAGCCAACACTAACCAGATGGTTATGG
ZM4_HR        ATCATGCTGAAGGTACTTGTACTTTTATGGTACTGCTAACACTAATCAGATGGTTATGG
ECOLI_NATIVE  ACCATGCGCCGGGAACATGTACTTCTACGGTACTGCCAACACCAACCAGATGGTGGTGG
                * *****       ** **  ** **  ** **   ** *****  ** *******   ***

ZM4_NATIVE    AAGTCCTCGGTCTTCATATGCCAGGTTCGGCATTTGTTACCCCGGGTACCCCGCTCCGCC
ZM4_MATCHED   AAGTTCTCGGTCTACATATGCCCGGTAGTGCCTTTGTTACTCCTGGTACTCCTCTCAGGC
ZM4_HR        AAGTTTTGGGTTTGCACATGCCAGGTAGTGCATTCGTTACTCCAGGTACTCCACTGAGAC
ECOLI_NATIVE  AGTTTATGGGGATGCAGTTGCCAGGCTCTTCTTTTGTTCATCCGGATTCTCCGCTGCGCG
                  * *    *  *   *  ** **   *  *    *  *       *

ZM4_NATIVE    AGGCTCTGACCCGTGCTGCTGTGCATCGCGTTGCTGAATTGGGTTGGAAGGGCGACGATT
ZM4_MATCHED   AAGCACTAACTAGGGCAGCAGTGCATAGGGTTGCAGAATTAGGTTGGAAGGGAGACGATT
ZM4_HR        AGGCTTTGACTAGAGCTGCTGTTCATAGAGTTGCAGAGTTGGGTTGGAAAGGTGATGATT
ECOLI_NATIVE  ATGCTTTGACCGCCGCAGCTGCGCGTCAGGTTACACGCATGACCGGTAATGGTAATGAAT
                * **  *  *  **  ** ** *   *  * *     * ** **  ** *   *  * **

ZM4_NATIVE    ATCGTCCGCTTGGTAAAATCATTGACGAAAAATCAATCGTCAATGCTATTGTTGGTCTGT
ZM4_MATCHED   ATAGGCCTCTAGGTAAAATTATTGACGAAAAAAGTATTGTTAATGCAATTGTTGGTCTAT
ZM4_HR        ATAGACCTTTGGGTAAAATTATTGATGAGAAATCTATTGTTAATGCTATTGTTGGTTTGT
ECOLI_NATIVE  GGATGCCGATCGGTAAGATGATCGATGAGAAAGTGGTGGTGAACGGTATCGTTGCACTGC
                      **    * ***** ** **  ** **   **      *  ** **   ** ****    *

ZM4_NATIVE    TGGCAACCGGTGGTTCCACCAACCATACCATGCATATTCCGGCCATTGCTCGTGCTGCTG
ZM4_MATCHED   TAGCCACTGGTGGTAGTACTAACCATACGATGCATATTCCTGCTATTGCAAGGGCAGCAG
ZM4_HR        TAGCTACAGGTGGTTCTACAAATCATACAATGCATATTCCGGCCATAGCTAGAGCAGCAG
ECOLI_NATIVE  TGGCGACCGGTGGTTCCACTAACCACACCATGCACCTGGTGGCGATGGCGCGCGCGGCCG
                * **  ** ******     **  **  ***** **  *  **   **  ** ** **  *

ZM4_NATIVE    GTGTTATCGTTAACTGGAATGACTTCCATGATCTTTCTGAAGTTGTTCCGTTGATTGCCC
ZM4_MATCHED   GTGTTATTGTTAACTGGAATGACTTCCATGATCTATCAGAAGTTGTTCCTTTAATTGCTA
ZM4_HR        GGGTTATAGTTAATTGGAATGATTTTCATGATTTGTCTGAAGTTGTTCCATTGATTGCTA
ECOLI_NATIVE  GTATTCAGATTAACTGGGATGACTTCTCTGACCTTTCTGATGTTGTACCGCTGATGGCAC
                *  **       **** **** ****    ***     * **  * **  **  ***   *  * *  **

ZM4_NATIVE    GCATTTACCCGAATGGCCCGCGCGACATCAATGAATTCCAGAATGCAGGCGGCATGGCTT
ZM4_MATCHED   GGATTTACCCTAATGGACCTAGGGACATTAACGAATTTCAAAATGCCGGAGGAATGGCAT
ZM4_HR        GAATTTATCCAAATGGTCCTAGAGATATAAATGAATTTCAAAATGCAGGAGGAATGGCTT
ECOLI_NATIVE  GTCTCTACCCGAACGGTCCGGCCGATATTAACCACTTCCAGCCGGCAGGTGGCGTACCGG
                *   * **  ** ** **   *    *  ** **   *    **    ** **  *        *

ZM4_NATIVE    ATGTCATCAAAGAACTGCTTTCTGCTAATCTGTTGAACCGTGATGTCACGACCATTGCCA
ZM4_MATCHED   ATGTTATTAAGGAACTACTATCAGCAAATCTACTAAACAGGGATGTTACAACTATTGCTA
ZM4_HR        ATGTAATTAAAGAATTGTTGAGTGCGAATTTGTTAAATAGAGATGTTACTACTATTGCTA
ECOLI_NATIVE  TTCTGGTGCGTGAACTGCTCAAAGCAGGCCTGCTGCATGAAGATGTCAATACGGTGGCAG
                    *    *  *** * *   **     *   *    *   ***** **   **  **
```

FIG. 6C (Cont. 1)

```
ZM4_NATIVE      AGGGCGGT--ATCGAAGAATACGCCAAGGCTCCGGCATTAAATGATGCTGGCGAATTGGT
ZM4_MATCHED     AGGGGAGGT--ATAGAAGAATACGCTAAGGCACCTGCCCTAAATGATGCAGGAGAATTAGT
ZM4_HR          AAGGAGGG--ATAGAAGAATATGCTAAAGCTCCAGCTCTGAACGATGCGGGTGAATTGGT
ECOLI_NATIVE    GTTTTGGTCTGTCTCGTTATACCCTTGAACCATGGC--TGAATAATG---GTGAACTGGA
                  **        *   *** *     *      **   * **  ***   * ***  * *

ZM4_NATIVE      CTGG----AAGCCAGCTGGCGAACCTGGTGATGACACCATTCTGCGTCCGGTTTCTAAT--
ZM4_MATCHED     TTGG---AAGCCCGCAGGAGAACCTGGTGATGACACTATTCTAAGGCCTGTTTCAAAT--
ZM4_HR          GTGG---AAACCGGCTGGCGAACCTGGGGACGACACAATTTTTGAGACCAGTATCTAAT--
ECOLI_NATIVE    CTGGCGGGAAGGGGCGGAAAAATCACTCGACAGCA--ATGTGATCGCTTCCTTCGAACAA
                 ***        *    *  **   *    **  **   **   *       ** **

ZM4_NATIVE      CCTTTCGCAAAAGATGGCGGTCTGCGTCTCTTGGAAGGTAACCTTGGCCGTGCAATGTAC
ZM4_MATCHED     CCTTTCGCCAAAGATGGAGGTCTAAGGCTCTTAGAAGGTAACCTAGGAAGGGCCATGTAC
ZM4_HR          CCATTTGCTAAAGATGGTGGTTTGCGTCTCTTGGAAGGTAATTTGGGTAGAGCAATGTAT
ECOLI_NATIVE    CCTTTCTCTCATCATGGTGGGACAAAAGTGTTAAGCGGTAACCTGGGCCGTGCGGT-TAT
                ** **   *  * ****  **        *  **   ***** *  **   * ** **

ZM4_NATIVE      -AAGGCCAGTGCGGT--TGATCCTAAATTCTGGACCATTGAAGCACCGGTTCGCGTCTTC
ZM4_MATCHED     -AAGGCTAGCGCCGT--TGATCCTAAATTCTGGACTATTGAAGCCCCTGTTAGGGTTTTC
ZM4_HR          -AAGGCTTCTGCTGT--AGATCCAAAATTCTGGACTATTGAAGCTCCCGTTAGAGTTTTC
ECOLI_NATIVE    GAAAACCTCTGCCGTGCCGGTTGAGAA--CCAGGTGATTGAAGCGCCAGCGGTTGTTTTT
                 **   *    **  *  **  *  *    **   * ******** ** **    * ***  ** **

ZM4_NATIVE      TCTGACCAAGACGATGTTCAGAAAGCCTTCAAGGCTGGCGAATTGAACAAAGACGTTATC
ZM4_MATCHED     TCAGACCAGGACGATGTTCAAAAAGCCTTCAAGGCAGGAGAACTAAACAAAGACGTTATT
ZM4_HR          TCTGATCAAGATGATGTTCAAAAGGCTTTTAAAGCAGGCGAGTTAAATAAAGATGTTATA
ECOLI_NATIVE    GAAAGCCAGCATGACGTTATGCCGGCCTTTGAAGCGGGTTTGCTGGACCGCGATTGTGTC
                       *    ** * *** *  ***  **  ** **   *    *         *  * **    *

ZM4_NATIVE      GTTGTTGTTCGTTTCCAGGGCCCGCGCGCAAACGGTATGCCTGAATTGCATAAGCTGACC
ZM4_MATCHED     GTTGTTGTTAGGTTCCAAGGACCTAGGGCCAACGGTATGCCTGAATTACATAAGCTAACT
ZM4_HR          GTTGTTGTTAGATTTCAAGGTCCTCGTGCTAATGGTATGCCTGAATTGCATAAGTTGACT
ECOLI_NATIVE    GTTGTTGTCCGTCATCAGGGGCCAAAAGCGAACGGAATGCCAGAATTACATAAACTCATG
                ********   *   ** **  **     ** ** ** ***** ***** *****     * *

ZM4_NATIVE      CCGGCTTTGGGTGTTCTGCAGGATAATGGCTACAAAGTTGCTTTGGTAACTGATGGTCGT
ZM4_MATCHED     CCTGCATTAGGTGTTCTACAAGATAATGGATACAAAGTTGCATTAGTGACGGATGGTAGG
ZM4_HR          CCTGCGCTAGGCGTATTGCAAGATAATGGTTATAAGGTTGCTTTAGTTACTGATGGTAGA
ECOLI_NATIVE    CCGCCACTTGGTGTATTATTGGACCGGTGTTTCAAAATTGCGTTAGTTACCGATGGACGA
                ** *   * * *** **  *          *   *  ** **    ** ** ***** *

ZM4_NATIVE      ATGTCCGGTGCTACCGGTAAAGTTCCGGTTGCTTTGCATGTCAGCCCAGAAGCTCTTGGC
ZM4_MATCHED     ATGAGTGGTGCAACTGGTAAAGTTCCTGTTGCATTACATGTTTCACCCGAAGCACTAGGA
ZM4_HR          ATGTCTGGTGCAACTGGTAAAGTACCGGTGGCTCTGCATGTTTCACCAGAGGCTTTAGGA
ECOLI_NATIVE    CTCTCCGGCGCTTCAGGTAAAGTGCCGTCAGCTATCCACGTAACACCAGAAGCCTACGAT
                    *  ** **   * ********  **  * **     **    **  ***  **       *

ZM4_NATIVE      GGTGGTGCCATCGGTAAAT-TACGTGATGGCGATATCGTCCGTATCTCGGTTGAAGAAGG
ZM4_MATCHED     GGTGGTGCTATTGGTAAAC-TTAGGGATGGAGATATTGTTAGGATTAGTGTTGAAGAAGG
ZM4_HR          GGTGGGGCGATTGGCAAGT-TGAGAGATGGCGATATAGTTAGAATTTCTGTTGAAGAAGG
ECOLI_NATIVE    GGCGG-GCTGCTGGCAAAAGTGCGCGACGGGGACATCATTCGTGTGAATGGACAGACAGG
                ** **   **    ** ** ** * ** **  ** **  ** *  ** ** *    * ***

ZM4_NATIVE      CAAACTTGAAGCTTTGGTTCCAGCTGATGA-GTGGAA-----TGCTCG---TCCGCATG-
ZM4_MATCHED     AAAACTTGAAGCACTCGTTCCCGCAGATGA-GTGGAA-----TGCAAG---GCCTCATG-
ZM4_HR          TAAATTAGAGGCTCTTGTCCCCGCCGACGA-GTGGAA-----TGCTAG---ACCACATG-
ECOLI_NATIVE    CGAACT-GACGCTGCTG-----GTAGACGAAGCGGAACTGGCTGCTCGCGAACCGCACAT
                  ** ** * **  * *       *    ** **  ** ****    ***   *   ** **
```

FIG. 6C (Cont. 2)

```
ZM4_NATIVE     --CTGAAAAACCGGCTTTCCGTCCGGGAACCGGACGCGAATTGTTTGATATCTTCCGTCA
ZM4_MATCHED    --CAGAAAAACCTGCATTCAGGCCTGGGACTGGGAGGGAATTATTTGATATTTTCAGGCA
ZM4_HR         --CTGAGAAGCCCGCTTTTAGACCTGGTACTGGGAGAGAATTGTTTGACATTTTTAGACA
ECOLI_NATIVE   TCCTGACCTGAGCGCGTCACGCGTGGGAACAGGACGTGAATTATTCAGCGCCTTGCGTGA
                 * **        ** *     *   ** ** **    * ***** **       ** *   *

ZM4_NATIVE     GAATGCTG-CTAAAGCTGAAGACGGTGCAGTCGCAATATATGCAGGTGCCGGTATC
ZM4_MATCHED    AAATGCAG-CAAAAGCAGAAGACGGTGCCGTTGCCATCTATGCCGGTGCTGGTATA
ZM4_HR         AAACGCTG-CTAAGGCTGAGGATGGTGCAGTTGCAATTTATGCTGGGGCAGGGATC
ECOLI_NATIVE   AAA-ACTGTCCGGTGCCGAACAGGG------CGCAACCTGTATCACTTTT------
                **   *   *        **  **   *  **            **   *   *   *
```

FIG. 6C (Cont. 3)

Protein Sequence Alignment for ZM4 Native, ZM4 Matched, ZM4 HR and *E.coli* Edd

```
ZM4_NATIVE      MTDLHSTVEKVTARVIERSRETRKAYLDLIQYEREKGVDRPNLSCSNLAHGFAAMN-GDK
ZM4_MATCHED     MTDLHSTVEKVTARVIERSRETRKAYLDLIQYEREKGVDRPNLSCSNLAHGFAAMN-GDK
ZM4_HR          MTDLHSTVEKVTARVIERSRETRKAYLDLIQYEREKGVDRPNLSCSNLAHGFAAMN-GDK
ECOLI_NATIVE    ---MNPQLLRVTNRIIERSRETRSAYLARIEQAKTSTVHRSQLACGNLAHGFAACQPEDK
                   :.  : :** *:*******.***  *:   :  . *.*.:*:*.********  : **

ZM4_NATIVE      PALRDFNRMNIGVVTSYNDMLSAHEPYYRYPEQMKVFAREVGATVQVAGGVPAMCDGVTQ
ZM4_MATCHED     PALRDFNRMNIGVVTSYNDMLSAHEPYYRYPEQMKVFAREVGATVQVAGGVPAMCDGVTQ
ZM4_HR          PALRDFNRMNIGVVTSYNDMLSAHEPYYRYPEQMKVFAREVGATVQVAGGVPAMCDGVTQ
ECOLI_NATIVE    ASLKSMLRNNIAIITSYNDMLSAHQPYEHYPEIIRKALHEANAVGQVAGGVPAMCDGVTQ
                .:*::.: * **.::**********:** :*** ::    :*..*. ************

ZM4_NATIVE      GQPGMEESLFSRDVIALATSVSLSHGMFEGAALLGICDKIVPGLLMGALRFGHLPTILVP
ZM4_MATCHED     GQPGMEESLFSRDVIALATSVSLSHGMFEGAALLGICDKIVPGLLMGALRFGHLPTILVP
ZM4_HR          GQPGMEESLFSRDVIALATSVSLSHGMFEGAALLGICDKIVPGLLMGALRFGHLPTILVP
ECOLI_NATIVE    GQDGMELSLLSREVIAMSAAVGLSHNMFDGALFLGVCDKIVPGLTMAALSFGHLPAVFVP
                ** *** **.**:**:::.*.***.**:.**:**:********* *.** *****::**

ZM4_NATIVE      SGPMTTGIPNKEKIRIRQLYAQGKIGQKELLDMEAACYHAEGTCTFYGTANTNQMVMEVL
ZM4_MATCHED     SGPMTTGIPNKEKIRIRQLYAQGKIGQKELLDMEAACYHAEGTCTFYGTANTNQMVMEVL
ZM4_HR          SGPMTTGIPNKEKIRIRQLYAQGKIGQKELLDMEAACYHAEGTCTFYGTANTNQMVMEVL
ECOLI_NATIVE    SGPMASGLPNKEKVRIRQLYAEGKVDRMALLESEAASYHAPGTCTFYGTANTNQMVVEFM
                ****::*:*****:*******:**:.   ***: **:*** ***************:*.:

ZM4_NATIVE      GLHMPGSAFVTPGTPLRQALTRAAVHRVAELGWKGDDYRPLGKIIDEKSIVNAIVGLLAT
ZM4_MATCHED     GLHMPGSAFVTPGTPLRQALTRAAVHRVAELGWKGDDYRPLGKIIDEKSIVNAIVGLLAT
ZM4_HR          GLHMPGSAFVTPGTPLRQALTRAAVHRVAELGWKGDDYRPLGKIIDEKSIVNAIVGLLAT
ECOLI_NATIVE    GMQLPGSSFVHPDSPLRDALTAAAARQVTRMTGNGNEWMPIGKMIDEKVVVNGIVALLAT
                *:::***:** *.:***:*** **.::: .:*:::  *:**:*****..**.**.****
```

FIG. 6D

```
ZM4_NATIVE      GGSTNHTMHIPAIARAAGVIVNWNDFEDLSEVVPLIARIYPNGPRDINEFQNAGGMAYVI
ZM4_MATCHED     GGSTNHTMHIPAIARAAGVIVNWNDFEDLSEVVPLIARIYPNGPRDINEFQNAGGMAYVI
ZM4_HR          GGSTNHTMHIPAIARAAGVIVNWNDFEDLSEVVPLIARIYPNGPRDINEFQNAGGMAYVI
ECOLI_NATIVE    GGSTNHTMHLVAMARAAGIQINWDDFSDLSDVVPLMARLYPNGPADINHFQAAGGVPVLV
                *********:.*:****:.:**:** ***:****:**:**** ***.** ***:. ::

ZM4_NATIVE      KELLSANLLNRDVTTIAKGGIEEYAKAPALNDAGELVWKPAGEPG-DDTILRPVSNPFAK
ZM4_MATCHED     KELLSANLLNRDVTTIAKGGIEEYAKAPALNDAGELVWKPAGEPG-DDTILRPVSNPFAK
ZM4_HR          KELLSANLLNRDVTTIAKGGIEEYAKAPALNDAGELVWKPAGEPG-DDTILRPVSNPFAK
ECOLI_NATIVE    RELLKAGLLHEDVNTVAGFGLSRYTLEPWLNN-GELDWREGAEKSLDSNVIASFEQPFSH
                :***.*.**:.**.*:*   *:...*:  * **: *** *: ..* .*...:: ...:**::

ZM4_NATIVE      DGGLRLLEGNLGRAMYKASAVDPKFWTIEAPVRVFSDQDDVQKAFKAGELNKDVIVVVRF
ZM4_MATCHED     DGGLRLLEGNLGRAMYKASAVDPKFWTIEAPVRVFSDQDDVQKAFKAGELNKDVIVVVRF
ZM4_HR          DGGLRLLEGNLGRAMYKASAVDPKFWTIEAPVRVFSDQDDVQKAFKAGELNKDVIVVVRF
ECOLI_NATIVE    HGGTKVLSGNLGRAVMKTSAVPVENQVIEAPAVVFESQHDVMPAFEAGLLDRDCVVVVRH
                .** ::*.******:*:*** :*.**:*.  :****. **..*.** **:** *:.* :****.

ZM4_NATIVE      QGPRANGMPELEKLTPALGVLQDNGYKVALVTDGRMSGATGKVPVALHVSPEALGGGAIG
ZM4_MATCHED     QGPRANGMPELEKLTPALGVLQDNGYKVALVTDGRMSGATGKVPVALHVSPEALGGGAIG
ZM4_HR          QGPRANGMPELEKLTPALGVLQDNGYKVALVTDGRMSGATGKVPVALHVSPEALGGGAIG
ECOLI_NATIVE    QGPKANGMPELEKLMPPLGVLLDRCFKIALVTDGRLSGASGKVPSAIHVTPEAYDGGLLA
                ***:*********** *.**** *. .:*:*******:***.**** *:***:*** .**  :.

ZM4_NATIVE      KLRDGDIVRISVEEGKLEALVPADEWNAR-PHA-EKPAFRPGTGRELFDIFRQNAAKAED
ZM4_MATCHED     KLRDGDIVRISVEEGKLEALVPADEWNAR-PHA-EKPAFRPGTGRELFDIFRQNAAKAED
ZM4_HR          KLRDGDIVRISVEEGKLEALVPADEWNAR-PHA-EKPAFRPGTGRELFDIFRQNAAKAED
ECOLI_NATIVE    KVRDGDIIRVNGQTGELTLLVDEAELAAREPHIPDLSASRVGTGRELFSALREKLSGAEQ
                *:*****:*:.. :  *:*  ** **    *  ** ** ** *******.  :*::  :  **:

ZM4_NATIVE      GAVAIYAGAGI
ZM4_MATCHED     GAVAIYAGAGI
ZM4_HR          GAVAIYAGAGI
ECOLI_NATIVE    GATCITF----
```

FIG. 6D (Cont.)

SEQUENCE LISTING

<160> NUMBER OF SEQ ID NOS: 461

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 1
aactgactag taaaaaaatg cgtgatatcg attcc                                35

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtaactcga gctactaggc aacagcagcg cgcttg                               36

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aactgactag taaaaaaatg actgatctgc attcaacg                             38

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtaactcga gctactagat accggcacct gcatatattg c                         41

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aactgactag taaaaaaatg aaaaactgga aaacaagtgc agaatc                    46

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtaactcga gctactacag cttagcgcct tctacagctt cacg                      44

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```
aactgactag taaaaaaatg aatccacaat tgttacgcgt aacaaatcg          49

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtaactcga gctactaaaa agtgatacag gttgcgccct gttcggcac          49

<210> SEQ ID NO 9
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgcatattcc gttcaatctt ataaagctgc catagatttt tacaccaagt cgtttttaaga     60 gcttggtgag cgcta                                              75

<210> SEQ ID NO 10
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttgccagtg aatgaccttt ggcattctca tggaaacttc agtttcatag tcgagttcaa     60
gagaaaaaaa aagaa                                              75

<210> SEQ ID NO 11
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgactgtta ctactccttt tgtgaatggt acttcttatt gtaccgtcac tgcatattcc     60
gttcaatctt ataaa                                              75

<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaatcaact ctctttcttc caaccaaatg gtcagcaatg agtctggtag cttgccagtg     60
aatgaccttt ggcat                                              75

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13
gactaactga actagtaaaa aaatgaccaa gccgcgcaca attaatcag                49

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 14
aagtgagtaa ctcgagttat taaccgctgt tgcgaagtgc cgtcgc                   46

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 15
atgtctcatc atcatcatca tcataccaag ccgcgcacaa ttaatcagaa c             51

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 16
gactaactga actagtaaaa aaatgtctca tcatcatcat catcatacca ag            52

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 17
atgtctcatc atcatcatca tcatatgacc aagccaagaa ctattaacca aaaccc        56

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 18
gactaactga actagtaaaa aaatgtctca tcatcatcat catcatatga ccaagccaag    60

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
aagtgagtaa ctcgagttat taaccggagt ttctcaaagc agtagcgata g        51

<210> SEQ ID NO 20
<211> LENGTH: 2679
<212> TYPE: DNA
<213> ORGANISM: Zymomonas mobilis

<400> SEQUENCE: 20

| | | | | | |
|---|---|---|---|---|---|
| actagtaaaa | aaatgaccaa | gccgcgcaca | attaatcaga | acccagacct | tcgctatttt | 60 |
| ggtaacctgc | tcggtcaggt | tattaaggaa | caaggcggag | agtctttatt | caaccagatc | 120 |
| gagcaaattc | gctctgccgc | gattagacgc | catcggggta | ttgttgacag | caccgagcta | 180 |
| agttctcgct | tagccgatct | cgaccttaat | gacatgttct | cttttgcaca | tgccttttg  | 240 |
| ctgttttcaa | tgctggccaa | tttggctgat | gatcgtcagg | gagatgccct | tgatcctgat | 300 |
| gccaatatgg | caagtgccct | taaggacata | aaagccaaag | gcgtcagtca | gcaggcgatc | 360 |
| attgatatga | tcgacaaagc | ctgcattgtg | cctgttctga | cagcacatcc | gaccgaagtc | 420 |
| cgtcggaaaa | gtatgcttga | ccattataat | cgcattgcag | gtttaatgcg | gttaaaagat | 480 |
| gctggacaaa | cggtgaccga | agatggtctt | ccgatcgaag | atgcgttaat | ccagcaaatc | 540 |
| acgatattat | ggcagactcg | tccgctcatg | ctgcaaaagc | tgaccgtggc | tgatgaaatc | 600 |
| gaaactgccc | tgtctttctt | aagagaaact | tttctgcctg | ttctgcccca | gatttatgca | 660 |
| gaatgggaaa | aattgcttgg | tagttctatt | ccaagcttta | tcagacctgg | taattggatt | 720 |
| ggtggtgacc | gtgacggtaa | ccccaatgtc | aatgccgata | cgatcatgct | gtctttgaag | 780 |
| cgcagctcgg | aaacggtatt | gacggattat | ctcaaccgtc | ttgataaact | gctttccaac | 840 |
| ctttcggtct | caaccgatat | ggtttcggta | tccgatgata | ttctacgtct | agccgataaa | 900 |
| agtggtacg  | atgctgcgat | ccgtgcggat | gaaccttatc | gtcgtgcctt | aaatggtatt | 960 |
| tatgaccgtt | tagccgctac | ctatcgtcag | atcgccggtc | gcaaccccttc | gcgcccagcc | 1020 |
| ttgcgttctg | cagaagccta | taaacggcct | caagaattgc | tggctgattt | gaagaccttg | 1080 |
| gccgaaggct | tgggtaaatt | ggcagaaggt | agttttaagg | cattgatccg | ttcggttgaa | 1140 |
| acctttggtt | tccatttggc | cacctcgat  | ctgcgtcaga | attcgcaggt | tcatgaagaa | 1200 |
| gttgtcaatg | aactgctacg | gacagccacc | gttgaagccg | attatttatc | tctatcggaa | 1260 |
| gaagatcgcg | ttaagctgtt | aagacgggaa | ttgtcgcagc | cgcggactct | attcgttccg | 1320 |
| cgcgccgatt | attccgaaga | aacgcgttct | gaacttgata | ttattcaggc | agcagcccgc | 1380 |
| gcccatgaaa | ttttggcccc | tgaatccatt | acgacttatt | tgatttcgaa | tggcaaagc  | 1440 |
| atttccgata | ttctggaagt | ctatttgctt | ttgaaagaag | cagggctgta | tcaaggggt  | 1500 |
| gctaagccaa | aagcggcgat | tgaagctgcg | cctttattcg | agacggtggc | cgatcttgaa | 1560 |
| aatgcgccaa | aggtcatgga | ggaatggttc | aagctgcctg | aagcgcaagc | cattgcaaag | 1620 |
| gcacatggcg | ttcaggaagt | gatggttggc | tattctgact | ccaataagga | cggcggatat | 1680 |
| ctgacctcgg | tttgggtct  | ttataaggct | tgcctcgctt | tggtgccgat | ttttgagaaa | 1740 |
| gccggtgtac | cgatccagtt | ttccatgga  | cggggtggtt | ccgttggtcg | cggtggtggt | 1800 |
| tccaacttta | atgccattct | gtcgcagcca | gccggagccg | tcaaagggcg | tatccgttat | 1860 |
| acagaacagg | gtgaagtcgt | ggcggccaaa | tatggcaccc | atgaaagcgc | tattgcccat | 1920 |
| ctggatgagg | ccgtagcggc | gactttgatt | acgtctttgg | aagcaccgac | cattgtcgag | 1980 |

-continued

| | |
|---|---|
| ccagagttta gtcgttaccg taaggccttg gatcagatct cagattcagc tttccaggcc | 2040 |
| tatcgccaat tggtctatgg aacgaagggc ttccgtaaat tctttagtga atttacgcct | 2100 |
| ttgccggaaa ttgccctgtt aaagatcggg tcacgcccac ctagccgcaa aaaatccgac | 2160 |
| cggattgaag atctacgcgc tattccttgg gtgtttagct ggtctcaagt tcgagtcatg | 2220 |
| ttacccggtt ggttcggttt cggtcaggct ttatatgact ttgaagatac cgagctgtta | 2280 |
| caggaaatgg caagccgttg ccgttttttc cgcacgacta ttcggaatat ggaacaggtg | 2340 |
| atggcacgtt ccgatatgac gatcgccaag cattatctgg ccttggttga ggatcagaca | 2400 |
| aatggtgagg ctatctatga ttctatcgcg gatggctgga ataaaggttg tgaaggtctg | 2460 |
| ttaaaggcaa cccagcagaa ttggctgttg gaacgctttc cggcggttga taattcggtg | 2520 |
| cagatgcgtc ggccttatct ggaaccgctt aattacttac aggtcgaatt gctgaagaaa | 2580 |
| tggcggggag gtgataccaa cccgcatatc ctcgaatcta ttcagctgac aatcaatgcc | 2640 |
| attgcgacgg cacttcgcaa cagcggttaa taactcgag | 2679 |

<210> SEQ ID NO 21
<211> LENGTH: 2679
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

| | |
|---|---|
| actagtaaaa aaatgaccaa gccaagaact attaaccaaa acccagactt gagatacttc | 60 |
| ggtaacttgt tgggtcaagt tatcaaggaa caaggtggtg aatctttgtt caaccaaatt | 120 |
| gaacaaatca gatccgctgc tattagaaga cacagaggta tcgtcgactc taccgaattg | 180 |
| tcctctagat tggctgactt ggacttgaac gacatgttct ccttcgctca cgctttcttg | 240 |
| ttgttctcta tgttggctaa cttggctgac gacagacaag gtgacgcttt ggacccagac | 300 |
| gctaacatgg cttccgcttt gaaggacatt aaggctaagg tgtttctca acaagctatc | 360 |
| attgacatga tcgacaaggc ttgtattgtc ccagttttga ctgctcaccc aaccgaagtc | 420 |
| agaagaaagt ccatgttgga ccactacaac agaatcgctg gtttgatgag attgaaggac | 480 |
| gctggtcaaa ctgttaccga agacggtttg ccaattgaag acgctttgat ccaacaaatt | 540 |
| actatcttgt ggcaaaccag accattgatg ttgcaaaagt tgactgtcgc tgacgaaatt | 600 |
| gaaaccgctt tgtctttctt gagagaaact ttcttgccag ttttgccaca aatctacgct | 660 |
| gaatgggaaa agttgttggg ttcctctatt ccatccttca tcagaccagg taactggatt | 720 |
| ggtggtgaca gagacggtaa cccaaaacgtc aacgctgaca ccatcatgtt gtcttttgaag | 780 |
| agatcctctg aaactgtttt gaccgactac ttgaacagat tggacaagtt gttgtccaac | 840 |
| ttgtctgtct ccactgacat ggtttctgtc tccgacgaca ttttgagatt ggctgacaag | 900 |
| tctggtgacg acgctgctat cagagctgac gaaccataca aagagctttt gaacggtatt | 960 |
| tacgacagat ggctgctac ctacagacaa atcgctggta aaacccatc cagaccagct | 1020 |
| ttgagatctg ctgaagctta caagagacca caagaattgt tggctgactt gaagactttg | 1080 |
| gctgaaggtt tgggtaagtt ggctgaaggt tccttcaagg ctttgattag atctgttgaa | 1140 |
| accttcggtt tccacttggc tactttggac ttgagacaaa actcccaagt ccacgaagaa | 1200 |
| gttgtcaacg aattgttgag aaccgctact gttgaagctg actacttgtc tttgtccgaa | 1260 |
| gaagacagag tcaagttgtt gagaagagaa ttgtctcaac caagaaccctt gttcgttcca | 1320 |
| agagctgact actccgaaga aactagatct gaattggaca tcattcaagc tgctgctaga | 1380 |

```
gctcacgaaa tcttcggtcc agaatccatt accacttact tgatctctaa cggtgaatcc   1440
atttctgaca tcttggaagt ctacttgttg ttgaaggaag ctggtttgta ccaaggtggt   1500
gctaagccaa aggctgctat tgaagctgct ccattgttcg aaaccgttgc tgacttggaa   1560
aacgctccaa aggtcatgga agaatggttc aagttgccag aagctcaagc tatcgctaag   1620
gctcacggtg ttcaagaagt catggttggt tactccgact ctaacaagga cggtggttac   1680
ttgacttccg tctggggttt gtacaaggct tgtttggctt tggttccaat tttcgaaaag   1740
gctggtgtcc caatccaatt cttccacggt agaggtggtt ctgttggtag aggtggtggt   1800
tccaacttca acgctatttt gtctcaacca gctggtgctg tcaagggtag aatcagatac   1860
accgaacaag gtgaagttgt cgctgctaag tacggtactc acgaatccgc tattgctcac   1920
ttggacgaag ctgttgctgc taccttgatc acttctttgg aagctccaac cattgtcgaa   1980
ccagaattct ccagatacag aaaggctttg gaccaaatct ctgactccgc tttccaagct   2040
tacagacaat tggtttacgg tactaagggt ttcagaaagt tcttctctga attcacccca   2100
ttgccagaaa ttgctttgtt gaagatcggt tccagaccac catctagaaa gaagtccgac   2160
agaattgaag acttgagagc tatcccatgg gtcttctctt ggtcccaagt tagagtcatg   2220
ttgccaggtt ggttcggttt cggtcaagct ttgtacgact tcgaagacac tgaattgttg   2280
caagaaatgg cttctagatg gccattcttc agaaccacta ttagaaacat ggaacaagtt   2340
atggctagat ccgacatgac catcgctaag cactacttgg ctttggtcga agaccaaact   2400
aacggtgaag ctatttacga ctctatcgct gacggttgga acaagggttg tgaaggtttg   2460
ttgaaggcta cccaacaaaa ctggttgttg gaaagattcc cagctgttga caactccgtc   2520
caaatgagaa gaccatactt ggaaccattg aactacttgc aagttgaatt gttgaagaag   2580
tggagaggtg gtgacactaa cccacacatt ttggaatcta tccaattgac cattaacgct   2640
atcgctactg ctttgagaaa ctccggttaa taactcgag                         2679

<210> SEQ ID NO 22
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggaatttt tcagcaatat cggtaaaatt cagtatcagg gaccaaaaag tactgatcct     60
ctctcattta agtactataa ccctgaagaa gtcatcaacg aaagacaat gcgcgagcat    120 ctgaagttcg ctctttcatg gtggcacaca atgggcggcg acggaacaga tatgttcggc    180
tgcggcacaa cagacaagac ctggggacag tccgatcccg ctgcaagagc aaaggctaag    240
gttgacgcag cattcgagat catggataag ctctccattg actactattg tttccacgat    300
cgcgatcttt ctcccgagta tggcagcctc aaggctacca acgatcagct tgacatagtt    360
acagactata tcaaggagaa gcagggcgac aagttcaagt gcctctgggg tacagcaaag    420
tgcttcgatc atccaagatt catgcacggt gcaggtacat ctccttctgc tgatgtattc    480
gctttctcag ctgctcagat caagaaggct ctggagtcaa cagtaaagct cggcggtaac    540
ggttacgttt tctggggcgg acgtgaaggc tatgagacac ttcttaatac aaatatggga    600
ctcgaactcg acaatatggc tcgtcttatg aagatggctg ttgagtatgg acgttcgatc    660
ggcttcaagg gcgacttcta tatcgagccc aagcccaagg agcccacaaa gcatcagtac    720
```

```
gatttcgata cagctactgt tctgggattc ctcagaaagt acggtctcga taaggatttc      780
aagatgaata tcgaagctaa ccacgctaca cttgctcagc atacattcca gcatgagctc      840
cgtgttgcaa gagacaatgg tgtgttcggt tctatcgacg caaaccaggg cgacgttctt      900
cttggatggg atacagacca gttccccaca aatatctacg atacaacaat gtgtatgtat      960
gaagttatca aggcaggcgg cttcacaaac ggcggtctca acttcgacgc taaggcacgc     1020
agagggagct tcactcccga ggatatcttc tacagctata tcgcaggtat ggatgcattt     1080
gctctgggct tcagagctgc tctcaagctt atcgaagacg gacgtatcga caagttcgtt     1140
gctgacagat acgcttcatg gaataccggt atcggtgcag acataatcgc aggtaaggca     1200
gatttcgcat ctcttgaaaa gtatgctctt gaaaagggcg aggttacagc ttcactctca     1260
agcggcagac aggaaatgct ggagtctatc gtaaataacg ttcttttcag tctgtaa       1317
```

<210> SEQ ID NO 23
<211> LENGTH: 1314
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atggagttct tttctaatat aggtaaaatt cagtatcaag gtccaaaatc tacagatcca       60 ttgtcttta aatattataa tccagaagaa gttataaatg gtaaaactat gagagaacat      120
ttaaaatttg ctttgtcttg gtggcatact atgggtggtg atggtactga tatgttcggt      180
tgtggtacta ctgataaaac ttggggtcaa tctgatccag ctgctagagc aaaagccaaa      240
gtagatgcag cctttgaaat tatggataaa ttgtctattg attattattg ttttcatgat      300
agagatttgt ctcctgaata tggttctta aaagcaacta atgatcaatt ggacattgtt      360
acggattata ttaaagaaaa acaaggtgat aaatttaaat gtttgtgggg cactgcgaaa      420 tgtttttgatc atccacgttt tatgcatggt gcggggacga gtccttctgc tgatgttttt      480
gctttttctg ccgctcaaat taagaaggca ttggaatcaa ctgttaaatt aggtgggaac      540
gggtatgtat tctggggagg aagggaaggt tatgaaacat tattaaacac taatatgggt      600
ttggaattgg ataatatggc tagattgatg aaaatggctg tagaatacgg aaggtctatt      660
ggttttaagg gtgactttta tattgaacca aaacctaaag agcctactaa acatcaatat      720
gattttgata ctgctacagt tttgggattc ttgagaaaat atggtctgga taaagatttt      780
aaaatgaata tagaagctaa tcatgcaaca ctcgcacaac atacttttca acatgaattg      840
agagttgcca gagataacgg agttttttgga tctatcgatg caaaccaggg agacgttttg      900
ctaggatggg atactgatca atttccaact aacatttatg tactactat gtgtatgtat      960 gaagtaatta aggcaggagg ctttactaat ggcggattaa actttgatgc gaaggctagg     1020
cgtggtagtt tcactccaga ggatatattc tattcttata ttgctggaat ggatgctttc     1080
gcgttaggtt tcagggcagc actaaaattg attgaagatg gtagaattga taagtttgta     1140
gctgatagat atgcttcttg gaatactgga ataggagcag atataatcgc tgggaaagcc     1200
gacttcgcca gtctggaaaa atatgcgctt gaaaaggag aagttactgc cagcttaagt     1260
tccggtcgtc aagaaatgtt ggaatctatt gtaaacaatg ttttattttc tctg          1314
```

<210> SEQ ID NO 24
<211> LENGTH: 1314
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 24
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt gcgccgaagg tgctgaccaa     180
ttcggtggag gtacaaagtc tttcccatgg aacgaaggta ctgatgctat gaaattgcc      240 aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccgtattaa gcttctctgg      420 agtactgcta acgtcttcgg tcacaagcgt tacatgaacg gtgcctccac taacccagac     480
tttgatgttg tcgcccgtgc tattgttcaa attaagaacg ccatagacgc cggtattgaa     540
cttggtgctg aaaactacgt cttctggggt ggtcgtgaag gttacatgag tctccttaac     600
actgaccaaa agcgtgaaaa ggaacacatg gccactatgc ttaccatggc tcgtgactac     660
gctcgttcca agggattcaa gggtactttc ctcattgaac caaagccaat ggaaccaacc     720
aagcaccaat acgatgttga cactgaaacc gctattggtt tccttaaggc ccacaactta     780
gacaaggact tcaaggtcaa cattgaagtt aaccacgcta ctcttgctgg tcacactttc     840
gaacacgaac ttgcctgtgc tgttgatgct ggtatgctcg gttccattga tgctaaccgt     900
ggtgactacc aaaacggttg ggatactgat caattcccaa ttgatcaata cgaactcgtc     960
caagcttgga tggaaatcat ccgtggtggt ggtttcgtta ctggtggtac caacttcgat    1020
gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga agaaggaacg ttacgcttcc ttcgacagtg gtattggtaa ggactttgaa    1200
gatggtaagc tcaccctcga acaagtttac gaatacggta agaagaacgg tgaaccaaag    1260
caaacttctg gtaagcaaga actctacgaa gctattgttg ccatgtacca ataa          1314

<210> SEQ ID NO 25
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggctaaag aatattttcc acaaattcag aaaattaaat ttgaaggtaa agattctaaa      60
aatccattgg ctttccatta ttatgatgct gaaaagaag ttatgggtaa aaagatgaaa      120
gattggttga gattcgctat ggcttggtgg catactctat gtgctgaagg agctgatcaa     180
tttggaggag gtactaaatc ttttccttgg aatgaaggta ctgacgctat gaaattgct      240 aagcagaaag tagacgcggg ttttgaaatt atgcaaaaat tgggaatacc atattattgt     300 ttcatgatg ttgatttggt atctgagggt aattctattg aagaatatga atctaattta      360
aaagctgttg ttgcttactt aaaagaaaaa caaaagaaa ctggaattaa attgttgtgg      420
tctacagcta atgttttcgg tcataaaaga tatatgaatg gtgcttctac aaatccagat     480
tttgatgttg tagctagagc tattgttcaa attaaaaatg ctagatagc aggaattgaa      540 ttaggtgccg aaaattatgt tttctgggga ggtagagaag ttatatgtc tttgttaaat     600
```

```
actgatcaaa aacgtgaaaa ggaacacatg gcaactatgt tgacaatggc tagggattat      660
gctagatcta aaggttttaa aggtactttc ttgattgagc aaaaacctat ggaaccaact      720
aaacatcaat atgacgttga cactgaaact gctattggtt tcttaaaagc tcataatttg      780
gataaagatt ttaaggttaa tatagaagtt aatcatgcta cactagctgg tcatactttt      840
gaacatgaat tagcttgtgc agttgatgcc ggtatgttag gttctatcga cgcaaataga      900
ggtgattatc aaaatggttg ggacacagat caatttccaa tagatcaata tgaattggtt      960
caagcatgga tggaaattat tagggtgga ggcttcgtta caggtggaac taattttgat     1020
gctaaaacta ggagaaattc tacagatctt gaagatataa ttattgctca tgtatctggt     1080
atggatgcga tggcccgtgc tttggaaaat gcagctaaat tacttcaaga atctccttat     1140
actaaaatga aaaggaaag atatgcttct tttgattctg gaataggtaa ggattttgaa     1200
gatggtaaat tgacattgga acaagtttat gaatatggta agaagaatgg agaaccaaaa     1260
caaacttctg gtaaacaaga attatatgag gctatagtag ctatgtatca ataa           1314

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acttgactac tagtatggag ttcttttcta ataggtaa aatt                          44

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agtcaagtct cgagcagaga aaataaaaca ttgtttacaa taga                        44

<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtcaagtct cgagctaatg atgatgatga tgatgcagag aaaataaaac attgtttac        59

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Lys Asp Asp Asp Asp Lys Gly
1               5

<210> SEQ ID NO 30
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Lys Pro Ile Pro Asn Pro Leu Leu Gly Leu Asp Ser Thr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Gln Lys Leu Ile Ser Glu Glu Asp Leu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Pro Glu Leu Ala Pro Glu Asp Pro Glu Asp
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Pro Tyr Asp Val Pro Asp Tyr Ala
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Thr Asp Ile Glu Met Asn Arg Leu Gly Lys
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 35

His His His His His His
```

```
<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid and this region may encompass
      1-3 residues

<400> SEQUENCE: 36

Cys Cys Xaa Xaa Xaa Cys Cys
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Cys Pro Gly Cys Cys
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Val Pro Arg Gly Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Asp Asp Asp Lys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Asn Leu Tyr Phe Gln Gly
1               5

<210> SEQ ID NO 41
<211> LENGTH: 8
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Glu Val Leu Phe Gln Gly Pro
1               5

<210> SEQ ID NO 42
<211> LENGTH: 627
<212> TYPE: DNA
<213> ORGANISM: Zymomonas mobilis

<400> SEQUENCE: 42

| | | | | | | |
|---|---|---|---|---|---|---|
| atgagagaca | ttgattctgt | tatgagattg | gctccagtta | tgccagtctt | ggttatagaa | 60 |
| gatatagctg | atgctaagcc | aattgctgag | gctttggttg | ctggtggttt | aaatgttttg | 120 |
| gaagttacat | tgagaactcc | atgtgctttg | aagctatta | aaattatgaa | ggaagttcca | 180 |
| ggtgctgttg | ttggtgctgg | tactgtttta | acgctaaaa | tgttggatca | agctcaagaa | 240 |
| gctggttgtg | agttctttgt | atcaccaggt | ttgactgctg | atttgggaaa | acatgctgtt | 300 |
| gctcaaaaag | cggctcttct | accaggggtt | gctaatgctg | ctgatgttat | gttgggattg | 360 |
| gatttggggtt | tggatagatt | taaattcttc | ccagctgaaa | atataggtgg | tttgccagct | 420 |
| ttaaaatcta | tggcttctgt | ttttagacaa | gttagatttt | gtccaactgg | aggaattact | 480 |
| ccgacttctg | ctccaaaata | tttggaaaat | ccatctattt | tgtgtgttgg | tggttcttgg | 540 |
| gttgttccag | cgggtaaacc | agatgttgcg | aaaattactg | ctttggctaa | agaggcttca | 600 |
| gcttttaaaa | gagctgctgt | ggcgtag | | | | 627 |

<210> SEQ ID NO 43
<211> LENGTH: 1824
<212> TYPE: DNA
<213> ORGANISM: Zymomonas mobilis

<400> SEQUENCE: 43

| | | | | | | |
|---|---|---|---|---|---|---|
| atgacggatt | tgcattcaac | tgttgagaaa | gtaactgcta | gagtaattga | aagatcaagg | 60 |
| gaaactagaa | aggcttattt | ggatttgata | caatatgaga | gggaaaaagg | tgttgataga | 120 |
| ccaaatttgt | cttgttctaa | tttggctcat | ggttttgctg | ctatgaatgg | tgataaacca | 180 |
| gctttgagag | atttaatag | aatgaatata | ggtgtagtta | cttcttataa | tgatatgttg | 240 |
| tctgctcatg | aaccatatta | tagatatcca | gaacaaatga | aggtttttgc | tcgtgaagtt | 300 |
| ggtgctacag | ttcaagttgc | tggtggtgtt | cctgcaatgt | gtgatggtgt | tactcaaggt | 360 |
| caaccaggta | tggaagaatc | tttgttttcc | agagatgtaa | ttgctttggc | tacatctgtt | 420 |
| tcattgtctc | acggaatgtt | tgaaggtgct | gcattgttgg | gaatttgtga | taaaattgtt | 480 |
| ccaggtttgt | tgatgggtgc | tttgaggttc | ggtcatttgc | caactatttt | ggttccatct | 540 |
| ggtccaatga | ctactggaat | cccaaataaa | gaaaagatta | gaattagaca | attgtatgct | 600 |
| caaggaaaaa | ttggtcaaaa | ggaattgttg | gatatggaag | ctgcctgtta | tcatgctgaa | 660 |
| ggtacttgta | cttttatgg | tactgctaac | actaatcaga | tggttatgga | agttttgggt | 720 |
| ttgcacatgc | caggtagtgc | attcgttact | ccaggtactc | cactgagaca | ggctttgact | 780 |
| agagctgctg | ttcatagagt | tgcagagttg | ggttggaaag | gtgatgatta | tagacctttg | 840 |
| ggtaaaatta | ttgatgagaa | atctattgtt | aatgctattg | ttggttttgtt | agctacaggt | 900 |
| ggttctacaa | atcatacaat | gcatattccg | gccatagcta | gagcagcagg | ggttatagtt | 960 |

```
aattggaatg attttcatga tttgtctgaa gttgttccat tgattgctag aatttatcca    1020
aatggtccta gagatataaa tgaatttcaa aatgcaggag gaatggctta tgtaattaaa    1080
gaattgttga gtgcgaattt gttaaataga gatgttacta ctattgctaa aggagggata    1140
gaagaatatg ctaaagctcc agctctgaac gatgcgggtg aattggtgtg gaaaccggct    1200
ggcgaacctg gggacgacac aattttgaga ccagtatcta atccatttgc taaagatggt    1260
ggtttgcgtc tcttggaagg taatttgggt agagcaatgt ataaggcttc tgctgtagat    1320
ccaaaattct ggactattga agctcccgtt agagttttct ctgatcaaga tgatgttcaa    1380
aaggctttta aagcaggcga gttaaataaa gatgttatag ttgttgttag atttcaaggt    1440
cctcgtgcta atggtatgcc tgaattgcat aagttgactc ctgcgctagg cgtattgcaa    1500
gataatggtt ataaggttgc tttagttact gatggtagaa tgtctggtgc aactggtaaa    1560
gtaccggtgg ctctgcatgt ttcaccagag gctttaggag gtggggcgat tggcaagttg    1620
agagatggcg atatagttag aatttctgtt gaagaaggta aattagaggc tcttgtcccc    1680
gccgacgagt ggaatgctag accacatgct gagaagcccg cttttagacc tggtactggg    1740
agagaattgt ttgacatttt tagacaaaac gctgctaagg ctgaggatgg tgcagttgca    1800
atttatgctg gggcagggat ctag                                            1824
```

<210> SEQ ID NO 44
<211> LENGTH: 627
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 44

```
atgagggata ttgatagtgt gatgaggtta gcccctgtta tgcctgttct cgttattgaa     60
gatattgcag atgccaaacc tattgccgaa gcactcgttg caggtggtct aaacgttcta    120
gaagtgacac taaggactcc ttgtgcacta gaagctatta agattatgaa ggaagttcct    180
ggtgctgttg ttggtgctgg tacagttcta aacgccaaaa tgctcgacca ggcacaagaa    240
gcaggttgcg aatttttcgt ttcacctggt ctaactgccg acctcggaaa gcacgcagtt    300
gctcaaaaag ccgcattact acccggtgtt gcaaatgcag cagatgtgat gctaggtcta    360
gacctaggtc tagataggtt caagttcttc cctgccgaaa acattggtgg tctacctgct    420
ctaaagagta tggcatcagt tttcaggcaa gttaggttct gccctactgg aggtataact    480
cctacaagtg cacctaaata tctagaaaac cctagtattc tatgcgttgg tggttcatgg    540
gttgttcctg ccggaaaacc cgatgttgcc aaaattacag ccctcgcaaa agaagcaagt    600
gcattcaaga gggcagcagt tgcttag                                         627
```

<210> SEQ ID NO 45
<211> LENGTH: 1824
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 45

```
atgacggatc tacatagtac agtggagaag gttactgcca gggttattga aaggagtagg     60
gaaactagga aggcatatct agatttaatt caatatgaga gggaaaaagg agtggacagg    120
cccaacctaa gttgtagcaa cctagcacat ggattcgccg caatgaatgg tgacaagccc    180
```

```
gcattaaggg acttcaacag gatgaatatt ggagttgtga cgagttacaa cgatatgtta     240
agtgcacatg aaccctatta taggtatcct gagcaaatga aggtgtttgc aagggaagtt     300
ggagccacag ttcaagttgc tggtggagtg cctgcaatgt gcgatggtgt gactcagggt     360
caacctggaa tggaagaatc cctattttca agggatgtta ttgcattagc aacttcagtt     420
tcattatcac atggtatgtt tgaagggggca gctctactcg gtatatgtga caagattgtt     480
cctggtctac taatgggagc actaaggttt ggtcacctac ctactattct agttcccagt     540
ggacctatga caacgggtat acctaacaaa gaaaaaatta ggattaggca actctatgca     600
caaggtaaaa ttgacaaaaa agaactacta gatatggaag ccgcatgcta ccatgcagaa     660
ggtacttgca ctttctatgg tacagccaac actaaccaga tggttatgga agttctcggt     720
ctacatatgc ccggtagtgc ctttgttact cctggtactc ctctcaggca agcactaact     780
agggcagcag tgcataggt tgcagaatta ggttggaagg gagacgatta taggcctcta     840
ggtaaaatta ttgacgaaaa aagtattgtt aatgcaattg ttggtctatt agccactggt     900
ggtagtacta accatacgat gcatattcct gctattgcaa gggcagcagg tgttattgtt     960
aactggaatg acttccatga tctatcagaa gttgttcctt taattgctag gatttaccct    1020
aatggaccta gggacattaa cgaatttcaa aatgccggag aatggcata tgttattaag     1080 gaactactat cagcaaatct actaaacagg gatgttacaa ctattgctaa gggaggtata    1140
gaagaatacg ctaaggcacc tgccctaaat gatgcaggag aattagtttg gaagcccgca    1200
ggagaacctg gtgatgacac tattctaagg cctgtttcaa atccttttcgc caaagatgga    1260 ggtctaaggc tcttagaagg taacctagga agggccatgt acaaggctag cgccgttgat    1320
cctaaattct ggactattga agccctgtt agggttttct cagaccagga cgatgttcaa     1380
aaagccttca aggcaggaga actaaacaaa gacgttattg ttgttgttag gttccaagga    1440
cctagggcca acggtatgcc tgaattacat aagctaactc ctgcattagg tgttctacaa    1500
gataatggat acaaagttgc attagtgacg gatggtagga tgagtggtgc aactggtaaa    1560
gttcctgttg cattacatgt ttcacccgaa gcactaggag gtggtgctat tggtaaactt    1620
agggatggag atattgttag gattagtgtt gaagaaggaa aacttgaagc actcgttccc    1680
gcagatgagt ggaatgcaag gcctcatgca gaaaaacctg cattcaggcc tgggactggg    1740
agggaattat ttgatatttt caggcaaaat gcagcaaaag cagaagacgg tgccgttgcc    1800
atctatgccg gtgctggtat atag                                           1824

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
actagtatgg ctaaggaata tttcccacaa attcaaaag                              39

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
```

```
ctcgagctac tattggtaca tggcaacaat agc                                    33

<210> SEQ ID NO 48
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctcgagctac taatgatgat gatgatgatg ttggtacatg gcaacaatag cttcg            55

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
actagtatgg ctaaagaata ttttccacaa attcag                                 36

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctcgagttat tgatacatag ctactatagc ctc                                    33

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctcgagttaa tgatgatgat gatgatgttg atacatagct actatagcct cattgtttac       60

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aatcgatcaa agcttctaaa tacaagacgt gcgatgacga ctatactgga c                51

<210> SEQ ID NO 53
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
taccgtacta cccgggtata tagtctttt gccctggtgt tccttaataa tttc              54
```

```
<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgctaatgac ccgggaattc cacttgcaat tacataaaaa attccggcgg                50

<210> SEQ ID NO 55
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atgatcattg agctcagctt cgcaagtatt cattttagac ccatggtgg                 49

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgctaatgag agctctcatt ttttggtgcg atatgttttt ggttgatg                  48

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aatgatcatg agctcgtcaa caagaactaa aaaattgttc aaaaatgc                  48

<210> SEQ ID NO 58
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctaaatacaa gacgtgcgat gacgactata ctgg                                 34

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtcaacaaga actaaaaaat tgttcaaaaa tgcaattgtc                           40
```

```
<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 60
tcrnnnnnna cg                                                            12

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(14)
<223> OTHER INFORMATION: a, c, t, g, unknown or other

<400> SEQUENCE: 61
cggnnnnnnn nnnnccg                                                       17

<210> SEQ ID NO 62
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 62
gaannttcnn gaa                                                           13

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aactgaactg actagtaaaa aaatgcaccc tcgtgtgctc gaagt                        45

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agtaaagtaa aagcttctac tagcgccagc cgttgaggct ct                           42
```

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
agtaaagtaa aagcttctac taatgatgat gatgatgatg gcgccagccg ttgaggctc      59

<210> SEQ ID NO 66
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
aactgaactg actagtaaaa aaatgcacaa ccttgaacag aagacc      46

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
agtaaagtaa ctcgagctat tagtgtctgc ggtgctcggc gaa      43

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
taaagtaact cgagctacta atgatgatga tgatgatggt gtctgcggtg ctcggcgaa      59

<210> SEQ ID NO 69
<211> LENGTH: 1830
<212> TYPE: DNA
<213> ORGANISM: Pseudomonas aeruginosa

<400> SEQUENCE: 69
atgcaccctc gtgtgctcga agtcacccgc cgcatccagg cccgtagcgc ggccactcgc      60
cagcgctacc tcgagatggt ccgggctgcg gccagcaagg ggccgcaccg cggcaccctg     120
ccgtgcggca acctcgccca cggggtcgcg gcctgtggcg aaagcgacaa gcagaccctg     180
cggctgatga accaggccaa cgtggccatc gtttccgcct acaacgacat gctctcggcg     240
caccagccgt tcgagcgctt tccggggctg atcaagcagg cgctgacgat gatcggttcg     300
gtcggccagt tcgccggcgg cgtgccggcc atgtgcgacg gggtgaccca gggcgagccg     360
ggcatggaac tgtcgctggc cagccgcgac gtgatcgcca tgtccaccgc catcgcgctg     420
tctcacaaca tgttcgatgc agcgctgtgc ctgggtgttt gcgacaagat cgtgccgggc     480
ctgctgatcg gctcgctgcg cttcggccac ctgcccaccg tgttcgtccc ggccgggccc     540
atgccgaccg gcatctccaa caaggaaaag gccgcggtgc gccaactgtt cgccgaaggc     600

```
aaggccactc gcgaagagct gctggcctcg gaaatggcct cctaccatgc acccggcacc    660
tgcaccttct atggcaccgc caataccaac cagttgctgg tggaggtgat gggcctgcac    720
ttgcccggtg cctccttcgt caacccgaac accccctgc gcgacgaact cacccgcgaa     780
gcggcacgcc aggccagccg gctgaccccc gagaacggca actacgtgcc gatggcggag    840
atcgtcgacg agaaggccat cgtcaactcg gtggtggcgc tgctcgccac cggcggctcg    900
accaaccaca ccctgcacct gctggcgatc gcccaggcgg cgggcatcca gttgacctgg    960
caggacatgt ccgagctgtc ccatgtggtg ccgaccctgg cgcgcatcta ccgaacggc    1020 caggccgaca tcaaccactt ccaggcggcc ggcggcatgt ccttcctgat ccgccaactg   1080
ctcgacggcg ggctgcttca cgaggacgta cagaccgtcg ccggccccgg cctgcgccgc   1140
tacacccgcg agccgttcct cgaggatggc cggctggtct ggcgcgaagg gccggaacgg   1200
agtctcgacg aagccatcct gcgtccgctg acaagccgt tctccgccga aggcggcttg    1260
cgcctgatgg agggcaacct cggtcgcggc gtgatgaagg tctcggcggt ggcgccggaa   1320
caccaggtgg tcgaggcgcc ggtacggatc ttccacgacc aggccagcct ggccgcggcc   1380
ttcaaggccg gcgagctgga gcgcgacctg gtcgccgtgg tgcgtttcca gggcccgcgg   1440
gcgaacggca tgccggagct gcacaagctc acgccgttcc tcgggtgtcct gcaggatcgt   1500 ggcttcaagg tggcgctggt caccgacggg cgcatgtccg gggcgtcggg caaggtgccc   1560
gcggccatcc atgtgagtcc ggaagccatc gccggcggtc cgctggcgcg cctgcgcgac   1620
ggcgaccggg tgcgggtgga tggggtgaac ggcgagttgc gggtgctggt cgacgacgcc   1680
gaatggcagg cgcgcagcct ggagccggcg ccgcaggacg gcaatctcgg ttgcggccgc   1740
gagctgttcg ccttcatgcg caacgccatg agcagcgcgg aagagggcgc ctgcagcttt   1800
accgagagcc tcaacggctg gcgctagtag                                   1830
```

<210> SEQ ID NO 70
<211> LENGTH: 608
<212> TYPE: PRT
<213> ORGANISM: Pseudomonas aeruginosa

<400> SEQUENCE: 70

```
Met His Pro Arg Val Leu Glu Val Thr Arg Ile Gln Ala Arg Ser
1               5                   10                  15

Ala Ala Thr Arg Gln Arg Tyr Leu Glu Met Val Arg Ala Ala Ser
                20                  25                  30

Lys Gly Pro His Arg Gly Thr Leu Pro Cys Gly Asn Leu Ala His Gly
                35                  40                  45

Val Ala Ala Cys Gly Glu Ser Asp Lys Gln Thr Leu Arg Leu Met Asn
        50                  55                  60

Gln Ala Asn Val Ala Ile Val Ser Ala Tyr Asn Asp Met Leu Ser Ala
65                  70                  75                  80

His Gln Pro Phe Glu Arg Phe Pro Gly Leu Ile Lys Gln Ala Leu His
                85                  90                  95

Glu Ile Gly Ser Val Gly Gln Phe Ala Gly Gly Val Pro Ala Met Cys
                100                 105                 110

Asp Gly Val Thr Gln Gly Glu Pro Gly Met Glu Leu Ser Leu Ala Ser
        115                 120                 125

Arg Asp Val Ile Ala Met Ser Thr Ala Ile Ala Leu Ser His Asn Met
    130                 135                 140

Phe Asp Ala Ala Leu Cys Leu Gly Val Cys Asp Lys Ile Val Pro Gly
145                 150                 155                 160
```

-continued

```
Leu Leu Ile Gly Ser Leu Arg Phe Gly His Leu Pro Thr Val Phe Val
                165                 170                 175

Pro Ala Gly Pro Met Pro Thr Gly Ile Ser Asn Lys Glu Lys Ala Ala
            180                 185                 190

Val Arg Gln Leu Phe Ala Glu Gly Lys Ala Thr Arg Glu Glu Leu Leu
        195                 200                 205

Ala Ser Glu Met Ala Ser Tyr His Ala Pro Gly Thr Cys Thr Phe Tyr
    210                 215                 220

Gly Thr Ala Asn Thr Asn Gln Leu Leu Val Glu Val Met Gly Leu His
225                 230                 235                 240

Leu Pro Gly Ala Ser Phe Val Asn Pro Asn Thr Pro Leu Arg Asp Glu
                245                 250                 255

Leu Thr Arg Glu Ala Ala Arg Gln Ala Ser Arg Leu Thr Pro Glu Asn
            260                 265                 270

Gly Asn Tyr Val Pro Met Ala Glu Ile Val Asp Glu Lys Ala Ile Val
        275                 280                 285

Asn Ser Val Val Ala Leu Leu Ala Thr Gly Gly Ser Thr Asn His Thr
    290                 295                 300

Leu His Leu Leu Ala Ile Ala Gln Ala Ala Gly Ile Gln Leu Thr Trp
305                 310                 315                 320

Gln Asp Met Ser Glu Leu Ser His Val Val Pro Thr Leu Ala Arg Ile
                325                 330                 335

Tyr Pro Asn Gly Gln Ala Asp Ile Asn His Phe Gln Ala Ala Gly Gly
            340                 345                 350

Met Ser Phe Leu Ile Arg Gln Leu Leu Asp Gly Gly Leu Leu His Glu
        355                 360                 365

Asp Val Gln Thr Val Ala Gly Pro Gly Leu Arg Arg Tyr Thr Arg Glu
    370                 375                 380

Pro Phe Leu Glu Asp Gly Arg Leu Val Trp Arg Glu Gly Pro Glu Arg
385                 390                 395                 400

Ser Leu Asp Glu Ala Ile Leu Arg Pro Leu Asp Lys Pro Phe Ser Ala
                405                 410                 415

Glu Gly Gly Leu Arg Leu Met Glu Gly Asn Leu Gly Arg Gly Val Met
            420                 425                 430

Lys Val Ser Ala Val Ala Pro Glu His Gln Val Val Glu Ala Pro Val
        435                 440                 445

Arg Ile Phe His Asp Gln Ala Ser Leu Ala Ala Ala Phe Lys Ala Gly
    450                 455                 460

Glu Leu Glu Arg Asp Leu Val Ala Val Val Arg Phe Gln Gly Pro Arg
465                 470                 475                 480

Ala Asn Gly Met Pro Glu Leu His Lys Leu Thr Pro Phe Leu Gly Val
                485                 490                 495

Leu Gln Asp Arg Gly Phe Lys Val Ala Leu Val Thr Asp Gly Arg Met
            500                 505                 510

Ser Gly Ala Ser Gly Lys Val Pro Ala Ala Ile His Val Ser Pro Glu
        515                 520                 525

Ala Ile Ala Gly Gly Pro Leu Ala Arg Leu Arg Asp Gly Asp Arg Val
    530                 535                 540

Arg Val Asp Gly Val Asn Gly Glu Leu Arg Val Leu Val Asp Asp Ala
545                 550                 555                 560

Glu Trp Gln Ala Arg Ser Leu Glu Pro Ala Pro Gln Asp Gly Asn Leu
                565                 570                 575

Gly Cys Gly Arg Glu Leu Phe Ala Phe Met Arg Asn Ala Met Ser Ser
            580                 585                 590
```

```
Ala Glu Glu Gly Ala Cys Ser Phe Thr Glu Ser Leu Asn Gly Trp Arg
        595                 600                 605
```

<210> SEQ ID NO 71
<211> LENGTH: 666
<212> TYPE: DNA
<213> ORGANISM: Pseudomonas aeruginosa

<400> SEQUENCE: 71

```
atgcacaacc ttgaacagaa gaccgcccgc atcgacacgc tgtgccggga ggcgcgcatc    60
ctcccggtga tcaccatcga ccgcgaggcg gacatcctgc cgatggccga tgccctcgcc   120
gccggcggcc tgaccgcccct ggagatcacc ctgcgcacgg cgcacgggct gaccgccatc   180
cggcgcctca gcgaggagcg cccgcacctg cgcatcggcg ccggcaccgt gctcgacccg   240
cggaccttcg ccgccgcgga aaaggccggg gcgagcttcg tggtcacccc gggttgcacc   300
gacgagttgc tgcgcttcgc cctggacagc gaagtcccgc tgttgcccgg cgtggccagc   360
gcttccgaga tcatgctcgc ctaccgccat ggctaccgcc gcttcaagct gtttcccgcc   420
gaagtcagcg gcgccccggc ggcgctgaag gcgttctcgg gaccattccc cgatatccgc   480
ttctgcccca ccggaggcgt cagcctgaac aatctcgccg actacctggc ggtacccaac   540
gtgatgtgcg tcggcggcac ctggatgctg cccaaggccg tggtcgaccg cggcgactgg   600
gcccaggtcg agcgcctcag ccgcgaagcc ctggagcgct cgccgagca ccgcagacac   660
taatag                                                              666
```

<210> SEQ ID NO 72
<211> LENGTH: 220
<212> TYPE: PRT
<213> ORGANISM: Pseudomonas aeruginosa

<400> SEQUENCE: 72

```
Met His Asn Leu Glu Gln Lys Thr Ala Arg Ile Asp Thr Leu Cys Arg
  1               5                  10                  15

Glu Ala Arg Ile Leu Pro Val Ile Thr Ile Asp Arg Glu Ala Asp Ile
            20                  25                  30

Leu Pro Met Ala Asp Ala Leu Ala Ala Gly Gly Leu Thr Ala Leu Glu
        35                  40                  45

Ile Thr Leu Arg Thr Ala His Gly Leu Thr Ala Ile Arg Arg Leu Ser
    50                  55                  60

Glu Glu Arg Pro His Leu Arg Ile Gly Ala Gly Thr Val Leu Asp Pro
 65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val
           100                 105                 110

Pro Leu Leu Pro Gly Val Ala Ser Ala Ser Glu Ile Met Leu Ala Tyr
       115                 120                 125

Arg His Gly Tyr Arg Arg Phe Lys Leu Phe Pro Ala Glu Val Ser Gly
   130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
               165                 170                 175

Ala Val Pro Asn Val Met Cys Val Gly Gly Thr Trp Met Leu Pro Lys
           180                 185                 190
```

-continued

Ala Val Val Asp Arg Gly Asp Trp Ala Gln Val Glu Arg Leu Ser Arg
        195                 200                 205

Glu Ala Leu Glu Arg Phe Ala Glu His Arg Arg His
    210                 215                 220

<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gttcactgca ctagtaaaaa aatgcactca gtcgttcaat ctg          43

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cttcgagatc tcgagttagt aaagttcatc gatggc               36

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gttcactgca ctagtaaaaa aatgcttgag aataactggt c            41

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cttcgagatc tcgagttaaa gtccgccaat cgcctc               36

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gttcactgca ctagtaaaaa aatgtctctg aatcccgtcg tc           42

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 78
cttcgagatc tcgagttagt gaatgtcgtc gccaac                              36

<210> SEQ ID NO 79
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gttcactgca ctagtaaaaa aatgatcgat actgccaaac tc                       42

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttcgagatc tcgagtcaga ccgtgaagag tgccgc                              36

<210> SEQ ID NO 81
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gttcactgca ctagtaaaaa aatgagcgat aatttttct gcg                       43

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cttcgagatc tcgagctatt tcctgttgat gatagc                              36

<210> SEQ ID NO 83
<211> LENGTH: 1827
<212> TYPE: DNA
<213> ORGANISM: Shewanella oneidensis

<400> SEQUENCE: 83
atgcactcag tcgttcaatc tgttactgac agaattattg cccgtagcaa agcatctcgt    60
gaagcatacc ttgctgcgtt aaacgatgcc cgtaaccatg gtgtacaccg aagttcctta   120
agttgcggta acttagccca cggttttgcg gcttgtaatc ccgatgacaa aaatgcattg   180
cgtcaattga cgaaggccaa tattgggatt atcaccgcat caacgatat gttatctgca    240 caccaaccct atgaaaccta tcctgatttg ctgaaaaaag cctgtcagga agtcggtagt   300
gttgcgcagg tggctggcgg tgttcccgcc atgtgtgacg gcgtgactca aggtcagccc   360
ggtatggaat tgagcttact gagccgtgaa gtgattgcga tggcaaccgc ggttggctta   420
tcacacaata tgtttgatgg agccttactc ctcggtattt gcgataaaat tgtaccgggt   480
```

```
ttactgattg gtgccttaag ttttggccat ttacctatgt tgtttgtgcc cgcaggccca    540
atgaaatcgg gtattcctaa taaggaaaaa gctcgcattc gtcagcaatt tgctcaaggt    600
aaggtcgata gagcacaact gctcgaagcg gaagcccagt cttaccacag tgcgggtact    660
tgtaccttct atggtaccgc taactcgaac caactgatgc tcgaagtgat ggggctgcaa    720
ttgccgggtt catcttttgt gaatccagac gatccactgc gcgaagcctt aaacaaaatg    780
gcggccaagc aggtttgtcg tttaactgaa ctaggcactc aatacagtcc gattggtgaa    840
gtcgttaacg aaaaatcgat agtgaatggt attgttgcat tgctcgcgac gggtggttca    900
acaaacttaa ccatgcacat tgtggcggcg gcccgtgctg caggtattat cgtcaactgg    960
gatgactttt cggaattatc cgatgcggtg cctttgctgg cacgtgttta tccaaacggt   1020
catgcggata ttaaccattt ccacgctgcg ggtggtatgg ctttccttat caagaattta   1080
ctcgatgcag gtttgctgca tgaggatgtc aatactgtcg cgggttatgg tctgcgccgt   1140
tacacccaag agcctaaact gcttgatggc gagctgcgct gggtcgatgg cccaacagtg   1200
agtttagata ccgaagtatt aacctctgtg gcaacaccat tccaaaacaa cggtggttta   1260
aagctgctga agggtaactt aggccgcgct gtgattaaag tgtctgccgt tcagccacag   1320
caccgtgtgg tggaagcgcc cgcagtggtg attgacgatc aaaacaaact cgatgcgtta   1380
tttaaatccg gcgcattaga cagggattgt gtggtggtgg tgaaaggcca agggccgaaa   1440
gccaacggta tgccagagct gcataaacta acgccgctgt taggttcatt gcaggacaaa   1500
ggctttaaag tggcactgat gactgatggt cgtatgtcgg gcgcatcggg caaagtacct   1560
gcggcgattc atttaacccc tgaagcgatt gatggcgggt taattgcaaa ggtacaagac   1620
ggcgatttaa tccgagttga tgcactgacc ggcgagctga gtttattagt ctctgacacc   1680
gagcttgcca ccagaactgc cactgaaatt gatttacgcc attctcgtta tggcatgggg   1740
cgtgagttat ttggagtact gcgttcaaac ttaagcagtc ctgaaaccgg tgcgcgtagt   1800
actagcgcca tcgatgaact ttactaa                                       1827
```

<210> SEQ ID NO 84
<211> LENGTH: 608
<212> TYPE: PRT
<213> ORGANISM: Shewanella oneidensis

<400> SEQUENCE: 84

```
Met His Ser Val Val Gln Ser Val Thr Asp Arg Ile Ile Ala Arg Ser
1               5                   10                  15

Lys Ala Ser Arg Glu Ala Tyr Leu Ala Ala Leu Asn Asp Ala Arg Asn
            20                  25                  30

His Gly Val His Arg Ser Ser Leu Ser Cys Gly Asn Leu Ala His Gly
        35                  40                  45

Phe Ala Ala Cys Asn Pro Asp Asp Lys Asn Ala Leu Arg Gln Leu Thr
    50                  55                  60

Lys Ala Asn Ile Gly Ile Ile Thr Ala Phe Asn Asp Met Leu Ser Ala
65                  70                  75                  80

His Gln Pro Tyr Glu Thr Tyr Pro Asp Leu Leu Lys Lys Ala Cys Gln
                85                  90                  95

Glu Val Gly Ser Val Ala Gln Val Ala Gly Gly Val Pro Ala Met Cys
            100                 105                 110

Asp Gly Val Thr Gln Gly Gln Pro Gly Met Glu Leu Ser Leu Leu Ser
        115                 120                 125

Arg Glu Val Ile Ala Met Ala Thr Ala Val Gly Leu Ser His Asn Met
    130                 135                 140
```

-continued

```
Phe Asp Gly Ala Leu Leu Gly Ile Cys Asp Lys Ile Val Pro Gly
145                 150                 155                 160

Leu Leu Ile Gly Ala Leu Ser Phe Gly His Leu Pro Met Leu Phe Val
            165                 170                 175

Pro Ala Gly Pro Met Lys Ser Gly Ile Pro Asn Lys Glu Lys Ala Arg
            180                 185                 190

Ile Arg Gln Gln Phe Ala Gln Gly Lys Val Asp Arg Ala Gln Leu Leu
            195                 200                 205

Glu Ala Glu Ala Gln Ser Tyr His Ser Ala Gly Thr Cys Thr Phe Tyr
210                 215                 220

Gly Thr Ala Asn Ser Asn Gln Leu Met Leu Glu Val Met Gly Leu Gln
225                 230                 235                 240

Leu Pro Gly Ser Ser Phe Val Asn Pro Asp Pro Leu Arg Glu Ala
            245                 250                 255

Leu Asn Lys Met Ala Ala Lys Gln Val Cys Arg Leu Thr Glu Leu Gly
            260                 265                 270

Thr Gln Tyr Ser Pro Ile Gly Glu Val Val Asn Glu Lys Ser Ile Val
            275                 280                 285

Asn Gly Ile Val Ala Leu Leu Ala Thr Gly Gly Ser Thr Asn Leu Thr
290                 295                 300

Met His Ile Val Ala Ala Arg Ala Ala Gly Ile Ile Val Asn Trp
305                 310                 315                 320

Asp Asp Phe Ser Glu Leu Ser Asp Ala Val Pro Leu Leu Ala Arg Val
                325                 330                 335

Tyr Pro Asn Gly His Ala Asp Ile Asn His Phe His Ala Ala Gly Gly
                340                 345                 350

Met Ala Phe Leu Ile Lys Glu Leu Leu Asp Ala Gly Leu Leu His Glu
            355                 360                 365

Asp Val Asn Thr Val Ala Gly Tyr Gly Leu Arg Arg Tyr Thr Gln Glu
370                 375                 380

Pro Lys Leu Leu Asp Gly Glu Leu Arg Trp Val Asp Gly Pro Thr Val
385                 390                 395                 400

Ser Leu Asp Thr Glu Val Leu Thr Ser Val Ala Thr Pro Phe Gln Asn
                405                 410                 415

Asn Gly Gly Leu Lys Leu Leu Lys Gly Asn Leu Gly Arg Ala Val Ile
            420                 425                 430

Lys Val Ser Ala Val Gln Pro Gln His Arg Val Val Glu Ala Pro Ala
            435                 440                 445

Val Val Ile Asp Asp Gln Asn Lys Leu Asp Ala Leu Phe Lys Ser Gly
            450                 455                 460

Ala Leu Asp Arg Asp Cys Val Val Val Lys Gly Gln Gly Pro Lys
465                 470                 475                 480

Ala Asn Gly Met Pro Glu Leu His Lys Leu Thr Pro Leu Leu Gly Ser
            485                 490                 495

Leu Gln Asp Lys Gly Phe Lys Val Ala Leu Met Thr Asp Gly Arg Met
            500                 505                 510

Ser Gly Ala Ser Gly Lys Val Pro Ala Ala Ile His Leu Thr Pro Glu
            515                 520                 525

Ala Ile Asp Gly Gly Leu Ile Ala Lys Val Gln Asp Gly Asp Leu Ile
530                 535                 540

Arg Val Asp Ala Leu Thr Gly Glu Leu Ser Leu Leu Val Ser Asp Thr
545                 550                 555                 560

Glu Leu Ala Thr Arg Thr Ala Thr Glu Ile Asp Leu Arg His Ser Arg
```

565                 570                 575
    Tyr Gly Met Gly Arg Glu Leu Phe Gly Val Leu Arg Ser Asn Leu Ser
                580                 585                 590
    Ser Pro Glu Thr Gly Ala Arg Ser Thr Ser Ala Ile Asp Glu Leu Tyr
                595                 600                 605

<210> SEQ ID NO 85
<211> LENGTH: 1848
<212> TYPE: DNA
<213> ORGANISM: Gluconobacter oxydans

<400> SEQUENCE: 85

| | | | | | | |
|---|---|---|---|---|---|---|
| atgtctctga | atcccgtcgt | cgagagcgtg | actgcccgta | tcatcgagcg | ttcgaaagtc | 60 |
| tcccgtcgcc | ggtatctcgc | cctgatggag | cgcaaccgcg | ccaagggtgt | gctccggccc | 120 |
| aagctggcct | gcggtaatct | ggcgcatgcc | atcgcagcgt | ccagccccga | caagccggat | 180 |
| ctgatgcgtc | ccaccgggac | caatatcggc | gtgatcacga | cctataacga | catgctctcg | 240 |
| gcgcatcagc | cgtatggccg | ctatcccgag | cagatcaagc | tgttcgcccg | tgaagtcggt | 300 |
| gcgacggccc | aggttgcagg | cggcgcacca | gcaatgtgtg | atggtgtgac | gcaggggcag | 360 |
| gagggcatgg | aactctccct | gttctcccgt | gacgtgatcg | ccatgtccac | ggcggtcggg | 420 |
| ctgagccacg | gcatgtttga | gggcgtggcg | ctgctgggca | tctgtgacaa | gattgtgccg | 480 |
| ggccttctga | tgggcgcgct | gcgcttcggt | catctcccgg | ccatgctgat | cccggcaggg | 540 |
| ccaatgccgt | ccggtcttcc | aaacaaggaa | aagcagcgca | tccgccagct | ctatgtgcag | 600 |
| ggcaaggtcg | ggcaggacga | gctgatggaa | gcggaaaacg | cctcctatca | cagcccgggc | 660 |
| acctgcacgt | tctatggcac | ggccaatacg | aaccagatga | tggtcgaaat | catgggtctg | 720 |
| atgatgccgg | actcggcttt | catcaatccc | aacacgaagc | tgcgtcaggc | aatgaccccgc | 780 |
| tcgggtattc | accgtctggc | cgaaatcggc | ctgaacggcg | aggatgtgcg | cccgctcgct | 840 |
| cattgcgtag | acgaaaaggc | catcgtgaat | gcggcggtcg | ggttgctggc | gacgggtggt | 900 |
| tcgaccaacc | attcgatcca | tcttcctgct | atcgcccgtg | ccgctggtat | cctgatcgac | 960 |
| tgggaagaca | tcagccgcct | gtcgtccgcg | gttccgctga | tcacccgtgt | ttatccgagc | 1020 |
| ggttccgagg | acgtgaacgc | gttcaaccgc | gtgggtggta | tgccgaccgt | gatcgccgaa | 1080 |
| ctgacgcgcg | ccgggatgct | gcacaaggac | attctgacgg | tctctcgtgg | cggttctcc | 1140 |
| gattatgccc | gtcgcgcatc | gctggaaggc | gatgagatcg | tctacaccca | cgcgaagccg | 1200 |
| tccacggaca | ccgatatcct | gcgcgatgtg | gctacgcctt | ccggcccgga | tggcggtatg | 1260 |
| cgcctgatga | ctggtaatct | gggccgcgcg | atctacaaga | gcagcgctat | tgcgcccgag | 1320 |
| cacctgaccg | ttgaagcgcc | ggcacgggtc | ttccaggacc | agcatgacgt | cctcacggcc | 1380 |
| tatcagaatg | gtgagcttga | gcgtgatgtt | gtcgtggtcg | tccggttcca | gggaccggaa | 1440 |
| gccaacggca | tgccggagct | tcacaagctg | accccgactc | tgggcgtgct | tcaggatcgc | 1500 |
| ggcttcaagg | tggccctgct | gacggatgga | cgcatgtccg | gtgcgagcgg | caaggtgccg | 1560 |
| gccgccattc | atgtcggtcc | cgaagcgcag | gttggcggtc | cgatcgcccg | cgtgcgggac | 1620 |
| ggcgacatga | tccgtgtctg | cgcggtgacg | ggacagatcg | aggctctggt | ggatgccgcc | 1680 |
| gagtgggaga | gccgcaagcc | ggtcccgccg | ccgctcccgg | cattgggaac | gggccgcgaa | 1740 |
| ctgttcgcgc | tgatgcgttc | ggtgcatgat | ccggccgagg | ctggcggatc | cgcgatgctg | 1800 |
| gcccagatgg | atcgcgtgat | cgaagccgtt | ggcgacgaca | ttcactaa | | 1848 |

<210> SEQ ID NO 86

<211> LENGTH: 615
<212> TYPE: PRT
<213> ORGANISM: Gluconobacter oxydans

<400> SEQUENCE: 86

```
Met Ser Leu Asn Pro Val Val Glu Ser Val Thr Ala Arg Ile Ile Glu
1               5                   10                  15

Arg Ser Lys Val Ser Arg Arg Tyr Leu Ala Leu Met Glu Arg Asn
            20                  25                  30

Arg Ala Lys Gly Val Leu Arg Pro Lys Leu Ala Cys Gly Asn Leu Ala
        35                  40                  45

His Ala Ile Ala Ala Ser Pro Asp Lys Pro Asp Leu Met Arg Pro
    50                  55                  60

Thr Gly Thr Asn Ile Gly Val Ile Thr Tyr Asn Asp Met Leu Ser
65                  70                  75                  80

Ala His Gln Pro Tyr Gly Arg Tyr Pro Glu Gln Ile Lys Leu Phe Ala
                85                  90                  95

Arg Glu Val Gly Ala Thr Ala Gln Val Ala Gly Ala Pro Ala Met
            100                 105                 110

Cys Asp Gly Val Thr Gln Gly Gln Glu Gly Met Glu Leu Ser Leu Phe
        115                 120                 125

Ser Arg Asp Val Ile Ala Met Ser Thr Ala Val Gly Leu Ser His Gly
    130                 135                 140

Met Phe Glu Gly Val Ala Leu Leu Gly Ile Cys Asp Lys Ile Val Pro
145                 150                 155                 160

Gly Leu Leu Met Gly Ala Leu Arg Phe Gly His Leu Pro Ala Met Leu
                165                 170                 175

Ile Pro Ala Gly Pro Met Pro Ser Gly Leu Pro Asn Lys Glu Lys Gln
            180                 185                 190

Arg Ile Arg Gln Leu Tyr Val Gln Gly Lys Val Gly Gln Asp Glu Leu
        195                 200                 205

Met Glu Ala Glu Asn Ala Ser Tyr His Ser Pro Gly Thr Cys Thr Phe
    210                 215                 220

Tyr Gly Thr Ala Asn Thr Asn Gln Met Met Val Glu Ile Met Gly Leu
225                 230                 235                 240

Met Met Pro Asp Ser Ala Phe Ile Asn Pro Asn Thr Lys Leu Arg Gln
                245                 250                 255

Ala Met Thr Arg Ser Gly Ile His Arg Leu Ala Glu Ile Gly Leu Asn
            260                 265                 270

Gly Glu Asp Val Arg Pro Leu Ala His Cys Val Asp Glu Lys Ala Ile
        275                 280                 285

Val Asn Ala Ala Val Gly Leu Leu Ala Thr Gly Gly Ser Thr Asn His
    290                 295                 300

Ser Ile His Leu Pro Ala Ile Ala Arg Ala Ala Gly Ile Leu Ile Asp
305                 310                 315                 320

Trp Glu Asp Ile Ser Arg Leu Ser Ser Ala Val Pro Leu Ile Thr Arg
                325                 330                 335

Val Tyr Pro Ser Gly Ser Glu Asp Val Asn Ala Phe Asn Arg Val Gly
            340                 345                 350

Gly Met Pro Thr Val Ile Ala Glu Leu Thr Arg Ala Gly Met Leu His
        355                 360                 365

Lys Asp Ile Leu Thr Val Ser Arg Gly Gly Phe Ser Asp Tyr Ala Arg
    370                 375                 380

Arg Ala Ser Leu Glu Gly Asp Glu Ile Val Tyr Thr His Ala Lys Pro
385                 390                 395                 400
```

Ser Thr Asp Thr Asp Ile Leu Arg Asp Val Ala Thr Pro Phe Arg Pro
            405                 410                 415

Asp Gly Gly Met Arg Leu Met Thr Gly Asn Leu Gly Arg Ala Ile Tyr
        420                 425                 430

Lys Ser Ser Ala Ile Ala Pro Glu His Leu Thr Val Glu Ala Pro Ala
    435                 440                 445

Arg Val Phe Gln Asp Gln His Asp Val Leu Thr Ala Tyr Gln Asn Gly
450                 455                 460

Glu Leu Glu Arg Asp Val Val Val Val Arg Phe Gln Gly Pro Glu
465                 470                 475                 480

Ala Asn Gly Met Pro Glu Leu His Lys Leu Thr Pro Thr Leu Gly Val
            485                 490                 495

Leu Gln Asp Arg Gly Phe Lys Val Ala Leu Leu Thr Asp Gly Arg Met
            500                 505                 510

Ser Gly Ala Ser Gly Lys Val Pro Ala Ala Ile His Val Gly Pro Glu
    515                 520                 525

Ala Gln Val Gly Gly Pro Ile Ala Arg Val Arg Asp Gly Asp Met Ile
    530                 535                 540

Arg Val Cys Ala Val Thr Gly Gln Ile Glu Ala Leu Val Asp Ala Ala
545                 550                 555                 560

Glu Trp Glu Ser Arg Lys Pro Val Pro Pro Leu Pro Ala Leu Gly
            565                 570                 575

Thr Gly Arg Glu Leu Phe Ala Leu Met Arg Ser Val His Asp Pro Ala
            580                 585                 590

Glu Ala Gly Gly Ser Ala Met Leu Ala Gln Met Asp Arg Val Ile Glu
    595                 600                 605

Ala Val Gly Asp Asp Ile His
    610                 615

<210> SEQ ID NO 87
<211> LENGTH: 1665
<212> TYPE: DNA
<213> ORGANISM: Ruminococcus flavefaciens

<400> SEQUENCE: 87
atgagcgata ttttttctg cgagggtgcg gataaagccc ctcagcgttc acttttcaat      60
gcactgggca tgactaaaga ggaaatgaag cgtcccctcg ttggtatcgt ttcttcctac    120
aatgagatcg ttcccggcca tatgaacatc gacaagctgg tcgaagccgt taagctgggt    180
gtagctatgg gcggcggcac tcctgttgtt ttccctgcta tcgctgtatg cgacggtatc    240
gctatgggtc acacaggcat gaagtacagc cttgttaccc gtgaccttat tgccgattct    300
acagagtgta tggctcttgc tcatcacttc gacgcactgg taatgatacc taactgcgac    360
aagaacgttc ccggcctgct tatggcggct gcacgtatca atgttcctac tgtattcgta    420
agcggcggcc ctatgcttgc aggccatgta aagggtaaga agacctctct ttcatccatg    480
ttcgaggctg taggcgctta cacagcaggc aagatagacg aggctgaact tgacgaattc    540
gagaacaaga cctgccctac ctgcggttca tgttcgggta tgtataccgc taactccatg    600
aactgcctca ctgaggtact gggtatgggt ctcagaggca acggcactat ccctgctgtt    660
tactccgagc gtatcaagct tgcaaagcag gcaggtatgc aggttatgga actctacaga    720
aagaatatcc gccctctcga tatcatgaca gagaaggctt ccagaacgc tctcacagct    780 gatatggctc ttgatgtttc cacaaacagt atgctccatc tccctgctat cgccaacgaa    840
tgcggcataa atatcaacct tgacatggct aacgagataa gcgccaagac tcctaacctc    900

-continued

```
tgccatcttg caccggcagg ccacacctac atggaagacc tcaacgaagc aggcggagtt    960
tatgcagttc tcaacgagct gagcaaaaag ggacttatca caccgactg catgactgtt   1020
acaggcaaga ccgtaggcga gaatatcaag ggctgcatca accgtgaccc tgagactatc   1080
cgtcctatcg acaacccata cagtgaaaca ggcggaatcg ccgtactcaa gggcaatctt   1140
gctcccgaca gatgtgttgt gaagagaagc gcagttgctc ccgaaatgct ggtacacaaa   1200
ggccctgcaa gagtattcga cagcgaggaa gaagctatca aggtcatcta tgagggcggt   1260
atcaaggcag cgacgttgt tgttatccgt tacgaaggcc ctgcaggcgg ccccggcatg   1320
agagaaatgc tctctcctac atcagctata cagggtgcag gtctcggctc aactgttgct   1380
ctaatcactg acggacgttt cagcggcgct cccgtggtg cggctatcgg acacgtatcc   1440
cccgaagctg taaacggcgg tactatcgca tatgtcaagg acggcgatat tatctccatc   1500
gacataccga attactccat cactcttgaa gtatccgacg aggagcttgc agagcgcaaa   1560
aaggcaatgc ctatcaagcg caaggagaac atcacaggct atctgaagcg ctatgcacag   1620
caggtatcat ccgcagacaa gggcgctatc atcaacagga aatag                   1665
```

<210> SEQ ID NO 88
<211> LENGTH: 554
<212> TYPE: PRT
<213> ORGANISM: Ruminococcus flavefaciens

<400> SEQUENCE: 88

```
Met Ser Asp Asn Phe Phe Cys Glu Gly Ala Asp Lys Ala Pro Gln Arg
1               5                   10                  15

Ser Leu Phe Asn Ala Leu Gly Met Thr Lys Glu Glu Met Lys Arg Pro
            20                  25                  30

Leu Val Gly Ile Val Ser Ser Tyr Asn Glu Ile Val Pro Gly His Met
        35                  40                  45

Asn Ile Asp Lys Leu Val Glu Ala Val Lys Leu Gly Val Ala Met Gly
    50                  55                  60

Gly Gly Thr Pro Val Val Phe Pro Ala Ile Ala Val Cys Asp Gly Ile
65                  70                  75                  80

Ala Met Gly His Thr Gly Met Lys Tyr Ser Leu Val Thr Arg Asp Leu
                85                  90                  95

Ile Ala Asp Ser Thr Glu Cys Met Ala Leu Ala His His Phe Asp Ala
            100                 105                 110

Leu Val Met Ile Pro Asn Cys Asp Lys Asn Val Pro Gly Leu Leu Met
        115                 120                 125

Ala Ala Ala Arg Ile Asn Val Pro Thr Val Phe Val Ser Gly Gly Pro
    130                 135                 140

Met Leu Ala Gly His Val Lys Gly Lys Lys Thr Ser Leu Ser Ser Met
145                 150                 155                 160

Phe Glu Ala Val Gly Ala Tyr Thr Ala Gly Lys Ile Asp Glu Ala Glu
                165                 170                 175

Leu Asp Glu Phe Glu Asn Lys Thr Cys Pro Thr Cys Gly Ser Cys Ser
            180                 185                 190

Gly Met Tyr Thr Ala Asn Ser Met Asn Cys Leu Thr Glu Val Leu Gly
        195                 200                 205

Met Gly Leu Arg Gly Asn Gly Thr Ile Pro Ala Val Tyr Ser Glu Arg
    210                 215                 220

Ile Lys Leu Ala Lys Gln Ala Gly Met Gln Val Met Glu Leu Tyr Arg
225                 230                 235                 240
```

```
        Lys Asn Ile Arg Pro Leu Asp Ile Met Thr Glu Lys Ala Phe Gln Asn
                    245                 250                 255

Ala Leu Thr Ala Asp Met Ala Leu Gly Cys Ser Thr Asn Ser Met Leu
                260                 265                 270

His Leu Pro Ala Ile Ala Asn Glu Cys Gly Ile Asn Ile Asn Leu Asp
                    275                 280                 285

Met Ala Asn Glu Ile Ser Ala Lys Thr Pro Asn Leu Cys His Leu Ala
            290                 295                 300

Pro Ala Gly His Thr Tyr Met Glu Asp Leu Asn Glu Ala Gly Gly Val
        305                 310                 315                 320

Tyr Ala Val Leu Asn Glu Leu Ser Lys Lys Gly Leu Ile Asn Thr Asp
                        325                 330                 335

Cys Met Thr Val Thr Gly Lys Thr Val Gly Glu Asn Ile Lys Gly Cys
                    340                 345                 350

Ile Asn Arg Asp Pro Glu Thr Ile Arg Pro Ile Asp Asn Pro Tyr Ser
                355                 360                 365

Glu Thr Gly Gly Ile Ala Val Leu Lys Gly Asn Leu Ala Pro Asp Arg
            370                 375                 380

Cys Val Val Lys Arg Ser Ala Val Ala Pro Glu Met Leu Val His Lys
        385                 390                 395                 400

Gly Pro Ala Arg Val Phe Asp Ser Glu Glu Ala Ile Lys Val Ile
                        405                 410                 415

Tyr Glu Gly Gly Ile Lys Ala Gly Asp Val Val Ile Arg Tyr Glu
                    420                 425                 430

Gly Pro Ala Gly Gly Pro Gly Met Arg Glu Met Leu Ser Pro Thr Ser
                435                 440                 445

Ala Ile Gln Gly Ala Gly Leu Gly Ser Thr Val Ala Leu Ile Thr Asp
            450                 455                 460

Gly Arg Phe Ser Gly Ala Thr Arg Gly Ala Ala Ile Gly His Val Ser
        465                 470                 475                 480

Pro Glu Ala Val Asn Gly Gly Thr Ile Ala Tyr Val Lys Asp Gly Asp
                        485                 490                 495

Ile Ile Ser Ile Asp Ile Pro Asn Tyr Ser Ile Thr Leu Glu Val Ser
                    500                 505                 510

Asp Glu Glu Leu Ala Glu Arg Lys Lys Ala Met Pro Ile Lys Arg Lys
                515                 520                 525

Glu Asn Ile Thr Gly Tyr Leu Lys Arg Tyr Ala Gln Gln Val Ser Ser
            530                 535                 540

Ala Asp Lys Gly Ala Ile Ile Asn Arg Lys
        545                 550

<210> SEQ ID NO 89
<211> LENGTH: 642
<212> TYPE: DNA
<213> ORGANISM: Shewanella oneidensis

<400> SEQUENCE: 89
atgcttgaga ataactggtc attacaacca caagatattt ttaaacgcag ccctattgtt      60
cctgttatgg tgattaacaa gattgaacat gcggtgccct agctaaagc gctggttgcc     120 ggagggataa gcgtgttgga agtgacatta cgcacgccat cgcccttga agctatcacc     180 aaaatcgcca aggaagtgcc tgaggcgctg gttggcgcgg gactatttt aaatgaagcc    240 cagcttggac aggctatcgc cgctggtgcg caatttatta tcactccagg tgcgacagtt    300
gagctgctca aagcgggcat gcaaggaccg gtgccgttaa ttccgggcgt tgccagtatt   360
```

```
tccgaggtga tgacgggcat ggcgctgggc tacactcact ttaaattctt ccctgctgaa      420
gcgtcaggtg gcgttgatgc gcttaaggct ttctctgggc cgttagcaga tatccgcttc      480
tgcccaacag gtggaattac cccgagcagc tataaagatt acttagcgct gaagaatgtc      540
gattgtattg gtggcagctg gattgctcct accgatgcga tggagcaggg cgattgggat      600
cgtatcactc agctgtgtaa agaggcgatt ggcggactt   aa                       642

<210> SEQ ID NO 90
<211> LENGTH: 213
<212> TYPE: PRT
<213> ORGANISM: Shewanella oneidensis

<400> SEQUENCE: 90

Met Leu Glu Asn Asn Trp Ser Leu Gln Pro Gln Asp Ile Phe Lys Arg
1               5                   10                  15

Ser Pro Ile Val Pro Val Met Val Ile Asn Lys Ile Glu His Ala Val
                20                  25                  30

Pro Leu Ala Lys Ala Leu Val Ala Gly Gly Ile Ser Val Leu Glu Val
            35                  40                  45

Thr Leu Arg Thr Pro Cys Ala Leu Glu Ala Ile Thr Lys Ile Ala Lys
        50                  55                  60

Glu Val Pro Glu Ala Leu Val Gly Ala Gly Thr Ile Leu Asn Glu Ala
65                  70                  75                  80

Gln Leu Gly Gln Ala Ile Ala Ala Gly Ala Gln Phe Ile Ile Thr Pro
                85                  90                  95

Gly Ala Thr Val Glu Leu Leu Lys Ala Gly Met Gln Gly Pro Val Pro
            100                 105                 110

Leu Ile Pro Gly Val Ala Ser Ile Ser Glu Val Met Thr Gly Met Ala
        115                 120                 125

Leu Gly Tyr Thr His Phe Lys Phe Phe Pro Ala Glu Ala Ser Gly Gly
    130                 135                 140

Val Asp Ala Leu Lys Ala Phe Ser Gly Pro Leu Ala Asp Ile Arg Phe
145                 150                 155                 160

Cys Pro Thr Gly Gly Ile Thr Pro Ser Ser Tyr Lys Asp Tyr Leu Ala
                165                 170                 175

Leu Lys Asn Val Asp Cys Ile Gly Gly Ser Trp Ile Ala Pro Thr Asp
            180                 185                 190

Ala Met Glu Gln Gly Asp Trp Asp Arg Ile Thr Gln Leu Cys Lys Glu
        195                 200                 205

Ala Ile Gly Gly Leu
    210

<210> SEQ ID NO 91
<211> LENGTH: 624
<212> TYPE: DNA
<213> ORGANISM: Gluconobacter oxydans

<400> SEQUENCE: 91
atgatcgata ctgccaaact cgacgccgtc atgagccgtt gtccggtcat gccggtgctg       60
gtggtcaatg atgtggctct ggcccgcccg atggccgagg ctctggtggc gggtggactg      120
tccacgctgg aagtcacgct gcgcacgccc tgcgcccttg aagctattga ggaaatgtcg      180
aaagtaccag gcgcgctggt cggtgccggt acggtgctga atccgtccga catggaccgt      240
gccgtgaagg cggtgcgcg cttcatcgtc agccccggcc tgaccgaggc gctggcaaag      300
gcgtcggttg agcatgacgt ccccttcctg ccaggcgttg ccaatgcggg tgacatcatg      360
```

```
cggggtctgg atctgggtct gtcacgcttc aagttcttcc cggctgtgac gaatggcggc    420
attcccgcgc tcaagagctt ggccagtgtt tttggcagca atgtccgttt ctgccccacg    480
ggcggcatta cggaagagag cgcaccggac tggctggcgc ttccctccgt ggcctgcgtc    540
ggcggatcct gggtgacggc cggcacgttc gatgcggaca aggtccgtca gcgcgccacg    600
gctgcggcac tcttcacggt ctga                                          624
```

<210> SEQ ID NO 92
<211> LENGTH: 207
<212> TYPE: PRT
<213> ORGANISM: Gluconobacter oxydans

<400> SEQUENCE: 92

```
Met Ile Asp Thr Ala Lys Leu Asp Ala Val Met Ser Arg Cys Pro Val
1               5                   10                  15

Met Pro Val Leu Val Val Asn Asp Val Ala Leu Ala Arg Pro Met Ala
            20                  25                  30

Glu Ala Leu Val Ala Gly Gly Leu Ser Thr Leu Glu Val Thr Leu Arg
        35                  40                  45

Thr Pro Cys Ala Leu Glu Ala Ile Glu Glu Met Ser Lys Val Pro Gly
    50                  55                  60

Ala Leu Val Gly Ala Gly Thr Val Leu Asn Pro Ser Asp Met Asp Arg
65                  70                  75                  80

Ala Val Lys Ala Gly Ala Arg Phe Ile Val Ser Pro Gly Leu Thr Glu
                85                  90                  95

Ala Leu Ala Lys Ala Ser Val Glu His Asp Val Pro Phe Leu Pro Gly
            100                 105                 110

Val Ala Asn Ala Gly Asp Ile Met Arg Gly Leu Asp Leu Gly Leu Ser
        115                 120                 125

Arg Phe Lys Phe Phe Pro Ala Val Thr Asn Gly Gly Ile Pro Ala Leu
    130                 135                 140

Lys Ser Leu Ala Ser Val Phe Gly Ser Asn Val Arg Phe Cys Pro Thr
145                 150                 155                 160

Gly Gly Ile Thr Glu Glu Ser Ala Pro Asp Trp Leu Ala Leu Pro Ser
                165                 170                 175

Val Ala Cys Val Gly Gly Ser Trp Val Thr Ala Gly Thr Phe Asp Ala
            180                 185                 190

Asp Lys Val Arg Gln Arg Ala Thr Ala Ala Leu Phe Thr Val
        195                 200                 205
```

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 93 tgatgtannt                                                          10

<210> SEQ ID NO 94
<211> LENGTH: 10
<212> TYPE: DNA
<213> ORGANISM: Artificial Sequence
<220> FEATURE:

```
<223> OTHER INFORMATION: Description of Artificial Sequence: Synthetic
      binding motif oligonucleotide
<220> FEATURE:
<221> NAME/KEY: modified_base
<222> LOCATION: (3)..(5)
<223> OTHER INFORMATION: a, c, t, g, unknown or other

<400> SEQUENCE: 94 ccnnnwwrgg                                                                 10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 95 wwwwsygggg                                                                 10

<210> SEQ ID NO 96
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 96
rmacccannc ayy                                                             13

<210> SEQ ID NO 97
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 97
tycgtnnrna rtgaya                                                          16

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 98
```

-continued rrraararaa nanraraa            18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 99
anagngagag agnggcag            18

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 100
tnnccwnttt ktttc            15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 101
aaaaararaa aarma            15

<210> SEQ ID NO 102
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(14)
<223> OTHER INFORMATION: a, c, t, g, unknown or other

<400> SEQUENCE: 102
ykytyttytt nnnnky            16

```
<210> SEQ ID NO 103
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 103
cgtccggcgc                                                                10

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 104
gaaaaagmaa aaaaa                                                          15

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 105
ttttyyttyt tkyntynt                                                       18

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 106
catkyttttt tkyty                                                          15

<210> SEQ ID NO 107
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 107 cacgtgacya                                                                10

<210> SEQ ID NO 108
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
```

```
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 108
cannnacaca sana                                                          14

<210> SEQ ID NO 109
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 109
ggnanannar narggcn                                                       17

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 110
tttkytktty nytttkty                                                      18

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 111 wttktttty tttttnt                                                        17
```

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 112
ttkttttytt c                                                            11

<210> SEQ ID NO 113
<211> LENGTH: 1665
<212> TYPE: DNA
<213> ORGANISM: Debaryomyces hansenii

<400> SEQUENCE: 113
atgtctcaag aagaatatag ttctggggta caaaccccag tttctaacca ttctggttta      60
gagaaagaag agcaacacaa gttagacggt ttagatgagg atgaaattgt cgatcaatta     120
ccttctttac cagaaaaatc agctaaggat tatttattaa tttctttctt ctgtgtatta     180
gttgcatttg gtggttttgt tttcggtttc gatactggta ctatctcagg tttcgttaac     240
atgagtgatt acttggaaag attcggtgag cttaatgcag atggtgaata tttcttatct     300
aatgttagaa ctggtttgat tgttgctatt tttaatgttg gttgtgctgt cggtggtatt     360
ttcttatcta agattgctga tgtttatggt agaagaattg gtcttatgtt ttccatgatt     420
atttatgtga ttggtataat tgttcaaatc tcagcttctg acaagtggta tcaaatcgtt     480
gttggtagag ctattgcagg tttagctgtt ggtaccgttt ctgtcttatc cccattattc     540
attggtgaat cagcacctaa aaccttaaga ggtactttag tgtgttgttt ccaattatgt     600
attaccttag gtatcttctt aggttactgt actacatatg gtactaaaac ctacaccgac     660
tctagacaat ggagaattcc attaggttta tgttttgttt gggctatcat gttggttatt     720
ggtatggttt gcatgccaga atcaccaaga tacttagttg tcaagaacaa gattgaagaa     780
gctaagaaat cgattggtag atccaacaag gtttcaccag aagatcctgc tgtttacacc     840
gaagtccaat tgattcaagc aggtattgaa agagaaagtt tagctggttc tgcctcttgg     900
accgaattgg ttactggtaa gccaagaatc tttcgtagag tcattatggg tattatgtta     960
caatctttac aacaattgac tggtgacaac tatttcttct actatggtac tactattttc    1020
caagctgtcg gtatgactga ttccttccaa acatctattg ttttaggtgt tgttaacttt    1080
gcatctacat ttctcggtat ctacacaatt gaaagattcg gtagaagatt atgtttgtta    1140
actggttctg tctgtatgtt cgtttgtttc atcattact ccattttggg tgttacaaac    1200
ttatatattg atggctacga tggtccaact tcggttccaa ccggtgatgc gatgattttc    1260
attactacct tatacatttt cttcttcgca tccacctggg ctggtggtgt ctactgtatc    1320
gtttccgaaa catacccatt gagaattaga tctaaggcca tgtccgttgc caccgctgct    1380
aactggattt ggggtttctt gatctctttc ttcactccat tcatcacctc ggctatccac    1440
ttctactacg gtttcgtttt cacaggatgt ttgttattct cgttcttta cgtttacttc    1500 tttgttgttg aaactaaggg attaacttta gaagaagttg atgaattgta tgcccaaggt    1560
gttgccccat ggagtcatcg aaatgggtt ccaccaacca aggaagaaat ggcccattct    1620
tcaggatatg ctgctgaagc caaacctcac gatcaacaag tataa                    1665

<210> SEQ ID NO 114
<211> LENGTH: 1725

```
<212> TYPE: DNA
<213> ORGANISM: Saccharomyces cerevisiae

<400> SEQUENCE: 114
atggcagttg aggagaacaa tatgcctgtt gtttcacagc aaccccaagc tggtgaagac      60
gtgatctctt cactcagtaa agattcccat ttaagcgcac aatctcaaaa gtattctaat     120
gatgaattga agccggtga gtcagggtct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg ggtttgttgt ccaaacagac     300
ttttgagaa ggtttggtat gaaacataag gatggtaccc actatttgtc aaacgtcaga     360
acaggtttaa tcgtcgccat tttcaatatt ggctgtgcct ttggtggtat tatactttcc     420
aaaggtggag atatgtatgg ccgtaaaaag ggtctttcga ttgtcgtctc ggtttatata     480
gttggtatta tcattcaaat tgcctctatc aacaagtggt accaatattt cattggtaga     540
atcatatctg gtttgggtgt cggcggcatc gccgtcttat gtcctatgtt gatctctgaa     600
attgctccaa agcacttgag aggcacacta gtttcttgtt atcagctgat gattactgca     660
ggtatctttt tgggctactg tactaattac ggtacaaaga ctattcgaa ctcagttcaa      720
tggagagttc cattagggct atgtttcgct tggtcattat ttatgattgg cgctttgacg     780
ttagttcctg aatccccacg ttatttatgt gaggtaataa ggtagaaga cgccaagcgt     840
tccattgcta agtctaacaa ggtgtcacca gaggatcctg ccgtccaggc agagttagat     900
ctgatcatgg ccgtatataga agctgaaaaa ctggctggca atgcgtcctg ggggaatta    960
ttttccacca agaccaaagt atttcaacgt tgttgatgg gtgtgtttgt tcaaatgttc    1020
caacaattaa ccgtaacaa ttattttttc tactacggta ccgttatttt caagtcagtt    1080
ggcctggatg attcctttga aacatccatt gtcattggtg tagtcaactt tgcctccact    1140
ttctttagtt tgtggactgt cgaaaacttg ggacatcgta aatgtttact tttgggcgct    1200
gccactatga tggcttgtat ggtcatctac gcctctgttg gtgttactag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcaccca ttcatcacat ctgccattaa cttctactac    1500
ggttatgtct tcatgggctg tttggttgcc atgttttttt atgtcttttt ctttgttcca    1560
gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa                    1725

<210> SEQ ID NO 115
<211> LENGTH: 750
<212> TYPE: DNA
<213> ORGANISM: Saccharomyces cerevisiae

<400> SEQUENCE: 115
atggtgacag tcggtgtgtt ttctgagagg gctagtttga cccatcaatt gggggaattc      60
atcgtcaaga aacaagatga ggcgctgcaa aagaagtcag actttaaagt ttccgttagc     120
ggtggctctt tgatcgatgc tctgtatgaa agtttagtag cggacgaatc actatcttct     180
cgagtgcaat ggtctaaatg gcaaatctac ttctctgatg aaagaattgt gccactgacg     240
gacgctgaca gcaattatgg tgccttcaag agagctgttc tagataaatt accctcgact     300
```

```
agtcagccaa acgtttatcc catggacgag tccttgattg gcagcgatgc tgaatctaac    360
aacaaaattg ctgcagagta cgagcgtatc gtacctcaag tgcttgattt ggtactgttg    420
ggctgtggtc ctgatggaca cacttgttcc ttattccctg agaaacaca  taggtacttg    480 ctgaacgaaa caaccaaaag agttgcttgg tgccacgatt ctcccaagcc tccaagtgac    540
agaatcacct tcactctgcc tgtgttgaaa gacgccaaag ccctgtgttt tgtggctgag    600
ggcagttcca acaaaatat  aatgcatgag atctttgact tgaaaaacga tcaattgcca    660
accgcattgg ttaacaaatt atttggtgaa aaaacatcct ggttcgttaa tgaggaagct    720
tttggaaaag ttcaaacgaa aacttttag                                      750
```

<210> SEQ ID NO 116
<211> LENGTH: 1518
<212> TYPE: DNA
<213> ORGANISM: Saccharomyces cerevisiae

<400> SEQUENCE: 116

```
atgagtgaag gccccgtcaa attcgaaaaa aataccgtca tatctgtctt tggtgcgtca    60
ggtgatctgg caagaagaa  gacttttccc gccttatttg gcttttcag  agaaggttac   120 cttgatccat ctaccaagat cttcggttat gcccggtcca aattgtccat ggaggaggac   180
ctgaagtccc gtgtcctacc ccacttgaaa aaacctcacg gtgaagccga tgactctaag   240
gtcgaacagt tcttcaagat ggtcagctac atttcgggaa attacgacac agatgaaggc   300
ttcgacgaat taagaacgca gatcgagaaa ttcgagaaaa gtgccaacgt cgatgtccca   360
caccgtctct tctatctggc cttgccgcca agcgtttttt tgacggtggc caagcagatc   420
aagagtcgtg tgtacgcaga gaatggcatc acccgtgtaa tcgtagagaa acctttcggc   480
cacgacctgg cctctgccag ggagctgcaa aaaaacctgg ggcccctctt taagaagaa    540 gagttgtaca gaattgacca ttacttgggt aagagttgg  tcaagaatct tttagtcttg   600
aggttcggta ccagtttttt gaatgcctcg tggaatagag acaacattca aagcgttcag   660
atttcgttta agagaggtt  cggcaccgaa ggccgtggcg ctatttcga  ctctataggc   720 ataatcagag acgtgatgca gaaccatctg ttacaaatca tgactctctt gactatggaa   780
agaccggtgt cttttgaccc ggaatctatt cgtgacgaaa aggttaaggt tctaaaggcc   840
gtggccccca tcgacacgga cgacgtcctc ttgggccagt acggtaaatc tgaggacggg   900
tctaagcccg cctacgtgga tgatgacact gtagacaagg actctaaatg tgtcactttt   960
gcagcaatga ctttcaacat cgaaaacgag cgttgggagg gcgtccccat catgatgcgt  1020
gccggtaagg ctttgaatga gtccaaggtg gagatcagac tgcagtacaa agcggtcgca  1080
tcgggtgtct tcaaagacat tccaaataac gaactggtca tcagagtgca gcccgatgcc  1140
gctgtgtacc taaagtttaa tgctaagacc cctggtctgt caaatgctac ccaagtcaca  1200
gatctgaatc taacttacgc aagcaggtac caagactttt ggattccaga ggcttacgag  1260
gtgttgataa gagacgccct actgggtgac cattccaact ttgtcagaga tgacgaattg  1320
gatatcagtt ggggcatatt caccccatta ctgaagcaca tagagcgtcc ggacggtcca  1380
acaccggaaa tttaccccta cggatcaaga ggtccaaagg gattgaagga atatatgcaa  1440
aaacacaagt atgttatgcc cgaaaagcac ccttacgctt ggcccgtgac taagccagaa  1500
gatacgaagg ataattag                                                1518
```

<210> SEQ ID NO 117
<211> LENGTH: 554

<212> TYPE: PRT
<213> ORGANISM: Debaryomyces hansenii

<400> SEQUENCE: 117

```
Met Ser Gln Glu Glu Tyr Ser Ser Gly Val Gln Thr Pro Val Ser Asn
1               5                   10                  15

His Ser Gly Leu Glu Lys Glu Gln His Lys Leu Asp Gly Leu Asp
            20                  25                  30

Glu Asp Glu Ile Val Asp Gln Leu Pro Ser Leu Pro Glu Lys Ser Ala
        35                  40                  45

Lys Asp Tyr Leu Leu Ile Ser Phe Phe Cys Val Leu Ala Phe Gly
50                  55                  60

Gly Phe Val Phe Gly Phe Asp Thr Gly Thr Ile Ser Gly Phe Val Asn
65                  70                  75                  80

Met Ser Asp Tyr Leu Glu Arg Phe Gly Glu Leu Asn Ala Asp Gly Glu
                85                  90                  95

Tyr Phe Leu Ser Asn Val Arg Thr Gly Leu Ile Val Ala Ile Phe Asn
            100                 105                 110

Val Gly Cys Ala Val Gly Gly Ile Phe Leu Ser Lys Ile Ala Asp Val
        115                 120                 125

Tyr Gly Arg Arg Ile Gly Leu Met Phe Ser Met Ile Tyr Val Ile
130                 135                 140

Gly Ile Ile Val Gln Ile Ser Ala Ser Asp Lys Trp Tyr Gln Ile Val
145                 150                 155                 160

Val Gly Arg Ala Ile Ala Gly Leu Ala Val Gly Thr Val Ser Val Leu
                165                 170                 175

Ser Pro Leu Phe Ile Gly Glu Ser Ala Pro Lys Thr Leu Arg Gly Thr
            180                 185                 190

Leu Val Cys Cys Phe Gln Leu Cys Ile Thr Leu Gly Ile Phe Leu Gly
        195                 200                 205

Tyr Cys Thr Thr Tyr Gly Thr Lys Thr Tyr Thr Asp Ser Arg Gln Trp
210                 215                 220

Arg Ile Pro Leu Gly Leu Cys Phe Val Trp Ala Ile Met Leu Val Ile
225                 230                 235                 240

Gly Met Val Cys Met Pro Glu Ser Pro Arg Tyr Leu Val Lys Asn
                245                 250                 255

Lys Ile Glu Glu Ala Lys Lys Ser Ile Gly Arg Ser Asn Lys Val Ser
            260                 265                 270

Pro Glu Asp Pro Ala Val Tyr Thr Glu Val Gln Leu Ile Gln Ala Gly
        275                 280                 285

Ile Glu Arg Glu Ser Leu Ala Gly Ser Ala Ser Trp Thr Glu Leu Val
290                 295                 300

Thr Gly Lys Pro Arg Ile Phe Arg Arg Val Ile Met Gly Ile Met Leu
305                 310                 315                 320

Gln Ser Leu Gln Gln Leu Thr Gly Asp Asn Tyr Phe Phe Tyr Tyr Gly
                325                 330                 335

Thr Thr Ile Phe Gln Ala Val Gly Met Thr Asp Ser Phe Gln Thr Ser
            340                 345                 350

Ile Val Leu Gly Val Val Asn Phe Ala Ser Thr Phe Leu Gly Ile Tyr
        355                 360                 365

Thr Ile Glu Arg Phe Gly Arg Arg Leu Cys Leu Leu Thr Gly Ser Val
370                 375                 380

Cys Met Phe Val Cys Phe Ile Ile Tyr Ser Ile Leu Gly Val Thr Asn
385                 390                 395                 400
```

```
Leu Tyr Ile Asp Gly Tyr Asp Gly Pro Thr Ser Val Pro Thr Gly Asp
            405                 410                 415
Ala Met Ile Phe Ile Thr Thr Leu Tyr Ile Phe Phe Ala Ser Thr
            420                 425                 430
Trp Ala Gly Gly Val Tyr Cys Ile Val Ser Glu Thr Tyr Pro Leu Arg
            435                 440                 445
Ile Arg Ser Lys Ala Met Ser Val Ala Thr Ala Ala Asn Trp Ile Trp
450                 455                 460
Gly Phe Leu Ile Ser Phe Phe Thr Pro Phe Ile Thr Ser Ala Ile His
465                 470                 475                 480
Phe Tyr Tyr Gly Phe Val Phe Thr Gly Cys Leu Leu Phe Ser Phe Phe
            485                 490                 495
Tyr Val Tyr Phe Phe Val Val Glu Thr Lys Gly Leu Thr Leu Glu Glu
            500                 505                 510
Val Asp Glu Leu Tyr Ala Gln Gly Val Ala Pro Trp Lys Ser Ser Lys
            515                 520                 525
Trp Val Pro Pro Thr Lys Glu Glu Met Ala His Ser Ser Gly Tyr Ala
            530                 535                 540
Ala Glu Ala Lys Pro His Asp Gln Gln Val
545                 550

<210> SEQ ID NO 118
<211> LENGTH: 574
<212> TYPE: PRT
<213> ORGANISM: Saccharomyces cerevisiae

<400> SEQUENCE: 118

Met Ala Val Glu Glu Asn Asn Met Pro Val Val Ser Gln Gln Pro Gln
1               5                   10                  15
Ala Gly Glu Asp Val Ile Ser Ser Leu Ser Lys Asp Ser His Leu Ser
            20                  25                  30
Ala Gln Ser Gln Lys Tyr Ser Asn Asp Glu Leu Lys Ala Gly Glu Ser
            35                  40                  45
Gly Ser Glu Gly Ser Gln Ser Val Pro Ile Glu Ile Pro Lys Lys Pro
            50                  55                  60
Met Ser Glu Tyr Val Thr Val Ser Leu Leu Cys Leu Cys Val Ala Phe
65              70                  75                  80
Gly Gly Phe Met Phe Gly Trp Asp Thr Gly Thr Ile Ser Gly Phe Val
                85                  90                  95
Val Gln Thr Asp Phe Leu Arg Arg Phe Gly Met Lys His Lys Asp Gly
            100                 105                 110
Thr His Tyr Leu Ser Asn Val Arg Thr Gly Leu Ile Val Ala Ile Phe
            115                 120                 125
Asn Ile Gly Cys Ala Phe Gly Gly Ile Ile Leu Ser Lys Gly Gly Asp
            130                 135                 140
Met Tyr Gly Arg Lys Lys Gly Leu Ser Ile Val Val Ser Val Tyr Ile
145                 150                 155                 160
Val Gly Ile Ile Ile Gln Ile Ala Ser Ile Asn Lys Trp Tyr Gln Tyr
                165                 170                 175
Phe Ile Gly Arg Ile Ile Ser Gly Leu Gly Val Gly Gly Ile Ala Val
            180                 185                 190
Leu Cys Pro Met Leu Ile Ser Glu Ile Ala Pro Lys His Leu Arg Gly
            195                 200                 205
Thr Leu Val Ser Cys Tyr Gln Leu Met Ile Thr Ala Gly Ile Phe Leu
            210                 215                 220
```

```
Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
            245                 250                 255

Gly Ala Leu Thr Leu Val Pro Glu Ser Pro Arg Tyr Leu Cys Glu Val
        260                 265                 270

Asn Lys Val Glu Asp Ala Lys Arg Ser Ile Ala Lys Ser Asn Lys Val
    275                 280                 285

Ser Pro Glu Asp Pro Ala Val Gln Ala Glu Leu Asp Leu Ile Met Ala
290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
        355                 360                 365

Ser Ile Val Ile Gly Val Val Asn Phe Ala Ser Thr Phe Phe Ser Leu
    370                 375                 380

Trp Thr Val Glu Asn Leu Gly His Arg Lys Cys Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
        435                 440                 445

Thr Trp Ala Pro Val Ala Trp Val Ile Thr Ala Glu Ser Phe Pro Leu
    450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
            500                 505                 510

Phe Tyr Val Phe Phe Phe Val Pro Glu Thr Lys Gly Leu Ser Leu Glu
        515                 520                 525

Glu Ile Gln Glu Leu Trp Glu Glu Gly Val Leu Pro Trp Lys Ser Glu
    530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570

<210> SEQ ID NO 119
<211> LENGTH: 505
<212> TYPE: PRT
<213> ORGANISM: Saccharomyces cerevisiae

<400> SEQUENCE: 119

Met Ser Glu Gly Pro Val Lys Phe Glu Lys Asn Thr Val Ile Ser Val
1               5                   10                  15

Phe Gly Ala Ser Gly Asp Leu Ala Lys Lys Lys Thr Phe Pro Ala Leu
            20                  25                  30
```

```
Phe Gly Leu Phe Arg Glu Gly Tyr Leu Asp Pro Ser Thr Lys Ile Phe
            35                  40                  45

Gly Tyr Ala Arg Ser Lys Leu Ser Met Glu Glu Asp Leu Lys Ser Arg
 50                  55                  60

Val Leu Pro His Leu Lys Lys Pro His Gly Glu Ala Asp Asp Ser Lys
 65                  70                  75                  80

Val Glu Gln Phe Phe Lys Met Val Ser Tyr Ile Ser Gly Asn Tyr Asp
                 85                  90                  95

Thr Asp Glu Gly Phe Asp Glu Leu Arg Thr Gln Ile Glu Lys Phe Glu
                100                 105                 110

Lys Ser Ala Asn Val Asp Val Pro His Arg Leu Phe Tyr Leu Ala Leu
            115                 120                 125

Pro Pro Ser Val Phe Leu Thr Val Ala Lys Gln Ile Lys Ser Arg Val
130                 135                 140

Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
                165                 170                 175

Phe Lys Glu Glu Glu Leu Tyr Arg Ile Asp His Tyr Leu Gly Lys Glu
                180                 185                 190

Leu Val Lys Asn Leu Leu Val Leu Arg Phe Gly Asn Gln Phe Leu Asn
            195                 200                 205

Ala Ser Trp Asn Arg Asp Asn Ile Gln Ser Val Gln Ile Ser Phe Lys
210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
                245                 250                 255

Leu Thr Met Glu Arg Pro Val Ser Phe Asp Pro Glu Ser Ile Arg Asp
                260                 265                 270

Glu Lys Val Lys Val Leu Lys Ala Val Ala Pro Ile Asp Thr Asp Asp
            275                 280                 285

Val Leu Leu Gly Gln Tyr Gly Lys Ser Glu Asp Gly Ser Lys Pro Ala
290                 295                 300

Tyr Val Asp Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
                325                 330                 335

Ile Met Met Arg Ala Gly Lys Ala Leu Asn Glu Ser Lys Val Glu Ile
                340                 345                 350

Arg Leu Gln Tyr Lys Ala Val Ala Ser Gly Val Phe Lys Asp Ile Pro
            355                 360                 365

Asn Asn Glu Leu Val Ile Arg Val Gln Pro Asp Ala Ala Val Tyr Leu
370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
                405                 410                 415

Glu Ala Tyr Glu Val Leu Ile Arg Asp Ala Leu Leu Gly Asp His Ser
                420                 425                 430

Asn Phe Val Arg Asp Asp Glu Leu Asp Ile Ser Trp Gly Ile Phe Thr
            435                 440                 445

Pro Leu Leu Lys His Ile Glu Arg Pro Asp Gly Pro Thr Pro Glu Ile
450                 455                 460
```

Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
            485                 490                 495

Thr Lys Pro Glu Asp Thr Lys Asp Asn
        500                 505

<210> SEQ ID NO 120
<211> LENGTH: 249
<212> TYPE: PRT
<213> ORGANISM: Saccharomyces cerevisiae

<400> SEQUENCE: 120

Met Val Thr Val Gly Val Phe Ser Glu Arg Ala Ser Leu Thr His Gln
1               5                   10                  15

Leu Gly Glu Phe Ile Val Lys Lys Gln Asp Glu Ala Leu Gln Lys Lys
            20                  25                  30

Ser Asp Phe Lys Val Ser Val Ser Gly Gly Ser Leu Ile Asp Ala Leu
        35                  40                  45

Tyr Glu Ser Leu Val Ala Asp Glu Ser Leu Ser Ser Arg Val Gln Trp
    50                  55                  60

Ser Lys Trp Gln Ile Tyr Phe Ser Asp Glu Arg Ile Val Pro Leu Thr
65                  70                  75                  80

Asp Ala Asp Ser Asn Tyr Gly Ala Phe Lys Arg Ala Val Leu Asp Lys
                85                  90                  95

Leu Pro Ser Thr Ser Gln Pro Asn Val Tyr Pro Met Asp Glu Ser Leu
            100                 105                 110

Ile Gly Ser Asp Ala Glu Ser Asn Asn Lys Ile Ala Ala Glu Tyr Glu
        115                 120                 125

Arg Ile Val Pro Gln Val Leu Asp Leu Val Leu Leu Gly Cys Gly Pro
    130                 135                 140

Asp Gly His Thr Cys Ser Leu Phe Pro Gly Glu Thr His Arg Tyr Leu
145                 150                 155                 160

Leu Asn Glu Thr Thr Lys Arg Val Ala Trp Cys His Asp Ser Pro Lys
                165                 170                 175

Pro Pro Ser Asp Arg Ile Thr Phe Thr Leu Pro Val Leu Lys Asp Ala
            180                 185                 190

Lys Ala Leu Cys Phe Val Ala Glu Gly Ser Ser Lys Gln Asn Ile Met
        195                 200                 205

His Glu Ile Phe Asp Leu Lys Asn Asp Gln Leu Pro Thr Ala Leu Val
    210                 215                 220

Asn Lys Leu Phe Gly Glu Lys Thr Ser Trp Phe Val Asn Glu Glu Ala
225                 230                 235                 240

Phe Gly Lys Val Gln Thr Lys Thr Phe
                245

<210> SEQ ID NO 121
<211> LENGTH: 2880
<212> TYPE: DNA
<213> ORGANISM: Saccharomyces cerevisiae

<400> SEQUENCE: 121
atgactgtta ctactccttt tgtgaatggt acttcttatt gtaccgtcac tgcatattcc      60
gttcaatctt ataaagctgc catagatttt tacaccaagt ttttgtcatt agaaaaccgc     120
tcttctccag atgaaaactc cactttattg tctaacgatt ccatctcttt gaagatcctt     180

```
ctacgtcctg atgaaaaaat caataaaaat gttgaggctc atttgaagga attgaacagt    240
attaccaaga ctcaagactg gagatcacat gccacccaat ccttggtatt taacacttcc    300
gacatcttgg cagtcaagga cactctaaat gctatgaacg ctcctcttca aggctaccca    360
acagaactat ttccaatgca gttgtacact ttgacccat taggtaacgt tgttggtgtt     420
acttctacta agaacgcagt ttcaaccaag ccaactccac caccagcacc agaagcttct    480
gctgagtctg tcttttcctc taaagttcac tcttacactg atttggctta ccgtatgaaa    540
accaccgaca cctatccatc tctgccaaag ccattgaaca ggcctcaaaa ggcaattgcc    600
gtcatgactt ccggtggtga tgctccaggt atgaactcta acgttagagc catcgtgcgt    660
tccgctatct tcaaaggttg tcgtgccttt gttgtcatgg aaggttatga aggtttggtt    720
cgtggtggtc cagaatacat caaggaattc cactgggaag acgtccgtgg ttggtctgct    780
gaaggtggta ccaacattgg tactgcccgt tgtatggaat tcaagaagcg cgaaggtaga    840
ttattgggtg cccaacattt gattgaggcc ggtgtcgatg ctttgatcgt ttgtggtggt    900
gacggttctt tgactggtgc tgatctgttt agatcagaat ggccttcttt gatcgaggaa    960
ttgttgaaaa caaacagaat ttccaacgaa caatacgaaa gaatgaagca tttgaatatt    1020
tgcggtactg tcggttctat tgataacgat atgtccacca cggatgctac tattggtgct    1080
tactctgcct tggacagaat ctgtaaggcc atcgattacg ttgaagccac tgccaactct    1140
cactcaagag ctttcgttgt tgaagttatg ggtagaaact gtggttggtt agctttatta    1200
gctggtatcg ccacttccgc tgactatatc tttattccag agaagccagc cacttccagc    1260
gaatggcaag atcaaatgtg tgacattgtc tccaagcaca gatcaagggg taagagaacc    1320
accattgttg ttgttgcaga aggtgctatc gctgctgact tgaccccaat ttctccaagc    1380
gacgtccaca aagttctagt tgacagatta ggtttggata caagaattac taccttaggt    1440
cacgttcaaa gaggtggtac tgctgttgct tacgaccgta tcttggctac tttacaaggt    1500
cttgaggccg ttaatgccgt tttggaatcc actccagaca ccccatcacc attgattgct    1560
gttaacgaaa acaaaattgt tcgtaaacca ttaatggaat ccgtcaagtt gaccaaagca    1620
gttgcagaag ccattcaagc taaggatttc aagagagcta tgtctttaag agacactgag    1680
ttcattgaac atttaaacaa tttcatggct atcaactctg ctgaccacaa cgaaccaaag    1740
ctaccaaagg acaagagact gaagattgcc attgttaatg tcggtgctcc agctggtggt    1800
atcaactctg ccgtctactc gatggctact tactgtatgt cccaaggtca cagaccatac    1860
gctatctaca atggttggtc tggttttggca agacatgaaa gtgttcgttc tttgaactgg    1920
aaggatatgt tgggttggca atcccgtggt ggttctgaaa tcggtactaa cagagtcact    1980
ccagaagaag cagatctagg tatgattgct tactatttcc aaaagtacga atttgatggt    2040
ttgatcatcg ttggtggttt cgaagctttt gaatctttac atcaattaga gagagcaaga    2100
gaaagttatc cagcttttcag aatcccaatg gtcttgatac cagctacttt gtctaacaat    2160
gttccaggta ctgaatactc ttttgggttct gataccgctt tgaatgctct aatggaatac    2220
tgtgatgttg ttaaacaatc cgcttcttca accagaggta gagccttcgt tgtcgattgt    2280
caaggtggta actcaggcta tttggccact tacgcttctt ggctgttgg tgctcaagtc    2340 tcttatgtcc cagaagaagg tatttctttg gagcaattgt ccgaggatat tgaatactta    2400
gctcaatctt ttgaaaaggc agaaggtaga ggtagatttg gtaaattgat tttgaagagt    2460
acaaacgctt ctaaggcttt atcagccact aaattggctg aagttattac tgctgaagcc    2520
gatggcagat ttgacgctaa gccagcttat ccaggtcatg tacaacaagg tggtttgcca    2580
```

```
tctccaattg atagaacaag agccactaga atggccatta aagctgtcgg cttcatcaaa    2640
gacaaccaag ctgccattgc tgaagctcgt gctgccgaag aaaacttcaa cgctgatgac    2700
aagaccattt ctgacactgc tgctgtcgtt ggtgttaagg gttcacatgt cgtttacaac    2760
tccattagac aattgtatga ctatgaaact gaagtttcca tgagaatgcc aaaggtcatt    2820
cactggcaag ctaccagact cattgctgac catttggttg gaagaaagag agttgattaa    2880
```

<210> SEQ ID NO 122
<211> LENGTH: 4179
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 122

```
atgactaacg aaaaggtctg gatagagaag ttggataatc caactctttc agtgttacca      60
catgactttt tacgcccaca acaagaacct tatacgaaac aagctacata ttcgttacag     120
ctacctcagc tcgatgtgcc tcatgatagt ttttctaaca aatacgctgt cgctttgagt     180
gtatgggctg cattgatata tagagtaacc ggtgacgatg atattgttct ttatattgcg     240
aataacaaaa tcttaagatt caatattcaa ccaacgtggt catttaatga gctgtattct     300
acaattaaca atgagttgaa caagctcaat tctattgagg ccaattttc ctttgacgag      360 ctagctgaaa aaattcaaag ttgccaagat ctggaaagga cccctcagtt gttccgtttg     420
gcctttttgg aaaaccaaga tttcaaatta gacgagttca agcatcattt agtggacttt     480
gctttgaatt tggataccag taataatgcg catgttttga acttaattta taacagctta     540
ctgtattcga atgaaagagt aaccattgtt gcggaccaat ttactcaata tttgactgct     600
gcgctaagcg atccatccaa ttgcataact aaaatctctc tgatcaccgc atcatccaag     660
gatagtttac ctgatccaac taagaacttg ggctggtgcg atttcgtggg gtgtattcac     720
gacattttcc aggacaatgc tgaagccttc ccagagagaa cctgtgttgt ggagactcca     780
acactaaatt ccgacaagtc ccgttctttc acttatcgcg acatcaaccg cacttctaac     840
atagttgccc attatttgat taaaacaggt atcaaaagag gtgatgtagt gatgatctat     900
tcttctaggg gtgtggattt gatggtatgt gtgatgggtg tcttgaaagc cggcgcaacc     960
ttttcagtta tcgaccctgc atatccccca gccagacaaa ccatttactt aggtgttgct    1020
aaaccacgtg ggttgattgt tattagagct gctggacaat tggatcaact agtagaagat    1080
tacatcaatg atgaattgga gattgtttca agaatcaatt ccatcgctat tcaagaaaat    1140
ggtaccattg aagtggcaa attggacaat ggcgaggatg ttttggctcc atatgatcac    1200
tacaaagaca ccagaacagg tgttgtagtt ggaccagatt ccaacccaac cctatctttc    1260
acatctggtt ccgaaggtat tcctaagggt gttcttggta acattttttc cttggcttat    1320
tatttcaatt ggatgtccaa aaggttcaac ttaacagaaa atgataaatt cacaatgctg    1380
agcggtattg cacatgatcc aattcaaaga gatatgttta caccattatt tttaggtgcc    1440
caattgtatg tccctactca agatgatatt ggtacaccgg gccgtttagc ggaatggatg    1500
agtaagtatg gttgcacagt tacccattta acacctgcca tgggtcaatt acttactgcc    1560
caagctacta caccattccc taagttacat catgcgttct ttgtgggtga cattttaaca    1620
aaacgtgatt gtctgaggtt acaaaccttg gcagaaaatt gccgtattgt taatatgtac    1680
ggtaccactg aaacacagcg tgcagtttct tatttcgaag ttaaatcaaa aaatgacgat    1740
ccaaactttt tgaaaaaatt gaaagatgtc atgcctgctg gtaaaggtat gttgaacgtt    1800
```

```
cagctactag ttgttaacag gaacgatcgt actcaaatat gtggtattgg cgaaataggt    1860
gagatttatg ttcgtgcagg tggtttggcc gaaggttata gaggattacc agaattgaat    1920
aaagaaaaat ttgtgaacaa ctggtttgtt gaaaaagatc actggaatta tttggataag    1980
gataatggtg aaccttggag acaattctgg ttaggtccaa gagatagatt gtacagaacg    2040
ggtgatttag gtcgttatct accaaacggt gactgtgaat gttgcggtag ggctgatgat    2100
caagttaaaa ttcgtgggtt cagaatcgaa ttaggagaaa tagatacgca catttcccaa    2160
catccattgg taagagaaaa cattacttta gttcgcaaaa atgccgacaa tgagccaaca    2220
ttgatcacat ttatggtccc aagatttgac aagccagatg acttgtctaa gttccaaagt    2280
gatgttccaa aggaggttga aactgaccct atagttaagg gcttaatcgg ttaccatctt    2340
ttatccaagg acatcaggac tttcttaaag aaaagattgg ctagctatgc tatgccttcc    2400
ttgattgtgg ttatggataa actaccattg aatccaaatg gtaaagttga taagcctaaa    2460
cttcaattcc caactcccaa gcaattaaat ttggtagctg aaaatacagt ttctgaaact    2520
gacgactctc agtttaccaa tgttgagcgc gaggttagag acttatggtt aagtatatta    2580
cctaccaagc cagcatctgt atcaccagat gattcgtttt tcgatttagg tggtcattct    2640
atcttggcta ccaaaatgat ttttacctta aagaaaaagc tgcaagttga tttaccattg    2700
ggcacaattt tcaagtatcc aacgataaag gcctttgccg cggaaattga cagaattaaa    2760
tcatcgggtg gatcatctca aggtgaggtc gtcgaaaatg tcactgcaaa ttatgcggaa    2820
gacgccaaga aattggttga gacgctacca agttcgtacc cctctcgaga atattttgtt    2880
gaacctaata gtgccgaagg aaaaacaaca attaatgtgt tgttaccggt tgtcacagga    2940
tttctgggct cctacatcct tgcagatttg ttaggacgtt ctccaaagaa ctacagtttc    3000
aaagtgtttg cccacgtcag ggccaaggat gaagaagctg catttgcaag attacaaaag    3060
gcaggtatca cctatggtac ttggaacgaa aaatttgcct caaatattaa agttgtatta    3120
ggcgatttat ctaaaagcca atttggtctt tcagatgaga agtggatgga tttggcaaac    3180
acagttgata taattatcca taatggtgcg ttagttcact gggtttatcc atatgccaaa    3240
ttgagggatc caaatgttat ttcaactatc aatgttatga gcttagccgc cgtcggcaag    3300
ccaaagttct ttgactttgt ttcctccact tctactcttg acactgaata ctactttaat    3360
ttgtcagata aacttgttag cgaagggaag ccaggcattt tagaatcaga cgatttaatg    3420
aactctgcaa gcgggctcac tggtggatat ggtcagtcca aatgggctgc tgagtacatc    3480
attagacgtg caggtgaaag gggcctacgt gggtgtattg tcagaccagg ttacgtaaca    3540
ggtgcctctg ccaatggttc ttcaaacaca gatgatttct tattgagatt tttgaaaggt    3600
tcagtccaat taggtaagat tccagatatc gaaaattccg tgaatatggt tccagtagat    3660
catgttgctc gtgttgttgt tgctacgtct ttgaatcctc ccaaagaaaa tgaattggcc    3720
gttgctcaag taacgggtca cccaagaata ttattcaaag actacttgta tactttacac    3780
gattatggtt acgatgtcga aatcgaaagc tattctaaat ggaagaaatc attggaggcg    3840
tctgttattg acaggaatga agaaaatgcg ttgtatcctt tgctacacat ggtcttagac    3900
aacttacctg aaagtaccaa agctccggaa ctagacgata ggaacgccgt ggcatcttta    3960
aagaaagaca ccgcatggac aggtgttgat tggtctaatg gaataggtgt tactccgaaa    4020
gaggttggta tatatattgc attttttaaac aaggttggat ttttacctcc accaactcat    4080
aatgacaaac ttccactgcc aagtatagaa ctaactcaag cgcaaataag tctagttgct    4140
tcaggtgctg gtgctcgtgg aagctccgca gcagcttaa                          4179
```

```
<210> SEQ ID NO 123
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Thr Thr Thr Arg Lys Lys Ser Lys Ala Leu Pro Ala Pro Pro Thr
1               5                   10                  15

Thr Leu Phe Leu Phe Gly Ala Arg Gly Asp Leu Val Lys Arg Leu Leu
            20                  25                  30

Met Pro Ala Leu Tyr Asn Leu Ser Arg Asp Gly Leu Leu Asp Glu Gly
        35                  40                  45

Leu Arg Ile Val Gly Val Asp His Asn Ala Val Ser Asp Ala Glu Phe
    50                  55                  60

Ala Thr Leu Leu Glu Asp Phe Leu Arg Asp Glu Val Leu Asn Lys Gln
65                  70                  75                  80

Gly Gln Gly Ala Ala Val Asp Ala Ala Val Trp Ala Arg Leu Thr Arg
                85                  90                  95

Gly Ile Asn Tyr Val Gln Gly Asp Phe Leu Asp Asp Ser Thr Tyr Ala
            100                 105                 110

Glu Leu Ala Ala Arg Ile Ala Ala Ser Gly Thr Gly Asn Ala Val Phe
        115                 120                 125

Tyr Leu Ala Thr Ala Pro Arg Phe Phe Ser Glu Val Val Arg Arg Leu
    130                 135                 140

Gly Ser Ala Gly Leu Leu Glu Glu Gly Pro Gln Ala Phe Arg Arg Val
145                 150                 155                 160

Val Ile Glu Lys Pro Phe Gly Ser Asp Leu Gln Thr Ala Glu Ala Leu
                165                 170                 175

Asn Gly Cys Leu Leu Lys Val Met Ser Glu Lys Gln Ile Tyr Arg Ile
            180                 185                 190

Asp His Tyr Leu Gly Lys Glu Thr Val Gln Asn Ile Leu Val Ser Arg
        195                 200                 205

Phe Ser Asn Ser Leu Phe Glu Ala Phe Trp Asn Asn His Tyr Ile Asp
    210                 215                 220

His Val Gln Ile Thr Ala Ala Glu Thr Val Gly Val Glu Thr Arg Gly
225                 230                 235                 240

Ser Phe Tyr Glu His Thr Gly Ala Leu Arg Asp Met Val Pro Asn His
                245                 250                 255

Leu Phe Gln Leu Leu Ala Met Val Ala Met Glu Pro Pro Ala Ala Phe
            260                 265                 270

Gly Ala Asp Ala Val Arg Gly Glu Lys Ala Lys Val Val Gly Ala Ile
        275                 280                 285

Arg Pro Trp Ser Val Glu Glu Ala Arg Ala Asn Ser Val Arg Gly Gln
    290                 295                 300

Tyr Ser Ala Gly Glu Val Ala Gly Lys Ala Leu Ala Gly Tyr Arg Glu
305                 310                 315                 320

Glu Ala Asn Val Ala Pro Asp Ser Ser Thr Glu Thr Tyr Val Ala Leu
                325                 330                 335

Lys Val Met Ile Asp Asn Trp Arg Trp Val Gly Val Pro Phe Tyr Leu
            340                 345                 350

Arg Thr Gly Lys Arg Met Ser Val Arg Asp Thr Glu Ile Val Ile Cys
        355                 360                 365
```

Phe Lys Pro Ala Pro Tyr Ala Gln Phe Arg Asp Thr Glu Val Glu Arg
        370                 375                 380

Leu Leu Pro Thr Tyr Leu Arg Ile Gln Ile Gln Pro Asn Glu Gly Met
385                 390                 395                 400

Trp Phe Asp Leu Leu Ala Lys Lys Pro Gly Pro Ser Leu Asp Met Ala
                405                 410                 415

Asn Ile Glu Leu Gly Phe Ala Tyr Arg Asp Phe Phe Gly Met Gln Pro
            420                 425                 430

Ser Thr Gly Tyr Glu Thr Leu Ile Tyr Asp Cys Leu Ile Gly Asp Gln
        435                 440                 445

Thr Leu Phe Gln Arg Ala Asp Asn Ile Glu Asn Gly Trp Arg Ala Val
    450                 455                 460

Gln Pro Phe Leu Asp Ala Trp Gln Gln Asp Ala Ser Leu Gln Asn Tyr
465                 470                 475                 480

Pro Ala Gly Val Asp Gly Pro Ala Ala Gly Asp Glu Leu Leu Ala Arg
                485                 490                 495

Asp Gly Arg Val Trp Arg Pro Leu Gly
                500                 505

<210> SEQ ID NO 124
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
atgaccacca cgcgaaagaa gtccaaggcg ttgccggcgc cgccgaccac gctgttcctg      60
ttcggcgccc gcggtgatct ggtcaagcgc ctgctgatgc cggcgctgta caacctcagc     120
cgcgacggtt tgctggatga ggggctgcgg attgtcggcg tcgaccacaa cgcggtgagc     180
gacgccgagt tcgccacgct gctggaagac ttccttcgcg atgaagtgct caacaagcaa     240 ggccagggg cggcggtgga tgccgccgtc tgggcccgcc tgacccgggg catcaactat      300
gtccagggcg atttcttcga cgactccacc tatgccgaac tggcggcgcg gattgccgcc     360
agcggcaccg gcaacgcggt gttctacctg gccaccgcac gcgcttcctt cagtgaagtg     420
gtgcgccgcc tgggcagcgc cgggttgctg gaggagggc cgcaggcttt cgccgggtg      480 gtgatcgaaa accccttcgg ctccgacctg cagaccgccg aagccctcaa cggctgcctg     540
ctcaaggtca tgagcgagaa gcagatctat cgcatcgacc attacctggg caaggaaacg     600
gtccagaaca tcctggtcag ccgttttttcc aacagcctgt tcgaggcatt ctggaacaac     660
cattacatcg accacgtgca gatcaccgcg gcggaaaccg tcggcgtgga aacccgtggc     720 agctttttatg aacacaccgg tgccctgcgg acatggtgc caaccaccct gttccagttg      780
ctggcgatgg tggccatgga gccgcccgct gcctttggcg ccgatgcggt acgtggcgaa     840
aaggccaagg tggtggggc tatccgcccc tggtccgtgg aagagcccg ggccaactcg      900 gtgcgcggcc agtacagcgc cggtgaagtg gccggcaagg ccctggcggg ctaccgcgag     960
gaagccaacg tggcgccgga cagcagcacc gaaacctacg ttgcgctgaa ggtgatgatc    1020
gacaactggc gctgggtcgg ggtgccgttc tacctgcgca ccggcaagcg catgagtgtg    1080
cgcgacaccg agatcgtcat ctgcttcaag ccggcgccct atgcacagtt ccgcgatacc    1140
gaggtcgagc gcctgttgcc gacctacctg cggatccaga tccagcccaa cgaaggcatg    1200
tggttcgacc tgctggcgaa aaagcccggg ccgagcctgg acatggccaa catcgaactg    1260

```
ggttttgcct accgcgactt tttcgagatg cagccctcca ccggctacga aaccctgatc   1320
tacgactgcc tgatcggcga ccagaccctg ttccagcgcg ccgacaacat cgagaacggc   1380
tggcgcgcgg tgcaacccett cctcgatgcc tggcaacagg acgccagctt gcagaactac   1440
ccggcgggcg tggatggccc ggcagccggg gatgaactgc tggcccggga tggccgcgta   1500
tggcgacccc tggggtga                                                1518
```

```
<210> SEQ ID NO 125
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125
```

```
Met Pro Ser Ile Thr Val Glu Pro Cys Thr Phe Ala Leu Phe Gly Ala
1               5                   10                  15

Leu Gly Asp Leu Ala Leu Arg Lys Leu Phe Pro Ala Leu Tyr Gln Leu
            20                  25                  30

Asp Ala Ala Gly Leu Leu His Asp Thr Arg Ile Leu Ala Leu Ala
        35                  40                  45

Arg Glu Pro Gly Ser Glu Gln Glu His Leu Ala Asn Ile Glu Thr Glu
    50                  55                  60

Leu His Lys Tyr Val Gly Asp Lys Asp Ile Asp Ser Gln Val Leu Gln
65                  70                  75                  80

Arg Phe Leu Val Arg Leu Ser Tyr Leu His Val Asp Phe Leu Lys Ala
                85                  90                  95

Glu Asp Tyr Val Ala Leu Ala Glu Arg Val Gly Ser Glu Gln Arg Leu
            100                 105                 110

Ile Ala Tyr Phe Ala Thr Pro Ala Ala Val Tyr Gly Ala Ile Cys Glu
        115                 120                 125

Asn Leu Ser Arg Val Gly Leu Asn Gln His Thr Arg Val Val Leu Glu
    130                 135                 140

Lys Pro Ile Gly Ser Asp Leu Asp Ser Ser Arg Lys Val Asn Asp Ala
145                 150                 155                 160

Val Ala Gln Phe Phe Pro Glu Thr Arg Ile Tyr Arg Ile Asp His Tyr
                165                 170                 175

Leu Gly Lys Glu Thr Val Gln Asn Leu Ile Ala Leu Arg Phe Ala Asn
            180                 185                 190

Ser Leu Phe Glu Thr Gln Trp Asn Gln Asn Tyr Ile Ser His Val Glu
        195                 200                 205

Ile Thr Val Ala Glu Lys Val Gly Ile Glu Gly Arg Trp Gly Tyr Phe
    210                 215                 220

Asp Lys Ala Gly Gln Leu Arg Asp Met Ile Gln Asn His Leu Leu Gln
225                 230                 235                 240

Leu Leu Cys Leu Ile Ala Met Asp Pro Pro Ala Asp Leu Ser Ala Asp
                245                 250                 255

Ser Ile Arg Asp Glu Lys Val Lys Val Leu Lys Ala Leu Ala Pro Ile
            260                 265                 270

Ser Pro Glu Gly Leu Thr Thr Gln Val Val Arg Gly Gln Tyr Ile Ala
        275                 280                 285

Gly His Ser Glu Gly Gln Ser Val Pro Gly Tyr Leu Glu Glu Glu Asn
    290                 295                 300

Ser Asn Thr Gln Ser Asp Thr Glu Thr Phe Val Ala Leu Arg Ala Asp
```

```
                305                 310                 315                 320
Ile Arg Asn Trp Arg Trp Ala Gly Val Pro Phe Tyr Leu Arg Thr Gly
                    325                 330                 335

Lys Arg Met Pro Gln Lys Leu Ser Gln Ile Val Ile His Phe Lys Glu
                340                 345                 350

Pro Ser His Tyr Ile Phe Ala Pro Glu Gln Arg Leu Gln Ile Ser Asn
            355                 360                 365

Lys Leu Ile Ile Arg Leu Gln Pro Asp Glu Gly Ile Ser Leu Arg Val
        370                 375                 380

Met Thr Lys Glu Gln Gly Leu Asp Lys Gly Met Gln Leu Arg Ser Gly
385                 390                 395                 400

Pro Leu Gln Leu Asn Phe Ser Asp Thr Tyr Arg Ser Ala Arg Ile Pro
                405                 410                 415

Asp Ala Tyr Glu Arg Leu Leu Leu Glu Val Met Arg Gly Asn Gln Asn
            420                 425                 430

Leu Phe Val Arg Lys Asp Glu Ile Glu Ala Ala Trp Lys Trp Cys Asp
        435                 440                 445

Gln Leu Ile Ala Gly Trp Lys Lys Ser Gly Asp Ala Pro Lys Pro Tyr
    450                 455                 460

Ala Ala Gly Ser Trp Gly Pro Met Ser Ser Ile Ala Leu Ile Thr Arg
465                 470                 475                 480

Asp Gly Arg Ser Trp Tyr Gly Asp Ile
                485

<210> SEQ ID NO 126
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
atgccttcga taacggttga accctgcacc tttgccttgt ttggcgcgct gggcgatctg      60
gcgctgcgta agctgtttcc tgccctgtac caactcgatg ccgccggttt gctgcatgac     120
gacacgcgca tcctggccct ggcccgcgag cctggcagcg agcaggaaca cctggcgaat     180
atcgaaaccg agctgcacaa gtatgtcggc gacaaggata tcgatagcca ggtcctgcag     240
cgttttctcg tccgcctgag ctacctgcat gtggacttcc tcaaggccga ggactacgtc     300
gccctggccg aacgtgtcgg cagcgagcag cgcctgattg cctacttcgc cacgccggcg     360
gcggtgtatg cgcgatctg cgaaaacctc tcccgggtcg gctcaacca gcacacccgt     420 gtggtcctgg aaaaacccat cggctcggac ctggattcat cacgcaaggt caacgacgcg     480
gtggcgcagt tcttcccgga aacccgcatc taccggatcg accactacct gggcaaggaa     540
acggtgcaga acctgattgc cctgcgtttc gccaacagcc tgttcgaaac ccagtggaac     600
cagaactaca tctcccacgt ggaaatcacc gtggccgaga aggtcggcat cgaaggtcgc     660
tggggctatt tcgacaaggc cggccaactg cgggacatga tccagaacca cttgctgcaa     720
ctgctctgcc tgatcgcgat ggacccgccg ccgaccttt cggccgacag catccgcgac     780
gagaaggtca aggtgctcaa ggccctggcg cccatcagcc cggaaggcct gaccacccag     840
gtggtgcgcg ccagtacat cgccggccac agcgaaggcc agtcggtgcc gggctacctg     900
gaggaagaaa actccaacac ccagagcgac accgagacct cgtcgccct gcgccgat     960 atccgcaact ggcgctgggc cggtgtgcct ttctacctgc gcaccggcaa gcgcatgcca    1020
```

```
cagaagctgt cgcagatcgt catccacttc aaggaaccct cgcactacat cttcgccccc    1080
gagcagcgcc tgcagatcag caacaagctg atcatccgcc tgcagccgga cgaaggtatc    1140
tcgttgcggg tgatgaccaa ggagcagggc ctggacaagg gcatgcaact gcgcagcggt    1200
ccgttgcagc tgaattttc cgataccta t cgcagtgcac ggatcccga t gcctacgag     1260 cggttgttgc tggaagtgat gcgcggcaat cagaacctgt ttgtgcgcaa agatgaaatc    1320
gaagccgcgt ggaagtggtg tgaccagttg attgccgggt ggaagaaatc cggcgatgcg    1380
cccaagccgt acgcggccgg gtcctggggg ccgatgagct ccattgcact gatcacgcgg    1440
gatgggaggt cttggtatgg cgatatctaa                                     1470
```

<210> SEQ ID NO 127
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

```
Met Pro Asp Val Arg Val Leu Pro Cys Thr Leu Ala Leu Phe Gly Ala
1               5                   10                  15

Leu Gly Asp Leu Ala Leu Arg Lys Leu Phe Pro Ala Leu Tyr Gln Leu
            20                  25                  30

Asp Arg Glu Asn Leu Leu His Arg Asp Thr Arg Val Leu Ala Leu Ala
        35                  40                  45

Arg Asp Glu Gly Ala Pro Ala Glu His Leu Ala Thr Leu Glu Gln Arg
    50                  55                  60

Leu Arg Leu Ala Val Pro Ala Lys Glu Trp Asp Asp Val Val Trp Gln
65                  70                  75                  80

Arg Phe Arg Glu Arg Leu Asp Tyr Leu Ser Met Asp Phe Leu Asp Pro
                85                  90                  95

Gln Ala Tyr Val Gly Leu Arg Glu Ala Val Asp Asp Glu Leu Pro Leu
            100                 105                 110

Val Ala Tyr Phe Ala Thr Pro Ala Ser Val Phe Gly Gly Ile Cys Glu
        115                 120                 125

Asn Leu Ala Ala Ala Gly Leu Ala Glu Arg Thr Arg Val Val Leu Glu
130                 135                 140

Lys Pro Ile Gly His Asp Leu Glu Ser Ser Arg Glu Val Asn Glu Ala
145                 150                 155                 160

Val Ala Arg Phe Phe Pro Glu Ser Arg Ile Tyr Arg Ile Asp His Tyr
                165                 170                 175

Leu Gly Lys Glu Thr Val Gln Asn Leu Ile Ala Leu Arg Phe Ala Asn
            180                 185                 190

Ser Leu Phe Glu Thr Gln Trp Asn Gln Asn His Ile Ser His Val Glu
        195                 200                 205

Ile Thr Val Ala Glu Lys Val Gly Ile Glu Gly Arg Trp Gly Tyr Phe
    210                 215                 220

Asp Gln Ala Gly Gln Leu Arg Asp Met Val Gln Asn His Leu Leu Gln
225                 230                 235                 240

Leu Leu Cys Leu Ile Ala Met Asp Pro Pro Ser Asp Leu Ser Ala Asp
                245                 250                 255

Ser Ile Arg Asp Glu Lys Val Lys Val Leu Arg Ala Leu Glu Pro Ile
            260                 265                 270

Pro Ala Glu Gln Leu Ala Ser Arg Val Val Arg Gly Gln Tyr Thr Ala
        275                 280                 285
```

```
Gly Phe Ser Asp Gly Lys Ala Val Pro Gly Tyr Leu Glu Glu Glu His
    290                 295                 300

Ala Asn Arg Asp Ser Asp Ala Glu Thr Phe Val Ala Leu Arg Val Asp
305                 310                 315                 320

Ile Arg Asn Trp Arg Trp Ser Gly Val Pro Phe Tyr Leu Arg Thr Gly
                325                 330                 335

Lys Arg Met Pro Gln Lys Leu Ser Gln Ile Val Ile His Phe Lys Glu
            340                 345                 350

Pro Pro His Tyr Ile Phe Ala Pro Glu Gln Arg Ser Leu Ile Ser Asn
        355                 360                 365

Arg Leu Ile Ile Arg Leu Gln Pro Asp Glu Gly Ile Ser Leu Gln Val
    370                 375                 380

Met Thr Lys Asp Gln Gly Leu Gly Lys Gly Met Gln Leu Arg Thr Gly
385                 390                 395                 400

Pro Leu Gln Leu Ser Phe Ser Glu Thr Tyr His Ala Ala Arg Ile Pro
                405                 410                 415

Asp Ala Tyr Glu Arg Leu Leu Leu Glu Val Thr Gln Gly Asn Gln Tyr
            420                 425                 430

Leu Phe Val Arg Lys Asp Glu Val Glu Phe Ala Trp Lys Trp Cys Asp
        435                 440                 445

Gln Leu Ile Ala Gly Trp Glu Arg Leu Ser Glu Ala Pro Lys Pro Tyr
    450                 455                 460

Pro Ala Gly Ser Trp Gly Pro Val Ala Ser Val Ala Leu Val Ala Arg
465                 470                 475                 480

Asp Gly Arg Ser Trp Tyr Gly Asp Phe
                485

<210> SEQ ID NO 128
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
atgcctgatg tccgcgttct gccttgcacg ttagcgctgt tcggtgcgct gggcgatctc      60
gccttgcgca agctgttccc ggcgctctac caactcgatc gtgagaacct gctgcaccgc     120 gataccgcg tcctggccct ggcccgtgac gaaggcgctc cgccgaaca cctggcgacg       180 ctggagcagc gcctgcgcct ggcagtgccg gcgaaggagt gggacgacgt ggtctggcag     240
cgtttccgcg aacgcctcga ctacctgagc atggacttcc tcgacccgca ggcctatgtc     300
ggcttgcgcg aggcggtgga tgacgaactg ccgctggtcg cctacttcgc cacgccggcc     360
tcggtgttcg gcggcatctg cgagaacctc gccgccgccg gtctcgccga gcgcaccccgg    420 gtggtgctgg agaagcccat cggtcatgac ctggagtcgt cccgcgaggt caacgaggca     480
gtcgcccggt tcttcccgga aagccgcatc taccggatcg accattacct gggcaaggag     540
acggtgcaga acctgatcgc cctgcgcttc gccaacagcc tcttcgagac ccagtggaac     600
cagaaccaca tctcccacgt ggagatcacc gtggccgaga aggtcggcat cgaaggccgc     660
tggggctact cgaccaggc cgggcaactg cgcgacatgg tgcagaacca cctgctgcaa     720
ctgctctgcc tgatcgccat ggatccgccc agcgaccttt cggcggacag cattcgcgac     780
gagaaggtca aggtcctccg cgccctcgag ccgattcccg cagaacaact ggcttcgcgc     840
gtggtgcgtg ggcagtacac cgccggtttc agcgacggca aggcagtgcc gggctacctg     900
```

```
gaggaggaac atgcgaatcg cgacagcgac gcggaaacct tcgtcgccct gcgcgtggac    960
atccgcaact ggcgctggtc gggcgtgccg ttctacctgc gcaccggcaa gcgcatgccg   1020
cagaagctgt cgcagatcgt catccacttc aaggagccgc cgcactacat cttcgctccc   1080
gagcagcgtt cgctgatcag caaccggctg atcatccgcc tgcagccgga cgaaggtatc   1140
tccctgcaag tgatgaccaa ggaccagggc ctgggcaagg gcatgcaatt gcgtaccggc   1200
ccgctgcaac tgagtttttc cgagacctac cacgcggcgc ggattcccga tgcctacgag   1260
cgtctgctgc tggaggtcac ccagggcaac cagtacctgt tcgtgcgcaa ggacgaggtg   1320
gagttcgcct ggaagtggtg cgaccagctg atcgctggct gggaacgcct gagcgaagcg   1380
cccaagccgt atccggcggg gagttggggg ccggtggcct cggtggccct ggtggcccgc   1440
gatgggagga gttggtatgg cgatttctga                                    1470
```

<210> SEQ ID NO 129
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Met Thr Asn Thr Val Ser Thr Met Ile Leu Phe Gly Ser Thr Gly Asp
1               5                   10                  15

Leu Ser Gln Arg Met Leu Leu Pro Ser Leu Tyr Gly Leu Asp Ala Asp
            20                  25                  30

Gly Leu Leu Ala Asp Asp Leu Arg Ile Val Cys Thr Ser Arg Ser Glu
        35                  40                  45

Tyr Asp Thr Asp Gly Phe Arg Asp Phe Ala Glu Lys Ala Leu Asp Arg
    50                  55                  60

Phe Val Ala Ser Asp Arg Leu Asn Asp Asp Ala Lys Ala Lys Phe Leu
65                  70                  75                  80

Asn Lys Leu Phe Tyr Ala Thr Val Asp Ile Thr Asp Pro Thr Gln Phe
                85                  90                  95

Gly Lys Leu Ala Asp Leu Cys Gly Pro Val Glu Lys Gly Ile Ala Ile
            100                 105                 110

Tyr Leu Ser Thr Ala Pro Ser Leu Phe Glu Gly Ala Ile Ala Gly Leu
        115                 120                 125

Lys Gln Ala Gly Leu Ala Gly Pro Thr Ser Arg Leu Ala Leu Glu Lys
    130                 135                 140

Pro Leu Gly Gln Asp Leu Ala Ser Ser Asp His Ile Asn Asp Ala Val
145                 150                 155                 160

Leu Lys Val Phe Ser Glu Lys Gln Val Tyr Arg Ile Asp His Tyr Leu
                165                 170                 175

Gly Lys Glu Thr Val Gln Asn Leu Leu Thr Leu Arg Phe Gly Asn Ala
            180                 185                 190

Leu Phe Glu Pro Leu Trp Asn Ser Lys Gly Ile Asp His Val Gln Ile
        195                 200                 205

Ser Val Ala Glu Thr Val Gly Leu Glu Gly Arg Ile Gly Tyr Phe Asp
    210                 215                 220

Gly Ser Gly Ser Leu Arg Asp Met Val Gln Ser His Ile Leu Gln Leu
225                 230                 235                 240

Val Ala Leu Val Ala Met Glu Pro Pro Ala His Met Glu Ala Asn Ala
                245                 250                 255
```

```
Val Arg Asp Glu Lys Val Lys Val Phe Arg Ala Leu Arg Pro Ile Asn
            260                 265                 270
Asn Asp Thr Val Phe Thr His Thr Val Thr Gly Gln Tyr Gly Ala Gly
            275                 280                 285
Val Ser Gly Gly Lys Glu Val Ala Gly Tyr Ile Asp Glu Leu Gly Gln
            290                 295                 300
Pro Ser Asp Thr Glu Thr Phe Val Ala Ile Lys Ala His Val Asp Asn
305                 310                 315                 320
Trp Arg Trp Gln Gly Val Pro Phe Tyr Ile Arg Thr Gly Lys Arg Leu
            325                 330                 335
Pro Ala Arg Arg Ser Glu Ile Val Val Gln Phe Lys Pro Val Pro His
            340                 345                 350
Ser Ile Phe Ser Ser Ser Gly Gly Ile Leu Gln Pro Asn Lys Leu Arg
            355                 360                 365
Ile Val Leu Gln Pro Asp Glu Thr Ile Gln Ile Ser Met Met Val Lys
            370                 375                 380
Glu Pro Gly Leu Asp Arg Asn Gly Ala His Met Arg Glu Val Trp Leu
385                 390                 395                 400
Asp Leu Ser Leu Thr Asp Val Phe Lys Asp Arg Lys Arg Ile Ala
            405                 410                 415
Tyr Glu Arg Leu Met Leu Asp Leu Ile Glu Gly Asp Ala Thr Leu Phe
            420                 425                 430
Val Arg Arg Asp Glu Val Glu Ala Gln Trp Val Trp Ile Asp Gly Ile
            435                 440                 445
Arg Glu Gly Trp Lys Ala Asn Ser Met Lys Pro Lys Thr Tyr Val Ser
            450                 455                 460
Gly Thr Trp Gly Pro Ser Thr Ala Ile Ala Leu Ala Glu Arg Asp Gly
465                 470                 475                 480
Val Thr Trp Tyr Asp
            485

<210> SEQ ID NO 130
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
atgacaaata ccgtttcgac gatgatattg tttggctcga ctggcgacct ttcacagcgt    60
atgctgttgc cgtcgcttta tggtcttgat gccgatggtt tgcttgcaga tgatctgcgt   120
atcgtctgca cctctcgtag cgaatacgac acagatggtt ccgtgatttt gcagaaaaa    180 gctttagatc gctttgtcgc ttctgaccgg ttaaatgatg acgctaaagc taaattcctt   240
aacaagcttt tctacgcgac ggtcgatatt acggatccga cccaattcgg aaaattagct   300
gacctttgtg gcccggtcga aaaaggtatc gccatttatc tttcgactgc gccttctttg   360
tttgaagggg caatcgctgg cctgaaacag gctggtctgg ctggtccaac ttctcgcctg   420
gcgcttgaaa aacctttagg tcaagatctt gcttcttccg atcatattaa tgatgcggtt   480
ttgaaagttt tctctgaaaa gcaagtttat cgtattgacc attatctggg taaagaaacg   540
gttcagaatc ttctgaccct gcgttttggt aatgctttgt ttgaaccgct ttggaattca   600
aaaggcattg accacgttca gatcagcgtt gctgaaacgg ttggtcttga aggtcgtatc   660
ggttatttcg acggttctgg cagcttgcgc gatatggttc aaagccatat ccttcagttg   720
```

```
gtcgctttgg ttgcaatgga accaccggct catatggaag ccaacgctgt tcgtgacgaa      780
aaggtaaaag ttttccgcgc tctgcgtccg atcaataacg acaccgtctt tacgcatacc      840
gttaccggtc aatatggtgc cggtgtttct ggtggtaaag aagttgccgg ttacattgac      900
gaactgggtc agccttccga taccgaaacc tttgttgcta tcaaagcgca tgttgataac      960
tggcgttggc agggtgttcc gttctatatc cgcactggta agcgtttacc tgcacgtcgt     1020
tctgaaatcg tggttcagtt taaacctgtt ccgcattcga ttttctcttc ttcaggtggt     1080
atcttgcagc cgaacaagct gcgtattgtc ttacagcctg atgaaaccat ccagatttct     1140
atgatggtga agaaccgggt cttgaccgt aacggtgcgc atatgcgtga agtttggctg     1200
gatctttccc tcacggatgt gtttaaagac cgtaaacgtc gtatcgctta tgaacgcctg     1260
atgcttgatc ttatcgaagg cgatgctact ttatttgtgc gtcgtgacga agttgaggcg     1320
cagtgggttt ggattgacgg aattcgtgaa ggctggaaag ccaacagtat gaagccaaaa     1380
acctatgtct ctggtacatg ggggccttca actgctatag ctctggccga acgtgatgga     1440
gtaacttggt atgactga                                                  1458

<210> SEQ ID NO 131
<211> LENGTH: 750
<212> TYPE: DNA
<213> ORGANISM: Saccharomyces cerevisiae

<400> SEQUENCE: 131
atggtgacag tcggtgtgtt ttctgagagg gctagtttga cccatcaatt gggggaattc       60
atcgtcaaga aacaagatga ggcgctgcaa aagaagtcag actttaaagt ttccgttagc      120
ggtggctctt tgatcgatgc tctgtatgaa agtttagtag cggacgaatc actatcttct      180
cgagtgcaat ggtctaaatg gcaaatctac ttctctgatg aaagaattgt gccactgacg      240
gacgctgaca gcaattatgg tgccttcaag agagctgttc tagataaatt accctcgact      300
agtcagccaa acgtttatcc catggacgag tccttgattg gcagcgatgc tgaatctaac      360
aacaaaattg ctgcagagta cgagcgtatc gtacctcaag tgcttgattt ggtactgttg      420
ggctgtggtc ctgatggaca cacttgttcc ttattccctg agaaacaca taggtacttg      480 ctgaacgaaa caaccaaaag agttgcttgg tgccacgatt ctcccaagcc tccaagtgac      540
agaatcacct tcactctgcc tgtgttgaaa gacgccaaag ccctgtgttt tgtggctgag      600
ggcagttcca acaaaatat aatgcatgag atctttgact tgaaaaacga tcaattgcca      660
accgcattgg ttaacaaatt atttggtgaa aaaacatcct ggttcgttaa tgaggaagct      720
tttggaaaag ttcaaacgaa aacttttag                                       750

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
```

<400> SEQUENCE: 132
aaannraang arraanar                                              18

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 133
gtgmaknmgr angng                                                 15

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 134
nttwacaycc rtacayny                                              18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 135
tttnctttky ttnytttt                                              18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

```
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 136
aaaranraaa naaarnaa                                                 18

<210> SEQ ID NO 137
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 137
cacacacaca cacacac                                                  17

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 138
ttgcttgaac gsatgcca                                                 18

<210> SEQ ID NO 139
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 139
yctttttttt yttyykg                                                  17

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 140
rrsccgmcgm grcgcgcs                                                 18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
```

-continued

```
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 141
aaanararnr aaaarrar                                                 18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 142
ggaagctgaa acgymwrr                                                 18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 143
ggagaggcat gatggggg                                                 18

<210> SEQ ID NO 144
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 144 ctncctttct                                                          10

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 145
gaaarraaaa aamrmara                                                 18

<210> SEQ ID NO 146
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
```

```
<222> LOCATION: (8)..(9)
<223> OTHER INFORMATION: a, c, t, g, unknown or other

<400> SEQUENCE: 146
gngccrsnnt m                                                          11

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 147 tttttyttt tynktttt                                                    18

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 148
yttcttttyt nyncnktn                                                   18

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 149
tnsykctttt cytty                                                      15

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
```

```
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 150
sttnytttyn ttytyyyy                                                 18

<210> SEQ ID NO 151
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 151 yknttttwyyt c                                                       11

<210> SEQ ID NO 152
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 152
aaaananaar arnag                                                    15

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 153
waaaaaagaa aanaaaar                                                 18

<210> SEQ ID NO 154
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
```

```
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 154
aaanggnara m                                                              11

<210> SEQ ID NO 155
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 155
tyttcyagaa nnttcy                                                         16

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 156
cacacacaca cacacaca                                                       18

<210> SEQ ID NO 157
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 157
tttycacatg c                                                              11

<210> SEQ ID NO 158
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 158
gnngcatgtg aaaa                                                           14

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
```

```
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 159
gaaaanaaaa aaaarana                                                 18

<210> SEQ ID NO 160
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 160
gaaaaaraar aanaa                                                    15

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other

<400> SEQUENCE: 161
yttktnnttt ttytyttt                                                 18

<210> SEQ ID NO 162
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 162 gcagngcagg                                                          10

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 163
tttytykttt nyyttttt                                                 18
```

```
<210> SEQ ID NO 164
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 164
tttccnaawn rggaaa                                                    16

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 165
yttyyttytt ttytyttc                                                  18

<210> SEQ ID NO 166
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 166 mttttytyt yttc                                                       14

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 167
tatacanagm krtatatg                                                  18

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
```

```
<220> FEATURE:
<221> NAME/KEY: modified_base
<222> LOCATION: (13)..(13)
<223> OTHER INFORMATION: a, c, t, g, unknown or other

<400> SEQUENCE: 168
tmtttntync ttntttwk                                                 18

<210> SEQ ID NO 169
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 169
ktnnttwtta ttccnc                                                   16

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 170
rnnaaaanra naaraaat                                                 18

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 171 tttttttttcw ctttkyc                                                 17

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
```

```
<220> FEATURE:
<221> NAME/KEY: modified_base
<222> LOCATION: (13)..(13)
<223> OTHER INFORMATION: a, c, t, g, unknown or other

<400> SEQUENCE: 172
tttynytktt tynyttyt                                                    18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 173
ttynnttytt nytttyyy                                                    18

<210> SEQ ID NO 174
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 174
tnygtgkryg tnyg                                                        14

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 175
ttyyyttttt yttttytt                                                    18

<210> SEQ ID NO 176
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 176
gamaaaaaar aaaar                                                       15

<210> SEQ ID NO 177
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 177
cycgggaagc sammnccg                                                 18

<210> SEQ ID NO 178
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 178
grtgyayggr tgy                                                      13

<210> SEQ ID NO 179
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 179
kmaaraaaaa raar                                                     14

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 180
aygraaaara raaaaraa                                                 18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 181
ggaksccntt tyngmrta                                                 18

<210> SEQ ID NO 182
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 182
ttttcnkttt yttttc                                                         17

<210> SEQ ID NO 183
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 183
araagmagaa arraa                                                          15

<210> SEQ ID NO 184
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 184
yttttctttt yntttt                                                         17

<210> SEQ ID NO 185
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 185
arraraaagg n                                                              11

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 186
```

```
ystnykntyt tnctcccm                                                18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 187
garanaaaar nraaraaa                                                18

<210> SEQ ID NO 188
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 188
cynnggssan c                                                       11

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 189
cacacacaca cacaya                                                  16

<210> SEQ ID NO 190
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 190
cttytwttkt tktsa                                                   15

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
```

```
<400> SEQUENCE: 191
yttyyytytt tytyyttt                                               18

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 192
amaaaaaraa rwaranaa                                               18

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 193
araaaarraa aaagnraa                                               18

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 194
raaraaaaar cmrsraaa                                               18

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 195
ttytktytyn tyykttty                                               18

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other
```

```
<220> FEATURE:
<221> NAME/KEY: modified_base
<222> LOCATION: (15)..(15)
<223> OTHER INFORMATION: a, c, t, g, unknown or other

<400> SEQUENCE: 196
gaaaamaana aaanaaa                                                  18

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 197
yaanaraara aaaanaam                                                 18

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 198 tynttttty tttttntk                                                  18

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 199
raaraaraaa naanrnaa                                                 18

<210> SEQ ID NO 200
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      binding motif oligonucleotide

<400> SEQUENCE: 200
cacacacaca cacacaca                                                      18

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 201
raarrraaaa anaaamaa                                                      18

<210> SEQ ID NO 202
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 202
gccagaccta c                                                             11

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 203
ttyttyttyt ttynytyt                                                      18

<210> SEQ ID NO 204
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 204
yksgcgcgyc kcgkcggs                                                      18

<210> SEQ ID NO 205
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 205
```

```
ttttyyttttt yyyyktt                                                17
```

<210> SEQ ID NO 206
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 206

```
ttcttktyyt ttt                                                     13
```

<210> SEQ ID NO 207
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 207

```
ttyttttyty ytttyttt                                                18
```

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 208

```
ttgcttgaac ggatgcca                                                18
```

<210> SEQ ID NO 209
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 209

```
mgnmcaaaaa taaaas                                                  16
```

<210> SEQ ID NO 210
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 210

```
tycgtnnrna rtgaya                                                  16
```

```
<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 211
gtgtgtgtgt gtgtg                                                         15

<210> SEQ ID NO 212
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 212
ytstysttnt tgytwtt                                                       17

<210> SEQ ID NO 213
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 213
gcatgaccat ccacg                                                         15

<210> SEQ ID NO 214
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 214
gsgayarmgg amaaaaa                                                       17

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 215
trccgagryw nsssgcgs                                                      18

<210> SEQ ID NO 216
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
```

```
<400> SEQUENCE: 216
cgtccggcgc                                                                    10

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 217
aarwtsgarg nanncsaa                                                           18

<210> SEQ ID NO 218
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other

<400> SEQUENCE: 218
csnccaatgk nncs                                                               14

<210> SEQ ID NO 219
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 219 gctnactaat                                                                    10

<210> SEQ ID NO 220
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 220 cacgtgacya                                                                    10

<210> SEQ ID NO 221
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 221
cayamrtgyn c                                                          11

<210> SEQ ID NO 222
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 222 tsgygrgasa                                                            10

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (6)..(8)
<223> OTHER INFORMATION: a, c, t, g, unknown or other

<400> SEQUENCE: 223
kncncnnnsc gctackgc                                                   18

<210> SEQ ID NO 224
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 224
srnggcmcgg cnssg                                                      15

<210> SEQ ID NO 225
<211> LENGTH: 15
<212> TYPE: DNA
<213> ORGANISM: Artificial Sequence
<220> FEATURE:
<223> OTHER INFORMATION: Description of Artificial Sequence: Synthetic
```

```
       binding motif oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 225
tacyacanca cawga                                                         15

<210> SEQ ID NO 226
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 226
ccytgnaytt cwncttc                                                       17

<210> SEQ ID NO 227
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 227
gtgmaknmgr angng                                                         15

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 228
nttwacaycc rtacayny                                                      18

<210> SEQ ID NO 229
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 229
aawnrtaaay arg                                                       13

<210> SEQ ID NO 230
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

<400> SEQUENCE: 230
ggnaawangt aaacaa                                                    16

<210> SEQ ID NO 231
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 231
sastkcwctc ktcgt                                                     15

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 232
ttgcttgaac gsatgcca                                                  18

<210> SEQ ID NO 233
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(13)
```

<223> OTHER INFORMATION: a, c, t, g, unknown or other

<400> SEQUENCE: 233
cggmnnncwn ynncccg                                           17

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 234
rgargtsacg cakrttct                                          18

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 235
ggaagctgaa acgymwrr                                          18

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 236
aggtgatgga gtgctcag                                          18

<210> SEQ ID NO 237
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 237
gkctrrnrgg agangm                                            16

<210> SEQ ID NO 238
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base

```
<222> LOCATION: (7)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 238
ngggsgntns ygtncga                                                17

<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 239
agnawgtttt tgwcaama                                               18

<210> SEQ ID NO 240
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 240
kcksgcaggc wttkytct                                               18

<210> SEQ ID NO 241
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 241
gnccsartng c                                                      11

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
```

-continued

```
<222> LOCATION: (13)..(13)
<223> OTHER INFORMATION: a, c, t, g, unknown or other

<400> SEQUENCE: 242
sgcgmgggnn ccngaccg                                               18

<210> SEQ ID NO 243
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 243
yctnattsgn cngs                                                   14

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 244
tnttsmttny tttccknc                                               18

<210> SEQ ID NO 245
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 245
ccacktksgs cctns                                                  15

<210> SEQ ID NO 246
<211> LENGTH: 11
<212> TYPE: DNA
<213> ORGANISM: Artificial Sequence
<220> FEATURE:
```

```
<223> OTHER INFORMATION: Description of Artificial Sequence: Synthetic
      binding motif oligonucleotide

<400> SEQUENCE: 246
crsgcywgkg c                                                          11

<210> SEQ ID NO 247
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 247
naaraagcng ggcacnc                                                    17

<210> SEQ ID NO 248
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 248
tyttcyagaa nnttcy                                                     16

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 249
cacacacaca cacacaca                                                   18

<210> SEQ ID NO 250
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 250
sckkcgckst ssttyaa                                                    17

<210> SEQ ID NO 251
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 251
gnngcatgtg aaaa                                                       14

<210> SEQ ID NO 252
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 252 cttttttttyy tsgcc                                                     15

<210> SEQ ID NO 253
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 253
gccggtmmcg sycnn                                                      15

<210> SEQ ID NO 254
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 254 annttttyt tkygc                                                       15

<210> SEQ ID NO 255
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 255
aaacntttat anataca                                                    17
```

```
<210> SEQ ID NO 256
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 256
caatntctnc k                                                              11

<210> SEQ ID NO 257
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 257
gnrrnanacg cgtnr                                                          15

<210> SEQ ID NO 258
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 258
tttccnaawn rggaaa                                                         16

<210> SEQ ID NO 259
<211> LENGTH: 1317
<212> TYPE: DNA
<213> ORGANISM: Ruminococcus flavefaciens

<400> SEQUENCE: 259 atggaattt tcagcaatat cggtaaaatt cagtatcagg gaccaaaaag tactgatcct          60
```

```
ctctcattta agtactataa ccctgaagaa gtcatcaacg aaagacaat gcgcgagcat       120 ctgaagttcg ctctttcatg gtggcacaca atgggcggcg acggaacaga tatgttcggc     180
tgcggcacaa cagacaagac ctggggacag tccgatcccg ctgcaagagc aaaggctaag     240
gttgacgcag cattcgagat catggataag ctctccattg actactattg tttccacgat    300
cgcgatcttt ctcccgagta tggcagcctc aaggctacca acgatcagct tgacatagtt    360
acagactata tcaaggagaa gcagggcgac aagttcaagt gcctctgggg tacagcaaag    420
tgcttcgatc atccaagatt catgcacggt gcaggtacat ctccttctgc tgatgtattc    480
gctttctcag ctgctcagat caagaaggct ctcgagtcaa cagtaaagct cggcggtaac    540
ggttacgttt tctggggcgg acgtgaaggc tatgagacac ttcttaatac aaatatggga   600
ctcgaactcg acaatatggc tcgtcttatg aagatggctg ttgagtatgg acgttcgatc    660
ggcttcaagg gcgacttcta tatcgagccc aagcccaagg agcccacaaa gcatcagtac    720
gatttcgata cagctactgt tctgggattc ctcagaaagt acggtctcga taaggatttc    780
aagatgaata tcgaagctaa ccacgctaca cttgctcagc atacattcca gcatgagctc    840
cgtgttgcaa gagacaatgg tgtgttcggt tctatcgacg caaaccaggg cgacgttctt    900
cttggatggg atacagacca gttccccaca aatatctacg atacaacaat gtgtatgtat    960
gaagttatca aggcaggcgg cttcacaaac ggcggtctca acttcgacgc taaggcacgc   1020
agagggagct tcactcccga ggatatcttc tacagctata tcgcaggtat ggatgcattt   1080
gctctgggct tcagagctgc tctcaagctt atcgaagacg gacgtatcga caagttcgtt   1140
gctgacagat acgcttcatg gaataccggt atcggtgcag acataatcgc aggtaaggca   1200
gatttcgcat ctcttgaaaa gtatgctctt gaaaagggcg aggttacagc ttcactctca   1260
agcggcagac aggaaatgct ggagtctatc gtaaataacg ttcttttcag tctgtaa      1317
```

<210> SEQ ID NO 260
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 260

```
atggaatttt tcagcaatat cggtaaaatt cagtatcagg gaccaaaaag tactgatcct      60
ctctcattta agtactataa ccctgaagaa gtcatcaacg aaagacaat gcgcgagcat       120 ctgaagttcg ctctttcatg gtggcacaca atgggcggcg acggaacaga tatgttcggc     180
tgcggcacaa cagacaagac ctggggacag tccgatcccg ctgcaagagc aaaggctaag     240
gttgacgcag cattcgagat catggataag ctctccattg actactattg tttccacgat    300
cgcgatcttt ctcccgagta tggcagcctc aaggctacca acgatcagct tgacatagtt    360
acagactata tcaaggagaa gcagggcgac aagttcaagt gcctctgggg tacagcaaag    420
tgcttcgatc atccaagatt catgcacggt gcaggtacat ctccttctgc tgatgtattc    480
gctttctcag ctgctcagat caagaaggct ctggagtcaa cagtaaagct cggcggtaac    540
ggttacgttt tctggggcgg acgtgaaggc tatgagacac ttcttaatac aaatatggga   600
ctcgaactcg acaatatggc tcgtcttatg aagatggctg ttgagtatgg acgttcgatc    660
ggcttcaagg gcgacttcta tatcgagccc aagcccaagg agcccacaaa gcatcagtac    720
gatttcgata cagctactgt tctgggattc ctcagaaagt acggtctcga taaggatttc    780
```

```
aagatgaata tcgaagctaa ccacgctaca cttgctcagc atacattcca gcatgagctc      840
cgtgttgcaa gagacaatgg tgtgttcggt tctatcgacg caaaccaggg cgacgttctt      900
cttggatggg atacagacca gttccccaca aatatctacg atacaacaat gtgtatgtat      960
gaagttatca aggcaggcgg cttcacaaac ggcggtctca acttcgacgc taaggcacgc     1020
agagggagct tcactcccga ggatatcttc tacagctata tcgcaggtat ggatgcattt     1080
gctctgggct tcagagctgc tctcaagctt atcgaagacg gacgtatcga caagttcgtt     1140
gctgacagat acgcttcatg aataccggt atcggtgcag acataatcgc aggtaaggca     1200
gatttcgcat ctcttgaaaa gtatgctctt gaaaagggcg aggttacagc ttcactctca     1260
agcggcagac aggaaatgct ggagtctatc gtaaataacg ttcttttcag tctgtaa       1317
```

<210> SEQ ID NO 261
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261

```
atggagttct tttctaatat aggtaaaatt cagtatcaag gtccaaaatc tacagatcca       60
ttgtctttta aatattataa tccagaagaa gttataaatg gtaaaactat gagagaacat      120
ttaaaatttg ctttgtcttg gtggcatact atgggtggtg atggtactga tatgttcggt      180
tgtggtacta ctgataaaac ttggggtcaa tctgatccag ctgctagagc aaaagccaaa      240
gtagatgcag cctttgaaat tatggataaa ttgtctattg attattattg ttttcatgat      300
agagatttgt ctcctgaata tggttcttta aaagcaacta atgatcaatt ggacattgtt      360
acggattata ttaagaaaa acaaggtgat aaatttaaat gtttgtgggg cactgcgaaa      420
tgttttgatc atccacgttt tatgcatggt gcggggacga gtccttctgc tgatgttttt      480 gcttttctg ccgctcaaat taagaaggca ttggaatcaa ctgttaaatt aggtgggaac      540
gggtatgtat tctggggagg aagggaaggt tatgaaacat tattaaacac taatatgggt      600
ttggaattgg ataatatggc tagattgatg aaaatggctg tagaatacgg aaggtctatt      660
ggttttaagg gtgacttta tattgaacca aaacctaaag agcctactaa acatcaatat      720
gattttgata ctgctacagt tttgggattc ttgagaaaat atggtctgga taaagatttt      780
aaaatgaata tagaagctaa tcatgcaaca ctcgcacaac atactttca acatgaattg      840 agagttgcca gagataacgg agttttgga tctatcgatg caaaccaggg agacgttttg      900
ctaggatggg atactgatca atttccaact aacatttatg atactactat gtgtatgtat      960
gaagtaatta aggcaggagg ctttactaat ggcggattaa actttgatgc gaaggctagg    1020
cgtggtagtt tcactccaga ggatatattc tattcttata ttgctggaat ggatgctttc    1080
gcgttaggtt tcagggcagc actaaaattg attgaagatg gtagaattga taagtttgta    1140
gctgatagat atgcttcttg gaatactgga ataggagcag atataatcgc tgggaaagcc    1200
gacttcgcca gtctggaaaa atatgcgctt gaaaaggag aagttactgc cagcttaagt    1260
tccggtcgtc aagaaatgtt ggaatctatt gtaaacaatg ttttatttc tctg           1314
```

<210> SEQ ID NO 262
<211> LENGTH: 1314
<212> TYPE: DNA
<213> ORGANISM: Piromyces sp.

<400> SEQUENCE: 262

```
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt gcgccgaagg tgctgaccaa     180
ttcggtggag gtacaaagtc tttcccatgg aacgaaggta ctgatgctat tgaaattgcc     240
aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccggtattaa gcttctctgg     420
agtactgcta acgtcttcgg tcacaagcgt tacatgaacg gtgcctccac taacccagac     480
tttgatgttg tcgcccgtgc tattgttcaa attaagaacg ccatagacgc cggtattgaa     540
cttggtgctg aaaactacgt cttctggggt ggtcgtgaag gttacatgag tctccttaac     600
actgaccaaa agcgtgaaaa ggaacacatg ccactatgc ttaccatggc tcgtgactac     660
gctcgttcca agggattcaa gggtactttc ctcattgaac caaagccaat ggaaccaacc     720
aagcaccaat acgatgttga cactgaaacc gctattggtt tccttaaggc ccacaactta     780
gacaaggact tcaaggtcaa cattgaagtt aaccacgcta ctcttgctgg tcacactttc     840
gaacacgaac ttgcctgtgc tgttgatgct ggtatgctcg gttccattga tgctaaccgt     900
ggtgactacc aaaacggttg ggatactgat caattcccaa ttgatcaata cgaactcgtc     960
caagcttgga tggaaatcat ccgtggtggt ggtttcgtta ctggtggtac caacttcgat    1020
gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga agaaggaacg ttacgcttcc ttcgacagtg gtattggtaa ggactttgaa    1200
gatggtaagc tcaccctcga caagtttac gaatacggta agaagaacgg tgaaccaaag    1260
caaacttctg gtaagcaaga actctacgaa gctattgttg ccatgtacca ataa           1314
```

<210> SEQ ID NO 263
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

```
atggctaaag aatatttttcc acaaattcag aaaattaaat ttgaaggtaa agattctaaa      60
aatccattgg ctttccatta ttatgatgct gaaaagaag ttatgggtaa aaagatgaaa     120
gattggttga gattcgctat ggcttggtgg catactctat gtgctgaagg agctgatcaa     180
tttggaggag gtactaaatc ttttccttgg aatgaaggta ctgacgctat tgaaattgct     240
aagcagaaag tagacgcggg ttttgaaatt atgcaaaaat tgggaatacc atattattgt     300
tttcatgatg ttgatttggt atctgagggt aattctattg aagaatatga atctaattta     360
aaagctgttg ttgcttactt aaaagaaaaa caaaagaaa ctggaattaa attgttgtgg     420
tctacagcta atgttttcgg tcataaaaga tatatgaatg gtgcttctac aaatccagat     480
tttgatgttg tagctagagc tattgttcaa attaaaaatg ctatagatgc aggaattgaa     540
ttaggtgccg aaaattatgt tttctgggga ggtagagaag gttatatgtc tttgttaaat     600
actgatcaaa aacgtgaaaa ggaacacatg gcaactatgt tgacaatggc tagggattat     660
gctagatcta aaggttttaa aggtactttc ttgattgagc caaaaccttat ggaaccaact     720
```

```
aaacatcaat atgacgttga cactgaaact gctattggtt tcttaaaagc tcataatttg    780
gataaagatt ttaaggttaa tatagaagtt aatcatgcta cactagctgg tcatactttt    840
gaacatgaat tagcttgtgc agttgatgcc ggtatgttag gttctatcga cgcaaataga    900
ggtgattatc aaaatggttg ggacacagat caatttccaa tagatcaata tgaattggtt    960
caagcatgga tggaaattat taggggtgga ggcttcgtta caggtggaac taattttgat   1020
gctaaaacta ggagaaattc tacagatctt gaagatataa ttattgctca tgtatctggt   1080
atggatgcga tggcccgtgc tttggaaaat gcagctaaat tacttcaaga atctccttat   1140
actaaaatga aaaaggaaag atatgcttct tttgattctg aataggtaa ggattttgaa    1200
```

(Note: line 1200 in image shows "actaaaatga aaaaggaaag atatgcttct tttgattctg aataggtaa ggattttgaa 1200")

```
gatggtaaat tgacattgga acaagtttat gaatatggta agaagaatgg agaaccaaaa   1260
caaacttctg gtaaacaaga attatatgag gctatagtag ctatgtatca ataa         1314

<210> SEQ ID NO 264
<211> LENGTH: 2679
<212> TYPE: DNA
<213> ORGANISM: Zymomonas mobilis

<400> SEQUENCE: 264
actagtaaaa aaatgaccaa gccgcgcaca attaatcaga acccagacct tcgctatttt     60
ggtaacctgc tcggtcaggt tattaaggaa caaggcggag agtctttatt caaccagatc    120
gagcaaattc gctctgccgc gattagacgc atcggggta ttgttgacag caccgagcta     180
agttctcgct tagccgatct cgaccttaat gacatgttct cttttgcaca tgccttttg     240 ctgttttcaa tgctggccaa tttggctgat gatcgtcagg gagatgccct tgatcctgat    300
gccaatatgg caagtgccct taaggacata aaagccaaag gcgtcagtca gcaggcgatc    360
attgatatga tcgacaaagc ctgcattgtg cctgttctga cagcacatcc gaccgaagtc    420
cgtcggaaaa gtatgcttga ccattataat cgcattgcag gtttaatgcg gttaaaagat    480
gctggacaaa cggtgaccga agatggtctt ccgatcgaag atgcgttaat ccagcaaatc    540
acgatattat ggcagactcg tccgctcatg ctgcaaaagc tgaccgtggc tgatgaaatc    600
gaaactgccc tgtctttctt aagagaaact tttctgcctg ttctgcccca gatttatgca    660
gaatgggaaa aattgcttgg tagttctatt ccaagcttta tcagacctgg taattggatt    720
ggtggtgacc gtgacggtaa ccccaatgtc aatgccgata cgatcatgct gtctttgaag    780
cgcagctcgg aaacggtatt gacggattat ctcaaccgtc ttgataaact gctttccaac    840 cttttcggtct caaccgatat ggtttcggta tccgatgata ttctacgtct agccgataaa    900
agtggtgacg atgctgcgat ccgtgcggat gaaccttatc gtcgtgcctt aaatggtatt    960
tatgaccgtt tagccgctac ctatcgtcag atcgccggtc gcaacccttc gcgcccagcc   1020
ttgcgttctg cagaagccta taacggcct caagaattgc tggctgattt gaagaccttg   1080
gccgaaggct tgggtaaatt ggcagaaggt agttttaagg cattgatccg ttcggttgaa   1140
acctttggtt tccatttggc caccctcgat ctgcgtcaga attcgcaggt tcatgaaaga   1200
gttgtcaatg aactgctacg gacagccacc gttgaagccg attatttatc tctatcggaa   1260
gaagatcgcg ttaagctgtt aagacgggaa ttgtcgcagc cgcggactct attcgttccg   1320
cgcgccgatt attccgaaga aacgcgttct gaacttgata ttattcaggc agcagcccgc   1380
gcccatgaaa ttttttggcc ctgaatccatt acgactatt tgatttcgaa tggcgaaagc   1440
atttccgata ttctgaagt ctatttgctt ttgaaagaag cagggctgta tcaagggggt   1500
gctaagccaa aagcggcgat tgaagctgcg ccttattcg agacggtggc cgatcttgaa   1560
```

| | | | | |
|---|---|---|---|---|
| aatgcgccaa | aggtcatgga | ggaatggttc | aagctgcctg | aagcgcaagc cattgcaaag | 1620 |
| gcacatggcg | ttcaggaagt | gatggttggc | tattctgact | ccaataagga cggcggatat | 1680 |
| ctgacctcgg | tttggggtct | ttataaggct | tgcctcgctt | tggtgccgat ttttgagaaa | 1740 |
| gccggtgtac | cgatccagtt | tttccatgga | cggggtggtt | ccgttggtcg cggtggtggt | 1800 |
| tccaacttta | atgccattct | gtcgcagcca | gccggagccg | tcaaagggcg tatccgttat | 1860 |
| acagaacagg | gtgaagtcgt | ggcggccaaa | tatggcaccc | atgaaagcgc tattgcccat | 1920 |
| ctggatgagg | ccgtagcggc | gactttgatt | acgtctttgg | aagcaccgac cattgtcgag | 1980 |
| ccagagttta | gtcgttaccg | taaggccttg | gatcagatct | cagattcagc tttccaggcc | 2040 |
| tatcgccaat | tggtctatgg | aacgaagggc | ttccgtaaat | tctttagtga atttacgcct | 2100 |
| ttgccggaaa | ttgccctgtt | aaagatcggg | tcacgcccac | ctagccgcaa aaaatccgac | 2160 |
| cggattgaag | atctacgcgc | tattccttgg | gtgtttagct | ggtctcaagt tcgagtcatg | 2220 |
| ttacccggtt | ggttcggttt | cggtcaggct | ttatatgact | ttgaagatac cgagctgtta | 2280 |
| caggaaatgg | caagccgttg | gccgtttttc | cgcacgacta | ttcggaatat ggaacaggtg | 2340 |
| atggcacgtt | ccgatatgac | gatcgccaag | cattatctgg | ccttggttga ggatcagaca | 2400 |
| aatggtgagg | ctatctatga | ttctatcgcg | gatggctgga | ataaaggttg tgaaggtctg | 2460 |
| ttaaaggcaa | cccagcagaa | ttggctgttg | gaacgctttc | cggcggttga taattcggtg | 2520 |
| cagatgcgtc | ggccttatct | ggaaccgctt | aattacttac | aggtcgaatt gctgaagaaa | 2580 |
| tggcggggag | gtgataccaa | cccgcatatc | ctcgaatcta | ttcagctgac aatcaatgcc | 2640 |
| attgcgacgg | cacttcgcaa | cagcggttaa | taactcgag | | 2679 |

<210> SEQ ID NO 265
<211> LENGTH: 2679
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 265

| | | | | |
|---|---|---|---|---|
| actagtaaaa | aaatgaccaa | gccaagaact | attaaccaaa | acccagactt gagatacttc | 60 |
| ggtaacttgt | tgggtcaagt | tatcaaggaa | caaggtggtg | aatctttgtt caaccaaatt | 120 |
| gaacaaatca | gatccgctgc | tattagaaga | cacagaggta | tcgtcgactc taccgaattg | 180 |
| tcctctagat | tggctgactt | ggacttgaac | gacatgttct | ccttcgctca cgctttcttg | 240 |
| ttgttctcta | tgttggctaa | cttggctgac | gacagacaag | gtgacgcttt ggacccagac | 300 |
| gctaacatgg | cttccgcttt | gaaggacatt | aaggctaagg | gtgtttctca acaagctatc | 360 |
| attgacatga | tcgacaaggc | ttgtattgtc | ccagttttga | ctgctcaccc aaccgaagtc | 420 |
| agaagaaagt | ccatgttgga | ccactacaac | agaatcgctg | gtttgatgag attgaaggac | 480 |
| gctggtcaaa | ctgttaccga | agacggtttg | ccaattgaag | acgctttgat ccaacaaatt | 540 |
| actatcttgt | ggcaaaccag | accattgatg | ttgcaaaagt | tgactgtcgc tgacgaaatt | 600 |
| gaaaccgctt | tgtctttctt | gagagaaact | ttcttgccag | ttttgccaca aatctacgct | 660 |
| gaatgggaaa | agttgttggg | ttcctctatt | ccatccttca | tcagaccagg taactggatt | 720 |
| ggtggtgaca | gagacggtaa | cccaaacgtc | aacgctgaca | ccatcatgtt gtctttgaag | 780 |
| agatcctctg | aaactgtttt | gaccgactac | ttgaacagat | ggacaagtt gttgtccaac | 840 |
| ttgtctgtct | ccactgacat | ggtttctgtc | tccgacgaca | ttttgagatt ggctgacaag | 900 |
| tctggtgacg | acgctgctat | cagagctgac | gaaccataca | aagagctttt gaacggtatt | 960 |

```
tacgacagat tggctgctac ctacagacaa atcgctggta gaaacccatc cagaccagct    1020
ttgagatctg ctgaagctta caagagacca caagaattgt tggctgactt gaagactttg    1080
gctgaaggtt tgggtaagtt ggctgaaggt tccttcaagg cttttgattag atctgttgaa    1140 accttcggtt tccacttggc tactttggac ttgagacaaa actcccaagt ccacgaaaga    1200
gttgtcaacg aattgttgag aaccgctact gttgaagctg actacttgtc tttgtccgaa    1260
gaagacagag tcaagttgtt gagaagagaa ttgtctcaac caagaacctt gttcgttcca    1320
agagctgact actccgaaga aactagatct gaattggaca tcattcaagc tgctgctaga    1380
gctcacgaaa tcttcggtcc agaatccatt accacttact tgatctctaa cggtgaatcc    1440
atttctgaca tcttggaagt ctacttgttg ttgaaggaag ctggttttgta ccaaggtggt    1500 gctaagccaa aggctgctat tgaagctgct ccattgttcg aaaccgttgc tgacttggaa    1560
aacgctccaa aggtcatgga agaatggttc aagttgccag aagctcaagc tatcgctaag    1620
gctcacggtg ttcaagaagt catggttggt tactccgact ctaacaagga cggtggttac    1680
ttgacttccg tctggggttt gtacaaggct tgtttggctt tggttccaat tttcgaaaag    1740
gctggtgtcc caatccaatt cttccacggt agaggtggtc ctgttggtag aggtggtggt    1800
tccaacttca cgctattttt gtctcaacca gctggtgctg tcaagggtag aatcagatac    1860
accgaacaag gtgaagttgt cgctgctaag tacggtactc acgaatccgc tattgctcac    1920
ttggacgaag ctgttgctgc taccttgatc acttctttgg aagctccaac cattgtcgaa    1980
ccagaattct ccagatacag aaaggctttg gaccaaatct ctgactccgc tttccaagct    2040
tacagacaat tggtttacgg tactaagggt ttcagaaagt tcttctctga attcaccccca    2100 ttgccagaaa ttgctttgtt gaagatcggt tccagaccac catctagaaa gaagtccgac    2160
agaattgaag acttgagagc tatcccatgg gtcttctctt ggtcccaagt tagagtcatg    2220
ttgccaggtt ggttcggttt cggtcaagct ttgtacgact tcgaagacac tgaattgttg    2280
caagaaatgg cttctagatg gccattcttc agaaccacta ttagaaacat ggaacaagtt    2340
atggctagat ccgacatgac catcgctaag cactacttgg cttttggtcga agaccaaact    2400 aacggtgaag ctatttacga ctctatcgct gacggttgga caagggttg tgaaggtttg    2460 ttgaaggcta cccaacaaaa ctggttgttg gaaagattcc cagctgttga caactccgtc    2520
caaatgagaa gaccatactt ggaaccattg aactacttgc aagttgaatt gttgaagaag    2580
tggagaggtg gtgacactaa cccacacatt ttggaatcta tccaattgac cattaacgct    2640
atcgctactg ctttgagaaa actccggttaa taactcgag                          2679
```

<210> SEQ ID NO 266
<211> LENGTH: 624
<212> TYPE: DNA
<213> ORGANISM: Zymomonas mobilis

<400> SEQUENCE: 266

```
atgcgtgata tcgattccgt aatgcgtttg gcaccggtta tgccggtcct cgtcattgaa      60
gatattgctg atgcaaaacc tatcgcagaa gctttggttg ctggtggtct gaacgttctt     120
gaagtaacgc ttcgcacccc ttgtgctctt gaagccatca agatcatgaa agaagttccg     180
ggtgccgttt tggtgccgg tacggttctg aacgcaaaaa tgctcgacca agctcaggaa     240
gctggttgcg aattttttcgt tagcccgggt ctgaccgctg acctcggcaa gcatgctgtt     300
gcccagaaag cagctttgct tccaggtgtt gctaatgctg ctgatgtgat gcttggtctt     360
gaccttggtc ttgatcgctt caaattcttc ccggctgaaa atatcggtgg tttacctgcc     420
```

```
ctgaagtcca tggcttctgt tttccgtcag gttcgtttct gcccgaccgg cggtatcacc    480
ccgacgtcag ctcctaaata tcttgaaaac ccgtccattc tttgcgtcgg tggtagctgg    540
gttgttccgg ctggcaaacc agatgtcgca aaaatcacgg cactcgctaa agaagcttct    600
gctttcaagc gcgctgctgt tgcc                                           624
```

<210> SEQ ID NO 267
<211> LENGTH: 624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267

```
atgagggata ttgatagtgt gatgaggtta gcccctgtta tgcctgttct cgttattgaa     60
gatattgcag atgccaaacc tattgccgaa gcactcgttg caggtggtct aaacgttcta    120
gaagtgacac taaggactcc ttgtgcacta gaagctatta gattatgaa ggaagttcct    180 ggtgctgttg ttggtgctgg tacagttcta acgccaaaa tgctcgacca ggcacaagaa    240
gcaggttgcg aattttttcgt ttcacctggt ctaactgccg acctcggaaa gcacgcagtt    300
gctcaaaaag ccgcattact acccggtgtt gcaaatgcag cagatgtgat gctaggtcta    360
gacctaggtc tagataggtt caagttcttc cctgccgaaa acattggtgg tctacctgct    420
ctaaagagta tggcatcagt tttcaggcaa gttaggttct gccctactgg aggtataact    480
cctacaagtg cacctaaata tctagaaaac cctagtattc tatgcgttgg tggttcatgg    540
gttgttcctg ccggaaaacc cgatgttgcc aaaattacag ccctcgcaaa agaagcaagt    600
gcattcaaga gggcagcagt tgct                                           624
```

<210> SEQ ID NO 268
<211> LENGTH: 624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 268

```
atgagagaca ttgattctgt tatgagattg gctccagtta tgccagtctt ggttatagaa     60
gatatagctg atgctaagcc aattgctgag gctttggttg ctggtggttt aaatgttttg    120
gaagttacat tgagaactcc atgtgctttg gaagctatta aaattatgaa ggaagttcca    180
ggtgctgttg ttggtgctgg tactgtttta aacgctaaaa tgttggatca agctcaagaa    240
gctggttgtg agttctttgt atcaccaggt ttgactgctg atttgggaaa acatgctgtt    300
gctcaaaaag cggctcttct accaggggtt gctaatgctg ctgatgttat gttgggattg    360
gatttgggtt tggatagatt taaattcttc ccagctgaaa atataggtgg tttgccagct    420
ttaaaatcta tggcttctgt ttttagacaa gttagatttt gtccaactgg aggaattact    480
ccgacttctg ctccaaaata tttggaaaat ccatctatt tgtgtgttgg tggttcttgg    540
gttgttccag cgggtaaacc agatgttgcg aaaattactg ctttggctaa agaggcttca    600
gcttttaaaa gagctgctgt ggcg                                           624
```

<210> SEQ ID NO 269
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269
atgaaaaact ggaaaacaag tgcagaatca atcctgacca ccggcccggt tgtaccggtt      60
atcgtggtaa aaaaactgga acacgcggtg ccgatggcaa aagcgttggt tgctggtggg     120
gtgcgcgttc tggaagtgac tctgcgtacc gagtgtgcag ttgacgctat ccgtgctatc     180
gccaaagaag tgcctgaagc gattgtgggt gccggtacgg tgctgaatcc acagcagctg     240
gcagaagtca ctgaagcggg tgcacagttc gcaattagcc cgggtctgac cgagccgctg     300
ctgaaagctg ctaccgaagg gactattcct ctgattccgg ggatcagcac tgtttccgaa     360
ctgatgctgg gtatggacta cggttttgaaa gagttcaaat tcttcccggc tgaagctaac     420
ggcggcgtga aagccctgca ggcgatcgcg ggtccgttct cccaggtccg tttctgcccg     480
acgggtggta tttctccggc taactaccgt gactacctgg cgctgaaaag cgtgctgtgc     540
atcggtggtt cctggctggt tccggcagat gcgctggaag cgggcgatta cgaccgcatt     600
actaagctgg cgcgtgaagc tgtagaaggc gctaagctg                            639

<210> SEQ ID NO 270
<211> LENGTH: 208
<212> TYPE: PRT
<213> ORGANISM: Zymomonas mobilis

<400> SEQUENCE: 270

Met Arg Asp Ile Asp Ser Val Met Arg Leu Ala Pro Val Met Pro Val
1               5                   10                  15

Leu Val Ile Glu Asp Ile Ala Asp Ala Lys Pro Ile Ala Glu Ala Leu
            20                  25                  30

Val Ala Gly Gly Leu Asn Val Leu Glu Val Thr Leu Arg Thr Pro Cys
        35                  40                  45

Ala Leu Glu Ala Ile Lys Ile Met Lys Glu Val Pro Gly Ala Val Val
    50                  55                  60

Gly Ala Gly Thr Val Leu Asn Ala Lys Met Leu Asp Gln Ala Gln Glu
65                  70                  75                  80

Ala Gly Cys Glu Phe Phe Val Ser Pro Gly Leu Thr Ala Asp Leu Gly
                85                  90                  95

Lys His Ala Val Ala Gln Lys Ala Ala Leu Leu Pro Gly Val Ala Asn
            100                 105                 110

Ala Ala Asp Val Met Leu Gly Leu Asp Leu Gly Leu Asp Arg Phe Lys
        115                 120                 125

Phe Phe Pro Ala Glu Asn Ile Gly Gly Leu Pro Ala Leu Lys Ser Met
    130                 135                 140

Ala Ser Val Phe Arg Gln Val Arg Phe Cys Pro Thr Gly Gly Ile Thr
145                 150                 155                 160

Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
            180                 185                 190

Thr Ala Leu Ala Lys Glu Ala Ser Ala Phe Lys Arg Ala Ala Val Ala
        195                 200                 205

<210> SEQ ID NO 271
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Met Arg Asp Ile Asp Ser Val Met Arg Leu Ala Pro Val Met Pro Val
1               5                   10                  15

Leu Val Ile Glu Asp Ile Ala Asp Ala Lys Pro Ile Ala Glu Ala Leu
            20                  25                  30

Val Ala Gly Gly Leu Asn Val Leu Glu Val Thr Leu Arg Thr Pro Cys
        35                  40                  45

Ala Leu Glu Ala Ile Lys Ile Met Lys Glu Val Pro Gly Ala Val Val
50                  55                  60

Gly Ala Gly Thr Val Leu Asn Ala Lys Met Leu Asp Gln Ala Gln Glu
65                  70                  75                  80

Ala Gly Cys Glu Phe Phe Val Ser Pro Gly Leu Thr Ala Asp Leu Gly
                85                  90                  95

Lys His Ala Val Ala Gln Lys Ala Ala Leu Leu Pro Gly Val Ala Asn
            100                 105                 110

Ala Ala Asp Val Met Leu Gly Leu Asp Leu Gly Leu Asp Arg Phe Lys
        115                 120                 125

Phe Phe Pro Ala Glu Asn Ile Gly Gly Leu Pro Ala Leu Lys Ser Met
130                 135                 140

Ala Ser Val Phe Arg Gln Val Arg Phe Cys Pro Thr Gly Gly Ile Thr
145                 150                 155                 160

Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
            180                 185                 190

Thr Ala Leu Ala Lys Glu Ala Ser Ala Phe Lys Arg Ala Ala Val Ala
        195                 200                 205

<210> SEQ ID NO 272
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Met Arg Asp Ile Asp Ser Val Met Arg Leu Ala Pro Val Met Pro Val
1               5                   10                  15

Leu Val Ile Glu Asp Ile Ala Asp Ala Lys Pro Ile Ala Glu Ala Leu
            20                  25                  30

Val Ala Gly Gly Leu Asn Val Leu Glu Val Thr Leu Arg Thr Pro Cys
        35                  40                  45

Ala Leu Glu Ala Ile Lys Ile Met Lys Glu Val Pro Gly Ala Val Val
50                  55                  60

Gly Ala Gly Thr Val Leu Asn Ala Lys Met Leu Asp Gln Ala Gln Glu
65                  70                  75                  80

Ala Gly Cys Glu Phe Phe Val Ser Pro Gly Leu Thr Ala Asp Leu Gly
                85                  90                  95

Lys His Ala Val Ala Gln Lys Ala Ala Leu Leu Pro Gly Val Ala Asn
            100                 105                 110

Ala Ala Asp Val Met Leu Gly Leu Asp Leu Gly Leu Asp Arg Phe Lys
        115                 120                 125

```
Phe Phe Pro Ala Glu Asn Ile Gly Gly Leu Pro Ala Leu Lys Ser Met
    130                 135                 140

Ala Ser Val Phe Arg Gln Val Arg Phe Cys Pro Thr Gly Gly Ile Thr
145                 150                 155                 160

Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
                180                 185                 190

Thr Ala Leu Ala Lys Glu Ala Ser Ala Phe Lys Arg Ala Ala Val Ala
                195                 200                 205

<210> SEQ ID NO 273
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
                20                  25                  30

Ala Lys Ala Leu Val Ala Gly Gly Val Arg Val Leu Glu Val Thr Leu
                35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
                100                 105                 110

Pro Gly Ile Ser Thr Val Ser Glu Leu Met Leu Gly Met Asp Tyr Gly
                115                 120                 125

Leu Lys Glu Phe Lys Phe Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
                180                 185                 190

Glu Ala Gly Asp Tyr Asp Arg Ile Thr Lys Leu Ala Arg Glu Ala Val
                195                 200                 205

Glu Gly Ala Lys Leu
                210

<210> SEQ ID NO 274
<211> LENGTH: 438
<212> TYPE: PRT
<213> ORGANISM: Ruminococcus flavefaciens

<400> SEQUENCE: 274

Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile
```

-continued

```
                    20                  25                  30
Asn Gly Lys Thr Met Arg Glu His Leu Lys Phe Ala Leu Ser Trp Trp
                35                  40                  45
His Thr Met Gly Gly Asp Gly Thr Asp Met Phe Gly Cys Gly Thr Thr
            50                  55                  60
Asp Lys Thr Trp Gly Gln Ser Asp Pro Ala Arg Ala Lys Ala Lys
65                  70                  75                  80
Val Asp Ala Ala Phe Glu Ile Met Asp Lys Leu Ser Ile Asp Tyr Tyr
                85                  90                  95
Cys Phe His Asp Arg Asp Leu Ser Pro Glu Tyr Gly Ser Leu Lys Ala
                100                 105                 110
Thr Asn Asp Gln Leu Asp Ile Val Thr Asp Tyr Ile Lys Glu Lys Gln
                115                 120                 125
Gly Asp Lys Phe Lys Cys Leu Trp Gly Thr Ala Lys Cys Phe Asp His
        130                 135                 140
Pro Arg Phe Met His Gly Ala Gly Thr Ser Pro Ser Ala Asp Val Phe
145                 150                 155                 160
Ala Phe Ser Ala Ala Gln Ile Lys Lys Ala Leu Glu Ser Thr Val Lys
                165                 170                 175
Leu Gly Gly Asn Gly Tyr Val Phe Trp Gly Gly Arg Glu Gly Tyr Glu
                180                 185                 190
Thr Leu Leu Asn Thr Asn Met Gly Leu Glu Leu Asp Asn Met Ala Arg
            195                 200                 205
Leu Met Lys Met Ala Val Glu Tyr Gly Arg Ser Ile Gly Phe Lys Gly
        210                 215                 220
Asp Phe Tyr Ile Glu Pro Lys Pro Lys Glu Pro Thr Lys His Gln Tyr
225                 230                 235                 240
Asp Phe Asp Thr Ala Thr Val Leu Gly Phe Leu Arg Lys Tyr Gly Leu
                245                 250                 255
Asp Lys Asp Phe Lys Met Asn Ile Glu Ala Asn His Ala Thr Leu Ala
                260                 265                 270
Gln His Thr Phe Gln His Glu Leu Arg Val Ala Arg Asp Asn Gly Val
            275                 280                 285
Phe Gly Ser Ile Asp Ala Asn Gln Gly Asp Val Leu Leu Gly Trp Asp
        290                 295                 300
Thr Asp Gln Phe Pro Thr Asn Ile Tyr Asp Thr Thr Met Cys Met Tyr
305                 310                 315                 320
Glu Val Ile Lys Ala Gly Gly Phe Thr Asn Gly Gly Leu Asn Phe Asp
                325                 330                 335
Ala Lys Ala Arg Arg Gly Ser Phe Thr Pro Glu Asp Ile Phe Tyr Ser
                340                 345                 350
Tyr Ile Ala Gly Met Asp Ala Phe Ala Leu Gly Phe Arg Ala Ala Leu
            355                 360                 365
Lys Leu Ile Glu Asp Gly Arg Ile Asp Lys Phe Val Ala Asp Arg Tyr
        370                 375                 380
Ala Ser Trp Asn Thr Gly Ile Gly Ala Asp Ile Ile Ala Gly Lys Ala
385                 390                 395                 400
Asp Phe Ala Ser Leu Glu Lys Tyr Ala Leu Glu Lys Gly Glu Val Thr
                405                 410                 415
Ala Ser Leu Ser Ser Gly Arg Gln Glu Met Leu Glu Ser Ile Val Asn
            420                 425                 430
Asn Val Leu Phe Ser Leu
        435
```

<210> SEQ ID NO 275
<211> LENGTH: 437
<212> TYPE: PRT
<213> ORGANISM: Piromyces sp.

<400> SEQUENCE: 275

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380
```

```
Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
            405                 410                 415

Gly Glu Pro Lys Gln Thr Ser Gly Lys Gln Glu Leu Tyr Glu Ala Ile
        420                 425                 430

Val Ala Met Tyr Gln
        435

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
taaaacgacg gccagtgaat                                                   20

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
tgcaggtcga ctctagagga t                                                 21

<210> SEQ ID NO 278
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gtgtgcgtgt atgtgtacac ctgtatttaa tttccttact cgcgggtttt tctaaaacga       60
cggccagtga at                                                           72

<210> SEQ ID NO 279
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tgtaccagtc tagaattcta ccaacaaatg gggaaatcaa agtaacttgg gctgcaggtc       60
gactctagag ga                                                           72

<210> SEQ ID NO 280
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
gtcgactgga aatctggaag gttggt                                            26
```

<210> SEQ ID NO 281
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gtcgacgctt tgctgcaagg attcat                                          26

<210> SEQ ID NO 282
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
actagtatga ctgttactac tccttttgtg aatggtac                             38

<210> SEQ ID NO 283
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
ctcgagttaa tcaactctct ttcttccaac caaatggtc                            39

<210> SEQ ID NO 284
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
aagcttttaa ttaatataac gctatgacgg tagttgaatg ttaaaaac                  48

<210> SEQ ID NO 285
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gaattcttaa ttaaagagaa caaagtattt aacgcacatg tataaatatt g              51

<210> SEQ ID NO 286
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
ggatccgcat gcggccggcc agcttttaat caaggaagta ataaataaag gac            53

<210> SEQ ID NO 287
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
ggatccgagc tcgcggccgc agcttttgaa caatgaattt tttgttcctt tc        52

<210> SEQ ID NO 288
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
gcggccgcag cttcgcaagt attcatttta gacccatg        38

<210> SEQ ID NO 289
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
ggccggccgg taccaattcc acttgcaatt acataaaaaa ttcc        44

<210> SEQ ID NO 290
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
ggatccgttt atcattatca atactcgcca tttcaaag        38

<210> SEQ ID NO 291
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
catatgttgg gtaccggccg caaattaaag ccttcgagcg        40

<210> SEQ ID NO 292
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
ggattcagtc agatcatatg gtaccccccg ggttaattaa ggcgcgccag atctg        55

<210> SEQ ID NO 293
<211> LENGTH: 60

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
gtcgacaggc ctactgtacg gctagcgaat tcgagctcgt tttcgacact ggatggcggc    60

<210> SEQ ID NO 294
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tctagactcg agtaataagc gaatttctta tgatttatg                           39

<210> SEQ ID NO 295
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
aagcttaggc ctggagcgat ttgcaggcat ttgc                               34

<210> SEQ ID NO 296
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
ggatccgcta gcaccgcgaa tccttacatc acaccc                             36

<210> SEQ ID NO 297
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tctagactcg agtaataagc gaatttctta tgatttatg                           39

<210> SEQ ID NO 298
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
gattgtactg agagtgcaca atatgcggtg tgaaatacc                           39

<210> SEQ ID NO 299
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 299
ggtatttcac accgcatatt gtgcactctc agtacaatc                            39

<210> SEQ ID NO 300
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gtgcgtcagg tgatctgggt aagaagaaga cttttccc                             38

<210> SEQ ID NO 301
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gggaaaagtc ttcttcttac ccagatcacc tgacgcac                             38

<210> SEQ ID NO 302
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gtgatctggg taagaagaag ggttttcccg ccttatttgg                           40

<210> SEQ ID NO 303
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
ccaaataagg cgggaaaacc cttcttctta cccagatcac                           40

<210> SEQ ID NO 304
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ccttgatcca tctaccaaga tcttcggtta taatcggtcc aaattgtcca t              51

<210> SEQ ID NO 305
<211> LENGTH: 51
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 305
atggacaatt tggaccgatt ataaccgaag atcttggtag atggatcaag g            51

<210> SEQ ID NO 306
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
atctaccaag atcttcggtt atgatcggtc caaattgtcc atg                     43

<210> SEQ ID NO 307
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
catggacaat ttggaccgat cataaccgaa gatcttggta gat                     43

<210> SEQ ID NO 308
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ggtgatctgg caaagaagaa gttttttccc gccttatttg gg                      42

<210> SEQ ID NO 309
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
cccaaataag gcgggaaaaa acttcttctt tgccagatca cc                      42

<210> SEQ ID NO 310
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
taccttgatc catctaccag aatcttcggt tatgcccggt                         40

<210> SEQ ID NO 311
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
accgggcata accgaagatt ctggtagatg gatcaaggta        40

<210> SEQ ID NO 312
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gggcttttca gagaaggttt gcttgatcca tctaccaaga        40

<210> SEQ ID NO 313
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcttggtaga tggatcaagc aaaccttctc tgaaaagccc        40

<210> SEQ ID NO 314
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gaagaagact tttcccgcct tatacgggct tttcagagaa g        41

<210> SEQ ID NO 315
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
cttctctgaa aagcccgtat aaggcgggaa aagtcttctt c        41

<210> SEQ ID NO 316
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gtcaggtgat ctggcaaaga agaagttgtt tcccgcctta tttgg        45

<210> SEQ ID NO 317
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317

```
ccaaataagg cgggaaacaa cttcttcttt gccagatcac ctgac            45
```

<210> SEQ ID NO 318
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318

```
cgaaaaaaat accgtcatat ctttgtttgg tgcgtcaggt gatctg           46
```

<210> SEQ ID NO 319
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319

```
cagatcacct gacgcaccaa acaaagatat gacggtattt ttttcg           46
```

<210> SEQ ID NO 320
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320

```
gacctgaagt cccgtgtcga accccacttg aaaaaacc                    38
```

<210> SEQ ID NO 321
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321

```
ggttttttca agtggggttc gacacgggac ttcaggtc                    38
```

<210> SEQ ID NO 322
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322

```
gtgcgtcagg tgatctgggt aagaagaaga cttttccc                    38
```

<210> SEQ ID NO 323
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323

```
gggaaaagtc ttcttcttac ccagatcacc tgacgcac                    38
```

<210> SEQ ID NO 324
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gtgcgtcagg tgatctgggt aagaagaaga cttttccc                          38

<210> SEQ ID NO 325
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gggaaaagtc ttcttcttac ccagatcacc tgacgcac                          38

<210> SEQ ID NO 326
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
accaagatct tcggttatgc cgattccaaa ttgtccatgg aggag                  45

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ctcctccatg gacaatttgg aatcggcata accgaagatc ttggt                  45

<210> SEQ ID NO 328
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tccatctacc aagatcttcg gttatgatgc ttccaaattg tccatggagg aggac       55

<210> SEQ ID NO 329
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gtcctcctcc atggacaatt tggaagcatc ataaccgaag atcttggtag atgga       55

<210> SEQ ID NO 330

```
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tccatctacc aagatcttcg gttatgatgc ttccaaattg tccatggagg aggac            55

<210> SEQ ID NO 331
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gtcctcctcc atggacaatt tggaagcatc ataaccgaag atcttggtag atgga            55

<210> SEQ ID NO 332
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tccatctacc aagatcttcg gttatgatgc ttccaaattg tccatggagg aggac            55

<210> SEQ ID NO 333
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gtcctcctcc atggacaatt tggaagcatc ataaccgaag atcttggtag atgga            55

<210> SEQ ID NO 334
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
aagatcttcg gttatgatca ttccaaattg tccatggagg                             40

<210> SEQ ID NO 335
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
cctccatgga caatttggaa tgatcataac cgaagatctt                             40

<210> SEQ ID NO 336
<211> LENGTH: 40
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 336
aagatcttcg gttatgccca ttccaaattg tccatggagg                              40

<210> SEQ ID NO 337
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
cctccatgga caatttggaa tgggcataac cgaagatctt                              40

<210> SEQ ID NO 338
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
gctagcatgg tgacagtcgg tgtgttttct gag                                    33

<210> SEQ ID NO 339
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
gtcgacctaa aaagttttcg tttgaacttt tcc                                    33

<210> SEQ ID NO 340
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ccaacactaa gaataattt cgccatttct tg                                      32

<210> SEQ ID NO 341
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gccaacaatt aaatccaagt tcacctattc tg                                     32

<210> SEQ ID NO 342
<211> LENGTH: 30
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 342
actagtatgt ctgacaagga acaaacgagc                                        30

<210> SEQ ID NO 343
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
ctcgagttaa aagattaccc tttcagtaga tggtaatg                               38

<210> SEQ ID NO 344
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
caagcctttg gtggtaccca gaatccaggg ttagctcc                               38

<210> SEQ ID NO 345
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
ggagctaacc ctggattctg ggtaccacca aaggcttg                               38

<210> SEQ ID NO 346
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
ggtacaacgc atatgcagat gttgctacaa agcagaa                                37

<210> SEQ ID NO 347
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
ttctgctttg tagcaacatc tgcatatgcg ttgtacc                                37

<210> SEQ ID NO 348
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 348
gacgacgtct agaaaagaat actggagaaa tgaaaagaaa ac                    42

<210> SEQ ID NO 349
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gcatgcttaa ttaatgcgag gcatatttat ggtgaagg                         38

<210> SEQ ID NO 350
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
ggccggccag atctgcggcc gcggccagca aaactaaaaa actgtattat aag        53

<210> SEQ ID NO 351
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
gcggccgcag atctggccgg ccgatttatc ttcgtttcct gcaggttttt g          51

<210> SEQ ID NO 352
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
gaattcttaa ttaacttttg ttccactact ttttggaact cttg                  44

<210> SEQ ID NO 353
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
gcatgcgcgg ccgcacgtcg gcaggcccg                                   29

<210> SEQ ID NO 354
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
```
cgaaggacgc gcgaccaagt ttatcattat caatactcgc catttc        46

<210> SEQ ID NO 355
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
gaaatggcga gtattgataa tgataaactt ggtcgcgcgt ccttcg        46

<210> SEQ ID NO 356
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
gtcgacccgc aaattaaagc cttcgagc        28

<210> SEQ ID NO 357
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
gtcgacgtac ccccgggtta attaaggcg        29

<210> SEQ ID NO 358
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gtcgaaaacg agctcgaatt cgacgtcggc aggcccg        37

<210> SEQ ID NO 359
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
cgggcctgcc gacgtcgaat tcgagctcgt tttcgac        37

<210> SEQ ID NO 360
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
ggatccgcgg ccgctggtcg cgcgtccttc g        31

<210> SEQ ID NO 361
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
gagggcacag ttaagccgct aaagg                                          25

<210> SEQ ID NO 362
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
gtcaacagta cccttagtat attctccagt agctagggag                          40

<210> SEQ ID NO 363
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
cgttacccaa ttgaacacgg tattgtcac                                      29

<210> SEQ ID NO 364
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gaagattgag cagcggtttg catttc                                         26

<210> SEQ ID NO 365
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
gcatgcgcgg ccgcacgtcg gcaggcccg                                      29

<210> SEQ ID NO 366
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
ggatccgcgg ccgctggtcg cgcgtccttc g                                   31

```
<210> SEQ ID NO 367
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
gagtcaaacg acgttgaaat tgaggctact gc                                   32

<210> SEQ ID NO 368
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
gattactgct gctgttccag cccatatcca ac                                   32

<210> SEQ ID NO 369
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
ggcaatcaaa ttgggaacga acaatg                                          26

<210> SEQ ID NO 370
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
cataacgaac cggtactcct atggaactc                                       29

<210> SEQ ID NO 371
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
gggtctacaa actgttgttg tcgaagaaga tg                                   32

<210> SEQ ID NO 372
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
cacgtgacag ttatttagta accttgactt ac                                   32

<210> SEQ ID NO 373
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
cctacccgcc tcggatccca gctacc                                          26

<210> SEQ ID NO 374
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
ggtagctggg atccgaggcg ggtagg                                          26

<210> SEQ ID NO 375
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
cctcccggca cagcgtgtcg atgc                                            24

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
cgaagccctg gagcgcttcg c                                               21

<210> SEQ ID NO 377
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
gtggtcagga ttgattctgc acttgttttc cag                                  33

<210> SEQ ID NO 378
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
cgcgtgaagc tgtagaaggc gctaag                                          26

<210> SEQ ID NO 379
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 379
gagctcggcc gcaaattaaa gccttcgag                                          29

<210> SEQ ID NO 380
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
ggccggccgt ttatcattat caatactcgc catttcaaag aatacg                       46

<210> SEQ ID NO 381
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
gttcactgca ctagtaaaaa aatgcttgag aataactggt c                            41

<210> SEQ ID NO 382
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
cttcgagatc tcgagttaaa gtccgccaat cgcctc                                  36

<210> SEQ ID NO 383
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
gttcactgca ctagtaaaaa aatgatcgat actgccaaac tc                           42

<210> SEQ ID NO 384
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
cttcgagatc tcgagtcaga ccgtgaagag tgccgc                                  36

<210> SEQ ID NO 385
<211> LENGTH: 43
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 385
gttcactgca ctagtaaaaa aatggtattg tcacacatcg aag            43

<210> SEQ ID NO 386
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
cttcgagatc tcgagttact gttttgctgc ttcaacaaat tg             42

<210> SEQ ID NO 387
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
gttcactgca ctagtaaaaa aatggagtcc aaagtcgttg aaaacc         46

<210> SEQ ID NO 388
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
cttcgagatc tcgagttaca cttggaaaac agcctgcaaa tcc            43

<210> SEQ ID NO 389
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
gttcactgca ctagtaaaaa aatgacaaac ctcgccccga cc             42

<210> SEQ ID NO 390
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
cttcgagatc tcgagtcagt ccagcagggc cagg                      34

<210> SEQ ID NO 391
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 391
gttcactgca ctagtaaaaa aatgacacag aacgaaaata atcagccgc          49

<210> SEQ ID NO 392
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
cttcgagatc tcgagtcagt caaacagcgc cagcgc                        36

<210> SEQ ID NO 393
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
gttcactgca ctagtaaaaa aatggctatt acaaagaat ttttagctcc ag        52

<210> SEQ ID NO 394
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
cttcgagatc tcgagttagc tagaaattt agcggtagtt gcc                  43

<210> SEQ ID NO 395
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
gttcactgca ctagtaaaaa aatgacgatt gcccagaccc ag                  42

<210> SEQ ID NO 396
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
cttcgagatc tcgagtcagc ccgcccgcac c                             31

<210> SEQ ID NO 397
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
```

```
gttcactgcc atatgaatcc acaattgtta cgcgtaacaa atcgaatcat tg        52
```

<210> SEQ ID NO 398
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398

```
cttcgagatc tcgagttaaa aagtgataca ggttgcgccc tgttcggc              48
```

<210> SEQ ID NO 399
<211> LENGTH: 630
<212> TYPE: DNA
<213> ORGANISM: Saccharophagus degradans

<400> SEQUENCE: 399

```
atggctatta caaagaatt tttagctcca gttggcgtaa tgcctgttgt ggttgtggat   60
cgtgtagaag atgcggtgcc tattacaaac gcattaaaag ccggcggtat taaagcagtt  120
gagattactt tacgtactcc tgcggcactg gatgctattc gcgctattaa agctgagtgt  180
gaagacatcc tggtgggggt aggtacggtt attaaccatc aaaaccttaa agatattgct  240
gcaattggtg ttgatttcgc cgtatctcct ggttacaccc caacattgct gaagcaagcg  300
caagatttgg gcgtagaaat gttgcctggt gtaacttcgc cttctgaagt tatgcttggt  360
atggagctag gttgtcttg cttcaagcta ttccctgcgg ttgcagtagg tggtttgcca  420
ttacttaagt ctattggtgg cccattacca caggtttcct tctgtccaac aggcggtttg  480
actatcgata ctttcaccga cttcttggca ttgcctaacg ttgcttgtgt gggtggtact  540
tggttggtgc ctgcagatgc tgttgcagct aaaaaactggc aagctattac tgatattgcg  600
gcggcaacta ccgctaaaat ttctagctaa                                   630
```

<210> SEQ ID NO 400
<211> LENGTH: 209
<212> TYPE: PRT
<213> ORGANISM: Saccharophagus degradans

<400> SEQUENCE: 400

```
Met Ala Ile Thr Lys Glu Phe Leu Ala Pro Val Gly Val Met Pro Val
1               5                   10                  15

Val Val Asp Arg Val Glu Asp Ala Val Pro Ile Thr Asn Ala Leu
            20                  25                  30

Lys Ala Gly Gly Ile Lys Ala Val Glu Ile Thr Leu Arg Thr Pro Ala
        35                  40                  45

Ala Leu Asp Ala Ile Arg Ala Ile Lys Ala Glu Cys Glu Asp Ile Leu
    50                  55                  60

Val Gly Val Gly Thr Val Ile Asn His Gln Asn Leu Lys Asp Ile Ala
65                  70                  75                  80

Ala Ile Gly Val Asp Phe Ala Val Ser Pro Gly Tyr Thr Pro Thr Leu
                85                  90                  95

Leu Lys Gln Ala Gln Asp Leu Gly Val Glu Met Leu Pro Gly Val Thr
            100                 105                 110

Ser Pro Ser Glu Val Met Leu Gly Met Glu Leu Gly Leu Ser Cys Phe
        115                 120                 125

Lys Leu Phe Pro Ala Val Ala Val Gly Gly Leu Pro Leu Leu Lys Ser
    130                 135                 140
```

Ile Gly Gly Pro Leu Pro Gln Val Ser Phe Cys Pro Thr Gly Gly Leu
145 150 155 160

Thr Ile Asp Thr Phe Thr Asp Phe Leu Ala Leu Pro Asn Val Ala Cys
165 170 175

Val Gly Gly Thr Trp Leu Val Pro Ala Asp Ala Val Ala Ala Lys Asn
180 185 190

Trp Gln Ala Ile Thr Asp Ile Ala Ala Ala Thr Thr Ala Lys Ile Ser
195 200 205

Ser

<210> SEQ ID NO 401
<211> LENGTH: 660
<212> TYPE: DNA
<213> ORGANISM: Xanthomonas axonopodis

<400> SEQUENCE: 401
atgacgattg cccagaccca gaacaccgcc gaacagttgc tgcgcgatgc cggcatcttg 60
cccgtggtca ccgtggacac gctggatcag gcgcgccgcg tcgccgatgc gttgctcgaa 120
ggcggcctgc ccgcgatcga gctgaccctt cgcacgccag tggcgatcga cgcgctggcg 180
atgctcaagc gcgagcttcc taacatcttg atcggtgccg gcaccgtgct gagcgaattg 240
cagctgcgtc agtcggtgga tgccggtgca gacttcctgg tgaccccggg cacgccggcg 300
ccgctggcgc gcctgctggc ggatgcgccg atcccggccg ttcccggcgc ggccactccg 360
accgagctgc tgaccttgat gggtcttggc tttcgcgtct gcaagctgtt cccggccacc 420
gccgtgggcg gtctgcagat gctcaggggc ctggccggcc cgctgtccga gctcaagctg 480
tgccccaccg gcggcatcag cgaggccaac gccgccgagt tcctgtcgca gccgaacgtg 540
ctgtgcatcg gcggttcgtg gatggtcccc aaggattggc tggcgcacgg ccaatgggac 600
aaggtcaagg aaagctcggc caaggcggcg gcgatcgtgc ggcaggtgcg ggcgggctga 660

<210> SEQ ID NO 402
<211> LENGTH: 219
<212> TYPE: PRT
<213> ORGANISM: Xanthomonas axonopodis

<400> SEQUENCE: 402

Met Thr Ile Ala Gln Thr Gln Asn Thr Ala Glu Gln Leu Leu Arg Asp
1 5 10 15

Ala Gly Ile Leu Pro Val Val Thr Val Asp Thr Leu Asp Gln Ala Arg
20 25 30

Arg Val Ala Asp Ala Leu Leu Glu Gly Gly Leu Pro Ala Ile Glu Leu
35 40 45

Thr Leu Arg Thr Pro Val Ala Ile Asp Ala Leu Ala Met Leu Lys Arg
50 55 60

Glu Leu Pro Asn Ile Leu Ile Gly Ala Gly Thr Val Leu Ser Glu Leu
65 70 75 80

Gln Leu Arg Gln Ser Val Asp Ala Gly Ala Asp Phe Leu Val Thr Pro
85 90 95

Gly Thr Pro Ala Pro Leu Ala Arg Leu Leu Ala Asp Ala Pro Ile Pro
100 105 110

Ala Val Pro Gly Ala Ala Thr Pro Thr Glu Leu Leu Thr Leu Met Gly
115 120 125

Leu Gly Phe Arg Val Cys Lys Leu Phe Pro Ala Thr Ala Val Gly Gly
130 135 140

Leu Gln Met Leu Arg Gly Leu Ala Gly Pro Leu Ser Glu Leu Lys Leu

```
                         145                 150                 155                 160
Cys Pro Thr Gly Gly Ile Ser Glu Ala Asn Ala Ala Glu Phe Leu Ser
                165                 170                 175

Gln Pro Asn Val Leu Cys Ile Gly Gly Ser Trp Met Val Pro Lys Asp
            180                 185                 190

Trp Leu Ala His Gly Gln Trp Asp Lys Val Lys Glu Ser Ser Ala Lys
        195                 200                 205

Ala Ala Ala Ile Val Arg Gln Val Arg Ala Gly
    210                 215

<210> SEQ ID NO 403
<211> LENGTH: 675
<212> TYPE: DNA
<213> ORGANISM: Pseudomonas syringiae

<400> SEQUENCE: 403
atgacacaga acgaaaataa tcagccgctc accagcatgg cgaacaagat tgcccggatc      60
gacgaactct gcgccaaggc aaagattctg ccggtcatca ccattgcccg tgatcaggac     120
gtattgccac tggccgacgc gctggccgct ggtggcatga cggctctgga aatcaccctg     180
cgctcggcgt tcggactgag tgcgatccgc attttgcgcg agcagcgccc agagctgtgc     240
actggcgccg ggaccattct ggaccgcaag atgctggccg acgccgaggc ggcgggctcg     300
caattcattg tgacccccgg cagcacgcag gaactgttgc aggcggcgct cgacagcccg     360
ttgcccctgt tgccaggcgt cagcagcgcg tcggaaatca tgatcggcta tgccttgggt     420
tatcgccgct tcaagctgtt cccggcagaa atcagcggcg gtgtggcagc gatcaaggcc     480
ttgggcgggc ctttcaacga ggtgcgtttc tgcccgacgg gcggcgtcaa cgagcagaac     540
ctcaagaact acatggcctt gcccaacgtc atgtgcgtcg gcgggacatg gatgattgat     600
aacgcctggg tcaagaatgg cgactggggc cgcattcagg aagccacggc acaggcgctg     660
gcgctgtttg actga                                                     675

<210> SEQ ID NO 404
<211> LENGTH: 224
<212> TYPE: PRT
<213> ORGANISM: Pseudomonas syringiae

<400> SEQUENCE: 404

Met Thr Gln Asn Glu Asn Asn Gln Pro Leu Thr Ser Met Ala Asn Lys
1               5                   10                  15

Ile Ala Arg Ile Asp Glu Leu Cys Ala Lys Ala Lys Ile Leu Pro Val
            20                  25                  30

Ile Thr Ile Ala Arg Asp Gln Asp Val Leu Pro Leu Ala Asp Ala Leu
        35                  40                  45

Ala Ala Gly Gly Met Thr Ala Leu Glu Ile Thr Leu Arg Ser Ala Phe
    50                  55                  60

Gly Leu Ser Ala Ile Arg Ile Leu Arg Glu Gln Arg Pro Glu Leu Cys
65                  70                  75                  80

Thr Gly Ala Gly Thr Ile Leu Asp Arg Lys Met Leu Ala Asp Ala Glu
                85                  90                  95

Ala Ala Gly Ser Gln Phe Ile Val Thr Pro Gly Ser Thr Gln Glu Leu
            100                 105                 110

Leu Gln Ala Ala Leu Asp Ser Pro Leu Pro Leu Pro Gly Val Ser
        115                 120                 125

Ser Ala Ser Glu Ile Met Ile Gly Tyr Ala Leu Gly Tyr Arg Arg Phe
    130                 135                 140
```

```
Lys Leu Phe Pro Ala Glu Ile Ser Gly Gly Val Ala Ala Ile Lys Ala
145                 150                 155                 160

Leu Gly Gly Pro Phe Asn Glu Val Arg Phe Cys Pro Thr Gly Gly Val
            165                 170                 175

Asn Glu Gln Asn Leu Lys Asn Tyr Met Ala Leu Pro Asn Val Met Cys
        180                 185                 190

Val Gly Gly Thr Trp Met Ile Asp Asn Ala Trp Val Lys Asn Gly Asp
    195                 200                 205

Trp Gly Arg Ile Gln Glu Ala Thr Ala Gln Ala Leu Ala Leu Phe Asp
210                 215                 220
```

<210> SEQ ID NO 405
<211> LENGTH: 642
<212> TYPE: DNA
<213> ORGANISM: Shewanella oneidensis

<400> SEQUENCE: 405

```
atgcttgaga ataactggtc attacaacca caagatattt ttaaacgcag ccctattgtt    60
cctgttatgg tgattaacaa gattgaacat gcggtgccct tagctaaagc gctggttgcc   120
ggagggataa gcgtgttgga agtgacatta cgcacgccat gcgcccttga agctatcacc   180
aaaatcgcca aggaagtgcc tgaggcgctg gttggcgcgg ggactatttt aaatgaagcc   240
cagcttggac aggctatcgc cgctggtgcg caatttatta tcactccagg tgcgacagtt   300
gagctgctca aagcgggcat gcaaggaccg gtgccgttaa ttccgggcgt tgccagtatt   360
tccgaggtga tgacgggcat ggcgctgggc tacactcact ttaaattctt ccctgctgaa   420
gcgtcaggtg gcgttgatgc gcttaaggct ttctctgggc cgttagcaga tatccgcttc   480
tgcccaacag gtggaattac cccgagcagc tataaagatt acttagcgct gaagaatgtc   540
gattgtattg gtggcagctg gattgctcct accgatgcga tggagcaggg cgattgggat   600
cgtatcactc agctgtgtaa agaggcgatt ggcggacttt aa                      642
```

<210> SEQ ID NO 406
<211> LENGTH: 213
<212> TYPE: PRT
<213> ORGANISM: Shewanella oneidensis

<400> SEQUENCE: 406

```
Met Leu Glu Asn Asn Trp Ser Leu Gln Pro Gln Asp Ile Phe Lys Arg
1               5                   10                  15

Ser Pro Ile Val Pro Val Met Val Ile Asn Lys Ile Glu His Ala Val
            20                  25                  30

Pro Leu Ala Lys Ala Leu Val Ala Gly Gly Ile Ser Val Leu Glu Val
        35                  40                  45

Thr Leu Arg Thr Pro Cys Ala Leu Glu Ala Ile Thr Lys Ile Ala Lys
    50                  55                  60

Glu Val Pro Glu Ala Leu Val Gly Ala Gly Thr Ile Leu Asn Glu Ala
65                  70                  75                  80

Gln Leu Gly Gln Ala Ile Ala Ala Gly Ala Gln Phe Ile Ile Thr Pro
            85                  90                  95

Gly Ala Thr Val Glu Leu Leu Lys Ala Gly Met Gln Gly Pro Val Pro
        100                 105                 110

Leu Ile Pro Gly Val Ala Ser Ile Ser Glu Val Met Thr Gly Met Ala
    115                 120                 125

Leu Gly Tyr Thr His Phe Lys Phe Phe Pro Ala Glu Ala Ser Gly Gly
130                 135                 140
```

```
Val Asp Ala Leu Lys Ala Phe Ser Gly Pro Leu Ala Asp Ile Arg Phe
145                 150                 155                 160

Cys Pro Thr Gly Gly Ile Thr Pro Ser Ser Tyr Lys Asp Tyr Leu Ala
                165                 170                 175

Leu Lys Asn Val Asp Cys Ile Gly Gly Ser Trp Ile Ala Pro Thr Asp
            180                 185                 190

Ala Met Glu Gln Gly Asp Trp Asp Arg Ile Thr Gln Leu Cys Lys Glu
        195                 200                 205

Ala Ile Gly Gly Leu
        210

<210> SEQ ID NO 407
<211> LENGTH: 666
<212> TYPE: DNA
<213> ORGANISM: Pseudomonas fluorescens

<400> SEQUENCE: 407
atgacaaacc tcgccccgac cgtttccatg gcggacaaag ttgccctgat cgacagcctc      60
tgcgccaagg cgcggatcct gccggtgatc accattgccc gcgagcagga tgtcctgccg     120
ctggccgatg ccctggcggc cggcggcctg accgccctgg aagtgaccct gcgttcgcag     180
ttcggcctca aggcgatcca gatcctgcgc aacagcgcc cggagctggt gaccggtgcc      240
ggcaccgtgc tcgacccgca gatgctggtg gcggcggaag cggcaggttc gcagttcatc     300
gtcaccccgg gcatcacccg cgacctgctg caagccagcg tggccagccc gattcccctg     360
ctgccgggga tcagcaatgc ctccgggatc atggagggtt atgccctggg ctaccgccgc     420
ttcaagctgt cccggcgga agtcagtggt ggcgtggcgg cgatcaaggc cctgggcggg      480
ccgttcggcg aggtcaagtt ctgccctacc ggcggcgtcg gccggccaa tatcaagagc      540 tacatggcgc tcaagaatgt gatgtgtgtc ggcggtagct ggatgctcga tcccgagtgg     600
atcaagaacg gcgactgggc acggatccag gagtgcacgg ccgaggccct ggccctgctg     660
gactga                                                                666

<210> SEQ ID NO 408
<211> LENGTH: 221
<212> TYPE: PRT
<213> ORGANISM: Pseudomonas fluorescens

<400> SEQUENCE: 408

Met Thr Asn Leu Ala Pro Thr Val Ser Met Ala Asp Lys Val Ala Leu
1               5                   10                  15

Ile Asp Ser Leu Cys Ala Lys Ala Arg Ile Leu Pro Val Ile Thr Ile
            20                  25                  30

Ala Arg Glu Gln Asp Val Leu Pro Leu Ala Asp Ala Leu Ala Ala Gly
        35                  40                  45

Gly Leu Thr Ala Leu Glu Val Thr Leu Arg Ser Gln Phe Gly Leu Lys
    50                  55                  60

Ala Ile Gln Ile Leu Arg Glu Gln Arg Pro Glu Leu Val Thr Gly Ala
65                  70                  75                  80

Gly Thr Val Leu Asp Pro Gln Met Leu Val Ala Ala Glu Ala Ala Gly
                85                  90                  95

Ser Gln Phe Ile Val Thr Pro Gly Ile Thr Arg Asp Leu Leu Gln Ala
            100                 105                 110

Ser Val Ala Ser Pro Ile Pro Leu Leu Pro Gly Ile Ser Asn Ala Ser
        115                 120                 125
```

Gly Ile Met Glu Gly Tyr Ala Leu Gly Tyr Arg Arg Phe Lys Leu Phe
        130                 135                 140

Pro Ala Glu Val Ser Gly Val Ala Ile Lys Ala Leu Gly Gly
145                 150                 155                 160

Pro Phe Gly Glu Val Lys Phe Cys Pro Thr Gly Gly Val Gly Pro Ala
                165                 170                 175

Asn Ile Lys Ser Tyr Met Ala Leu Lys Asn Val Met Cys Val Gly Gly
            180                 185                 190

Ser Trp Met Leu Asp Pro Glu Trp Ile Lys Asn Gly Asp Trp Ala Arg
        195                 200                 205

Ile Gln Glu Cys Thr Ala Glu Ala Leu Ala Leu Leu Asp
    210                 215                 220

<210> SEQ ID NO 409
<211> LENGTH: 591
<212> TYPE: DNA
<213> ORGANISM: Bacillus subtilis

<400> SEQUENCE: 409
atggagtcca aagtcgttga aaaccgtctg aaagaagcaa agctgattgc agtcattcgt      60
tcaaaggata agcaggaggc ctgtcagcag attgagagtt tattagataa agggattcgt     120
gcagttgaag tgacgtatac gaccccgggg catcagata ttatcgaatc cttccgtaat     180
agggaagata ttttaattgg cgcgggtacg gtcatcagcg cgcagcaagc tggggaagct     240
gctaaggctg gcgcgcagtt tattgtcagt ccgggttttt cagctgatct tgctgaacat     300
ctatcttttg taaagacaca ttatatcccc ggcgtcttga ctccgagcga aattatggaa     360
gcgctgacat tcggttttac gacattaaag ctgttcccaa gcggtgtgtt tggcattccg     420
tttatgaaaa atttagcggg tccttttccg caggtgacct ttattccgac aggcgggata     480
catccgtctg aagtgcctga ttggcttaga gccggagctg gcgccgtcgg agtcggcagc     540
cagttgggca gctgttcaaa agaggatttg caggctgttt ccaagtgta a              591

<210> SEQ ID NO 410
<211> LENGTH: 196
<212> TYPE: PRT
<213> ORGANISM: Bacillus subtilis

<400> SEQUENCE: 410

Met Glu Ser Lys Val Val Glu Asn Arg Leu Lys Glu Ala Lys Leu Ile
1               5                   10                  15

Ala Val Ile Arg Ser Lys Asp Lys Gln Glu Ala Cys Gln Gln Ile Glu
            20                  25                  30

Ser Leu Leu Asp Lys Gly Ile Arg Ala Val Glu Val Thr Tyr Thr Thr
        35                  40                  45

Pro Gly Ala Ser Asp Ile Ile Glu Ser Phe Arg Asn Arg Glu Asp Ile
    50                  55                  60

Leu Ile Gly Ala Gly Thr Val Ile Ser Ala Gln Gln Ala Gly Glu Ala
65                  70                  75                  80

Ala Lys Ala Gly Ala Gln Phe Ile Val Ser Pro Gly Phe Ser Ala Asp
                85                  90                  95

Leu Ala Glu His Leu Ser Phe Val Lys Thr His Tyr Ile Pro Gly Val
            100                 105                 110

Leu Thr Pro Ser Glu Ile Met Glu Ala Leu Thr Phe Gly Phe Thr Thr
        115                 120                 125

Leu Lys Leu Phe Pro Ser Gly Val Phe Gly Ile Pro Phe Met Lys Asn
    130                 135                 140

Leu Ala Gly Pro Phe Pro Gln Val Thr Phe Ile Pro Thr Gly Gly Ile
145                 150                 155                 160

His Pro Ser Glu Val Pro Asp Trp Leu Arg Ala Gly Ala Gly Ala Val
            165                 170                 175

Gly Val Gly Ser Gln Leu Gly Ser Cys Ser Lys Glu Asp Leu Gln Ala
        180                 185                 190

Val Phe Gln Val
        195

<210> SEQ ID NO 411
<211> LENGTH: 624
<212> TYPE: DNA
<213> ORGANISM: Bacillus licheniformis

<400> SEQUENCE: 411
atggtattgt cacacatcga agaacaaaaa ctgattgcga tcatccgcgg atacaatccg      60
gaggaggcag tgagcattgc cggcgcctta aaagcgggcg gcatcaggct tgtggagatt     120
acgcttaatt cccctcaagc gatcaaagcg attgaagcgg tttcagagca ttttggggac     180
gaaatgcttg tcggagcggg aaccgtactt gatcccgaat ctgcgagagc ggcgctttta     240
gccggcgcgc ggtttatcct gtctccgacc gtcaatgaag agacgatcaa gctgacaaaa     300
cggtatggag cggtcagcat tccaggcgct tttaccccga ctgaaatatt gacggcgtat     360
gaaagcgggg agacatcat caaggtattt cccggaacaa tggggcctgg ctatatcaag     420
gatatccacg gaccgcttcc gcatattccg ctgcttccga ctggaggagt cggattggaa     480
aaccttcacg agtttctgca ggccggtgcg gtcggagcgg gaatcggcgg ttcgcttgtt     540
cgggctaata aagatgttaa tgacgcgttt ttagaagagc tgtccaaaaa agcaaagcaa     600
tttgttgaag cagcaaaaca gtaa                                            624

<210> SEQ ID NO 412
<211> LENGTH: 207
<212> TYPE: PRT
<213> ORGANISM: Bacillus licheniformis

<400> SEQUENCE: 412

Met Val Leu Ser His Ile Glu Glu Gln Lys Leu Ile Ala Ile Arg
1               5                   10                  15

Gly Tyr Asn Pro Glu Glu Ala Val Ser Ile Ala Gly Ala Leu Lys Ala
            20                  25                  30

Gly Gly Ile Arg Leu Val Glu Ile Thr Leu Asn Ser Pro Gln Ala Ile
        35                  40                  45

Lys Ala Ile Glu Ala Val Ser Glu His Phe Gly Asp Glu Met Leu Val
    50                  55                  60

Gly Ala Gly Thr Val Leu Asp Pro Glu Ser Ala Arg Ala Ala Leu Leu
65                  70                  75                  80

Ala Gly Ala Arg Phe Ile Leu Ser Pro Thr Val Asn Glu Glu Thr Ile
                85                  90                  95

Lys Leu Thr Lys Arg Tyr Gly Ala Val Ser Ile Pro Gly Ala Phe Thr
            100                 105                 110

Pro Thr Glu Ile Leu Thr Ala Tyr Glu Ser Gly Gly Asp Ile Ile Lys
        115                 120                 125

Val Phe Pro Gly Thr Met Gly Pro Gly Tyr Ile Lys Asp Ile His Gly
    130                 135                 140

Pro Leu Pro His Ile Pro Leu Leu Pro Thr Gly Gly Val Gly Leu Glu
145                 150                 155                 160

Asn Leu His Glu Phe Leu Gln Ala Gly Ala Val Gly Ala Gly Ile Gly
                165                 170                 175

Gly Ser Leu Val Arg Ala Asn Lys Asp Val Asn Asp Ala Phe Leu Glu
            180                 185                 190

Glu Leu Ser Lys Lys Ala Lys Gln Phe Val Glu Ala Ala Lys Gln
        195                 200                 205

<210> SEQ ID NO 413
<211> LENGTH: 624
<212> TYPE: DNA
<213> ORGANISM: Gluconobacter oxydans

<400> SEQUENCE: 413
atgatcgata ctgccaaact cgacgccgtc atgagccgtt gtccggtcat gccggtgctg      60
gtggtcaatg atgtggctct ggcccgcccg atggccgagg ctctggtggc gggtggactg     120
tccacgctgg aagtcacgct gcgcacgccc tgcgcccttg aagctattga ggaaatgtcg     180
aaagtaccag gcgcgctggt cggtgccggt acggtgctga atccgtccga catggaccgt     240
gccgtgaagg cgggtgcgcg cttcatcgtc agccccggcc tgaccgaggc gctggcaaag     300
gcgtcggttg agcatgacgt ccccttcctg ccaggcgttg ccaatgcggg tgacatcatg     360
cggggtctgg atctgggtct gtcacgcttc aagttcttcc cggctgtgac gaatggcggc     420
attcccgcgc tcaagagctt ggccagtgtt tttggcagca atgtccgttt ctgccccacg     480
ggcggcatta cggaagagag cgcaccggac tggctggcgc ttccctccgt ggcctgcgtc     540
ggcggatcct gggtgacggc cggcacgttc gatgcggaca aggtccgtca gcgcgccacg     600
gctgcggcac tcttcacggt ctga                                            624

<210> SEQ ID NO 414
<211> LENGTH: 207
<212> TYPE: PRT
<213> ORGANISM: Gluconobacter oxydans

<400> SEQUENCE: 414

Met Ile Asp Thr Ala Lys Leu Asp Ala Val Met Ser Arg Cys Pro Val
1               5                   10                  15

Met Pro Val Leu Val Val Asn Asp Val Ala Leu Ala Arg Pro Met Ala
            20                  25                  30

Glu Ala Leu Val Ala Gly Gly Leu Ser Thr Leu Glu Val Thr Leu Arg
        35                  40                  45

Thr Pro Cys Ala Leu Glu Ala Ile Glu Glu Met Ser Lys Val Pro Gly
    50                  55                  60

Ala Leu Val Gly Ala Gly Thr Val Leu Asn Pro Ser Asp Met Asp Arg
65                  70                  75                  80

Ala Val Lys Ala Gly Ala Arg Phe Ile Val Ser Pro Gly Leu Thr Glu
                85                  90                  95

Ala Leu Ala Lys Ala Ser Val Glu His Asp Val Pro Phe Leu Pro Gly
            100                 105                 110

Val Ala Asn Ala Gly Asp Ile Met Arg Gly Leu Asp Leu Gly Leu Ser
        115                 120                 125

Arg Phe Lys Phe Phe Pro Ala Val Thr Asn Gly Gly Ile Pro Ala Leu
    130                 135                 140

Lys Ser Leu Ala Ser Val Phe Gly Ser Asn Val Arg Phe Cys Pro Thr
145                 150                 155                 160

Gly Gly Ile Thr Glu Glu Ser Ala Pro Asp Trp Leu Ala Leu Pro Ser
                165                 170                 175

Val Ala Cys Val Gly Gly Ser Trp Val Thr Ala Gly Thr Phe Asp Ala
            180                 185                 190

Asp Lys Val Arg Gln Arg Ala Thr Ala Ala Ala Leu Phe Thr Val
        195                 200                 205

<210> SEQ ID NO 415
<211> LENGTH: 642
<212> TYPE: DNA
<213> ORGANISM: Pseudomonas aeruginosa

<400> SEQUENCE: 415
atgaaaaact ggaaaacaag tgcagaatca atcctgacca ccggcccggt tgtaccggtt      60
atcgtggtaa aaaaactgga acacgcggtg ccgatggcaa aagcgttggt tgctggtggg     120
gtgcgcgttc tggaagtgac tctgcgtacc gagtgtgcag ttgacgctat ccgtgctatc     180
gccaaagaag tgcctgaagc gattgtgggt gccggtacgg tgctgaatcc acagcagctg     240
gcagaagtca ctgaagcggg tgcacagttc gcaattagcc cgggtctgac cgagccgctg     300
ctgaaagctg ctaccgaagg gactattcct ctgattccgg ggatcagcac tgtttccgaa     360
ctgatgctgg gtatggacta cggtttgaaa gagttcaaat tcttcccggc tgaagctaac     420
ggcggcgtga aagccctgca ggcgatcgcg ggtccgttct cccaggtccg tttctgcccg     480
acgggtggta tttctccggc taactaccgt gactacctgg cgctgaaaag cgtgctgtgc     540
atcggtggtt cctggctggt tccggcagat gcgctggaag cgggcgatta cgaccgcatt     600
actaagctgg cgcgtgaagc tgtagaaggc gctaagctgt aa                       642

<210> SEQ ID NO 416
<211> LENGTH: 213
<212> TYPE: PRT
<213> ORGANISM: Pseudomonas aeruginosa

<400> SEQUENCE: 416

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

```
Glu Ala Gly Asp Tyr Asp Arg Ile Thr Lys Leu Ala Arg Glu Ala Val
        195                 200                 205

Glu Gly Ala Lys Leu
    210

<210> SEQ ID NO 417
<211> LENGTH: 682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417
atgaaaaact ggaaacagaa gaccgcccgc atcgacacgc tgtgccggga ggcgcgcatc      60
ctcccggtga tcaccatcga ccgcgaggcg gacatcctgc cgatggccga tgccctcgcc     120
gccggcggcc tgaccgccct ggagatcacc ctgcgcacgg cgcacgggct gaccgccatc     180
cggcgcctca gcgaggagcg cccgcacctg cgcatcggcg ccggcaccgt gctcgacccg     240
cggaccttcg ccgccgcgga aaaggccggg gcgagcttcg tggtcacccc gggttgcacc     300
gacgagttgc tgcgcttcgc cctggacagc gaagtcccgc tgttgcccgg cgtggccagc     360
gcttccgaga tcatgctcgc ctaccgccat ggctaccgcc gcttcaagct gtttcccgcc     420
gaagtcagcg gcggcccggc ggcgctgaag gcgttctcgg gaccattccc cgatatccgc     480
ttctgcccca ccgaggcgt cagcctgaac aatctcgccg actacctggc ggtacccaac     540
gtgatgtgcg tcggcggcac ctggatgctg cccaaggccg tggtcgaccg cggcgactgg     600
gcccaggtcg agcgcctcag ccgcgaagcc ctggagcgct cgccgagca ccgcagacac     660 taatagctcg agttacttta ct                                              682

<210> SEQ ID NO 418
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Met Lys Asn Trp Lys Gln Lys Thr Ala Arg Ile Asp Thr Leu Cys Arg
1               5                   10                  15

Glu Ala Arg Ile Leu Pro Val Ile Thr Ile Asp Arg Glu Ala Asp Ile
            20                  25                  30

Leu Pro Met Ala Asp Ala Leu Ala Ala Gly Gly Leu Thr Ala Leu Glu
        35                  40                  45

Ile Thr Leu Arg Thr Ala His Gly Leu Thr Ala Ile Arg Arg Leu Ser
    50                  55                  60

Glu Glu Arg Pro His Leu Arg Ile Gly Ala Gly Thr Val Leu Asp Pro
65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val
            100                 105                 110

Pro Leu Leu Pro Gly Val Ala Ser Ala Ser Glu Ile Met Leu Ala Tyr
        115                 120                 125

Arg His Gly Tyr Arg Arg Phe Lys Leu Phe Pro Ala Glu Val Ser Gly
    130                 135                 140
```

Gly Pro Ala Ala Leu Lys Ala Phe Ser Gly Pro Phe Pro Asp Ile Arg
145                 150                 155                 160

Phe Cys Pro Thr Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg Arg His
210                 215                 220

<210> SEQ ID NO 419
<211> LENGTH: 682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419
atgaaaaact ggaaaacaag tgcagaatca atcgacacgc tgtgccggga ggcgcgcatc      60
ctcccggtga tcaccatcga ccgcgaggcg acatcctgc cgatggccga tgccctcgcc     120
gccggcggcc tgaccgccct ggagatcacc ctgcgcacgg cgcacgggct gaccgccatc     180
cggcgcctca gcgaggagcg cccgcacctg cgcatcggcg ccggcaccgt gctcgacccg     240
cggaccttcg ccgccgcgga aaaggccggg gcgagcttcg tggtcacccc gggttgcacc     300
gacgagttgc tgcgcttcgc cctggacagc gaagtcccgc tgttgcccgg cgtggccagc     360
gcttccgaga tcatgctcgc ctaccgccat ggctaccgcc gcttcaagct gtttcccgcc     420
gaagtcagcg gcggcccggc ggcgctgaag gcgttctcgg gaccattccc cgatatccgc     480
ttctgcccca ccggaggcgt cagcctgaac aatctcgccg actacctggc ggtacccaac     540
gtgatgtgcg tcgcggcac ctggatgctg cccaaggccg tggtcgaccg cggcgactgg     600
gcccaggtcg agcgcctcag ccgcgaagcc ctggagcgct tcgccgagca ccgcagacac     660
taatagctcg agttacttta ct                                             682

<210> SEQ ID NO 420
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Met Lys Asn Trp Lys Thr Ser Ala Glu Ser Ile Asp Thr Leu Cys Arg
1               5                   10                  15

Glu Ala Arg Ile Leu Pro Val Ile Thr Ile Asp Arg Glu Ala Asp Ile
            20                  25                  30

Leu Pro Met Ala Asp Ala Leu Ala Ala Gly Gly Leu Thr Ala Leu Glu
        35                  40                  45

Ile Thr Leu Arg Thr Ala His Gly Leu Thr Ala Ile Arg Arg Leu Ser
    50                  55                  60

Glu Glu Arg Pro His Leu Arg Ile Gly Ala Gly Thr Val Leu Asp Pro
65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val

-continued

Pro Leu Leu Pro Gly Val Ala Ser Ala Ser Glu Ile Met Leu Ala Tyr
            115                 120                 125

Arg His Gly Tyr Arg Arg Phe Lys Leu Phe Pro Ala Glu Val Ser Gly
        130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg Arg His
    210                 215                 220

<210> SEQ ID NO 421
<211> LENGTH: 682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 421
atgaaaaact ggaaaacaag tgcagaatca atcctgacca ccggccggga ggcgcgcatc    60
ctcccggtga tcaccatcga ccgcgaggcg gacatcctgc cgatggccga tgccctcgcc   120
gccggcggcc tgaccgccct ggagatcacc ctgcgcacgg cgcacgggct gaccgccatc   180
cggcgcctca gcgaggagcg cccgcacctg cgcatcggcg ccggcaccgt gctcgacccg   240
cggaccttcg ccgccgcgga aaaggccggg gcgagcttcg tggtcacccc gggttgcacc   300
gacgagttgc tgcgcttcgc cctggacagc gaagtcccgc tgttgcccgg cgtggccagc   360
gcttccgaga tcatgctcgc ctaccgccat ggctaccgcc gcttcaagct gtttcccgcc   420
gaagtcagcg gcggcccggc ggcgctgaag gcgttctcgg gaccattccc cgatatccgc   480
ttctgcccca ccggaggcgt cagcctgaac aatctcgccg actacctggc ggtacccaac   540
gtgatgtgcg tcggcggcac ctggatgctg cccaaggccg tggtcgaccg cggcgactgg   600
gcccaggtcg agcgcctcag ccgcgaagcc ctggagcgct tcgccgagca ccgcagacac   660
taatagctcg agttacttta ct                                            682

<210> SEQ ID NO 422
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Met Lys Asn Trp Lys Thr Ser Ala Glu Ser Ile Leu Thr Thr Gly Arg
1               5                   10                  15

Glu Ala Arg Ile Leu Pro Val Ile Thr Ile Asp Arg Glu Ala Asp Ile
            20                  25                  30

Leu Pro Met Ala Asp Ala Leu Ala Ala Gly Gly Leu Thr Ala Leu Glu
        35                  40                  45

Ile Thr Leu Arg Thr Ala His Gly Leu Thr Ala Ile Arg Arg Leu Ser
    50                  55                  60

```
Glu Glu Arg Pro His Leu Arg Ile Gly Ala Gly Thr Val Leu Asp Pro
 65                  70                  75                  80

Arg Thr Phe Ala Ala Ala Glu Lys Ala Gly Ala Ser Phe Val Val Thr
                 85                  90                  95

Pro Gly Cys Thr Asp Glu Leu Leu Arg Phe Ala Leu Asp Ser Glu Val
            100                 105                 110

Pro Leu Leu Pro Gly Val Ala Ser Ala Ser Glu Ile Met Leu Ala Tyr
        115                 120                 125

Arg His Gly Tyr Arg Arg Phe Lys Leu Phe Pro Ala Glu Val Ser Gly
    130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg Arg His
    210                 215                 220

<210> SEQ ID NO 423
<211> LENGTH: 1665
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 423
atgtccaata actcattcac taacttcaaa ctggccactg aattgccagc ctggtctaag      60
ttgcaaaaaa tttatgaatc tcaaggtaag actttgtctg tcaagcaaga attccaaaaa     120
gatgccaagc gttttgaaaa attgaacaag actttcacca actatgatgg ttccaaaatc     180
ttgttcgact actcaaagaa cttggtcaac gatgaaatat tgctgcatt gattgaactg      240 gccaaggagg ctaacgtcac cggtttgaga gatgctatgt tcaaaggtga acacatcaac     300
tccactgaag atcgtgctgt ctaccacgtc gcattgagaa acagagctaa caagccaatg     360
tacgttgatg gtgtcaacgt tgctccagaa gtcgactctg tcttgaagca catgaaggag     420
ttctctgaac aagttcgttc tggtgaatgg aagggttata ccgtaagaa gatcaccgat      480 gttgttaaca tcggtattgg tggttccgat ttgggtccag tcatggtcac tgaggctttg     540
aagcactacg ctggtgtctt ggatgtccac ttcgtttcca acattgacgg tactcacatt     600
gctgaaacct tgaaggttgt tgacccagaa actactttgt ttttgattgc ttccaagact     660
ttcactaccg ctgaaactat cactaacgct aacactgcca gaactggtt cttgtcgaag      720 acaggtaatg atccatctca cattgctaag catttcgctg ctttgtccac taacgaaacc     780
gaagttgcca gttcggtat tgacaccaaa aacatgtttg gtttcgaaag ttgggtcggt      840
ggtcgttact ctgtctggtc ggctattggt ttgtctgttg ccttgtacat ggctatgac      900 aactttgagg ctttcttgaa gggtgctgaa gccgtcgaca ccacttcac ccaaacccca      960 ttggaagaca cattccatt gttgggtggt tgttgtctg tctggtacaa caacttcttt      1020
ggtgctcaaa cccatttggt tgctccattc gaccaatact tgcacagatt cccagcctac    1080
ttgcaacaat tgtcaatgga atctaacggt aagtctgtta ccagaggtaa cgtgtttact    1140
```

-continued

```
gactactcta ctggttctat cttgtttggt gaaccagcta ccaacgctca acactctttc    1200
ttccaattgg ttcaccaagg taccaagttg attccatctg atttcatctt agctgctcaa    1260
tctcataacc caattgagaa caaattacat caaagatgt tggcttcaaa cttctttgct     1320
caagctgaag ctttaatggt tggtaaggat gaagaacaag ttaaggctga aggtgccact    1380
ggtggtttgg tcccacacaa ggtcttctca ggtaacagac caactacctc tatcttggct    1440
caaaagatta ctccagctac tttgggtgct tgattgcct actacgaaca tgttactttc     1500
actgaaggtg ccatttggaa tatcaactct ttcgaccaat ggggtgttga attgggtaaa    1560
gtcttggcta aagtcatcgg caaggaattg gacaactcct ccaccatttc tacccacgat    1620
gcttctacca acggtttaat caatcaattc aaggaatgga tgtga                   1665
```

<210> SEQ ID NO 424
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 424

```
atgtctgctg atttcggttt gattggtttg gccgtcatgg gtcaaaattt gatcttgaac    60
gctgctgacc acgtttcac tgtttgtgct tacaacagaa ctcaatccaa ggtcgaccat    120
ttcttggcca atgaagctaa gggcaaatct atcatcggtg ctacttccat gaagatttc    180 atctccaaat tgaagagacc tagaaaggtc atgctttttgg ttaaagctgg tgctccagtt    240
gacgctttga tcaaccaaat cgtcccactt ttggaaaagg gtgatattat catcgatggt    300
ggtaactctc acttcccaga ttctaataga cgttacgaag aattgaagaa aagggtatt    360 cttttcgttg gttctggtgt ctccggtggt gaggaaggtg cccgttacgg tccatctttg    420
atgccaggtg gttctgaaga agcttggcca catattaaga acatcttcca atccatctct    480
gctaaatccg acggtgaacc atgttgcgaa tgggttggcc cagccggtgc tggtcactac    540
gtcaagatgg ttcacaacgg tattgaatac ggtgatatgc aattgatttg tgaagcttat    600
gacatcatga agagattggg tgggtttacc gataaggaaa tcagtgacgt ttttgccaaa    660 tgaacaatg tgtcttgga ttccttcttg gtcgaaatta ccagagatat tttgaaattc    720
gacgacgtcg acggtaagcc attagttgaa aaaatcatgg atactgctgg tcaaaagggt    780
actggtaagt ggactgccat caacgccttg gatttgggta tgccagttac tttgattggt    840
gaagctgtct tgcccgttg tctatctgct ttgaagaacg agagaattag agcctccaag    900
gtcttaccag gcccagaagt tccaaaagac gccgtcaagg acagaaaca atttgtcgat    960 gatttggaac aagctttgta tgcttccaag attatttctt acgctcaagg tttcatgttg    1020
atccgtgaag ctgctgctac ttatggctgg aaactaaaca ccctgccat cgctttgatg    1080 tggagaggtg gttgtatcat tagatctgtt ttcttgggtc aaatcacaaa ggcctacaga    1140
gaagaaccag atttgaaaaa cttgttgttc aacaagttct tcgctgatgc cgtcaccaag    1200
gctcaatctg gttggagaaa gtcaattgcg ttggctacca cctacggtat cccaacacca    1260
gccttttcca ccgctttgtc tttctacgat gggtacagat ctgaaagatt gccagccaac    1320
ttactacaag ctcaacgtga ctactttggt gctcacactt tcagagtgtt gccagaatgt    1380
gcttctgaca acttgccagt agacaaggat atccatatca actggactgg ccacggtggt    1440
aatgtttctt cctctacata ccaagcttaa                                     1470
```

<210> SEQ ID NO 425
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 425

```
atgtcaaagg cagtaggtga tttaggctta gttggtttag ccgtgatggg tcaaaatttg      60
atcttaaacg cagcggatca cggatttacc gtggttgctt ataataggac gcaatcaaag     120
gtagataggt ttctagctaa tgaggcaaaa ggaaaatcaa taattggtgc aacttcaatt     180
gaggacttgg ttgcgaaact aaagaaacct agaaagatta tgcttttaat caaagccggt     240
gctccggtcg acactttaat aaaggaactt gtaccacatc ttgataaagg cgacattatt     300
atcgacggtg gtaactcaca tttcccggac actaacagac gctacgaaga gctaacaaag     360
caaggaattc tttttgtggg ctctggtgtc tcaggcggtg aagatggtgc acgttttggt     420
ccatctttaa tgcctggtgg gtcagcagaa gcatggccgc acatcaagaa catctttcaa     480
tctattgccg ccaaatcaaa cggtgagcca tgctgcgaat gggtggggcc tgccggttct     540
ggtcactatg tgaagatggt acacaacggt atcgagtacg tgatatgca gttgatttgc      600
gaggcttacg atatcatgaa acgaattggc cggtttacgg ataaagagat cagtgaagta     660
tttgacaagt ggaacactgg agttttggat tctttcttga ttgaaatcac gagggacatt     720
ttaaaattcg atgacgtcga cggtaagcca ttggtggaaa aaattatgga tactgccggt     780
caaaagggta ctggtaaatg gactgcaatc aacgccttgg atttaggaat gccagtcact     840
ttaattgggg aggctgtttt cgctcgttgt ttgtcagcca taaggacga acgtaaaaga     900
gcttcgaaac ttctggcagg accaacagta ccaaggatg caatacatga tagagaacaa     960
tttgtgtatg atttggaaca agcattatac gcttcaaaga ttatttcata tgctcaaggt    1020
ttcatgctga tccgcgaagc tgccagatca tacggctgga aattaaacaa cccagctatt    1080
gctctaatgt ggagaggtgg ctgtataatc agatctgtgt tcttagctga gattacgaag    1140
gcttataggg acgatccaga tttggaaaat ttattattca acgagttctt cgcttctgca    1200
gttactaagg cccaatccgg ttggagaaga actattgccc ttgctgctac ttacggtatt    1260
ccaactccag ctttctctac tgcttttagcg ttttacgacg gctatagatc tgagaggcta    1320
ccagcaaact gttacaagc gcaacgtgat tatttggcg ctcatacatt tagaatttta    1380
cctgaatgtg cttctgccca tttgccagta gacaaggata ttcatatcaa ttggactggg    1440
cacggaggta atatatcttc ctcaacctac caagcttaa                            1479
```

<210> SEQ ID NO 426
<211> LENGTH: 1008
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 426

```
atgtctgaac cagctcaaaa gaaacaaaag gttgctaaca actctctaga acaattgaaa      60
gcctccggca ctgtcgttgt tgccgacact ggtgatttcg gctctattgc caagtttcaa     120
cctcaagact ccacaactaa cccatcattg atcttggctg ctgccaagca accaacttac     180
gccaagttga tcgatgttgc cgtggaatac ggtaagaagc atggtaagac caccgaagaa     240
caagtcgaaa atgctgtgga cagattgtta gtcgaattcg gtaaggagat cttaaagatt     300
```

```
gttccaggca gagtctccac cgaagttgat gctagattgt cttttgacac tcaagctacc    360
attgaaaagg ctagacatat cattaaattg tttgaacaag aaggtgtctc caaggaaaga    420
gtccttatta aaattgcttc cacttgggaa ggtattcaag ctgccaaaga attggaagaa    480
aaggacggta tccactgtaa tttgactcta ttattctcct tcgttcaagc agttgcctgt    540
gccgaggccc aagttacttt gatttcccca tttgttggta gaattctaga ctggtacaaa    600
tccagcactg gtaaagatta caagggtgaa gccgacccag gtgttatttc cgtcaagaaa    660
atctacaact actacaagaa gtacggttac aagactattg ttatgggtgc ttctttcaga    720
agcactgacg aaatcaaaaa cttggctggt gttgactatc taacaatttc tccagcttta    780
ttggacaagt tgatgaacag tactgaacct ttcccaagag ttttggaccc tgtctccgct    840
aagaaggaag ccggcgacaa gatttcttac atcagcgacg aatctaaatt cagattcgac    900
ttgaatgaag acgctatggc cactgaaaaa ttgtccgaag gtatcagaaa attctctgcc    960
gatattgtta ctctattcga cttgattgaa aagaaagtta ccgcttaa              1008
```

<210> SEQ ID NO 427
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

```
Met Ser Glu Pro Ala Gln Lys Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Ile Tyr Asn Tyr
    210                 215                 220

Tyr Lys Lys Tyr Gly Tyr Lys Thr Ile Val Met Gly Ala Ser Phe Arg
225                 230                 235                 240
```

```
Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
    290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335
```

<210> SEQ ID NO 428
<211> LENGTH: 2043
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 428

```
atgactcaat tcactgacat tgataagcta gccgtctcca ccataagaat tttggctgtg      60
gacaccgtat ccaaggccaa ctcaggtcac ccaggtgctc cattgggtat ggcaccagct     120
gcacacgttc tatggagtca aatgcgcatg aacccaacca acccagactg gatcaacaga     180
gatagatttg tcttgtctaa cggtcacgcg gtcgctttgt tgtattctat gctacatttg     240
actggttacg atctgtctat tgaagacttg aaacagttca gacagttggg ttccagaaca     300
ccaggtcatc ctgaatttga gttgccaggt gttgaagtta ctaccggtcc attaggtcaa     360
ggtatctcca acgctgttgg tatggccatg gctcaagcta acctggctgc cacttacaac     420
aagccgggct taccttgtc tgacaactac acctatgttt cttgggtga cggttgttg       480
caagaaggta tttcttcaga agcttcctcc ttggctggtc atttgaaatt gggtaacttg     540
attgccatct acgatgacaa caagatcact atcgatggtg ctaccagtat ctcattcgat     600
gaagatgttg ctaagagata cgaagcctac ggttgggaag ttttgtacgt agaaaatggt     660
aacgaagatc tagccggtat tgccaaggct attgctcaag ctaagttatc caaggacaaa     720
ccaactttga tcaaaatgac cacaaccatt ggttacggtt ccttgcatgc cggctctcac     780
tctgtgcacg gtgccccatt gaaagcagat gatgttaaac aactaaagag caaattcggt     840
ttcaacccag acaagtcctt tgttgttcca caagaagttt acgaccacta ccaaaagaca     900
attttaaagc aggtgtcga agccaacaac aagtggaaca agttgttcag cgaataccaa     960
aagaaattcc cagaattagg tgctgaattg ctagaagat tgagcggcca actacccgca    1020
aattgggaat ctaagttgcc aacttacacc gccaaggact ctgccgtggc cactagaaaa    1080
ttatcagaaa ctgttcttga ggatgtttac aatcaattgc cagagttgat tggtggttct    1140
gccgatttaa caccttctaa cttgaccaga tggaaggaag cccttgactt ccaacctcct    1200
tcttccggtt caggtaacta ctctggtaga tacattaggt acggtattag agaacacgct    1260
atgggtgcca taatgaacgg tatttcagct ttcggtgcca actacaaacc atacggtggt    1320
actttcttga acttcgtttc ttatgctgct ggtgccgtta gattgtccgc tttgtctggc    1380
cacccagtta tttgggttgc tacacatgac tctatcggtg tcggtgaaga tggtccaaca    1440
catcaaccta ttgaaacttt agcacacttc agatccctac caaacattca agtttggaga    1500
```

-continued

```
ccagctgatg gtaacgaagt ttctgccgcc tacaagaact ctttagaatc caagcatact    1560
ccaagtatca ttgctttgtc cagacaaaac ttgccacaat tggaaggtag ctctattgaa    1620
agcgcttcta agggtggtta cgtactacaa gatgttgcta acccagatat tattttagtg    1680
gctactggtt ccgaagtgtc tttgagtgtt gaagctgcta agactttggc cgcaaagaac    1740
atcaaggctc gtgttgtttc tctaccagat ttcttcactt ttgacaaaca accctagaa     1800 tacagactat cagtcttacc agacaacgtt ccaatcatgt ctgttgaagt tttggctacc    1860
acatgttggg gcaaatacgc tcatcaatcc ttcggtattg acagatttgg tgcctccggt    1920
aaggcaccag aagtcttcaa gttcttcggt ttcaccccag aaggtgttgc tgaaagagct    1980
caaaagacca ttgcattcta agggtgac    aagctaattt ctcctttgaa aaaagctttc   2040
taa                                                                  2043
```

<210> SEQ ID NO 429
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

```
Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45

Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
```

```
                    260                 265                 270
Lys Gln Leu Lys Ser Lys Phe Gly Phe Asn Pro Asp Lys Ser Phe Val
                275                 280                 285
Val Pro Gln Glu Val Tyr Asp His Tyr Gln Lys Thr Ile Leu Lys Pro
290                 295                 300
Gly Val Glu Ala Asn Asn Lys Trp Asn Lys Leu Phe Ser Glu Tyr Gln
305                 310                 315                 320
Lys Lys Phe Pro Glu Leu Gly Ala Glu Leu Ala Arg Arg Leu Ser Gly
                325                 330                 335
Gln Leu Pro Ala Asn Trp Glu Ser Lys Leu Pro Thr Tyr Thr Ala Lys
                340                 345                 350
Asp Ser Ala Val Ala Thr Arg Lys Leu Ser Glu Thr Val Leu Glu Asp
                355                 360                 365
Val Tyr Asn Gln Leu Pro Glu Leu Ile Gly Gly Ser Ala Asp Leu Thr
                370                 375                 380
Pro Ser Asn Leu Thr Arg Trp Lys Glu Ala Leu Asp Phe Gln Pro Pro
385                 390                 395                 400
Ser Ser Gly Ser Gly Asn Tyr Ser Gly Arg Tyr Ile Arg Tyr Gly Ile
                405                 410                 415
Arg Glu His Ala Met Gly Ala Ile Met Asn Gly Ile Ser Ala Phe Gly
                420                 425                 430
Ala Asn Tyr Lys Pro Tyr Gly Gly Thr Phe Leu Asn Phe Val Ser Tyr
                435                 440                 445
Ala Ala Gly Ala Val Arg Leu Ser Ala Leu Ser Gly His Pro Val Ile
                450                 455                 460
Trp Val Ala Thr His Asp Ser Ile Gly Val Gly Glu Asp Gly Pro Thr
465                 470                 475                 480
His Gln Pro Ile Glu Thr Leu Ala His Phe Arg Ser Leu Pro Asn Ile
                485                 490                 495
Gln Val Trp Arg Pro Ala Asp Gly Asn Glu Val Ser Ala Ala Tyr Lys
                500                 505                 510
Asn Ser Leu Glu Ser Lys His Thr Pro Ser Ile Ile Ala Leu Ser Arg
                515                 520                 525
Gln Asn Leu Pro Gln Leu Glu Gly Ser Ser Ile Glu Ser Ala Ser Lys
                530                 535                 540
Gly Gly Tyr Val Leu Gln Asp Val Ala Asn Pro Asp Ile Ile Leu Val
545                 550                 555                 560
Ala Thr Gly Ser Glu Val Ser Leu Ser Val Glu Ala Ala Lys Thr Leu
                565                 570                 575
Ala Ala Lys Asn Ile Lys Ala Arg Val Val Ser Leu Pro Asp Phe Phe
                580                 585                 590
Thr Phe Asp Lys Gln Pro Leu Glu Tyr Arg Leu Ser Val Leu Pro Asp
                595                 600                 605
Asn Val Pro Ile Met Ser Val Glu Val Leu Ala Thr Thr Cys Trp Gly
                610                 615                 620
Lys Tyr Ala His Gln Ser Phe Gly Ile Asp Arg Phe Gly Ala Ser Gly
625                 630                 635                 640
Lys Ala Pro Glu Val Phe Lys Phe Phe Gly Phe Thr Pro Glu Gly Val
                645                 650                 655
Ala Glu Arg Ala Gln Lys Thr Ile Ala Phe Tyr Lys Gly Asp Lys Leu
                660                 665                 670
Ile Ser Pro Leu Lys Lys Ala Phe
                675                 680
```

<210> SEQ ID NO 430
<211> LENGTH: 1830
<212> TYPE: DNA
<213> ORGANISM: Saccharophagus degradans

<400> SEQUENCE: 430

| | | | | | |
|---|---|---|---|---|---|
| atgaatagcg | taatcgaagc | tgtaactcag | cgaattattg | agcgcagtcg | acattctcgt | 60 |
| caggcgtatt | tgaatttaat | gcgcaacacc | atggagcagc | atcctcctaa | aaagcgtcta | 120 |
| tcttgcggca | atttggctca | tgcctatgca | gcatgtggtc | aatccgataa | gcaaacaatt | 180 |
| cgtttaatgc | aaagtgcaaa | cataagtatt | actacggcat | taacgatat | gctttcggcg | 240 |
| catcagcctt | tagaaacata | ccctcaaata | atcaaagaaa | ctgcgcgtgc | aatgggttca | 300 |
| actgctcaag | ttgcaggcgg | cgtgccggca | atgtgtgatg | tgtaactca | aggccagccc | 360 |
| ggtatggagc | tgagtttgtt | tagccgcgaa | gttgtagcaa | tggctacagc | agtaggcctt | 420 |
| tcgcacaata | tgtttgatgg | caatatgttt | tgggtgtat | gcgataaaat | tgttcctggc | 480 |
| atgctaattg | gcgcgttgca | gtttggtcat | attcctgggg | tgtttgtgcc | tgccggacca | 540 |
| atgccttctg | gtattcccaa | caaagaaaaa | gcaaaagttc | gtcagcaata | tcggcgggc | 600 |
| attgtggggg | aagataagct | tttagaaacc | gagtcggctt | cctatcacag | tgcaggcacg | 660 |
| tgtactttt | acggtacagc | gaatacaaac | caaatgatgg | ttgaaatgtt | gggtgttcag | 720 |
| ttgcctggct | cgtcgtttgt | ttaccccggt | actgagttgc | gtgatgcctt | aacgagagct | 780 |
| gctgttgaaa | agttggtaaa | aatcacagat | tcagccggta | actaccgtcc | gctctacgaa | 840 |
| gtcattacgg | aaaaatccat | cgtcaattca | ataattggtt | tgttggctac | cggcggttct | 900 |
| actaaccaca | cgctacacat | tgttgctgtg | gctcgcgctg | cgggtataga | ggttacgtgg | 960 |
| gcagatatgg | acgagctttc | gcgtgctgtg | ccattacttg | cacgtgttta | ccctaacggc | 1020 |
| gaagctgatg | ttaaccaatt | ccagcaggct | ggcggcatgg | cttatttagt | aagagagctg | 1080 |
| cgcagcggcg | gtttgctaaa | tgaagatgtg | gttactatta | tgggtgaggg | cctcgaggcc | 1140 |
| tacgaaaaag | agcccatgct | taacgataag | gggcaggctg | aatgggtaaa | tgatgtacct | 1200 |
| gttagccgcg | acgataccgt | tgtgcgtcca | gttacctcgc | ctttcgataa | agagggtggg | 1260 |
| ttgcgtctac | tcaagggtaa | cttagggcag | ggcgtaatca | aaatttctgc | ggtagcgcca | 1320 |
| gaaaatcgcg | ttgttgaggc | cccatgtatt | gtattcgagg | cccaagaaga | gctaatagct | 1380 |
| gcgtttaagc | gtggtgagct | cgaaaaagac | tttgttgcgg | tagtgcgctt | ccaagggcct | 1440 |
| tctgccaatg | gcatgccaga | acttcataaa | atgaccccgc | ctttaggtgt | gcttcaagat | 1500 |
| aagggtttca | aggtagcgtt | agttaccgat | ggcagaatgt | ctggtgcatc | tggtaaagtg | 1560 |
| ccggccggta | tacacttgtc | gccagaagcg | agtaagggtg | gcctgttgaa | taagctgcgc | 1620 |
| acgggtgatg | tgattcgctt | cgatgccgaa | gcgggcgtta | ttcaagcgct | tgttagtgat | 1680 |
| gaagagttag | ctgcgcgtga | gccagctgtg | caaccggtcg | tggagcagaa | cctcggacgc | 1740 |
| tctctgtttg | gtggtttgcg | cgatttggct | ggtgtatcgc | tacaaggcgg | aacagttttc | 1800 |
| gattttgaaa | gagagtttgg | cgaaaaatag | | | | 1830 |

<210> SEQ ID NO 431
<211> LENGTH: 609
<212> TYPE: PRT
<213> ORGANISM: Saccharophagus degradans

<400> SEQUENCE: 431

Met Asn Ser Val Ile Glu Ala Val Thr Gln Arg Ile Ile Glu Arg Ser
1               5                   10                  15

```
Arg His Ser Arg Gln Ala Tyr Leu Asn Leu Met Arg Asn Thr Met Glu
         20                  25                  30

Gln His Pro Lys Lys Arg Leu Ser Cys Gly Asn Leu Ala His Ala
         35                  40                  45

Tyr Ala Ala Cys Gly Gln Ser Asp Lys Gln Thr Ile Arg Leu Met Gln
 50                  55                  60

Ser Ala Asn Ile Ser Ile Thr Thr Ala Phe Asn Asp Met Leu Ser Ala
 65                  70                  75                  80

His Gln Pro Leu Glu Thr Tyr Pro Gln Ile Ile Lys Glu Thr Ala Arg
                 85                  90                  95

Ala Met Gly Ser Thr Ala Gln Val Ala Gly Val Pro Ala Met Cys
                100                 105                 110

Asp Gly Val Thr Gln Gly Gln Pro Gly Met Glu Leu Ser Leu Phe Ser
                115                 120                 125

Arg Glu Val Val Ala Met Ala Thr Ala Val Gly Leu Ser His Asn Met
    130                 135                 140

Phe Asp Gly Asn Met Phe Leu Gly Val Cys Asp Lys Ile Val Pro Gly
145                 150                 155                 160

Met Leu Ile Gly Ala Leu Gln Phe Gly His Ile Pro Gly Val Phe Val
                165                 170                 175

Pro Ala Gly Pro Met Pro Ser Gly Ile Pro Asn Lys Glu Lys Ala Lys
                180                 185                 190

Val Arg Gln Gln Tyr Ala Ala Gly Ile Val Gly Glu Asp Lys Leu Leu
    195                 200                 205

Glu Thr Glu Ser Ala Ser Tyr His Ser Ala Gly Thr Cys Thr Phe Tyr
    210                 215                 220

Gly Thr Ala Asn Thr Asn Gln Met Met Val Glu Met Leu Gly Val Gln
225                 230                 235                 240

Leu Pro Gly Ser Ser Phe Val Tyr Pro Gly Thr Glu Leu Arg Asp Ala
                245                 250                 255

Leu Thr Arg Ala Ala Val Glu Lys Leu Val Lys Ile Thr Asp Ser Ala
            260                 265                 270

Gly Asn Tyr Arg Pro Leu Tyr Glu Val Ile Thr Glu Lys Ser Ile Val
            275                 280                 285

Asn Ser Ile Ile Gly Leu Leu Ala Thr Gly Gly Ser Thr Asn His Thr
290                 295                 300

Leu His Ile Val Ala Val Ala Arg Ala Ala Gly Ile Glu Val Thr Trp
305                 310                 315                 320

Ala Asp Met Asp Glu Leu Ser Arg Ala Val Pro Leu Leu Ala Arg Val
                325                 330                 335

Tyr Pro Asn Gly Glu Ala Asp Val Asn Gln Phe Gln Gln Ala Gly Gly
            340                 345                 350

Met Ala Tyr Leu Val Arg Glu Leu Arg Ser Gly Gly Leu Leu Asn Glu
            355                 360                 365

Asp Val Val Thr Ile Met Gly Glu Gly Leu Glu Ala Tyr Glu Lys Glu
            370                 375                 380

Pro Met Leu Asn Asp Lys Gly Gln Ala Glu Trp Val Asn Asp Val Pro
385                 390                 395                 400

Val Ser Arg Asp Asp Thr Val Arg Pro Val Thr Ser Pro Phe Asp
            405                 410                 415

Lys Glu Gly Gly Leu Arg Leu Leu Lys Gly Asn Leu Gly Gln Gly Val
            420                 425                 430

Ile Lys Ile Ser Ala Val Ala Pro Glu Asn Arg Val Val Glu Ala Pro
```

```
        435                 440                 445

Cys Ile Val Phe Glu Ala Gln Glu Glu Leu Ile Ala Ala Phe Lys Arg
    450                 455                 460

Gly Glu Leu Glu Lys Asp Phe Val Ala Val Val Arg Phe Gln Gly Pro
465                 470                 475                 480
Ser Ala Asn Gly Met Pro Glu Leu His Lys Met Thr Pro Pro Leu Gly
                485                 490                 495
Val Leu Gln Asp Lys Gly Phe Lys Val Ala Leu Val Thr Asp Gly Arg
            500                 505                 510
Met Ser Gly Ala Ser Gly Lys Val Pro Ala Gly Ile His Leu Ser Pro
        515                 520                 525
Glu Ala Ser Lys Gly Gly Leu Leu Asn Lys Leu Arg Thr Gly Asp Val
    530                 535                 540
Ile Arg Phe Asp Ala Glu Ala Gly Val Ile Gln Ala Leu Val Ser Asp
545                 550                 555                 560
Glu Glu Leu Ala Ala Arg Glu Pro Ala Val Gln Pro Val Val Glu Gln
                565                 570                 575
Asn Leu Gly Arg Ser Leu Phe Gly Gly Leu Arg Asp Leu Ala Gly Val
            580                 585                 590
Ser Leu Gln Gly Gly Thr Val Phe Asp Phe Glu Arg Glu Phe Gly Glu
        595                 600                 605
Lys

<210> SEQ ID NO 432
<211> LENGTH: 1917
<212> TYPE: DNA
<213> ORGANISM: Xanthomonas axonopodis

<400> SEQUENCE: 432
atgagcctgc atccgaatat ccaagccgtc accgaccgta tccgcaagcg cagtgctccc      60
tcgcgcgcgg cgtatctggc cggcctcgat gccgccctgc gtgagggccc gttccgtagc     120
cggttgagct gcggcaatct cgcgcatggc ttcgctgcgt ccgagccggg cgacaaatcg     180
cgcctgcgcg gtgcggccac gccgaacctg ggcatcatca ctgcctataa cgacatgttg     240
tcggcacatc agccgttcga gcactacccg cagctgatcc gcgaaaccgc gcgctcactt     300
ggcgccactg cgcaggtggc cggcggcgtg ccggcgatgt gtgacggcgt gacccagggc     360
cgcgccggca tggagctgtc gctgttctcg cgcgacaaca tcgctcaggc tgcggccatt     420
ggcctgagcc atgacatgtt cgacagcgtg gtgtacctgg gggtgtgcga caagatcgtg     480
ccgggtctgc tgatcggtgc gctggcgttt ggccatttgc cggcgatctt catgccggct     540
ggtccgatga ccccgggcat cccgaacaag cagaaagccg aagtccgcga acgctacgcc     600
gctggcgaag ccacccgcgc cgaattgctg gaggccgaat cctcgtctta tcactcgccc     660
ggcacctgca cctttacgg cacggcgaac tccaaccagg tgttgctcga agcgatgggc     720
gtgcagttgc ccggcgcctc gttcgtcaat ccggagctgc cgctgcgcga tgcactgacc     780
cgcgaaggca ccgcacgcgc attggcgatc tccgcgctgg gcgatgactt ccgccccgttc    840 ggtcgtttga tcgacgaacg ggccatcgtc aatgccgtgg tcgcgctgat ggcgaccggc     900
ggttcgacca accacaccat ccactggatc gcagtggcgc gtgcggccgg catcgtgttg     960
acctgggacg acatggatct gatctcgcag accgtgccgc tgttgacacg catctacccg    1020
aacggcgaag ccgacgtgaa ccgcttccag gccgcaggcg gcacggcgtt cgtgttccgc    1080
gaattgatgg acgccggcta catgcacgac gacctgccga ccatcgtcga aggcggcatg    1140
```

```
cgcgcgtacg tcaacgaacc gcgcctgcag gacggcaagg tgacctacgt gcccggcacc   1200
gcgaccactg ccgacgacag cgtcgcgcgt ccggtcagcg atgcattcga atcacaaggc   1260
ggcctgcgcc tgctgcgcgg caacctcggc cgctcgttga tcaagctgtc ggcggtcaag   1320
ccgcagcacc gcagcatcca agcgccagcg gtggtgatcg acaccccgca agtgctcaac   1380
aaactgcatg cggcgggcgt actgccgcac gatttcgtgg tggtactgcg ctatcagggc   1440
ccacgcgcaa acggcatgcc ggagctgcat tcgatggcgc cgctactggg cctgctgcag   1500
aaccagggcc ggcgcgtggc gttggtcacc gacggccgtc tgtccggcgc ctcgggcaag   1560
ttcccggcgg cgatccacat gaccccggaa gccgcacgcg gcggcccgat cgggcgcgta   1620
cgcgaaggcg acatcgtgcg actggacggc gaagccggca ccttggaagt gctggtttcg   1680
gccgaagaat gggcatcgcg cgaggtcgca ccgaacactg cgttggccgg caacgacctg   1740
ggccgcaacc tgttcgccat caaccgccag gtggttggcc cggccgacca gggcgcgatt   1800
tccatttcct gcggcccgac ccatccggac ggtgcgctgt ggagctacga cgccgagtac   1860
gaactcggtg ccgatgcagc tgcagccgcc gcgccgcacg agtccaagga cgcctga      1917
```

```

<210> SEQ ID NO 433
<211> LENGTH: 638
<212> TYPE: PRT
<213> ORGANISM: Xanthomonas axonopodis

<400> SEQUENCE: 433

Met Ser Leu His Pro Asn Ile Gln Ala Val Thr Asp Arg Ile Arg Lys
1               5                   10                  15

Arg Ser Ala Pro Ser Arg Ala Ala Tyr Leu Ala Gly Ile Asp Ala Ala
            20                  25                  30

Leu Arg Glu Gly Pro Phe Arg Ser Arg Leu Ser Cys Gly Asn Leu Ala
        35                  40                  45

His Gly Phe Ala Ala Ser Glu Pro Thr Asp Lys Ser Arg Leu Arg Gly
    50                  55                  60

Ala Ala Thr Pro Asn Leu Gly Ile Ile Thr Ala Tyr Asn Asp Met Leu
65                  70                  75                  80

Ser Ala His Gln Pro Phe Glu His Tyr Pro Gln Leu Ile Arg Glu Thr
                85                  90                  95

Ala Arg Ser Leu Gly Ala Thr Ala Gln Val Ala Gly Gly Val Pro Ala
            100                 105                 110

Met Cys Asp Gly Val Thr Gln Gly Arg Ala Gly Met Glu Leu Ser Leu
        115                 120                 125

Phe Ser Arg Asp Asn Ile Ala Gln Ala Ala Ala Ile Gly Leu Ser His
    130                 135                 140

Asp Met Phe Asp Ser Val Val Tyr Leu Gly Val Cys Asp Lys Ile Val
145                 150                 155                 160

Pro Gly Leu Leu Ile Gly Ala Leu Ala Phe Gly His Leu Pro Ala Ile
                165                 170                 175

Phe Met Pro Ala Gly Pro Met Thr Pro Gly Ile Pro Asn Lys Gln Lys
            180                 185                 190

Ala Glu Val Arg Glu Arg Tyr Ala Ala Gly Glu Ala Thr Arg Ala Glu
        195                 200                 205

Leu Leu Glu Ala Glu Ser Ser Ser Tyr His Ser Pro Gly Thr Cys Thr
    210                 215                 220

Phe Tyr Gly Thr Ala Asn Ser Asn Gln Val Leu Leu Glu Ala Met Gly
225                 230                 235                 240

Val Gln Leu Pro Gly Ala Ser Phe Val Asn Pro Glu Leu Pro Leu Arg
```

```
                      245                 250                 255
Asp Ala Leu Thr Arg Glu Gly Thr Ala Arg Ala Leu Ala Ile Ser Ala
                260                 265                 270

Leu Gly Asp Asp Phe Arg Pro Phe Gly Arg Leu Ile Asp Glu Arg Ala
            275                 280                 285

Ile Val Asn Ala Val Val Ala Leu Met Ala Thr Gly Gly Ser Thr Asn
        290                 295                 300

His Thr Ile His Trp Ile Ala Val Ala Arg Ala Ala Gly Ile Val Leu
    305                 310                 315                 320

Thr Trp Asp Asp Met Asp Leu Ile Ser Gln Thr Val Pro Leu Leu Thr
                325                 330                 335

Arg Ile Tyr Pro Asn Gly Glu Ala Asp Val Asn Arg Phe Gln Ala Ala
            340                 345                 350

Gly Gly Thr Ala Phe Val Phe Arg Glu Leu Met Asp Ala Gly Tyr Met
        355                 360                 365

His Asp Asp Leu Pro Thr Ile Val Glu Gly Met Arg Ala Tyr Val
    370                 375                 380

Asn Glu Pro Arg Leu Gln Asp Gly Lys Val Thr Tyr Val Pro Gly Thr
385                 390                 395                 400

Ala Thr Thr Ala Asp Asp Ser Val Ala Arg Pro Val Ser Asp Ala Phe
                405                 410                 415

Glu Ser Gln Gly Gly Leu Arg Leu Arg Gly Asn Leu Gly Arg Ser
            420                 425                 430

Leu Ile Lys Leu Ser Ala Val Lys Pro Gln His Arg Ser Ile Gln Ala
        435                 440                 445

Pro Ala Val Val Ile Asp Thr Pro Gln Val Leu Asn Lys Leu His Ala
    450                 455                 460

Ala Gly Val Leu Pro His Asp Phe Val Val Leu Arg Tyr Gln Gly
465                 470                 475                 480

Pro Arg Ala Asn Gly Met Pro Glu Leu His Ser Met Ala Pro Leu Leu
                485                 490                 495

Gly Leu Leu Gln Asn Gln Gly Arg Arg Val Ala Leu Val Thr Asp Gly
            500                 505                 510

Arg Leu Ser Gly Ala Ser Gly Lys Phe Pro Ala Ala Ile His Met Thr
        515                 520                 525

Pro Glu Ala Ala Arg Gly Gly Pro Ile Gly Arg Val Arg Glu Gly Asp
    530                 535                 540

Ile Val Arg Leu Asp Gly Glu Ala Gly Thr Leu Glu Val Leu Val Ser
545                 550                 555                 560

Ala Glu Glu Trp Ala Ser Arg Glu Val Ala Pro Asn Thr Ala Leu Ala
                565                 570                 575

Gly Asn Asp Leu Gly Arg Asn Leu Phe Ala Ile Asn Arg Gln Val Val
            580                 585                 590

Gly Pro Ala Asp Gln Gly Ala Ile Ser Ile Ser Cys Gly Pro Thr His
        595                 600                 605

Pro Asp Gly Ala Leu Trp Ser Tyr Asp Ala Glu Tyr Glu Leu Gly Ala
    610                 615                 620

Asp Ala Ala Ala Ala Ala Pro His Glu Ser Lys Asp Ala
625                 630                 635

<210> SEQ ID NO 434
<211> LENGTH: 1827
<212> TYPE: DNA
<213> ORGANISM: Pseudomonas syringae
```

<400> SEQUENCE: 434

```
atgcatcccc gcgtccttga agtaaccgag cggctcattg ctcgcagtcg cgatacccgt    60
cagcgctacc ttcaattgat tcgaggcgca gcgagcgatg gcccgatgcg cggcaagctt   120
caatgtgcca actttgctca cggcgtcgcc gcctgcggac cggaggacaa gcaaagcctg   180
cgtttgatga acgccgccaa cgtggcaatc gtctcttcct acaatgaaat gctctcggcg   240
catcagccct acgagcactt tcctgcacag atcaaacagg cgttacgtga cattggttcg   300
gtcggtcagt ttgccggcgg cgtgcctgcc atgtgcgatg gcgtgactca gggtgagccg   360
ggcatggaac tggccattgc cagccgcgaa gtgattgcca tgtccacggc aattgccttg   420
tcacacaata tgttcgacgc cgccatgatg ctgggtatct gcgacaagat cgtccccggc   480
ctgatgatgg gggcgttgcg tttcggtcat ctgccgacca tcttcgtgcc gggcgggccg   540
atggtgtcag gtatctccaa caaggaaaaa gccgacgtac ggcagcgtta cgctgaaggc   600
aaggccagcc gtgaagagct gctggactcg gaaatgaagt cctatcacgg cccgggaacc   660
tgcacgttct acggcaccgc caacaccaat cagttggtga tggaagtcat gggcatgcac   720
cttcccggtg cctcgttcgt caatccctac acaccactgc gtgatgcgct gacagctgaa   780
gcggctcgtc aggtcacgcg tctgaccatg caaagcggca gtttcatgcc gattggtgaa   840
atcgtcgacg agcgctcgct ggtcaattcc atcgttgcgc tgcacgccac cggcggctcg   900
accaaccaca cgctgcacat gccggcgatt gctcaggctg cgggtattca gctgacctgg   960
caggacatgg ccgacctctc cgaagtggtg ccgaccctca gtcacgtcta ccccaacggc  1020
aaggccgaca tcaaccattt ccaggccgca ggcggcatgt cgttcctgat cgcgagctg   1080
ctggcagccg gtctgctgca cgaaaacgtt aacaccgtgg ccggttatgg cctgagccgc  1140
tacaccaaag agccattcct ggaggatggc aaactggtct ggcgtgaagg cccgctggac  1200
agcctggatg aaaacatcct gcgcccggtg gcgcgtccgt ctcccctga aggcggtttg   1260
cgggtcatgg aaggcaacct gggtcgcggt gtcatgaaag tatcggccgt tgcgctggag  1320
catcagattg tcgaagcgcc agcccgagtg tttcaggatc agaaggagct ggccgatgcg  1380
ttcaaggccg gcgagctgga atgtgatttc gtcgccgtca tgcgttttca gggcccgcgc  1440
tgcaacggca tgcccgaact gcacaagatg accccgtttc tgggcgtgct gcaggatcgt  1500
ggtttcaaag tggcgctggt caccgatgga cggatgtcgg gcgcctcagg caagattccg  1560
gcggcgattc acgtctgccc ggaagcgttc gatggtggcc cgttggcact ggtacgcgac  1620
ggcgatgtga tccgcgtgga tggcgtaaaa ggcacgttac aagtgctggt cgaagcgtca  1680
gaattggccg cccgagaacc ggccatcaac cagatcgaca acagtgtcgg ctgcggtcgc  1740
gagcttttg gattcatgcg catggccttc agctccgcag agcaaggcgc cagcgccttt  1800
acctctagtc tggagacgct caagtga                                     1827
```

<210> SEQ ID NO 435
<211> LENGTH: 608
<212> TYPE: PRT
<213> ORGANISM: Pseudomonas syringae

<400> SEQUENCE: 435

```
Met His Pro Arg Val Leu Glu Val Thr Glu Arg Leu Ile Ala Arg Ser
1               5                   10                  15

Arg Asp Thr Arg Gln Arg Tyr Leu Gln Leu Ile Arg Gly Ala Ala Ser
            20                  25                  30

Asp Gly Pro Met Arg Gly Lys Leu Gln Cys Ala Asn Phe Ala His Gly
        35                  40                  45
```

```
Val Ala Ala Cys Gly Pro Glu Asp Lys Gln Ser Leu Arg Leu Met Asn
 50                  55                  60

Ala Ala Asn Val Ala Ile Val Ser Ser Tyr Asn Glu Met Leu Ser Ala
 65                      70                  75                  80

His Gln Pro Tyr Glu His Phe Pro Ala Gln Ile Lys Gln Ala Leu Arg
                     85                  90                  95

Asp Ile Gly Ser Val Gly Gln Phe Ala Gly Gly Val Pro Ala Met Cys
                100                 105                 110

Asp Gly Val Thr Gln Gly Glu Pro Gly Met Glu Leu Ala Ile Ala Ser
            115                 120                 125

Arg Glu Val Ile Ala Met Ser Thr Ala Ile Ala Leu Ser His Asn Met
            130                 135                 140

Phe Asp Ala Ala Met Met Leu Gly Ile Cys Asp Lys Ile Val Pro Gly
145                 150                 155                 160

Leu Met Met Gly Ala Leu Arg Phe Gly His Leu Pro Thr Ile Phe Val
                165                 170                 175

Pro Gly Gly Pro Met Val Ser Gly Ile Ser Asn Lys Glu Lys Ala Asp
                180                 185                 190

Val Arg Gln Arg Tyr Ala Glu Gly Lys Ala Ser Arg Glu Glu Leu Leu
            195                 200                 205

Asp Ser Glu Met Lys Ser Tyr His Gly Pro Gly Thr Cys Thr Phe Tyr
210                 215                 220

Gly Thr Ala Asn Thr Asn Gln Leu Val Met Glu Val Met Gly Met His
225                 230                 235                 240

Leu Pro Gly Ala Ser Phe Val Asn Pro Tyr Thr Pro Leu Arg Asp Ala
                245                 250                 255

Leu Thr Ala Glu Ala Ala Arg Gln Val Thr Arg Leu Thr Met Gln Ser
            260                 265                 270

Gly Ser Phe Met Pro Ile Gly Glu Ile Val Asp Glu Arg Ser Leu Val
            275                 280                 285

Asn Ser Ile Val Ala Leu His Ala Thr Gly Gly Ser Thr Asn His Thr
290                 295                 300

Leu His Met Pro Ala Ile Ala Gln Ala Ala Gly Ile Gln Leu Thr Trp
305                 310                 315                 320

Gln Asp Met Ala Asp Leu Ser Glu Val Val Pro Thr Leu Ser His Val
                325                 330                 335

Tyr Pro Asn Gly Lys Ala Asp Ile Asn His Phe Gln Ala Ala Gly Gly
            340                 345                 350

Met Ser Phe Leu Ile Arg Glu Leu Leu Ala Ala Gly Leu Leu His Glu
            355                 360                 365

Asn Val Asn Thr Val Ala Gly Tyr Gly Leu Ser Arg Tyr Thr Lys Glu
370                 375                 380

Pro Phe Leu Glu Asp Gly Lys Leu Val Trp Arg Glu Gly Pro Leu Asp
385                 390                 395                 400

Ser Leu Asp Glu Asn Ile Leu Arg Pro Val Ala Arg Pro Phe Ser Pro
                405                 410                 415

Glu Gly Gly Leu Arg Val Met Glu Gly Asn Leu Gly Arg Gly Val Met
            420                 425                 430

Lys Val Ser Ala Val Ala Leu Glu His Gln Ile Val Glu Ala Pro Ala
            435                 440                 445

Arg Val Phe Gln Asp Gln Lys Glu Leu Ala Asp Ala Phe Lys Ala Gly
450                 455                 460

Glu Leu Glu Cys Asp Phe Val Ala Val Met Arg Phe Gln Gly Pro Arg
```

```
                       465                 470                 475                 480
    Cys Asn Gly Met Pro Glu Leu His Lys Met Thr Pro Phe Leu Gly Val
                   485                 490                 495

Leu Gln Asp Arg Gly Phe Lys Val Ala Leu Val Thr Asp Gly Arg Met
                500                 505                 510

Ser Gly Ala Ser Gly Lys Ile Pro Ala Ala Ile His Val Cys Pro Glu
                515                 520                 525

Ala Phe Asp Gly Pro Leu Ala Leu Val Arg Asp Gly Asp Val Ile
                530                 535                 540

Arg Val Asp Gly Val Lys Gly Thr Leu Gln Val Leu Val Glu Ala Ser
    545                 550                 555                 560

Glu Leu Ala Ala Arg Glu Pro Ala Ile Asn Gln Ile Asp Asn Ser Val
                    565                 570                 575

Gly Cys Gly Arg Glu Leu Phe Gly Phe Met Arg Met Ala Phe Ser Ser
                    580                 585                 590

Ala Glu Gln Gly Ala Ser Ala Phe Thr Ser Ser Leu Glu Thr Leu Lys
                    595                 600                 605

<210> SEQ ID NO 436
<211> LENGTH: 1827
<212> TYPE: DNA
<213> ORGANISM: Pseudomonas fluorescens

<400> SEQUENCE: 436
atgcatcccc gcgttcttga ggtcaccgaa cggcttatcg cccgtagtcg cgccactcgc     60
caggcctatc tcgcgctgat ccgcgatgcc gccagcgacg gcccgcagcg gggcaagctg    120
caatgtgcga acttcgccca cggcgtggcc ggttgcggca ccgacgacaa gcacaacctg    180
cggatgatga atgcggccaa cgtggcaatt gtttcgtcat ataacgacat gttgtcggcg    240
caccagcctt acgaggtgtt ccccgagcag atcaagcgcg ccctgcgcga gatcggctcg    300
gtgggccagt tcgccggcgg cacccccggcc atgtgcgatg gcgtgaccca gggcgaggcc    360
ggtatggaac tgagcctgcc gagccgtgaa gtgatcgccc tgtctacggc ggtggccctc    420
tctcacaaca tgttcgatgc cgcgctgatg ctggggatct gcgacaagat tgtcccgggg    480
ttgatgatgg gcgctctgcg cttcggtcac ctgccgacca tcttcgttcc gggcgggccc    540
atggtctcgg gcatttccaa caagcagaaa gccgacgtgc ccagcgtta cgccgaaggc    600 aaggccagcc gcgaggaact gctggagtcg gaaatgaagt cctaccacag ccccggcacc    660
tgcactttct acggcaccgc caacaccaac cagttgctga tggaagtgat gggcctgcac    720
ctgccgggcg cctctttcgt caaccccaat cgccgctgc gcgacgccct gacccatgag    780
gcggcgcagc aggtcacgcg cctgaccaag cagagcgggg ccttcatgcc gattggcgag    840
atcgtcgacg agcgcgtgct ggtcaactcc atcgttgccc tgcacgccac gggcggctcc    900
accaaccaca ccctgcacat gccggccatc gcccaggcgg cgggcatcca gctgacctgg    960
caggacatgg ccgacctctc cgaggtggtg ccgaccctgt ccacgtctta tccaaacggc   1020
aaggccgata tcaaccactt ccaggcggcg ggcggcatgt cttttcctgat ccgcgagctg   1080 ctggaagccg gcctgctcca cgaagacgtc aataccgtgg ccggccgcgg cctgagccgc   1140 tatcccagg aacccttcct ggacaacggc aagctggtgt ggcgcgacgg cccgattgaa   1200
agcctggacg aaaacatcct cgcccggtg gcccgggcgt tctctgcgga gggcggcttg   1260
cgggtcatgg aaggcaacct cggtcgcggc gtgatgaagg tttccgccgt ggccccggag   1320
caccagatcg tcgaggcccc ggccgtggtg ttccaggacc agcaggacct ggccgatgcc   1380
```

-continued

```
ttcaaggccg gcctgctgga gaaggacttc gtcgcggtga tgcgcttcca gggcccgcgc    1440
tccaacggca tgcccgagct gcacaagatg acccccttcc tcggggtgct gcaggaccgc    1500
ggcttcaagg tggcgctggt caccgacggg cgcatgtccg gcgcttcggg caagattccg    1560
gcagcgatcc atgtcagccc cgaagcccag gtgggtggcg cgctggcccg ggtgctggac    1620
ggcgatatca tccgagtgga tggcgtcaag ggcaccctgg agcttaaggt agacgccgca    1680
gaattcgccg cccgggagcc ggccaagggc ctgctgggca caacgttgg caccggccgc     1740 gaactcttcg ccttcatgcg catggccttc agctcggcag agcagggcgc cagcgccttt    1800
acctctgccc tggagacgct caagtga                                        1827
```

<210> SEQ ID NO 437
<211> LENGTH: 608
<212> TYPE: PRT
<213> ORGANISM: Pseudomonas fluorescens

<400> SEQUENCE: 437

```
Met His Pro Arg Val Leu Glu Val Thr Glu Arg Leu Ile Ala Arg Ser
1               5                   10                  15

Arg Ala Thr Arg Gln Ala Tyr Leu Ala Leu Ile Arg Asp Ala Ala Ser
                20                  25                  30

Asp Gly Pro Gln Arg Gly Lys Leu Gln Cys Ala Asn Phe Ala His Gly
            35                  40                  45

Val Ala Gly Cys Gly Thr Asp Asp Lys His Asn Leu Arg Met Met Asn
        50                  55                  60

Ala Ala Asn Val Ala Ile Val Ser Ser Tyr Asn Asp Met Leu Ser Ala
65                  70                  75                  80

His Gln Pro Tyr Glu Val Phe Pro Glu Gln Ile Lys Arg Ala Leu Arg
                85                  90                  95

Glu Ile Gly Ser Val Gly Gln Phe Ala Gly Gly Thr Pro Ala Met Cys
            100                 105                 110

Asp Gly Val Thr Gln Gly Glu Ala Gly Met Glu Leu Ser Leu Pro Ser
        115                 120                 125

Arg Glu Val Ile Ala Leu Ser Thr Ala Val Ala Leu Ser His Asn Met
    130                 135                 140

Phe Asp Ala Ala Leu Met Leu Gly Ile Cys Asp Lys Ile Val Pro Gly
145                 150                 155                 160

Leu Met Met Gly Ala Leu Arg Phe Gly His Leu Pro Thr Ile Phe Val
                165                 170                 175

Pro Gly Gly Pro Met Val Ser Gly Ile Ser Asn Lys Gln Lys Ala Asp
            180                 185                 190

Val Arg Gln Arg Tyr Ala Glu Gly Lys Ala Ser Arg Glu Glu Leu Leu
        195                 200                 205

Glu Ser Glu Met Lys Ser Tyr His Ser Pro Gly Thr Cys Thr Phe Tyr
    210                 215                 220

Gly Thr Ala Asn Thr Asn Gln Leu Leu Met Glu Val Met Gly Leu His
225                 230                 235                 240

Leu Pro Gly Ala Ser Phe Val Asn Pro Asn Thr Pro Leu Arg Asp Ala
                245                 250                 255

Leu Thr His Glu Ala Ala Gln Gln Val Thr Arg Leu Thr Lys Gln Ser
            260                 265                 270

Gly Ala Phe Met Pro Ile Gly Glu Ile Val Asp Glu Arg Val Leu Val
        275                 280                 285

Asn Ser Ile Val Ala Leu His Ala Thr Gly Gly Ser Thr Asn His Thr
    290                 295                 300
```

```
Leu His Met Pro Ala Ile Ala Gln Ala Gly Ile Gln Leu Thr Trp
305                 310                 315                 320

Gln Asp Met Ala Asp Leu Ser Glu Val Val Pro Thr Leu Ser His Val
            325                 330                 335

Tyr Pro Asn Gly Lys Ala Asp Ile Asn His Phe Gln Ala Ala Gly Gly
        340                 345                 350

Met Ser Phe Leu Ile Arg Glu Leu Leu Glu Ala Gly Leu Leu His Glu
    355                 360                 365

Asp Val Asn Thr Val Ala Gly Arg Gly Leu Ser Arg Tyr Thr Gln Glu
370                 375                 380

Pro Phe Leu Asp Asn Gly Lys Leu Val Trp Arg Asp Gly Pro Ile Glu
385                 390                 395                 400

Ser Leu Asp Glu Asn Ile Leu Arg Pro Val Ala Arg Ala Phe Ser Ala
            405                 410                 415

Glu Gly Gly Leu Arg Val Met Glu Gly Asn Leu Gly Arg Gly Val Met
        420                 425                 430

Lys Val Ser Ala Val Ala Pro Glu His Gln Ile Val Glu Ala Pro Ala
    435                 440                 445

Val Val Phe Gln Asp Gln Gln Asp Leu Ala Asp Ala Phe Lys Ala Gly
450                 455                 460

Leu Leu Glu Lys Asp Phe Val Ala Val Met Arg Phe Gln Gly Pro Arg
465                 470                 475                 480

Ser Asn Gly Met Pro Glu Leu His Lys Met Thr Pro Phe Leu Gly Val
            485                 490                 495

Leu Gln Asp Arg Gly Phe Lys Val Ala Leu Val Thr Asp Gly Arg Met
        500                 505                 510

Ser Gly Ala Ser Gly Lys Ile Pro Ala Ala Ile His Val Ser Pro Glu
    515                 520                 525

Ala Gln Val Gly Gly Ala Leu Ala Arg Val Leu Asp Gly Asp Ile Ile
530                 535                 540

Arg Val Asp Gly Val Lys Gly Thr Leu Glu Leu Lys Val Asp Ala Ala
545                 550                 555                 560

Glu Phe Ala Ala Arg Glu Pro Ala Lys Gly Leu Leu Gly Asn Asn Val
            565                 570                 575

Gly Thr Gly Arg Glu Leu Phe Ala Phe Met Arg Met Ala Phe Ser Ser
        580                 585                 590

Ala Glu Gln Gly Ala Ser Ala Phe Thr Ser Ala Leu Glu Thr Leu Lys
    595                 600                 605

<210> SEQ ID NO 438
<211> LENGTH: 1677
<212> TYPE: DNA
<213> ORGANISM: Bacillus subtilis

<400> SEQUENCE: 438
atggcagaat tacgcagtaa tatgatcaca caaggaatcg atagagctcc gcaccgcagt      60
ttgcttcgtg cagcagggt aaaagaagag gatttcggca agccgtttat tgcggtgtgt     120
aattcataca ttgatatcgt tcccggtcat gttcacttgc aggagtttgg gaaaatcgta     180
aaagaagcaa tcagagaagc aggggcgtt ccgtttgaat ttaataccat ggggtagat       240 gatggcatcg caatggggca tatcggtatg agatattcgc tgccaagccg tgaaattatc     300
gcagactctg tggaaacggt tgtatccgca cactggtttg acggaatggt ctgtattccg     360
aactgcgaca aaatcacacc gggaatgctt atggcggcaa tgcgcatcaa cattccgacg     420
```

```
atttttgtca gcggcggacc gatggcggca ggaagaacaa gttacgggcg aaaaatctcc   480
ctttcctcag tattcgaagg ggtaggcgcc taccaagcag ggaaaatcaa cgaaaacgag   540
cttcaagaac tagagcagtt cggatgccca acgtgcgggt cttgctcagg catgtttacg   600
gcgaactcaa tgaactgtct gtcagaagca cttggtcttg ctttgccggg taatggaacc   660
attctggcaa catctccgga acgcaaagag tttgtgagaa atcggctgc gcaattaatg    720
gaaacgattc gcaaagatat caaaccgcgt gatattgtta cagtaaaagc gattgataac   780
gcgtttgcac tcgatatggc gctcggaggt tctacaaata ccgttcttca taccctttgcc  840
cttgcaaacg aagccggcgt tgaatactct ttagaacgca ttaacgaagt cgctgagcgc   900
gtgccgcact tggctaagct ggcgcctgca tcggatgtgt ttattgaaga tcttcacgaa   960
gcgggcggcg tttcagcggc tctgaatgag ctttcgaaga agaaggagc gcttcattta   1020
gatgcgctga ctgttacagg aaaaaactctt ggagaaacca ttgccggaca tgaagtaaag  1080
gattatgacg tcattcaccc gctggatcaa ccattcactg aaaagggagg ccttgctgtt  1140
ttattcggta atctagctcc ggacggcgct atcattaaaa caggcggcgt acagaatggg   1200
attacaagac acgaagggcc ggctgtcgta ttcgattctc aggacgaggc gcttgacggc   1260
attatcaacc gaaaagtaaa agaaggcgac gttgtcatca tcagatacga agggccaaaa   1320
ggcggacctg gcatgccgga aatgctggcg ccaacatccc aaatcgttgg aatgggactc   1380
gggccaaaag tggcattgat tacggacgga cgttttttccg gagcctcccg tggcctctca   1440
atcggccacg tatcacctga ggccgctgag ggcgggccgc ttgcctttgt tgaaaacgga   1500
gaccatatta tcgttgatat tgaaaaacgc atcttggatg tacaagtgcc agaagaagag   1560
tgggaaaaac gaaaagcgaa ctggaaaggt tttgaaccga agtgaaaaac cggctacctg   1620
gcacgttatt ctaaacttgt gacaagtgcc aacaccggcg gtattatgaa aatctag      1677
```

<210> SEQ ID NO 439
<211> LENGTH: 558
<212> TYPE: PRT
<213> ORGANISM: Bacillus subtilis

<400> SEQUENCE: 439

```
Met Ala Glu Leu Arg Ser Asn Met Ile Thr Gln Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
65                  70                  75                  80

Asp Gly Ile Ala Met Gly His Ile Gly Met Arg Tyr Ser Leu Pro Ser
                85                  90                  95

Arg Glu Ile Ile Ala Asp Ser Val Glu Thr Val Val Ser Ala His Trp
            100                 105                 110

Phe Asp Gly Met Val Cys Ile Pro Asn Cys Asp Lys Ile Thr Pro Gly
        115                 120                 125

Met Leu Met Ala Ala Met Arg Ile Asn Ile Pro Thr Ile Phe Val Ser
    130                 135                 140

Gly Gly Pro Met Ala Ala Gly Arg Thr Ser Tyr Gly Arg Lys Ile Ser
145                 150                 155                 160
```

Leu Ser Ser Val Phe Glu Gly Val Gly Ala Tyr Gln Ala Gly Lys Ile
            165                 170                 175

Asn Glu Asn Glu Leu Gln Glu Leu Glu Gln Phe Gly Cys Pro Thr Cys
        180                 185                 190

Gly Ser Cys Ser Gly Met Phe Thr Ala Asn Ser Met Asn Cys Leu Ser
            195                 200                 205

Glu Ala Leu Gly Leu Ala Leu Pro Gly Asn Gly Thr Ile Leu Ala Thr
    210                 215                 220

Ser Pro Glu Arg Lys Glu Phe Val Arg Lys Ser Ala Ala Gln Leu Met
225                 230                 235                 240

Glu Thr Ile Arg Lys Asp Ile Lys Pro Arg Asp Ile Val Thr Val Lys
            245                 250                 255

Ala Ile Asp Asn Ala Phe Ala Leu Asp Met Ala Leu Gly Gly Ser Thr
        260                 265                 270

Asn Thr Val Leu His Thr Leu Ala Leu Ala Asn Glu Ala Gly Val Glu
        275                 280                 285

Tyr Ser Leu Glu Arg Ile Asn Glu Val Ala Glu Arg Val Pro His Leu
    290                 295                 300

Ala Lys Leu Ala Pro Ala Ser Asp Val Phe Ile Glu Asp Leu His Glu
305                 310                 315                 320

Ala Gly Gly Val Ser Ala Ala Leu Asn Glu Leu Ser Lys Lys Glu Gly
            325                 330                 335

Ala Leu His Leu Asp Ala Leu Thr Val Thr Gly Lys Thr Leu Gly Glu
        340                 345                 350

Thr Ile Ala Gly His Glu Val Lys Asp Tyr Asp Val Ile His Pro Leu
        355                 360                 365

Asp Gln Pro Phe Thr Glu Lys Gly Gly Leu Ala Val Leu Phe Gly Asn
    370                 375                 380

Leu Ala Pro Asp Gly Ala Ile Ile Lys Thr Gly Gly Val Gln Asn Gly
385                 390                 395                 400

Ile Thr Arg His Glu Gly Pro Ala Val Val Phe Asp Ser Gln Asp Glu
            405                 410                 415

Ala Leu Asp Gly Ile Ile Asn Arg Lys Val Lys Glu Gly Asp Val Val
        420                 425                 430

Ile Ile Arg Tyr Glu Gly Pro Lys Gly Gly Pro Gly Met Pro Glu Met
    435                 440                 445

Leu Ala Pro Thr Ser Gln Ile Val Gly Met Gly Leu Gly Pro Lys Val
    450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Glu Gly Gly Pro Leu Ala Phe
            485                 490                 495

Val Glu Asn Gly Asp His Ile Ile Val Asp Ile Glu Lys Arg Ile Leu
        500                 505                 510

Asp Val Gln Val Pro Glu Glu Glu Trp Glu Lys Arg Lys Ala Asn Trp
    515                 520                 525

Lys Gly Phe Glu Pro Lys Val Lys Thr Gly Tyr Leu Ala Arg Tyr Ser
530                 535                 540

Lys Leu Val Thr Ser Ala Asn Thr Gly Gly Ile Met Lys Ile
545                 550                 555

<210> SEQ ID NO 440
<211> LENGTH: 1677
<212> TYPE: DNA
<213> ORGANISM: Bacillus licheniformis

<400> SEQUENCE: 440

```
atgacaggtt tacgcagtga catgattaca aaagggatcg acagagcgcc gcaccgcagt      60
ttgctgcgcg cggctggggt aaaagaagag gacttcggca aaccgtttat tgccgtttgc     120
aactcataca tcgatatcgt accgggtcat gtccatttgc aggagtttgg aaaaatcgtc     180
aaagaggcga tcagagaggc cggcggtgtt ccgtttgaat ttaatacaat cggggtcgac     240
gacggaattg cgatggggca catcggaatg aggtattctc tcccgagccg cgaaatcatc     300
gcagattcag tggaaacggt tgtatcggcg cactggtttg acggaatggt atgtattcca     360
aactgtgata aaatcacacc gggcatgatc atggcggcaa tgcggatcaa cattccgacc     420
gtgtttgtca gcggggggcc gatggaagcg gaagaacga gcgacggacg aaaaatctcg     480
ctttcctctg tatttgaagg cgttggcgct tatcaatcag gcaaaatcga tgagaaagga     540
ctcgaggagc ttgaacagtt cggctgtccg acttgcggat catgctcggg catgtttacg     600
gcgaactcga tgaactgtct ttctgaagct cttggcatcg ccatgccggg caacggcacc     660
attttggcga catcgcccga ccgcagggaa tttgccaaac agtcggcccg ccagctgatg     720
gagctgatca agtcggatat caaaccgcgc gacatcgtga ccgaaaaagc gatcgacaac     780
gcgttcgctt tagacatggc gctcggcgga tcaacgaata cgatccttca tacgcttgcg     840
atcgccaatg aagcgggtgt agactattcg cttgaacgga tcaatgaggt agcggcaagg     900
gttccgcatt tatcgaagct tgcaccggct tccgatgtgt ttattgaaga tttgcatgaa     960
gcaggaggcg tatcggcagt cttaaacgag ctgtcgaaaa aagaaggcgc gcttcacttg    1020
gatacgctga ctgtaacggg gaaaacgctt ggcgaaaata ttgccggacg cgaagtgaaa    1080
gattacgagg tcattcatcc gatcgatcag ccgtttttcag agcaaggcgg actcgccgtc    1140
ctgttcggca acctggctcc tgacggtgcg atcattaaaa cgggcggcgt ccaagacggg    1200
attcccgcc atgaaggacc tgcggttgtc tttgattcac aggaagaagc gcttgacggc    1260
atcatcaacc gtaaagtaaa agcgggagat gtcgtcatca tccgctatga aggccctaaa    1320
ggcggaccgg gaatgcctga aatgcttgcg ccgacttcac agatcgtcgg aatgggcctc    1380
ggcccgaaag tcgccttgat taccgacggc cgcttttcag gagcctcccg cggtctttcg    1440
atcggccacg tttcaccgga agcagccgaa ggcggcccgc ttgctttcgt agaaaacggc    1500
gaccatatcg ttgtcgatat cgaaaagcgg attttaaaca tcgaaatctc cgatgaggaa    1560
tgggaaaaaa gaaagcaaa ctggcccggc tttgaaccga aagtgaaaac gggctatctc    1620
gccaggtatt caaagcttgt gacatctgcc aataccggcg gcattatgaa aatctag       1677
```

<210> SEQ ID NO 441
<211> LENGTH: 558
<212> TYPE: PRT
<213> ORGANISM: Bacillus licheniformis

<400> SEQUENCE: 441

```
Met Thr Gly Leu Arg Ser Asp Met Ile Thr Lys Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
```

```
              65                  70                  75                  80
Asp Gly Ile Ala Met Gly His Ile Gly Met Arg Tyr Ser Leu Pro Ser
                    85                  90                  95

Arg Glu Ile Ile Ala Asp Ser Val Glu Thr Val Ser Ala His Trp
                100                 105                 110

Phe Asp Gly Met Val Cys Ile Pro Asn Cys Asp Lys Ile Thr Pro Gly
                115                 120                 125

Met Ile Met Ala Ala Met Arg Ile Asn Ile Pro Thr Val Phe Val Ser
        130                 135                 140

Gly Gly Pro Met Glu Ala Gly Arg Thr Ser Asp Gly Arg Lys Ile Ser
145                 150                 155                 160

Leu Ser Ser Val Phe Glu Gly Val Gly Ala Tyr Gln Ser Gly Lys Ile
                    165                 170                 175

Asp Glu Lys Gly Leu Glu Glu Leu Glu Gln Phe Gly Cys Pro Thr Cys
                180                 185                 190

Gly Ser Cys Ser Gly Met Phe Thr Ala Asn Ser Met Asn Cys Leu Ser
                195                 200                 205

Glu Ala Leu Gly Ile Ala Met Pro Gly Asn Gly Thr Ile Leu Ala Thr
        210                 215                 220

Ser Pro Asp Arg Arg Glu Phe Ala Lys Gln Ser Ala Arg Gln Leu Met
225                 230                 235                 240

Glu Leu Ile Lys Ser Asp Ile Lys Pro Arg Asp Ile Val Thr Glu Lys
                    245                 250                 255

Ala Ile Asp Asn Ala Phe Ala Leu Asp Met Ala Leu Gly Gly Ser Thr
                260                 265                 270

Asn Thr Ile Leu His Thr Leu Ala Ile Ala Asn Glu Ala Gly Val Asp
                275                 280                 285

Tyr Ser Leu Glu Arg Ile Asn Glu Val Ala Ala Arg Val Pro His Leu
        290                 295                 300

Ser Lys Leu Ala Pro Ala Ser Asp Val Phe Ile Glu Asp Leu His Glu
305                 310                 315                 320

Ala Gly Gly Val Ser Ala Val Leu Asn Glu Leu Ser Lys Lys Glu Gly
                    325                 330                 335

Ala Leu His Leu Asp Thr Leu Thr Val Thr Gly Lys Thr Leu Gly Glu
                340                 345                 350

Asn Ile Ala Gly Arg Glu Val Lys Asp Tyr Glu Val Ile His Pro Ile
                355                 360                 365

Asp Gln Pro Phe Ser Glu Gln Gly Gly Leu Ala Val Leu Phe Gly Asn
        370                 375                 380

Leu Ala Pro Asp Gly Ala Ile Ile Lys Thr Gly Gly Val Gln Asp Gly
385                 390                 395                 400

Ile Thr Arg His Glu Gly Pro Ala Val Val Phe Asp Ser Gln Glu Glu
                    405                 410                 415

Ala Leu Asp Gly Ile Ile Asn Arg Lys Val Lys Ala Gly Asp Val Val
                420                 425                 430

Ile Ile Arg Tyr Glu Gly Pro Lys Gly Gly Pro Gly Met Pro Glu Met
                435                 440                 445

Leu Ala Pro Thr Ser Gln Ile Val Gly Met Gly Leu Gly Pro Lys Val
        450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Glu Gly Gly Pro Leu Ala Phe
                    485                 490                 495
```

```
Val Glu Asn Gly Asp His Ile Val Asp Ile Glu Lys Arg Ile Leu
            500                 505                 510
Asn Ile Glu Ile Ser Asp Glu Trp Glu Lys Arg Lys Ala Asn Trp
            515                 520                 525
Pro Gly Phe Glu Pro Lys Val Lys Thr Gly Tyr Leu Ala Arg Tyr Ser
            530                 535                 540
Lys Leu Val Thr Ser Ala Asn Thr Gly Gly Ile Met Lys Ile
545                 550                 555

<210> SEQ ID NO 442
<211> LENGTH: 1827
<212> TYPE: DNA
<213> ORGANISM: Sewanella oneidensis

<400> SEQUENCE: 442
atgcactcag tcgttcaatc tgttactgac agaattattg cccgtagcaa agcatctcgt        60
gaagcatacc ttgctgcgtt aaacgatgcc cgtaaccatg gtgtacaccg aagttcctta       120
agttgcggta acttagccca cggttttgcg gcttgtaatc ccgatgacaa aaatgcattg       180
cgtcaattga cgaaggccaa tattgggatt atcaccgcat tcaacgatat gttatctgca       240
caccaaccct atgaaaccta tcctgatttg ctgaaaaaag cctgtcagga agtcggtagt       300
gttgcgcagg tggctggcgg tgttcccgcc atgtgtgacg gcgtgactca aggtcagccc       360
ggtatggaat tgagcttact gagccgtgaa gtgattgcga tggcaaccgc ggttggctta       420
tcacacaata tgtttgatgg agccttactc tcggtatttt gcgataaaat tgtaccgggt       480
ttactgattg gtgccttaag ttttggccat ttacctatgt tgtttgtgcc cgcaggccca       540
atgaaatcgg gtattcctaa taaggaaaaa gctcgcattc gtcagcaatt tgctcaaggt       600
aaggtcgata gagcacaact gctcgaagcg gaagcccagt cttaccacag tgcgggtact       660
tgtaccttct atggtaccgc taactcgaac caactgatgc tcgaagtgat ggggctgcaa       720
ttgccgggtt catcttttgt gaatccagac gatccactgc gcgaagcctt aaacaaaatg       780
gcggccaagc aggtttgtcg tttaactgaa ctaggcactc aatacagtcc gattggtgaa       840
gtcgttaacg aaaaatcgat agtgaatggt attgttgcat tgctcgcgac gggtggttca       900
acaaacttaa ccatgcacat tgtggcggcg gcccgtgctg caggtattat cgtcaactgg       960
gatgactttt cggaattatc cgatgcggtg cctttgctgg cacgtgttta tccaaacggt      1020
catgcggata ttaaccattt ccacgctgcg ggtggtatgg ctttccttat caagaattac      1080
ctcgatgcag tttgctgca tgaggatgtc aatactgtcg cgggttatgg tctgcgccgt      1140
tacacccaag agcctaaact gcttgatggc gagctgcgct gggtcgatgg cccaacagtg      1200
agtttagata ccgaagtatt aacctctgtg caacaccat tccaaaacaa cggtggttta      1260
aagctgctga agggtaactt aggccgcgct gtgattaaag tgtctgccgt tcagccacag      1320
caccgtgtgg tggaagcgcc cgcagtggtg attgacgatc aaaacaaact cgatgcgtta      1380
tttaaatccg gcgcattaga cagggattgt gtggtggtgg tgaaaggcca agggccgaaa      1440
gccaacggta tgccagagct gcataaaacta acgccgctgt taggttcatt gcaggacaaa      1500
ggctttaaag tggcactgat gactgatggt cgtatgtcgg gcgcatcggg caaagtacct      1560
gcggcgattc atttaacccc tgaagcgatt gatggcgggt taattgcaaa ggtacaagac      1620
ggcgatttaa tccgagttga tgcactgacc ggcgagctga gtttattagt ctctgacacc      1680
gagcttgcca ccagaactgc cactgaaatt gatttacgcc attctcgtta tggcatgggg      1740
cgtgagttat ttggagtact gcgttcaaac ttaagcagtc tgaaaccggt gcgcgtagt       1800
```
actagcgcca tcgatgaact ttactaa                                           1827

<210> SEQ ID NO 443
<211> LENGTH: 608
<212> TYPE: PRT
<213> ORGANISM: Sewanella oneidensis

<400> SEQUENCE: 443

Met His Ser Val Val Gln Ser Val Thr Asp Arg Ile Ile Ala Arg Ser
1               5                   10                  15

Lys Ala Ser Arg Glu Ala Tyr Leu Ala Ala Leu Asn Asp Ala Arg Asn
            20                  25                  30

His Gly Val His Arg Ser Ser Leu Ser Cys Gly Asn Leu Ala His Gly
        35                  40                  45

Phe Ala Ala Cys Asn Pro Asp Asp Lys Asn Ala Leu Arg Gln Leu Thr
    50                  55                  60

Lys Ala Asn Ile Gly Ile Ile Thr Ala Phe Asn Asp Met Leu Ser Ala
65                  70                  75                  80

His Gln Pro Tyr Glu Thr Tyr Pro Asp Leu Leu Lys Lys Ala Cys Gln
                85                  90                  95

Glu Val Gly Ser Val Ala Gln Val Ala Gly Val Pro Ala Met Cys
            100                 105                 110

Asp Gly Val Thr Gln Gly Gln Pro Gly Met Glu Leu Ser Leu Leu Ser
        115                 120                 125

Arg Glu Val Ile Ala Met Ala Thr Ala Val Gly Leu Ser His Asn Met
    130                 135                 140

Phe Asp Gly Ala Leu Leu Gly Ile Cys Asp Lys Ile Val Pro Gly
145                 150                 155                 160

Leu Leu Ile Gly Ala Leu Ser Phe Gly His Leu Pro Met Leu Phe Val
                165                 170                 175

Pro Ala Gly Pro Met Lys Ser Gly Ile Pro Asn Lys Glu Lys Ala Arg
            180                 185                 190

Ile Arg Gln Gln Phe Ala Gln Gly Lys Val Asp Arg Ala Gln Leu Leu
        195                 200                 205

Glu Ala Glu Ala Gln Ser Tyr His Ser Ala Gly Thr Cys Thr Phe Tyr
    210                 215                 220

Gly Thr Ala Asn Ser Asn Gln Leu Met Leu Glu Val Met Gly Leu Gln
225                 230                 235                 240

Leu Pro Gly Ser Ser Phe Val Asn Pro Asp Asp Pro Leu Arg Glu Ala
                245                 250                 255

Leu Asn Lys Met Ala Ala Lys Gln Val Cys Arg Leu Thr Glu Leu Gly
            260                 265                 270

Thr Gln Tyr Ser Pro Ile Gly Val Val Asn Glu Lys Ser Ile Val
        275                 280                 285

Asn Gly Ile Val Ala Leu Leu Ala Thr Gly Gly Ser Thr Asn Leu Thr
    290                 295                 300

Met His Ile Val Ala Ala Ala Arg Ala Ala Gly Ile Ile Val Asn Trp
305                 310                 315                 320

Asp Asp Phe Ser Glu Leu Ser Asp Ala Val Pro Leu Leu Ala Arg Val
                325                 330                 335

Tyr Pro Asn Gly His Ala Asp Ile Asn His Phe His Ala Ala Gly Gly
            340                 345                 350

Met Ala Phe Leu Ile Lys Glu Leu Leu Asp Ala Gly Leu Leu His Glu
        355                 360                 365

Asp Val Asn Thr Val Ala Gly Tyr Gly Leu Arg Arg Tyr Thr Gln Glu

```
         370              375              380
Pro Lys Leu Leu Asp Gly Glu Leu Arg Trp Val Asp Gly Pro Thr Val
385                 390                 395                 400

Ser Leu Asp Thr Glu Val Leu Thr Ser Val Ala Thr Pro Phe Gln Asn
                405                 410                 415

Asn Gly Gly Leu Lys Leu Leu Lys Gly Asn Leu Gly Arg Ala Val Ile
            420                 425                 430

Lys Val Ser Ala Val Gln Pro Gln His Arg Val Glu Ala Pro Ala
                435                 440                 445

Val Val Ile Asp Asp Gln Asn Lys Leu Asp Ala Leu Phe Lys Ser Gly
450                 455                 460

Ala Leu Asp Arg Asp Cys Val Val Val Lys Gly Gln Gly Pro Lys
465                 470                 475                 480

Ala Asn Gly Met Pro Glu Leu His Lys Leu Thr Pro Leu Leu Gly Ser
                485                 490                 495

Leu Gln Asp Lys Gly Phe Lys Val Ala Leu Met Thr Asp Gly Arg Met
                500                 505                 510

Ser Gly Ala Ser Gly Lys Val Pro Ala Ala Ile His Leu Thr Pro Glu
            515                 520                 525

Ala Ile Asp Gly Gly Leu Ile Ala Lys Val Gln Asp Gly Asp Leu Ile
530                 535                 540

Arg Val Asp Ala Leu Thr Gly Glu Leu Ser Leu Val Ser Asp Thr
545                 550                 555                 560

Glu Leu Ala Thr Arg Thr Ala Thr Glu Ile Asp Leu Arg His Ser Arg
                565                 570                 575

Tyr Gly Met Gly Arg Glu Leu Phe Gly Val Leu Arg Ser Asn Leu Ser
                580                 585                 590

Ser Pro Glu Thr Gly Ala Arg Ser Thr Ser Ala Ile Asp Glu Leu Tyr
            595                 600                 605

<210> SEQ ID NO 444
<211> LENGTH: 1848
<212> TYPE: DNA
<213> ORGANISM: Gluconobacter oxydans

<400> SEQUENCE: 444
atgtctctga atcccgtcgt cgagagcgtg actgcccgta tcatcgagcg ttcgaaagtc      60
tcccgtcgcc ggtatctcgc cctgatggag cgcaaccgcg ccaagggtgt gctccggccc     120
aagctggcct gcggtaatct ggcgcatgcc atcgcagcgt ccagccccga caagccggat     180
ctgatgcgtc ccaccgggac caatatcggc gtgatcacga cctataacga catgctctcg     240
gcgcatcagc cgtatggccg ctatcccgag cagatcaagc tgttcgcccg tgaagtcggt     300
gcgacggccc aggttgcagg cggcgcacca gcaatgtgtg atggtgtgac gcaggggcag     360
gagggcatgg aactctccct gttctcccgt gacgtgatcg ccatgtccac ggcggtcggg     420
ctgagccacg gcatgtttga gggcgtggcg ctgctgggca tctgtgacaa gattgtgccg     480
ggccttctga tgggcgcgct cgcgcttcgg catctcccgg ccatgctgat cccggcaggg     540
ccaatgccgt ccggtcttcc aaacaaggaa aagcagcgca tccgccagct ctatgtgcag     600
ggcaaggtcg gcaggacga gctgatgaa gcggaaaacg cctcctatca gcccgggc      660 acctgcacgt tctatggcac ggccaatacg aaccagatga tggtcgaaat catgggtctg     720
atgatgccgg actcggcttt catcaatccc aacacgaagc tgcgtcaggc aatgacccgc     780
tcgggtattc accgtctggc cgaaatcggc ctgaacggcg aggatgtgcg cccgctcgct     840
```

-continued

```
cattgcgtag acgaaaaggc catcgtgaat gcggcggtcg ggttgctggc gacgggtggt    900
tcgaccaacc attcgatcca tcttcctgct atcgcccgtg ccgctggtat cctgatcgac    960
tgggaagaca tcagccgcct gtcgtccgcg gttccgctga tcacccgtgt ttatccgagc   1020
ggttccgagg acgtgaacgc gttcaaccgc gtgggtggta tgccgaccgt gatcgccgaa   1080
ctgacgcgcg ccgggatgct gcacaaggac attctgacgg tctctcgtgg cggtttctcc   1140
gattatgccc gtcgcgcatc gctggaaggc gatgagatcg tctacaccca cgcgaagccg   1200
tccacggaca ccgatatcct gcgcgatgtg gctacgcctt ccggcccgga tgcggtatg    1260 cgcctgatga ctggtaatct gggccgcgcg atctacaaga gcagcgctat gcgcccgag    1320 cacctgaccg ttgaagcgcc ggcacgggtc ttccaggacc agcatgacgt cctcacggcc   1380
tatcagaatg gtgagcttga gcgtgatgtt gtcgtggtcg tccggttcca gggaccggaa   1440
gccaacggca tgccggagct tcacaagctg accccgactc tgggcgtgct tcaggatcgc   1500
ggcttcaagg tggccctgct gacggatgga cgcatgtccg gtgcgagcgg caaggtgccg   1560
gccgccattc atgtcggtcc cgaagcgcag gttggcggtc cgatcgcccg cgtgcgggac   1620
ggcgacatga tccgtgtctg cgcggtgacg ggacagatcg aggctctggt ggatgccgcc   1680
gagtgggaga gccgcaagcc ggtcccgccg ccgctcccgg cattgggaac gggccgcgaa   1740
ctgttcgcgc tgatgcgttc ggtgcatgat ccggccgagg ctggcggatc cgcgatgctg   1800
gcccagatgg atcgcgtgat cgaagccgtt ggcgacgaca ttcactaa              1848
```

<210> SEQ ID NO 445
<211> LENGTH: 615
<212> TYPE: PRT
<213> ORGANISM: Gluconobacter oxydans

<400> SEQUENCE: 445

```
Met Ser Leu Asn Pro Val Val Glu Ser Val Thr Ala Arg Ile Ile Glu
1               5                   10                  15

Arg Ser Lys Val Ser Arg Arg Tyr Leu Ala Leu Met Glu Arg Asn
            20                  25                  30

Arg Ala Lys Gly Val Leu Arg Pro Lys Leu Ala Cys Gly Asn Leu Ala
        35                  40                  45

His Ala Ile Ala Ala Ser Ser Pro Asp Lys Pro Asp Leu Met Arg Pro
    50                  55                  60

Thr Gly Thr Asn Ile Gly Val Ile Thr Thr Tyr Asn Asp Met Leu Ser
65                  70                  75                  80

Ala His Gln Pro Tyr Gly Arg Tyr Pro Glu Gln Ile Lys Leu Phe Ala
                85                  90                  95

Arg Glu Val Gly Ala Thr Ala Gln Val Ala Gly Gly Ala Pro Ala Met
            100                 105                 110

Cys Asp Gly Val Thr Gln Gly Gln Glu Gly Met Glu Leu Ser Leu Phe
        115                 120                 125

Ser Arg Asp Val Ile Ala Met Ser Thr Ala Val Gly Leu Ser His Gly
    130                 135                 140

Met Phe Glu Gly Val Ala Leu Leu Gly Ile Cys Asp Lys Ile Val Pro
145                 150                 155                 160

Gly Leu Leu Met Gly Ala Leu Arg Phe Gly His Leu Pro Ala Met Leu
                165                 170                 175

Ile Pro Ala Gly Pro Met Pro Ser Gly Leu Pro Asn Lys Glu Lys Gln
            180                 185                 190

Arg Ile Arg Gln Leu Tyr Val Gln Gly Lys Val Gly Gln Asp Glu Leu
        195                 200                 205
```

```
Met Glu Ala Glu Asn Ala Ser Tyr His Ser Pro Gly Thr Cys Thr Phe
    210                 215                 220

Tyr Gly Thr Ala Asn Thr Asn Gln Met Met Val Glu Ile Met Gly Leu
225                 230                 235                 240

Met Met Pro Asp Ser Ala Phe Ile Asn Pro Asn Thr Lys Leu Arg Gln
            245                 250                 255

Ala Met Thr Arg Ser Gly Ile His Arg Leu Ala Glu Ile Gly Leu Asn
            260                 265                 270

Gly Glu Asp Val Arg Pro Leu Ala His Cys Val Asp Glu Lys Ala Ile
            275                 280                 285

Val Asn Ala Ala Val Gly Leu Leu Ala Thr Gly Gly Ser Thr Asn His
        290                 295                 300

Ser Ile His Leu Pro Ala Ile Ala Arg Ala Ala Gly Ile Leu Ile Asp
305                 310                 315                 320

Trp Glu Asp Ile Ser Arg Leu Ser Ser Ala Val Pro Leu Ile Thr Arg
                325                 330                 335

Val Tyr Pro Ser Gly Ser Glu Asp Val Asn Ala Phe Asn Arg Val Gly
            340                 345                 350

Gly Met Pro Thr Val Ile Ala Glu Leu Thr Arg Ala Gly Met Leu His
            355                 360                 365

Lys Asp Ile Leu Thr Val Ser Arg Gly Gly Phe Ser Asp Tyr Ala Arg
370                 375                 380

Arg Ala Ser Leu Glu Gly Asp Glu Ile Val Tyr Thr His Ala Lys Pro
385                 390                 395                 400

Ser Thr Asp Thr Asp Ile Leu Arg Asp Val Ala Thr Pro Phe Arg Pro
                405                 410                 415

Asp Gly Gly Met Arg Leu Met Thr Gly Asn Leu Gly Arg Ala Ile Tyr
            420                 425                 430

Lys Ser Ser Ala Ile Ala Pro Glu His Leu Thr Val Glu Ala Pro Ala
            435                 440                 445

Arg Val Phe Gln Asp Gln His Asp Val Leu Thr Ala Tyr Gln Asn Gly
    450                 455                 460

Glu Leu Glu Arg Asp Val Val Val Val Arg Phe Gln Gly Pro Glu
465                 470                 475                 480

Ala Asn Gly Met Pro Glu Leu His Lys Leu Thr Pro Thr Leu Gly Val
            485                 490                 495

Leu Gln Asp Arg Gly Phe Lys Val Ala Leu Leu Thr Asp Gly Arg Met
        500                 505                 510

Ser Gly Ala Ser Gly Lys Val Pro Ala Ala Ile His Val Gly Pro Glu
    515                 520                 525

Ala Gln Val Gly Gly Pro Ile Ala Arg Val Arg Asp Gly Asp Met Ile
    530                 535                 540

Arg Val Cys Ala Val Thr Gly Gln Ile Glu Ala Leu Val Asp Ala Ala
545                 550                 555                 560

Glu Trp Glu Ser Arg Lys Pro Val Pro Pro Leu Pro Ala Leu Gly
                565                 570                 575

Thr Gly Arg Glu Leu Phe Ala Leu Met Arg Ser Val His Asp Pro Ala
            580                 585                 590

Glu Ala Gly Gly Ser Ala Met Leu Ala Gln Met Asp Arg Val Ile Glu
            595                 600                 605

Ala Val Gly Asp Asp Ile His
            610                 615
```

<210> SEQ ID NO 446
<211> LENGTH: 1665
<212> TYPE: DNA
<213> ORGANISM: Ruminococcus flavefaciens

<400> SEQUENCE: 446

```
atgagcgata attttttctg cgagggtgcg gataaagccc ctcagcgttc acttttcaat      60
gcactgggca tgactaaaga ggaaatgaag cgtcccctcg ttggtatcgt ttcttcctac     120
aatgagatcg ttcccggcca tatgaacatc gacaagctgg tcgaagccgt taagctgggt     180
gtagctatgg gcggcggcac tcctgttgtt ttccctgcta tcgctgtatg cgacggtatc     240
gctatgggtc acacaggcat gaagtacagc cttgttaccc gtgaccttat tgccgattct     300
acagagtgta tggctcttgc tcatcacttc gacgcactgg taatgatacc taactgcgac     360
aagaacgttc ccggcctgct tatggcggct gcacgtatca atgttcctac tgtattcgta     420
agcggcggcc ctatgcttgc aggccatgta aagggtaaga agacctctct ttcatccatg     480
ttcgaggctg taggcgctta cacagcaggc aagatagacg aggctgaact tgacgaattc     540
gagaacaaga cctgccctac ctgcggttca tgttcgggta tgtataccgc taactccatg     600
aactgcctca ctgaggtact gggtatgggt ctcagaggca acggcactat ccctgctgtt     660
tactccgagc gtatcaagct tgcaaagcag gcaggtatgc aggttatgga actctacaga     720
aagaatatcc gccctctcga tatcatgaca gagaaggctt tccagaacgc tctcacagct     780
gatatggctc ttggatgttc cacaaacagt atgctccatc ccctgctat cgccaacgaa      840
tgcggcataa atatcaacct tgacatggct aacgagataa cgccaagac tcctaacctc      900
tgccatcttg caccggcagg ccacacctac atggaagacc tcaacgaagc aggcggagtt     960
tatgcagttc tcaacgagct gagcaaaaag ggacttatca caccgactg catgactgtt      1020
acaggcaaga ccgtaggcga gaatatcaag ggctgcatca accgtgaccc tgagactatc     1080
cgtcctatcg acaacccata cagtgaaaca ggcggaatcg ccgtactcaa gggcaatctt     1140
gctcccgaca gatgtgttgt gaagagaagc gcagttgctc ccgaaatgct ggtacacaaa     1200
ggccctgcaa gagtattcga cagcgaggaa gaagctatca aggtcatcta tgagggcggt     1260
atcaaggcag gcgacgttgt tgttatccgt tacgaaggcc ctgcaggcgg ccccggcatg     1320
agagaaatgc tctctcctac atcagctata caggtgcag gtctcggctc aactgttgct      1380
ctaatcactg acggacgttt cagcggcgct acccgtggtg cggctatcgg acacgtatcc     1440
cccgaagctg taaacggcgg tactatcgca tatgtcaagg acggcgatat tatctccatc     1500
gacataccga attactccat cactcttgaa gtatccgacg aggagcttgc agagcgcaaa     1560
aaggcaatgc ctatcaagcg caaggagaac atcacaggct atctgaagcg ctatgcacag     1620
caggtatcat ccgcagacaa gggcgctatc atcaacagga aatag                    1665
```

<210> SEQ ID NO 447
<211> LENGTH: 554
<212> TYPE: PRT
<213> ORGANISM: Ruminococcus flavefaciens

<400> SEQUENCE: 447

```
Met Ser Asp Asn Phe Phe Cys Glu Gly Ala Asp Lys Ala Pro Gln Arg
1               5                  10                  15

Ser Leu Phe Asn Ala Leu Gly Met Thr Lys Glu Met Lys Arg Pro
            20                  25                  30

Leu Val Gly Ile Val Ser Ser Tyr Asn Glu Ile Val Pro Gly His Met
        35                  40                  45
```

-continued

```
Asn Ile Asp Lys Leu Val Glu Ala Val Lys Leu Gly Val Ala Met Gly
 50                  55                  60

Gly Gly Thr Pro Val Val Phe Pro Ala Ile Ala Val Cys Asp Gly Ile
 65                  70                  75                  80

Ala Met Gly His Thr Gly Met Lys Tyr Ser Leu Val Thr Arg Asp Leu
                 85                  90                  95

Ile Ala Asp Ser Thr Glu Cys Met Ala Leu Ala His His Phe Asp Ala
            100                 105                 110

Leu Val Met Ile Pro Asn Cys Asp Lys Asn Val Pro Gly Leu Leu Met
        115                 120                 125

Ala Ala Ala Arg Ile Asn Val Pro Thr Val Phe Val Ser Gly Gly Pro
    130                 135                 140

Met Leu Ala Gly His Val Lys Gly Lys Thr Ser Leu Ser Ser Met
145                 150                 155                 160

Phe Glu Ala Val Gly Ala Tyr Thr Ala Gly Lys Ile Asp Glu Ala Glu
                165                 170                 175

Leu Asp Glu Phe Glu Asn Lys Thr Cys Pro Thr Cys Gly Ser Cys Ser
            180                 185                 190

Gly Met Tyr Thr Ala Asn Ser Met Asn Cys Leu Thr Glu Val Leu Gly
        195                 200                 205

Met Gly Leu Arg Gly Asn Gly Thr Ile Pro Ala Val Tyr Ser Glu Arg
    210                 215                 220

Ile Lys Leu Ala Lys Gln Ala Gly Met Gln Val Met Glu Leu Tyr Arg
225                 230                 235                 240

Lys Asn Ile Arg Pro Leu Asp Ile Met Thr Glu Lys Ala Phe Gln Asn
                245                 250                 255

Ala Leu Thr Ala Asp Met Ala Leu Gly Cys Ser Thr Asn Ser Met Leu
            260                 265                 270

His Leu Pro Ala Ile Ala Asn Glu Cys Gly Ile Asn Ile Asn Leu Asp
        275                 280                 285

Met Ala Asn Glu Ile Ser Ala Lys Thr Pro Asn Leu Cys His Leu Ala
    290                 295                 300

Pro Ala Gly His Thr Tyr Met Glu Asp Leu Asn Glu Ala Gly Gly Val
305                 310                 315                 320

Tyr Ala Val Leu Asn Glu Leu Ser Lys Lys Gly Leu Ile Asn Thr Asp
                325                 330                 335

Cys Met Thr Val Thr Gly Lys Thr Val Gly Glu Asn Ile Lys Gly Cys
            340                 345                 350

Ile Asn Arg Asp Pro Glu Thr Ile Arg Pro Ile Asp Asn Pro Tyr Ser
        355                 360                 365

Glu Thr Gly Gly Ile Ala Val Leu Lys Gly Asn Leu Ala Pro Asp Arg
    370                 375                 380

Cys Val Val Lys Arg Ser Ala Val Ala Pro Glu Met Leu Val His Lys
385                 390                 395                 400

Gly Pro Ala Arg Val Phe Asp Ser Glu Glu Ala Ile Lys Val Ile
                405                 410                 415

Tyr Glu Gly Gly Ile Lys Ala Gly Asp Val Val Val Ile Arg Tyr Glu
            420                 425                 430

Gly Pro Ala Gly Gly Pro Gly Met Arg Glu Met Leu Ser Pro Thr Ser
        435                 440                 445

Ala Ile Gln Gly Ala Gly Leu Gly Ser Thr Val Ala Leu Ile Thr Asp
    450                 455                 460

Gly Arg Phe Ser Gly Ala Thr Arg Gly Ala Ala Ile Gly His Val Ser
465                 470                 475                 480
```

```
Pro Glu Ala Val Asn Gly Gly Thr Ile Ala Tyr Val Lys Asp Gly Asp
                485                 490                 495

Ile Ile Ser Ile Asp Ile Pro Asn Tyr Ser Ile Thr Leu Glu Val Ser
        500                 505                 510

Asp Glu Glu Leu Ala Glu Arg Lys Lys Ala Met Pro Ile Lys Arg Lys
    515                 520                 525

Glu Asn Ile Thr Gly Tyr Leu Lys Arg Tyr Ala Gln Gln Val Ser Ser
    530                 535                 540

Ala Asp Lys Gly Ala Ile Ile Asn Arg Lys
545                 550

<210> SEQ ID NO 448
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 448
gcgtccatac cggaccgtcc atccgtcccg gcgggctatc gttagtcccc gcgagcggat      60
tccgaggtgt cgatgacgcg ctcggtcccc gcatctcggg gtggcccgca cctagcttaa     120
gcggactacg aagcgcgggg cgagcggcga cgatcgcgta ctcacactcg gacctcgcgg     180
gtcggctcgg agccctggtc a                                               201

<210> SEQ ID NO 449
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 449
agcggtcagt gcacgggacg cgatcgggca ccctcgacgc agcgatgggc cgtgcgtcgt      60
gtagtccgat agtgccggcg tcgctcggta agcccttat acctgcgcgc tggcgagaga     120
tgggttcgcg agtctagcgc gatcgctcta gagggtccag gagtacctac acggcgcgag    180
gcgcggacat cctagggcgc a                                               201

<210> SEQ ID NO 450
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 450
cccctgcgtt tgccgagcga cgagtcctac accctgtccg cgcccgagca gggtcgtccc      60
cgcgaaccga cggatgcgcg gcccgaatcg cctagacccc tacggggcgg ctcgctcggc    120
cccgcctgac cggtcgatcc cacgagaccc cgccctatag ggagagcacc gacccgcctc    180
ctcgggcctt acggcgtgcg a                                               201

<210> SEQ ID NO 451
<211> LENGTH: 201
<212> TYPE: DNA
<213> ORGANISM: Artificial Sequence
<220> FEATURE:
<223> OTHER INFORMATION: Description of Artificial Sequence: Synthetic
```

```
                                   polynucleotide

<400> SEQUENCE: 451
gccagtgtag agatccgggg atccccagcg cctggagcta ggcccacggc gtctgaccgg      60
gtgtaccggg cccctagga cgggtgcgcc cgtagtccgt ctgcgagggg gccgtccggt     120
cgggggcatc cggcgctccg cggggaggcg ctacgtgccc gaccggggga gtcgagtctc     180
tatgctcgcg accgcgtgcg a                                               201

<210> SEQ ID NO 452
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 452
aagcgcgcac tacgtcaggc atagcgtact gggcttgcgg agccacgcgg gcgcggagcg      60
ggccggttga gtgcgggata gacggaccgt acgcatgcct caagtcgacg gtacgggggg     120
cagggtagct gggatccgag gcgggtaggc gtcggccgcg actgtgcccg tacgacggga     180 gaacccccg cgcgagttgg a                                                201

<210> SEQ ID NO 453
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 453
acgtcggcag gcccgctcgg ttccgagcac cggatcgacg ctacacgagg cccgacacta      60
ggcgcgtact ccggggggt ccgcctccgt cccgtgagta tcgcgggcgg gaacagggcg     120
ggctgccggg gccgaccggt gtggggcgtg actccgaccg actcgggcga gggccgccta     180
gtcgcgaagg acgcgcgacc a                                               201

<210> SEQ ID NO 454
<211> LENGTH: 1821
<212> TYPE: DNA
<213> ORGANISM: Zymomonas mobilis

<400> SEQUENCE: 454
atgactgatc tgcattcaac ggtagaaaag gttaccgcgc gcgttattga acgctcgcgg      60
gaaacccgta aggcttatct ggatttgatc cagtatgagc gggaaaaagg cgtagaccgt     120
ccaaacctgt cctgtagtaa ccttgctcat ggctttgcgg ctatgaatgg tgacaagcca     180
gctttgcgcg acttcaaccg catgaatatc ggcgtcgtga cttcctacaa cgatatgttg     240
tcggctcatg aaccatatta tcgctatccg gagcagatga agtatttgc tcgcgaagtt     300 ggcgcaacgg ttcaggtcgc cggtggcgtg cctgctatgt gcgatggtgt gacccaaggt     360
cagccgggca tggaagaatc cctgtttagc cgcgatgtta tcgctttggc taccagcgtt     420
tctttgtctc atggtatgtt tgaagggct gcccttctcg gtatctgtga caagattgtc     480
cctggtctgt tgatgggcgc tctgcgcttt ggtcacctgc cgaccattct ggtcccatca     540
ggcccgatga cgactggtat cccgaacaaa gaaaaaatcc gtatccgtca gctctatgct     600
cagggtaaaa tcggccagaa agaacttctg gatatggaag cggcttgcta ccatgctgaa     660
```

| | |
|---|---|
| ggtacctgca ccttctatgg tacggcaaac accaaccaga tggttatgga agtcctcggt | 720 |
| cttcatatgc caggttcggc atttgttacc ccgggtaccc cgctccgcca ggctctgacc | 780 |
| cgtgctgctg tgcatcgcgt tgctgaattg ggttggaagg gcgacgatta tcgtccgctt | 840 |
| ggtaaaatca ttgacgaaaa atcaatcgtc aatgctattg ttggtctgtt ggcaaccggt | 900 |
| ggttccacca accataccat gcatattccg gccattgctc gtgctgctgg tgttatcgtt | 960 |
| aactggaatg acttccatga tctttctgaa gttgttccgt tgattgcccg catttacccg | 1020 |
| aatggcccgc gcgacatcaa tgaattccag aatgcaggcg catggctta tgtcatcaaa | 1080 |
| gaactgcttt ctgctaatct gttgaaccgt gatgtcacga ccattgccaa gggcggtatc | 1140 |
| gaagaatacg ccaaggctcc ggcattaaat gatgctggcg aattggtctg gaagccagct | 1200 |
| ggcgaacctg gtgatgacac cattctgcgt ccggtttcta atccttcgc aaaagatggc | 1260 |
| ggtctgcgtc tcttggaagg taaccttggc cgtgcaatgt acaaggccag tgcggttgat | 1320 |
| cctaaattct ggaccattga agcaccggtt cgcgtcttct ctgaccaaga cgatgttcag | 1380 |
| aaagccttca aggctggcga attgaacaaa gacgttatcg ttgttgttcg tttccagggc | 1440 |
| ccgcgcgcaa acggtatgcc tgaattgcat aagctgaccc cggctttggg tgttctgcag | 1500 |
| gataatggct acaaagttgc tttggtaact gatggtcgta tgtccggtgc taccggtaaa | 1560 |
| gttccggttg ctttgcatgt cagcccagaa gctcttggcg tggtgccat cggtaaatta | 1620 |
| cgtgatggcg atatcgtccg tatctcggtt gaagaaggca aacttgaagc tttggttcca | 1680 |
| gctgatgagt ggaatgctcg tccgcatgct gaaaaaccgg cttccgtcc gggaaccgga | 1740 |
| cgcgaattgt ttgatatctt ccgtcagaat gctgctaaag ctgaagacgg tgcagtcgca | 1800 |
| atatatgcag gtgccggtat c | 1821 |

<210> SEQ ID NO 455
<211> LENGTH: 1821
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 455

| | |
|---|---|
| atgacggatc tacatagtac agtggagaag gttactgcca gggttattga aaggagtagg | 60 |
| gaaactagga aggcatatct agatttaatt caatatgaga gggaaaaagg agtggacagg | 120 |
| cccaacctaa gttgtagcaa cctagcacat ggattcgccg caatgaatgg tgacaagccc | 180 |
| gcattaaggg acttcaacag gatgaatatt ggagttgtga cgagttacaa cgatatgtta | 240 |
| agtgcacatg aaccctatta taggtatcct gagcaaatga aggtgtttgc aagggaagtt | 300 |
| ggagccacag ttcaagttgc tggtgagtg cctgcaatgt gcgatggtgt gactcagggt | 360 |
| caacctggaa tggaagaatc cctatttca agggatgtta ttgcattagc aacttcagtt | 420 |
| tcattatcac atggtatgtt tgaagggca gctctactcg gtatatgtga caagattgtt | 480 |
| cctggtctac taatgggagc actaaggttt ggtcacctac ctactattct agttcccagt | 540 |
| ggacctatga caacgggtat acctaacaaa gaaaaaatta ggattaggca actctatgca | 600 |
| caaggtaaaa ttggacaaaa agaactacta gatatggaag ccgcatgcta ccatgcagaa | 660 |
| ggtacttgca ctttctatgg tacagccaac actaaccaga tggttatgga agttctcggt | 720 |
| ctacatatgc ccggtagtgc ctttgttact cctggtactc ctctcaggca agcactaact | 780 |
| agggcagcag tgcataggt tgcagaatta ggttggaagg gagacgatta taggcctcta | 840 |
| ggtaaaatta ttgacgaaaa agtattgtt aatgcaattg ttggtctatt agccactggt | 900 |

-continued

```
ggtagtacta accatacgat gcatattcct gctattgcaa gggcagcagg tgttattgtt      960
aactggaatg acttccatga tctatcagaa gttgttcctt taattgctag gatttaccct     1020
aatggaccta gggacattaa cgaatttcaa aatgccggag gaatggcata tgttattaag     1080
gaactactat cagcaaatct actaaacagg gatgttacaa ctattgctaa gggaggtata     1140
gaagaatacg ctaaggcacc tgccctaaat gatgcaggag aattagtttg gaagcccgca     1200
ggagaacctg gtgatgacac tattctaagg cctgtttcaa atccttttcgc caaagatgga    1260 ggtctaaggc tcttagaagg taacctagga agggccatgt acaaggctag cgccgttgat     1320
cctaaattct ggactattga agcccctgtt agggttttct cagaccagga cgatgttcaa     1380
aaagccttca aggcaggaga actaaacaaa gacgttattg ttgttgttag gttccaagga     1440
cctagggcca acggtatgcc tgaattacat aagctaactc ctgcattagg tgttctacaa     1500
gataatggat acaaagttgc attagtgacg gatggtagga tgagtggtgc aactggtaaa     1560
gttcctgttg cattacatgt ttcacccgaa gcactaggag gtggtgctat tggtaaactt     1620
agggatggag atattgttag gattagtgtt gaagaaggaa aacttgaagc actcgttccc     1680
gcagatgagt ggaatgcaag gcctcatgca gaaaaacctg cattcaggcc tgggactggg     1740
agggaattat ttgatatttt caggcaaaat gcagcaaaag cagaagacgg tgccgttgcc     1800
atctatgccg gtgctggtat a                                                1821

<210> SEQ ID NO 456
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456
atgacggatt tgcattcaac tgttgagaaa gtaactgcta gagtaattga agatcaagg       60 gaaactagaa aggcttattt ggatttgata caatatgaga gggaaaaagg tgttgataga     120
ccaaatttgt cttgttctaa tttggctcat ggttttgctg ctatgaatgg tgataaacca     180
gctttgagag atttaatag aatgaatata ggtgtagtta cttcttataa tgatatgttg     240
tctgctcatg aaccatatta tagatatcca gaacaaatga aggttttgc tcgtgaagtt     300 ggtgctacag ttcaagttgc tggtggtgtt cctgcaatgt gtgatggtgt tactcaaggt   360
caaccaggta tggaagaatc tttgtttttcc agagatgtaa ttgctttggc tacatctgtt   420
tcattgtctc acggaatgtt tgaaggtgct gcattgttgg gaatttgtga taaaattgtt    480 ccaggttttgt tgatgggtgc tttgaggttc ggtcatttgc caactatttt ggttccatct    540
ggtccaatga ctactggaat cccaaataaa gaaaagatta gaattagaca attgtatgct    600
caaggaaaaa ttggtcaaaa ggaattgttg gatatggaag ctgcctgtta tcatgctgaa    660
ggtacttgta ctttttatgg tactgctaac actaatcaga tggttatgga agttttgggt   720
ttgcacatgc caggtagtgc attcgttact ccaggtactc cactgagaca ggcttttgact  780 agagctgctg ttcatagagt tgcagagttg ggttggaaag tgatgattta agacccttg    840 ggtaaaatta ttgatgagaa atctattgtt aatgctattg ttggttttgtt agctacaggt  900 ggttctacaa atcatacaat gcatattccg gccatagcta gagcagcagg ggttatagtt    960
aattggaatg attttcatga tttgtctgaa gttgttccat tgattgctag aatttatcca  1020
aatggtccta gagatataaa tgaatttcaa aatgcaggag gaatggctta tgtaattaaa   1080
```

```
gaattgttga gtgcgaattt gttaaataga gatgttacta ctattgctaa aggagggata    1140
gaagaatatg ctaaagctcc agctctgaac gatgcgggtg aattggtgtg gaaaccggct    1200
ggcgaacctg gggacgacac aattttgaga ccagtatcta atccatttgc taaagatggt    1260
ggtttgcgtc tcttggaagg taatttgggt agagcaatgt ataaggcttc tgctgtagat    1320
ccaaaattct ggactattga agctcccgtt agagttttct ctgatcaaga tgatgttcaa    1380
aaggctttta aagcaggcga gttaaataaa gatgttatag ttgttgttag atttcaaggt    1440
cctcgtgcta atggtatgcc tgaattgcat aagttgactc ctgcgctagg cgtattgcaa    1500
gataatggtt ataaggttgc tttagttact gatggtagaa tgtctggtgc aactggtaaa    1560
gtaccggtgg ctctgcatgt ttcaccagag gctttaggag gtgggggcgat tggcaagttg    1620 agagatggcg atatagttag aatttctgtt gaagaaggta aattagaggc tcttgtcccc    1680
gccgacgagt ggaatgctag accacatgct gagaagcccg cttttagacc tggtactggg    1740
agagaattgt ttgacatttt tagacaaaac gctgctaagg ctgaggatgg tgcagttgca    1800
atttatgctg gggcagggat c                                              1821

<210> SEQ ID NO 457
<211> LENGTH: 1809
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 457
atgaatccac aattgttacg cgtaacaaat cgaatcattg aacgttcgcg cgagactcgc      60
tctgcttatc tcgcccggat agaacaagcg aaaacttcga ccgttcatcg ttcgcagttg     120
gcatgcggta acctggcaca cggtttcgct gcctgccagc cagaagacaa agcctctttg     180
aaaagcatgt tgcgtaacaa tatcgccatc atcacctcct ataacgacat gctctccgcg     240
caccagcctt atgaacacta tccagaaatc attcgtaaag ccctgcatga agcgaatgcg     300
gttggtcagg ttgcgggcgg tgttccggcg atgtgtgatg tgtcaccca ggggcaggat     360 ggaatggaat tgtcgctgct aagccgcgaa gtgatagcga tgtctgcggc ggtggggctg     420
tcccataaca tgtttgatgg tgctctgttc ctcggtgtgt cgacaagat tgtcccgggt     480 ctgacgatgg cagccctgtc gtttggtcat ttgcctgcgg tgtttgtgcc gtctggaccg     540
atggcaagcg gtttgccaaa taagaaaaaa gtgcgtattc gccagctta tgccgaaggt     600 aaagtggacc gcatggcctt actggagtca gaagccgcgt cttaccatgc gccgggaaca     660
tgtactttct acggtactgc caacaccaac cagatggtgg tggagtttat ggggatgcag     720
ttgccaggct cttcttttgt tcatccggat tctccgctgc gcgatgcttt gaccgccgca     780
gctgcgcgtc aggttacacg catgaccggt aatggtaatg aatggatgcc gatcggtaag     840
atgatcgatg agaaagtggt ggtgaacggt atcgttcac tgctggcgac cggtggttcc     900
actaaccaca ccatgcacct ggtggcgatg gcgcgcgcgg ccggtattca gattaactgg     960
gatgacttct ctgaccttc tgatgttgta ccgctgatgg cacgtctcta cccgaacggt    1020
ccggccgata ttaaccactt ccaggcggca ggtggcgtac cggttctggt cgtgaactg    1080 ctcaaagcag gcctgctgca tgaagatgtc aatacggtgg caggttttgg tctgtctcgt    1140
tatacccttg aaccatggct gaataatggt gaactggact ggcgggaagg ggcggaaaaa    1200
tcactcgaca gcaatgtgat cgcttccttc gaacaacctt tctctcatca tggtgggaca    1260
aaagtgttaa gcggtaacct gggccgtgcg gttatgaaaa cctctgccgt gccggttgag    1320
```

```
aaccaggtga ttgaagcgcc agcggttgtt tttgaaagcc agcatgacgt tatgccggcc    1380
tttgaagcgg gtttgctgga ccgcgattgt gtcgttgttg tccgtcatca ggggccaaaa    1440
gcgaacggaa tgccagaatt acataaactc atgccgccac ttggtgtatt attggaccgg    1500
tgtttcaaaa ttgcgttagt taccgatgga cgactctccg gcgcttcagg taaagtgccg    1560
tcagctatcc acgtaacacc agaagcctac gatggcgggc tgctggcaaa agtgcgcgac    1620
ggggacatca ttcgtgtgaa tggacagaca ggcgaactga cgctgctggt agacgaagcg    1680
gaactggctg ctcgcgaacc gcacattcct gacctgagcg cgtcacgcgt gggaacagga    1740
cgtgaattat tcagcgcctt gcgtgaaaaa ctgtccggtg ccgaacaggg cgcaacctgt    1800
atcactttt                                                            1809
```

<210> SEQ ID NO 458
<211> LENGTH: 607
<212> TYPE: PRT
<213> ORGANISM: Zymomonas mobilis

<400> SEQUENCE: 458

```
Met Thr Asp Leu His Ser Thr Val Glu Lys Val Thr Ala Arg Val Ile
1               5                   10                  15

Glu Arg Ser Arg Glu Thr Arg Lys Ala Tyr Leu Asp Leu Ile Gln Tyr
            20                  25                  30

Glu Arg Glu Lys Gly Val Asp Arg Pro Asn Leu Ser Cys Ser Asn Leu
        35                  40                  45

Ala His Gly Phe Ala Ala Met Asn Gly Asp Lys Pro Ala Leu Arg Asp
    50                  55                  60

Phe Asn Arg Met Asn Ile Gly Val Val Thr Ser Tyr Asn Asp Met Leu
65                  70                  75                  80

Ser Ala His Glu Pro Tyr Tyr Arg Tyr Pro Glu Gln Met Lys Val Phe
                85                  90                  95

Ala Arg Glu Val Gly Ala Thr Val Gln Val Ala Gly Val Pro Ala
            100                 105                 110

Met Cys Asp Gly Val Thr Gln Gly Gln Pro Gly Met Glu Glu Ser Leu
        115                 120                 125

Phe Ser Arg Asp Val Ile Ala Leu Ala Thr Ser Val Ser Leu Ser His
    130                 135                 140

Gly Met Phe Glu Gly Ala Ala Leu Leu Gly Ile Cys Asp Lys Ile Val
145                 150                 155                 160

Pro Gly Leu Leu Met Gly Ala Leu Arg Phe Gly His Leu Pro Thr Ile
                165                 170                 175

Leu Val Pro Ser Gly Pro Met Thr Thr Gly Ile Pro Asn Lys Glu Lys
            180                 185                 190

Ile Arg Ile Arg Gln Leu Tyr Ala Gln Gly Lys Ile Gly Gln Lys Glu
        195                 200                 205

Leu Leu Asp Met Glu Ala Ala Cys Tyr His Ala Glu Gly Thr Cys Thr
    210                 215                 220

Phe Tyr Gly Thr Ala Asn Thr Asn Gln Met Val Met Glu Val Leu Gly
225                 230                 235                 240

Leu His Met Pro Gly Ser Ala Phe Val Thr Pro Gly Thr Pro Leu Arg
                245                 250                 255

Gln Ala Leu Thr Arg Ala Ala Val His Arg Val Ala Glu Leu Gly Trp
            260                 265                 270

Lys Gly Asp Asp Tyr Arg Pro Leu Gly Lys Ile Ile Asp Glu Lys Ser
        275                 280                 285
```

Ile Val Asn Ala Ile Val Gly Leu Leu Ala Thr Gly Gly Ser Thr Asn
        290                 295                 300

His Thr Met His Ile Pro Ala Ile Ala Arg Ala Ala Gly Val Ile Val
305                 310                 315                 320

Asn Trp Asn Asp Phe His Asp Leu Ser Glu Val Val Pro Leu Ile Ala
                325                 330                 335

Arg Ile Tyr Pro Asn Gly Pro Arg Asp Ile Asn Glu Phe Gln Asn Ala
            340                 345                 350

Gly Gly Met Ala Tyr Val Ile Lys Glu Leu Leu Ser Ala Asn Leu Leu
        355                 360                 365

Asn Arg Asp Val Thr Thr Ile Ala Lys Gly Gly Ile Glu Glu Tyr Ala
    370                 375                 380

Lys Ala Pro Ala Leu Asn Asp Ala Gly Glu Leu Val Trp Lys Pro Ala
385                 390                 395                 400

Gly Glu Pro Gly Asp Asp Thr Ile Leu Arg Pro Val Ser Asn Pro Phe
                405                 410                 415

Ala Lys Asp Gly Gly Leu Arg Leu Leu Glu Gly Asn Leu Gly Arg Ala
            420                 425                 430

Met Tyr Lys Ala Ser Ala Val Asp Pro Lys Phe Trp Thr Ile Glu Ala
        435                 440                 445

Pro Val Arg Val Phe Ser Asp Gln Asp Val Gln Lys Ala Phe Lys
    450                 455                 460

Ala Gly Glu Leu Asn Lys Asp Val Ile Val Val Arg Phe Gln Gly
465                 470                 475                 480

Pro Arg Ala Asn Gly Met Pro Glu Leu His Lys Leu Thr Pro Ala Leu
                485                 490                 495

Gly Val Leu Gln Asp Asn Gly Tyr Lys Val Ala Leu Val Thr Asp Gly
            500                 505                 510

Arg Met Ser Gly Ala Thr Gly Lys Val Pro Val Ala Leu His Val Ser
        515                 520                 525

Pro Glu Ala Leu Gly Gly Gly Ala Ile Gly Lys Leu Arg Asp Gly Asp
    530                 535                 540

Ile Val Arg Ile Ser Val Glu Glu Gly Lys Leu Glu Ala Leu Val Pro
545                 550                 555                 560

Ala Asp Glu Trp Asn Ala Arg Pro His Ala Glu Lys Pro Ala Phe Arg
                565                 570                 575

Pro Gly Thr Gly Arg Glu Leu Phe Asp Ile Phe Arg Gln Asn Ala Ala
            580                 585                 590

Lys Ala Glu Asp Gly Ala Val Ala Ile Tyr Ala Gly Ala Gly Ile
        595                 600                 605

<210> SEQ ID NO 459
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Met Thr Asp Leu His Ser Thr Val Glu Lys Val Thr Ala Arg Val Ile
1               5                   10                  15

Glu Arg Ser Arg Glu Thr Arg Lys Ala Tyr Leu Asp Leu Ile Gln Tyr
            20                  25                  30

Glu Arg Glu Lys Gly Val Asp Arg Pro Asn Leu Ser Cys Ser Asn Leu
        35                  40                  45

```
Ala His Gly Phe Ala Ala Met Asn Gly Asp Lys Pro Ala Leu Arg Asp
     50                  55                  60
Phe Asn Arg Met Asn Ile Gly Val Val Thr Ser Tyr Asn Asp Met Leu
65                  70                  75                  80
Ser Ala His Glu Pro Tyr Tyr Arg Tyr Pro Glu Gln Met Lys Val Phe
                 85                  90                  95
Ala Arg Glu Val Gly Ala Thr Val Gln Val Ala Gly Gly Val Pro Ala
                100                 105                 110
Met Cys Asp Gly Val Thr Gln Gly Gln Pro Gly Met Glu Glu Ser Leu
                115                 120                 125
Phe Ser Arg Asp Val Ile Ala Leu Ala Thr Ser Val Ser Leu Ser His
    130                 135                 140
Gly Met Phe Glu Gly Ala Ala Leu Leu Gly Ile Cys Asp Lys Ile Val
145                 150                 155                 160
Pro Gly Leu Leu Met Gly Ala Leu Arg Phe Gly His Leu Pro Thr Ile
                165                 170                 175
Leu Val Pro Ser Gly Pro Met Thr Thr Gly Ile Pro Asn Lys Glu Lys
                180                 185                 190
Ile Arg Ile Arg Gln Leu Tyr Ala Gln Gly Lys Ile Gly Gln Lys Glu
                195                 200                 205
Leu Leu Asp Met Glu Ala Ala Cys Tyr His Ala Glu Gly Thr Cys Thr
    210                 215                 220
Phe Tyr Gly Thr Ala Asn Thr Asn Gln Met Val Met Glu Val Leu Gly
225                 230                 235                 240
Leu His Met Pro Gly Ser Ala Phe Val Thr Pro Gly Thr Pro Leu Arg
                245                 250                 255
Gln Ala Leu Thr Arg Ala Ala Val His Arg Val Ala Glu Leu Gly Trp
                260                 265                 270
Lys Gly Asp Asp Tyr Arg Pro Leu Gly Lys Ile Ile Asp Glu Lys Ser
                275                 280                 285
Ile Val Asn Ala Ile Val Gly Leu Leu Ala Thr Gly Gly Ser Thr Asn
                290                 295                 300
His Thr Met His Ile Pro Ala Ile Ala Arg Ala Ala Gly Val Ile Val
305                 310                 315                 320
Asn Trp Asn Asp Phe His Asp Leu Ser Glu Val Val Pro Leu Ile Ala
                325                 330                 335
Arg Ile Tyr Pro Asn Gly Pro Arg Asp Ile Asn Glu Phe Gln Asn Ala
                340                 345                 350
Gly Gly Met Ala Tyr Val Ile Lys Glu Leu Leu Ser Ala Asn Leu Leu
                355                 360                 365
Asn Arg Asp Val Thr Thr Ile Ala Lys Gly Gly Ile Glu Glu Tyr Ala
                370                 375                 380
Lys Ala Pro Ala Leu Asn Asp Ala Gly Glu Leu Val Trp Lys Pro Ala
385                 390                 395                 400
Gly Glu Pro Gly Asp Asp Thr Ile Leu Arg Pro Val Ser Asn Pro Phe
                405                 410                 415
Ala Lys Asp Gly Gly Leu Arg Leu Leu Glu Gly Asn Leu Gly Arg Ala
                420                 425                 430
Met Tyr Lys Ala Ser Ala Val Asp Pro Lys Phe Trp Thr Ile Glu Ala
                435                 440                 445
Pro Val Arg Val Phe Ser Asp Gln Asp Val Gln Lys Ala Phe Lys
    450                 455                 460
Ala Gly Glu Leu Asn Lys Asp Val Ile Val Val Val Arg Phe Gln Gly
```

```
                     465                 470                 475                 480
Pro Arg Ala Asn Gly Met Pro Glu Leu His Lys Leu Thr Pro Ala Leu
                485                 490                 495
Gly Val Leu Gln Asp Asn Gly Tyr Lys Val Ala Leu Val Thr Asp Gly
            500                 505                 510
Arg Met Ser Gly Ala Thr Gly Lys Val Pro Val Ala Leu His Val Ser
        515                 520                 525
Pro Glu Ala Leu Gly Gly Ala Ile Gly Lys Leu Arg Asp Gly Asp
    530                 535                 540
Ile Val Arg Ile Ser Val Glu Glu Gly Lys Leu Glu Ala Leu Val Pro
545                 550                 555                 560
Ala Asp Glu Trp Asn Ala Arg Pro His Ala Glu Lys Pro Ala Phe Arg
                565                 570                 575
Pro Gly Thr Gly Arg Glu Leu Phe Asp Ile Phe Arg Gln Asn Ala Ala
            580                 585                 590
Lys Ala Glu Asp Gly Ala Val Ala Ile Tyr Ala Gly Ala Gly Ile
        595                 600                 605

<210> SEQ ID NO 460
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Met Thr Asp Leu His Ser Thr Val Glu Lys Val Thr Ala Arg Val Ile
1               5                   10                  15
Glu Arg Ser Arg Glu Thr Arg Lys Ala Tyr Leu Asp Leu Ile Gln Tyr
            20                  25                  30
Glu Arg Glu Lys Gly Val Asp Arg Pro Asn Leu Ser Cys Ser Asn Leu
        35                  40                  45
Ala His Gly Phe Ala Ala Met Asn Gly Asp Lys Pro Ala Leu Arg Asp
    50                  55                  60
Phe Asn Arg Met Asn Ile Gly Val Val Thr Ser Tyr Asn Asp Met Leu
65                  70                  75                  80
Ser Ala His Glu Pro Tyr Tyr Arg Tyr Pro Glu Gln Met Lys Val Phe
                85                  90                  95
Ala Arg Glu Val Gly Ala Thr Val Gln Val Ala Gly Gly Val Pro Ala
            100                 105                 110
Met Cys Asp Gly Val Thr Gln Gly Gln Pro Gly Met Glu Glu Ser Leu
        115                 120                 125
Phe Ser Arg Asp Val Ile Ala Leu Ala Thr Ser Val Ser Leu Ser His
    130                 135                 140
Gly Met Phe Glu Gly Ala Ala Leu Leu Gly Ile Cys Asp Lys Ile Val
145                 150                 155                 160
Pro Gly Leu Leu Met Gly Ala Leu Arg Phe Gly His Leu Pro Thr Ile
                165                 170                 175
Leu Val Pro Ser Gly Pro Met Thr Thr Gly Ile Pro Asn Lys Glu Lys
            180                 185                 190
Ile Arg Ile Arg Gln Leu Tyr Ala Gln Gly Lys Ile Gly Gln Lys Glu
        195                 200                 205
Leu Leu Asp Met Glu Ala Ala Cys Tyr His Ala Glu Gly Thr Cys Thr
    210                 215                 220
Phe Tyr Gly Thr Ala Asn Thr Asn Gln Met Val Met Glu Val Leu Gly
```

```
              225                 230                 235                 240
Leu His Met Pro Gly Ser Ala Phe Val Thr Pro Gly Thr Pro Leu Arg
                    245                 250                 255

Gln Ala Leu Thr Arg Ala Ala Val His Arg Val Ala Glu Leu Gly Trp
                260                 265                 270

Lys Gly Asp Asp Tyr Arg Pro Leu Gly Lys Ile Ile Asp Glu Lys Ser
            275                 280                 285

Ile Val Asn Ala Ile Val Gly Leu Leu Ala Thr Gly Gly Ser Thr Asn
        290                 295                 300

His Thr Met His Ile Pro Ala Ile Ala Arg Ala Ala Gly Val Ile Val
305                 310                 315                 320

Asn Trp Asn Asp Phe His Asp Leu Ser Glu Val Val Pro Leu Ile Ala
                325                 330                 335

Arg Ile Tyr Pro Asn Gly Pro Arg Asp Ile Asn Glu Phe Gln Asn Ala
                340                 345                 350

Gly Gly Met Ala Tyr Val Ile Lys Glu Leu Leu Ser Ala Asn Leu Leu
            355                 360                 365

Asn Arg Asp Val Thr Thr Ile Ala Lys Gly Gly Ile Glu Glu Tyr Ala
        370                 375                 380

Lys Ala Pro Ala Leu Asn Asp Ala Gly Glu Leu Val Trp Lys Pro Ala
385                 390                 395                 400

Gly Glu Pro Gly Asp Asp Thr Ile Leu Arg Pro Val Ser Asn Pro Phe
                405                 410                 415

Ala Lys Asp Gly Gly Leu Arg Leu Leu Glu Gly Asn Leu Gly Arg Ala
                420                 425                 430

Met Tyr Lys Ala Ser Ala Val Asp Pro Lys Phe Trp Thr Ile Glu Ala
            435                 440                 445

Pro Val Arg Val Phe Ser Asp Gln Asp Val Gln Lys Ala Phe Lys
        450                 455                 460

Ala Gly Glu Leu Asn Lys Asp Val Ile Val Val Arg Phe Gln Gly
465                 470                 475                 480

Pro Arg Ala Asn Gly Met Pro Glu Leu His Lys Leu Thr Pro Ala Leu
                485                 490                 495

Gly Val Leu Gln Asp Asn Gly Tyr Lys Val Ala Leu Val Thr Asp Gly
            500                 505                 510

Arg Met Ser Gly Ala Thr Gly Lys Val Pro Val Ala Leu His Val Ser
        515                 520                 525

Pro Glu Ala Leu Gly Gly Gly Ala Ile Gly Lys Leu Arg Asp Gly Asp
530                 535                 540

Ile Val Arg Ile Ser Val Glu Glu Gly Lys Leu Glu Ala Leu Val Pro
545                 550                 555                 560

Ala Asp Glu Trp Asn Ala Arg Pro His Ala Glu Lys Pro Ala Phe Arg
                565                 570                 575

Pro Gly Thr Gly Arg Glu Leu Phe Asp Ile Phe Arg Gln Asn Ala Ala
                580                 585                 590

Lys Ala Glu Asp Gly Ala Val Ala Ile Tyr Ala Gly Ala Gly Ile
            595                 600                 605

<210> SEQ ID NO 461
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 461

Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu
    50                  55                  60

Arg Asn Asn Ile Ala Ile Ile Thr Ser Tyr Asn Asp Met Leu Ser Ala
65                  70                  75                  80

His Gln Pro Tyr Glu His Tyr Pro Glu Ile Ile Arg Lys Ala Leu His
                85                  90                  95

Glu Ala Asn Ala Val Gly Gln Val Ala Gly Val Pro Ala Met Cys
            100                 105                 110

Asp Gly Val Thr Gln Gly Gln Asp Gly Met Glu Leu Ser Leu Ser
            115                 120                 125

Arg Glu Val Ile Ala Met Ser Ala Ala Val Gly Leu Ser His Asn Met
130                 135                 140

Phe Asp Gly Ala Leu Phe Leu Gly Val Cys Asp Lys Ile Val Pro Gly
145                 150                 155                 160

Leu Thr Met Ala Ala Leu Ser Phe Gly His Leu Pro Ala Val Phe Val
                165                 170                 175

Pro Ser Gly Pro Met Ala Ser Gly Leu Pro Asn Lys Glu Lys Val Arg
            180                 185                 190

Ile Arg Gln Leu Tyr Ala Glu Gly Lys Val Asp Arg Met Ala Leu Leu
        195                 200                 205

Glu Ser Glu Ala Ala Ser Tyr His Ala Pro Gly Thr Cys Thr Phe Tyr
    210                 215                 220

Gly Thr Ala Asn Thr Asn Gln Met Val Val Glu Phe Met Gly Met Gln
225                 230                 235                 240

Leu Pro Gly Ser Ser Phe Val His Pro Asp Ser Pro Leu Arg Asp Ala
                245                 250                 255

Leu Thr Ala Ala Ala Ala Arg Gln Val Thr Arg Met Thr Gly Asn Gly
            260                 265                 270

Asn Glu Trp Met Pro Ile Gly Lys Met Ile Asp Glu Lys Val Val Val
        275                 280                 285

Asn Gly Ile Val Ala Leu Leu Ala Thr Gly Gly Ser Thr Asn His Thr
    290                 295                 300

Met His Leu Val Ala Met Ala Arg Ala Ala Gly Ile Gln Ile Asn Trp
305                 310                 315                 320

Asp Asp Phe Ser Asp Leu Ser Asp Val Val Pro Leu Met Ala Arg Leu
                325                 330                 335

Tyr Pro Asn Gly Pro Ala Asp Ile Asn His Phe Gln Ala Ala Gly Gly
            340                 345                 350

Val Pro Val Leu Val Arg Glu Leu Leu Lys Ala Gly Leu Leu His Glu
        355                 360                 365

Asp Val Asn Thr Val Ala Gly Phe Gly Leu Ser Arg Tyr Thr Leu Glu
    370                 375                 380

Pro Trp Leu Asn Asn Gly Glu Leu Asp Trp Arg Glu Gly Ala Glu Lys
385                 390                 395                 400

Ser Leu Asp Ser Asn Val Ile Ala Ser Phe Glu Gln Pro Phe Ser His
                405                 410                 415

-continued

```
His Gly Gly Thr Lys Val Leu Ser Gly Asn Leu Gly Arg Ala Val Met
            420                 425                 430
Lys Thr Ser Ala Val Pro Val Glu Asn Gln Val Ile Glu Ala Pro Ala
        435                 440                 445
Val Val Phe Glu Ser Gln His Asp Val Met Pro Ala Phe Glu Ala Gly
    450                 455                 460
Leu Leu Asp Arg Asp Cys Val Val Val Arg His Gln Gly Pro Lys
465                 470                 475                 480
Ala Asn Gly Met Pro Glu Leu His Lys Leu Met Pro Pro Leu Gly Val
                485                 490                 495
Leu Leu Asp Arg Cys Phe Lys Ile Ala Leu Val Thr Asp Gly Arg Leu
            500                 505                 510
Ser Gly Ala Ser Gly Lys Val Pro Ser Ala Ile His Val Thr Pro Glu
        515                 520                 525
Ala Tyr Asp Gly Gly Leu Leu Ala Lys Val Arg Asp Gly Asp Ile Ile
    530                 535                 540
Arg Val Asn Gly Gln Thr Gly Glu Leu Thr Leu Leu Val Asp Glu Ala
545                 550                 555                 560
Glu Leu Ala Ala Arg Glu Pro His Ile Pro Asp Leu Ser Ala Ser Arg
                565                 570                 575
Val Gly Thr Gly Arg Glu Leu Phe Ser Ala Leu Arg Glu Lys Leu Ser
            580                 585                 590
Gly Ala Glu Gln Gly Ala Thr Cys Ile Thr Phe
        595                 600
```

ENGINEERED MICROORGANISMS WITH ENHANCED FERMENTATION ACTIVITY

RELATED PATENT APPLICATION(S)

This patent application is a continuation application which claims the benefit of international patent application no. PCT/US2010/041607 filed on Jul. 9, 2010, entitled ENGINEERED MICROORGANISMS WITH ENHANCED FERMENTATION ACTIVITY, naming Stephen Picataggio, Kirsty Anne Lily Salmon and Jose Miguel LaPlaza as inventors, which claims the benefit of (i) U.S. provisional patent application No. 61/224,430 filed on Jul. 9, 2009, entitled ENGINEERED MICROORGANISMS WITH ENHANCED FERMENTATION ACTIVITY, naming Stephen Picataggio as inventor; (ii) U.S. provisional patent application No. 61/316,780 filed on Mar. 23, 2010, entitled ENGINEERED MICROORGANISMS WITH ENHANCED FERMENTATION ACTIVITY, naming Stephen Picataggio as inventor; and (iii) U.S. provisional patent application No. 61/334,097 filed on May 12, 2010, entitled ENGINEERED MICROORGANISMS WITH ENHANCED FERMENTATION ACTIVITY, naming Stephen Picataggio as inventor. The entire content of the foregoing patent applications is incorporated herein by reference, including, without limitation, all text, tables and drawings.

SEQUENCE LISTING

The instant application contains a Sequence Listing which has been submitted in ASCII format via EFS-Web and is hereby incorporated by reference in its entirety. Said ASCII copy, created on Feb. 23, 2011, is named VRD12CT4.txt and is 410,477 bytes in size.

FIELD

The technology relates in part to genetically modified microorganisms that have enhanced fermentation activity, and methods for making and using such microorganisms.

BACKGROUND

Microorganisms employ various enzyme-driven biological pathways to support their own metabolism and growth. A cell synthesizes native proteins, including enzymes, in vivo from deoxyribonucleic acid (DNA). DNA first is transcribed into a complementary ribonucleic acid (RNA) that comprises a ribonucleotide sequence encoding the protein. RNA then directs translation of the encoded protein by interaction with various cellular components, such as ribosomes. The resulting enzymes participate as biological catalysts in pathways involved in production of molecules utilized or secreted by the organism.

These pathways can be exploited for the harvesting of the naturally produced products. The pathways also can be altered to increase production or to produce different products that may be commercially valuable. Advances in recombinant molecular biology methodology allow researchers to isolate DNA from one organism and insert it into another organism, thus altering the cellular synthesis of enzymes or other proteins. Such genetic engineering can change the biological pathways within the host organism, causing it to produce a desired product. Microorganic industrial production can minimize the use of caustic chemicals and production of toxic byproducts, thus providing a "clean" source for certain products.

SUMMARY

Provided herein are engineered microorganisms having enhanced fermentation activity. In certain non-limiting embodiments, such microorganisms are capable of generating a target product with enhanced fermentation efficiency by, for example, (i) preferentially utilizing a particular glycolysis pathway, which increases yield of a target product, upon a change in fermentation conditions; (ii) reducing cell division rates upon a change in fermentation conditions, thereby diverting nutrients towards production of a target product; (iii) having the ability to readily metabolize five-carbon sugars; and/or (iv) having the ability to readily metabolize carbon dioxide; and combinations of the foregoing. In some embodiments, a target product is ethanol or succinic acid.

Thus, provided in certain embodiments are engineered microorganisms that comprise: (a) a functional Embden-Meyerhoff glycolysis pathway that metabolizes six-carbon sugars under aerobic fermentation conditions, and (b) a genetic modification that reduces an Embden-Meyerhoff glycolysis pathway member activity upon exposure of the engineered microorganism to anaerobic fermentation conditions, whereby the engineered microorganisms preferentially metabolize six-carbon sugars by the Enter-Doudoroff pathway under the anaerobic fermentation conditions. In some embodiments, the genetic modification is insertion of a promoter into genomic DNA in operable linkage with a polynucleotide that encodes the Embden-Meyerhoff glycolysis pathway member activity. In certain embodiments, the genetic modification is provision of a heterologous promoter polynucleotide in operable linkage with a polynucleotide that encodes the Embden-Meyerhoff glycolysis pathway member activity. In some embodiments, the genetic modification is a deletion or disruption of a polynucleotide that encodes, or regulates production of, the Embden-Meyerhoff glycolysis pathway member, and the microorganism comprises a heterologous nucleic acid that includes a polynucleotide encoding the Embden-Meyerhoff glycolysis pathway member operably linked to a polynucleotide that down-regulates production of the member under anaerobic fermentation conditions. In certain embodiments, the Embden-Meyerhoff glycolysis pathway member activity is a phosphofructokinase activity. In some embodiments, the activity of one or more (e.g., 2, 3, 4, 5 or more) pathway members in an EM pathway is reduced or removed to undetectable levels.

Also provided in some embodiments are engineered microorganisms that comprise a genetic modification that inhibits cell division upon exposure to a change in fermentation conditions, where: the genetic modification comprises introduction of a heterologous promoter operably linked to a polynucleotide encoding a polypeptide that regulates the cell cycle of the microorganism; and the promoter activity is altered by the change in fermentation conditions. Provided also in certain embodiments are engineered microorganisms that comprise a genetic modification that inhibits cell division and/or cell proliferation upon exposure of the microorganisms to a change in fermentation conditions. In certain embodiments, the genetic modification inhibits cell division, inhibits cell proliferation, inhibits the cell cycle and/or induces cell cycle arrest. In some embodiments, the change in fermentation conditions is a switch to anaerobic fermentation conditions, and in certain embodiments, the change in fermentation conditions is a switch to an elevated temperature. In some embodiments, the polypeptide that regulates the cell cycle has thymidylate synthase activity. In certain embodiments, the promoter activity is reduced by the change in fermentation conditions. In some embodiments, the genetic modification is a temperature sensitive mutation.

Provided also in some embodiments are methods for manufacturing a target product produced by an engineered microorganism, which comprise: (a) culturing an engineered microorganism described herein under aerobic conditions; and (b) culturing the engineered microorganism after (a) under anaerobic conditions, whereby the engineered microorganism produces the target product. Also provided in some embodiments are methods for producing a target product by an engineered microorganism, which comprise: (a) culturing an engineered microorganism described herein under a first set of fermentation conditions; and (b) culturing the engineered microorganism after (a) under a second set of fermentation conditions different than the first set of fermentation conditions, whereby the second set of fermentation conditions inhibits cell division and/or cell proliferation of the engineered microorganism. In certain embodiments, the target product is ethanol or succinic acid. In some embodiments, the host microorganism from which the engineered microorganism is produced does not produce a detectable amount of the target product. In certain embodiments, the culture conditions comprise fermentation conditions, comprise introduction of biomass, comprise introduction of a six-carbon sugar (e.g., glucose), and/or comprise introduction of a five-carbon sugar (e.g., xylulose, xylose); or combinations of the foregoing. In some embodiments, the target product is produced with a yield of greater than about 0.3 grams per gram of glucose added, and in certain embodiments, a method comprises purifying the target product from the cultured microorganisms. In some embodiments, a method comprises modifying the target product, thereby producing modified target product. In certain embodiments, a method comprises placing the cultured microorganisms, the target product or the modified target product in a container, and in certain embodiments, a method comprises shipping the container. In some embodiments, the second set of fermentation conditions comprises an elevated temperature as compared to the temperature in the first set of fermentation conditions. In certain embodiments, the genetic modification inhibits the cell cycle of the engineered microorganism upon exposure to the second set of fermentation conditions. In some embodiments, the genetic modification inhibits cell proliferation, inhibits cell division, inhibits the cell cycle and/or induces cell cycle arrest upon exposure to the second set of fermentation conditions. In certain embodiments, the genetic modification inhibits thymidylate synthase activity upon exposure to the change in fermentation conditions, and sometimes the genetic modification comprises a temperature sensitive mutation.

Also provided in certain embodiments are methods for manufacturing an engineered microorganism, which comprise: (a) introducing a genetic modification to a host microorganism that reduces an Embden-Meyerhoff glycolysis pathway member activity upon exposure of the engineered microorganism to anaerobic conditions; and (b) selecting for engineered microorganisms that (i) metabolize six-carbon sugars by the Embden-Meyerhoff glycolysis pathway under aerobic fermentation conditions, and (ii) preferentially metabolize six-carbon sugars by the Enter-Doudoroff pathway under the anaerobic fermentation conditions. In some embodiments, the genetic modification is insertion of a promoter into genomic DNA in operable linkage with a polynucleotide that encodes the Embden-Meyerhoff glycolysis pathway member activity. The genetic modification sometimes is provision of a heterologous promoter polynucleotide in operable linkage with a polynucleotide that encodes the Embden-Meyerhoff glycolysis pathway member activity. In certain embodiments, the genetic modification is a deletion or disruption of a polynucleotide that encodes, or regulates production of, the Embden-Meyerhoff glycolysis pathway member, and the microorganism comprises a heterologous nucleic acid that includes a polynucleotide encoding the Embden-Meyerhoff glycolysis pathway member operably linked to a polynucleotide that down-regulates production of the member under anaerobic fermentation conditions. In some embodiments, the Embden-Meyerhoff glycolysis pathway member activity is a phosphofructokinase activity. In certain embodiments, the activity of one or more (e.g., 2, 3, 4, 5 or more) pathway members in an EM pathway is reduced or removed to undetectable levels. Provided also in some embodiments are methods for manufacturing an engineered microorganism, which comprise: (a) introducing a genetic modification to a host microorganism that inhibits cell division upon exposure to a change in fermentation conditions, thereby producing engineered microorganisms; and (b) selecting for engineered microorganisms with inhibited cell division upon exposure of the engineered microorganisms to the change in fermentation conditions. In certain embodiments, the change in fermentation conditions comprises a change to anaerobic fermentation conditions. The change in fermentation conditions sometimes comprises a change to an elevated temperature. In some embodiments, the genetic modification inhibits the cell cycle of the engineered microorganism upon exposure to the change in fermentation conditions. The genetic modification sometimes inhibits cell division, inhibits the cell cycle, inhibits cell proliferation and/or induces cell cycle arrest upon exposure to the change in fermentation conditions. In some embodiments, the genetic modification inhibits thymidylate synthase activity upon exposure to the change in fermentation conditions, and in certain embodiments, the genetic modification comprises a temperature sensitive mutation.

In certain embodiments pertaining to engineered microorganisms, and methods of making or using such microorganisms, the microorganism comprises a genetic modification that adds or alters a five-carbon sugar metabolic activity. In some embodiments, the microorganism comprises a genetic alteration that adds or alters xylose isomerase activity. In certain embodiments, the microorganism comprises a genetic alteration that adds or alters five-carbon sugar transporter activity, and sometimes the transporter activity is a transporter facilitator activity or an active transporter activity. In some embodiments, the microorganism comprises a genetic alteration that adds or alters carbon dioxide fixation activity, and sometimes the genetic alteration that adds or alters phosphoenolpyruvate (PEP) carboxylase activity. In certain embodiments, the microorganism comprises a genetic modification that reduces or removes an alcohol dehydrogenase 2 activity. In some embodiments the microorganism is an engineered yeast, such as a *Saccharomyces* yeast (e.g., *S. cerevisiae*), for example.

Additional embodiments can be found in Example 29: Examples of the embodiments. Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

In FIG. 2 the activity of an enzyme in the Embden-Meyerhoff pathway, phosphofructokinase (e.g., PFK) is permanently or temporarily reduced or eliminated. The inactivation is shown as the "X" in FIG. 2. Disruption of the activity of PFK serves to inactivate the Embden-Meyerhoff pathway (EM pathway). To allow cells to survive with a non-functional PFK, two activities from the Entner-Doudoroff pathway (ED pathway) have been introduced into a host organism engineered with the reduced or non-functional EM pathway. The introduced activities allow survival with an inactivated EM pathway in addition to increased efficiency of ethanol production.

FIG. 6 shows DNA and amino acid sequence alignments for the nucleotide sequences of EDA (FIG. 6A (SEQ ID NOS 266-269, respectively, in order of appearance), 6B (SEQ ID NOS 270-273, respectively, in order of appearance)) and EDD (FIG. 6C (SEQ ID NOS 454-457, respectively, in order of appearance), 6D (SEQ ID NOS 458-461, respectively, in order of appearance)) genes from *Zymomonas mobilis* (native and optimized) and *Escherichia coli*.

FIG. 11A illustrates the fermentation data for engineered strain BF428 (BY4742 with vector controls), and FIG. 11B illustrates the fermentation data for engineered strain BF591 (BY4742 with EDD-PAO1/EDA-PAO1). Experimental conditions and results are described in Example 12.

FIG. 12A illustrates the fermentation data for engineered strain BF738 (BY4742 tal1 with vector controls p426GPD and p425GPD). FIG. 12B illustrates the fermentation data for engineered strain BF741 (BY4742 tal1 with plasmids pBF290 (EDD- PAO1) and pBF292 (EDA-PAO1). Experimental conditions and results are described in Example 13.

FIG. 13A illustrates the fermentation data for BF740 grown on 2% dextrose, and FIG. 13B illustrates the fermentation data for BF743 grown on 2% dextrose. Strain descriptions, experimental conditions and results are described in Example 14.

DETAILED DESCRIPTION

Figure 1:
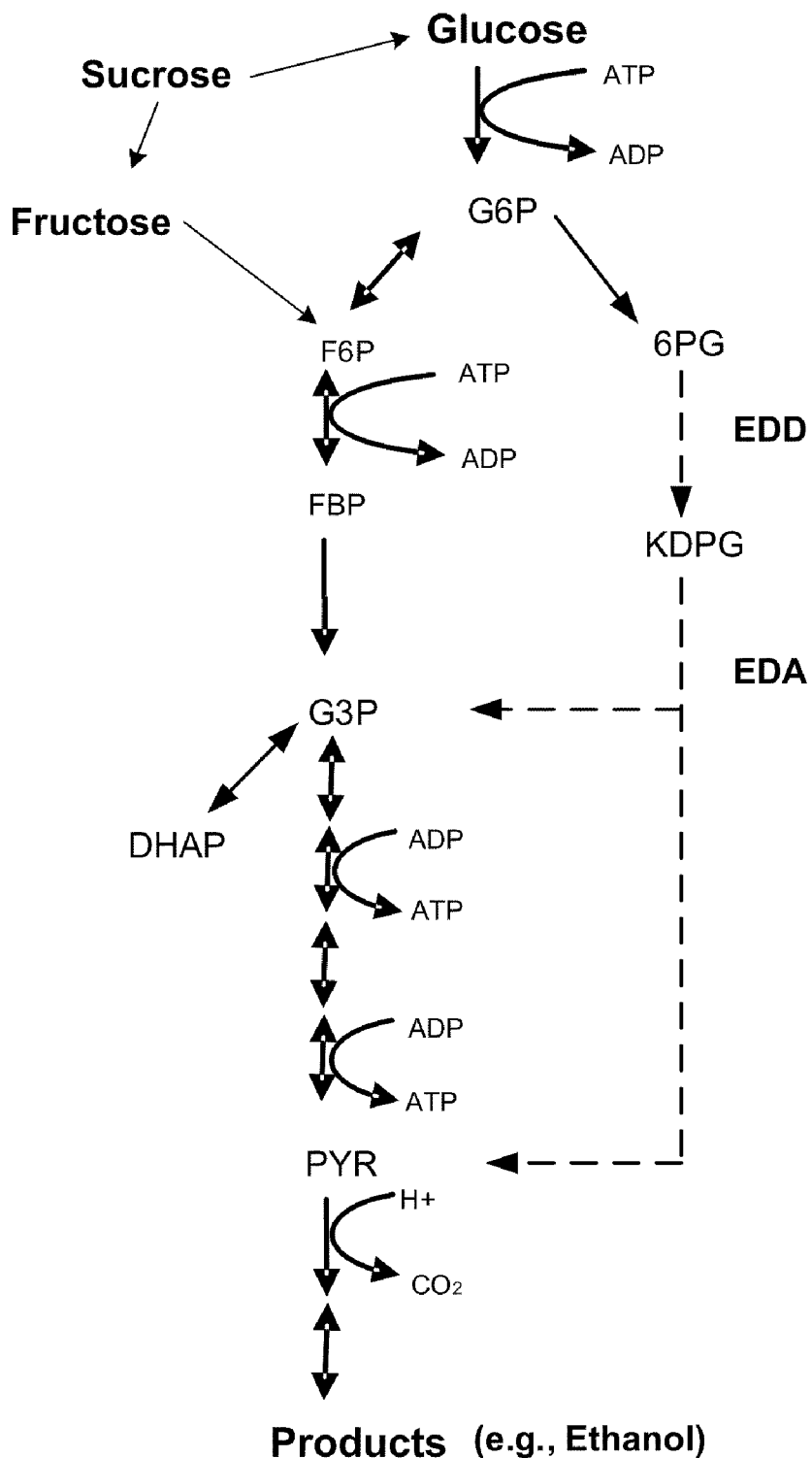
FIG. 1 depicts a metabolic pathway that produces ethanol as by product of cellular respiration. The solid lines represent activities present in the Embden-Meyerhoff pathway (e.g., aerobic respiration). Dashed lines represent activities associated with the Entner-Doudoroff pathway (e.g., anaerobic respiration). One or both pathways often can be operational in a microorganism. The level of activity of each pathway can vary from organism to organism. The arrow from FBP (e.g., Fructose-1,6-bisphosphate, also referred to as F-1,6-BP) to G3P (e.g., glcyeraldehyde-3-phosphate), illustrates wild type levels of conversion of FBP to two molecules of G3P. In the embodiments shown in FIGS. 2, 3 and 5 a smaller arrow from FBP to G3P is illustrated, indicating reduced or no conversion of FBP to G3P. The reduction in conversion of FBP to G3P illustrated in FIGS. 2, 3 and 5 is a result of the reduction or elimination of the previous activity that converts fructose-6-phosphate (F6P) to FBP (e.g., the activity of PFK).
Figure 2:
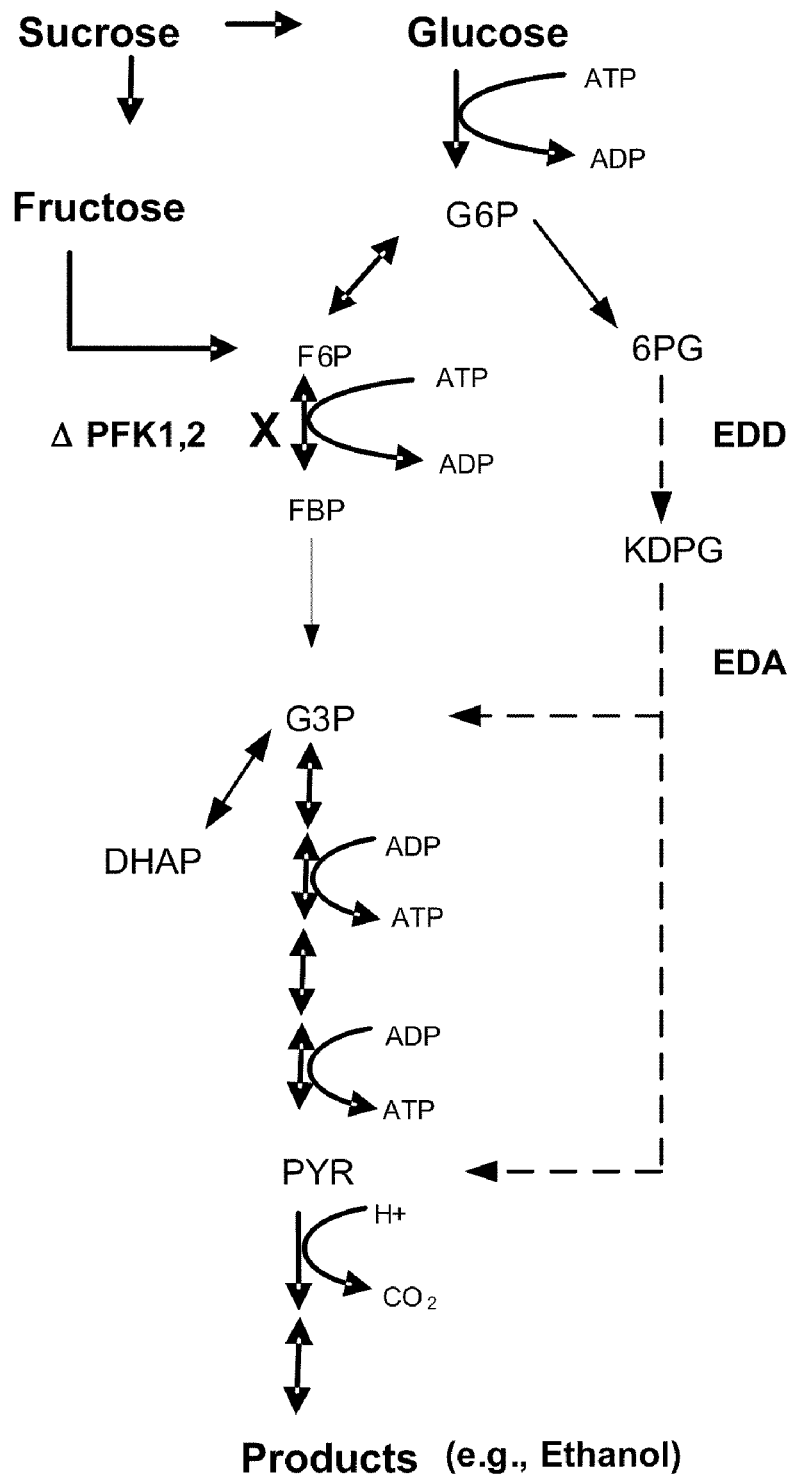
FIG. 2 depicts an engineered metabolic pathway that can be used to produce ethanol more efficiently in a host microorganism in which the pathway has been engineered. The solid lines in FIGS. 2-5 represent the metabolic pathway naturally found in a host organism (e.g., Saccharomyces cerevisiae, for example). The dashed lines in FIGS. 2-5 represent a novel activity or pathway engineered into a microorganism to allow increased ethanol production efficiency.
Figure 3:
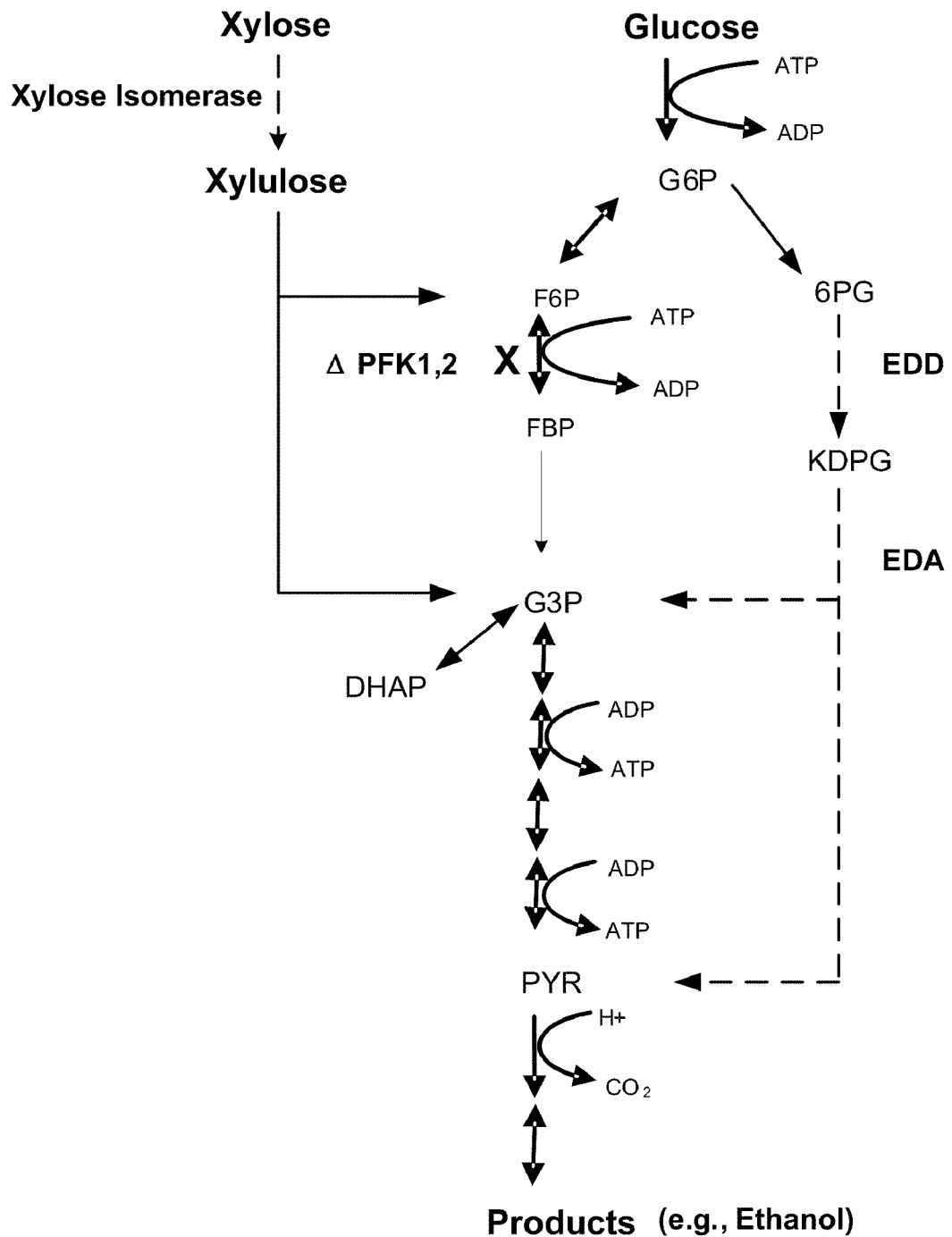
FIG. 3 depicts an engineered metabolic pathway that can be used to produce ethanol using xylose as a carbon source by introducing the activity into a microorganism. The engineered microorganism can convert xylose to xylulose in a single reaction using the introduced xylose isomerase activity. Xylulose then can be fermented to ethanol by entering the EM pathway. Engineered microorganisms also can use the increased efficiency of ethanol production associated with inactivation of the EM pathway and introduction of activities of the ED pathway, shown in FIG. 2 and discussed below. The ability to utilize xylose efficiently (e.g., concurrently with six-carbon sugars or prior to the depletion of six-carbon sugars) can be provided by the introduction of the novel activity, xylose isomerase.

Ethanol is a two carbon, straight chain, primary alcohol that can be produced from fermentation (e.g., cellular respiration processes) or as a by-product of petroleum refining. Ethanol has widespread use in medicine, consumables, and in industrial processes where it often is used as an essential solvent and a precursor, or feedstock, for the synthesis of other products (e.g., ethyl halides, ethyl esters, diethyl ether, acetic acid, ethyl amines and to a lesser extent butadiene, for example). The largest use of ethanol, worldwide, is as a motor fuel and fuel additive. Greater than 90% of the cars produced world wide can run efficiently on hydrous ethanol (e.g., 95% ethanol and 5% water). Ethanol also is commonly used for production of heat and light.

World production of ethanol exceeds 50 gigaliters (e.g., $1.3 \times 10^{10}$ US gallons), with 69% of the world supply coming from Brazil and the United States. The United States fuel ethanol industry is based largely on corn biomass. The use of corn biomass for ethanol production may not yield a positive net energy gain, and further has the potential of diverting land that could be used for food production into ethanol production. It is possible that cellulosic crops may displace corn as the main fuel crop for producing bio-ethanol. Non-limiting examples of cellulosic crops and waste materials include switchgrass and wood pulp waste from paper production and wood milling industries.

Biomass produced in the paper pulping and wood milling industries contains both 5 and six-carbon sugars. Use of this wasted biomass could allow production of significant amounts of bio-fuels and products, while reducing the use of land that could be used for food production. Predominant forms of sugars in the biomass produced in wood and paper pulping and wood milling industries are glucose and xylose.

Provided herein are methods for producing ethanol, ethanol derivatives and/or conjugates and other organic chemical intermediates (e.g., pyruvate, acetaldehyde, glyceraldehyde-3-phosphate, and the like) using biological systems. Such production systems may have significantly less environmental impact and could be economically competitive with current manufacturing systems. Thus, provided herein are methods for manufacturing ethanol and other organic chemical intermediates by engineered microorganisms. In some embodiments microorganisms are engineered to contain at least one heterologous gene encoding an enzyme, where the enzyme is a member of a novel pathway engineered into the microorganism. In certain embodiments, an organism may be selected for elevated activity of a native enzyme.

Genetically engineered microorganisms described herein produce organic molecules for industrial uses. The organisms are designed to be "feedstock flexible" in that they can use five-carbon sugars (e.g., pentose sugars such as xylose, for example), six-carbon sugars (e.g., hexose sugars such as glucose or fructose, for example) or both as carbon sources. Further, the organisms described herein have been designed to be highly efficient in their use of hexose sugars to produce desired organic molecules. To that end, the microorganisms described herein are "pathway flexible" such that the microorganisms are able to direct hexose sugars primarily to either (i) the traditional glycolysis pathway (the Embden-Meyerhoff pathway) thereby generating ATP energy for cell growth and division at certain times, or (ii) a separate glycolytic pathway (the Entner-Doudoroff pathway) thereby producing significant levels of pyruvic acid, a key 3-carbon intermediate for producing many desired industrial organic molecules.

Pathway selection in the microorganism can be directed via one or more environmental switches such as a temperature change, oxygen level change, addition or subtraction of a component of the culture medium, or combinations thereof. The metabolic pathway flexibility of microorganisms described herein allow the microorganisms to efficiently use hexose sugars, which ultimately can lead to microorganisms capable of producing a greater amount of industrial chemical product per gram of feedstock as compared with conventional microorganisms (e.g., the organism from which the engineered organism was generated, for example). In some embodiments, the metabolic pathway flexibility of the engineered microorganisms described herein is generated by adding or increasing metabolic activities associated with the Entner-Doudoroff pathway. In certain embodiments the metabolic activities added are phosphogluconate dehydratase (e.g., EDD gene), 2-keto-3-deoxygluconate-6-phosphate aldolase (e.g., EDA gene) or both.

A number of industrially useful microorganisms (e.g., microorganisms used in fermentation processes, yeast for example), metabolize xylose inefficiently or are incapable of metabolizing xylose. Many organisms that can metabolize xylose do so only after all glucose and/or other six-carbon sugars have been depleted. The microorganisms described herein have been engineered to efficiently utilize five-carbon sugars (e.g., xylose, for example) as an alternative or additional source of carbon, concurrently with and/or prior to six-carbon sugar usage, by the incorporation of a heterologous nucleic acid (e.g., gene) encoding a xylose isomerase, in some embodiments. Xylose isomerase converts the five-carbon sugar xylose to xylulose. Xylulose can ultimately be converted to pyruvic acid or to ethanol through metabolism via the Embden-Meyerhoff or Entner-Doudoroff pathways.

Many non-photosynthetic organisms are not capable of incorporating inorganic atmospheric carbon into organic carbon compounds, via carbon fixation pathways, to any appreciable degree, or at all. Often, microorganisms used in industrial fermentation process also are incapable of significant carbon fixation. The ability to incorporate atmospheric carbon dioxide, or carbon dioxide waste from respiration in fermentation processes, can increase the amount of industrial chemical product produced per gram of feedstock, in certain embodiments. Thus, the microorganisms described herein also can be modified to add or increase the ability to incorporate carbon from carbon dioxide into industrial chemical products, in some embodiments. In certain embodiments, the microorganisms described herein are engineered to express enzymes such as phosphoenolpyruvate carboxylase ("PEP" carboxylase) and/or ribulose 1,5-bis-phosphate carboxylase ("Rubisco"), thus allowing the use of carbon dioxide as an additional source of carbon.

A particularly useful industrial chemical product produced by fermentation is ethanol. Ethanol is an end product of cellular respiration and is produced from acetaldehyde by an alcohol dehydrogenase activity (e.g., by an enzyme like alcohol dehydrogenase 1 or ADH1, for example). However, ethanol can readily be converted back to acetaldehyde by the action of the enzyme alcohol dehydrogenase 2 (e.g., ADH2), thus lowering the yield of ethanol produced. In some embodiments, microorganisms described herein are modified to reduce or eliminate the activity of ADH2, to allow increased yields of ethanol. In certain embodiments, the engineered microorganisms described herein also are modified to have a higher tolerance to alcohol, thus enabling even higher yields of alcohol as a fermentation product without inhibition of cellular processes due to increased levels of alcohol in the growth medium.

Microorganisms

A microorganism selected often is suitable for genetic manipulation and often can be cultured at cell densities useful for industrial production of a target product. A microorganism selected often can be maintained in a fermentation device.

The term "engineered microorganism" as used herein refers to a modified microorganism that includes one or more activities distinct from an activity present in a microorganism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Thus, an engineered microorganism has been altered directly or indirectly by a human being. A host microorganism sometimes is a native microorganism, and at times is a microorganism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba).

Any suitable yeast may be selected as a host microorganism, engineered microorganism or source for a heterologous polynucleotide. Yeast include, but are not limited to, *Yarrowia* yeast (e.g., *Y. lipolytica* (formerly classified as *Candida lipolytica*)), *Candida* yeast (e.g., *C. revkaufi, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a yeast is a *S. cerevisiae* strain including, but not limited to, YGR240CBY4742 (ATCC accession number 4015893) and BY4742 (ATCC accession number 201389). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *C. tropicalis* strain that includes, but is not limited to, ATCC20336, ATCC20913, SU-2 (ura3-/ura3-), ATCC20962, H5343 (beta oxidation blocked; U.S. Pat. No. 5,648,247) strains.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*), *Orpinomyces* or *Piromyces*. In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium, B. stearothermophilus*), *Bacteroides* bacteria (e.g., *Bacteroides uniformis, Bacteroides thetaiotaomicron*), *Clostridium* bacteria (e.g., *C. phytofermentans, C. thermohydrosulfuricum, C. cellulyticum* (H10)), *Acinetobacter* bacteria, *Norcardia* bacteria, *Lactobacillus* bacterial (e.g., *Lactobacillus pentosus*), *Xanthobacter* bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188))), *Streptomyces* bacteria (e.g., *Streptomyces rubiginosus, Streptomyces murinus*), *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Thermus* bacteria (e.g., *Thermus thermophilus*), and *Thermotoga* bacteria (e.g., *Thermotoga maritiima, Thermotoga neopolitana*) and *Ruminococcus* (e.g., *Ruminococcus* environmental samples, *Ruminococcus albus, Ruminococcus bromii, Ruminococcus callidus, Ruminococcus flavefaciens, Ruminococcus gauvreauii, Ruminococcus gnavus, Ruminococcus lactaris, Ruminococcus obeum, Ruminococcus* sp., *Ruminococcus* sp. 14531, *Ruminococcus* sp. 15975, *Ruminococcus* sp. 16442, *Ruminococcus* sp. 18P13, *Ruminococcus* sp. 25F6, *Ruminococcus* sp. 25F7, *Ruminococcus* sp. 25F8, *Ruminococcus* sp. 4_1_47FAA, *Ruminococcus* sp. 5, *Ruminococcus* sp. 5_1_39BFAA, *Ruminococcus* sp. 7L75, *Ruminococcus* sp. 8_1_37FAA, *Ruminococcus* sp. 9SE51, *Ruminococcus* sp. C36, *Ruminococcus* sp. CB10, *Ruminococcus* sp. CB3, *Ruminococcus* sp. CCUG 37327 A, *Ruminococcus* sp. CE2, *Ruminococcus* sp. CJ60, *Ruminococcus* sp. CJ63, *Ruminococcus* sp. CO1, *Ruminococcus* sp. CO12, *Ruminococcus* sp. CO22, *Ruminococcus* sp. CO27, *Ruminococcus* sp. CO28, *Ruminococcus* sp. CO34, *Ruminococcus* sp. CO41, *Ruminococcus* sp. CO47, *Ruminococcus* sp. CO7, *Ruminococcus* sp. CS1, *Ruminococcus* sp. CS6, *Ruminococcus* sp. DJF_VR52, *Ruminococcus* sp. DJF_VR66, *Ruminococcus* sp. DJF_VR67, *Ruminococcus* sp. DJF_VR70k1, *Ruminococcus* sp. DJF_VR87, *Ruminococcus* sp. Eg2, *Ruminococcus* sp. Egf, *Ruminococcus* sp. END-1, *Ruminococcus* sp. FD1, *Ruminococcus* sp. GM2/1, *Ruminococcus* sp. ID1, *Ruminococcus* sp. ID8, *Ruminococcus* sp. K-1, *Ruminococcus* sp. KKA Seq234, *Ruminococcus* sp. M-1, *Ruminococcus* sp. M10, *Ruminococcus* sp. M22, *Ruminococcus* sp. M23, *Ruminococcus* sp. M6, *Ruminococcus* sp. M73, *Ruminococcus* sp. M76, *Ruminococcus* sp. MLG080-3, *Ruminococcus* sp. NML 00-0124, *Ruminococcus* sp. Pei041, *Ruminococcus* sp. SC101, *Ruminococcus* sp. SC103, *Ruminococcus* sp. Siijpesteijn 1948, *Ruminococcus* sp. WAL 17306, *Ruminococcus* sp. YE281, *Ruminococcus* sp. YE58, *Ruminococcus* sp. YE71, *Ruminococcus* sp. ZS2-15, *Ruminococcus torques*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. lutecium*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.).

Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Six-Carbon Sugar Metabolism and Activities

Six-carbon or hexose sugars can be metabolized using one of two pathways in many organisms. One pathway, the Embden-Meyerhoff pathway (EM pathway), operates primarily under aerobic (e.g., oxygen rich) conditions. The other pathway, the Entner-Doudoroff pathway (ED pathway), operates primarily under anaerobic (e.g., oxygen poor) conditions, producing pyruvate that can be converted to lactic acid. Lactic acid can be further metabolized upon a return to appropriate conditions. The EM pathway produces two ATP for each six-carbon sugar metabolized, as compared to one ATP produced for each six-carbon sugar metabolized in the ED pathway. Thus the ED pathway yields ethanol more efficiently than the EM pathway with respect to a given amount of input carbon, as seen by the lower net energy yield. However, yeast preferentially use the EM pathway for metabolism of six-carbon sugars, thereby preferentially using the pathway that yields more energy and less desired product.

The following steps and enzymatic activities metabolize six-carbon sugars via the EM pathway. Six-carbon sugars (glucose, sucrose, fructose, hexose and the like) are converted to glucose-6-phosphate by hexokinase or glucokinase (e.g., HXK or GLK, respectively). Glucose-6-phosphate can be converted to fructose-6-phosphate by phosphoglucoisomerase (e.g., PGI). Fructose-6-phosphate can be converted to fructose-1,6-bisphosphate by phosphofructokinase (e.g., PFK). Fructose-1,6-bisphosphate (F1,6BP) represents a key intermediate in the metabolism of six-carbon sugars, as the next enzymatic reaction converts the six-carbon sugar into two 3 carbon sugars. The reaction is catalyzed by fructose bisphosphate aldolase and yields a mixture of dihydroxyacetone phosphate (DHAP) and glyceraldehyde-3-phosphate (G-3-P). The mixture of the two 3 carbon sugars is preferentially converted to glyceraldehyde-3-phosphate by the action of triosephosphate isomerase. G-3-P is converted is converted to 1,3-diphosphoglycerate (1,3-DPG) by glyceraldehyde-3-phosphate dehydrogenase (GLD). 1,3-DPG is converted to 3-phosphoglycerate (3-P-G by phosphoglycerate kinase (PGK). 3-P-G is converted to 2-phosphoglycerate (2-P-G) by phophoglycero mutase (GPM). 2-P-G is converted to phosphoenolpyruvate (PEP) by enolase (ENO). PEP is converted to pyruvate (PYR) by pyruvate kinase (PYK). PYR is converted to acetaldehyde by pyruvate dicarboxylase (PDC). Acetaldehyde is converted to ethanol by alcohol dehydrogenase 1 (ADH1).

Many enzymes in the EM pathway are reversible. The enzymes in the EM pathway that are not reversible, and provide a useful activity with which to control six-carbon sugar metabolism, via the EM pathway, include, but are not limited to phosphofructokinase and alcohol dehydrogenase. In some embodiments, reducing or eliminating the activity of phosphofructokinase may inactivate the EM pathway. Engineering microorganisms with modified activities in PFK and/or ADH may yield increased product output as compared to organisms with the wild type activities, in certain embodiments. In some embodiments, modifying a reverse activity (e.g., the enzyme responsible for catalyzing the reverse activity of ADH, for example) may also yield an increase in product yield by reducing or eliminating the back conversion of products by the backwards reaction. The activity which catalyzes the conversion of ethanol to acetaldehyde is alcohol dehydrogenase 2 (ADH2). Reducing or eliminating the activity of ADH2 can increase the yield of ethanol per unit of carbon input due to the inactivation of the conversion of ethanol to acetaldehyde, in certain embodiments. In addition to enzyme activities that are not reversible, certain reversible activities also can be used to control six-carbon sugar metabolism via the EM pathway, in some embodiments. A non-limiting example of a reversible enzymatic activity that can be utilized to control six-carbon sugar metabolism includes phosphoglucose isomerase (PGI).

A microorganism may be engineered to include or regulate one or more activities in the Embden-Meyerhoff pathway, for example. In some embodiments, one or more of these activities may be altered such that the activity or activities can be increased or decreased according to a change in environmental conditions. In certain embodiments, one or more of the activities (e.g., PGI, PFK or ADH2) can be altered to allow regulated control and an alternative pathway for more efficient carbon metabolism can be provided (e.g., one or more activities from the ED pathway, for example). An engineered organism with the EM pathway under regulatable control and a novel or enhanced ED pathway would be useful for producing significantly more ethanol or other end product from a given amount of input feedstock. The term "activity" as used herein refers to the functioning of a microorganism's natural or engineered biological pathways to yield various products including ethanol and its precursors. Ethanol (or other product) producing activity can be provided by any non-mammalian source in certain embodiments. Such sources include, without limitation, eukaryotes such as yeast and fungi and prokaryotes such as bacteria. In some embodiments, the activity of one or more (e.g., 2, 3, 4, 5 or more) pathway members in an EM pathway is reduced or removed to undetectable levels.

An engineered microorganism may, in some embodiments, preferentially metabolize six-carbon sugars via the ED pathway as opposed to the EM pathway under certain conditions. Such engineered microorganisms may metabolize about 60% or more of the available six-carbon sugars via the ED pathway (e.g., about 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing), and such fraction of the available six-carbon sugars are not metabolized by the EM pathway, under certain conditions. A microorganism may metabolize six-carbon sugars substantially via the ED pathway, and not the EM pathway, in certain embodiments (e.g., 99% or greater, or 100%, of the available six-carbon sugars are metabolized via the ED pathway). A six-carbon sugar is deemed as being metabolized via a particular pathway when the sugar is converted to end metabolites of the pathway, and not intermediate metabolites only, of the particular pathway. A microorganism may preferentially metabolize certain sugars under the ED pathway after a certain time after the microorganism is exposed to a certain set of conditions (e.g., there may be a time delay after a microorganism is exposed to a certain set of conditions before the microorganism preferentially metabolizes sugars by the ED pathway).

Certain novel activities involved in the metabolism of six-carbon sugars by the ED pathway can be engineered into a desired yeast strain to increase the efficiency of ethanol (or other products) production. Yeast do not have an activity that converts 6-phophogluconate to 2-keto-3-deoxy-6-p-gluconate or an activity that converts 2-keto-3-deoxy-6-p-gluconate to pyruvate. Addition of these activities to engineered yeast can allow the engineered microorganisms to increase fermentation efficiency by allowing yeast to ferment ethanol under anaerobic condition without having to use the EM pathway and expend additional energy. Therefore, by providing novel activities associated with converting 6-phosphogluconate to 2-keto-3-deoxy-6-p-gluconate and 2-keto-3-deoxy-6-p-gluconate to pyruvate, the engineered microorganism can benefit by producing ethanol more efficiently, with respect to a given amount of input carbon, than by using the native EM pathway.

Bacteria often have enzymatic activities that confer the ability to anaerobically metabolize six-carbon sugars to ethanol. These activities are associated with the ED pathway and include, but are not limited to, phosphogluconate dehydratase (e.g., the EDD gene, for example), and 2-keto-3-deoxygluconate-6-phosphate aldolase (e.g., the EDA gene, for example). Phosphogluconate dehydratase converts 6-phophogluconate to 2-keto-3-deoxy-6-p-gluconate. 2-keto-3-deoxygluconate-6-phosphate aldolase converts 2-keto-3-deoxy-6-p-gluconate to pyruvate. In some embodiments, these activities can be introduced into a host organism to generate an engineered microorganism which gains the ability to use the ED pathway to produce ethanol more efficiently than the non-engineered starting organism, by virtue of the lower net energy yield by the ED pathway. A microorganism may be engineered to include or regulate one or more activities in the Entner-Doudoroff pathway. In some embodiments, one or more of these activities may be altered such that the activity or activities can be increased or decreased according to a change in environmental conditions. Nucleic acid sequences encoding Embden-Meyerhoff pathway and Entner-Doudoroff pathway activities can be obtained from any suitable organism (e.g., plants, bacteria, and other microorganisms, for example) and any of these activities can be used herein with the proviso that the nucleic acid sequence is naturally active in the chosen microorganism when expressed, or can be altered or modified to be active.

Yeast also can have endogenous or heterologous enzymatic activities that enable the organism to anaerobically metabolize six carbon sugars. Saccharomyces cerevisiae used in fermentation often convert glucose-6-phosphate (G-6-P) to fructose-6-phosphate (F-6-P) via phosphoglucose isomerase (EC 5.3.1.9), up to 95% of G-6-P is converted to F-6-P in this manner for example. Only a minor proportion of G-6-P is converted to 6-phophoglucono-lactone (6-PGL) by an alternative enzyme, glucose-6-phosphate dehydrogenase (EC 1.1.1.49). Yeast engineered to carry both Entner-Doudoroff (ED) and Embden-Meyerhoff (EM) pathways often covert sugars to ethanol using the EM pathway preferentially. Inactivation of one or more activities in the EM pathway can result in conversion of sugars to ethanol using the ED pathway preferentially, in some embodiments.

Phosphoglucose isomerase (EC 5.3.1.9) catalyzes the reversible interconversion of glucose-6-phosphate and fructose-6-phosphate. Phosphoglucose isomerase is encoded by the PGI1 gene in *S. cerevisiae*. The proposed mechanism for sugar isomerization involves several steps and is thought to occur via general acid/base catalysis. Since glucose 6-phosphate and fructose 6-phosphate exist predominantly in their cyclic forms, PGI is believed to catalyze first the opening of the hexose ring to yield the straight chain form of the substrates. Glucose 6-phosphate and fructose 6-phosphate then undergo isomerization via formation of a cis-enediol intermediate with the double bond located between C-1 and C-2. Phosphoglucose isomerase sometimes also is referred to as glucose-6-phosphate isomerase or phosphohexose isomerase.

PGI is involved in different pathways in different organisms. In some higher organisms PGI is involved in glycolysis, and in mammals PGI also is involved in gluconeogenesis. In plants PGI is involved in carbohydrate biosynthesis, and in some bacteria PGI provides a gateway for fructose into the Entner-Doudoroff pathway. PGI also is known as neuroleukin (a neurotrophic factor that mediates the differentiation of neurons), autocrine motility factor (a tumor-secreted cytokine that regulates cell motility), differentiation and maturation mediator and myofibril-bound serine proteinase inhibitor, and has different roles inside and outside the cell. In the cytoplasm, PGI catalyses the second step in glycolysis, while outside the cell it serves as a nerve growth factor and cytokine. PGI activity is involved in cell cycle progression and completion of the gluconeogenic events of sporulation in *S. cerevisiae*.

In certain embodiments, phosphoglucose isomerase activity is altered in an engineered microorganism. In some embodiments phosphoglucose isomerase activity is decreased or disrupted in an engineered microorganism. In certain embodiments, decreasing or disrupting phosphoglucose isomerase activity may be desirable to decrease or eliminate the isomerization of glucose-6-phosphate to fructose-6-phosphate, thereby increasing the proportion of glucose-6-phosphate converted to gluconolactone-6-phosphate by the activity encoded by ZWF1 (e.g., glucose-6-phosphate dehydrogenase). Increased levels of gluconolactone-6-phosphate can be further metabolized and thereby improve fermentation of sugar to ethanol via activities in the Entner-Doudoroff pathway, even in the presence of the enzymes comprising the Embden-Meyerhoff pathway. Decreased or disrupted phosphoglucose isomerase (EC 5.3.1.9) activity in yeast may be achieved by any suitable method, or as described herein. Non-limiting examples of methods suitable for decreasing or disrupting the activity of phosphoglucose isomerase include use of a regulated promoter, use of a weak constitutive promoter, disruption of one of the two copies of the gene in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof. In some embodiments, a gene used to knockout one activity can also introduce or increase another activity. PGI1 genes may be native to *S. cerevisiae*, or may be obtained from a heterologous source.

Glucose-6-phosphate dehydrogenase (EC 1.1.1.49) catalyzes the first step of the pentose phosphate pathway, and is encoded by the *S. cerevisiae* gene, zwf1. The reaction for the first step in the PPP pathway is;

D-glucose 6-phosphate+NADP$^+$=D-glucono-1,5-lactone 6-phosphate+NADPH+H$^+$

This reaction is irreversible and rate-limiting for efficient fermentation of sugar via the Entner-Doudoroff pathway. The enzyme regenerates NADPH from NADP+ and is important both for maintaining cytosolic levels of NADPH and protecting yeast against oxidative stress. Zwf1p expression in yeast is constitutive, and the activity is inhibited by NADPH such that processes that decrease the cytosolic levels of NADPH stimulate the oxidative branch of the pentose phosphate pathway. Amplification of glucose-6-phosphate dehydrogenase activity in yeast may be desirable to increase the proportion of glucose-6-phosphate converted to 6-phosphoglucono-lactone and thereby improve fermentation of sugar to ethanol via the Entner-Doudoroff pathway, even in the presence of the enzymes comprising the Embden-Meyerhoff pathway.

Glucose-6-phosphate dehydrogenase (EC 1.1.1.49) activity in yeast may be amplified by over-expression of the zwf1 gene by any suitable method. Non-limiting examples of methods suitable to amplify or over express zwf1 include amplifying the number of ZWF1 genes in yeast following transformation with a high-copy number plasmid (e.g., such as one containing a 2 uM origin of replication), integration of multiple copies of ZWF1 into the yeast genome, over-expression of the ZWF1 gene directed by a strong promoter, the like or combinations thereof. The ZWF1 gene may be native to *S. cerevisiae*, or it may be obtained from a heterologous source. 6-phosphogluconolactonase (EC 3.1.1.31) catalyzes the second step of the ED (e.g., pentose phosphate pathway), and is encoded by *S. cerevisiae* genes SOL3 and SOL4. The reaction for the second step of the pentose phosphate pathway is;

6-phospho-D-glucono-1,5-lactone+H2O=6-phospho-D-gluconate

Amplification of 6-phosphogluconolactonase activity in yeast may be desirable to increase the proportion of 6-phospho-D-glucono-1,5-lactone converted to 6-phospho-D-gluconate and thereby improve fermentation of sugar to ethanol via the Entner-Doudoroff pathway, even in the presence of the enzymes comprising the Embden-Meyerhoff pathway. For example, over expression of SOL3 is known to increase the rate of carbon source utilization to result in faster growth on xylose than wild type.

The *Saccharomyces cerevisiae* SOL protein family includes Sol3p and Sol4p. Both localize predominantly in the cytosol, exhibit 6-phosphogluconolactonase activity and function in the pentose phosphate pathway. 6-phosphogluconolactonase (EC 3.1.1.31) activity in yeast may be amplified by over-expression of the SOL3 and/or SOL4 gene(s) by any suitable method. Non-limiting examples of methods to amplify or over express SOL3 and SOL4 include increasing the number of SOL3 and/or SOL4 genes in yeast by transformation with a high-copy number plasmid, integration of multiple copies of SOL3 and/or SOL4 gene(s) into the yeast genome, over-expression of the SOL3 and/or SOL4 gene(s) directed by a strong promoter, the like or combinations thereof. The SOL3 and/or SOL4 gene(s) may be native to *S. cerevisiae*, or may be obtained from a heterologous source. For example, Sol3p and Sol4p have similarity to each other, and to *Candida albicans* Sol1p, *Schizosaccharomyces pombe* Sol1p, human PGLS which is associated with 6-phosphogluconolactonase deficiency, and human H6PD which is associated with cortisone reductase deficiency. Sol3p and Sol4p are also similar to the 6-phosphogluconolactonases in bacteria (*Pseudomonas aeruginosa*) and eukaryotes (*Drosophila melanogaster, Arabidopsis thaliana*, and *Trypanosoma brucei*), to the glucose-6-phosphate dehydrogenase enzymes from bacteria (*Mycobacterium leprae*) and eukaryotes (*Plasmodium falciparum* and rabbit liver microsomes), and have regions of similarity to proteins of the Nag family, including human GNPI and *Escherichia coli* NagB.

Phosphogluconate dehydrogenase (EC:1.1.1.44) catalyzes the second oxidative reduction of NADP+ to NADPH in the cytosolic oxidative branch of the pentose phosphate pathway, and is encoded by the *S. cerevisiae* genes GND1 and GND2. GND1 encodes the major isoform of the enzyme accounting for up to 80% of phosphogluconate dehydrogenase activity, while GND2 encodes the minor isoform of the enzyme. Phosphogluconate dehydrogenase sometimes also is referred to as phosphogluconic acid dehydrogenase, 6-phosphogluconic dehydrogenase, 6-phosphogluconic carboxylase, 6-phosphogluconate dehydrogenase (decarboxylating), and 6-phospho-D-gluconate dehydrogenase. Phosphogluconate dehydrogenase belongs to the family of oxidoreductases, specifically those acting on the CH—OH group of donor with NAD$^+$ or NADP$^+$ as the acceptor. The reaction for the second oxidative reduction of NADP+ to NADPH in the cytosolic oxidative branch of the pentose phosphate pathway is;

6-phospho-D-gluconate+NADP$^+$ ⇌ D-ribulose 5-phosphate+CO$_2$+NADPH

Decreasing the level of 6-phosphogluconolactonase activity in yeast may be desirable to decrease the proportion of 6-phospho-D-gluconate converted to D-ribulose 5-phosphate thereby increasing the levels of the intermediate gluconate-6-phosphate available for conversion to 6-dehydro-3-deoxy-gluconate-6-phosphate, in some embodiments involving engineered microorganisms including increased EDA and EDD activities, thereby improving fermentation of sugar to ethanol via the Entner-Doudoroff pathway, even in the presence of the enzymes comprising the Embden-Meyerhoff pathway.

Decreasing or disrupting 6-phosphogluconolactonase activity in yeast may be achieved by any suitable method, or as described herein. Non-limiting examples of methods suitable for decreasing the activity of 6-phosphogluconate dehydrogenase include use of a regulated promoter, use of a weak constitutive promoter, disruption of one of the two copies of the gene in a diploid yeast (e.g., partial gene knockout), disrupting both copies of the gene in a diploid yeast (e.g., complete gene knockout) expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof. In some embodiments, a gene used to knockout one activity can also introduce or increase another activity. GND1 and/or GND2 gene(s) may be native to *S. cerevisiae*, or may be obtained from a heterologous source. For example, *S. cerevisiae* GND1 and GND2 have similarity to each other, and to the phosphogluconate dehydrogenase nucleotide sequences of *Candida parapsilosis, Cryptococcus neoformans* and humans.

Five-Carbon Sugar Metabolism and Activities

As noted above, five-carbon sugars are the second most predominant form of sugars in lignocelluosic waste biomass produced in wood pulp and wood milling industries. Furthermore, xylose is the second most abundant carbohydrate in nature. However, the conversion of biomass to energy (e.g., ethanol, for example) has not proven economically attractive because many organisms cannot metabolize hemicellulose. Biomass and waste biomass contain both cellulose and hemicellulose. Many industrially applicable organisms can metabolize five-carbon sugars (e.g., xylose, pentose and the like), but may do so at low efficiency, or may not begin metabolizing five-carbon sugars until all six-carbon sugars have been depleted from the growth medium. Many yeast and fungus grow slowly on xylose and other five-carbon sugars. Some yeast, such as *S. cerevisiae* do not naturally use xylose, or do so only if there are no other carbon sources. An engineered microorganism (e.g., yeast, for example) that could grow rapidly on xylose and provide ethanol and/or other products as a result of fermentation of xylose can be useful due to the ability to use a feedstock source that is currently underutilized while also reducing the need for petrochemicals.

The pentose phosphate pathway (PPP), which is a biochemical route for xylose metabolism, is found in virtually all cellular organisms where it provides D-ribose for nucleic acid biosynthesis, D-erythrose 4-phosphate for the synthesis of aromatic amino acids and NADPH for anabolic reactions. The PPP is thought of as having two phases. The oxidative phase converts the hexose, D-glucose 6P, into the pentose, D-ribulose 5P, plus CO2 and NADPH. The non-oxidative phase converts D-ribulose 5P into D-ribose 5P, D-xylulose 5P, D-sedoheptulose 7P, D-erythrose 4P, D-fructose 6P and D-glyceraldehyde 3P. D-Xylose and L-arabinose enter the PPP through D-xylulose.

Certain organisms (e.g., yeast, filamentous fungus and other eukaryotes, for example) require two or more activities to convert xylose to a usable from that can be metabolized in the pentose phosphate pathway. The activities are a reduction and an oxidation carried out by xylose reductase (XYL1) and xylitol dehydrogenase (XYL2), respectively. Xylose reductase converts D-xylose to xylitol. Xylitol dehydrogenase converts xylitol to D-xylulose. The use of these activities sometimes can inhibit cellular function due to cofactor and metabolite imbalances.

Some organisms (e.g., certain bacteria, for example) require only one activity, xylose isomerase (xylA). Xylose isomerase converts xylose directly to xylulose. Xylulose can then be converted to xylulose-5-phosphate by xylulose kinase. Phosphorylation of xylulose then allows the five-carbon sugar to be further converted by transketolase (e.g., TKL1/TKL2) to enter the EM pathway for further metabolism at either fructose-6-phosphate or glyceraldehyde-3-phosphate. In some embodiments, where the EM pathway is inactivated, five-carbon sugars enter the EM pathway and are further converted for use by the ED pathway. Therefore, engineering a microorganism with xylose isomerase activity may allow rapid growth on xylose when compared to the non-engineered microorganism, while avoiding cofactor and metabolite imbalances.

A microorganism may be engineered to include or regulate one or more activities in a five-carbon sugar metabolism pathway (e.g., pentose phosphate pathway, for example). In some embodiments, an engineered microorganism can comprise a xylose isomerase activity. In some embodiments, the xylose isomerase activity may be altered such that the activity can be increased or decreased according to a change in environmental conditions. Nucleic acid sequences encoding xylose isomerase activities can be obtained from any suitable bacteria (e.g., *Piromyces, Orpinomyces, Bacteroides thetaiotaomicron, Clostridium phytofermentans, Thermus thermophilus* and *Ruminococcus* (e.g., *R. flavefaciens*) and any of these activities can be used herein with the proviso that the nucleic acid sequence is naturally active in the chosen microorganism when expressed, or can be altered or modified to be active.

Carbon Dioxide Metabolism and Activities

Microorganisms grown in fermentors often are grown under anaerobic conditions, with limited or no gas exchange. Therefore the atmosphere inside fermentors sometimes is carbon dioxide rich. Unlike photosynthetic organisms, many microorganisms suitable for use in industrial fermentation processes do not incorporate atmospheric carbon (e.g., $CO_2$) to any significant degree, or at all. Thus, to ensure that increasing levels of carbon dioxide do not inhibit cell growth and the fermentation process, methods to remove carbon dioxide from the interior of fermentors can be useful.

Photosynthetic organisms make use of atmospheric carbon by incorporating the carbon available in carbon dioxide into organic carbon compounds by a process known as carbon fixation. The activities responsible for a photosynthetic organism's ability to fix carbon dioxide include phosphoenolpyruvate carboxylase (e.g., PEP carboxylase) or ribulose 1,5-bis-phosphate carboxylase (e.g., Rubisco). PEP carboxylase catalyzes the addition of carbon dioxide to phosphoenolpyruvate to generate the four-carbon compound oxaloacetate. Oxaloacetate can be used in other cellular processes or be further converted to yield several industrially useful products (e.g., malate, succinate, citrate and the like). Rubisco catalyzes the addition of carbon dioxide and ribulose-1,5-bisphosphate to generate 2 molecules of 3-phosphoglycerate. 3-phosphoglycerate can be further converted to ethanol via cellular fermentation or used to produce other commercially useful products. Nucleic acid sequences encoding PEP carboxylase and Rubisco activities can be obtained from any suitable organism (e.g., plants, bacteria, and other microorganisms, for example) and any of these activities can be used herein with the proviso that the nucleic acid sequence is either naturally active in the chosen microorganism when expressed, or can be altered or modified to be active.

Examples of Altered Activities

In some embodiments, engineered microorganisms can include modifications to one or more (e.g., 1, 2, 3, 4, 5, 6 or all) of the following activities: phosphofructokinase activity (PFK1 A subunit, PFK2 B subunit), phosphogluconate dehydratase activity (EDD), 2-keto-3-deoxygluconate-6-phosphate aldolase activity (EDA), xylose isomerase activity (xylA), phosphoenolpyruvate carboxylase activity (PEP carboxylase), alcohol dehydrogenase 2 activity (ADH2), thymidylate synthase activity, phosphoglucose isomerase activity (PGI1), transaldolase activity (TAL1), transketolase activity (TKL1, TKL2), 6-phosphogluconolactonase activity (SOL3, SOL4), Glucose-6-phosphate dehydrogenase activity (ZWF1), 6-phosphogluconate dehydrogenase (decarboxylating) activity (GND1, GND2), galactose permease activity (GAL2), high affinity glucose transport activity (HXT7), glucose/xylose transport activity (GXS1, GXF1) and combinations of the foregoing.

The term "phosphofructokinase activity" as used herein refers to conversion of fructose-6-phosphate to fructose-1,6-bisphosphate. Phosphofructokinase activity may be provided by an enzyme that includes one or two subunits (referred to hereafter as "subunit A" and/or "subunit B"). The term "inactivating the Embden-Meyerhoff pathway" as used herein refers to reducing or eliminating the activity of one or more activities in the Embden-Meyerhoff pathway, including but not limited to phosphofructokinase activity. In some embodiments, the phosphofructokinase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the phosphofructokinase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of phosphofructokinase activity can have sequences partially or substantially complementary to sequences described herein. Presence or absence of the amount of phosphofructokinase activity can be detected by any suitable method known in the art, including requiring a five-carbon sugar carbon source or a functional Entner-Doudoroff pathway for growth. Inactivation of the Embden-Meyerhoff pathway is described in further detail below. As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

The term "phosphogluconate dehydratase activity" as used herein refers to conversion of 6-phophogluconate to 2-keto-3-deoxy-6-p-gluconate. The phosphogluconate dehydratase activity can be provided by a polypeptide. In some embodiments, the polypeptide is encoded by a heterologous nucleotide sequence introduced to a host microorganism. Nucleic acid sequences conferring phosphogluconate dehydratase activity can be obtained from a number of sources, including *Zymomonas mobilis* and *Escherichia coli*. Examples of an amino acid sequence of a polypeptide having phosphogluconate dehydratase activity, and a nucleotide sequence of a polynucleotide that encodes the polypeptide, are presented below in tables. Presence, absence or amount of phosphogluconate dehydratase activity can be detected by any suitable method known in the art, including western blot analysis.

The term "2-keto-3-deoxygluconate-6-phosphate aldolase activity" as used herein refers to conversion of 2-keto-3-deoxy-6-p-gluconate to pyruvate. The 2-keto-3-deoxygluconate-6-phosphate aldolase activity can be provided by a polypeptide. In some embodiments, the polypeptide is encoded by a heterologous nucleotide sequence introduced to a host microorganism. Nucleic acid sequences conferring 2-keto-3-deoxygluconate-6-phosphate aldolase activity can be obtained from a number of sources, including *Zymomonas mobilis* and *Escherichia coli*. Examples of an amino acid sequence of a polypeptide having 2-keto-3-deoxygluconate-6-phosphate aldolase activity, and a nucleotide sequence of a polynucleotide that encodes the polypeptide, are presented below in tables. Presence, absence or amount of 2-keto-3-deoxygluconate-6-phosphate aldolase activity can be detected by any suitable method known in the art, including western blot analysis.

The term "xylose isomerase activity" as used herein refers to conversion of xylose to xylulose. The xylose isomerase activity can be provided by a polypeptide. In some embodiments, the polypeptide is encoded by a heterologous nucleotide sequence introduced to a host microorganism. Nucleic acid sequences conferring xylose isomerase activity can be obtained from a number of sources, including *Piromyces, Orpinomyces, Bacteroides* (e.g., *B. thetaiotaomicron, B. uniformis, B. stercoris*), *Clostralies* (e.g., *Clostrialies* BVAB3), *Clostridium* (e.g., *C. phytofermentans, C. thermohydrosulfuricum, C. cellulyticum*), *Thermus thermophilus, Eschericia coli, Streptomyces* (e.g., *S. rubiginosus, S. murinus*), *Bacillus stearothermophilus, Lactobacillus pentosus, Thermotoga* (e.g., *T. maritime, T. neopolitana*) and *Ruminococcus* (e.g., *Ruminococcus* environmental samples, *Ruminococcus albus, Ruminococcus bromii, Ruminococcus callidus, Ruminococcus flavefaciens, Ruminococcus gauvreauii, Ruminococcus gnavus, Ruminococcus lactaris, Ruminococcus obeum, Ruminococcus* sp., *Ruminococcus* sp. 14531, *Ruminococcus* sp. 15975, *Ruminococcus* sp. 16442, *Ruminococcus* sp. 18P13, *Ruminococcus* sp. 25F6, *Ruminococcus* sp. 25F7, *Ruminococcus* sp. 25F8, *Ruminococcus* sp. 4_1_47FAA, *Ruminococcus* sp. 5, *Ruminococcus* sp. 5_1_39BFAA, *Ruminococcus* sp. 7L75, *Ruminococcus* sp. 8_1_37FAA, *Ruminococcus* sp. 9SE51, *Ruminococcus* sp. C36, *Ruminococcus* sp. CB10, *Ruminococcus* sp. CB3, *Ruminococcus* sp. CCUG 37327 A, *Ruminococcus* sp. CE2, *Ruminococcus* sp. CJ60, *Ruminococcus* sp. CJ63, *Ruminococcus* sp. CO1, *Ruminococcus* sp. CO12, *Ruminococcus* sp. CO22, *Ruminococcus* sp. CO27, *Ruminococcus* sp. CO28, *Ruminococcus* sp. CO34, *Ruminococcus* sp. CO41, *Ruminococcus* sp. CO47, *Ruminococcus* sp. CO7, *Ruminococcus* sp. CS1, *Ruminococcus* sp. CS6, *Ruminococcus* sp. DJF_VR52, *Ruminococcus* sp. DJF_VR66, *Ruminococcus* sp. DJF_VR67, *Ruminococcus* sp. DJF_VR70k1, *Ruminococcus* sp. DJF_VR87, *Ruminococcus* sp. Eg2, *Ruminococcus* sp. Egf, *Ruminococcus* sp. END-1, *Ruminococcus* sp. FD1, *Ruminococcus* sp. GM2/1, *Ruminococcus* sp. ID1, *Ruminococcus* sp. ID8, *Ruminococcus* sp. K-1, *Ruminococcus* sp. KKA Seq234, *Ruminococcus* sp. M-1, *Ruminococcus* sp. M10, *Ruminococcus* sp. M22, *Ruminococcus* sp. M23, *Ruminococcus* sp. M6, *Ruminococcus* sp. M73, *Ruminococcus* sp. M76, *Ruminococcus* sp. MLG080-3, *Ruminococcus* sp. NML 00-0124, *Ruminococcus* sp. Pei041, *Ruminococcus* sp. SC101, *Ruminococcus* sp. SC103, *Ruminococcus* sp. Siijpesteijn 1948, *Ruminococcus* sp. WAL 17306, *Ruminococcus* sp. YE281, *Ruminococcus* sp. YE58, *Ruminococcus* sp. YE71, *Ruminococcus* sp. ZS2-15, *Ruminococcus torques*). Examples of an amino acid sequence of a polypeptide having xylose isomerase activity, and a nucleotide sequence of a polynucleotide that encodes the polypeptide, are presented below in tables. Presence, absence or amount of xylose isomerase activity can be detected by any suitable method known in the art, including western blot analysis.

The term "phosphoenolpyruvate carboxylase activity" as used herein refers to the addition of carbon dioxide to phosphoenolpyruvate to generate the four-carbon compound oxaloacetate. The phosphoenolpyruvate carboxylase activity can be provided by a polypeptide. In some embodiments, the polypeptide is encoded by a heterologous nucleotide sequence introduced to a host microorganism. Nucleic acid sequences conferring phosphoenolpyruvate carboxylase activity can be obtained from a number of sources, including *Zymomonas mobilis*. Examples of an amino acid sequence of a polypeptide having phosphoenolpyruvate carboxylase activity, and a nucleotide sequence of a polynucleotide that encodes the polypeptide, are presented below in tables. Presence, absence or amount of xylose isomerase activity can be detected by any suitable method known in the art.

The term "alcohol dehydrogenase 2 activity" as used herein refers to conversion of ethanol to acetaldehyde, which is the reverse of the forward action catalyzed by alcohol dehydrogenase 1. The term "inactivation of the conversion of ethanol to acetaldehyde" refers to a reduction or elimination in the activity of alcohol dehydrogenase 2. Reducing or eliminating the activity of alcohol dehydrogenase 2 activity can lead to an increase in ethanol production. In some embodiments, the alcohol dehydrogenase 2 activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the alcohol dehydrogenase 2 activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a non-functional polypeptide or protein. Nucleic acid sequences that can be used to reduce or eliminate the activity of alcohol dehydrogenase 2 can have sequences partially or substantially complementary to nucleic acid sequences that encode alcohol dehydrogenase 2 activity. Presence or absence of the amount of alcohol dehydrogenase 2 activity can be detected by any suitable method known in the art, including inability to grown in media with ethanol as the sole carbon source.

The term "thymidylate synthase activity" as used herein refers to a reductive methylation, where deoxyuridine monophosphate (dUMP) and N5,N10-methylene tetrahydrofolate are together used to generate thymidine monophosphate (dTMP), yielding dihydrofolate as a secondary product. The term "temporarily inactivate thymidylate synthase activity" refers to a temporary reduction or elimination in the activity of thymidylate synthase when the modified organism is shifted to a non-permissive temperature. The activity can return to normal upon return to a permissive temperature. Temporarily inactivating thymidylate synthase uncouples cell growth from cell division while under the non permissive temperature. This inactivation in turn allows the cells to continue fermentation without producing biomass and dividing, thus increasing the yield of product produced during fermentation.

In some embodiments, the thymidylate synthase activity can be temporarily reduced or eliminated by genetic modification, as described below. In certain embodiments, the genetic modification renders the activity responsive to changes in the environment. Nucleic acid sequences conferring temperature sensitive thymidylate synthase activity can be obtained from *S. cerevisiae* strain 172066 (accession number 208583). The cdc21 mutation in *S. cerevisiae* strain 172066 has a point mutation at position G139S relative to the initiating methionine. Examples of nucleotide sequences used to PCR amplify the polynucleotide encoding the temperature sensitive polypeptide, are presented below in tables. Presence, absence or amount of thymidylate synthase activity can be detected by any suitable method known in the art, including growth arrest at the non-permissive temperature.

Thymidylate synthase is one of many polypeptides that regulate the cell cycle. The cell cycle may be inhibited in engineered microorganisms under certain conditions (e.g., temperature shift, dissolved oxygen shift), which can result in inhibited or reduced cell proliferation, inhibited or reduced cell division, and sometimes cell cycle arrest (collectively "cell cycle inhibition"). Upon exposure to triggering conditions, a microorganism may display cell cycle inhibition after a certain time after the microorganism is exposed to the triggering conditions (e.g., there may be a time delay after a microorganism is exposed to a certain set of conditions before the microorganism displays cell cycle inhibition). Where cell cycle inhibition results in reduced cell proliferation, cell proliferation rates may be reduced by about 50% or greater, for example (e.g., reduced by about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Where cell cycle inhibition results a reduced number of cells undergoing cell division, the rate of cell division may be reduced by about 50% or greater, for example (e.g., the number of cells undergoing division is reduced by about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Where cell cycle inhibition results in cell cycle arrest, cells may be arrested at any stage of the cell cycle (e.g., resting $G_0$ phase, interphase (e.g., $G_1$, S, $G_2$ phases), mitosis (e.g., prophase, prometaphase, metaphase, anaphase, telophase)) and different percentages of cells in a population can be arrested at different stages of the cell cycle.

The term "phosphoglucose isomerase activity" as used herein refers to the conversion of glucose-6-phosphate to fructose-6-phosphate. The term "inactivation of the conversion of glucose-6-phosphate to fructose-6-phosphate" refers to a reduction or elimination in the activity of phosphoglucose isomerase. Reducing or eliminating the activity of phosphoglucose isomerase activity can lead to an increase in ethanol production. In some embodiments, the phosphoglucose isomerase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the phosphoglucose isomerase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a non-functional polypeptide or protein. Nucleic acid sequences that can be used to reduce or eliminate the activity of phosphoglucose isomerase can have sequences partially or substantially complementary to nucleic acid sequences that encode phosphoglucose isomerase activity. Presence or absence of the amount of phosphoglucose isomerase activity can be detected by any suitable method known in the art, including nucleic acid based analysis and western blot analysis.

The term "glucose-6-phosphate dehydrogenase activity" as used herein refers to conversion of glucose-6-phosphate to gluconolactone-6-phosphate coupled with the generation of NADPH. The glucose-6-phosphate dehydrogenase aldolase activity can be provided by a polypeptide. In some embodiments, the polypeptide is encoded by a heterologous nucleotide sequence introduced to a host microorganism. Nucleic acid sequences conferring glucose-6-phosphate dehydrogenase activity can be obtained from a number of sources, including, but not limited to *S. cerevisiae* Examples of a nucleotide sequence of a polynucleotide that encodes the polypeptide, are presented below in tables. Presence, absence or amount of glucose-6-phosphate dehydrogenase activity can be detected by any suitable method known in the art, including western blot analysis.

The term "6-phosphogluconolactonase activity" as used herein refers to conversion of gluconolactone-6-phosphate to gluconate-6-phosphate. The 6-phosphogluconolactonase activity can be provided by a polypeptide. In some embodiments, the polypeptide is encoded by a heterologous nucleotide sequence introduced to a host microorganism. Nucleic acid sequences conferring 6-phosphogluconolactonase activity can be obtained from a number of sources, including, but not limited to *S. cerevisiae*. Examples of an amino acid sequence of a polypeptide having 6-phosphogluconolactonase activity, and a nucleotide sequence of a polynucleotide that encodes the polypeptide, are presented below in tables. Presence, absence or amount of 6-phosphogluconolactonase activity can be detected by any suitable method known in the art, including nucleic acid based analysis and western blot analysis.

The term "6-phosphogluconate dehydrogenase (decarboxylating) activity" as used herein refers to the conversion of gluconate-6-phosphate to ribulose-5-phosphate. The term "inactivation of the conversion of gluconate-6-phosphate to ribulose-5-phosphate" refers to a reduction or elimination in the activity of 6-phosphogluconate dehydrogenase. Reducing or eliminating the activity of 6-phosphogluconate dehydrogenase (decarboxylating) activity can lead to an increase in ethanol production. In some embodiments, the 6-phosphogluconate dehydrogenase (decarboxylating) activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the 6-phosphogluconate dehydrogenase (decarboxylating) activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of 6-phosphogluconate dehydrogenase (decarboxylating) can have sequences partially or substantially complementary to nucleic acid sequences that encode 6-phosphogluconate dehydrogenase (decarboxylating) activity. Presence or absence of the amount of 6-phosphogluconate dehydrogenase (decarboxylating) activity can be detected by any suitable method known in the art, including nucleic acid based analysis and western blot analysis.

The term "transketolase activity" as used herein refers to conversion of xylulose-5-phosphate and ribose-5-phosphate to sedoheptulose-7-phosphate and glyceraldehyde-3-phosphate. The transketolase activity can be provided by a polypeptide. In some embodiments, the polypeptide is encoded by a heterologous nucleotide sequence introduced to a host microorganism. Nucleic acid sequences conferring transketolase activity can be obtained from a number of sources, including, but not limited to *S. cerevisiae, Kluyveromyces, Pichia, Escherichia, Bacillus, Ruminococcus, Schizosaccharomyces*, and *Candida*. Examples of an amino acid sequence of a polypeptide having transketolase activity, and a nucleotide sequence of a polynucleotide that encodes the polypeptide, are presented below in the examples. The term "inactivation of the conversion of xylulose-5-phosphate and ribose-5-phosphate to sedoheptulose-7-phosphate and glyceraldehyde-3-phosphate" refers to a reduction or elimination in the activity of transketolase. Reducing or eliminating the activity of transketolase activity can lead to an increase in ethanol production. In some embodiments, the transketolase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the transketolase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of transketolase can have sequences partially or substantially complementary to nucleic acid sequences that encode transketolase activity. Presence, absence or amount of transketolase activity can be detected by any suitable method known in the art, including nucleic acid based analysis and western blot analysis.

The term "transaldolase activity" as used herein refers to conversion of sedoheptulose 7-phosphate and glyceraldehyde 3-phosphate to erythrose 4-phosphate and fructose 6-phosphate. The transaldolase activity can be provided by a polypeptide. In some embodiments, the polypeptide is encoded by a heterologous nucleotide sequence introduced to a host microorganism. Nucleic acid sequences conferring transaldolase activity can be obtained from a number of sources, including, but not limited to *S. cerevisiae, Kluyveromyces, Pichia, Escherichia, Bacillus, Ruminococcus, Schizosaccharomyces*, and *Candida*. Examples of an amino acid sequence of a polypeptide having transaldolase activity, and a nucleotide sequence of a polynucleotide that encodes the polypeptide, are presented below in the examples. The term "inactivation of the conversion of sedoheptulose 7-phosphate and glyceraldehyde 3-phosphate to erythrose 4-phosphate and fructose 6-phosphate" refers to a reduction or elimination in the activity of transaldolase. Reducing or eliminating the activity of transaldolase activity can lead to an increase in ethanol production. In some embodiments, the transaldolase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the transaldolase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of transaldolase can have sequences partially or substantially complementary to nucleic acid sequences that encode transaldolase activity. Presence, absence or amount of transaldolase activity can be detected by any suitable method known in the art, including nucleic acid based analysis and western blot analysis.

The term "galactose permease activity" as used herein refers to the import of galactose into a cell or organism by an activity that transports galactose across cell membranes. The galactose permease activity can be provided by a polypeptide. In some embodiments, the polypeptide is encoded by a heterologous nucleotide sequence introduced to a host microorganism. Nucleic acid sequences conferring galactose permease activity can be obtained from a number of sources, including, but not limited to *S. cerevisiae, Candida albicans, Debaryomyces hansenii, Schizosaccharomyces pombe, Arabidopsis thaliana*, and *Colwellia psychrerythraea*. Examples of an amino acid sequence of a polypeptide having galactose permease activity, and a nucleotide sequence of a polynucleotide that encodes the polypeptide, are presented below in the Examples. Presence, absence or amount of galactose permease activity can be detected by any suitable method known in the art, including nucleic acid based analysis and western blot analysis.

The term "glucose/xylose transport activity" as used herein refers to the import of glucose and/or xylose into a cell or organism by an activity that transports glucose and/or xylose across cell membranes. The glucose/xylose transport activity can be provided by a polypeptide. In some embodiments, the polypeptide is encoded by a heterologous nucleotide sequence introduced to a host microorganism. Nucleic acid sequences conferring glucose/xylose transport activity can be obtained from a number of sources, including, but not limited to *Pichia* yeast, *Saccharomyces cerevisiae, Candida albicans, Debaryomyces hansenii, Schizosaccaromyces pombe*. Examples of an amino acid sequence of a polypeptide having glucose/xylose transport activity, and a nucleotide sequence of a polynucleotide that encodes the polypeptide, are presented below in the Examples. Presence, absence or amount of glucose/xylose transport activity can be detected by any suitable method known in the art, including nucleic acid based analysis and western blot analysis.

The terms "high affinity glucose transport activity" and "hexose transport activity" as used herein refer to the import of glucose and other hexose sugars into a cell or organism by an activity that transports glucose and other hexose sugars across cell membranes. The high affinity glucose transport activity or hexose transport activity can be provided by a polypeptide. In some embodiments, the polypeptide is encoded by a heterologous nucleotide sequence introduced to a host microorganism. Nucleic acid sequences conferring high affinity glucose transport activity or hexose transport activity can be obtained from a number of sources, including, but not limited to *S. cerevisiae, Pichia* yeast, *Candida albicans, Debaryomyces hansenii, Schizosaccaromyces pombe*. Presence, absence or amount of glucose/xylose transport activity can be detected by any suitable method known in the art, including nucleic acid based analysis and western blot analysis.

Activities described herein can be modified to generate microorganisms engineered to allow a method of independently regulating or controlling (e.g., ability to independently turn on or off, or increase or decrease, for example) six-carbon sugar metabolism, five-carbon sugar metabolism, atmospheric carbon metabolism (e.g., carbon dioxide fixation) or combinations thereof. In some embodiments, regulated control of a desired activity can be the result of a genetic modification. In certain embodiments, the genetic modification can be modification of a promoter sequence. In some embodiments the modification can increase of decrease an activity encoded by a gene operably linked to the promoter element. In certain embodiments, the modification to the promoter element can add or remove a regulatory sequence. In some embodiments the regulatory sequence can respond to a change in environmental or culture conditions. Non-limiting examples of culture conditions that could be used to regulate an activity in this manner include, temperature, light, oxygen, salt, metals and the like. Additional methods for altering an activity by modification of a promoter element are given below.

In some embodiments, the genetic modification can be to an ORF. In certain embodiments, the modification of the ORF can increase or decrease expression of the ORF. In some embodiments modification of the ORF can alter the efficiency of translation of the ORF. In certain embodiments, modification of the ORF can alter the activity of the polypeptide or protein encoded by the ORF. Additional methods for altering an activity by modification of an ORF are given below.

In some embodiments, the genetic modification can be to an activity associated with cell division (e.g., cell division cycle or CDC activity, for example). In certain embodiments the cell division cycle activity can be thymidylate synthase activity. In certain embodiments, regulated control of cell division can be the result of a genetic modification. In some embodiments, the genetic modification can be to a nucleic acid sequence that encodes thymidylate synthase. In certain embodiments, the genetic modification can temporarily inactivate thymidylate synthase activity by rendering the activity temperature sensitive (e.g., heat resistant, heat sensitive, cold resistant, cold sensitive and the like).

In some embodiments, the genetic modification can modify a promoter sequence operably linked to a gene encoding an activity involved in control of cell division. In some embodiments the modification can increase of decrease an activity encoded by a gene operably linked to the promoter element. In certain embodiments, the modification to the promoter element can add or remove a regulatory sequence. In some embodiments the regulatory sequence can respond to a change in environmental or culture conditions. Non-limiting examples of culture conditions that could be used to regulate an activity in this manner include, temperature, light, oxygen, salt, metals and the like. In some embodiments, an engineered microorganism comprising one or more activities described above or below can be used in to produce ethanol by inhibiting cell growth and cell division by use of a temperature sensitive cell division control activity while allowing cellular fermentation to proceed, thereby producing a significant increase in ethanol yield when compared to the native organism.

Polynucleotides and Polypeptides

A nucleic acid (e.g., also referred to herein as nucleic acid reagent, target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). A nucleic acid can also comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Deoxyribonucleotides include deoxyadenosine, deoxycytidine, deoxyguanosine and deoxythymidine. For RNA, the uracil base is uridine.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like). The terms "amplify", "amplification", "amplification reaction", or "amplifying" as used herein, refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can comprise certain elements often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments.

A promoter often interacts with a RNA polymerase. A polymerase is an enzyme that catalyses synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein. The term "operably linked" as used herein with respect to promoters refers to a nucleic acid sequence (e.g., a coding sequence) present on the same nucleic acid molecule as a promoter element and whose expression is under the control of said promoter element.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments the activity can be altered using recombinant DNA and genetic techniques known to the artisan. Methods for engineering microorganisms are further described herein. Tables herein provide non-limiting lists of yeast promoters that are up-regulated by oxygen, yeast promoters that are down-regulated by oxygen, yeast transcriptional repressors and their associated genes, DNA binding motifs as determined using the MEME sequence analysis software. Potential regulator binding motifs can be identified using the program MEME to search intergenic regions bound by regulators for overrepresented sequences. For each regulator, the sequences of intergenic regions bound with p-values less than 0.001 were extracted to use as input for motif discovery. The MEME software was run using the following settings: a motif width ranging from 6 to 18 bases, the "zoops" distribution model, a 6th order Markov background model and a discovery limit of 20 motifs. The discovered sequence motifs were scored for significance by two criteria: an E-value calculated by MEME and a specificity score. The motif with the best score using each metric is shown for each regulator. All motifs presented are derived from datasets generated in rich growth conditions with the exception of a previously published dataset for epitope-tagged Gal4 grown in galactose In some embodiments, the altered activity can be found by screening the organism under conditions that select for the desired change in activity. For example, certain microorganisms can be adapted to increase or decrease an activity by selecting or screening the organism in question on a media containing substances that are poorly metabolized or even toxic. An increase in the ability of an organism to grow a substance that is normally poorly metabolized would result in an increase in the growth rate on that substance, for example. A decrease in the sensitivity to a toxic substance might be manifested by growth on higher concentrations of the toxic substance, for example. Genetic modifications that are identified in this manner sometimes are referred to as naturally occurring mutations or the organisms that carry them can sometimes be referred to as naturally occurring mutants. Modifications obtained in this manner are not limited to alterations in promoter sequences. That is, screening microorganisms by selective pressure, as described above, can yield genetic alterations that can occur in non-promoter sequences, and sometimes also can occur in sequences that are not in the nucleotide sequence of interest, but in a related nucleotide sequences (e.g., a gene involved in a different step of the same pathway, a transport gene, and the like). Naturally occurring mutants sometimes can be found by isolating naturally occurring variants from unique environments, in some embodiments.

In addition to the regulated promoter sequences, regulatory sequences, and coding polynucleotides provided herein, a nucleic acid reagent may include a polynucleotide sequence 70% or more identical to the foregoing (or to the complementary sequences). That is, a nucleotide sequence that is at least 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address at world wide web uniform resource locator gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address at world wide web uniform resource locator gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

As noted above, nucleic acid reagents may also comprise one or more 5' UTR's, and one or more 3'UTR's. A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5 'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., http address at world wide web uniform resource locator interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can comprise a target nucleotide sequence. A "target nucleotide sequence" as used herein encodes a nucleic acid, peptide, polypeptide or protein of interest, and may be a ribonucleotide sequence or a deoxyribonucleotide sequence.

A target nucleic acid sometimes can comprise a chimeric nucleic acid (or chimeric nucleotide sequence), which can encode a chimeric protein (or chimeric amino acid sequence). The term "chimeric" as used herein refers to a nucleic acid or nucleotide sequence, or encoded product thereof, containing sequences from two or more different sources. Any suitable source can be selected, including, but not limited to, a sequence from a nucleic acid, nucleotide sequence, ribosomal nucleic acid, RNA, DNA, regulatory nucleotide sequence (e.g., promoter, URL, enhancer, repressor and the like), coding nucleic acid, gene, nucleic acid linker, nucleic acid tag, amino acid sequence, peptide, polypeptide, protein, chromosome, and organism. A chimeric molecule can include a sequence of contiguous nucleotides or amino acids from a source including, but not limited to, a virus, prokaryote, eukaryote, genus, species, homolog, ortholog, paralog and isozyme, nucleic acid linkers, nucleic acid tags, the like and combinations thereof). A chimeric molecule can be generated by placing in juxtaposition fragments of related or unrelated nucleic acids, nucleotide sequences or DNA segments, in some embodiments. In certain embodiments the nucleic acids, nucleotide sequences or DNA segments can be native or wild type sequences, mutant sequences or engineered sequences (completely engineered or engineered to a point, for example).

In some embodiments, a chimera includes about 1, 2, 3, 4 or 5 sequences (e.g., contiguous nucleotides, contiguous amino acids) from one organism and 1, 2, 3, 4 or 5 sequences (e.g., contiguous nucleotides, contiguous amino acids) from another organism. The organisms sometimes are a microbe, such as a bacterium (e.g., gram positive, gram negative), yeast or fungus (e.g., aerobic fungus, anaerobic fungus), for example. In some embodiments, the organisms are bacteria, the organisms are yeast or the organisms are fungi (e.g., different species), and sometimes one organism is a bacterium or yeast and another is a fungus. A chimeric molecule may contain up to about 99% of sequences from one organism (e.g., about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99%) and the balance percentage from one or more other organisms. In certain embodiments, a chimeric molecule includes altered codons (in the case of a chimeric nucleic acid) and one or more mutations (e.g., point mutations, nucleotide substitutions, amino acid substitutions).

A chimera sometimes is the result of recombination between two or more nucleic acids, nucleotide sequences or genes, and sometimes is the result of genetic manipulation (e.g., designed and/or generated by the hand of a human being). Any suitable nucleic acid or nucleotide sequence and method for combining nucleic acids or nucleotide sequences can be used to generate a chimeric nucleic acid or nucleotide sequence. Non-limiting examples of nucleic acid and nucleotide sequence sources and methods for generating chimeric nucleic acids and nucleotide sequences are presented herein.

In some embodiments, fragments used to generate a chimera can be juxtaposed as units (e.g., nucleic acid from the sources are combined end to end and not interspersed. In embodiments where a chimera includes one stretch of contiguous nucleotides for each organism, nucleotide sequence combinations can be noted as DNA source 1 DNA source 2 or DNA source 1/DNA source 2/DNA source 3, the like and combinations thereof, for example. In certain embodiments, fragments used to generate a chimera can be juxtaposed such that one or more fragments from one or more sources can be interspersed with other fragments used to generate the chimera (e.g., DNA source 1/DNA source 2/DNA source 1/DNA source 3/DNA source 2/DNA source 1). In some embodiments, the nucleotide sequence length of the fragments used to generate a chimera can be in the range from about 5 base pairs to about 5,000 base pairs (e.g., about 5 base pairs (bp), about 10 bp, about 15 bp, about 20 bp, about 25 bp, about 30 bp, about 35 bp, about 40 bp, about 45 bp, about 50 bp, about 55 bp, about 60 bp, about bp, about 65 bp, about 70 bp, about 75 bp, about 80 bp, about 85 bp, about 90 bp, about 95 bp, about 100 bp, about 125 bp, about 150 bp, about 175 bp, about 200 bp, about 250 bp, about 300 bp, about 350 bp, about 400 bp, about 450 bp, about 500 bp, about 550 bp, about 600 bp, about 650 bp, about 700 bp, about 750 bp, about 800 bp, about 850 bp, about 900 bp, about 950 bp, about 1000 bp, about 1500 bp, about 2000 bp, about 2500 bp, about 3000 bp, about 3500 bp, about 4000 bp, about 4500 bp, or about 5000 bp).

In certain embodiments, a chimeric nucleic acid or nucleotide sequence encodes the same activity as the activity encoded by the source nucleic acids or nucleotide sequences. In some embodiments, a chimeric nucleic acid or nucleotide sequence has a similar or the same activity, but the amount of the activity, or kinetics of the activity, are altered (e.g., increased, decreased). In certain embodiments, a chimeric nucleic acid or nucleotide sequence encodes a different activity, and in some embodiments a chimeric nucleic acid or nucleotide sequences encodes a chimeric activity (e.g., a combination of two or more activities).

A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

Any peptides, polypeptides or proteins, or an activity catalyzed by one or more peptides, polypeptides or proteins may be encoded by a target nucleotide sequence and may be selected by a person of ordinary skill in the art. Representative proteins include enzymes (e.g., phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like, for example), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity) include phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like for example. The term "enzyme" as used herein refers to a protein which can act as a catalyst to induce a chemical change in other compounds, thereby producing one or more products from one or more substrates.

Specific polypeptides (e.g., enzymes) useful for embodiments described herein are listed hereafter. The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail below in Engineering and Alteration Methods), a genetic modification can result in a modification (e.g., increase, substantially increase, decrease or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG (SEQ ID NO: 29)), V5 (e.g., GKPIPNPLLGLDST (SEQ ID NO: 30)), c-MYC (e.g., EQKLISEEDL (SEQ ID NO: 31)), HSV (e.g., QPELAPEDPED (SEQ ID NO: 32)), influenza hemaglutinin, HA (e.g., YPYDVPDYA (SEQ ID NO: 33)), VSV-G (e.g., YTDIEMNRLGK (SEQ ID NO: 34)), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 35)) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 36), wherein X is any amino acid and n is 1 to 3, and the cysteine-rich sequence sometimes is CCPGCC (SEQ ID NO: 37). In certain embodiments, the tag comprises a cysteine-rich element and a polyhistidine element (e.g., CCPGCC (SEQ ID NO: 37) and His6 (SEQ ID NO: 35)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3, 2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS (SEQ ID NO: 38)), enterokinase (e.g., recognition site DDDDK (SEQ ID NO: 39)), TEV protease (e.g., recognition site ENLYFQG (SEQ ID NO: 40)) or PreScission™ protease (e.g., recognition site LEVLFQGP (SEQ ID NO: 41)), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and Salmonella Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address at world wide web uniform resource locator invitrogen.com/content/sfs/manuals/tagondemand_supernatant_man.pdf; Tag-On-Demand™ Gateway® Vector Instruction Manual, Version B, 20 Jun., 2003 at http address at world wide web uniform resource locator invitrogen.com/content/sfs/manuals/tagondemand_vectors_man.pdf; and Capone et al., Amber, ochre and opal suppressor tRNA genes derived from a human serine tRNA gene. EMBO J. 4:213, 1985).

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described hereafter. In some embodiments, a cloning strategy can be combined with genetic manipulation such as recombination (e.g., recombination of a nucleic acid reagent with a nucleic acid sequence of interest into the genome of the organism to be modified, as described further below). In some embodiments, the cloned ORF(s) can produce (directly or indirectly) a desired product, by engineering a microorganism with one or more ORFs of interest, which microorganism comprises one or more altered activities selected from the group consisting of phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity, sugar transport activity, phosphoglucoisomerase activity, transaldolase activity, transketolase activity, glucose-6-phosphate dehydrogenase activity, 6-phosphogluconolactonase activity, 6-phosphogluconate dehydrogenase (decarboxylating) activity, and thymidylate synthase activity.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the ura3 gene (e.g., for *S. cerevisiae* and *C. albicans*, for example) or ura4 and ura5 genes (e.g., for *S. pombe*, for example) and toxicity of the nucleotide analogue 5-Fluoroorotic acid (5-FOA). The ura3 or ura4 and ura5 genes encode orotine-5'-monophosphate (OMP) dicarboxylase. Yeast with an active ura3 or ura4 and ura5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may comprise the URA3 gene or cassette (for *S. cerevisiae*), flanked on either side by the same nucleotide sequence in the same orientation. The ura3 cassette comprises a promoter, the ura3 gene and a functional transcription terminator. Target sequences which direct the construct to a particular nucleic acid region of interest in the organism to be engineered are added such that the target sequences are adjacent to and abut the flanking sequences on either side of the ura3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the ura3 cassette out of the construct, leaving a disrupted gene and an identifiable footprint (e.g., nucleic acid sequence) that can be use to verify the presence of the disrupted gene. The technique described is useful for disrupting or "knocking out" gene function, but also can be used to insert genes or constructs into a host organisms genome in a targeted, sequence specific manner. Further detail will be described below in the engineering section and in the example section.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T) CCTT-PO4-TOPO, a complex of the topoisomerase covalently bound to the 3' phosphate via a tyrosine in the topoisomerase (e.g., Shuman, J. Biol. Chem. 266:11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA *E. coli* topoisomerase III. An element to be inserted often is combined with topoisomerase-reacted template and thereby incorporated into the nucleic acid reagent (e.g., http address at world wide web uniform resource locator invitrogen.com/downloads/F-13512_Topo_Flyer.pdf; http address at world wide web uniform resource locator invitrogen.com/content/sfs/brochures/710_021849%20_B_TOPOCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address world wide web uniform resource locator devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid reagent, protein reagent, protein fragment reagent or other reagent described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Engineering and Alteration Methods

Methods and compositions (e.g., nucleic acid reagents) described herein can be used to generate engineered microorganisms. As noted above, the term "engineered microorganism" as used herein refers to a modified organism that includes one or more activities distinct from an activity present in a microorganism utilized as a starting point for modification (e.g., host microorganism or unmodified organism). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like. The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include, deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis, T., E. F. Fritsch and J. Sambrook (1982) Molecular Cloning: a Laboratory Manual; Cold Spring Harbor Laboratory, Cold Spring Harbor, N.Y.

The term "genetic modification" as used herein refers to any suitable nucleic acid addition, removal or alteration that facilitates production of a target product (e.g., phosphogluconate dehydratase activity, 2-keto-3-deoxygluconate-6-phosphate aldolase activity, xylose isomerase activity, or phosphoenolpyruvate carboxylase activity, for example). in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous polynucleotide" as used herein refers to a nucleotide sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous polynucleotide is from a different organism in some embodiments, and in certain embodiments, is from the same type of organism but from an outside source (e.g., a recombinant source).

The term "altered activity" as used herein refers to an activity in an engineered microorganism that is added or modified relative to the host microorganism (e.g., added, increased, reduced, inhibited or removed activity). An activity can be altered by introducing a genetic modification to a host microorganism that yields an engineered microorganism having added, increased, reduced, inhibited or removed activity.

An added activity often is an activity not detectable in a host microorganism. An increased activity generally is an activity detectable in a host microorganism that has been increased in an engineered microorganism. An activity can be increased to any suitable level for production of a target product (e.g., adipic acid, 6-hydroxyhexanoic acid), including but not limited to less than 2-fold (e.g., about 10% increase to about 99% increase; about 20%, 30%, 40%, 50%, 60%, 70%, 80%, 90% increase), 2-fold, 3-fold, 4-fold, 5-fold, 6-fold, 7-fold, 8-fold, 9-fold, of 10-fold increase, or greater than about 10-fold increase. A reduced or inhibited activity generally is an activity detectable in a host microorganism that has been reduced or inhibited in an engineered microorganism. An activity can be reduced to undetectable levels in some embodiments, or detectable levels in certain embodiments. An activity can be decreased to any suitable level for production of a target product (e.g., adipic acid, 6-hydroxyhexanoic acid), including but not limited to less than 2-fold (e.g., about 10% decrease to about 99% decrease; about 20%, 30%, 40%, 50%, 60%, 70%, 80%, 90% decrease), 2-fold, 3-fold, 4-fold, 5-fold, 6-fold, 7-fold, 8-fold, 9-fold, of 10-fold decrease, or greater than about 10-fold decrease.

An altered activity sometimes is an activity not detectable in a host organism and is added to an engineered organism. An altered activity also may be an activity detectable in a host organism and is increased in an engineered organism. An activity may be added or increased by increasing the number of copies of a polynucleotide that encodes a polypeptide having a target activity, in some embodiments. In certain embodiments an activity can be added or increased by inserting into a host microorganism a heterologous polynucleotide that encodes a polypeptide having the added activity. In certain embodiments, an activity can be added or increased by inserting into a host microorganism a heterologous polynucleotide that is (i) operably linked to another polynucleotide that encodes a polypeptide having the added activity, and (ii) up regulates production of the polynucleotide. Thus, an activity can be added or increased by inserting or modifying a regulatory polynucleotide operably linked to another polynucleotide that encodes a polypeptide having the target activity. In certain embodiments, an activity can be added or increased by subjecting a host microorganism to a selective environment and screening for microorganisms that have a detectable level of the target activity. Examples of a selective environment include, without limitation, a medium containing a substrate that a host organism can process and a medium lacking a substrate that a host organism can process.

An altered activity sometimes is an activity detectable in a host organism and is reduced, inhibited or removed (i.e., not detectable) in an engineered organism. An activity may be reduced or removed by decreasing the number of copies of a polynucleotide that encodes a polypeptide having a target activity, in some embodiments. In some embodiments, an activity can be reduced or removed by (i) inserting a polynucleotide within a polynucleotide that encodes a polypeptide having the target activity (disruptive insertion), and/or (ii) removing a portion of or all of a polynucleotide that encodes a polypeptide having the target activity (deletion or knock out, respectively). In certain embodiments, an activity can be reduced or removed by inserting into a host microorganism a heterologous polynucleotide that is (i) operably linked to another polynucleotide that encodes a polypeptide having the target activity, and (ii) down regulates production of the polynucleotide. Thus, an activity can be reduced or removed by inserting or modifying a regulatory polynucleotide operably linked to another polynucleotide that encodes a polypeptide having the target activity.

An activity also can be reduced or removed by (i) inhibiting a polynucleotide that encodes a polypeptide having the activity or (ii) inhibiting a polynucleotide operably linked to another polynucleotide that encodes a polypeptide having the activity. A polynucleotide can be inhibited by a suitable technique known in the art, such as by contacting an RNA encoded by the polynucleotide with a specific inhibitory RNA (e.g., RNAi, siRNA, ribozyme). An activity also can be reduced or removed by contacting a polypeptide having the activity with a molecule that specifically inhibits the activity (e.g., enzyme inhibitor, antibody). In certain embodiments, an activity can be reduced or removed by subjecting a host microorganism to a selective environment and screening for microorganisms that have a reduced level or removal of the target activity.

In some embodiments, an untranslated ribonucleic acid, or a cDNA can be used to reduce the expression of a particular activity or enzyme. For example, a microorganism can be engineered by genetic modification to express a nucleic acid reagent that reduces the expression of an activity by producing an RNA molecule that is partially or substantially homologous to a nucleic acid sequence of interest which encodes the activity of interest. The RNA molecule can bind to the nucleic acid sequence of interest and inhibit the nucleic acid sequence from performing its natural function, in certain embodiments. In some embodiments, the RNA may alter the nucleic acid sequence of interest which encodes the activity of interest in a manner that the nucleic acid sequence of interest is no longer capable of performing its natural function (e.g., the action of a ribozyme for example).

In certain embodiments, nucleotide sequences sometimes are added to, modified or removed from one or more of the nucleic acid reagent elements, such as the promoter, 5'UTR, target sequence, or 3'UTR elements, to enhance, potentially enhance, reduce, or potentially reduce transcription and/or translation before or after such elements are incorporated in a nucleic acid reagent. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, S95936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences).

An AU-rich element (ARE, e.g., AUUUA repeats) and/or splicing junction that follows a non-sense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that increase, potentially increase, reduce or potentially reduce translation efficiency are present in the elements, and adding, removing or modifying one or more of such sequences if they are identified. Certain embodiments are directed to a process comprising: determining whether any nucleotide sequences that increase or potentially increase translation efficiency are not present in the elements, and incorporating such sequences into the nucleic acid reagent.

In some embodiments, an activity can be altered by modifying the nucleotide sequence of an ORF. An ORF sometimes is mutated or modified (for example, by point mutation, deletion mutation, insertion mutation, PCR based mutagenesis and the like) to alter, enhance or increase, reduce, substantially reduce or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA's preferentially used in the host organism or engineered organism). To determine the relative activity, the activity from the product of the mutated ORF (or cell containing it) can be compared to the activity of the product or protein encoded by the unmodified ORF (or cell containing it).

In some embodiments, an ORF nucleotide sequence sometimes is mutated or modified to alter the triplet nucleotide sequences used to encode amino acids (e.g., amino acid codon triplets, for example). Modification of the nucleotide sequence of an ORF to alter codon triplets sometimes is used to change the codon found in the original sequence to better match the preferred codon usage of the organism in which the ORF or nucleic acid reagent will be expressed. For example, the codon usage, and therefore the codon triplets encoded by a nucleic acid sequence from bacteria may be different from the preferred codon usage in eukaryotes like yeast or plants. Preferred codon usage also may be different between bacterial species. In certain embodiments an ORF nucleotide sequences sometimes is modified to eliminate codon pairs and/or eliminate mRNA secondary structures that can cause pauses during translation of the mRNA encoded by the ORF nucleotide sequence. Translational pausing sometimes occurs when nucleic acid secondary structures exist in an mRNA, and sometimes occurs due to the presence of codon pairs that slow the rate of translation by causing ribosomes to pause. In some embodiments, the use of lower abundance codon triplets can reduce translational pausing due to a decrease in the pause time needed to load a charged tRNA into the ribosome translation machinery. Therefore, to increase transcriptional and translational efficiency in bacteria (e.g., where transcription and translation are concurrent, for example) or to increase translational efficiency in eukaryotes (e.g., where transcription and translation are functionally separated), the nucleotide sequence of a nucleotide sequence of interest can be altered to better suit the transcription and/or translational machinery of the host and/or genetically modified microorganism. In certain embodiment, slowing the rate of translation by the use of lower abundance codons, which slow or pause the ribosome, can lead to higher yields of the desired product due to an increase in correctly folded proteins and a reduction in the formation of inclusion bodies.

Codons can be altered and optimized according to the preferred usage by a given organism by determining the codon distribution of the nucleotide sequence donor organism and comparing the distribution of codons to the distribution of codons in the recipient or host organism. Techniques described herein (e.g., site directed mutagenesis and the like) can then be used to alter the codons accordingly. Comparisons of codon usage can be done by hand, or using nucleic acid analysis software commercially available to the artisan.

Modification of the nucleotide sequence of an ORF also can be used to correct codon triplet sequences that have diverged in different organisms. For example, certain yeast (e.g., *C. tropicalis* and *C. maltosa*) use the amino acid triplet CUG (e.g., CTG in the DNA sequence) to encode serine. CUG typically encodes leucine in most organisms. In order to maintain the correct amino acid in the resultant polypeptide or protein, the CUG codon must be altered to reflect the organism in which the nucleic acid reagent will be expressed. Thus, if an ORF from a bacterial donor is to be expressed in either *Candida* yeast strain mentioned above, the heterologous nucleotide sequence must first be altered or modified to the appropriate leucine codon. Therefore, in some embodiments, the nucleotide sequence of an ORF sometimes is altered or modified to correct for differences that have occurred in the evolution of the amino acid codon triplets between different organisms. In some embodiments, the nucleotide sequence can be left unchanged at a particular amino acid codon, if the amino acid encoded is a conservative or neutral change in amino acid when compared to the originally encoded amino acid.

In some embodiments, an activity can be altered by modifying translational regulation signals, like a stop codon for example. A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., World Wide Web URL iupac.org/news/prize/2003/wang.pdf).

Depending on the portion of a nucleic acid reagent (e.g., Promoter, 5' or 3' UTR, ORI, ORF, and the like) chosen for alteration (e.g., by mutagenesis, introduction or deletion, for example) the modifications described above can alter a given activity by (i) increasing or decreasing feedback inhibition mechanisms, (ii) increasing or decreasing promoter initiation, (iii) increasing or decreasing translation initiation, (iv) increasing or decreasing translational efficiency, (v) modifying localization of peptides or products expressed from nucleic acid reagents described herein, or (vi) increasing or decreasing the copy number of a nucleotide sequence of interest, (vii) expression of an anti-sense RNA, RNAi, siRNA, ribozyme and the like. In some embodiments, alteration of a nucleic acid reagent or nucleotide sequence can alter a region involved in feedback inhibition (e.g., 5' UTR, promoter and the like). A modification sometimes is made that can add or enhance binding of a feedback regulator and sometimes a modification is made that can reduce, inhibit or eliminate binding of a feedback regulator.

In certain embodiments, alteration of a nucleic acid reagent or nucleotide sequence can alter sequences involved in transcription initiation (e.g., promoters, 5' UTR, and the like). A modification sometimes can be made that can enhance or increase initiation from an endogenous or heterologous promoter element. A modification sometimes can be made that removes or disrupts sequences that increase or enhance transcription initiation, resulting in a decrease or elimination of transcription from an endogenous or heterologous promoter element.

In some embodiments, alteration of a nucleic acid reagent or nucleotide sequence can alter sequences involved in translational initiation or translational efficiency (e.g., 5' UTR, 3' UTR, codon triplets of higher or lower abundance, translational terminator sequences and the like, for example). A modification sometimes can be made that can increase or decrease translational initiation, modifying a ribosome binding site for example. A modification sometimes can be made that can increase or decrease translational efficiency. Removing or adding sequences that form hairpins and changing codon triplets to a more or less preferred codon are non-limiting examples of genetic modifications that can be made to alter translation initiation and translation efficiency.

In certain embodiments, alteration of a nucleic acid reagent or nucleotide sequence can alter sequences involved in localization of peptides, proteins or other desired products (e.g., adipic acid, for example). A modification sometimes can be made that can alter, add or remove sequences responsible for targeting a polypeptide, protein or product to an intracellular organelle, the periplasm, cellular membranes, or extracellularly. Transport of a heterologous product to a different intracellular space or extracellularly sometimes can reduce or eliminate the formation of inclusion bodies (e.g., insoluble aggregates of the desired product).

In some embodiments, alteration of a nucleic acid reagent or nucleotide sequence can alter sequences involved in increasing or decreasing the copy number of a nucleotide sequence of interest. A modification sometimes can be made that increases or decreases the number of copies of an ORF stably integrated into the genome of an organism or on an epigenetic nucleic acid reagent. Non-limiting examples of alterations that can increase the number of copies of a sequence of interest include, adding copies of the sequence of interest by duplication of regions in the genome (e.g., adding additional copies by recombination or by causing gene amplification of the host genome, for example), cloning additional copies of a sequence onto a nucleic acid reagent, or altering an ORI to increase the number of copies of an epigenetic nucleic acid reagent. Non-limiting examples of alterations that can decrease the number of copies of a sequence of interest include, removing copies of the sequence of interest by deletion or disruption of regions in the genome, removing additional copies of the sequence from epigenetic nucleic acid reagents, or altering an ORI to decrease the number of copies of an epigenetic nucleic acid reagent.

In certain embodiments, increasing or decreasing the expression of a nucleotide sequence of interest can also be accomplished by altering, adding or removing sequences involved in the expression of an anti-sense RNA, RNAi, siRNA, ribozyme and the like. The methods described above can be used to modify expression of anti-sense RNA, RNAi, siRNA, ribozyme and the like.

Engineered microorganisms can be prepared by altering, introducing or removing nucleotide sequences in the host genome or in stably maintained epigenetic nucleic acid reagents, as noted above. The nucleic acid reagents use to alter, introduce or remove nucleotide sequences in the host genome or epigenetic nucleic acids can be prepared using the methods described herein or available to the artisan.

Nucleic acid sequences having a desired activity can be isolated from cells of a suitable organism using lysis and nucleic acid purification procedures available in Maniatis, T., E. F. Fritsch and J. Sambrook (1982) Molecular Cloning: a Laboratory Manual; Cold Spring Harbor Laboratory, Cold Spring Harbor, N.Y. or with commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

Protocols for conducting the various type of PCR listed above are readily available to the artisan. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein Amplified, isolated and/or purified nucleic acids can be cloned into the recombinant DNA vectors described in Figures herein or into suitable commercially available recombinant DNA vectors. Cloning of nucleic acid sequences of interest into recombinant DNA vectors can facilitate further manipulations of the nucleic acids for preparation of nucleic acid reagents, (e.g., alteration of nucleotide sequences by mutagenesis, homologous recombination, amplification and the like, for example). Standard cloning procedures (e.g., enzymic digestion, ligation, and the like) are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

In some embodiments, nucleic acid sequences prepared by isolation or amplification can be used, without any further modification, to add an activity to a microorganism and thereby generate a genetically modified or engineered microorganism. In certain embodiments, nucleic acid sequences prepared by isolation or amplification can be genetically modified to alter (e.g., increase or decrease, for example) a desired activity. In some embodiments, nucleic acids, used to add an activity to an organism, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleic acid sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

Site directed mutagenesis is a procedure in which a specific nucleotide or specific nucleotides in a DNA molecule are mutated or altered. Site directed mutagenesis typically is performed using a nucleic acid sequence of interest cloned into a circular plasmid vector. Site-directed mutagenesis requires that the wild type sequence be known and used a platform for the genetic alteration. Site-directed mutagenesis sometimes is referred to as oligonucleotide-directed mutagenesis because the technique can be performed using oligonucleotides which have the desired genetic modification incorporated into the complement a nucleotide sequence of interest. The wild type sequence and the altered nucleotide are allowed to hybridize and the hybridized nucleic acids are extended and replicated using a DNA polymerase. The double stranded nucleic acids are introduced into a host (e.g., E. coli, for example) and further rounds of replication are carried out in vivo. The transformed cells carrying the mutated nucleic acid sequence are then selected and/or screened for those cells carrying the correctly mutagenized sequence. Cassette mutagenesis and PCR-based site-directed mutagenesis are further modifications of the site-directed mutagenesis technique. Site-directed mutagenesis can also be performed in vivo (e.g., transplacement "pop-in pop-out", In vivo site-directed mutagenesis with synthetic oligonucleotides and the like, for example).

PCR-based mutagenesis can be performed using PCR with oligonucleotide primers that contain the desired mutation or mutations. The technique functions in a manner similar to standard site-directed mutagenesis, with the exception that a thermocycler and PCR conditions are used to replace replication and selection of the clones in a microorganism host. As PCR-based mutagenesis also uses a circular plasmid vector, the amplified fragment (e.g., linear nucleic acid molecule) containing the incorporated genetic modifications can be separated from the plasmid containing the template sequence after a sufficient number of rounds of thermocycler amplification, using standard electrophorectic procedures. A modification of this method uses linear amplification methods and a pair of mutagenic primers that amplify the entire plasmid. The procedure takes advantage of the E. coli Dam methylase system which causes DNA replicated in vivo to be sensitive to the restriction endonucleases DpnI. PCR synthesized DNA is not methylated and is therefore resistant to DpnI. This approach allows the template plasmid to be digested, leaving the genetically modified, PCR synthesized plasmids to be isolated and transformed into a host bacteria for DNA repair and replication, thereby facilitating subsequent cloning and identification steps. A certain amount of randomness can be added to PCR-based sited directed mutagenesis by using partially degenerate primers.

Recombination sometimes can be used as a tool for mutagenesis. Homologous recombination allows the artisan to specifically target regions of known sequence for insertion of heterologous nucleotide sequences using the host organisms natural DNA replication and repair enzymes. Homologous recombination methods sometimes are referred to as "pop in pop out" mutagenesis, transplacement, knock out mutagenesis or knock in mutagenesis. Integration of a nucleic acid sequence into a host genome is a single cross over event, which inserts the entire nucleic acid reagent (e.g., pop in). A second cross over event excises all but a portion of the nucleic acid reagent, leaving behind a heterologous sequence, often referred to as a "footprint" (e.g., pop out). Mutagenesis by insertion (e.g., knock in) or by double recombination leaving behind a disrupting heterologous nucleic acid (e.g., knock out) both server to disrupt or "knock out" the function of the gene or nucleic acid sequence in which insertion occurs. By combining selectable markers and/or auxotrophic markers with nucleic acid reagents designed to provide the appropriate nucleic acid target sequences, the artisan can target a selectable nucleic acid reagent to a specific region, and then select for recombination events that "pop out" a portion of the inserted (e.g., "pop in") nucleic acid reagent.

Such methods take advantage of nucleic acid reagents that have been specifically designed with known target nucleic acid sequences at or near a nucleic acid or genomic region of interest. Popping out typically leaves a "foot print" of left over sequences that remain after the recombination event. The left over sequence can disrupt a gene and thereby reduce or eliminate expression of that gene. In some embodiments, the method can be used to insert sequences, upstream or downstream of genes that can result in an enhancement or reduction in expression of the gene. In certain embodiments, new genes can be introduced into the genome of a host organism using similar recombination or "pop in" methods. An example of a yeast recombination system using the ura3 gene and 5-FOA were described briefly above and further detail is presented herein.

A method for modification is described in Alani et al., "A method for gene disruption that allows repeated use of URA3 selection in the construction of multiply disrupted yeast strains", Genetics 116(4):541-545 August 1987. The original method uses a Ura3 cassette with 1000 base pairs (bp) of the same nucleotide sequence cloned in the same orientation on either side of the URA3 cassette. Targeting sequences of about 50 bp are added to each side of the construct. The double stranded targeting sequences are complementary to sequences in the genome of the host organism. The targeting sequences allow site-specific recombination in a region of interest. The modification of the original technique replaces the two 1000 bp sequence direct repeats with two 200 bp direct repeats. The modified method also uses 50 bp targeting sequences. The modification reduces or eliminates recombination of a second knock out into the 1000 bp repeat left behind in a first mutagenesis, therefore allowing multiply knocked out yeast. Additionally, the 200 bp sequences used herein are uniquely designed, self-assembling sequences that leave behind identifiable footprints. The technique used to design the sequences incorporate design features such as low identity to the yeast genome, and low identity to each other. Therefore a library of the self-assembling sequences can be generated to allow multiple knockouts in the same organism, while reducing or eliminating the potential for integration into a previous knockout.

As noted above, the URA3 cassette makes use of the toxicity of 5-FOA in yeast carrying a functional URA3 gene. Uracil synthesis deficient yeast are transformed with the modified URA3 cassette, using standard yeast transformation protocols, and the transformed cells are plated on minimal media minus uracil. In some embodiments, PCR can be used to verify correct insertion into the region of interest in the host genome, and certain embodiments the PCR step can be omitted. Inclusion of the PCR step can reduce the number of transformants that need to be counter selected to "pop out" the URA3 cassette. The transformants (e.g., all or the ones determined to be correct by PCR, for example) can then be counter-selected on media containing 5-FOA, which will select for recombination out (e.g., popping out) of the URA3 cassette, thus rendering the yeast ura3 deficient again, and resistant to 5-FOA toxicity. Targeting sequences used to direct recombination events to specific regions are presented herein. A modification of the method described above can be used to integrate genes in to the chromosome, where after recombination a functional gene is left in the chromosome next to the 200 bp footprint.

In some embodiments, other auxotrophic or dominant selection markers can be used in place of URA3 (e.g., an auxotrophic selectable marker), with the appropriate change in selection media and selection agents. Auxotrophic selectable markers are used in strains deficient for synthesis of a required biological molecule (e.g., amino acid or nucleoside, for example). Non-limiting examples of additional auxotrophic markers include; HIS3, TRP1, LEU2, LEU2-d, and LYS2. Certain auxotrophic markers (e.g., URA3 and LYS2) allow counter selection to select for the second recombination event that pops out all but one of the direct repeats of the recombination construct. HIS3 encodes an activity involved in histidine synthesis. TRP1 encodes an activity involved in tryptophan synthesis. LEU2 encodes an activity involved in leucine synthesis. LEU2-d is a low expression version of LEU2 that selects for increased copy number (e.g., gene or plasmid copy number, for example) to allow survival on minimal media without leucine. LYS2 encodes an activity involved in lysine synthesis, and allows counter selection for recombination out of the LYS2 gene using alpha-amino adipate (α-amino adipate).

Dominant selectable markers are useful because they also allow industrial and/or prototrophic strains to be used for genetic manipulations. Additionally, dominant selectable markers provide the advantage that rich medium can be used for plating and culture growth, and thus growth rates are markedly increased. Non-limiting examples of dominant selectable markers include; Tn903 kan$^r$, Cm$^r$, Hyg$^r$, CUP1, and DHFR. Tn903 kan$^r$ encodes an activity involved in kanamycin antibiotic resistance (e.g., typically neomycin phosphotransferase II or NPTII, for example). Cm$^r$ encodes an activity involved in chloramphenicol antibiotic resistance (e.g., typically chloramphenicol acetyl transferase or CAT, for example). Hyg$^r$ encodes an activity involved in hygromycin resistance by phosphorylation of hygromycin B (e.g., hygromycin phosphotransferase, or HPT). CUP1 encodes an activity involved in resistance to heavy metal (e.g., copper, for example) toxicity. DHFR encodes a dihydrofolate reductase activity which confers resistance to methotrexate and sulfanilamide compounds.

In contrast to site-directed or specific mutagenesis, random mutagenesis does not require any sequence information and can be accomplished by a number of widely different methods. Random mutagenesis often is used to generate mutant libraries that can be used to screen for the desired genotype or phenotype. Non-limiting examples of random mutagenesis include; chemical mutagenesis, UV-induced mutagenesis, insertion element or transposon-mediated mutagenesis, DNA shuffling, error-prone PCR mutagenesis, and the like.

Chemical mutagenesis often involves chemicals like ethyl methanesulfonate (EMS), nitrous acid, mitomycin C, N-methyl-N-nitrosourea (MNU), diepoxybutane (DEB), 1,2,7,8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamino)-acridinedihydrochloride (ICR-170), 2-amino purine (2AP), and hydroxylamine (HA), provided herein as non-limiting examples. These chemicals can cause base-pair substitutions, frameshift mutations, deletions, transversion mutations, transition mutations, incorrect replication, and the like. In some embodiments, the mutagenesis can be carried out in vivo. Sometimes the mutagenic process involves the use of the host organisms DNA replication and repair mechanisms to incorporate and replicate the mutagenized base or bases.

Another type of chemical mutagenesis involves the use of base-analogs. The use of base-analogs cause incorrect base pairing which in the following round of replication is corrected to a mismatched nucleotide when compared to the starting sequence. Base analog mutagenesis introduces a small amount of non-randomness to random mutagenesis, because specific base analogs can be chose which can be incorporated at certain nucleotides in the starting sequence. Correction of the mispairing typically yields a known substitution. For example, Bromo-deoxyuridine (BrdU) can be incorporated into DNA and replaces T in the sequence. The host DNA repair and replication machinery can sometime correct the defect, but sometimes will mispair the BrdU with a G. The next round of replication then causes a G-C transversion from the original A-T in the native sequence.

Ultra violet (UV) induced mutagenesis is caused by the formation of thymidine dimers when UV light irradiates chemical bonds between two adjacent thymine residues. Excision repair mechanism of the host organism correct the lesion in the DNA, but occasionally the lesion is incorrectly repaired typically resulting in a C to T transition.

Insertion element or transposon-mediated mutagenesis makes use of naturally occurring or modified naturally occurring mobile genetic elements. Transposons often encode accessory activities in addition to the activities necessary for transposition (e.g., movement using a transposase activity, for example). In many examples, transposon accessory activities are antibiotic resistance markers (e.g., see Tn903 kan$^r$ described above, for example). Insertion elements typically only encode the activities necessary for movement of the nucleic acid sequence. Insertion element and transposon mediated mutagenesis often can occur randomly, however specific target sequences are known for some transposons. Mobile genetic elements like IS elements or Transposons (Tn) often have inverted repeats, direct repeats or both inverted and direct repeats flanking the region coding for the transposition genes. Recombination events catalyzed by the transposase cause the element to remove itself from the genome and move to a new location, leaving behind a portion of an inverted or direct repeat. Classic examples of transposons are the "mobile genetic elements" discovered in maize. Transposon mutagenesis kits are commercially available which are designed to leave behind a 5 codon insert (e.g., Mutation Generation System kit, Finnzymes, World Wide Web URL finnzymes.us, for example). This allows the artisan to identify the insertion site, without fully disrupting the function of most genes.

DNA shuffling is a method which uses DNA fragments from members of a mutant library and reshuffles the fragments randomly to generate new mutant sequence combinations. The fragments are typically generated using DNaseI, followed by random annealing and re-joining using self priming PCR. The DNA overhanging ends, from annealing of random fragments, provide "primer" sequences for the PCR process. Shuffling can be applied to libraries generated by any of the above mutagenesis methods.

Error prone PCR and its derivative rolling circle error prone PCR uses increased magnesium and manganese concentrations in conjunction with limiting amounts of one or two nucleotides to reduce the fidelity of the Taq polymerase. The error rate can be as high as 2% under appropriate conditions, when the resultant mutant sequence is compared to the wild type starting sequence. After amplification, the library of mutant coding sequences must be cloned into a suitable plasmid. Although point mutations are the most common types of mutation in error prone PCR, deletions and frameshift mutations are also possible. There are a number of commercial error-prone PCR kits available, including those from Stratagene and Clontech (e.g., World Wide Web URL strategene.com and World Wide Web URL clontech.com, respectively, for example). Rolling circle error-prone PCR is a variant of error-prone PCR in which wild-type sequence is first cloned into a plasmid, the whole plasmid is then amplified under error-prone conditions.

As noted above, organisms with altered activities can also be isolated using genetic selection and screening of organisms challenged on selective media or by identifying naturally occurring variants from unique environments. For example, 2-Deoxy-D-glucose is a toxic glucose analog. Growth of yeast on this substance yields mutants that are glucose-deregulated. A number of mutants have been isolated using 2-Deoxy-D-glucose including transport mutants, and mutants that ferment glucose and galactose simultaneously instead of glucose first then galactose when glucose is depleted. Similar techniques have been used to isolate mutant microorganisms that can metabolize plastics (e.g., from landfills), petrochemicals (e.g., from oil spills), and the like, either in a laboratory setting or from unique environments.

Similar methods can be used to isolate naturally occurring mutations in a desired activity when the activity exists at a relatively low or nearly undetectable level in the organism of choice, in some embodiments. The method generally consists of growing the organism to a specific density in liquid culture, concentrating the cells, and plating the cells on various concentrations of the substance to which an increase in metabolic activity is desired. The cells are incubated at a moderate growth temperature, for 5 to 10 days. To enhance the selection process, the plates can be stored for another 5 to 10 days at a low temperature. The low temperature sometimes can allow strains that have gained or increased an activity to continue growing while other strains are inhibited for growth at the low temperature. Following the initial selection and secondary growth at low temperature, the plates can be replica plated on higher or lower concentrations of the selection substance to further select for the desired activity.

A native, heterologous or mutagenized polynucleotide can be introduced into a nucleic acid reagent for introduction into a host organism, thereby generating an engineered microorganism. Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents comprise two replication origins to allow the same nucleic acid reagent to be manipulated in bacterial before final introduction of the final product into the host organism (e.g., yeast or fungus for example). Standard molecular biology and recombinant DNA methods available to one of skill in the art can be found in Maniatis, T., E. F. Fritsch and J. Sambrook (1982) Molecular Cloning: a Laboratory Manual; Cold Spring Harbor Laboratory, Cold Spring Harbor, N.Y.

Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595,899) can increase the uptake of DNA in cells typically though to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

Culture, Production and Process Methods

Engineered microorganisms often are cultured under conditions that optimize yield of a target molecule. A non-limiting example of such a target molecule is ethanol. Culture conditions often can alter (e.g., add, optimize, reduce or eliminate, for example) activity of one or more of the following activities: phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activities. In general, conditions that may be optimized include the type and amount of carbon source, the type and amount of nitrogen source, the carbon-to-nitrogen ratio, the oxygen level, growth temperature, pH, length of the biomass production phase, length of target product accumulation phase, and time of cell harvest.

The term "fermentation conditions" as used herein refers to any culture conditions suitable for maintaining a microorganism (e.g., in a static or proliferative state). Fermentation conditions can include several parameters, including without limitation, temperature, oxygen content, nutrient content (e.g., glucose content), pH, agitation level (e.g., revolutions per minute), gas flow rate (e.g., air, oxygen, nitrogen gas), redox potential, cell density (e.g., optical density), cell viability and the like. A change in fermentation conditions (e.g., switching fermentation conditions) is an alteration, modification or shift of one or more fermentation parameters. For example, one can change fermentation conditions by increasing or decreasing temperature, increasing or decreasing pH (e.g., adding or removing an acid, a base or carbon dioxide), increasing or decreasing oxygen content (e.g., introducing air, oxygen, carbon dioxide, nitrogen) and/or adding or removing a nutrient (e.g., one or more sugars or sources of sugar, biomass, vitamin and the like), or combinations of the foregoing. Examples of fermentation conditions are described herein. Aerobic conditions often comprise greater than about 50% dissolved oxygen (e.g., about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Anaerobic conditions often comprise less than about 50% dissolved oxygen (e.g., about 1%, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48%, or less than any one of the foregoing).

Culture media generally contain a suitable carbon source. Carbon sources may include, but are not limited to, monosaccharides (e.g., glucose, fructose, xylose), disaccharides (e.g., lactose, sucrose), oligosaccharides, polysaccharides (e.g., starch, cellulose, hemicellulose, other lignocellulosic materials or mixtures thereof), sugar alcohols (e.g., glycerol), and renewable feedstocks (e.g., cheese whey permeate, cornsteep liquor, sugar beet molasses, barley malt). Carbon sources also can be selected from one or more of the following non-limiting examples: linear or branched alkanes (e.g., hexane), linear or branched alcohols (e.g., hexanol), fatty acids (e.g., about 10 carbons to about 22 carbons), esters of fatty acids, monoglycerides, diglycerides, triglycerides, phospholipids and various commercial sources of fatty acids including vegetable oils (e.g., soybean oil) and animal fats. A carbon source may include one-carbon sources (e.g., carbon dioxide, methanol, formaldehyde, formate and carbon-containing amines) from which metabolic conversion into key biochemical intermediates can occur. It is expected that the source of carbon utilized may encompass a wide variety of carbon-containing sources and will only be limited by the choice of the engineered microorganism(s).

Nitrogen may be supplied from an inorganic (e.g., $(NH_4)_2SO_4$) or organic source (e.g., urea or glutamate). In addition to appropriate carbon and nitrogen sources, culture media also can contain suitable minerals, salts, cofactors, buffers, vitamins, metal ions (e.g., $Mn^{+2}$, $Co^{+2}$, $Zn^{+2}$, $Mg^{+2}$) and other components suitable for culture of microorganisms. Engineered microorganisms sometimes are cultured in complex media (e.g., yeast extract-peptone-dextrose broth (YPD)). In some embodiments, engineered microorganisms are cultured in a defined minimal media that lacks a component necessary for growth and thereby forces selection of a desired expression cassette (e.g., Yeast Nitrogen Base (DIFCO Laboratories, Detroit, Mich.)). Culture media in some embodiments are common commercially prepared media, such as Yeast Nitrogen Base (DIFCO Laboratories, Detroit, Mich.). Other defined or synthetic growth media may also be used and the appropriate medium for growth of the particular microorganism are known.

A variety of host organisms can be selected for the production of engineered microorganisms. Non-limiting examples include yeast and fungi. In specific embodiments, yeast are cultured in YPD media (10 g/L Bacto Yeast Extract, 20 g/L Bacto Peptone, and 20 g/L Dextrose). Filamentous fungi, in particular embodiments, are grown in CM (Complete Medium) containing 10 g/L Dextrose, 2 g/L Bacto Peptone, 1 g/L Bacto Yeast Extract, 1 g/L Casamino acids, 50 mL/L 20× Nitrate Salts (120 g/L $NaNO_3$, 10.4 g/L KCl, 10.4 g/L $MgSO_4.7\ H_2O$), 1 mL/L 1000× Trace Elements (22 g/L $ZnSO_4.7\ H_2O$, 11 g/L $H_3BO_3$, 5 g/L $MnCl_2.7\ H_2O$, 5 g/L $FeSO_4.7\ H_2O$, 1.7 g/L $CoCl_2.6\ H_2O$, 1.6 g/L $CuSO_4.5\ H_2O$, 1.5 g/L $Na_2MoO_4.2\ H_2O$, and 50 g/L $Na_4EDTA$), and 1 mL/L Vitamin Solution (100 mg each of Biotin, pyridoxine, thiamine, riboflavin, p-aminobenzoic acid, and nicotinic acid in 100 mL water).

A suitable pH range for the fermentation often is between about pH 4.0 to about pH 8.0, where a pH in the range of about pH 5.5 to about pH 7.0 sometimes is utilized for initial culture conditions. Culturing may be conducted under aerobic or anaerobic conditions, where microaerobic conditions sometimes are maintained. A two-stage process may be utilized, where one stage promotes microorganism proliferation and another state promotes production of target molecule. In a two-stage process, the first stage may be conducted under aerobic conditions (e.g., introduction of air and/or oxygen) and the second stage may be conducted under anaerobic conditions (e.g., air or oxygen are not introduced to the culture conditions).

A variety of fermentation processes may be applied for commercial biological production of a target product. In some embodiments, commercial production of a target product from a recombinant microbial host is conducted using a batch, fed-batch or continuous fermentation process, for example.

A batch fermentation process often is a closed system where the media composition is fixed at the beginning of the process and not subject to further additions beyond those required for maintenance of pH and oxygen level during the process. At the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die.

A variation of the standard batch process is the fed-batch process, where the carbon source is continually added to the fermentor over the course of the fermentation process. Fed-batch processes are useful when catabolite repression is apt to inhibit the metabolism of the cells or where it is desirable to have limited amounts of carbon source in the media at any one time. Measurement of the carbon source concentration in fed-batch systems may be estimated on the basis of the changes of measurable factors such as pH, dissolved oxygen and the partial pressure of waste gases (e.g., CO.sub.2). Batch and fed-batch culturing methods are known in the art. Examples of such methods may be found in Thomas D. Brock in Biotechnology: A Textbook of Industrial Microbiology, 2.sup.nd ed., (1989) Sinauer Associates Sunderland, Mass. and Deshpande, Mukund V., Appl. Biochem. Biotechnol., 36:227 (1992).

In continuous fermentation process a defined media often is continuously added to a bioreactor while an equal amount of culture volume is removed simultaneously for product recovery. Continuous cultures generally maintain cells in the log phase of growth at a constant cell density. Continuous or semi-continuous culture methods permit the modulation of one factor or any number of factors that affect cell growth or end product concentration. For example, an approach may limit the carbon source and allow all other parameters to moderate metabolism. In some systems, a number of factors affecting growth may be altered continuously while the cell concentration, measured by media turbidity, is kept constant. Continuous systems often maintain steady state growth and thus the cell growth rate often is balanced against cell loss due to media being drawn off the culture. Methods of modulating nutrients and growth factors for continuous culture processes, as well as techniques for maximizing the rate of product formation, are known and a variety of methods are detailed by Brock, supra.

In various embodiments ethanol may be purified from the culture media or extracted from the engineered microorganisms. Culture media may be tested for ethanol concentration and drawn off when the concentration reaches a predetermined level. Detection methods are known in the art, including but not limited to the use of a hydrometer and infrared measurement of vibrational frequency of dissolved ethanol using the CH band at 2900 $cm^{-1}$. Ethanol may be present at a range of levels as described herein.

A target product sometimes is retained within an engineered microorganism after a culture process is completed, and in certain embodiments, the target product is secreted out of the microorganism into the culture medium. For the latter embodiments, (i) culture media may be drawn from the culture system and fresh medium may be supplemented, and/or (ii) target product may be extracted from the culture media during or after the culture process is completed. Engineered microorganisms may be cultured on or in solid, semi-solid or liquid media. In some embodiments media is drained from cells adhering to a plate. In certain embodiments, a liquid-cell mixture is centrifuged at a speed sufficient to pellet the cells but not disrupt the cells and allow extraction of the media, as known in the art. The cells may then be resuspended in fresh media. Target product may be purified from culture media according to methods known in the art.

In certain embodiments, target product is extracted from the cultured engineered microorganisms. The microorganism cells may be concentrated through centrifugation at speed sufficient to shear the cell membranes. In some embodiments, the cells may be physically disrupted (e.g., shear force, sonication) or chemically disrupted (e.g., contacted with detergent or other lysing agent).

The phases may be separated by centrifugation or other method known in the art and target product may be isolated according to known methods.

Commercial grade target product sometimes is provided in substantially pure form (e.g., 90% pure or greater, 95% pure or greater, 99% pure or greater or 99.5% pure or greater). In some embodiments, target product may be modified into any one of a number of downstream products. For example, ethanol may be derivatized or further processed to produce ethyl halides, ethyl esters, diethyl ether, acetic acid, ethyl amines, butadiene, solvents, food flavorings, distilled spirits and the like.

Target product may be provided within cultured microbes containing target product, and cultured microbes may be supplied fresh or frozen in a liquid media or dried. Fresh or frozen microbes may be contained in appropriate moisture-proof containers that may also be temperature controlled as necessary. Target product sometimes is provided in culture medium that is substantially cell-free. In some embodiments target product or modified target product purified from microbes is provided, and target product sometimes is provided in substantially pure form. In certain embodiments, ethanol can be provided in anhydrous or hydrous forms. Ethanol may be transported in a variety of containers including pints, quarts, liters, gallons, drums (e.g., 10 gallon or 55 gallon, for example) and the like.

In certain embodiments, a target product (e.g., ethanol, succinic acid) is produced with a yield of about 0.30 grams of target product, or greater, per gram of glucose added during a fermentation process (e.g., about 0.31 grams of target product per gram of glucose added, or greater; about 0.32 grams of target product per gram of glucose added, or greater; about 0.33 grams of target product per gram of glucose added, or greater; about 0.34 grams of target product per gram of glucose added, or greater; about 0.35 grams of target product per gram of glucose added, or greater; about 0.36 grams of target product per gram of glucose added, or greater; about 0.37 grams of target product per gram of glucose added, or greater; about 0.38 grams of target product per gram of glucose added, or greater; about 0.39 grams of target product per gram of glucose added, or greater; about 0.40 grams of target product per gram of glucose added, or greater; about 0.41 grams of target product per gram of glucose added, or greater; 0.42 grams of target product per gram of glucose added, or greater; 0.43 grams of target product per gram of glucose added, or greater; 0.44 grams of target product per gram of glucose added, or greater; 0.45 grams of target product per gram of glucose added, or greater; 0.46 grams of target product per gram of glucose added, or greater; 0.47 grams of target product per gram of glucose added, or greater; 0.48 grams of target product per gram of glucose added, or greater; 0.49 grams of target product per gram of glucose added, or greater; 0.50 grams of target product per gram of glucose added, or greater; 0.51 grams of target product per gram of glucose added, or greater; 0.52 grams of target product per gram of glucose added, or greater; 0.53 grams of target product per gram of glucose added, or greater; 0.54 grams of target product per gram of glucose added, or greater; 0.55 grams of target product per gram of glucose added, or greater; 0.56 grams of target product per gram of glucose added, or greater; 0.57 grams of target product per gram of glucose added, or greater; 0.58 grams of target product per gram of glucose added, or greater; 0.59 grams of target product per gram of glucose added, or greater; 0.60 grams of target product per gram of glucose added, or greater; 0.61 grams of target product per gram of glucose added, or greater; 0.62 grams of target product per gram of glucose added, or greater; 0.63 grams of target product per gram of glucose added, or greater; 0.64 grams of target product per gram of glucose added, or greater; 0.65 grams of target product per gram of glucose added, or greater; 0.66 grams of target product per gram of glucose added, or greater; 0.67 grams of target product per gram of glucose added, or greater; 0.68 grams of target product per gram of glucose added, or greater; 0.69 or 0.70 grams of target product per gram of glucose added or greater). In some embodiments, 0.45 grams of target product per gram of glucose added, or greater, is produced during the fermentation process.

EXAMPLES

The examples set forth below illustrate certain embodiments and do not limit the technology. Certain examples set forth below utilize standard recombinant DNA and other biotechnology protocols known in the art. Many such techniques are described in detail in Maniatis, T., E. F. Fritsch and J. Sambrook (1982) *Molecular Cloning: a Laboratory Manual*; Cold Spring Harbor Laboratory, Cold Spring Harbor, N.Y. DNA mutagenesis can be accomplished using the Stratagene (San Diego, Calif.) "QuickChange" kit according to the manufacturer's instructions, or by one of the other types of mutagenesis described above.

Example 1

Activation of the Entner-Doudoroff Pathway in Yeast Cells

Genomic DNA from *Zymomonas mobilis* (ZM4) was obtained from the American Type Culture Collection (ATCC accession number 31821D-5). The genes encoding phosphogluconate dehydratase EC 4.2.1.12 (referred to as "edd") and 2-keto-3-deoxygluconate-6-phosphate aldolase EC 4.2.1.14 (referred to as "eda") were isolated from the ZM4 genomic DNA using the following oligonucleotides:

The ZM4 eda gene:
(SEQ ID No: 1)
5'-aactgactagtaaaaaaatgcgtgatatcgattcc-3'

(SEQ ID No: 2)
5'-agtaactcgagctactaggcaacagcagcgcgcttg-3'

The ZM4 edd gene:
(SEQ ID NO: 3)
5'-aactgactagtaaaaaaatgactgatctgcattcaacg-3'

(SEQ ID NO: 4)
5'-agtaactcgagctactagataccggcacctgcatatattgc-3'

E. coli genomic DNA was prepared using Qiagen DNeasy blood and tissue kit according to the manufacture's protocol. The E. coli edd and eda constructs were isolated from E. coli genomic DNA using the following oligonucleotides:

The E. coli eda gene:
(SEQ ID NO: 5)
5'-aactgactagtaaaaaaatgaaaaactggaaaacaagtgcaga
atc-3'

(SEQ ID NO: 6)
5'-agtaactcgagctactacagcttagcgccttctacagcttcacg-3'

The E. coli edd gene:
(SEQ ID NO: 7)
5'-aactgactagtaaaaaaatgaatccacaattgttacgcgtaaca
aatcg-3'

(SEQ ID NO: 8)
5'agtaactcgagctactaaaaagtgatacaggttgcgccctgttc
ggcac-3'

All oligonucleotides set forth above were purchased from Integrated DNA technologies ("IDT", Coralville, Iowa). These oligonucleotides were designed to incorporate a SpeI restriction endonuclease cleavage site upstream and a XhoI restriction endonuclease cleavage site downstream of the edd and eda gene constructs such that these sites could be used to clone these genes into yeast expression vectors p426GPD (ATCC accession number 87361) and p425GPD (ATCC accession number 87359). In addition to incorporating restriction endonuclease cleavage sites, the forward oligonucleotides were designed to incorporate six consecutive AAAAAA nucleotides immediately upstream of the ATG initiation codon. This ensured that there was a conserved kozak sequence important for efficient translation initiation in yeast.

Cloning the edd and eda genes from ZM4 and *E. coli* genomic DNA was accomplished using the following procedure: About 100 ng of ZM4 or *E. coli* genomic DNA, 1 μM of the oligonucleotide primer set listed above, 2.5 U of PfuUltra High-Fidelity DNA polymerase (Stratagene), 300 μM dNTPs (Roche), and 1× PfuUltra reaction buffer was mixed in a final reaction volume of 50 μl. A BIORAD DNA Engine Tetrad 2 Peltier thermal cycler was used for the PCR reactions and the following cycle conditions were used: 5 min denaturation step at 95° C., followed by 30 cycles of 20 sec at 95° C., 20 sec at 55° C., and 1 min at 72° C., and a final step of 5 min at 72° C.

In an attempt to maximize expression of the ZM4 edd and eda genes in yeast, two different approaches were undertaken to optimize the ZM4 edd and eda genes. The first approach was to remove translational pauses from the polynucleotide sequence by designing the gene to incorporate only codons that are preferred in yeast. This optimization is referred to as the "hot rod" optimization. In the second approach, translational pauses which are present in the native organism gene sequence are matched in the heterologous expression host organism by substituting the codon usage pattern of that host organism. This optimization is referred to as the "matched" optimization. The final gene and protein sequences for edd and eda from the ZM4 native, hot rod (HR) and matched versions, as well as the *E. coli* native are shown in FIG. 6. Certain sequences in FIG. 6 are presented at the end of this Example 1. The matched version of ZM4 edd and ZM4 eda genes were synthesized by IDT, and the hot rod version was constructed using methods described in Larsen et al. (*Int. J. Bioinform. Res. Appl;* 2008:4[3]; 324-336).

Each version of each edd and eda gene was inserted into the yeast expression vector p426GPD (GPD promoter, 2 micron, URA3) (ATCC accession number 87361) between the SpeI and XhoI cloning sites. Each version of the eda gene was also inserted into the SpeI and XhoI sites of the yeast expression vector p425GPD (GPD promoter, 2 micron, LEU3) (ATCC accession number 87359). For each edd and eda version, 3' His tagged and non tagged p426 GPD constructs were made. Please refer to table 1 for all oligonucleotides used for PCR amplification of edd and eda constructs for cloning into p425 and p426 GPD vectors. All cloning procedures were conducted according to standard cloning procedures described by Maniatis et al.

Each edd and eda p426GPD construct was transformed into *Saccharomyces cerevisiae* strain BY4742 (MATalpha his3delta1 leu2delta0 lys2delta0 ura3delta0) (ATCC accession number 201389). This strain has a deletion of the his3 gene, an imidazoleglycerol-phosphate dehydratase which catalyzes the sixth step in histidine biosynthesis; a deletion of leu2 gene, a beta-isopropylmalate dehydrogenase which catalyzes the third step in the leucine biosynthesis pathway; a deletion of the lys2 gene, an alpha aminoadipate reductase which catalyzes the fifth step in biosynthesis of lysine; and a deletion of the ura3 gene, an orotidine-5'-phosphate decarboxylase which catalyzes the sixth enzymatic step in the de novo biosynthesis of pyrimidines. The genotype of BY4742 makes it an auxotroph for histidine, leucine, lysine and uracil.

Transformation of the p426GPD plasmids containing an edd or an eda variant gene into yeast strain BY4742 was accomplished using the Zymo Research frozen-EZ yeast transformation II kit according to the manufacturer's protocol. The transformed BY4742 cells were selected by growth on a synthetic dextrose medium (SD) (0.67% yeast nitrogen base-2% dextrose) containing complete amino acids minus uracil (Krackeler Scientific Inc). Plates were incubated at about 30° C. for about 48 hours. Transformant colonies for each edd and eda variant were inoculated onto 5 ml of SD minus uracil medium and cells were grown at about 30° C. and shaken at about 250 rpm for about 24 hours. Cells were harvested by centrifugation at 1000×g for about 5 minutes, after which protein crude extract was prepared with Y-PER Plus (Thermo Scientific) according to the manufacturer's instructions. Whole cell extract protein concentrations were determined using the Coomassie Plus Protein Assay (Thermo Scientific) according to the manufacturer's directions. For each edd and eda variant His-tagged construct, about 10 µg of soluble and insoluble fractions were loaded on 4-12% NuPAGE Novex Bis-Tris protein gels (Invitrogen) and proteins were analyzed by western using anti-(His)$_6$ mouse monoclonal antibody ('(His)$_6$' disclosed as SEQ ID NO: 35) (Abcam) and HRP-conjugated secondary antibody (Abcam). Supersignal West Pico Chemiluminescent substrate (Thermo Scientific) was used for western detection according to manufacturer's instructions. All edd variants showed expression in both soluble and insoluble fractions whereas only the *E. coli* eda variant showed expression in the soluble fraction.

In order to confirm that edd and eda variants were functional in yeast, the combined edd and eda activities were assayed by the formation of pyruvate, coupled to the NADH-dependent activity of lactate dehydrogenase. Transformation of combined edd (in p426GPD) and edd (in p425GPD) constructs was accomplished with the Zymo Research frozen-EZ yeast transformation II kit based on manufacturer's protocol. As a negative control, p425GPD and p426GPD vectors were also transformed into BY4742. Transformants (16 different combinations total including the variant edd and eda combinations plus vector controls) were selected on synthetic dextrose medium (SD) (0.67% yeast nitrogen base-2% dextrose) containing complete amino acids minus uracil and leucine. Transformants of edd and eda variant combinations were inoculated onto 5 ml of SD minus uracil and leucine and cells were grown at about 30° C. in shaker flasks at about 250 rpm for about 24 hours. Fresh overnight culture was used to inoculate about 100 ml of (SD media minus uracil and leucine containing about 0.01 g ergosterol/L and about 400 µl of Tween80) to an initial inoculum OD$_{600nm}$ of about 0.1 and grown anaerobically at about 30° C. for approximately 14 hours until cells reached an OD$_{600nm}$ of 3-4. The cells were centrifuged at about 3000 g for about 10 minutes. The cells were then washed with 25 ml deionized H$_2$O and centrifuged at 3000 g for 10 min. the cells were resuspended at about 2 ml/g of cell pellet) in lysis buffer (50 mM TrisCl pH7, mM MgCl$_2$, 1× Calbiochem protease inhibitor cocktail set III). Approximately 900 µl of glass beads were added and cells were lysed by vortexing at maximum speed for 4×30 seconds. Cell lysate was removed from the glass beads, placed into fresh tubes and spun at about 10,000 g for about 10 minutes at about 4° C. The supernatant containing whole cell extract (WCE) was transferred to a fresh tube. WCE protein concentrations were measured using the Coomassie Plus Protein Assay (Thermo Scientific) according to the manufacturer's directions. A total of about 750 µg of WCE was used for the edd and eda coupled assay. For this assay, about 750 µg of WCE was mixed with about 2 mM 6-phosphogluconate and about 4.5 U lactate dehydrogenase in a final volume of about 400 µl. A total of about 100 µl of NADH was added to this reaction to a final molarity of about 0.3 mM, and NADH oxidation was monitored for about 10 minutes at about 340 nM using a DU800 spectrophotometer.

```
ZM4 HR EDA GENE
                                                          (SEQ ID NO: 42)
ATGAGAGACATTGATTCTGTTATGAGATTGGCTCCAGTTATGCCAGTCTTGGTTATAGAA

GATATAGCTGATGCTAAGCCAATTGCTGAGGCTTTGGTTGCTGGTGGTTTAAATGTTTT

GGAAGTTACATTGAGAACTCCATGTGCTTTGGAAGCTATTAAAATTATGAAGGAAGTTCC

AGGTGCTGTTGTTGGTGCTGGTACTGTTTTAAACGCTAAAATGTTGGATCAAGCTCAAG

AAGCTGGTTGTGAGTTCTTTGTATCACCAGGTTTGACTGCTGATTTGGGAAAACATG

CTGTTGCTCAAAAAGCGGCTCTTCTACCAGGGGTTGCTAATGCTGCTGATGTTATG

TTGGGATTGGATTTGGGTTTGGATAGATTTAAATTCTTCCCAGCTGAAAATATAGGTGGT

TTGCCAGCTTTAAAATCTATGGCTTCTGTTTTTAGACAAGTTAGATTTTGTCCAACT

GGAGGAATTACTCCGACTTCTGCTCCAAAATATTTGGAAAATCCATCTATTTTGTGTGTT

GGTGGTTCTTGGGTTGTTCCAGCGGGTAAACCAGATGTTGCGAAAATTACTGCTTTGGC

TAAAGAGGCTTCAGCTTTTAAAAGAGCTGCTGTGGCGTAG
```

ZM4 HR EDD GENE (SEQ ID NO: 43)

ATGACGGATTTGCATTCAACTGTTGAGAAAGTAACTGCTAGAGTAATTGAAAGATC

AAGGGAAACTAGAAAGGCTTATTTGGATTTGATACAATATGAGAGGGAAAAAGGTG

TTGATAGACCAAATTTGTCTTGTTCTAATTTGGCTCATGGTTTTGCTGCTATGAAT

GGTGATAAACCAGCTTTGAGAGATTTTAATAGAATGAATATAGGTGTAGTTACTTC

TTATAATGATATGTTGTCTGCTCATGAACCATATTATAGATATCCAGAACAAATGA

AGGTTTTTGCTCGTGAAGTTGGTGCTACAGTTCAAGTTGCTGGTGGTGTTCCTGCA

ATGTGTGATGGTGTTACTCAAGGTCAACCAGGTATGGAAGAATCTTTGTTTTCCAG

AGATGTAATTGCTTTGGCTACATCTGTTTCATTGTCTCACGGAATGTTTGAAGGTG

CTGCATTGTTGGGAATTTGTGATAAAATTGTTCCAGGTTTGTTGATGGGTGCTTTG

AGGTTCGGTCATTTGCCAACTATTTTGGTTCCATCTGGTCCAATGACTACTGGAAT

CCCAAATAAAGAAAGATTAGAATTAGACAATTGTATGCTCAAGGAAAAATTGGTC

AAAAGGAATTGTTGGATATGGAAGCTGCCTGTTATCATGCTGAAGGTACTTGTACT

TTTTATGGTACTGCTAACACTAATCAGATGGTTATGGAAGTTTTGGGTTTGCACAT

GCCAGGTAGTGCATTCGTTACTCCAGGTACTCCACTGAGACAGGCTTTGACTAGAG

CTGCTGTTCATAGAGTTGCAGAGTTGGGTTGGAAAGGTGATGATTATAGACCTTTG

GGTAAAATTATTGATGAGAAATCTATTGTTAATGCTATTGTTGGTTTGTTAGCTAC

AGGTGGTTCTACAAATCATACAATGCATATTCCGGCCATAGCTAGAGCAGCAGGGG

TTATAGTTAATTGGAATGATTTTCATGATTGTCTGAAGTTGTTCCATTGATTGCT

AGAATTTATCCAAATGGTCCTAGAGATATAAATGAATTTCAAAATGCAGGAGGAAT

GGCTTATGTAATTAAAGAATTGTTGAGTGCGAATTTGTTAAATAGAGATGTTACTA

CTATTGCTAAAGGAGGGATAGAAGAATATGCTAAAGCTCCAGCTCTGAACGATGCG

GGTGAATTGGTGTGGAAACCGGCTGGCGAACCTGGGGACGACACAATTTTGAGACC

AGTATCTAATCCATTTGCTAAAGATGGTGGTTTGCGTCTCTTGGAAGGTAATTTGG

GTAGAGCAATGTATAAGGCTTCTGCTGTAGATCCAAAATTCTGGACTATTGAAGCT

CCCGTTAGAGTTTTCTCTGATCAAGATGATGTTCAAAAGGCTTTTAAAGCAGGCGA

GTTAAATAAAGATGTTATAGTTGTTGTTAGATTTCAAGGTCCTCGTGCTAATGGTA

TGCCTGAATTGCATAAGTTGACTCCTGCGCTAGGCGTATTGCAAGATAATGGTTAT

AAGGTTGCTTTAGTTACTGATGGTAGAATGTCTGGTGCAACTGGTAAAGTACCGGT

GGCTCTGCATGTTTCACCAGAGGCTTTAGGAGGTGGGGCGATTGGCAAGTTGAGAG

ATGGCGATATAGTTAGAATTTCTGTTGAAGAAGGTAAATTAGAGGCTCTTGTCCCC

GCCGACGAGTGGAATGCTAGACCACATGCTGAGAAGCCCGCTTTTAGACCTGGTAC

TGGGAGAGAATTGTTTGACATTTTTAGACAAAACGCTGCTAAGGCTGAGGATGGTG

CAGTTGCAATTTATGCTGGGGCAGGGATCTAG

ZM4 MATCHED EDA GENE (SEQ ID NO: 44)

ATGAGGGATATTGATAGTGTGATGAGGTTAGCCCCTGTTATGCCTGTTCTCGTTAT

TGAAGATATTGCAGATGCCAAACCTATTGCCGAAGCACTCGTTGCAGGTGGTCTAA

ACGTTCTAGAAGTGACACTAAGGACTCCTTGTGCACTAGAAGCTATTAAGATTATG

AAGGAAGTTCCTGGTGCTGTTGTTGGTGCTGGTACAGTTCTAAACGCCAAAATGCT

CGACCAGGCACAAGAAGCAGGTTGCGAATTTTTCGTTTCACCTGGTCTAACTGCCG

-continued

ACCTCGGAAAGCACGCAGTTGCTCAAAAAGCCGCATTACTACCCGGTGTTGCAAAT

GCAGCAGATGTGATGCTAGGTCTAGACCTAGGTCTAGATAGGTTCAAGTTCTTCCC

TGCCGAAAACATTGGTGGTCTACCTGCTCTAAAGAGTATGGCATCAGTTTTCAGGC

AAGTTAGGTTCTGCCCTACTGGAGGTATAACTCCTACAAGTGCACCTAAATATCTA

GAAAACCCTAGTATTCTATGCGTTGGTGGTTCATGGGTTGTTCCTGCCGGAAAACC

CGATGTTGCCAAAATTACAGCCCTCGCAAAAGAAGCAAGTGCATTCAAGAGGGCAG

CAGTTGCTTAG

ZM4 MATCHED EDD GENE (SEQ ID NO: 45)
ATGACGGATCTACATAGTACAGTGGAGAAGGTTACTGCCAGGGTTATTGAAAGGAG

TAGGGAAACTAGGAAGGCATATCTAGATTTAATTCAATATGAGAGGGAAAAAGGAG

TGGACAGGCCCAACCTAAGTTGTAGCAACCTAGCACATGGATTCGCCGCAATGAAT

GGTGACAAGCCCGCATTAAGGGACTTCAACAGGATGAATATTGGAGTTGTGACGAG

TTACAACGATATGTTAAGTGCACATGAACCCTATTATAGGTATCCTGAGCAAATGA

AGGTGTTTGCAAGGGAAGTTGGAGCCACAGTTCAAGTTGCTGGTGGAGTGCCTGCA

ATGTGCGATGGTGTGACTCAGGGTCAACCTGGAATGGAAGAATCCCTATTTTCAAG

GGATGTTATTGCATTAGCAACTTCAGTTTCATTATCACATGGTATGTTTGAAGGGG

CAGCTCTACTCGGTATATGTGACAAGATTGTTCCTGGTCTACTAATGGGAGCACTA

AGGTTTGGTCACCTACCTACTATTCTAGTTCCCAGTGGACCTATGACAACGGGTAT

ACCTAACAAAGAAAAATTAGGATTAGGCAACTCTATGCACAAGGTAAAATTGGAC

AAAAAGAACTACTAGATATGGAAGCCGCATGCTACCATGCAGAAGGTACTTGCACT

TTCTATGGTACAGCCAACACTAACCAGATGGTTATGGAAGTTCTCGGTCTACATAT

GCCCGGTAGTGCCTTTGTTACTCCTGGTACTCCTCTCAGGCAAGCACTAACTAGGG

CAGCAGTGCATAGGGTTGCAGAATTAGGTTGGAAGGGAGACGATTATAGGCCTCTA

GGTAAAATTATTGACGAAAAAAGTATTGTTAATGCAATTGTTGGTCTATTAGCCAC

TGGTGGTAGTACTAACCATACGATGCATATTCCTGCTATTGCAAGGGCAGCAGGTG

TTATTGTTAACTGGAATGACTTCCATGATCTATCAGAAGTTGTTCCTTTAATTGCT

AGGATTTACCCTAATGGACCTAGGGACATTAACGAATTTCAAAATGCCGGAGGAAT

GGCATATGTTATTAAGGAACTACTATCAGCAAATCTACTAAACAGGGATGTTACAA

CTATTGCTAAGGGAGGTATAGAAGAATACGCTAAGGCACCTGCCCTAAATGATGCA

GGAGAATTAGTTTGGAAGCCCGCAGGAGAACCTGGTGATGACACTATTCTAAGGCC

TGTTTCAAATCCTTTCGCCAAAGATGGAGGTCTAAGGCTCTTAGAAGGTAACCTAG

GAAGGGCCATGTACAAGGCTAGCGCCGTTGATCCTAAATTCTGGACTATTGAAGCC

CCTGTTAGGGTTTTCTCAGACCAGGACGATGTTCAAAAAGCCTTCAAGGCAGGAGA

ACTAAACAAAGACGTTATTGTTGTTGTTAGGTTCCAAGGACCTAGGGCCAACGGTA

TGCCTGAATTACATAAGCTAACTCCTGCATTAGGTGTTCTACAAGATAATGGATAC

AAAGTTGCATTAGTGACGGATGGTAGGATGAGTGGTGCAACTGGTAAAGTTCCTGT

TGCATTACATGTTTCACCCGAAGCACTAGGAGGTGGTGCTATTGGTAAACTTAGGG

ATGGAGATATTGTTAGGATTAGTGTTGAAGAAGGAAAACTTGAAGCACTCGTTCCC

GCAGATGAGTGGAATGCAAGGCCTCATGCAGAAAAACCTGCATTCAGGCCTGGGAC

TGGGAGGGAATTATTTGATATTTTCAGGCAAAATGCAGCAAAAGCAGAAGACGGTG

CCGTTGCCATCTATGCCGGTGCTGGTATATAG

Example 2

Inactivation of the Embden-Meyerhof Pathway in Yeast

*Saccharomyces cerevisiae* strain YGR240CBY4742 was obtained from the ATCC (accession number 4015893). This strain is genetically identical to *S. cerevisiae* strain BY4742, except that YGR420C, the gene encoding the PFK1 enzyme, which is the alpha subunit of heterooctameric phosphofructokinase, has been deleted. A DNA construct designed to delete the gene encoding the PFK2 enzyme via homologous recombination was prepared. This construct substituted the gene encoding HIS3 (imidazoleglycerol-phosphate dehydratase, an enzyme required for synthesis of histidine) for the PFK2 gene. The DNA construct comprised, in the 5' to 3' direction, 100 bases of the 5' end of the open reading frame of PFK2, followed by the HIS3 promoter, HIS3 open reading frame, HIS3 terminator, and 100 bp of the 3' end of the PFK2 open reading frame.

This construct was prepared by two rounds of PCR. In the first round, about 100 ng of BY4742 genomic DNA was used as a template. The genomic DNA was prepared from cells using the Zymo Research Yeastar kit according to the manufacturer's instructions. PCR was performed using the following primers:

(SEQ ID NO: 9)
5'-tgcatattccgttcaatcttataaagctgccatagatttttacac caagtcgttttaagagcttggtgagcgcta-3'

(SEQ ID NO: 10)
5'-cttgccagtgaatgacctttggcattctcatggaaacttcagtttc atagtcgagttcaagagaaaaaaaagaa-3'

The PCR reaction conditions were the same as those set forth in Example 1 for preparing the edd and eda genes.

For the second round of PCR, approximately 1 µl of the first PCR product was used as a template. The second round of PCR reaction was performed with the following primer set:
5'-atgactgttactactccttttgtgaatg-
gtacttcttattgtaccgtcactgcatattccgttcaatcttataaa-3' (SEQ ID NO:11)
5'-ttaatcaactctctttcttccaac-
caaatggtcagcaatgagtctggtagcttgccagtgaatgacctttggcat-3' (SEQ ID NO:12)

PCR conditions for this reaction were the same as for the first reaction immediately above. The final PCR product was separated by agarose gel electrophoresis, excised, and purified using MP Biomedicals Geneclean II kit according to the manufacturer's instructions.

Approximately 2 µg of the purified DNA was used for transformation of the yeast strain YGR240CBY4742 by lithium acetate procedure as described by Shiestl and Gietz with an additional recovery step added after the heat shock step. Essentially after heat shock, cells were centrifuged at 500×g for 2 min and resuspended in 1 ml of YP-Ethanol (1% yeast extract-2% peptone-2% ethanol) and incubated at 30° C. for 2 hours prior to plating on selective media containing SC-Ethanol (0.67% yeast nitrogen base-2% ethanol) containing complete amino acids minus histidine. The engineered transformant strain referred to as YGR420CBY4742ΔPFK2 has PFK1 and PFK2 genes deleted and is an auxotroph for leucine, uracil and lysine.

The YGR420CBY4742ΔPFK2 strain was used for transformation of the combination of edd-p426 GPD (edd variants in p426 GPD) and eda-p425 GPD (eda variants in p425 GPD) variant constructs. A total of 16 combinations of edd-p426 GPD and eda-p425 GPD variant constructs were tested. Each combination was transformed into YGR420CBY4742ΔPFK2. For all transformation, 1 µg of edd-p426 GPD and 1 µg of eda-p425 GPD was used. All transformants from each edd-p426 GPD and eda-p425 GPD construct combination were selected on SC-Ethanol (0.67% yeast nitrogen base-2% ethanol) containing complete amino acids minus uracil and leucine.

To confirm that the edd and eda variants are functional in yeast, a complementation test for growth of YGR420CBY4742ΔPFK2 strain on YPD (1% yeast extract-2% peptone-2% dextrose) and YPGluconate (1% yeast extract-2% peptone-2% gluconate) was performed. Viable colonies of edd-p426 GPD and eda-p425 GPD variant construct combinations grown on SC-Ethanol minus uracil and leucine were patched to plates containing SC-ethanol minus uracil and leucine and incubated at 30° C. for 48 hrs. These patches were used to inoculate 5 ml of YPD media to an initial inoculum $OD_{600nm}$ of 0.1 and the cells were grown anaerobically at 30° C. for 3 to 7 days.

Example 3

Preparation of Carbon Dioxide Fixing Yeast Cells

Total genomic DNA from *Zymomonas mobilis* was obtained from ATCC (ATCC Number 31821). The *Z. mobilis* gene encoding the enzyme phosphoenolpyruvate carboxylase ("PEP carboxylase") was isolated from this genomic DNA and cloned using PCR amplification. PCR was performed in a total volume of about 50 micro-liters in the presence of about 20 nanograms of *Z. mobilis* genomic DNA, about 0.2 mM of 5' forward primer, about 0.2 mM of 3' reverse primer, about 0.2 mM of dNTP, about 1 micro-liter of pfu UltraII DNA polymerase (Stratagene, La Jolla, Calif.), and 1×PCR buffer (Stratagene, La Jolla, Calif.). PCR was carried out in a thermocycler using the following program: Step One "95° C. for 10 minutes" for 1 cycle, followed by Step Two "95° C. for 20 seconds, 65° C. for 30 seconds, and 72° C. for 45 seconds" for 35 cycles, followed by Step Three "72° C. for 5 minutes" for 1 cycle, and then Step Four "4° C. Hold" to stop the reaction. The primers for the PCR reaction were:

(SEQ ID NO: 13)
5' GACTAACTGAACTAGTAAAAAAATGACCAAGCCGCGCACAATTAAT

CAG-3'

(SEQ ID NO: 14)
5' AAGTGAGTAACTCGAGTTATTAACCGCTGTTGCGAAGTGCCGTCG

C-3'

The DNA sequence of native *Z. Mobilis* PEP carboxylase is set forth as SEQ ID NO:20.

The cloned gene was inserted into the vector pGPD426 (ATCC Number: 87361) in between the SpeI and XhoI sites. The final plasmid containing the PEP carboxylase gene was named pGPD426 PEPC.

Separately, a similar plasmid, referred to as pGPD426 N-his PEPC was constructed to insert a six-histidine tag (SEQ ID NO: 35) at the N-terminus of the PEPC sequence for protein expression verification in yeast. This plasmid was constructed using two rounds of PCR to extend the 5' end of the PEPC gene to incorporate a six-histidine tag (SEQ ID NO:

35) at the N-terminus of the PEPC protein. The two 5' forward primers used sequentially were:

(SEQ ID NO: 15)
5'ATGTCTCATCATCATCATCATCATACCAAGCCGCGCACAATTAATC AGAAC-3' and (SEQ ID NO: 16)
5'GACTAACTGAACTAGTAAAAAAATGTCTCATCATCATCATCAT ACCAAG-3'

The same 3' primer was used as described above. The PCR was performed in a total volume of about 50 micro-liters in the presence of about 20 nanograms of Z. Mobilis PEP carboxylase polynucleotide, about 0.2 mM of 5' forward primer, about 0.2 mM of 3' reverse primer, about 0.2 mM of dNTP, about 1 micro-liter of pfu UltraII DNA polymerase (Stratagene, La Jolla, Calif.), and 1×PCR buffer (Stratagene, La Jolla, Calif.). The PCR was carried out in a thermocycler using the following program: Step One "95° C. for 10 minutes" for 1 cycle, followed by Step Two "95° C. for 20 seconds, 65° C. for 30 seconds, and 72° C. for 45 seconds" for 35 cycles, followed Step Three "72° C. for 5 minutes" for 1 cycle, and then Step Four "4° C. Hold" to stop the reaction.

To increase protein expression level of Z. Mobilis PEP carboxylase in yeast, the PEPC coding sequence was optimized to incorporate frequently used codons obtained from yeast glycolytic genes. The resulting PEP carboxylase amino acid sequence remains identical to the wild type.

The codon optimized PEP carboxylase DNA sequence was ordered from IDT and was inserted into the vector pGPD426 at the SpeI and XhoI site. The final plasmid containing the codon optimized PEP carboxylase gene was named pGPD426 PEPC_opti. A similar plasmid, named pGPD426 N-his PEPC_opti was constructed to insert a six-histidine tag (SEQ ID NO: 35) at the N-terminus of the optimized PEPC gene for protein expression verification in yeast.

To construct pGPD426 N-his PEPC_opti, two rounds of PCR were performed to extend the 5' end of the codon optimized PEPC gene to incorporate the six-histidine tag (SEQ ID NO: 35) at the N-terminus of the PEPC protein. Two 5' forward primers used in sequential order were:

(SEQ ID NO: 17)
5'ATGTCTCATCATCATCATCATCATATGACCAAGCCAAGAACTATTAA CCAAAACCC-3' and (SEQ ID NO: 18)
5'GACTAACTGAACTAGTAAAAAAATGTCTCATCATCATCATCAT ATGACCAAGCCAAG 3'

The 3' reverse primer sequence used for both PCR reactions was:

(SEQ ID NO: 19)
5'AAGTGAGTAACTCGAGTTATTAACCGGAGTTTCTCAAAGCAGTAGC GATAG3'

Both PCR reactions were performed in a total volume of about 50 micro-liters in the presence of about 20 nanograms of the codon optimized PEP carboxylase polynucleotide, about 0.2 mM of 5' forward primer, about 0.2 mM of 3' reverse primer, about 0.2 mM of dNTP, about 1 micro-liter of pfu UltraII DNA polymerase (Stratagene, La Jolla, Calif.), and 1×PCR buffer (Stratagene, La Jolla, Calif.). PCR reactions were carried out in a thermocycler using the following program: Step One "95° C. for 10 minutes" for 1 cycle, followed by Step Two "95° C. for 20 seconds, 65° C. for 30 seconds, and 72° C. for 45 seconds" for 35 cycles, followed Step Three "72° C. for 5 minutes" for 1 cycle, and then Step Four "4° C. Hold" to stop the reaction.

Saccharomyces cerevisiae strain BY4742 was cultured in YPD medium to an OD of about 1.0, and then prepared for transformation using the Frozen-EZ Yeast Transformation II kit (Zymo Research, Orange, Calif.) and following the manufacturer's instructions. Approximately 500 micrograms of each plasmid was added to the cells, and transformation was accomplished by addition of PEG solution ("Solution 3" in the Frozen-EZ Yeast Transformation II kit) and incubation at about 30° C. for an hour. After transformation, the cells were plated on synthetic complete medium (described in Example IV below) minus uracil (sc-ura) medium, grown for about 48 hours at about 30° C., and transformants were selected based on auxotrophic complementation.

Following a similar procedure, the same plasmids were individually transformed using the procedure described above into the following yeast mutant strains: YKR097W (ATCC Number 4016013, ΔPCK, in the phosphoenolpyruvate carboxykinase gene is deleted), YGL062W (ATCC Number 4014429, ΔPYC1, in which the pyruvate carboxylase 1 gene is deleted), and YBR218C (ATCC Number 4013358, ΔPYC2, in which the pyruvate carboxylase 2 gene is deleted).

The transformed yeast cells were grown aerobically in a shake flask in synthetic complete medium minus uracil (see Example IV) containing 1% glucose to mid-log phase (an OD of 2.0). The mid-log phase cultures were then used to inoculate a fresh culture (in sc-ura medium with 1% glucose) to an initial OD of 0.1 at which time the cultures were then grown anaerobically in a serum bottle. Culture samples were drawn periodically to monitor the level of glucose consumption and ethanol production.

```
DNA sequence of the native Z. mobilis PEP carboxylase gene (SEQ ID NO: 20):
ACTAGTAAAAAAATGACCAAGCCGCGCACAATTAATCAGAACCCAGACCTTCGCTATTTTGGT

AACCTGCTCGGTCAGGTTATTAAGGAACAAGGCGGAGAGTCTTTATTCAACCAGATCGAGCAA

ATTCGCTCTGCCGCGATTAGACGCCATCGGGGTATTGTTGACAGCACCGAGCTAAGTTCTCG

CTTAGCCGATCTCGACCTTAATGACATGTTCTCTTTTGCACATGCCTTTTTGCTGTTTTCAATG

CTGGCCAATTTGGCTGATGATCGTCAGGGAGATGCCCTTGATCCTGATGCCAATATGGCAAGT

GCCCTTAAGGACATAAAAGCCAAAGGCGTCAGTCAGCAGGCGATCATTGATATGATCGACAAA

GCCTGCATTGTGCCTGTTCTGACAGCACATCCGACCGAAGTCCGTCGGAAAAGTATGCTTGA
```

```
CCATTATAATCGCATTGCAGGTTTAATGCGGTTAAAAGATGCTGGACAAACGGTGACCGAAGA
TGGTCTTCCGATCGAAGATGCGTTAATCCAGCAAATCACGATATTATGGCAGACTCGTCCGCT
CATGCTGCAAAAGCTGACCGTGGCTGATGAAATCGAAACTGCCCTGTCTTTCTTAAGAGAAAC
TTTTCTGCCTGTTCTGCCCCAGATTTATGCAGAATGGGAAAAATTGCTTGGTAGTTCTATTCCA
AGCTTTATCAGACCTGGTAATTGGATTGGTGGTGACCGTGACGGTAACCCCAATGTCAATGCC
GATACGATCATGCTGTCTTTGAAGCGCAGCTCGGAAACGGTATTGACGGATTATCTCAACCGT
CTTGATAAACTGCTTTCCAACCTTTCGGTCTCAACCGATATGGTTTCGGTATCCGATGATATTC
TACGTCTAGCCGATAAAAGTGGTGACGATGCTGCGATCCGTGCGGATGAACCTTATCGTCGT
GCCTTAAATGGTATTTATGACCGTTTAGCCGCTACCTATCGTCAGATCGCCGGTCGCAACCCT
TCGCGCCCAGCCTTGCGTTCTGCAGAAGCCTATAAACGGCCTCAAGAATTGCTGGCTGATTT
GAAGACCTTGGCCGAAGGCTTGGGTAAATTGGCAGAAGGTAGTTTTAAGGCATTGATCCGTTC
GGTTGAAACCTTTGGTTTCCATTTGGCCACCCTCGATCTGCGTCAGAATTCGCAGGTTCATGA
AAGAGTTGTCAATGAACTGCTACGGACAGCCACCGTTGAAGCCGATTATTTATCTCTATCGGA
AGAAGATCGCGTTAAGCTGTTAAGACGGGAATTGTCGCAGCCGCGGACTCTATTCGTTCCGC
GCGCCGATTATTCCGAAGAAACGCGTTCTGAACTTGATATTATTCAGGCAGCAGCCCGCGCC
CATGAAATTTTTGGCCCTGAATCCATTACGACTTATTTGATTTCGAATGGCGAAAGCATTTCCG
ATATTCTGGAAGTCTATTTGCTTTTGAAAGAAGCAGGGCTGTATCAAGGGGGTGCTAAGCCAA
AAGCGGCGATTGAAGCTGCGCCTTTATTCGAGACGGTGGCCGATCTTGAAAATGCGCCAAAG
GTCATGGAGGAATGGTTCAAGCTGCCTGAAGCGCAAGCCATTGCAAAGGCACATGGCGTTCA
GGAAGTGATGGTTGGCTATTCTGACTCCAATAAGGACGGCGGATATCTGACCTCGGTTTGGG
GTCTTTATAAGGCTTGCCTCGCTTTGGTGCCGATTTTTGAGAAAGCCGGTGTACCGATCCAGT
TTTTCCATGGACGGGGTGGTTCCGTTGGTCGCGGTGGTGGTTCCAACTTTAATGCCATTCTGT
CGCAGCCAGCCGGAGCCGTCAAAGGGCGTATCCGTTATACAGAACAGGGTGAAGTCGTGGC
GGCCAAATATGGCACCCATGAAAGCGCTATTGCCCATCTGGATGAGGCCGTAGCGGCGACTT
TGATTACGTCTTTGGAAGCACCGACCATTGTCGAGCCAGAGTTTAGTCGTTACCGTAAGGCCT
TGGATCAGATCTCAGATTCAGCTTTCCAGGCCTATCGCCAATTGGTCTATGGAACGAAGGGCT
TCCGTAAATTCTTTAGTGAATTTACGCCTTTGCCGGAAATTGCCCTGTTAAAGATCGGGTCACG
CCCACCTAGCCGCAAAAAATCCGACCGGATTGAAGATCTACGCGCTATTCCTTGGGTGTTTAG
CTGGTCTCAAGTTCGAGTCATGTTACCCGGTTGGTTCGGTTTCGGTCAGGCTTTATATGACTT
TGAAGATACCGAGCTGTTACAGGAAATGGCAAGCCGTTGGCCGTTTTTCCGCACGACTATTCG
GAATATGGAACAGGTGATGGCACGTTCCGATATGACGATCGCCAAGCATTATCTGGCCTTGGT
TGAGGATCAGACAAATGGTGAGGCTATCTATGATTCTATCGCGGATGGCTGGAATAAAGGTTG
TGAAGGTCTGTTAAAGGCAACCCAGCAGAATTGGCTGTTGGAACGCTTTCCGGCGGTTGATA
ATTCGGTGCAGATGCGTCGGCCTTATCTGGAACCGCTTAATTACTTACAGGTCGAATTGCTGA
AGAAATGGCGGGGAGGTGATACCAACCCGCATATCCTCGAATCTATTCAGCTGACAATCAATG
CCATTGCGACGGCACTTCGCAACAGCGGTTAATAACTCGAG
```

DNA sequence of the codon optimized PEP carboxylase gene (SEQ ID NO: 21):
```
ACTAGTAAAAAAATGACCAAGCCAAGAACTATTAACCAAAACCCAGACTTGAGATACTTCGGTA
ACTTGTTGGGTCAAGTTATCAAGGAACAAGGTGGTGAATCTTTGTTCAACCAAATTGAACAAAT
CAGATCCGCTGCTATTAGAAGACACAGAGGTATCGTCGACTCTACCGAATTGTCCTCTAGATT
GGCTGACTTGGACTTGAACGACATGTTCTCCTTCGCTCACGCTTTCTTGTTGTTCTCTATGTTG
```

```
GCTAACTTGGCTGACGACAGACAAGGTGACGCTTTGGACCCAGACGCTAACATGGCTTCCGC

TTTGAAGGACATTAAGGCTAAGGGTGTTTCTCAACAAGCTATCATTGACATGATCGACAAGGC

TTGTATTGTCCCAGTTTTGACTGCTCACCCAACCGAAGTCAGAAGAAAGTCCATGTTGGACCA

CTACAACAGAATCGCTGGTTTGATGAGATTGAAGGACGCTGGTCAAACTGTTACCGAAGACG

GTTTGCCAATTGAAGACGCTTTGATCCAACAAATTACTATCTTGTGGCAAACCAGACCATTGAT

GTTGCAAAAGTTGACTGTCGCTGACGAAATTGAAACCGCTTTGTCTTTCTTGAGAGAAACTTTC

TTGCCAGTTTTGCCACAAATCTACGCTGAATGGGAAAAGTTGTTGGGTTCCTCTATTCCATCCT

TCATCAGACCAGGTAACTGGATTGGTGGTGACAGAGACGGTAACCCAAACGTCAACGCTGAC

ACCATCATGTTGTCTTTGAAGAGATCCTCTGAAACTGTTTTGACCGACTACTTGAACAGATTGG

ACAAGTTGTTGTCCAACTTGTCTGTCTCCACTGACATGGTTTCTGTCTCCGACGACATTTTGAG

ATTGGCTGACAAGTCTGGTGACGACGCTGCTATCAGAGCTGACGAACCATACAGAAGAGCTT

TGAACGGTATTTACGACAGATTGGCTGCTACCTACAGACAAATCGCTGGTAGAAACCCATCCA

GACCAGCTTTGAGATCTGCTGAAGCTTACAAGAGACCACAAGAATTGTTGGCTGACTTGAAGA

CTTTGGCTGAAGGTTTGGGTAAGTTGGCTGAAGGTTCCTTCAAGGCTTTGATTAGATCTGTTG

AAACCTTCGGTTTCCACTTGGCTACTTTGGACTTGAGACAAAACTCCCAAGTCCACGAAAGAG

TTGTCAACGAATTGTTGAGAACCGCTACTGTTGAAGCTGACTACTTGTCTTTGTCCGAAGAAG

ACAGAGTCAAGTTGTTGAGAAGAGAATTGTCTCAACCAAGAACCTTGTTCGTTCCAAGAGCTG

ACTACTCCGAAGAAACTAGATCTGAATTGGACATCATTCAAGCTGCTGCTAGAGCTCACGAAA

TCTTCGGTCCAGAATCCATTACCACTTACTTGATCTCTAACGGTGAATCCATTTCTGACATCTT

GGAAGTCTACTTGTTGTTGAAGGAAGCTGGTTTGTACCAAGGTGGTGCTAAGCCAAAGGCTG

CTATTGAAGCTGCTCCATTGTTCGAAACCGTTGCTGACTTGGAAAACGCTCCAAAGGTCATGG

AAGAATGGTTCAAGTTGCCAGAAGCTCAAGCTATCGCTAAGGCTCACGGTGTTCAAGAAGTCA

TGGTTGGTTACTCCGACTCTAACAAGGACGGTGGTTACTTGACTTCCGTCTGGGGTTTGTACA

AGGCTTGTTTGGCTTTGGTTCCAATTTTCGAAAAGGCTGGTGTCCCAATCCAATTCTTCCACG

GTAGAGGTGGTTCTGTTGGTAGAGGTGGTGGTTCCAACTTCAACGCTATTTTGTCTCAACCAG

CTGGTGCTGTCAAGGGTAGAATCAGATACACCGAACAAGGTGAAGTTGTCGCTGCTAAGTAC

GGTACTCACGAATCCGCTATTGCTCACTTGGACGAAGCTGTTGCTGCTACCTTGATCACTTCT

TTGGAAGCTCCAACCATTGTCGAACCAGAATTCTCCAGATACAGAAAGGCTTTGGACCAAATC

TCTGACTCCGCTTTCCAAGCTTACAGACAATTGGTTTACGGTACTAAGGGTTTCAGAAAGTTCT

TCTCTGAATTCACCCCATTGCCAGAAATTGCTTTGTTGAAGATCGGTTCCAGACCACCATCTAG

AAAGAAGTCCGACAGAATTGAAGACTTGAGAGCTATCCCATGGGTCTTCTCTTGGTCCCAAGT

TAGAGTCATGTTGCCAGGTTGGTTCGGTTTCGGTCAAGCTTTGTACGACTTCGAAGACACTGA

ATTGTTGCAAGAAATGGCTTCTAGATGGCCATTCTTCAGAACCACTATTAGAAACATGGAACAA

GTTATGGCTAGATCCGACATGACCATCGCTAAGCACTACTTGGCTTTGGTCGAAGACCAAACT

AACGGTGAAGCTATTTACGACTCTATCGCTGACGGTTGGAACAAGGGTTGTGAAGGTTTGTTG

AAGGCTACCCAACAAAACTGGTTGTTGGAAAGATTCCCAGCTGTTGACAACTCCGTCCAAATG

AGAAGACCATACTTGGAACCATTGAACTACTTGCAAGTTGAATTGTTGAAGAAGTGGAGAGGT

GGTGACACTAACCCACACATTTTGGAATCTATCCAATTGACCATTAACGCTATCGCTACTGCTT

TGAGAAACTCCGGTTAATAACTCGAG
```

Example 4

Production of Pentose Sugar Utilizing Yeast Cells

The full length gene encoding the enzyme xylose isomerase from *Ruminococcus flavefaciens* strain 17 (also known as *Ruminococcus flavefaciens* strain Siijpesteijn 1948) with a substitution at position 513 (in which cytidine was replaced by guanidine) was synthesized by Integrated DNA Technologies, Inc. ("IDT", Coralville, Iowa; http address at world wide web uniform resource locator idtdna-.com). The sequence of this gene is set forth below as SEQ ID NO:22.

```
                                              SEQ ID NO: 22
atggaattttcagcaatatcggtaaaattcagtatcagggaccaaaaa gtactgatcctctctcatttaagtactataaccctgaagaagtcatcaa cggaaagacaatgcgcgagcatctgaagttcgctcttcatggtggcac acaatgggcggcgacggaacagatatgttcggctgcggcacaacagac aagacctggggacagtccgatcccgctgcaagagcaaaggctaaggtt gacgcagcattcgagatcatggataagctctccattgactactattgtt tccacgatcgcgatctttctcccgagtatggcagcctcaaggctacc aacgatcagcttgacatagttacagactatatcaaggagaagcag ggcgacaagttcaagtgcctctggggtacagcaaagtgcttcgat catccaagattcatgcacggtgcaggtacatctccttctgctgatgta ttcgctttctcagctgctcagatcaagaaggctctGgagtcaacag taaagctcggcggtaacggttacgttttctggggcggacgtgaag gctatgagacacttcttaatacaaatgggactcgaactcgacaat atggctcgtcttatgaagatggctgttgagtatggacgttcgatcggct tcaagggcgacttctatatcgagcccaagcccaaggagcccaca aagcatcagtacgatttcgatacagctactgttctgggattcctcaga aagtacggtctcgataaggatttcaagatgaatatcgaagctaacc acgctacacttgctcagcatacattccagcatgagctccgtgttgca agagacaatggtgtgttcggttctatcgacgcaaaccagggcgac gttcttcttggatgggatacagaccagttccccacaaatatctacgat acaacaatgtgtatgtatgaagttatcaaggcaggcggcttcacaa acggcggtctcaacttcgacgctaaggcacgcagagggagcttc actcccgaggatatcttctacagctatatcgcaggtatggatgcattt gctctgggcttcagagctgctctcaagcttatcgaagacggacgta tcgacaagttcgttgctgacagatacgcttcatggaataccggtatc ggtgcagacataatcgcaggtaaggcagatttcgcatctcttgaaa agtatgctcttgaaaagggcgaggttacagcttcactctcaagcgg cagacaggaaatgctggagtctatcgtaaataacgttcttttcagtct gtaa
```

Separately, PCR was conducted to add a DNA sequence encoding 6 histidines (SEQ ID NO: 35) to the 3' terminus of this gene.

Two variants designed to remove the translational pauses in the gene were prepared using the DNA self-assembly method of Larsen et al., supra. One variant contained DNA sequence encoding a 6-histidine tag (SEQ ID NO: 35) at the 5' terminus, and the other version did not. The annealing temperature for the self assembly reactions was about 48 degrees Celsius. This gene variant is referred to as a "Hot Rod" or "HR" gene variant. The sequence of this HR gene is set forth below as SEQ ID NO: 23:

```
                                              SEQ ID NO: 23
ATGGAGTTCTTTTCTAATATAGGTAAAATTCAGTATCAAGGTCCAAAATC

TACAGATCCATTGTCTTTTAAATATTATAATCCAGAAGAAGTTATAAATG

GTAAAACTATGAGAGAACATTTAAAATTTGCTTTGTCTTGGTGGCATACT

ATGGGTGGTGATGGTACTGATATGTTCGGTTGTGGTACTACTGATAAAAC

TTGGGGTCAATCTGATCCAGCTGCTAGAGCAAAAGCCAAAGTAGATGCAG

CCTTTGAAATTATGGATAAATTGTCTATTGATTATTATTGTTTTCATGAT

AGAGATTTGTCTCCTGAATATGGTTCTTTAAAAGCAACTAATGATCAATT

GGACATTGTTACGGATTATATTAAAGAAAAACAAGGTGATAAATTTAAAT

GTTTGTGGGGCACTGCGAAATGTTTTGATCATCCACGTTTTATGCATGGT

GCGGGGACGAGTCCTTCTGCTGATGTTTTTGCTTTTTCTGCCGCTCAAAT

TAAGAAGGCATTGGAATCAACTGTTAAATTAGGTGGGAACGGGTATGTAT

TCTGGGAGGAAGGGAAGGTTATGAAACATTATTAAACACTAATATGGGT

TTGGAATTGGATAATATGGCTAGATTGATGAAAATGGCTGTAGAATACGG

AAGGTCTATTGGTTTTAAGGGTGACTTTTATATTGAACCAAAACCTAAAG

AGCCTACTAAACATCAATATGATTTTGATACTGCTACAGTTTTGGGATTC

TTGAGAAAATATGGTCTGGATAAAGATTTTAAAATGAATATAGAAGCTAA

TCATGCAACACTCGCACAACATACTTTTCAACATGAATTGAGAGTTGCCA

GAGATAACGGAGTTTTTGGATCTATCGATGCAAACCAGGGAGACGTTTTG

CTAGGATGGGATACTGATCAATTTCCAACTAACATTTATGATACTACTAT

GTGTATGTATGAAGTAATTAAGGCAGGAGGCTTTACTAATGGCGGATTAA

ACTTTGATGCGAAGGCTAGGCGTGGTAGTTTCACTCCAGAGGATATATTC

TATTCTTATATTGCTGGAATGGATGCTTTCGCGTTAGGTTTCAGGGCAGC

ACTAAAATTGATTGAAGATGGTAGAATTGATAAGTTTGTAGCTGATAGAT

ATGCTTCTTGGAATACTGGAATAGGAGCAGATATAATCGCTGGGAAAGCC

GACTTCGCCAGTCTGGAAAAATATGCGCTTGAAAAAGGAGAAGTTACTGC

CAGCTTAAGTTCCGGTCGTCAAGAAATGTTGGAATCTATTGTAAACAATG

TTTTATTTTCTCTG
```

For cloning purposes, PCR was used to engineer a unique SpeI restriction site into the 5' end of each of the xylose isomerase genes, and to engineer a unique XhoI restriction site at the 3' end. In addition, a version of each gene was created that contained a 6-HIS tag (SEQ ID NO: 35) at the 3' end of each gene to enable detection of the proteins using Western analysis.

PCR amplifications were performed in about 50 μl reactions containing 1×PfuII Ultra reaction buffer (Stratagene, San Diego, Calif.), 0.2 mM dNTPs, 0.2 μM specific 5' and 3' primers, and 1 U PfuUltra II polymerase (Stratagene, San Diego, Calif.). The reactions were cycled at 95° C. for 10 minutes, followed by 30 rounds of amplification (95° C. for 30 seconds, 62° C. for 30 seconds, 72° C. for 30 seconds) and a final extension incubation at 72° C. for 5 minutes. Amplified PCR products were cloned into pCR Blunt II TOPO (Life Sciences, Carlsbad, Calif.) and confirmed by sequencing (GeneWiz, La Jolla, Calif.). The PCR primers for these reactions were:

```
                                                   (SEQ ID NO: 26)
5'ACTTGACTACTAGTATGGAGTTCTTTTCTAATATAGGTAAAATT
3' (without the His tag):
                                                   (SEQ ID NO: 27)
AGTCAAGTCTCGAGCAGAGAAAATAAAACATTGTTTACAATAGA 3' (with the His tag):
                                                   (SEQ ID NO: 28)
AGTCAAGTCTCGAGCTAATGATGATGATGATGCAGAGAAAATAAA
ACATTGTTTAC
```

Separately, the xylose isomerase gene from *Piromyces*, strain E2 (Harhangi et al., *Arch. Microbiol.*, 180(2): 134-141 (2003)) was synthesized by IDT. The sequence of this gene is set forth below as SEQ ID NO: 24.

```
   1 atggctaagg aatatttccc acaaattcaa aagattaagt tcgaaggtaa ggattctaag
  61 aatccattag ccttccacta ctacgatgct gaaaaggaag tcatgggtaa gaaaatgaag
 121 gattggttac gtttcgccat ggcctggtgg cacactcttt gcgccgaagg tgctgaccaa
 181 ttcggtggag gtacaaagtc tttcccatgg aacgaaggta ctgatgctat tgaaattgcc
 241 aagcaaaagg ttgatgctgg tttcgaaatc atgcaaaagc ttggtattcc atactactgt
 301 ttccacgatg ttgatcttgt ttccgaaggt aactctattg aagaatacga atccaacctt
 361 aaggctgtcg ttgcttacct caaggaaaag caaaaggaaa ccggtattaa gcttctctgg
 421 agtactgcta acgtcttcgg tcacaagcgt tacatgaacg gtgcctccac taacccagac
 481 tttgatgttg tcgcccgtgc tattgttcaa attaagaacg ccatagacgc cggtattgaa
 541 cttggtgctg aaaactacgt cttctggggt ggtcgtgaag gttacatgag tctccttaac
 601 actgaccaaa agcgtgaaaa ggaacacatg gccactatgc ttaccatggc tcgtgactac
 661 gctcgttcca agggattcaa gggtactttc ctcattgaac aaagccaat ggaaccaacc
 721 aagcaccaat acgatgttga cactgaaacc gctattggtt tccttaaggc ccacaactta
 781 gacaaggact tcaaggtcaa cattgaagtt aaccacgcta ctcttgctgg tcacactttc
 841 gaacacgaac ttgcctgtgc tgttgatgct ggtatgctcg gttccattga tgctaaccgt
 901 ggtgactacc aaaacggttg ggatactgat caattcccaa ttgatcaata cgaactcgtc
 961 caagcttgga tggaaatcat ccgtggtggt ggtttcgtta ctggtggtac caacttcgat
1021 gccaagactc gtcgtaactc tactgacctc gaagacatca tcattgccca cgtttctggt
1081 atggatgcta tggctcgtgc tcttgaaaac gctgccaagc tcctccaaga atctccatac
1141 accaagatga agaaggaacg ttacgcttcc ttcgacagtg gtattggtaa ggactttgaa
1201 gatggtaagc tcaccctcga acaagtttac gaatacggta agaagaacgg tgaaccaaag
1261 caaacttctg gtaagcaaga actctacgaa gctattgttg ccatgtacca ataa
```

Two hot rod ("HR") versions of the *Piromyces xylose* isomerase gene were prepared using the method of Larsen et al., supra. One version contained DNA sequence encoding a 6-histidine tag (SEQ ID NO: 35) at the 5' terminus and the other did not. The annealing temperature for the self-assembling oligonucleotides was about 48 degrees Celsius. The sequence of this gene is set forth below as SEQ ID NO: 25.
```
ATGGCTAAAGAATATTTTCCACAAATTCAGAAAATTAAATTTGAAGGTAAAGATTCTAAAAATCCATTGGCTTTCCATTA

TTATGATGCTGAAAAAGAAGTTATGGGTAAAAAGATGAAAGATTGGTTGAGATTCGCTATGGCTTGGTGGCATACTCTAT

GTGCTGAAGGAGCTGATCAATTTGGAGGAGGTACTAAATCTTTTCCTTGGAATGAAGGTACTGACGCTATTGAAATTGCT

AAGCAGAAAGTAGACGCGGGTTTTGAAATTATGCAAAAATTGGGAATACCATATTATTGTTTTCATGATGTTGATTTGGT

ATCTGAGGGTAATTCTATTGAAGAATATGAATCTAATTTAAAAGCTGTTGTTGCTTACTTAAAAGAAAAACAAAAGAAA

CTGGAATTAAATTGTTGTGGTCTACAGCTAATGTTTTCGGTCATAAAAGATATATGAATGGTGCTTCTACAAATCCAGAT

TTTGATGTTGTAGCTAGAGCTATTGTTCAAATTAAAAATGCTATAGATGCAGGAATTGAATTAGGTGCCGAAAATTATGT

TTTCTGGGGAGGTAGAGAAGGTTATATGTCTTTGTTAAATACTGATCAAAAACGTGAAAAGGAACACATGGCAACTATGT

TGACAATGGCTAGGGATTATGCTAGATCTAAAGGTTTTAAAGGTACTTTCTTGATTGAGCCAAAACCTATGGAACCAACT

AAACATCAATATGACGTTGACACTGAAACTGCTATTGGTTTCTTAAAAGCTCATAATTTGGATAAAGATTTTAAGGTTAA

TATAGAAGTTAATCATGCTACACTAGCTGGTCATACTTTTGAACATGAATTAGCTTGTGCAGTTGATGCCGGTATGTTAG

GTTCTATCGACGCAAATAGAGGTGATTATCAAATGGTTGGGACACAGATCAATTTCCAATAGATCAATATGAATTGGTT

CAAGCATGGATGGAAATTATTAGGGGTGGAGGCTTCGTTACAGGTGGAACTAATTTTGATGCTAAAACTAGGAGAAATTC

TACAGATCTTGAAGATATAATTATTGCTCATGTATCTGGTATGGATGCGATGGCCCGTGCTTTGGAAAATGCAGCTAAAT

TACTTCAAGAATCTCCTTATACTAAAATGAAAAAGGAAAGATATGCTTCTTTTGATTCTGGAATAGGTAAGGATTTTGAA

GATGGTAAATTGACATTGGAACAAGTTTATGAATATGGTAAGAAGAATGGAGAACCAAAACAAACTTCTGGTAAACAAGA

ATTATATGAGGCTATAGTAGCTATGTATCAAtaa
```

For cloning purposes, a unique SpeI restriction site was engineered at the 5' end of each of the XI genes, and a unique XhoI restriction site was engineered at the 3' end. When needed, a 6-HIS tag (SEQ ID NO: 35) was engineered at the 3' end of each gene sequence to enable detection of the proteins using Western analysis. The primers are listed in Table X. PCR amplifications were performed in 50 μl reactions containing 1×PfuII Ultra reaction buffer (Stratagene, San Diego, Calif.), 0.2 mM dNTPs, 0.2 μM specific 5' and 3' primers, and 1 U PfuUltra II polymerase (Stratagene, San Diego, Calif.). The reactions were cycled at 95° C. for 10 minutes, followed by 30 rounds of amplification (95° C. for 30 seconds, 62° C. for 30 seconds, 72° C. for 30 seconds) and a final extension incubation at 72° C. for 5 minutes. Amplified PCR products were cloned into pCR Blunt II TOPO (Life Sciences, Carlsbad, Calif.) and confirmed by sequencing (GeneWiz).

The primers used for PCR were:

5' (native gene)
(SEQ ID NO: 46)
ACTAGTATGGCTAAGGAATATTTCCCACAAATTCAAAAG

3' (native gene)
(SEQ ID NO: 47)
CTCGAGCTACTATTGGTACATGGCAACAATAGC

3' (native gene plus His tag)
(SEQ ID NO: 48)
CTCGAGCTACTAATGATGATGATGATGATGTTGGTACATGGCAACAAT

AGCTTCG

5' (hot rod gene)
(SEQ ID NO: 49)
ACTAGTATGGCTAAAGAATATTTTCCACAAATTCAG

3' (hot rod gene)
(SEQ ID NO: 50)
CTCGAGTTATTGATACATAGCTACTATAGCCTC

3' (hot rod gene plus His tag)
(SEQ ID NO: 51)
CTCGAGTTAATGATGATGATGATGATGTTGATACATAGCTACTATAGCC

TCATTGTTTAC

The genes encoding the native and HR versions of xylose isomerase were separately inserted into the vector p426GDP (ATCC catalog number 87361).

*Saccharomyces cerevisiae* strain BY4742 cells (ATCC catalog number 201389) were cultured in YPD media (10 g Yeast Extract, 20 g Bacto-Peptone, 20 g Glucose, 1 L total) at about 30° C. Separate aliquots of the cells were transformed with the plasmid constructs containing the various xylose isomerase constructs or with the vector alone. Transformation was accomplished using the Zymo kit (Catalog number T2001; Zymo Research Corp., Orange, Calif. 92867) using about 1 μg plasmid DNA and cultured on SC media (set forth below) containing glucose but no uracil (20 g glucose; 2.21 g SC dry mix, 6.7 g Yeast Nitrogen Base, 1 L total) for 2-3 days at about 30° C.

Synthetic Complete Medium mix (minus uracil) contained:

| | |
|---|---|
| 0.4 g | Adenine hemisulfate |
| 3.5 g | Arginine |
| 1 g | Glutamic Acid |
| 0.433 g | Histidine |
| 0.4 g | Myo-Inositol |
| 5.2 g | Isoleucine |
| 2.63 g | Leucine |
| 0.9 g | Lysine |

-continued

| 1.5 g | Methionine |
| 0.8 g | Phenylalanine |
| 1.1 g | Serine |
| 1.2 g | Threonine |
| 0.8 g | Tryptophan |
| 0.2 g | Tyrosine |
| 1.2 g | Valine |

Figure 7:
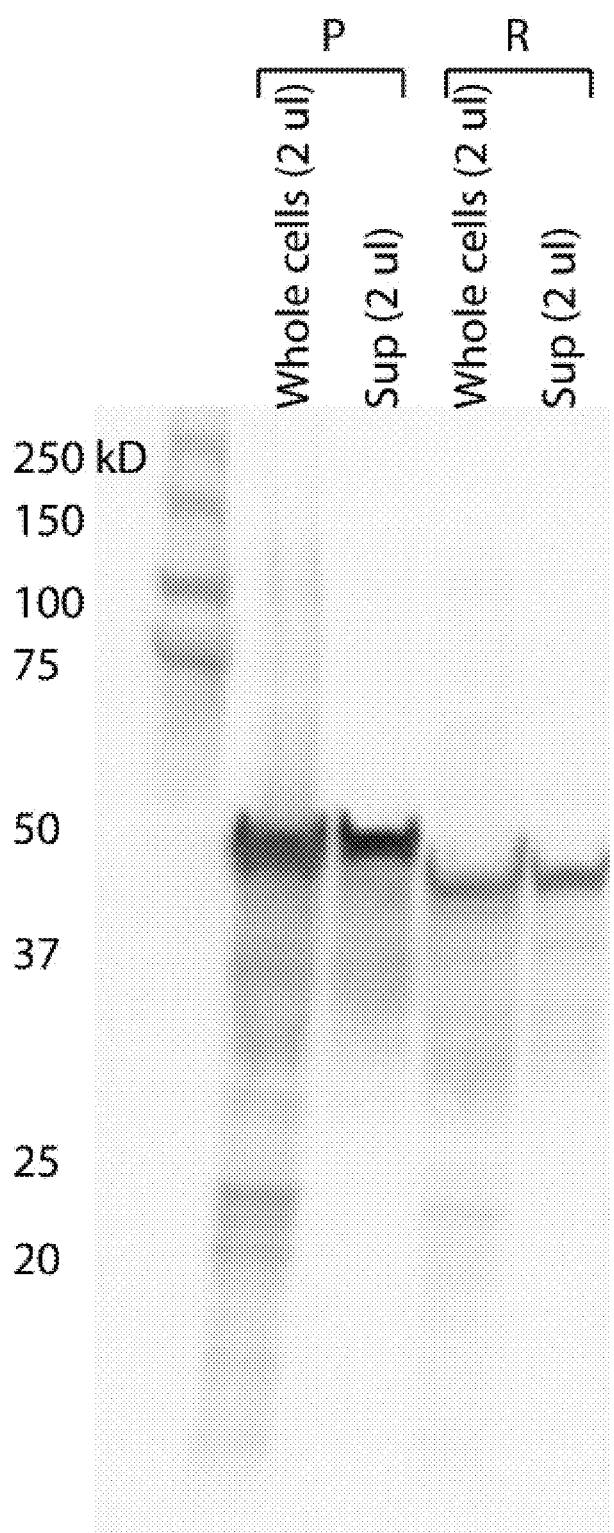
FIG. 7 shows a representative western blot used to detect the presence of an enzyme associated with an activity described herein.

For expression and activity analysis, transformed cells containing the various xylose isomerase constructs were selected from the cultures and grown in about 100 ml of SC-Dextrose (minus uracil) to an $OD_{600}$ of about 4.0. The *S. cerevisiae* cultures that were transformed with the various xylose isomerase-histidine constructs were then lysed using YPER-Plus reagent (Thermo Scientific, catalog number 78999) according to the manufacturer's directions. Protein quantitation of the lysates was performed using the Coomassie-Plus kit (Thermo Scientific, catalog number 23236) as directed by the manufacturer. Denaturing and native Western blot analyses were then conducted. To detect his-tagged xylose isomerase polypeptides Western analysis was employed. Gels were transferred onto a nitrocellulose membrane (0.45 micron, Thermo Scientific, San Diego, Calif.) using Western blotting filter paper (Thermo Scientific) using a Bio-Rad Mini Trans-Blot Cell (BioRad, Hercules, Calif.) system for approximately 90 minutes at 40V. Following transfer, the membrane was washed in 1×PBS (EMD, San Diego, Calif.), 0.05% Tween-20 (Fisher Scientific, Fairlawn, N.J.) for 2-5 minutes with gentle shaking. The membrane was blocked in 3% BSA dissolved in 1×PBS and 0.05% Tween-20 at room temperature for about 2 hours with gentle shaking. The membrane was washed once in 1×PBS and 0.05% Tween-20 for about 5 minutes with gentle shaking. The membrane was then incubated at room temperature with the 1:5000 dilution of primary antibody (Ms mAB to 6× His Tag (SEQ ID NO: 35), AbCam, Cambridge, Mass.) in 0.3% BSA (Fraction V, EMD, San Diego, Calif.) dissolved in 1×PBS and 0.05% Tween-20 with gentle shaking. Incubation was allowed to proceed for about 1 hour with gentle shaking. The membrane was then washed three times for 5 minutes each with 1×PBS and 0.05% Tween-20 with gentle shaking. The secondary antibody [Dnk pAb to Ms IgG (HRP), AbCam, Cambridge, Mass.] was used at 1:15000 dilution in 0.3% BSA and allowed to incubate for about 90 minutes at room temperature with gentle shaking. The membrane was washed three times for about 5 minutes using 1×PBS and 0.05% Tween-20 with gentle shaking. The membrane was then incubated with 5 ml of Supersignal West Pico Chemiluminescent substrate (Thermo Scientific, San Diego, Calif.) for 1 minute and then was exposed to a phosphorimager (Bio-Rad Universal Hood II, Bio-Rad, Hercules, Calif.) for about 10-100 seconds. The results are shown in FIG. 7. As can be seen, both *Piromyces* ("P" in FIG. 7) and *Ruminococcus* ("R" in FIG. 7) xylose isomerases are expressed in both the soluble and insoluble fractions of the yeast cells.

To measure activity of the various xylose isomerase constructs, assays were performed according to Kuyper et al. (*FEMS Yeast Res.*, 4:69 [2003]). About 20 μg of soluble whole cell extract was incubated in the presence of 100 mM Tris, pH 7.5, 10 mM $MgCl_2$, 0.15 mM NADH (Sigma, St. Louis, Mo.), and about 2 U sorbitol dehydrogenase (Roche) at about 30° C. To start the reaction, about 100 μl of xylose was added at various final concentrations of 40-500 mM. A Beckman DU-800 was utilized with an Enzyme Mechanism software package (Beckman Coulter, Inc.), and the change in the $A_{340}$ was monitored for 2-3 minutes.

Example 5

Preparation of Selective Growth Yeast

The yeast gene cdc21 encodes thymidylate synthase, which is required for de novo synthesis of pyrimidine deoxyribonucleotides. A cdc 21 mutant, strain 17206, (ATCC accession number 208583) has a point mutation G139S relative to the initiating methionine. The restrictive temperature of this temperature sensitive mutant is 37° C., which arrests cell division at S phase, so that little or no cell growth and division occurs at or above this temperature.

*Saccharomyces cerevisiae* strain YGR420CBY4742ΔPFK2 was used as the starting cell line to create the cdc21 growth sensitive mutant. A construct for homologous recombination was prepared to replace the wild type thymidylate synthase YGR420CBY4742ΔPFK2 for the cdc21 mutant. This construct was made in various steps. First, the cdc21 mutant region from *Saccharomyces cerevisiae* strain 17206 was PCR amplified using the following primers:

```
                                        (SEQ ID NO: 52)
CDC21_fwd: 5'-aatcgatcaaagcttctaaatacaagacgtgcga tgacgactatactggac-3'
                                        (SEQ ID NO: 53)
CDC21_rev: 5'-taccgtactacccgggtatatagtcttttttgccct ggtgttccttaataatttc-3'
```

For this PCR amplification reaction *Saccharomyces cerevisiae* 17206 genomic DNA was used. The genomic DNA was extracted using Zymo research YeaStar Genomic DNA kit according to instructions. In the PCR amplification reaction 100 ng of 17206 genomic DNA, 1 μM of the oligonucleotide primer set listed above, 2.5 U of PfuUltra High-Fidelity DNA polymerase (Stratagene), 300 μM dNTPs (Roche), and 1×PfuUltra reaction buffer was mixed in a final reaction volume of 50 μl. Using a BIORAD DNA Engine Tetrad 2 Peltier thermal cycler the following cycle conditions were used: 5 min denaturation step at 95° C., followed by 30 cycles of 20 sec at 95° C., 20 sec at 50° C., and 1 min at 72° C., and a final step of 5 min at 72° C. This PCR product was digested with HindIII and XmaI restriction endonucleases and cloned in the HindIII and XmaI sites of PUC19 (NEB) according to standard cloning procedures described by Maniatis in Molecular Cloning.

The genomic DNA of BR214-4a (ATTC accession number 208600) was extracted using Zymo research YeaStar Genomic DNA kit according to instructions. The lys2 gene with promoter and terminator regions was PCR amplified from BR214-4a genomic DNA using the following primers:
Lys2Fwd: 5'-tgctaatgacccgggaattccacttgcaattaca taaaaattc-cggcgg-3' (SEQ ID NO: 54)
Lys2Rev: 5'-atgatcattgagctcagcttcgcaagtattcatttta gacccatg-gtgg-3'. (SEQ ID NO: 55)

The PCR cycle was identical to that just described above but with genomic DNA of BR214-4a instead. XmaI and SacI restriction sites were designed to flank this DNA construct to clone it into the XmaI and SacI sites of the PUC19-cdc21 vector according to standard cloning procedures described by Maniatis in Molecular Cloning. The new construct with the cdc21 mutation with a lys2 directly downstream of that will be referred to as PUC19-cdc21-lys2.

The final step involved the cloning of the downstream region of thymidylate synthase into the PUC19-cdc21-lys2 vector immediately downstream of the lys2 gene. The downstream region of the thymidylate synthase was amplified from BY4742 genomic DNA (ATCC accession number 201389D-5 using the following primers:

(SEQ ID NO: 56)
ThymidylateSynthase_DownFwd: 5'-tgctaatgagagctctc atttttggtgcgatatgtttttggttgatg-3'
and (SEQ ID NO: 57)
ThymidylateSynthatse_DownRev: 5'-aatgatcatgagctcg tcaacaagaactaaaaaattgttcaaaaatgc-3'.

This final construct is referred as PUC19-cdc21-lys2-ThymidylateSynthase_down. The sequence is set forth in the tables. A final PCR amplification reaction of this construct was performed using the following PCR primers:

(SEQ ID NO: 58)
ThymidylateSynthase::cdc21 fwd: 5'-ctaaatacaagacg tgcgatgacgactatactgg-3'
and (SEQ ID NO: 59)
ThymidylateSynthase::cdc21 rev: 5'-gtcaacaagaacta aaaaattgttcaaaaatgcaattgtc-3'.

The PCR reaction was identical to that described above but using 100 ng of the PUC19-cdc2'-lys2-ThymidylateSynthase_down construct as a template.

The final PCR product was separated by agarose gel electrophoresis, excised, and purified using MP Biomedicals Geneclean II kit as recommended. Homologous recombination of YGR420CBY4742ΔPFK2 to replace the wt thymidylate synthase for the cdc21 mutant was accomplished using 10 µg of the purified PCR product to transform YGR420CBY4742ΔPFK2 strain using same transformation protocol described above. Transformants were selected by culturing the cells on selective media containing SC-Ethanol (0.67% yeast nitrogen base-2% ethanol) containing complete amino acids minus lysine.

The genome of this final engineered strain contains the mutated cdc21 gene, and has both the PFK1 and PFK2 genes deleted. This final engineered strain will be transformed with the best combination of edd-p426 GPD and eda-p425 GPD variant constructs. Ethanol and glucose measurements will be monitored during aerobic and anaerobic growth conditions using Roche ethanol and glucose kits according to instructions.

Example 6

Examples of Polynucleotide Regulators

Provided in the tables hereafter are non-limiting examples of regulator polynucleotides that can be utilized in embodiments herein. Such polynucleotides may be utilized in native form or may be modified for use herein. Examples of regulatory polynucleotides include those that are regulated by oxygen levels in a system (e.g., up-regulated or down-regulated by relatively high oxygen levels or relatively low oxygen levels)

Regulated Yeast Promoters—Up-Regulated by Oxygen

| ORF name | Gene name | Relative mRNA level (Aerobic) | Relative mRNA level (Anaerobic) | Ratio |
|---|---|---|---|---|
| YPL275W | | 4389 | 30 | 219.5 |
| YPL276W | | 2368 | 30 | 118.4 |
| YDR256C | CTA1 | 2076 | 30 | 103.8 |
| YHR096C | HXT5 | 1846 | 30 | 72.4 |
| YDL218W | | 1189 | 30 | 59.4 |
| YCR010C | | 1489 | 30 | 48.8 |
| YOR161C | | 599 | 30 | 29.9 |
| YPL200W | | 589 | 30 | 29.5 |
| YGR110W | | 1497 | 30 | 27 |
| YNL237W | YTP1 | 505 | 30 | 25.2 |
| YBR116C | | 458 | 30 | 22.9 |
| YOR348C | PUT4 | 451 | 30 | 22.6 |
| YBR117C | TKL2 | 418 | 30 | 20.9 |
| YLL052C | | 635 | 30 | 20 |
| YNL195C | | 1578 | 30 | 19.4 |
| YPR193C | | 697 | 30 | 15.7 |
| YDL222C | | 301 | 30 | 15 |
| YNL335W | | 294 | 30 | 14.6 |
| YPL036W | PMA2 | 487 | 30 | 12.8 |
| YML122C | | 206 | 30 | 10.3 |
| YGR067C | | 236 | 30 | 10.2 |
| YPR192W | | 204 | 30 | 10.2 |
| YNL014W | | 828 | 30 | 9.8 |
| YFL061W | | 256 | 30 | 9.1 |
| YNR056C | | 163 | 30 | 8.1 |
| YOR186W | | 153 | 30 | 7.6 |
| YDR222W | | 196 | 30 | 6.5 |
| YOR338W | | 240 | 30 | 6.3 |
| YPR200C | | 113 | 30 | 5.7 |
| YMR018W | | 778 | 30 | 5.2 |
| YOR364W | | 123 | 30 | 5.1 |
| YNL234W | | 93 | 30 | 4.7 |
| YNR064C | | 85 | 30 | 4.2 |
| YGR213C | RTA1 | 104 | 30 | 4 |
| YCL064C | CHA1 | 80 | 30 | 4 |
| YOL154W | | 302 | 30 | 3.9 |
| YPR150W | | 79 | 30 | 3.9 |
| YPR196W | MAL63 | 30 | 30 | 3.6 |
| YDR420W | HKR1 | 221 | 30 | 3.5 |
| YJL216C | | 115 | 30 | 3.5 |
| YNL270C | ALP1 | 67 | 30 | 3.3 |
| YHL016C | DUR3 | 224 | 30 | 3.2 |
| YOL131W | | 230 | 30 | 3 |
| YOR077W | RTS2 | 210 | 30 | 3 |
| YDR536W | STL1 | 55 | 30 | 2.7 |
| YNL150W | | 78 | 30 | 2.6 |
| YHR212C | | 149 | 30 | 2.4 |
| YJL108C | | 106 | 30 | 2.4 |
| YGR069W | | 49 | 30 | 2.4 |
| YDR106W | | 60 | 30 | 2.3 |
| YNR034W | SOL1 | 197 | 30 | 2.2 |
| YEL073C | | 104 | 30 | 2.1 |
| YOL141W | | 81 | 30 | 1.8 |

Regulated Yeast Promoters—Down-Regulated by Oxygen

| ORF name | Gene name | Relative mRNA level (Aerobic) | Relative mRNA level (Anaerobic) | Ratio |
|---|---|---|---|---|
| YJR047C | ANB1 | 30 | 4901 | 231.1 |
| YMR319C | FET4 | 30 | 1159 | 58 |
| YPR194C | | 30 | 982 | 49.1 |
| YIR019C | STA1 | 30 | 981 | 22.8 |
| YHL042W | | 30 | 608 | 12 |
| YHR210C | | 30 | 552 | 27.6 |
| YHR079B | SAE3 | 30 | 401 | 2.7 |
| YGL162W | STO1 | 30 | 371 | 9.6 |
| YHL044W | | 30 | 334 | 16.7 |
| YOL015W | | 30 | 320 | 6.1 |

| ORF name | Gene name | Relative mRNA level (Aerobic) | Relative mRNA level (Anaerobic) | Ratio |
|---|---|---|---|---|
| YCLX07W |  | 30 | 292 | 4.2 |
| YIL013C | PDR11 | 30 | 266 | 10.6 |
| YDR046C |  | 30 | 263 | 13.2 |
| YBR040W | FIG1 | 30 | 257 | 12.8 |
| YLR040C |  | 30 | 234 | 2.9 |
| YOR255W |  | 30 | 231 | 11.6 |
| YOL014W |  | 30 | 229 | 11.4 |
| YAR028W |  | 30 | 212 | 7.5 |
| YER089C |  | 30 | 201 | 6.2 |
| YFL012W |  | 30 | 193 | 9.7 |
| YDR539W |  | 30 | 187 | 3.4 |
| YHL043W |  | 30 | 179 | 8.9 |
| YJR162C |  | 30 | 173 | 6 |
| YMR165C | SMP2 | 30 | 147 | 3.5 |
| YER106W |  | 30 | 145 | 7.3 |
| YDR541C |  | 30 | 140 | 7 |
| YCRX07W |  | 30 | 138 | 3.3 |
| YHR048W |  | 30 | 137 | 6.9 |
| YCL021W |  | 30 | 136 | 6.8 |
| YOL160W |  | 30 | 136 | 6.8 |
| YCRX08W |  | 30 | 132 | 6.6 |
| YMR057C |  | 30 | 109 | 5.5 |
| YDR540C |  | 30 | 83 | 4.2 |
| YOR378W |  | 30 | 78 | 3.9 |
| YBR085W | AAC3 | 45 | 1281 | 28.3 |
| YER188W |  | 47 | 746 | 15.8 |
| YLL065W | GIN11 | 50 | 175 | 3.5 |
| YDL241W |  | 58 | 645 | 11.1 |
| YBR238C |  | 59 | 274 | 4.6 |
| YCR048W | ARE1 | 60 | 527 | 8.7 |
| YOL165C |  | 60 | 306 | 5.1 |
| YNR075W |  | 60 | 251 | 4.2 |
| YJL213W |  | 60 | 250 | 4.2 |
| YPL265W | DIP5 | 61 | 772 | 12.7 |
| YDL093W | PMT5 | 62 | 353 | 5.7 |
| YKR034W | DAL80 | 63 | 345 | 5.4 |
| YKR053C |  | 66 | 1268 | 19.3 |
| YJR147W |  | 68 | 281 | 4.1 |

Known and Putative DNA Binding Motifs

| Regulator | Known Consensus Motif | SEQ ID NO: |
|---|---|---|
| Abf1 | TCRNNNNNNACG | 60 |
| Cbf1 | RTCACRTG |  |
| Gal4 | CGGNNNNNNNNNNNNCCG | 61 |
| Gcn4 | TGACTCA |  |
| Gcr1 | CTTCC |  |
| Hap2 | CCAATNA |  |
| Hap3 | CCAATNA |  |
| Hap4 | CCAATNA |  |
| Hsf1 | GAANNTTCNNGAA | 62 |
| Ino2 | ATGTGAAA |  |
| Mata(A1) | TGATGTANNT | 93 |
| Mcm1 | CCNNNWWRGG | 94 |
| Mig1 | WWWWSYGGGG | 95 |
| Pho4 | CACGTG |  |
| Rap1 | RMACCCANNCAYY | 96 |
| Reb1 | CGGGTRR |  |
| Ste12 | TGAAACA |  |
| Swi4 | CACGAAA |  |
| Swi6 | CACGAAA |  |
| Yap1 | TTACTAA |  |

| Putative DNA Binding Motifs Regulator | Best Motif (scored by E-value) | SEQ ID NO: | Best Motif (scored by Hypergeometric) | SEQ ID NO: |
|---|---|---|---|---|
| Abf1 | TYCGT--R-ARTGAYA | 97 | TYCGT--R-ARTGAYA | 210 |
| Ace2 | RRRAARARAA-A-RARAA | 98 | GTGTGTGTGTGTGTG | 211 |

| | | | | | |
|---|---|---|---|---|---|
| Adr1 | A-AG-GAGAGAG-GGCAG | 99 | YTSTYSTT-TTGYTWTT | 212 | |
| Arg80 | T--CCW-TTTKTTTC | 100 | GCATGACCATCCACG | 213 | |
| Arg81 | AAAAARARAAAARMA | 101 | GSGAYARMGGAMAAAAA | 214 | |
| Aro80 | YKYTYTTYTT----KY | 102 | TRCCGAGRYW-SSSGCGS | 215 | |
| Ash1 | CGTCCGGCGC | 103 | CGTCCGGCGC | 216 | |
| Azf1 | GAAAAAGMAAAAAAA | 104 | AARWTSGARG-A--CSAA | 217 | |
| Bas1 | TTTTYYTTYTTKY-TY-T | 105 | CS-CCAATGK--CS | 218 | |
| Cad1 | CATKYTTTTTKYTY | 106 | GCT-ACTAAT | 219 | |
| Cbf1 | CACGTGACYA | 107 | CACGTGACYA | 220 | |
| Cha4 | CA---ACACASA-A | 108 | CAYAMRTGY-C | 221 | |
| Cin5 | none | | none | | |
| Crz1 | GG-A-A--AR-ARGGC- | 109 | TSGYGRGASA | 222 | |
| Cup9 | TTTKYTKTTY-YTTTKTY | 110 | K-C-C---SCGCTACKGC | 223 | |
| Dal81 | WTTKTTTTYTTTTT-T | 111 | SR-GGCMCGGC-SSG | 224 | |
| Dal82 | TTKTTTTYTTC | 112 | TACYACA-CACAWGA | 225 | |
| Dig1 | AAA--RAA-GARRAA-AR | 132 | CCYTG-AYTTCW-CTTC | 226 | |
| Dot6 | GTGMAK-MGRA-G-G | 133 | GTGMAK-MGRA-G-G | 227 | |
| Fhl1 | -TTWACAYCCRTACAY-Y | 134 | -TTWACAYCCRTACAY-Y | 228 | |
| Fkh1 | TTT-CTTTKYTT-YTTTT | 135 | AAW-RTAAAYARG | 229 | |
| Fkh2 | AAAARA-RAAA-AAAR-AA | 136 | GG-AAWA-GTAAACAA | 230 | |
| Fzf1 | CACACACACACACAC | 137 | SASTKCWCTCKTCGT | 231 | |
| Gal4 | TTGCTTGAACGSATGCCA | 138 | TTGCTTGAACGSATGCCA | 232 | |
| Gal4 (Gal) | YCTTTTTTTTYTTYYKG | 139 | CGGM---CW-Y--CCCG | 233 | |
| Gat1 | none | | none | | |
| Gat3 | RRSCCGMCGMGRCGCGCS | 140 | RGARGTSACGCAKRTTCT | 234 | |
| Gcn4 | AAA-ARAR-RAAAARRAR | 141 | TGAGTCAY | | |
| Gcr1 | GGAAGCTGAAACGYMWRR | 142 | GGAAGCTGAAACGYMWRR | 235 | |
| Gcr2 | GGAGAGGCATGATGGGGG | 143 | AGGTGATGGAGTGCTCAG | 236 | |
| Gln3 | CT-CCTTTCT | 144 | GKCTRR-RGGAGA-GM | 237 | |
| Grf10 | GAAARRAAAAAMRMARA | 145 | -GGGSG-T-SYGT-CGA | 238 | |
| Gts1 | G-GCCRS--TM | 146 | AG-AWGTTTTTGWCAAMA | 239 | |
| Haa1 | none | | none | | |
| Hal9 | TTTTTYTTTTY-KTTTT | 147 | KCKSGCAGGCWTTKYTCT | 240 | |
| Hap2 | YTTCTTTTYT-Y-C-KT- | 148 | G-CCSART-GC | 241 | |
| Hap3 | T-SYKCTTTTCYTTY | 149 | SGCGMGGG--CC-GACCG | 242 | |
| Hap4 | STT-YTTTY-TTYTYYYY | 150 | YCT-ATTSG-C-GS | 243 | |
| Hap5 | YK-TTTWYYTC | 151 | T-TTSMTT-YTTTCCK-C | 244 | |
| Hir1 | AAAA-A-AARAR-AG | 152 | CCACKTKSGSCCT-S | 245 | |
| Hir2 | WAAAAAGAAAA-AAAR | 153 | CRSGCYWGKGC | 246 | |
| Hms1 | AAA-GG-ARAM | 154 | -AARAGC-GGGCAC-C | 247 | |

| | | | | | |
|---|---|---|---|---|---|
| Hsf1 | TYTTCYAGAA--TTCY | 155 | TYTTCYAGAA--TTCY | 248 |
| Ime4 | CACACACACACACACA | 156 | CACACACACACACACA | 249 |
| Ino2 | TTTYCACATGC | 157 | SCKKCGCKSTSSTTYAA | 250 |
| Ino4 | G--GCATGTGAAAA | 158 | G--GCATGTGAAAA | 251 |
| Ixr1 | GAAAA-AAAAAAARA-A | 159 | CTTTTTTYYTSGCC | 252 |
| Leu3 | GAAAARAARAA-AA | 160 | GCCGGTMMCGSYC-- | 253 |
| Mac1 | YTTKT--TTTTTYTYTTT | 161 | A--TTTTYTTKYGC | 254 |
| Mal13 | GCAG-GCAGG | 162 | AAAC-TTTATA-ATACA | 255 |
| Mal33 | none | | none | |
| Mata1 | GCCC-C | | CAAT-TCT-CK | 256 |
| Mbp1 | TTTYTYKTTT-YYTTTTT | 163 | G-RR-A-ACGCGT-R | 257 |
| Mcm1 | TTTCC-AAW-RGGAAA | 164 | TTTCC-AAW-RGGAAA | 258 |
| Met31 | YTTYYTTYTTTTYTYTTC | 165 | | |
| Met4 | MTTTTTYTYTYTTC | 166 | | |
| Mig1 | TATACA-AGMKRTATATG | 167 | | |
| Mot3 | TMTTT-TY-CTT-TTTWK | 168 | | |
| Msn1 | KT--TTWTTATTCC-C | 169 | | |
| Msn2 | ACCACC | | | |
| Msn4 | R--AAAA-RA-AARAAAT | 170 | | |
| Mss11 | TTTTTTTTCWCTTTKYC | 171 | | |
| Ndd 1 | TTTY-YTKTTTY-YTTYT | 172 | | |
| Nrg1 | TTY--TTYTT-YTTTYYY | 173 | | |
| Pdr1 | T-YGTGKRYGT-YG | 174 | | |
| Phd1 | TTYYYTTTTTYTTTTYTT | 175 | | |
| Pho4 | GAMAAAAARAAAAR | 176 | | |
| Put3 | CYCGGGAAGCSAMM-CCG | 177 | | |
| Rap1 | GRTGYAYGGRTGY | 178 | | |
| Rcs1 | KMAARAAAARAAR | 179 | | |
| Reb1 | RTTACCCGS | | | |
| Rfx1 | AYGRAAAARARAAAARAA | 180 | | |
| Rgm1 | GGAKSCC-TTTY-GMRTA | 181 | | |
| Rgt1 | CCCTCC | | | |
| Rim101 | GCGCCGC | | | |
| Rlm1 | TTTTC-KTTTYTTTTC | 182 | | |
| Rme1 | ARAAGMAGAAARRAA | 183 | | |
| Rox1 | YTTTTCTTTTY-TTTTT | 184 | | |
| Rph1 | ARRARAAAGG- | 185 | | |
| Rtg1 | YST-YK-TYTT-CTCCCM | 186 | | |
| Rtg3 | GARA-AAAAR-RAARAAA | 187 | | |
| Sfl1 | CY--GGSSA-C | 188 | | |

| | | |
|---|---|---|
| Sfp1 | CACACACACACACAYA | 189 |
| Sip4 | CTTYTWTTKTTKTSA | 190 |
| Skn7 | YTTYYYTYTTTYTYYTTT | 191 |
| Sko1 | none | |
| Smp1 | AMAAAAARAARWARA-AA | 192 |
| Sok2 | ARAAAARRAAAAG-RAA | 193 |
| Stb1 | RAARAAAARCMRSRAAA | 194 |
| Ste12 | TTYTKTYTY-TYYKTTTY | 195 |
| Stp1 | GAAAAMAA-AAAAA-AAA | 196 |
| Stp2 | YAA-ARAARAAAAA-AAM | 197 |
| Sum1 | TY-TTTTTYTTTTT-TK | 198 |
| Swi4 | RAARAARAAA-AA-R-AA | 199 |
| Swi5 | CACACACACACACACA | 200 |
| Swi6 | RAARRAAAAA-AAAMAA | 201 |
| Thi2 | GCCAGACCTAC | 202 |
| Uga3 | GG-GGCT | |
| Yap1 | TTYTTYTTYTTTY-YTYT | 203 |
| Yap3 | none | |
| Yap5 | YKSGCGCGYCKCGKCGGS | 204 |
| Yap6 | TTTTYYTTTTYYYYKTT | 205 |
| Yap7 | none | |
| Yfl044c | TTCTTKTYYTTTT | 206 |
| Yjl206c | TTYTTTTYTYYTTTYTTT | 207 |
| Zap1 | TTGCTTGAACGGATGCCA | 208 |
| Zms1 | MG-MCAAAAATAAAAS | 209 |

Transcriptional Repressors

| Associated Gene(s) | Description(s) |
|---|---|
| WHI5 | Repressor of G1 transcription that binds to SCB binding factor (SBF) at SCB target promoters in early G1; phosphorylation of Whi5p by the CDK, Cln3p/Cdc28p relieves repression and promoter binding by Whi5; periodically expressed in G1 |
| TUP1 | General repressor of transcription, forms complex with Cyc8p, involved in the establishment of repressive chromatin structure through interactions with histones H3 and H4, appears to enhance expression of some genes |
| ROX1 | Heme-dependent repressor of hypoxic genes; contains an HMG domain that is responsible for DNA bending activity |
| SFL1 | Transcriptional repressor and activator; involved in repression of flocculation-related genes, and activation of stress responsive genes; negatively regulated by cAMP-dependent protein kinase A subunit Tpk2p |
| RIM101 | Transcriptional repressor involved in response to pH and in cell wall construction; required for alkaline pH-stimulated haploid invasive growth and sporulation; activated by proteolytic processing; similar to A. nidulans PacC |
| RDR1 | Transcriptional repressor involved in the control of multidrug resistance; negatively regulates expression of the PDR5 gene; member of the Gal4p family of zinc cluster proteins |

| Associated Gene(s) | Description(s) |
|---|---|
| SUM1 | Transcriptional repressor required for mitotic repression of middle sporulation-specific genes; also acts as general replication initiation factor; involved in telomere maintenance, chromatin silencing; regulated by pachytene checkpoint |
| XBP1 | Transcriptional repressor that binds to promoter sequences of the cyclin genes, CYS3, and SMF2; expression is induced by stress or starvation during mitosis, and late in meiosis; member of the Swi4p/Mbp1p family; potential Cdc28p substrate |
| NRG2 | Transcriptional repressor that mediates glucose repression and negatively regulates filamentous growth; has similarity to Nrg1p |
| NRG1 | Transcriptional repressor that recruits the Cyc8p-Tup1p complex to promoters; mediates glucose repression and negatively regulates a variety of processes including filamentous growth and alkaline pH response |
| CUP9 | Homeodomain-containing transcriptional repressor of PTR2, which encodes a major peptide transporter; imported peptides activate ubiquitin-dependent proteolysis, resulting in degradation of Cup9p and de-repression of PTR2 transcription |
| YOX1 | Homeodomain-containing transcriptional repressor, binds to Mcm1p and to early cell cycle boxes (ECBs) in the promoters of cell cycle-regulated genes expressed in M/G1 phase; expression is cell cycle-regulated; potential Cdc28p substrate |
| RFX1 | Major transcriptional repressor of DNA-damage-regulated genes, recruits repressors Tup1p and Cyc8p to their promoters; involved in DNA damage and replication checkpoint pathway; similar to a family of mammalian DNA binding RFX1-4 proteins |
| MIG3 | Probable transcriptional repressor involved in response to toxic agents such as hydroxyurea that inhibit ribonucleotide reductase; phosphorylation by Snf1p or the Mec1p pathway inactivates Mig3p, allowing induction of damage response genes |
| RGM1 | Putative transcriptional repressor with proline-rich zinc fingers; overproduction impairs cell growth |
| YHP1 | One of two homeobox transcriptional repressors (see also Yox1p), that bind to Mcm1p and to early cell cycle box (ECB) elements of cell cycle regulated genes, thereby restricting ECB-mediated transcription to the M/G1 interval |
| HOS4 | Subunit of the Set3 complex, which is a meiotic-specific repressor of sporulation specific genes that contains deacetylase activity; potential Cdc28p substrate |
| CAF20 | Phosphoprotein of the mRNA cap-binding complex involved in translational control, repressor of cap-dependent translation initiation, competes with eIF4G for binding to eIF4E |
| SAP1 | Putative ATPase of the AAA family, interacts with the Sin1p transcriptional repressor in the two-hybrid system |
| SET3 | Defining member of the SET3 histone deacetylase complex which is a meiosis-specific repressor of sporulation genes; necessary for efficient transcription by RNAPII; one of two yeast proteins that contains both SET and PHD domains |
| RPH1 | JmjC domain-containing histone demethylase which can specifically demethylate H3K36 tri- and dimethyl modification states; transcriptional repressor of PHR1; Rph1p phosphorylation during DNA damage is under control of the MEC1-RAD53 pathway |
| YMR181C | Protein of unknown function; mRNA transcribed as part of a bicistronic transcript with a predicted transcriptional repressor RGM1/YMR182C; mRNA is destroyed by nonsense-mediated decay (NMD); YMR181C is not an essential gene |
| YLR345W | Similar to 6-phosphofructo-2-kinase/fructose-2,6-bisphosphatase enzymes responsible for the metabolism of fructoso-2,6-bisphosphate; mRNA expression is repressed by the Rfx1p-Tup1p-Ssn6p repressor complex; YLR345W is not an essential gene |
| MCM1 | Transcription factor involved in cell-type-specific transcription and pheromone response; plays a central role in the formation of both repressor and activator complexes |
| PHR1 | DNA photolyase involved in photoreactivation, repairs pyrimidine dimers in the presence of visible light; induced by DNA damage; regulated by transcriptional repressor Rph1p |
| HOS2 | Histone deacetylase required for gene activation via specific deacetylation of lysines in H3 and H4 histone tails; subunit of the Set3 complex, a meiotic-specific repressor of sporulation specific genes that contains deacetylase activity |
| RGT1 | Glucose-responsive transcription factor that regulates expression of several glucose transporter (HXT) genes in response to glucose; binds to promoters and acts both as a transcriptional activator and repressor |
| SRB7 | Subunit of the RNA polymerase II mediator complex; associates with core polymerase subunits to form the RNA polymerase II |

-continued

| Associated Gene(s) | Description(s) |
|---|---|
| | holoenzyme; essential for transcriptional regulation; target of the global repressor Tup1p |
| GAL11 | Subunit of the RNA polymerase II mediator complex; associates with core polymerase subunits to form the RNA polymerase II holoenzyme; affects transcription by acting as target of activators and repressors |

Transcriptional Activators

| Associated Gene(s) | Description(s) |
|---|---|
| SKT5 | Activator of Chs3p (chitin synthase III), recruits Chs3p to the bud neck via interaction with Bni4p; has similarity to Shc1p, which activates Chs3p during sporulation |
| MSA1 | Activator of G1-specific transcription factors, MBF and SBF, that regulates both the timing of G1-specific gene transcription, and cell cycle initiation; potential Cdc28p substrate |
| AMA1 | Activator of meiotic anaphase promoting complex (APC/C); Cdc20p family member; required for initiation of spore wall assembly; required for Clb1p degradation during meiosis |
| STB5 | Activator of multidrug resistance genes, forms a heterodimer with Pdr1p; contains a Zn(II)2Cys6 zinc finger domain that interacts with a PDRE (pleotropic drug resistance element) in vitro; binds Sin3p in a two-hybrid assay |
| RRD2 | Activator of the phosphotyrosyl phosphatase activity of PP2A,peptidyl-prolyl cis/trans-isomerase; regulates G1 phase progression, the osmoresponse, microtubule dynamics; subunit of the Tap42p-Pph21p-Rrd2p complex |
| BLM10 | Proteasome activator subunit; found in association with core particles, with and without the 19S regulatory particle; required for resistance to bleomycin, may be involved in protecting against oxidative damage; similar to mammalian PA200 |
| SHC1 | Sporulation-specific activator of Chs3p (chitin synthase III), required for the synthesis of the chitosan layer of ascospores; has similarity to Skt5p, which activates Chs3p during vegetative growth; transcriptionally induced at alkaline pH |
| NDD1 | Transcriptional activator essential for nuclear division; localized to the nucleus; essential component of the mechanism that activates the expression of a set of late-S-phase-specific genes |
| IMP2' | Transcriptional activator involved in maintenance of ion homeostasis and protection against DNA damage caused by bleomycin and other oxidants, contains a C-terminal leucine-rich repeat |
| LYS14 | Transcriptional activator involved in regulation of genes of the lysine biosynthesis pathway; requires 2-aminoadipate semialdehyde as co-inducer |
| MSN1 | Transcriptional activator involved in regulation of invertase and glucoamylase expression, invasive growth and pseudohyphal differentiation, iron uptake, chromium accumulation, and response to osmotic stress; localizes to the nucleus |
| HAA1 | Transcriptional activator involved in the transcription of TPO2, YRO2, and other genes putatively encoding membrane stress proteins; involved in adaptation to weak acid stress |
| UGA3 | Transcriptional activator necessary for gamma-aminobutyrate (GABA)-dependent induction of GABA genes (such as UGA1, UGA2, UGA4); zinc-finger transcription factor of the Zn(2)-Cys(6) binuclear cluster domain type; localized to the nucleus |
| GCR1 | Transcriptional activator of genes involved in glycolysis; DNA-binding protein that interacts and functions with the transcriptional activator Gcr2p |
| GCR2 | Transcriptional activator of genes involved in glycolysis; interacts and functions with the DNA-binding protein Gcr1p |
| GAT1 | Transcriptional activator of genes involved in nitrogen catabolite repression; contains a GATA-1-type zinc finger DNA-binding motif; activity and localization regulated by nitrogen limitation and Ure2p |
| GLN3 | Transcriptional activator of genes regulated by nitrogen catabolite repression (NCR), localization and activity regulated by quality of nitrogen source |
| PUT3 | Transcriptional activator of proline utilization genes, constitutively binds PUT1 and PUT2 promoter sequences and undergoes a conformational change to form the active state; has a Zn(2)-Cys(6) binuclear cluster domain |

-continued

| Associated Gene(s) | Description(s) |
|---|---|
| ARR1 | Transcriptional activator of the basic leucine zipper (bZIP) family, required for transcription of genes involved in resistance to arsenic compounds |
| PDR3 | Transcriptional activator of the pleiotropic drug resistance network, regulates expression of ATP-binding cassette (ABC) transporters through binding to cis-acting sites known as PDREs (PDR responsive elements) |
| MSN4 | Transcriptional activator related to Msn2p; activated in stress conditions, which results in translocation from the cytoplasm to the nucleus; binds DNA at stress response elements of responsive genes, inducing gene expression |
| MSN2 | Transcriptional activator related to Msn4p; activated in stress conditions, which results in translocation from the cytoplasm to the nucleus; binds DNA at stress response elements of responsive genes, inducing gene expression |
| PHD1 | Transcriptional activator that enhances pseudohyphal growth; regulates expression of FLO11, an adhesin required for pseudohyphal filament formation; similar to StuA, an A. nidulans developmental regulator; potential Cdc28p substrate |
| FHL1 | Transcriptional activator with similarity to DNA-binding domain of Drosophila forkhead but unable to bind DNA in vitro; required for rRNA processing; isolated as a suppressor of splicing factor prp4 |
| VHR1 | Transcriptional activator, required for the vitamin H-responsive element (VHRE) mediated induction of VHT1 (Vitamin H transporter) and BIO5 (biotin biosynthesis intermediate transporter) in response to low biotin concentrations |
| CDC20 | Cell-cycle regulated activator of anaphase-promoting complex/cyclosome (APC/C), which is required for metaphase/anaphase transition; directs ubiquitination of mitotic cyclins, Pds1p, and other anaphase inhibitors; potential Cdc28p substrate |
| CDH1 | Cell-cycle regulated activator of the anaphase-promoting complex/cyclosome (APC/C), which directs ubiquitination of cyclins resulting in mitotic exit; targets the APC/C to specific substrates including Cdc20p, Ase1p, Cin8p and Fin1p |
| AFT2 | Iron-regulated transcriptional activator; activates genes involved in intracellular iron use and required for iron homeostasis and resistance to oxidative stress; similar to Aft1p |
| MET4 | Leucine-zipper transcriptional activator, responsible for the regulation of the sulfur amino acid pathway, requires different combinations of the auxiliary factors Cbf1p, Met28p, Met31p and Met32p |
| CBS2 | Mitochondrial translational activator of the COB mRNA; interacts with translating ribosomes, acts on the COB mRNA 5'-untranslated leader |
| CBS1 | Mitochondrial translational activator of the COB mRNA; membrane protein that interacts with translating ribosomes, acts on the COB mRNA 5'-untranslated leader |
| CBP6 | Mitochondrial translational activator of the COB mRNA; phosphorylated |
| PET111 | Mitochondrial translational activator specific for the COX2 mRNA; located in the mitochondrial inner membrane |
| PET494 | Mitochondrial translational activator specific for the COX3 mRNA, acts together with Pet54p and Pet122p; located in the mitochondrial inner membrane |
| PET122 | Mitochondrial translational activator specific for the COX3 mRNA, acts together with Pet54p and Pet494p; located in the mitochondrial inner membrane |
| RRD1 | Peptidyl-prolyl cis/trans-isomerase, activator of the phosphotyrosyl phosphatase activity of PP2A; involved in G1 phase progression, microtubule dynamics, bud morphogenesis and DNA repair; subunit of the Tap42p-Sit4p-Rrd1p complex |
| YPR196W | Putative maltose activator |
| POG1 | Putative transcriptional activator that promotes recovery from pheromone induced arrest; inhibits both alpha-factor induced G1 arrest and repression of CLN1 and CLN2 via SCB/MCB promoter elements; potential Cdc28p substrate; SBF regulated |
| MSA2 | Putative transcriptional activator, that interacts with G1-specific transcription factor, MBF and G1-specific promoters; ortholog of Msa2p, an MBF and SBF activator that regulates G1-specific transcription and cell cycle initiation |
| PET309 | Specific translational activator for the COX1 mRNA, also influences stability of intron-containing COX1 primary transcripts; localizes to the mitochondrial inner membrane; contains seven pentatricopeptide repeats (PPRs) |
| TEA1 | Ty1 enhancer activator required for full levels of Ty enhancer-mediated transcription; C6 zinc cluster DNA-binding protein |
| PIP2 | Autoregulatory oleate-specific transcriptional activator of peroxisome proliferation, contains Zn(2)-Cys(6) cluster domain, forms heterodimer |

-continued

| Associated Gene(s) | Description(s) |
|---|---|
| | with Oaf1p, binds oleate response elements (OREs), activates beta-oxidation genes |
| CHA4 | DNA binding transcriptional activator, mediates serine/threonine activation of the catabolic L-serine (L-threonine) deaminase (CHA1); Zinc-finger protein with Zn[2]-Cys[6] fungal-type binuclear cluster domain |
| SFL1 | Transcriptional repressor and activator; involved in repression of flocculation-related genes, and activation of stress responsive genes; negatively regulated by cAMP-dependent protein kinase A subunit Tpk2p |
| RDS2 | Zinc cluster transcriptional activator involved in conferring resistance to ketoconazole |
| CAT8 | Zinc cluster transcriptional activator necessary for derepression of a variety of genes under non-fermentative growth conditions, active after diauxic shift, binds carbon source responsive elements |
| ARO80 | Zinc finger transcriptional activator of the Zn2Cys6 family; activates transcription of aromatic amino acid catabolic genes in the presence of aromatic amino acids |
| SIP4 | C6 zinc cluster transcriptional activator that binds to the carbon source-responsive element (CSRE) of gluconeogenic genes; involved in the positive regulation of gluconeogenesis; regulated by Snf1p protein kinase; localized to the nucleus |
| SPT10 | Putative histone acetylase, sequence-specific activator of histone genes, binds specifically and highly cooperatively to pairs of UAS elements in core histone promoters, functions at or near the TATA box |
| MET28 | Basic leucine zipper (bZIP) transcriptional activator in the Cbf1p-Met4p-Met28p complex, participates in the regulation of sulfur metabolism |
| GCN4 | Basic leucine zipper (bZIP) transcriptional activator of amino acid biosynthetic genes in response to amino acid starvation; expression is tightly regulated at both the transcriptional and translational levels |
| CAD1 | AP-1-like basic leucine zipper (bZIP) transcriptional activator involved in stress responses, iron metabolism, and pleiotropic drug resistance; controls a set of genes involved in stabilizing proteins; binds consensus sequence TTACTAA |
| INO2 | Component of the heteromeric Ino2p/Ino4p basic helix-loop-helix transcription activator that binds inositol/choline-responsive elements (ICREs), required for derepression of phospholipid biosynthetic genes in response to inositol depletion |
| THI2 | Zinc finger protein of the Zn(II)2Cys6 type, probable transcriptional activator of thiamine biosynthetic genes |
| SWI4 | DNA binding component of the SBF complex (Swi4p-Swi6p), a transcriptional activator that in concert with MBF (Mbp1-Swi6p) regulates late G1-specific transcription of targets including cyclins and genes required for DNA synthesis and repair |
| HAP5 | Subunit of the heme-activated, glucose-repressed Hap2/3/4/5 CCAAT-binding complex, a transcriptional activator and global regulator of respiratory gene expression; required for assembly and DNA binding activity of the complex |
| HAP3 | Subunit of the heme-activated, glucose-repressed Hap2p/3p/4p/5p CCAAT-binding complex, a transcriptional activator and global regulator of respiratory gene expression; contains sequences contributing to both complex assembly and DNA binding |
| HAP2 | Subunit of the heme-activated, glucose-repressed Hap2p/3p/4p/5p CCAAT-binding complex, a transcriptional activator and global regulator of respiratory gene expression; contains sequences sufficient for both complex assembly and DNA binding |
| HAP4 | Subunit of the heme-activated, glucose-repressed Hap2p/3p/4p/5p CCAAT-binding complex, a transcriptional activator and global regulator of respiratory gene expression; provides the principal activation function of the complex |
| YML037C | Putative protein of unknown function with some characteristics of a transcriptional activator; may be a target of Dbf2p-Mob1p kinase; GFP-fusion protein co-localizes with clathrin-coated vesicles; YML037C is not an essential gene |
| TRA1 | Subunit of SAGA and NuA4 histone acetyltransferase complexes; interacts with acidic activators (e.g., Gal4p) which leads to transcription activation; similar to human TRRAP, which is a cofactor for c-Myc mediated oncogenic transformation |
| YLL054C | Putative protein of unknown function with similarity to Pip2p, an oleate-specific transcriptional activator of peroxisome proliferation; YLL054C is not an essential gene |
| RTG2 | Sensor of mitochondrial dysfunction; regulates the subcellular location of Rtg1p and Rtg3p, transcriptional activators of the retrograde (RTG) and TOR pathways; Rtg2p is inhibited by the phosphorylated form of Mks1p |

-continued

Figure 4:
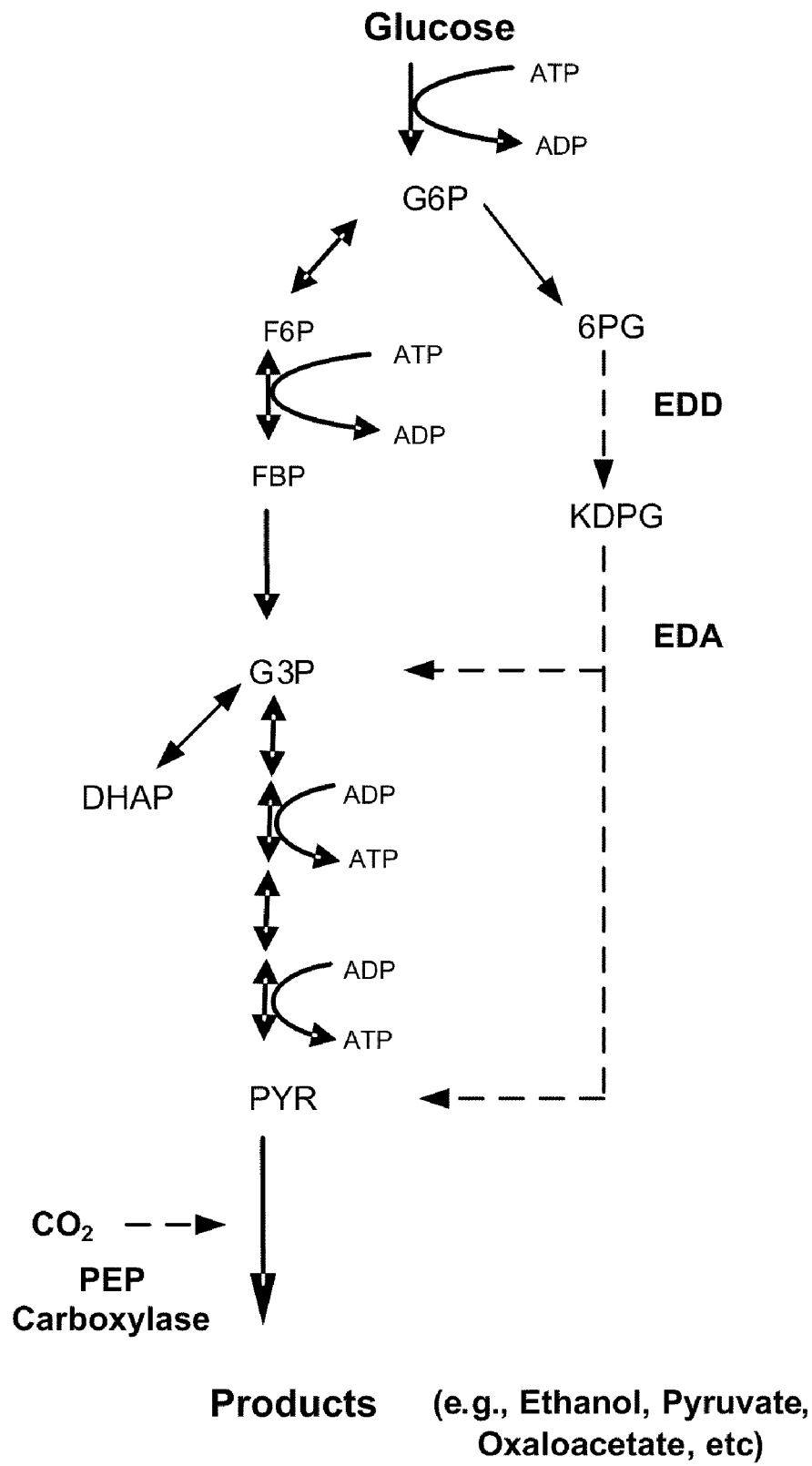
FIG. 4 depicts an engineered metabolic pathway that can be used to increase the efficiency of ethanol production (and other products) by introducing the ability to fix atmospheric carbon dioxide into a microorganism. The engineered microorganism can incorporate or fix atmospheric carbon dioxide into organic molecules using the introduced phosphoenolpyruvate carboxylase activity. Carbon dioxide incorporated in this manner can be used as an additional carbon source that can increase production of many organic molecules, including ethanol. Non-limiting examples of other products whose production can benefit from carbon fixation include; pyruvate, oxaloacetate, glyceraldehyde-3-phosphate and the like. The pathway depicted in FIG. 4 illustrates the introduction of the novel carbon dioxide fixation activity in the background of a fully functional EM pathway, and an introduced ED pathway. It is understood the introduction of the carbon fixation activity can benefit microorganisms that have no other modifications to any metabolic pathways. It also is understood that microorganism modified in one, or multiple, other metabolic pathways can benefit from the introduction of a carbon fixation activity.
Figure 5:
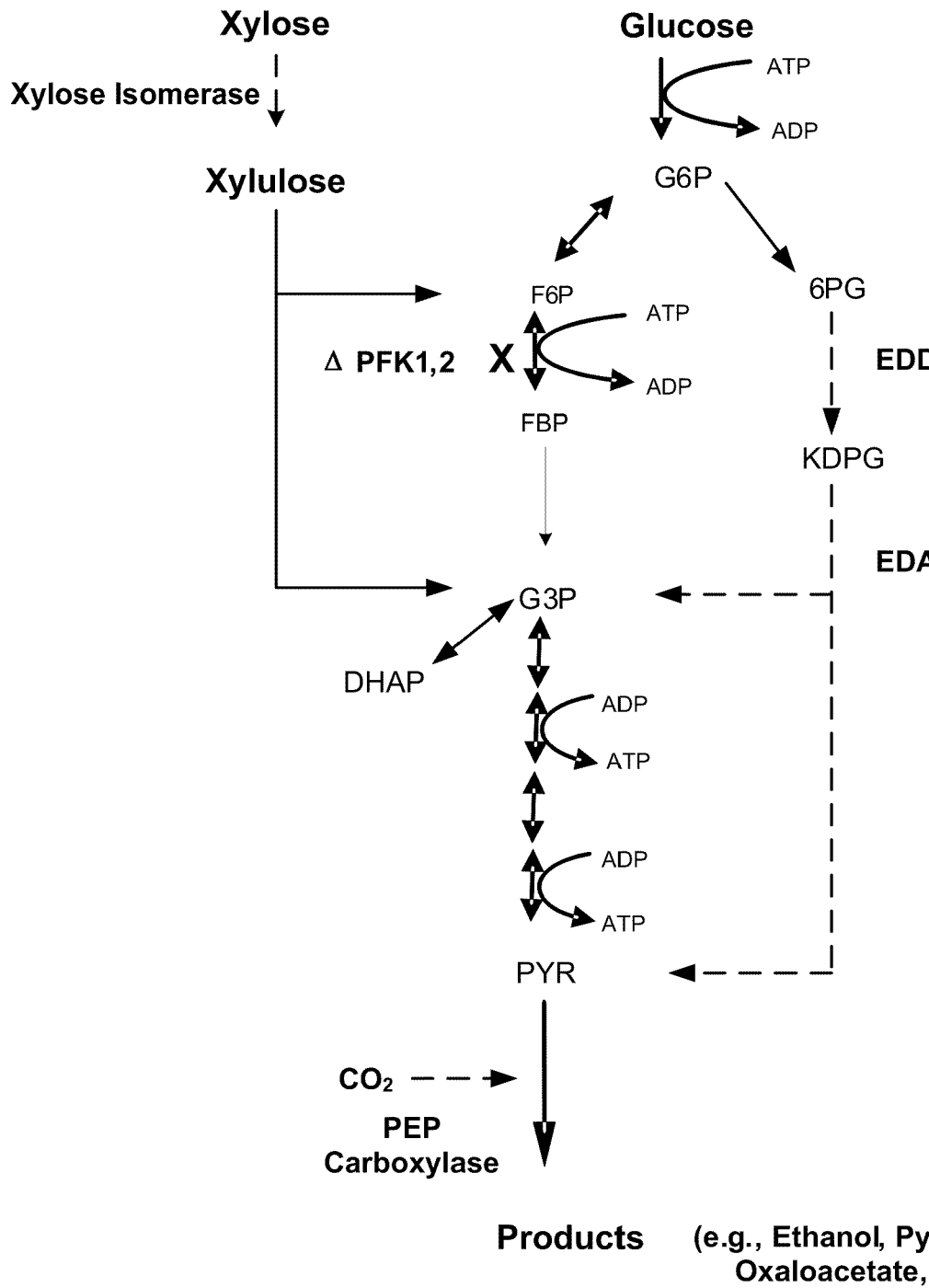
FIG. 5 shows a combination of some engineered metabolic pathways described herein. The combination of engineered metabolic pathways shown in FIG. 5 can provide significant increases in the production of ethanol (or other products) when compared to the wild type organism or organisms lacking one, two, three or more of the modifications. Other combinations of engineered metabolic pathways not shown in FIG. 5 are possible, including but not limited to, combinations including increased alcohol tolerance, modified alcohol dehydrogenase 2 activity and/or modified thymidylate synthase activity, as described herein. Therefore, FIG. 5 also illustrates an embodiment of a method for generating an engineered microorganism with the ability to produce a greater amount of target product comprising expressing one or more genetically modified activities, described herein, in a host organism that produces the desired target (e.g., ethanol, pyruvate, oxaloacetate and the like, for example) via one or more metabolic pathways. In some embodiments, the combination of metabolic pathways includes those depicted in FIG. 5 in addition to combinations including one, two or three of the following activities; increased alcohol tolerance, modified alcohol dehydrogenase 2 activity and modified thymidylate synthase activity.

| Associated Gene(s) | Description(s) |
|---|---|
| YBR012C | Dubious open reading frame, unlikely to encode a functional protein; expression induced by iron-regulated transcriptional activator Aft2p |
| JEN1 | Lactate transporter, required for uptake of lactate and pyruvate; phosphorylated; expression is derepressed by transcriptional activator Cat8p during respiratory growth, and repressed in the presence of glucose, fructose, and mannose |
| MRP1 | Mitochondrial ribosomal protein of the small subunit; MRP1 exhibits genetic interactions with PET122, encoding a COX3-specific translational activator, and with PET123, encoding a small subunit mitochondrial ribosomal protein |
| MRP17 | Mitochondrial ribosomal protein of the small subunit; MRP17 exhibits genetic interactions with PET122, encoding a COX3-specific translational activator |
| TPI1 | Triose phosphate isomerase, abundant glycolytic enzyme; mRNA half-life is regulated by iron availability; transcription is controlled by activators Reb1p, Gcr1p, and Rap1p through binding sites in the 5' non-coding region |
| PKH3 | Protein kinase with similarity to mammalian phosphoinositide-dependent kinase 1 (PDK1) and yeast Pkh1p and Pkh2p, two redundant upstream activators of Pkc1p; identified as a multicopy suppressor of a pkh1 pkh2 double mutant |
| YGL079W | Putative protein of unknown function; green fluorescent protein (GFP)-fusion protein localizes to the endosome; identified as a transcriptional activator in a high-throughput yeast one-hybrid assay |
| TFB1 | Subunit of TFIIH and nucleotide excision repair factor 3 complexes, required for nucleotide excision repair, target for transcriptional activators |
| PET123 | Mitochondrial ribosomal protein of the small subunit; PET123 exhibits genetic interactions with PET122, which encodes a COX3 mRNA-specific translational activator |
| MHR1 | Protein involved in homologous recombination in mitochondria and in transcription regulation in nucleus; binds to activation domains of acidic activators; required for recombination-dependent mtDNA partitioning |
| MCM1 | Transcription factor involved in cell-type-specific transcription and pheromone response; plays a central role in the formation of both repressor and activator complexes |
| EGD1 | Subunit beta1 of the nascent polypeptide-associated complex (NAC) involved in protein targeting, associated with cytoplasmic ribosomes; enhances DNA binding of the Gal4p activator; homolog of human BTF3b |
| STE5 | Pheromone-response scaffold protein; binds Ste11p, Ste7p, and Fus3p kinases, forming a MAPK cascade complex that interacts with the plasma membrane and Ste4p-Ste18p; allosteric activator of Fus3p that facilitates Ste7p-mediated activation |
| RGT1 | Glucose-responsive transcription factor that regulates expression of several glucose transporter (HXT) genes in response to glucose; binds to promoters and acts both as a transcriptional activator and repressor |
| TYE7 | Serine-rich protein that contains a basic-helix-loop-helix (bHLH) DNA binding motif; binds E-boxes of glycolytic genes and contributes to their activation; may function as a transcriptional activator in Ty1-mediated gene expression |
| VMA13 | Subunit H of the eight-subunit V1 peripheral membrane domain of the vacuolar H+-ATPase (V-ATPase), an electrogenic proton pump found throughout the endomembrane system; serves as an activator or a structural stabilizer of the V-ATPase |
| GAL11 | Subunit of the RNA polymerase II mediator complex; associates with core polymerase subunits to form the RNA polymerase II holoenzyme; affects transcription by acting as target of activators and repressors |
| VAC14 | Protein involved in regulated synthesis of PtdIns(3,5)P(2), in control of trafficking of some proteins to the vacuole lumen via the MVB, and in maintenance of vacuole size and acidity; interacts with Fig4p; activator of Fab1p |

Example 7

Heterologous Xylose Isomerase Expression in Yeast

Provided hereafter are non-limiting examples of certain organisms from which nucleic acids that encode a polypeptide having xylose isomerase activity can be obtained. Certain nucleic acid encoded polypeptides having active xylose isomerase activity can be expressed in an engineered yeast (*S. cerevisiae*).

| Donor Organism | Active? (yes/no) | Xylose isomerase type (Type 1/Type 2) |
|---|---|---|
| *Piromyces* | Yes | Type 2 |
| *Orpinomyces* | Yes | |
| *Bacteroides thetaiotaomicron* | Yes | |
| *Clostridium phytofermentans* | Yes | |
| *Thermus thermophilus* | Yes | Type 1 |

| Donor Organism | Active? (yes/no) | Xylose isomerase type (Type 1/Type 2) |
|---|---|---|
| *Ruminococcus flavefaciens* | Yes | |
| *Escherichia coli* | No | |
| *Bacillus subtilis* | No | |
| *Lactobacillus pentoses* | No | |
| *Leifsoria xyli* subsp. *Cynodontis* | No | |
| *Clostridium thermosulfurogenes* | No | |
| *Bacillus licheniformis* | No | |
| *Burkholderia xenovorans* | No | |
| *Psudomonas savastanoi* | No | |
| *Robiginitalea biformata* | No | |
| *Saccharophagus degradans* | No | |
| *Staphylococcus xylosus* | No | |
| *Streptomyces diastaticus* subsp *diastaticus* | No | |
| *Xanthomonas campestris* | No | |
| *Salmonella enterica* serovar Typhimurium | No | |
| *Agrobacterium tumefaciens* | No | |
| *Arabidopsis thaliana* | No | |
| *Pseudomonas syringae* | No | |
| *Actinoplanes missouriensis* | No | |
| *Streptomyces rubiginosus* | No | |
| *Epilopiscium* | No | |

Example 8

Examples of Nucleic Acid and Amino Acid Sequences

Provided hereafter and non-limiting examples of certain nucleic acid sequences.

| Gene Name | Organism/ ATCC identifier | Nucleic acid Accession No. or other identifier | Nucleotide Sequence |
|---|---|---|---|
| Xylose Isomerase (XI-RF Native) | Ruminococcus flavefaciens strain 17 | AJ132472 | atggaattttt tcagcaatat cggtaaaatt cagtatcagg gaccaaaaag tactgatcct ctctcattta agtactatta ccctgaagaa gtcatcaacg gaagacaat gcgcgacgt ctgaagttcg ctctttcatg gtggcacaca atggcgggc acgaacaga tatgttcggc tgcggcacaa cagacaagac ctgggacag tcgatcccg ctgcaagagc aaaggctaag gttgacgcag cattcggaga catggataag ctctccattg actactattg tttccacgat cgcgatcttt ctcccagta tgcagcctc aaggcagtca acgatcagct tgcacatgat acagactata tcaaggagaa gcaggcgac aagtcaagt gcctctggg tacagcaag tgcttcgatc atccaagatt catgcacggt gcagtacat ctcctttgc tgatgattc gttttccag ctgctcagat caagaaggct tcgagtcaa cagtaaagct cggcggtaac ggtacgttt tctggggcg tatgagccg tcttcttatg aagatggctg ttgatatgg acgttcgatc ctcgaacctg acaatatgc tgtcttatg agcccaagg agcccacaa gcatcagtac ggcttcaagg gcgacttcta tatgcagccc tctgagacgt acgtctcga taaggattc gattcgata cagctactgt tctgggattc tctgctcagc ctgctcagc atacattcca gcatgagctc aagatgaata tcgaagctaa caccgtcag caaccaggt cgacgttctt cggttgcaa gagacaatgg tgtgttcggt tctatcgcg caacccaggt tacagttcgt cttggatggg atacagacca gttcccaca aatatctacg atacaacat gtgtatgtat gaagttatca aggcaggcgg cttcacaaac ggcgtctca acttcgacgc taaggcacgc agagggagct tcactcccga ggatatcttc tacagctata tcgcaggtat ggatgcattt gcctcgggct tcagagctgc tctcaagctc atcgaagacg gactatcga caagtcgtt gctgacagat acgcttcatg gaataccggt atcgtgcac acataatcgc agtaaggca gattccgcat ctctgaaaa gtatgctctt gaaaagggcg agttacgc ttcactctca acgggcgac aggaatgct ggagtctatc ggaataacg ttctttcag tctgtaa (SEQ ID NO: 259) |
| Xylose isomerase (point mutation) | Based on Ruminococcus flavefaciens strain 17 | Based on AJ132472 | atggaatttttcagcaatatcgtaaaattcagtatcaggaccaaaaagtactgatcctctctcattaagtactataacc ctgaagaagtcatcaacgaaagcaatgcgcgagcactgaagctcgctctttcatgtggcacaatggcggc gacgaacagatatgtcggctcgacgcagcatgttggcacaactgggacagaagaccgggacgatccgatccctgcaagagcaaa ggctaaggtgacgcagcagcagcattcgagatcgagatggataagctctccatttccacgatcgcgatctttctccc gagtatgcgcagctcaaggccagtcaacgatcagctgcacatgatacagactatatcaaggagaagcaggcgaca agttcgcttctccgatgcctgtcagatcaagaaggctctGgagtcaacagtcaagctcggctggtggttcggttttct gggcggacgcatggaatgatggacgatgagacactctctaatacaaatatggcgcaatatggctcgtcttatga agtggcgtgagtacgattcgatacagctcgatcagtgttctgggattcctcagcatatctcagcatgagctccgtgttgcagccca tatcgagctaaccacggctactgtctgcagcagttcctcttgaaggtatgcagccgctccacaaaccgcctcaactcgacgtaagc gagag aatgtgtatgatgaagttatcaaggccagcggctactacagtttctacagcttcgatggatgcttccagcggtctctcaa ggagcttctcttcgagttcagagctgccacagtctttacacagttgttcgatctcatcacagttttacgaggttcatctccttggcttcagagctgctcagacata gctgactcgaagacagtcgcatggaatacgcatcgggctctattggggcttcagacttgtctgactacgcttacagctcgcaagctgctcagac atcgcaggtaaggcgaatgtgagtctgaaatatgctcttgaaataacgtcttttcagtcgtaa (SEQ ID NO: 260) |
| Xylose isomerase (XI-RF_HR) | | | atggagttctttctaatatagtaaattcagtatcaaggtccaaatc tacagatccatgcttgtcttaaatataatcagagaagttataaatg gtaaaactagagaacattaaatttgcttgtctgtgcatact atggtggtatggtactgatgtcgttgtgtcgataaaac ttgggcaatcgatcgatccagctgctagcaaaagcaaagtagatgcag cctttgaaattatgcgaaattatgtcgattgattattgttttcatgat |

| Gene Name | Organism/ ATCC identifier | Nucleic acid Accession No. or other identifier | Nucleotide Sequence |
|---|---|---|---|
| | | | agagattgtctcctgaatatgtcttaaagcaactaatgatcaatt ggacattgttacggattatattaagaaaacaagtgataaatttaaat gttgtgggcactgcgaaatgttttgatcatccacgtttatgcatgt gcgggacgagtccctcgctgatgttttgctttttctgccgctcaaat taagaaggcaattggaatcaactgtaaattaggtgggaacggtatgtat tctgggaggaaggaaggttatgaaacattattaaacactaatatggt ttggaatgataatatgcgtagatgatgaaaatggctgtagaatacgg aagtccattgtgtttaaggtgtactttatattgaaccaaaacctaaag agcctactacaaaatcaatattaggttaatggtaaatgaataaaggtata tgagaaaatatggtctggataaagatttaaaatgaatatagaagtaa tcatgcaactcgcaacaactcttttcaactgaatgagagttgcca gaataacggagttttggatctatcgatgcaaccaggagacgtttg ctagatgggactgatcaattccaactaacattatgatactactat gtgtatgtgaagtaattaagcaggaggcttactaatgcggattaa acttgatgcgaaggctaggcgtgtagtttcactccgaggatatattc tattcctatattctgaatgatgtctagaaattgatagttgtagctagat actaaaattgattgaagatggaataggacagatataacgctgggaaagcc atgtttcttggaatactggaataggacctgaaaaggaaaactatgc gacttcgcagtctgaaaatatgcgcttgaaaaggaagaagttactgc cagcttaagtccgctgctgcaagaaatgttgaatcttattgtaacaatg ttttatttctctg (SEQ ID NO: 261) |
| Xylose isomerase (XI-P Native) | Piromyces sp. E2 | AJ249909 | atggctaagg aatattcccc acaaattcaa aagattaagt tcgaagtcaa ggattctaag aatccattag cctccacta ctacgatgct gaaaaggaag tcatgggtaa gaaaatgaag gattggttac gttcgccat ggcctggtgg cacactcttt ggcccgaagg tgctgaccaa ttcggtggag gtacaaagtc tttccatgg aacgaaggta ctgatgctat tgaaattgcc agccaaaagg ttgatgctgg tttcgaaatc atgcaaaagc ttggtattcc atactactgt ttccacgatg ttgatctgt tccgaaagt aactctattg aagaatacca atccaacctt tccacactcg tcgctagtgct gctcctctcg aggctgtcg tgcttacct caagaacgt tactgaacgt gtccctcac taaccagac agtactgtta cgtcctcgg tcacaagcgt tattgttcaa attaagaacg ccatagacgc cggtattgaa cttgtgctg aaaactcgt cttctgggt ggtcggtaaa gtacatgag tctcctaac actgaccaaa agcgtgaaaa ggaacacatg gccactatgc ttaccatgc tcgtgactac gctcgtccaa aggattcaa ggtactttc ctcattgtt tccttaaggc ccacacttc aagcaccaat acgtgttga cactgaaacc gctgaaagtt aaccagcta cttctgctg tcacacttc gacaaggact ttgcctgtc caagagtt caattgcgta accgaagcta cttctgctg tcacacttc gaacacgaac ttgcctgc tgttgatgct tgtgatgct gttccattga tgctaaccgt ggtgactacc aaaacggttg ggaatccat ccgtggtggt ggtttcgtta cggtggtac cgctctcggt caagctgcc gccaagatc cgtgtaactc gaagcatca cattgcccca cgtttctggt gccaagactg gctgtaactc tactgacctc gaagcatca cattgcccca cgtttctggt atggatgcta tggcctaact ggctgcaagc ttcgacagtg tcctccaaga actccatac accaagatga agaaggaacg ttacgcttcc tcgacagtg gtattgtaa ggacttgaa gatggtaagc tcaccctcga acaagtttac aaagttac catgttgtg agaagaacgt tgaccttgaa caacttctg gtaagcaaga actctacgaa gctattgtg ccatgtacca ata (SEQ ID NO: 262) |
| Xylose Isomerase (XI-P-HR1) | Based on Piromyces sp. E2 | | ATGGCTAAGAATATTTCCACAAATTCAGAAATTAAATTTGAAGTAAAGATTC TAAAAATCCATTGGCTTTCCATTATTATGATGCTGAAAAGAAGTTATGGGTAAAA AGATGAAGATTGGTTAGATTCGCTATGGCTTGGTGGCATACTCTATGTGCTG AAGGAGCTGATCAATTGGAGGAGGTACTAAATCTTTTCCTTGAATGAAGGTA |

| Gene Name | Organism/ ATCC identifier | Nucleic acid Accession No. or other identifier | Nucleotide Sequence |
|---|---|---|---|
| | | | CTGACGCTATTGAAATGCTAAGCAGAAAGTAGACGCGGGTTTTGAAATTATGC AAAAATTGGAATACCATATTATTGTTTTCATGATGTTGATTTGGTATCTGAGGGT AATTCTATTGAAGAATATGAATCTAATTTAAAAGCTGTTGTTGCTTACTACTAAAGA AAAACAAAAAGAAACTGAATTAAATTGTTGGTCTACAGCTAATGTTTTCGGT CATAAAAGATATATGAATGGTGCTTCTACAAATCCAGATTTTGATGTTGTAGCTA GAGCTATTGTTCAAATTAAAAATGCTATAGATGCAGAATTGAATTAGGTGCCGA AAATTATGTTTTCGGGAGGTAGAAGAGTACTTTCTTGTTTAAATACTGAT CAAAACGTGAAAAGGAACACATGGCAACTATGTTGACAATGGCTAGGGATTAT GCTAGATCTAAAGGTTTTAAAGGTACTTTCTTGATTGAGCCAAAACTATGAAC CAACTAAAACATCAATATGACGTTGACACTGAAACTGCTATTGGTTCTAAAAGC TCATAATTGGATAAAGATTTTAAGGTTAATATAGAAGTTAATCATGCTACTACTAG CTGGTCATACTTTTGAACATGAAGGTGATTATCAAAATGGTGCAGTTGATGCCGGTATGTTAGG TTCTATCGACGCAAATAGAGGTGATTATCAAGCATGGAGAAATTATTAGGGGTGA GGCTTCGTTACAGGTGGAACTAATTTTGATGCTAAAACTAGGAGAAATTCTACAG AICTTGAAGATAAATAATTATTGCTCTATGCTCATGTATCTGTATGATGCGATGCCCGTGC TTTGGAAAATGCAGCTAATATTCTCCAAGAATCTCCTATACTAAAATGAAAAAGG AAAGATATGCTTCTTTTGATTCTGGAATAGGTAAGGATTTTGAAGATGGTAAATT GACATTGGAACAAGTTTATGAATATGGTAAGAGAAATGGAGAACCAAAACAAACT TCTGGTAAACAAGAATTATATGAGGCTATAGTAGCTATGTATCAAtaa (SEQ ID NO: 263) |
| PEP Carboxylase (PEPC-Native) | Zymomonas mobilis | ATCC 31821 | ACTAGTAAAAAATGACCAAGCCGCGCACAATTAATCAGAACCCAGACCTTCGC TATTTGGTAACCTGCTCGGTCAGGTTATTAAGGAACAAGGCGGAGAGTCTTTAT TCAACCAGATCGAGCAAATTCGCTCTGCCGCGATTAGACGCCATCGGGTATTG TGACAGCCACCGAGCTAAGTTCTCGCTTAGCCGATCTCGACCTTAATGACATGT TCTCTTTTGCACATGCCTTTTGCTGTCTGTTTTCAATGCTGGCCAATTGGCTGATGA TCGTCAGGGAGATGCCCTTGATCGTGATGCCAATATGGCAAGTGCCCTTAAGGA CATAAAAGCCAAAGGCGTCAGTTCGACAGCACATCCGACGAGTCATTGATATGACAAAGC CTGCATTGTCCTGTTTGACAGCACATCCGAGCGTTAATGCGTTAAAGATGCTGGACAA ACGTGACCAAGATGGTCTTCCGATGCAAGAATGCGTTAATCAGCAAATCACG AIATTATGGCAGACTCGTCCGCTCATGCTGCAAAAGCTGACCGTGACTGATGAA ATCGAAACTGCCCTGCTTCGCCGCATGCAAGCTGAAGCTGAAGAATCTCTTATCAGACC TGCAATTGGATTGGTGAACGTGACGGTAACCCCATGCATGCAATGCCAGACC TGCAATTGCGTCTTTGAAGCGCAGCTCCGAGAAAACGGTATTGACGGATTATCCAA CCGTTCTTGATAACTGCTTTCAAACCTTTCGGTCAACCTTTGGTCTGACCGATATGTTTCGTA TCCGATGATATTCTACGTCTAGCCGCAATAAAAGTGGTGACGATGCTGCCAGCCGT GCGGATGAACCTTACGTCGTGCCTGCCATGAAAGGTATTTATGACCGTTTAGCCGCTA CCTATCGTCAGATCAAACGCCCGTCCAGATCGCCCAGCCTTGCGTTCTGCA GAAGCCTATAACGGCTTCAAGAATTGCTGGCTAGTTTAAGGCATTGATCCGTTGGTTGAA ACCTTTGGTTTCCATTTGGCAGAAGGTAGTTTTAAGGGATTTCGCAGGTTCAT GAAAGAGTTGTCAATGAACTGCTACGGACCAGCCACCGTTGAAGCCGATTATTTA TCTCTATCCGAAGAAGATCGCCTTAAGCTGTTAAGACGGAATTGTCGCAGCCG CGGACTCTATTTGAAGCATTCGCCGCGCCGATTATCCGAAGAAAACGCGTTCGAACTT GATATTATTCAGGCAGCCAGCCCCCATGCAGCTTTGGCCCTGAATCCATT ACGACTTATTTGATTTCGAATGCGAAAGCATTTCGATATTCGATGAAGTCTATT |

| Gene Name | Organism/ ATCC identifier | Nucleic acid Accession No. or other identifier | Nucleotide Sequence |
|---|---|---|---|
| | | | TGCTTTTGAAAGAAGCAGGGCTGTATCAAGGGGTGTAAGCCAAAGCGCG<br>AATTGAAGCTGCGCCTTTATTCGAGACGTGGCCGATCTGAAAATGCGCCAAAG<br>GTCATGGAGGAATGGTTCAAGCTGCCTGAAGCCAATCTGCAAAGGCACA<br>TGGCGTTCAGGAAGTGATGGTTGGCTATTCTGACTCCAATAAGGACGGCGATA<br>TCTGACCTCGGTTTGGGGTCTTTATAAGGCTTGCCTCGCTTTGGTGCCGATTTTT<br>GAGAAAGCCGGTGTACCGATCCAGTTTTTCCATGGACGGGGTGGTTCCGTTGG<br>TCGCGGTGGTGGTCCAACTTTAATGCCATTCTGTCGCAGCCAGCGAGCCG<br>TCAAAGGGCGTATCCGTTATACAGAACAGGGTGAAGTCTGGCGGCCAAATAT<br>GGCACCCATGAAAGCGTATTGCCCATCTGGATGAGGCCTGGCGGCGACTTT<br>GATTACGTCTTTGAAGCACCGACCATTGTCGAGCCAGAGTTTAGTCGTTACCG<br>TAAGGCCTTGGATCAGATCTCAGATTCAGCTTCCAGCCTATCGCCAATTGT<br>CTATGGAACGAAGGGCTTCCGTAAATTCTTTAGTGAATTACCGCCTTTGCCGAA<br>AATTGCCCTGTTAAAGATCTACGGCTATTCCTTGGGTGTTTAGCTGGTCTCAAGTTCGACT<br>CATGTTACCCGGCTGGTTCGGTTTCAGGCTTTATATGACTTTGAAGATACC<br>GAGCTGTTTACAGGAAATGGCAAGCCGTTGGCCGTTTTTCCGCACGACTATTCGG<br>AATATGGAACAGGTGATGGCACGTTCCGATATGACAGATCGCCAAGCATTATCTG<br>GCCTTGGTTGAGGATCAGCAAATGGTGAGGCTATCTATGATTCTATCGCGAT<br>GGCTGGAATAAAGGTTGTGAAGGTCTGTTAAAGGCAACCCAGCAGAATTGGCTG<br>TTGGAACGCTTTCCGGCCGTTGATAATTCGGTGCAGATGCGTCGGCCTTATCTG<br>GAACCGCTTAATTACTTACAGGTCGAATTGCTGAAGAAATGCTGAAGAAATGGCGGGAGGTGAT<br>ACCAACCCGCATATCCTCGAATCTATTCAGCTGACAATCAATGCCATTGCGACG<br>GCACTTCCAACGCGGTTAATAACTCGAG (SEQ ID NO: 264) |
| PEP Carboxylase (PEPC-HR) | Based on Zymomonas mobilis | | ACTAGTAAAAAAATGACCAAGCCAAGACTATTAACCAAAACCCAGACTTGAGAT<br>ACTTCGGTAACTTGTTGGGTCAAGTTATCAAGGAACAAGGTGTGAATCTTTGTT<br>CAACCAAATTGAACAAATCAGATCCGCTGCTATTAGAGAACAGAGGTATCGT<br>CGACTCTACCGAATTGTCCTCTAGATTGGCTGTCTGACTTGAACGACATGTT<br>CTCCTTCGCTCACGCTTTCTTGTTCTCTATGTTGGCTAACTTGGCTGACGAC<br>AGACAAGGTGACCGTTTGGACCCAGACGCTAACATGGCTTCCGCTTTGAAGGA<br>CATTAAGGCTAAGGTGTTTCTCAACAAGCTATCATTGACTGATCGACAAGGCT<br>TGTATTGTCCCAGTTTTGACTGCTGACTCACCCAACCGAAGTCAGAAGAAGTCCATG<br>TTGGACCACTACAACAGAATCGCTGGTTTGATGAGATTGAAGGACGCTGGTCAA<br>ACTGTTACCGAAGACGGTTTGCCAATTGAAGAACGCTTTGATCCAACAAATTACTA<br>TCTTGTGCAAACCAGACCATTGATGTTGCAAAAGTTGACTGTCGCTGACGAAA<br>TTGAAACCGCTTGTCTTCTTTGAGAGAAACTTCTTGTCCAGTTTGCCACAAAT<br>CTACGCTGAATGGGAAAAGTTGTTGGGTTCCTCTATTCCATCCTTCATCAGACCA<br>GGTAACTGGATTGGTGGTGACAGAGAGATCCTGAAACTGTTTTGACGACTACTTGAAC<br>CATCATGTTGTCTTTGAAGAGATCCTCTGAAACTGTTTTGACGACTACTTGAAC<br>AGATTGACAAGTTGTTCAACTTGTCTGTCTCCACTGACTTGTTTTCTGTCT<br>CCGACGACATTTTGAGATTGGCTGACAAGTCTGGTGACGACGTGCTATCAGAG<br>CTGACGAACCATACAGAAGAGCTTTGAACGGTATTTACGACAGATTGGCTGCTA<br>CCTACAGACAAATCGCTGGTAGACAAATCGTGCTGACTTGAGATCTGCTG<br>AAGCTTACAAGAGACCACAAGAATTGTTGGCTGACTTGAAGACTTTGGCTGAAG<br>GTTTGGGTAAGTTGGCTGAAGGTTCCTTGAGACTTGAGACAAAACTCCCAAGTCCACGA<br>CTTCGGTTTCCACTTGGCTACTTTGGACTTGAGAACCGCTACTGTTGAAGCTGACTACTTGTCT<br>AAGAGTTGTCAACGAATTGTTGAGAACAGAGTCAAGTTGTTGAGAAGAATTGTCTCAACCAGA<br>TTGTCCGAAGAAGACAGAGTCAAGTTGTTGAGAAGAATTGTCTCAACCAGA<br>ACCTTGTTCGTTCAAGAGCTGACTACTCCGAAGAAGAACTAGATCTGAATTGGAC |

-continued

| Gene Name | Organism/ ATCC identifier | Nucleic acid Accession No. or other identifier | Nucleotide Sequence |
|---|---|---|---|
| | | | ATCATTCAAGCTGCTGCTAGAGCTCAGAAATCTTCGTCCAGAATCCATTACCA CTTACTTGATCTCTAACGGTGAATCCATTCTGACATCTTGGAAGTCTACTTGTT GTTGAAGGAAGCTGGTTTGTACCAAGGTGGTGTAAGCAAAGGCTGCTATTGA AGCTGCTCCATTGTTCGAAACCGTTGCTGACTTGGAAAACGCTCCAAAGGTCAT GAAGAATGGTTCAAGTTGCCAGAAGCTCAAGCTATCGCTAAGGCTCACGGTGT TCAAGAAGTCATGGTTGTTACTCCGACTTGTTGGCTTTGGCTTTCAATTTCGAAAAG GCTGGTGTCCCAATCCAATTCTTCCACGGTAGAGGTGGTTCTGTTGGTAGAGGT GGTGGTTCCAACTTCAACGCTATTTTGTTCTCAACCACTGGTGCTGTCAAGGGT AGAATCCGATACACCGAACAAGGTGAAGTTGTCGCTGACTACGGTACTCAC GAATCCGCTATTGCTCTTGGACGAAGCTGTTGCTGCTACCTTGATCACTTCTT TGGAAGCTCCAACCATTGTCGAACCAGAATTCTCCAGATACAGAAAGGCTTTGG ACCAAATCTCTGACTCCGCTTTCTCTGAATTCACCCCATTGCCAGAACAATTGT GGGTTTCAGAAAGTTCTTCTGAGAAGAAGAGTCCGACAGAATTGAAGACTTG AAGATCGGTTCCGACACCACCATCGCTAGAAAGAAGTCCTAAGCACTACTTGGCTTGTCTGAAGG AGAGCTATCCCATGGGTCTTCTTGGTCTACGACTTAGAGTCATGTTGCCAGGT TGGTTCGGTTTCGGTCAAGCTTTGAAGGCTACCACCAAACAAACTGGTTGTTGGAACAAGG GAAATGGCTTCTAGATGCCATTCTTCAGAACCACTATTAGAAACATGGAACAAG TTATGGCTAGATCGCGACATGACCATCGCTAAGCACTACTGGCTTGCTTGTCGAAG ACCAAACTAACGGTGAAGCTATTTACGACTCTATCGCTGACGGTTGGAACAAG GTTGTGAAGGTTTGTTGACACCTCCGTCAATGAAGGCTACCAAATGAAGAAGACCATTACTTGGAACCATTGAACT CAGCTGTTGACAACTCCGTCCAACAAGCTGATGAAGATGAAGACCATTACTTGGAACCATTGAACT ACTTGCAAGTTGAATTGTTGAAGAAGTTGAAGGAGGTGGTGACACTAACCACACA TTTTGGAATCTATCCAATTGACCATTAACGCTATCGCTATCGCTTCTGCTTTGAGAAACTC CGGTTAATAACTCGAG (SEQ ID NO: 265) |
| EDA Primers | Zymomonas mobilis (ZM4) | 31821D-5 | 5'-aactgactagtaaaaaaatgcgtgatatcgattcc-3' (SEQ ID No: 1) 5'-agtaactcgagctactaggcaacagcgcgcttg-3' (SEQ ID No: 2) |
| EDD Primers | Zymomonas mobilis (ZM4) | 31821D-5 | 5'-aactgactagtaaaaaaatgactgactcgcattcaacg-3' (SEQ ID NO: 3) 5'-agtaactcgagctactagataccggcacctgcatatattgc-3' (SEQ ID NO: 4) |
| EDA Primers | Escherichia coli | | 5'-aactgactagtaaaaaaatgaaaactgaaaacaagtgcagaatc-3' (SEQ ID NO: 5) 5'-agtaactcgagctactacagttagcgccttctcacagttcacg-3' (SEQ ID NO: 6) |
| EDD Primers | Escherichia coli | | 5'-aactgactagtaaaaaaatgaatccacaagttacgcgtaacaaatg-3' (SEQ ID NO: 7) 5'-agtaactcgagctactaaaaagtgataacagggtgccccgttccggcac-3' (SEQ ID NO: 8) |
| PFK primers | Saccharomyces cerevisiae YGR240CBY4742 | 4015893 | 5'-tgcatattccgttcaatcttataagctgccataagtatttcacaccaagtcgttttaagagctcgttggtgagcgcta-3' (SEQ ID NO: 9) 5'-cttgcagtgaatgacctttggcattctcatgtttcatagtcgagttcaagagagaaaaagaa-3' (SEQ ID NO: 10) 5'-atgactgtactactcctttgtgaatgtactcttattgtaccgtcactgcatattccgtcaatccttataa-3' (SEQ ID NO: 11) 5'-ttaatcaactctctttcttcctccaaccaaatggtcagcaatgagtcgagttgccagtgaatgaccctttggcat-3' (SEQ ID NO: 12) |

-continued

| Gene Name | Organism/ ATCC identifier | Nucleic acid Accession No. or other identifier | Nucleotide Sequence |
|---|---|---|---|
| Thymidilate synthase (cdc21) | Saccharomyces cerevisiae strain 17206 | 208583 | CDC21_fwd: 5'-aatcgatcaaagcttctaaatacaagacgtgcgatgacgactatactggac-3' (SEQ ID NO: 52)<br>CDC21_rev: 5'-taccgtactacccgggtatatagtcttttgccctgtgttcctaataattc-3' (SEQ ID NO: 53)<br>ThymidylateSynthase::cdc21 fwd: 5'-ctaaatacaagacgtgcgatgacgactatactgg-3' (SEQ ID NO: 58)<br>ThymidylateSynthase::cdc21 rev: 5'-gtcaacaagaactaaaaatgttcaaaatgcaattgtc-3' (SEQ ID NO: 59). |
| LYS2 | BR214-4a | 208600 | Lys2Fwd: 5'-tgctaatgacccgggaattccactgcaattacataaaaattccggcgg-3' (SEQ ID NO: 54)<br>Lys2Rev: 5'-atgatcattgagctcagctcgcaagtattcatttagaccatggtgg-3' (SEQ ID NO: 55). |
| PEPC Primers | Zymomonas mobilis | | 5' forward (5'-GACTAACTGAACTAGTAAAAAAATGACCAAGCCGCCACAATTAATCAG-3' (SEQ ID NO: 13)<br>3' reverse (5'-AAGTGAGTAACTCGAGTTATTAACCGCTGTTGCGAAGTGCCGTCGC-3') (SEQ ID NO: 14). |

Provided hereafter are non-limiting examples of certain amino acid sequences.

| Gene Name | Organism/ATCC identifier | Amino acid Accession No. or other identifier | Amino Acid Sequence |
|---|---|---|---|
| Xylose Isomerase (XI-RF Native) | *Ruminococcus flavefaciens* strain 17 | CAB51938.1 | MEFFSNIGKIQYQGPKSTDPLSFKYYNPEEVINGKTMREHLKFALSWWHTMGGDGTDM FGCGTTDKTWGQSDPAARAKAKVDAAFEIMDKLSIDYYCFHDRDLSPEYGSLKATNDQL DIVTDYIKEKQGDKFKCLWGTAKCFDHPRFMHGAGTSPSADVFAFSAAQIKKALESTVKL GGNGYVFWGGREGYETLLNTNMGLELDNMARLMKMAVEYGRSIGFKGDFYIEPKPKEP TKHQYDFDTATVLGFLRKYGLDKDFKMNIEANHATLAQHTFQHELRVARDNGVFGSIDA NQGDVLLGWDTDQFPTNIYDTTMCMYEVIKAGGFTNGGLNFDAKARRGSFTPEDIFYSY IAGMDAFALGFRAALKLIEDGRIDKFVADRYASWNTGIGADIIAGKADFASLEKYALEKGEVT ASLSSGRQEMLESIVNNVLFSL (SEQ ID NO: 274) |
| Xylose isomerase (XI-P Native) | *Piromyces* sp. E2 | CAB76571.1 | MAKEYFPQIQKIKFEGKDSKNPLAFHYYDAEKEVMGKKMKDWLR FAMAWWHTLCAEGADQFGGGTKSFPWNEGTDAIEIAKQKVDAGFEIMQKLGIPYYCFH DVDLVSEGNSIEEYESNLKAVVAYLKEKQKETGIKLLWSTANVFGHKRYMNGASTNPD FDVVARAIVQIKNAIDAGIELGAENYVFWGGREGYMSLLNTDQKREKEHMATMLTMAR DYARSKGFKGTFLIEPKPMEPTKHQYDVDTETAIGFLKAHNLDKDFKVNIEVNHATLA GHTFEHELACAVDAGMLGSIDANRGDYQNGWDTDQFPIDQYELVQAWMEIIRGGGFVT GGTNFDAKTRRNSTDLEDIIIAHVSGMDAMARALENAAKLLQESPYTKMKKERYASFDSGI GKDFEDGKLTLEQVYEYGKKNGEPKQTSGKQELYEAIVAMYQ (SEQ ID NO: 275) |

Example 9

Activation of the Entner-Doudoroff Pathway in Yeast Cells Using edd and eda Genes from *Pseudomonas aeruginosa* Strain PAO1

*Pseudomonas aeruginosa* strain PAO1 DNA was prepared using Qiagen DNeasy Blood and Tissue kit (Qiagen, Valencia, Calif.) according to the manufacture's instructions. The *P. aeruginosa* edd and eda constructs were isolated from *P. aeruginosa* genomic DNA using the following oligonucleotides:

The *P. aeruginosa* edd gene:
(SEQ ID NO: 63)
5'-aactgaactgactagtaaaaaaatgcaccctcgtgtgctcgaagt-3'

(SEQ ID NO: 64)
5'-agtaaagtaaaagcttctactagcgccagccgttgaggctct-3'

The *P. aeruginosa* edd gene with 6-HIS c-terminal tag (SEQ ID NO: 35):
(SEQ ID NO63)
5'-aactgaactgactagtaaaaaaatgcaccctcgtgtgctcgaagt-3'

(SEQ ID NO: 65)
5'-agtaaagtaaaagcttctactaatgatgatgatgatgatggcgcc agccgttgaggctc-3'

The *P. aeruginosa* eda gene:
(SEQ ID NO: 66)
5'-aactgaactgactagtaaaaaaatgcacaaccttgaacagaagacc-3'

(SEQ ID NO: 67)
5'-agtaaagtaactcgagctattagtgtctgcggtgctcggcgaa-3'

The *P. aeruginosa* eda gene with 6-HIS c-terminal tag (SEQ ID NO: 35):
(SEQ ID NO: 66)
5'-aactgaactgactagtaaaaaaatgcacaaccttgaacagaagacc-3'

(SEQ ID NO: 68)
5'-taaagtaactcgagctactaatgatgatgatgatggtgtctgcg gtgctcggcgaa-3'

All oligonucleotides set forth above were purchased from Integrated technologies ("IDT", Coralville, Iowa). These oligonucleotides were designed to incorporate a SpeI restriction endonuclease cleavage site upstream of a HindIII restriction endonuclease cleavage site or downstream of an XhoI restriction endonuclease cleavage site, with respect to the edd and eda gene constructs. These restriction endonuclease sites could be used to clone the edd and eda genes into yeast expression vectors p426GPD (ATCC accession number 87361) and p425GPD (ATCC accession number 87359). In addition to incorporating restriction endonuclease cleavage sites, the forward oligonucleotides also incorporate six consecutive A nucleotides (e.g., AAAAAA) immediately upstream of the ATG initiation codon. The six consecutive A nucleotides ensured that there was a conserved ribosome binding sequence for efficient translation initiation in yeast.

PCR amplification of the genes were performed as follows: about 100 ng of the genomic *P. aeruginosa* PAO1 DNA was added to 1×Pfu Ultra II buffer, 0.3 mM dNTPs, 0.3 µmol gene-specific primers (SEQ. ID. NOS: 63-68, and combinations as indicated), and 1 U Pfu Ultra II polymerase (Agilent, La Jolla, Calif.) in a 50 µl reaction mix. This was cycled as follows: 95° C. 10 minutes followed by 30 rounds of 95° C. for 20 seconds, 50° C. (eda amplifications) or 53° C. (edd amplifications) for 30 seconds, and 72° C. for 15 seconds (eda amplifications) or 30 seconds (edd amplifications). A final 5 minute extension reaction at 72° C. also was included. The about 670 bp (eda) or 1830 bp product (edd) was TOPO cloned into the pCR Blunt II TOPO vector (Life Technologies, Carlsbad, Calif.) according to the manufacturer's recommendations.

The nucleotide and amino acid sequences of the *P. aeruginosa* edd and eda genes are given below as SEQ ID NOS. 69-72.

*P. aeruginosa* edd nucleotide sequence:

SEQ ID NO: 69

ATGCACCCTCGTGTGCTCGAAGTCACCCGCCGCATCCAGGCCCGTAGCGCGGCCACTCGCC

AGCGCTACCTCGAGATGGTCCGGGCTGCGGCCAGCAAGGGGCCGCACCGCGGCACCCTGC

CGTGCGGCAACCTCGCCCACGGGGTCGCGGCCTGTGGCGAAAGCGACAAGCAGACCCTGC

GGCTGATGAACCAGGCCAACGTGGCCATCGTTTCCGCCTACAACGACATGCTCTCGGCGCAC

CAGCCGTTCGAGCGCTTTCCGGGGCTGATCAAGCAGGCGCTGCACGAGATCGGTTCGGTCG

GCCAGTTCGCCGGCGGCGTGCCGGCCATGTGCGACGGGGTGACCCAGGGCGAGCCGGGCA

TGGAACTGTCGCTGGCCAGCCGCGACGTGATCGCCATGTCCACCGCCATCGCGCTGTCTCA

CAACATGTTCGATGCAGCGCTGTGCCTGGGTGTTTGCGACAAGATCGTGCCGGGCCTGCTGA

TCGGCTCGCTGCGCTTCGGCCACCTGCCCACCGTGTTCGTCCCGGCCGGGCCGATGCCGAC

CGGCATCTCCAACAAGGAAAAGGCCGCGGTGCGCCAACTGTTCGCCGAAGGCAAGGCCACT

CGCGAAGAGCTGCTGGCCTCGGAAATGGCCTCCTACCATGCACCCGGCACCTGCACCTTCTA

TGGCACCGCCAATACCAACCAGTTGCTGGTGGAGGTGATGGGCCTGCACTTGCCCGGTGCC

TCCTTCGTCAACCCGAACACCCCCTGCGCGACGAACTCACCCGCGAAGCGGCACGCCAGG

CCAGCCGGCTGACCCCCGAGAACGGCAACTACGTGCCGATGGCGGAGATCGTCGACGAGAA

GGCCATCGTCAACTCGGTGGTGGCGCTGCTCGCCACCGGCGGCTCGACCAACCACACCCTG

CACCTGCTGGCGATCGCCCAGGCGGCGGGCATCCAGTTGACCTGGCAGGACATGTCCGAGC

TGTCCCATGTGGTGCCGACCCTGGCGCGCATCTATCCGAACGGCCAGGCCGACATCAACCA

CTTCCAGGCGGCCGGCGGCATGTCCTTCCTGATCCGCCAACTGCTCGACGGCGGGCTGCTT

CACGAGGACGTACAGACCGTCGCCGGCCCCGGCCTGCGCCGCTACACCCGCGAGCCGTTC

CTCGAGGATGGCCGGCTGGTCTGGCGCGAAGGGCCGGAACGGAGTCTCGACGAAGCCATC

CTGCGTCCGCTGGACAAGCCGTTCTCCGCCGAAGGCGGCTTGCGCCTGATGGAGGGCAACC

TCGGTCGCGGCGTGATGAAGGTCTCGGCGGTGGCGCCGGAACACCAGGTGGTCGAGGCGC

CGGTACGGATCTTCCACGACCAGGCCAGCCTGGCCGCGGCCTTCAAGGCCGGCGAGCTGGA

GCGCGACCTGGTCGCCGTGGTGCGTTTCCAGGGCCCGCGGGCGAACGGCATGCCGGAGCT

GCACAAGCTCACGCCGTTCCTCGGGGTCCTGCAGGATCGTGGCTTCAAGGTGGCGCTGGTC

ACCGACGGGCGCATGTCCGGGGCGTCGGGCAAGGTGCCCGCGGCCATCCATGTGAGTCCG

GAAGCCATCGCCGGCGGTCCGCTGGCGCGCCTGCGCGACGGCGACCGGGTGCGGGTGGAT

GGGGTGAACGGCGAGTTGCGGGTGCTGGTCGACGACGCCGAATGGCAGGCGCGCAGCCTG

GAGCCGGCGCCGCAGGACGGCAATCTCGGTTGCGGCCGCGAGCTGTTCGCCTTCATGCGCA

ACGCCATGAGCAGCGCGGAAGAGGGCGCCTGCAGCTTTACCGAGAGCCTCAACGGCTGGCG

CTAGTAG

*P. aeruginosa* edd amino sequence:

SEQ ID NO: 70

MHPRVLEVTRRIQARSAATRQRYLEMVRAAASKGPHRGTLPCGNLAHGVAACGESDKQTLRLMN

QANVAIVSAYNDMLSAHQPFERFPGLIKQALHEIGSVGQFAGGVPAMCDGVTQGEPGMELSLASR

DVIAMSTAIALSHNMFDAALCLGVCDKIVPGLLIGSLRFGHLPTVFVPAGPMPTGISNKEKAAVRQL

FAEGKATREELLASEMASYHAPGTCTFYGTANTNQLLVEVMGLHLPGASFVNPNTPLRDELTREA

ARQASRLTPENGNYVPMAEIVDEKAIVNSVVALLATGGSTNHTLHLLAIAQAAGIQLTWQDMSELS

HVVPTLARIYPNGQADINHFQAAGGMSFLIRQLLDGGLLHEDVQTVAGPGLRRYTREPFLEDGRLV

WREGPERSLDEAILRPLDKPFSAEGGLRLMEGNLGRGVMKVSAVAPEHQVVEAPVRIFHDQASLA

AAFKAGELERDLVAVVRFQGPRANGMPELHKLTPFLGVLQDRGFKVALVTDGRMSGASGKVPAAI

-continued

HVSPEAIAGGPLARLRDGDRVRVDGVNGELRVLVDDAEWQARSLEPAPQDGNLGCGRELFAFM

RNAMSSAEEGACSFTESLNGWR

P. aeruginosa eda nucleotide sequence:
SEQ ID NO: 71
ATGCACAACCTTGAACAGAAGACCGCCCGCATCGACACGCTGTGCCGGGAGGCGCGCATCC

TCCCGGTGATCACCATCGACCGCGAGGCGGACATCCTGCCGATGGCCGATGCCCTCGCCGC

CGGCGGCCTGACCGCCCTGGAGATCACCCTGCGCACGGCGCACGGGCTGACCGCCATCCG

GCGCCTCAGCGAGGAGCGCCCGCACCTGCGCATCGGCGCCGGCACCGTGCTCGACCCGCG

GACCTTCGCCGCCGCGGAAAAGGCCGGGGCGAGCTTCGTGGTCACCCCGGGTTGCACCGA

CGAGTTGCTGCGCTTCGCCCTGGACAGCGAAGTCCCGCTGTTGCCCGGCGTGGCCAGCGCT

TCCGAGATCATGCTCGCCTACCGCCATGGCTACCGCCGCTTCAAGCTGTTTCCCGCCGAAGT

CAGCGGCGGCCCGGCGGCGCTGAAGGCGTTCTCGGGACCATTCCCCGATATCCGCTTCTGC

CCCACCGGAGGCGTCAGCCTGAACAATCTCGCCGACTACCTGGCGGTACCCAACGTGATGT

GCGTCGGCGGCACCTGGATGCTGCCCAAGGCCGTGGTCGACCGCGGCGACTGGGCCCAGG

TCGAGCGCCTCAGCCGCGAAGCCCTGGAGCGCTTCGCCGAGCACCGCAGACACTAATAG

P. aeruginosa eda amino sequence:
SEQ ID NO: 72
MHNLEQKTARIDTLCREARILPVITIDREADILPMADALAAGGLTALEITLRTAHGLTAIRRLSEERPH

LRIGAGTVLDPRTFAAAEKAGASFVVTPGCTDELLRFALDSEVPLLPGVASASEIMLAYRHGYRRF

KLFPAEVSGGPAALKAFSGPFPDIRFCPTGGVSLNNLADYLAVPNVMCVGGTWMLPKAVVDRGD

WAQVERLSREALERFAEHRRH

Cloning of PAO1 edd and eda Genes into Yeast Expression Vectors

Following sequence confirmation (GeneWiz), the about 670 bp SpeI-XhoI eda and about 1830 bp SpeI-HindIII edd fragments were cloned into the corresponding restriction sites in plasmids p425GPD and p426GPD vectors (Mumberg et al., 1995, Gene 156: 119-122; obtained from ATCC #87361; PubMed: 7737504), respectively. Briefly, about 50 ng of SpeI-XhoI-digested p425GPD vector was ligated to about 50 ng of SpeI/XhoI-restricted eda fragment in a 10 µl reaction with 1×T4 DNA ligase buffer and 1 U T4 DNA ligase (Fermentas) overnight at 16° C. About 3 µl of this reaction was used to transform DH5α competent cells (Zymo Research) and plated onto LB agar media containing 100 µg/ml ampicillin. Similarly, about 50 ng of SpeI-HindIII-digested p426GPD vector was ligated to about 42 ng of SpeI/HindIII-restricted edd fragment in a 10 µl reaction with 1×T4 DNA ligase buffer and 1 U T4 DNA ligase (Fermentas) overnight at 16° C. About 3 µl of this reaction was used to transform DH5α competent cells (Zymo Research) and plated onto LB agar media containing 100 µg/ml ampicillin.

A haploid Saccharomyces cerevisiae strain (BY4742; ATCC catalog number 201389) was cultured in YPD media (10 g Yeast Extract, 20 g Bacto-Peptone, 20 g Glucose, 1 L total) at about 30° C. Separate aliquots of these cultured cells were transformed with a plasmid construct(s) containing the eda gene alone, the eda and edd genes, or with vector alone. Transformation was accomplished using the Zymo frozen yeast transformation kit (Catalog number T2001; Zymo Research Corp., Orange, Calif.). To 50 µl of cells was added approximately 0.5-1 µg plasmid DNA and the cells were cultured on SC drop out media with glucose minus leucine (eda), minus uracil and minus leucine (eda and edd) (about 20 g glucose; about 2.21 g SC drop-out mix [described below], about 6.7 g yeast nitrogen base, all in about 1 L of water); this mixture was cultured for 2-3 days at about 30° C. SC drop-out mix contained the following ingredients (Sigma); all indicated weights are approximate:

| | |
|---|---|
| 0.4 g | Adenine hemisulfate |
| 3.5 g | Arginine |
| 1 g | Glutamic Acid |
| 0.433 g | Histidine |
| 0.4 g | Myo-Inositol |
| 5.2 g | Isoleucine |
| 2.63 g | Leucine |
| 0.9 g | Lysine |
| 1.5 g | Methionine |
| 0.8 g | Phenylalanine |
| 1.1 g | Serine |
| 1.2 g | Threonine |
| 0.8 g | Tryptophan |
| 0.2 g | Tyrosine |
| 0.2 g | Uracil |
| 1.2 g | Valine |

Activity and Western Analyses

Cell lysates of the various EDD and EDA expressing strains were prepared as follows. About 50 to 100 ml of SCD-ura-leu media containing 10 mM MnCl2 was used to culture strains containing the desired plasmid constructs. When cultured aerobically, strains were grown in a 250 ml baffled shaker flask. When grown anaerobically, 400 µl/L Tween-80 (British Drug Houses, Ltd., West Chester, Pa.) plus 0.01 g/L Ergosterol (Alef Aesar, Ward Hill, Mass.) were added and the culture was grown in a 250 ml serum bottle outfitted with a butyl rubber stopper with an aluminum crimp cap. Each strain was inoculated at an initial $OD_{600}$ of about 0.2 and grown to an $OD_{600}$ of about 3-4. Cells were grown at 30° C. at 200 rpm.

Yeast cells were harvested by centrifugation at 1046×g (e.g., approximately 3000 rpm) for 5 minutes at 4° C. The supernatant was discarded and the cells were resuspended in 25 mL cold sterile water. This wash step was repeated once. Washed cell pellets were resuspended in 1 mL sterile water, transferred to 1.5 mL screw cap tube, and centrifuged at 16,100×g (e.g., approximately 13,200 rpm) for 3 minutes at 4° C.

Cell pellets were resuspended in about 800-1000 μl of freshly prepared lysis buffer (50 mM Tris-Cl pH 7.0, 10 mM $MgCl_2$, 1× protease inhibitor cocktail EDTA-free (Thermo Scientific, Waltham, Mass.) and the tube filled with zirconia beads to avoid any headspace in the tube. The tubes were placed in a Mini BeadBeater (Bio Spec Products, Inc., Bartlesville, Okla.) and vortexed twice for 30 seconds at room temperature. The supernatant was transferred to a new 1.5 mL microcentrifuge tube and centrifuged twice to remove cell debris at 16,100×g (e.g., approximately 13,200 rpm) for 10 minutes, at 4° C. Quantification of the lysates was performed using the Coomassie-Plus kit (Thermo Scientific, San Diego, Calif.) as directed by the manufacturer ('6-HIS' below disclosed as SEQ ID NO: 35).

| Strain | EDD | EDA |
|---|---|---|
| BF428 | p426GPD (vector control) | p425GPD (vector control) |
| BF604 | E. coli native | E. coli native |
| BF460 | E. coli native with 6-HIS | E. coli native with 6-HIS |
| BF591 | PAO1 native | PAO1 native |
| BF568 | PAO1 native with 6-HIS | PAO1 native with 6-HIS |
| BF592 | PAO1 native | E. coli native |
| BF603 | E. coli native | PAO1 native |

About 5-10 μg of total cell extract was used for SDS-gel [NuPage 4-12% Bis-Tris gels (Life Technologies, Carlsbad, Calif.)] electrophoresis and Western blot analyses.

SDS-PAGE gels were performed according to the manufacturer's recommendation using NuPage MES-SDS Running Buffer at 1× concentration with the addition of NuPage antioxidant into the cathode chamber at a 1× concentration. Novex Sharp Protein Standards (Life Technologies, Carlsbad, Calif.) were used as standards. For Western analysis, gels were transferred onto a nitrocellulose membrane (0.45 micron, Thermo Scientific, San Diego, Calif.) using Western blotting filter paper (Thermo Scientific) using a Bio-Rad Mini Trans-Blot Cell (BioRad, Hercules, Calif.) system for approximately 90 minutes at 40V. Following transfer, the membrane was washed in 1×PBS (EMD, San Diego, Calif.), 0.05% Tween-20 (Fisher Scientific, Fairlawn, N.J.) for 2-5 minutes with gentle shaking. The membrane was blocked in 3% BSA dissolved in 1×PBS and 0.05% Tween-20 at room temperature for about 2 hours with gentle shaking. The membrane was washed once in 1×PBS and 0.05% Tween-20 for about 5 minutes with gentle shaking. The membrane was then incubated at room temperature with the 1:5000 dilution of primary antibody (Ms mAB to 6×His Tag (SEQ ID NO: 35), AbCam, Cambridge, Mass.) in 0.3% BSA (Fraction V, EMD, San Diego, Calif.) dissolved in 1×PBS and 0.05% Tween-20 with gentle shaking.

Incubation was allowed to proceed for about 1 hour with gentle shaking. The membrane was then washed three times for 5 minutes each with 1×PBS and 0.05% Tween-20 with gentle shaking. The secondary antibody [Dnk pAb to Ms IgG (HRP), AbCam, Cambridge, Mass.] was used at 1:15000 dilution in 0.3% BSA and allowed to incubate for about 90 minutes at room temperature with gentle shaking. The membrane was washed three times for about 5 minutes using 1×PBS and 0.05% Tween-20 with gentle shaking. The membrane incubated with 5 ml of Supersignal West Pico Chemiluminescent substrate (Thermo Scientific, San Diego, Calif.) for 1 minute and then was exposed to a phosphorimager (Bio-Rad Universal Hood II, Bio-Rad, Hercules, Calif.) for about 10-100 seconds.

Figure 8A:
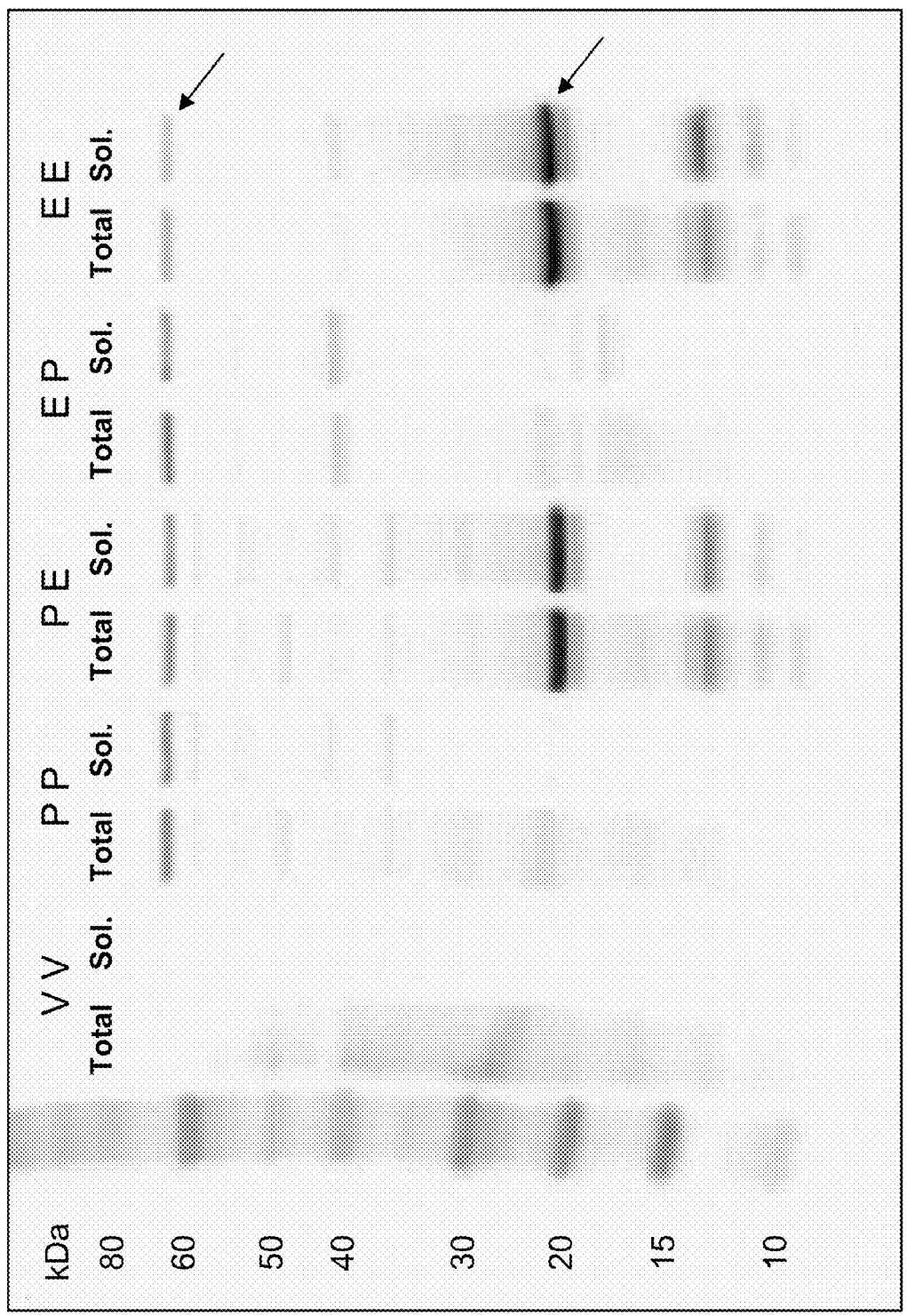
FIGS. 8A and 8B show representative Western blots used to detect levels of various exogenous EDD and EDA gene combinations expressed in a host organism. Experimental conditions and results are described in Example 9.
Figure 8B:
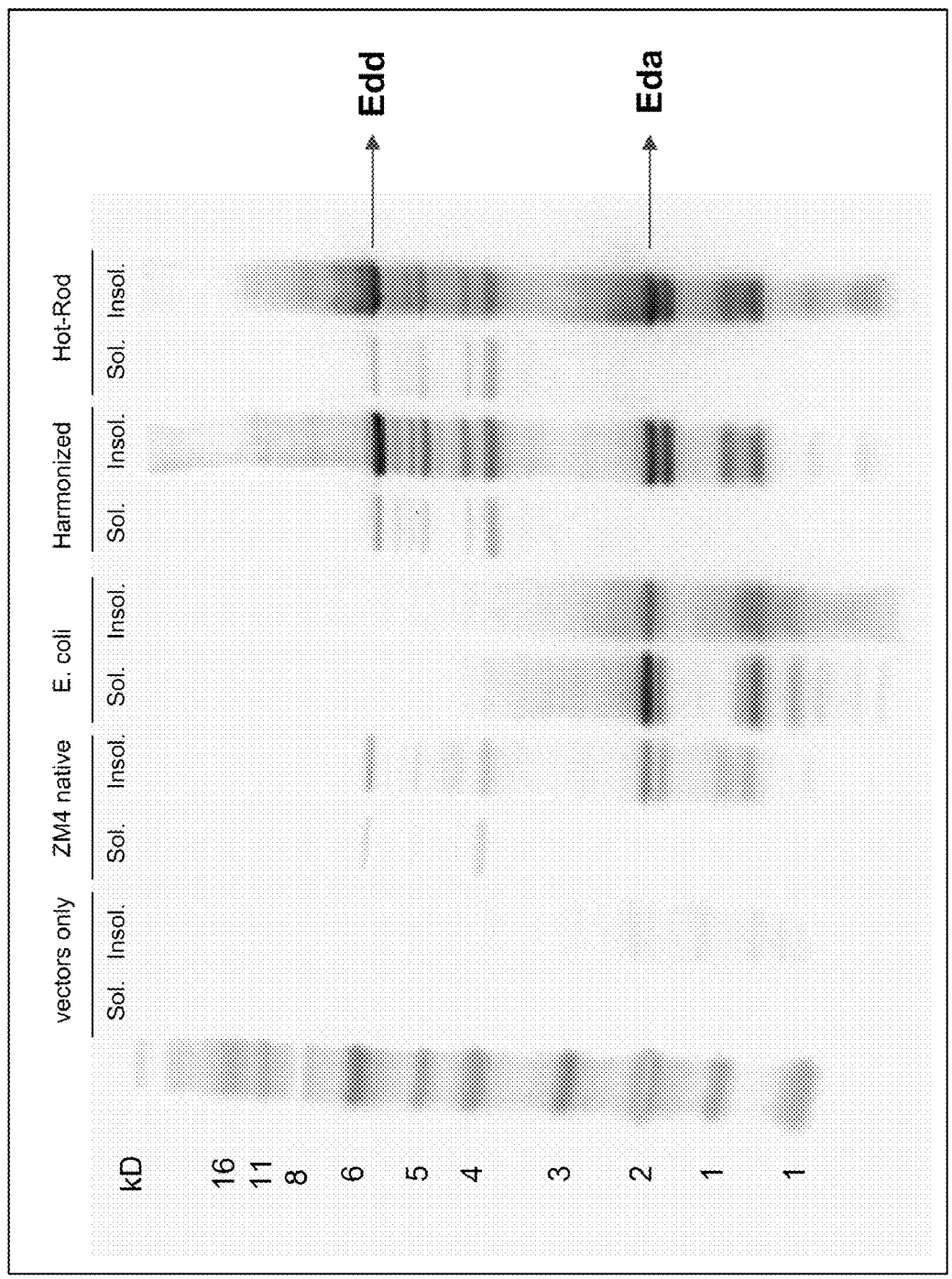

The results of the Western blots, shown in FIGS. 8A and 8B. Included in the expression data are engineered and/or optimized versions of certain eda and edd genes. The genes were modified to include a C-terminal HIS tag to facilitate purification. The two letters refer to the EDD and EDA source, respectively. P is from *P. aeruginosa*, PAO1, E is from *E. coli*, Z is from *Zymomonas mobilis* ZM4, hot rod is the optimized version of *Zymomonas mobilis*, Harmonized is the codon harmonized version of *Zymomonas mobilis*, V refers to the vector(s). Both total crude extract and the solubilized extract are shown. The results presented in FIGS. 8A and 8B indicate that the PAO1 EDD protein is expressed and soluble in *S. cerevisiae*. The results also demonstrate that the *E. coli* EDA protein is expressed and soluble. It was not clear from these experiments if the PAO1 EDA was soluble in yeast.

Example 10

EDD and EDA Activity Assays

Cell lysates of the various EDD and EDA expressing strains were prepared as follows. About 50 to 100 ml of SCD-ura-leu media containing 10 mM MnCl2 was used. When cultured aerobically, strains were grown in a 250 ml baffled shake flask. When grown anaerobically, 400 μl/L Tween-80 (British Drug Houses, Ltd., West Chester, Pa.) plus 0.01 g/L Ergosterol (Alef Aesar, Ward Hill, Mass.) were added and the culture was grown in a 250 ml serum bottle outfitted with a butyl rubber stopper with an aluminum crimp cap. Each strain was inoculated at an initial $OD_{600}$ of about 0.2 and grown to an $OD_{600}$ of about 3-4. Cells were grown at 30° C. at 200 rpm.

Yeast cells were harvested by centrifugation at 1046×g (3000 rpm) for 5 minutes at 4° C. The supernatant was discarded and the cells were resuspended in 25 mL cold sterile water. This wash step was repeated once. Washed cell pellets were resuspended in 1 mL sterile water, transferred to 1.5 mL screw cap tube, and centrifuged at 16,100×g (13,200 rpm) for 3 minutes at 4° C. Cell pellets were resuspended in about 800-1000 μl of freshly prepared lysis buffer (50 mM Tris-Cl pH 7.0, 10 mM $MgCl_2$, 1× protease inhibitor cocktail EDTA-free (Thermo Scientific, Waltham, Mass.) and the tube filled with zirconia beads to avoid any headspace in the tube. The tubes were placed in a Mini BeadBeater (Bio Spec Products, Inc., Bartlesville, Okla.) and vortexed twice for 30 seconds at room temperature. The supernatant was transferred to a new 1.5 mL microcentrifuge tube and centrifuged twice to remove cell debris at 16,100×g (13,200 rpm) for 10 minutes, at 4° C. Quantification of the lysates was performed using the Coomassie-Plus kit (Thermo Scientific, San Diego, Calif.) as directed by the manufacturer.

About 750 μg of crude extract was assayed using 1× assay buffer (50 mM Tris-Cl pH 7.0, 10 mM MgCl2), 3 U lactate dehydrogenase (5 μg/μL in 50 mM Tris-Cl pH 7.0), and 10 μl mM 6-phosphogluconate dissolved in 50 mM Tris-Cl pH 7.0 were mixed in a reaction of about 400 μl. This reaction mix was transferred to a 1 ml Quartz cuvette and allowed to incubate about 5 minutes at 30° C. To this reaction, 100 μl of 1.5 mM NADH (prepared in 50 mM Tris-Cl pH 7.0) was added, and the change in $Abs_{340nm}$ over the course of 5 minutes at 30° C. was monitored in a Beckman DU-800 spectrophotometer using the Enzyme Mechanism software package (Beckman Coulter, Inc, Brea, Calif.).

The table below presents the relative specific activities for BY4742 strains expressing EDD and EDA from either *P. aeruginosa* (PAO1) or *E. coli* sources. The results presented in the table below indicate that each of the listed combinations of EDD and EDA genes, when expressed in *S. cerevisiae* strain BY4742, confers activity.

| Gene Combination | Km ($M^{-1}$) | Vmax (mmol $min^{-1}$) | Specific Activity (mmol $min^{-1}$ $mg^{-1}$) |
|---|---|---|---|
| EDD-P/EDA-P | $1.04 \times 10^{-3}$ | 0.21930 | 0.3451 |
| EDD-P/EDA-E | $2.06 \times 10^{-3}$ | 0.27280 | 0.3637 |
| EDD-E/EDA-P | $1.43 \times 10^{-3}$ | 0.09264 | 0.1235 |
| EDD-E/EDA-E | $0.839 \times 10^{-3}$ | 0.16270 | 0.2169 |

Figure 9:
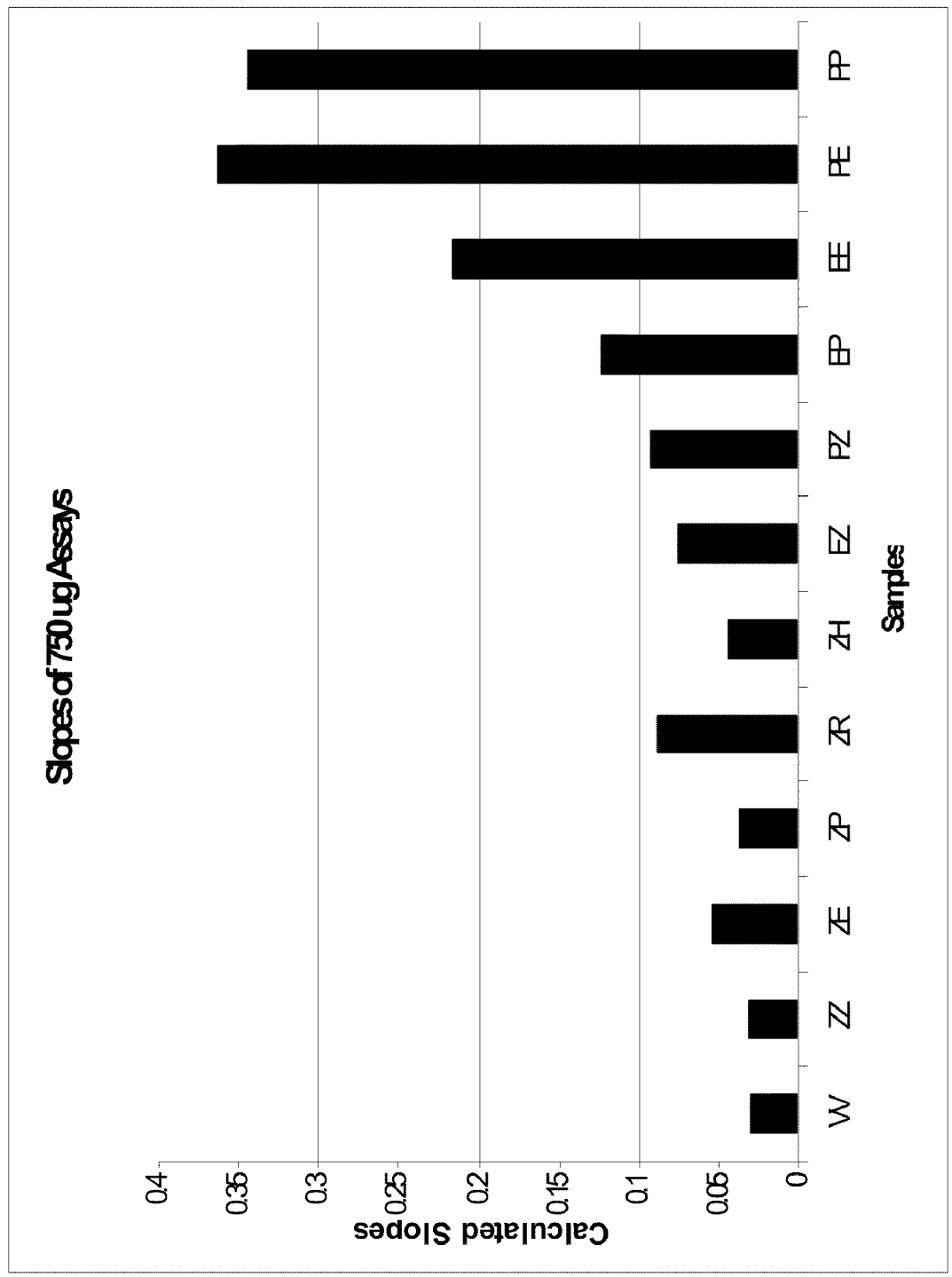
FIG. 9 graphically displays the relative activities of the various EDD/EDA combinations generated as described in Example 10.

The data presented above is also presented graphically in FIG. 9. FIG. 9 graphically displays the relative activities of the various EDD/EDA combinations presented in the table above, as measured in assays using 750 micrograms of crude extract. From the height of the PE bar in FIG. 9, and the data presented in the table above, it is evident that the combinations conferring the highest level of activity were the EDD-P/EDA-E (e.g., PE) and EDD-P/EDA-P (e.g., PP) combinations.

Example 11

Improved Ethanol Yield from Yeast Strains Expressing edd and eda Constructs

Figure 10:
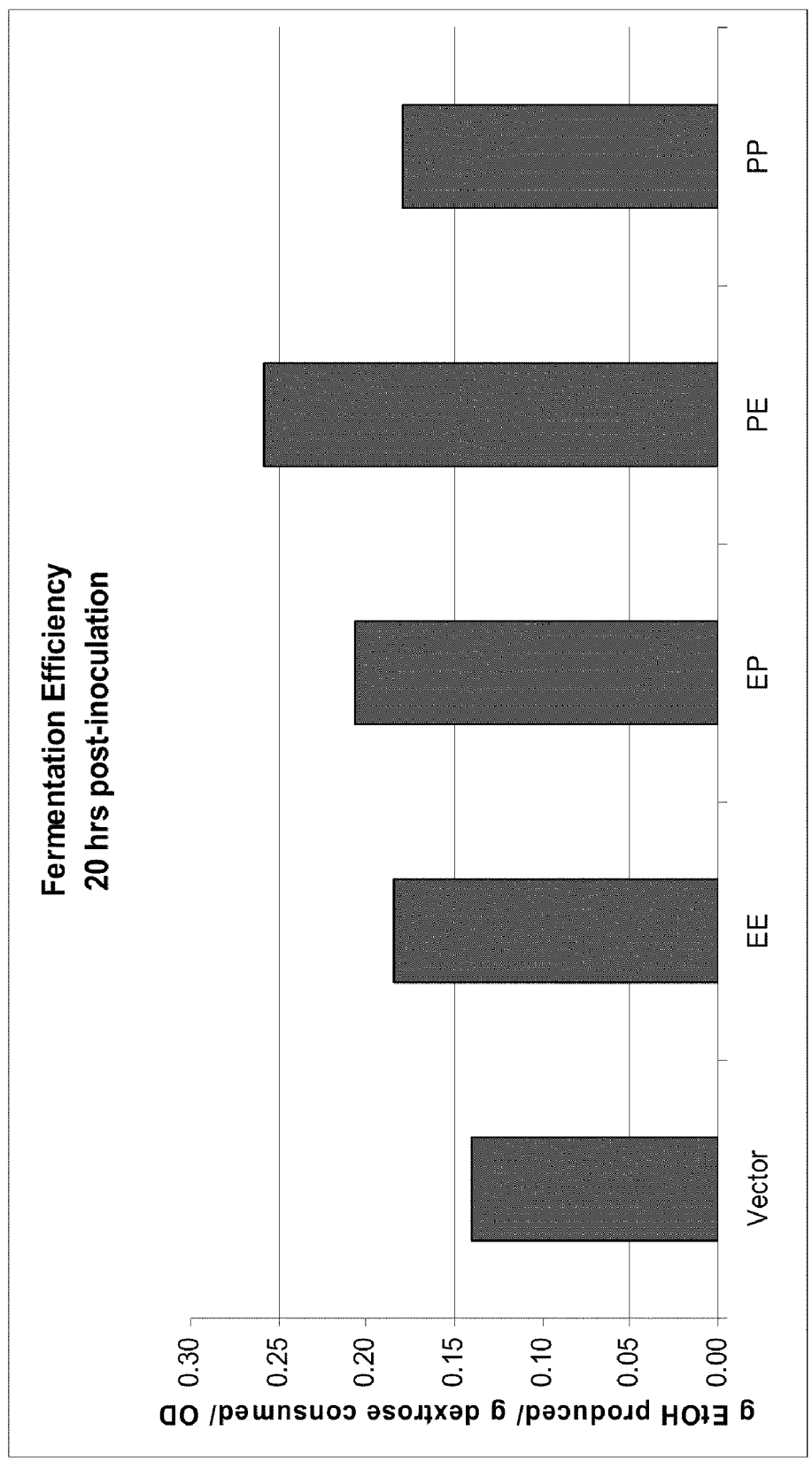
FIG. 10 graphically represents the fermentation efficiency of engineered yeast strains carrying exogenous EDD/EDA gene combinations. Vector=p426GPD/p425GPD; EE=EDD-*E. coli*/EDA-*E. coli*, EP=EDD-*E. coli*/EDA-PAO1; PE=EDD-PAO1/EDA-*E. coli*, PP=EDD-PAO1/EDA-PAO1. Experimental conditions and results are described in Example 11.

Strains BF428 (vector control), BF591 (EDD-PAO1/EDA-PAO1), BF592 (EDD-PAO1/EDA-*E. coli*), BF603 (EDD-*E. coli*/EDA-PAO1) and BF604 (EDD-*E. coli*/EDA-*E. coli*) were inoculated into 15 ml SCD-ura-leu media containing 400 μl/L Tween-80 (British Drug Houses, Ltd., West Chester, Pa.) plus 0.01 g/L Ergosterol (EMD, San Diego, Calif.) in 20 ml Hungate tubes outfitted with a butyl rubber stopper and sealed with an aluminum crimped cap to prevent oxygen from entering the culture at an initial $OD_{600}$ of 0.5 and grown for about 20 hours. Glucose and ethanol in the culture media were assayed using YSI 2700 BioAnalyzer instruments (world wide web uniform resource locator ysi.com), according to the manufacturer's recommendations at 0 and 20 hours post inoculation. The results of the fermentation of glucose to ethanol are showing graphically in FIG. 10. The results presented in FIG. 9 indicate that the presence of the EDD/EDA combinations in *S. cerevisiae* increase the yield of ethanol produced, when compared to a vector-only control. The EDD/EDA combinations that showed the greatest fermentation efficiency in yeast were EDD-P/EDA-E (e.g., PE) and EDD-E/EDA-P (e.g., EP).

Example 12

Improved Ethanol Yield from Yeast Strains Expressing EDD and EDA from PAO1 in Fermentors A fermentation test of the strain BF591 [BY4742 with plasmids pBF290 (p426GPD-EDD_PAO1) and pBF292 (p425GPD-EDA_PAO1)] was conducted against BF428 (BY4742 p426GPD/p425GPD) control strain in 700 ml w.v. Multifors multiplexed fermentors. The fermentation medium was SC-Ura-Leu with about 2% glucose. Vessels were inoculated with about a 6.25% inoculum from overnight cultures grown in about 50 ml SC-Ura-Leu with about 2% glucose.

The cultures were grown aerobically at about 30° C. with about 250 rpm agitation, 1 vvm sparge of process air, (21% O2). The pH was controlled at around 5.0 with 0.25 N NaOH. Once glucose concentrations dropped below 0.5 g/L the fermentation was switched to anaerobic conditions. Before changing to anaerobic conditions, samples were taken to measure glucose concentrations and biomass by $OD_{600}$ as reported in Table B. Ethanol and glucose concentrations in the fermentation broth were monitored using YSI 2700 BioAnalyzer instruments.

The table below presents the elapsed fermentation time (EFT), the biomass and glucose at the start of anaerobic fermentation in a 400 ml fermentor. The edd and eda combinations carried by the strains are described above.

| Strain | EFT (hrs) | $OD_{600\,nm}$ | Glucose (g/L) |
|---|---|---|---|
| BF591 | 32 | 4.50 | .047 |
| BF428 | 27 | 4.81 | .062 |

At the beginning of the anaerobic portion of the fermentation, a bolus of 20 g/L glucose plus 3.35 g/L of yeast nitrogen base without amino acids was added to the fermentors. In addition, 4 ml/L of 2.5 g/L ergosterol in ethanol, 0.4 ml/L Tween 80, and 0.01% AF-204 were added to each fermentor. Oxygen was purged with 100% N2 sparged at about 1 vvm until pO2 was below 1%.

Samples were taken every 2 to 7 hours and measured for ethanol and glucose concentrations and $OD_{600}$. The fermentation was harvested when the glucose concentration was below 0.05 g/L, at 50 hours elapsed fermentation time (EFT). Ethanol and glucose concentrations and $OD_{600}$ of the final sample are reported in the table below.

| Strain | $OD_{600\,nm}$ | Ethanol (g/L) | Glucose (g/L) |
|---|---|---|---|
| BF591 | 5.6 | 17.1 | .04 |
| BF428 | 5.6 | 15.8 | 0 |

Figure 11A:
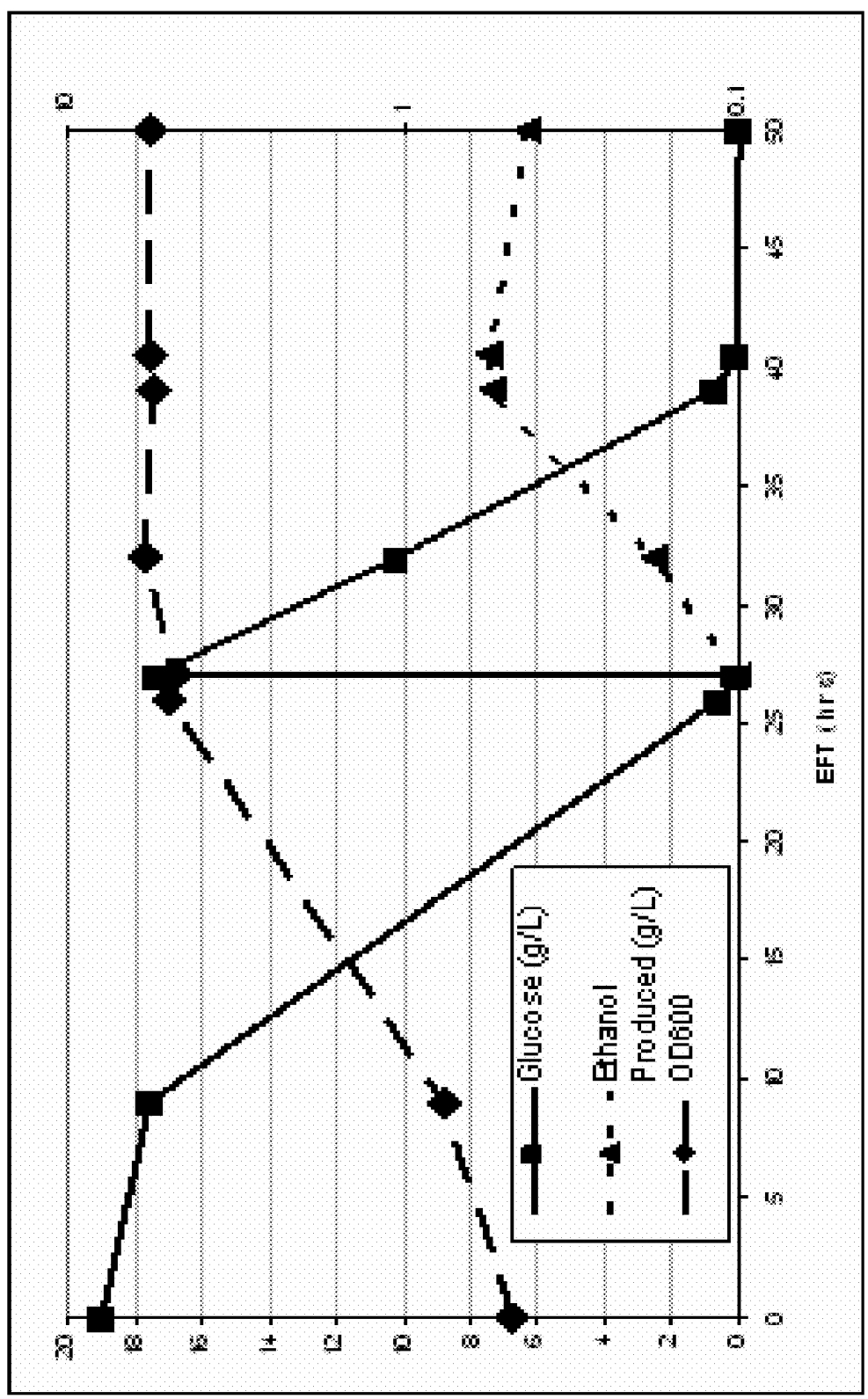
FIGS. 11A and 11B graphically illustrate fermentation data (e.g., cell growth, glucose usage and ethanol production) for engineered yeast strains generated as described herein.
Figure 11B:
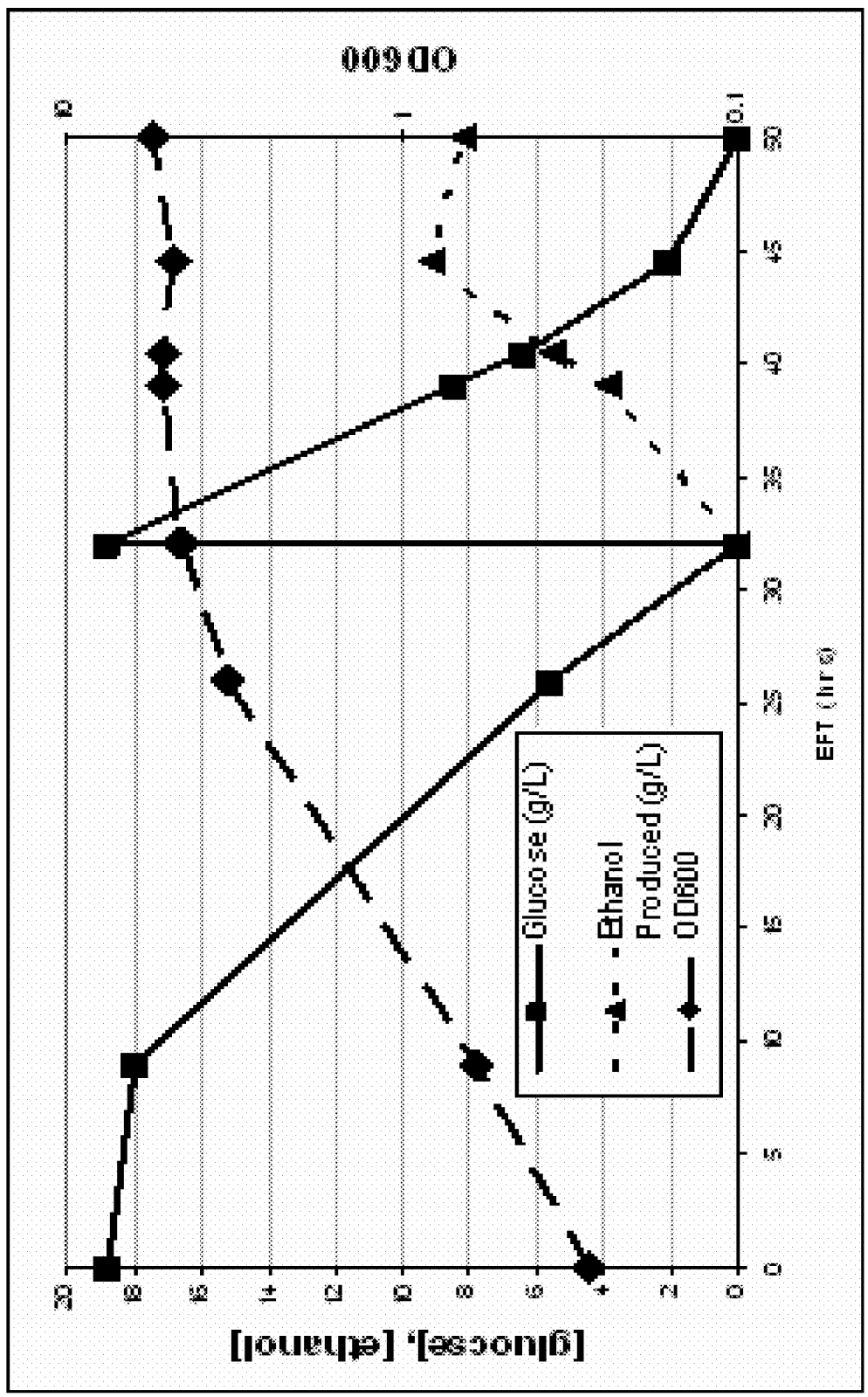

The data presented in the table above also is presented graphically in FIGS. 11A and 11B. FIG. 11A presents the fermentation data from strain BF428 (BY4742 with vector controls) and FIG. 11B presents the fermentation data from strain BF591 (BY4742 with EDD-PAO1/EDA-PAO1). Fermentation profiles for strains BF 428 and BF 591, grown on 2% dextrose, were calculated and are presented in the table below.

| Strain | Yx/s | Yp/s | Yp/x | Qp | qp |
|---|---|---|---|---|---|
| BF428 | 0.24 | 0.40 | 7.19 | 0.02 | 0.05 |
| BF591 | 0.23 | 0.43 | 7.44 | 0.02 | 0.07 |

Yx/s = OD/g glucose
Yp/s = g ethanol/g glucose
Yp/x = g ethanol/OD
Qp = g ethanol/$Lh^{-1}$
qp = g ethanol/$ODh^{-1}$ The results from the fermentation show that the BF591 has a higher ethanol yield (triangles, compare FIG. 11A and FIG. 11B) than the control BF428 strain. The calculated yield of ethanol was also determined to be higher in the engineered BF591 strain (0.43 g ethanol/g glucose) than that of the BF428 control strain (0.40 g ethanol/g glucose).

Example 13

Improved Ethanol Yield in a tal1 Strain of *S. cerevisiae* Expressing EDD and EDA from PAO1

To generate BY4741 and BY4742 tal1 mutant strains, the following procedure was used:

```
Oligonucleotides
#350
                                          (SEQ ID NO: 276)
5'-TAAAACGACGGCCAGTGAAT-3'

#351
                                          (SEQ ID NO: 277)
5'-TGCAGGTCGACTCTAGAGGAT-3'

#352
                                          (SEQ ID NO: 278)
5'-GTGTGCGTGTATGTGTACACCTGTATTTAATTTCCTTACTCGCG
GGTTTTTCTAAAACGACGGCCAGTGAAT-3'

#353
                                          (SEQ ID NO: 279)
5'-TGTACCAGTCTAGAATTCTACCAACAAATGGGGAAATCAAAGTA
ACTTGGGCTGCAGGTCGACTCTAGAGGA-3'
```

All oligonucleotides set forth above were purchased from Integrated Technologies ("IDT", Coralville, Iowa). PCR amplification of the genes were performed as follows: about 50 ng of the pBFU-719 DNA (e.g., plasmid with unique 200-mer sequence) was added to 1×Pfu Ultra II buffer, 0.3 mM dNTPs, 0.3 μmol gene-specific primers (#350/#351 in the first round), and 1 U Pfu Ultra II polymerase (Agilent, La Jolla, Calif.) in a 50 μl reaction mix. The reaction mixture was cycled as follows: 95° C. 10 minutes followed by 30 rounds of 95° C. for 20 seconds, 60° C. for 30 seconds, and 72° C. for 45 seconds. A final 5 minute extension reaction at 72° C. was also included. A second round of PCR amplification was done using 50 ng of the first round PCR amplification with 1×Pfu Ultra II buffer, 0.3 mM dNTPs, 0.3 μmol gene-specific primers (#352/#353 in the second round), and 1 U Pfu UltraII polymerase (Agilent, La Jolla, Calif.) in a 50 μl reaction mix. The second reaction mixture was cycled as follows: 95° C. 10 minutes followed by 30 rounds of 95° C. for 20 seconds, 60° C. for 30 seconds, and 72° C. for 45 seconds. A final 5 minute extension reaction at 72° C. was also included. The final PCR product was purified using the Zymo Research DNA Clean & Concentrator-25 kit (Zymo Research, Orange, Calif.).

Transformation was accomplished by a high-efficiency competency method. A 5 ml culture of the BY4742 or BY4741 strain was grown overnight at about 30° C. with shaking at about 200 rpm. A suitable amount of this overnight culture was added to 60 ml of YPD media to obtain an initial OD600 of about 0.2 (approximately 2×10$^6$ cells/ml). The cells were allowed to grow at 30° C. with agitation (about 200 rpm) until the $OD_{600}$ was about 1. The cells were then centrifuged at 3000 rpm for 5 min, washed with 10 ml sterile water and re-centrifuged. The cell pellet was resuspended in 1 ml sterile water, transferred to a 1.5 ml sterile microcentrifuge tube and spun down at 4000×g for about 5 minutes. This cell pellet was resuspended in 1 ml sterile 1×TE/LiOAC solution (10 mM Tris-HCl, 1 mM EDTA, 100 mM LiOAc, pH7.5) and re-centrifuged at about 4000×g for about 5 minutes. The cell pellet was resuspended in 0.25 ml 1×TE/LiOAc solution. For the transformation, 50 μl of these cells were aliquoted to a 1.5 ml microcentrifuge tube and about 1 μg purified PCR product and 5 μl of salmon sperm DNA that had been previously boiled for about 5 minutes and placed on ice. 300 μl of a sterile PEG solution was then added (40% PEG 3500, 10 mM Tris-HCl, 1 mM EDTA, 100 mM LiOAc, pH7.5). This mixture was allowed to incubate at 30° C. for about one hour with gentle mixing every 15 minutes. About 40 μl DMSO (Sigma, St. Louis, Mo.) was added to the incubating mixture, and the mixture heat shocked at about 42° C. for about 15 minutes. The cells were pelleted in a microcentrifuge at 13000 rpm for about 30 seconds and the supernatant removed. The cells were resuspended in 1 ml 1×TE (10 mM Tris-HCl, 1 mM EDTA, pH 7.5), centrifuged at 13000 rpm for about 30 seconds and resuspended in 1 ml 1×TE. About 100-200 μl of cells were plated onto SCD-URA media, as described above, and allowed to grow at about 30° C. for about 3 days. After 3 days, transformed colonies were streaked for single colonies on SCD-URA plates and allowed to grow at about 30° C. for about 3 days. From these plates, single colonies were streaked onto SCD agar plates (20 g/L agar in SCD media) containing 1 g/L 5-FOA (Research Products International Corp, Mt. Prospect, Ill.), and also inoculated into YPD liquid broth. The plates were allowed to grow at about 30° C. for about 4 days and the liquid culture was grown overnight at about 30° C. with agitation of about 200 rpm.

To confirm that integration of the construct was correct, genomic DNA was prepared from the YPD overnight cultures. Briefly, the yeast cells were pelleted by centrifugation at room temperature for 5 minutes at approximately 3000 rpm. The cell pellet was resuspended in 200 μl of breaking buffer (2% Triton X-100, 1% SDS, 100 mM NaCl, 10 mM Tris pH8, 1 mM EDTA) and placed into a 1.5 ml microcentrifuge tube containing about 200 μl glass beads and about 200 μl of phenol:chloroform:isoamyl alcohol (Ambion, Austin, Tex.). The mixture was vortexed for about 2 to 5 minutes at room temperature. About 200 μl of sterile water was then added and the mixture vortexed again. The mixture was centrifuged for about 10 minutes at about 13000 rpm and the aqueous layer transferred to a new microcentrifuge tube. About ⅒th of the aqueous layers volume of 3M NaOAc ((British Drug Houses, Ltd., West Chester, Pa.) was added to the aqueous layer and 2.5× the total volume of the mixture of ethanol was added and mixed well. The genomic DNA was then precipitated by placing the tubes at −80° C. for at least one hour (or in a dry ice/ethanol bath for about 30 minutes). The tubes were then centrifuged at about 13000 rpm for 5 minutes at about 4° C. to pellet the DNA. The DNA pellet was then washed two times or more times with about 200 μl of 70% ethanol and re-centrifuged. The DNA pellet was dried using vacuum assisted air drying and resuspended in about 50 to 200 μl 1×TE.

The genomic DNA isolated as described above was used in a PCR amplification reaction consisting of about 50 ng of the genomic DNA was added to 1×Pfu Ultra II buffer, 0.3 mM dNTPs, 0.3 μmol gene-specific primers (#276/#277), and 1 U Pfu UltraII polymerase (Agilent, La Jolla, Calif.) in a 50 μl reaction mix. The reaction mix was cycled as follows: 95° C. 10 minutes followed by 30 rounds of 95° C. for 20 seconds, 60° C. for 30 seconds, and 72° C. for 45 seconds. A final 5 minute extension reaction at 72° C. was also included. A second round of PCR amplification was done using 50 ng of the first round PCR amplification with 1×Pfu Ultra II buffer, 0.3 mM dNTPs, 0.3 μmol gene-specific primers (#352/#353 in the second round), and 1 U Pfu UltraII polymerase (Agilent, La Jolla, Calif.) in a 50 μl reaction mix. The second mixture was cycled as follows: 95° C. 10 minutes followed by 30 rounds of 95° C. for 20 seconds, 55° C. for 30 seconds, and 72° C. for about 30 seconds. A final 5 minute extension reaction at 72° C. was also included.

Positive colonies from the screen in YPD that had a PCR product of about 1600 bp indicating the insertion of the integration construct in the TAL1 locus, and that grew on the plates containing 5-FOA were grown overnight in YPD at about 30° C. with agitation of about 200 rpm. Genomic DNA was prepared as above and checked by PCR amplification using primers #276 and #277 (described below). Positive clones were identified which had a PCR product of 359 bp indicating the deletion of the tal1 locus and the remaining portion of the 200-mer tag. The strain carrying the correct traits was labeled as BF716. The BY4741 version was labeled as BF717.

```
Oligonucleotides
                                           (SEQ ID NO: 280)
#276      5'-GTCGACTGGAAATCTGGAAGGTTGGT-3'

(SEQ ID NO: 281)
#277      5'-GTCGACGCTTTGCTGCAAGGATTCAT-3'
```

The BY4742 tal1 strain was then made competent using the high efficiency competent method as described above. About 500 ng of plasmids pBF290 and pBF292 or with plasmids p426GPD and p425GPD were used to transform the BY4742 tal1 strain. The final transformation mixture was plated onto SCD-ura-leu plates and grown at about 30° C. for about 3 days. Strain BF716 (BY4742 tal1) with p426GPD/p425GPD was labeled as BF738. Strain BF716 with pBF290/pBF292 was labeled as BF741.

A fermentation test of the BF738 was conducted against BF741 in a 400 ml multiplexed fermentor. The fermentation medium utilized was SC-Ura-Leu with 2% glucose. Cultures were grown overnight in 50 ml SC-Ura-Leu 2% glucose and used to inoculate the fermentors at 4 to 5% inoculum. $OD_{600}$ readings of the inoculum are shown in the table below.

| Strain | $OD_{600\,nm}$ |
|---|---|
| BF741 (tal1 PP) | 3.70 |
| BF738 (tal1 VV) | 3.80 |

The cultures were grown aerobically at about 30° C. with about 250 rpm agitation, 0.5 vvm sparge of process air, 21% $O_2$. pH was controlled at 5.0 with 1N NaOH. Glucose concentrations in the fermentation broth were monitored by YSI 2700 BioAnalyzers during aerobic fermentation. Once glucose was depleted the fermentation was switched to anaerobic conditions. Before changing to anaerobic conditions samples were taken to measure glucose usage. Biomass was measured by monitoring the optical density of the growth medium at 600 nanometers (e.g., $OD_{600}$). EFT at glucose depletion, glucose concentrations and $OD_{600}$ are shown in the table below. The table below reports the amount of biomass in the fermentor and the amount of ethanol produced in grams per liter, after the specified amount of time (EFT), by the respective strains.

| Strain | EFT (hrs) | $OD_{600\,nm}$ | Glucose (g/L) |
|---|---|---|---|
| BF741 (tal1 PP) | 43.5 | 2.50 | 0.045 |
| BF738 (tal1 VV) | 31 | 2.95 | 0.192 |

At the beginning of anaerobic fermentation, about 19 g/L glucose, 3.7 g/L YNB, 4 ml/L of 2.5 g/L ergosterol (in ethanol), 0.4 ml/L Tween 80, and 0.01% AF-204 were added to each fermentor. Oxygen was purged with 100% $N_2$ sparged at 0.25 vvm for the remainder of the fermentation. Samples were taken every 4 to 12 hours and analyzed for ethanol production and glucose utilization using the YSI Bioanalyzers, and amount of biomass by $OD_{600}$. The fermentations were harvested when the glucose bolus was depleted. Anaerobic ethanol produced, anaerobic glucose consumption and $OD_{600}$ of the final sample are shown in the table below.

| Strain | $OD_{600\,nm}$ | Ethanol Produced (g/L) | Glucose Consumed (g/L) |
|---|---|---|---|
| BF741 (tal1 PP) | 3.75 | 8.1 | 18.99 |
| BF738 (tal1 VV) | 3.6 | 6.5 | 18.168 |

Figure 12A:
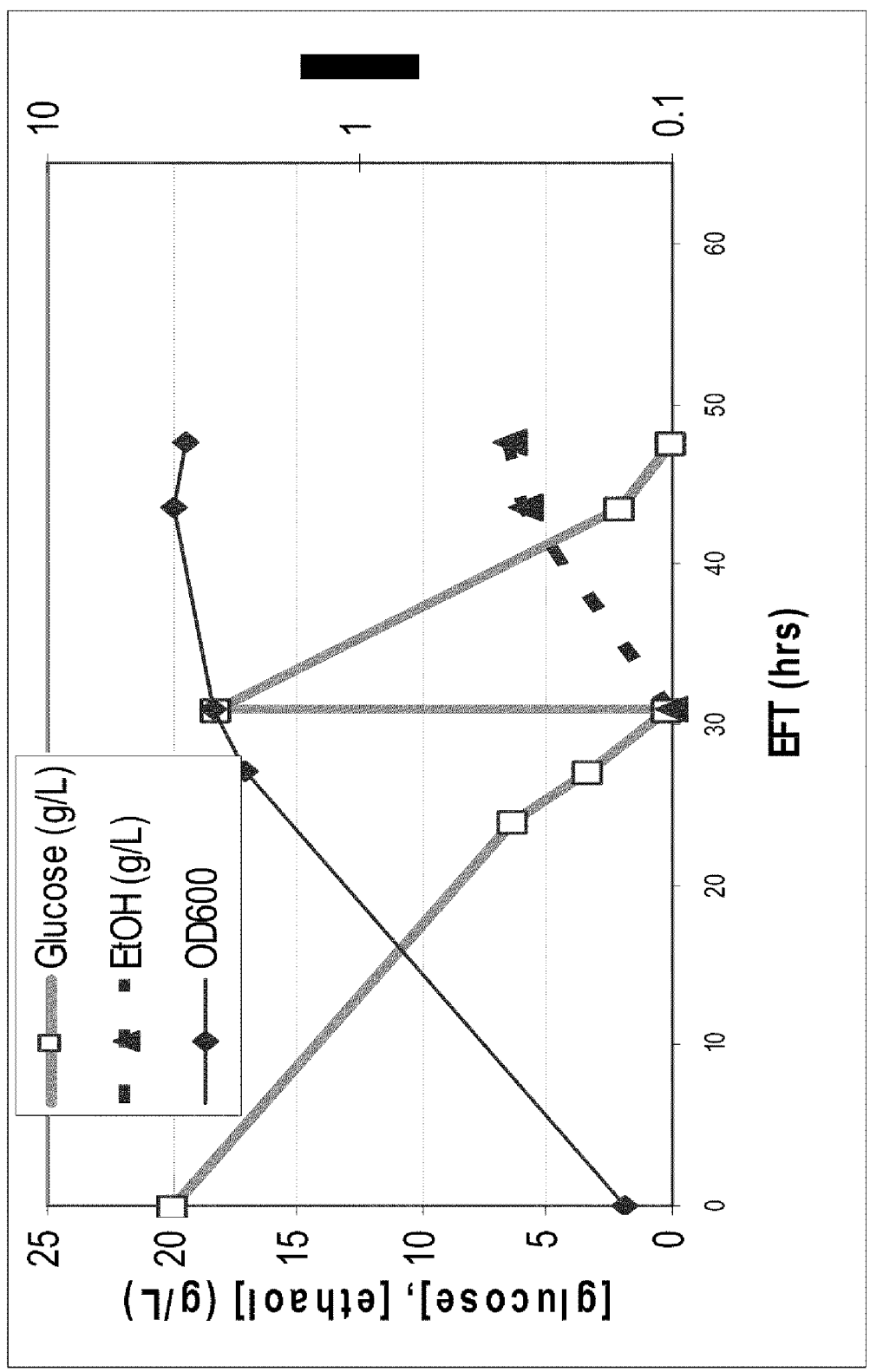
FIGS. 12A and 12B graphically illustrate fermentation data for engineered yeast strains described herein.
Figure 12B:
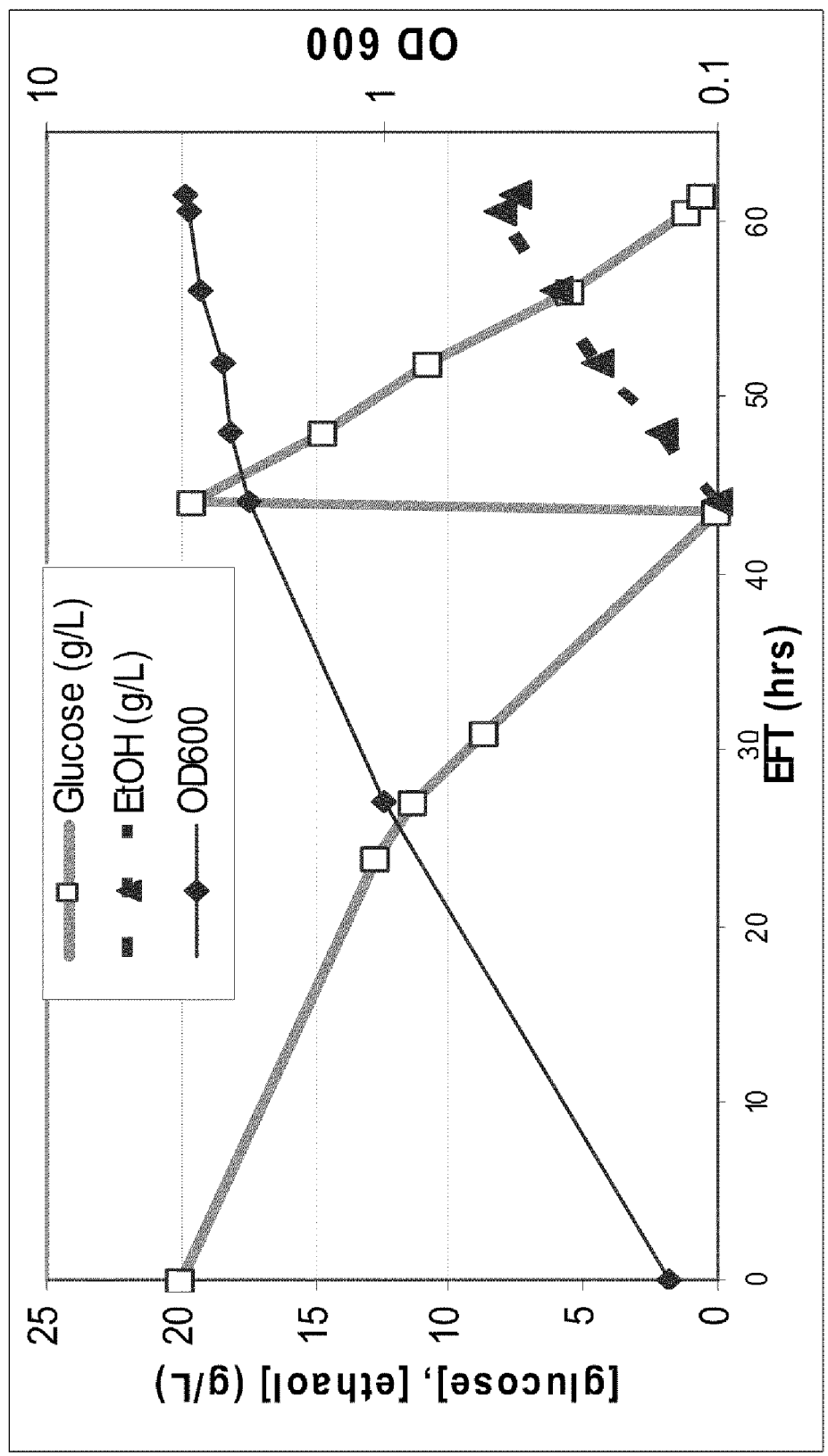

The results are also presented graphically in FIGS. 12A and 12B. FIG. 12A illustrates the fermentation data for strain BF738 (BY4742 tal1 with vector controls p426GPD and p425GPD) and FIG. 12B illustrates the fermentation data for strain BF741 (BY4742 tal1 with plasmids pBF290 (EDD-PAO1) and pBF292 (EDA-PAO1). The results presented above and in FIGS. 12A and 12B indicate that strain BF741, which expresses the activities encoded by the eda and edd genes, yields more ethanol than control strain BF738. Strain BF741 produced about 0.43 g ethanol per gram of glucose consumed whereas strain BF738 produced only 0.36 g ethanol per gram of glucose consumed. Fermentation profiles were calculated for strains BF738 and BF741 and are presented below.

| Strain | Yx/s | Yp/s | Yp/x | Qp | qp |
|---|---|---|---|---|---|
| BF738 | 0.198 | 0.358 | 3.76 | 0.371 | 0.103 |
| BF741 | 0.203 | 0.439 | 2.16 | 0.439 | 0.131 |

Yx/s = OD/g glucose,
Yp/s = q ethanol/g glucose,
Yp/x = g ethanol/OD
Qp = g ethanol/Lh$^{-1}$
qp = g ethanol/ODh$^{-1}$ Example 14

Complementation and Improved Ethanol Yield in a pfk1 Strain of *S. cerevisiae* Expressing the EDA and EDD Genes from *P. aeruginosa*

Strain BF205 (YGR240C/BY4742, ATCC Cat. No. 4015893; PubMed: 10436161) was transformed with plasmids p426GPD and p425GPD or with plasmids pBF290 (p426GPD/EDD-PAO1) and pBF292 (p426GPD/EDA-PAO1), generating strains BF740 (vector controls) and BF743, respectively. Transformation was accomplished by a high-efficiency competency method using 500 ng of plasmids p426GPD and p425GPD or plasmids pBF290 and pBF292. Transformants were plated onto SCD-ura-leu agar plates and grown at about 30° C. for about 3 days. The final strains were named BF740 (BY4742 pfk1 with plasmids p426GPD and p425GPD) and BF743 (BY4742-pfk1, pBF290/pBF292).

A fermentation test of the control strain BF740 (BY4742 pfk1 with plasmids p426GPD and p425GPD) was conducted against BF743 (BY4742-pfk1, pBF290/pBF292) in 400 ml w.v. Multifors multiplexed fermentors. The fermentation medium was SC-Ura-Leu with 2% glucose. Vessels were inoculated with about a 10% inoculum from overnight cultures grown in about 50 ml SC-Ura-Leu with about 2% glucose and normalized to 0.5 $OD_{600}$. The actual inoculated ODs for the fermentations are shown in the table below.

| Strain | $OD_{600\,nm}$ |
|---|---|
| BF740 (pfk1 VV) | 0.571 |
| BF743 (pfk1 PP) | 0.535 |

The cultures were grown aerobically at about 30° C. with about 250 rpm agitation, 1 vvm sparge of process air, (21% $O_2$). The pH was controlled at around 5.0 with 0.25 N NaOH. Once glucose concentrations dropped below 0.5 g/L the fermentation was switched to anaerobic conditions. Before changing to anaerobic conditions, samples were taken to measure glucose concentrations and biomass by $OD_{600}$ as shown in the table below. The table below shows the beginning cell biomass and glucose concentration (in grams per liter of nutrient broth). Ethanol and glucose concentrations in the fermentation broth were monitored using a YSI 2700 BioAnalyzer.

| Strain | $OD_{600\,nm}$ | Ethanol (g/L) | Glucose (g/L) |
|---|---|---|---|
| BF740 | 5.94 | 5.67 | 0.033 |
| BF743 | 5.82 | 5.82 | 0.034 |

At the beginning of the anaerobic portion of the fermentation, a bolus of about 18 g/L glucose plus about 4 ml/L of 2.5 g/L ergosterol in Ethanol, 0.4 ml/L Tween 80, and 0.01% AF-204 were added to each fermentor. Oxygen was purged with 100% $N_2$ sparged at about 1 vvm until $pO_2$ was below 1%. Samples were taken every 4 to 8 hours and measured for ethanol and glucose concentrations and biomass ($OD_{600}$). The fermentation was harvested when the glucose concentration was below 0.05 g/L, at about 42 hours elapsed fermentation time (EFT). Ethanol and glucose concentrations and $OD_{600}$ of the final sample are shown in the table below.

| Strain | $OD_{600\,nm}$ | Ethanol (g/L) | Glucose (g/L) |
|---|---|---|---|
| BF740 | 6.4 | 5.07 | 14.6 |
| BF743 | 5.09 | 13.37 | 0.042 |

Figure 13A:
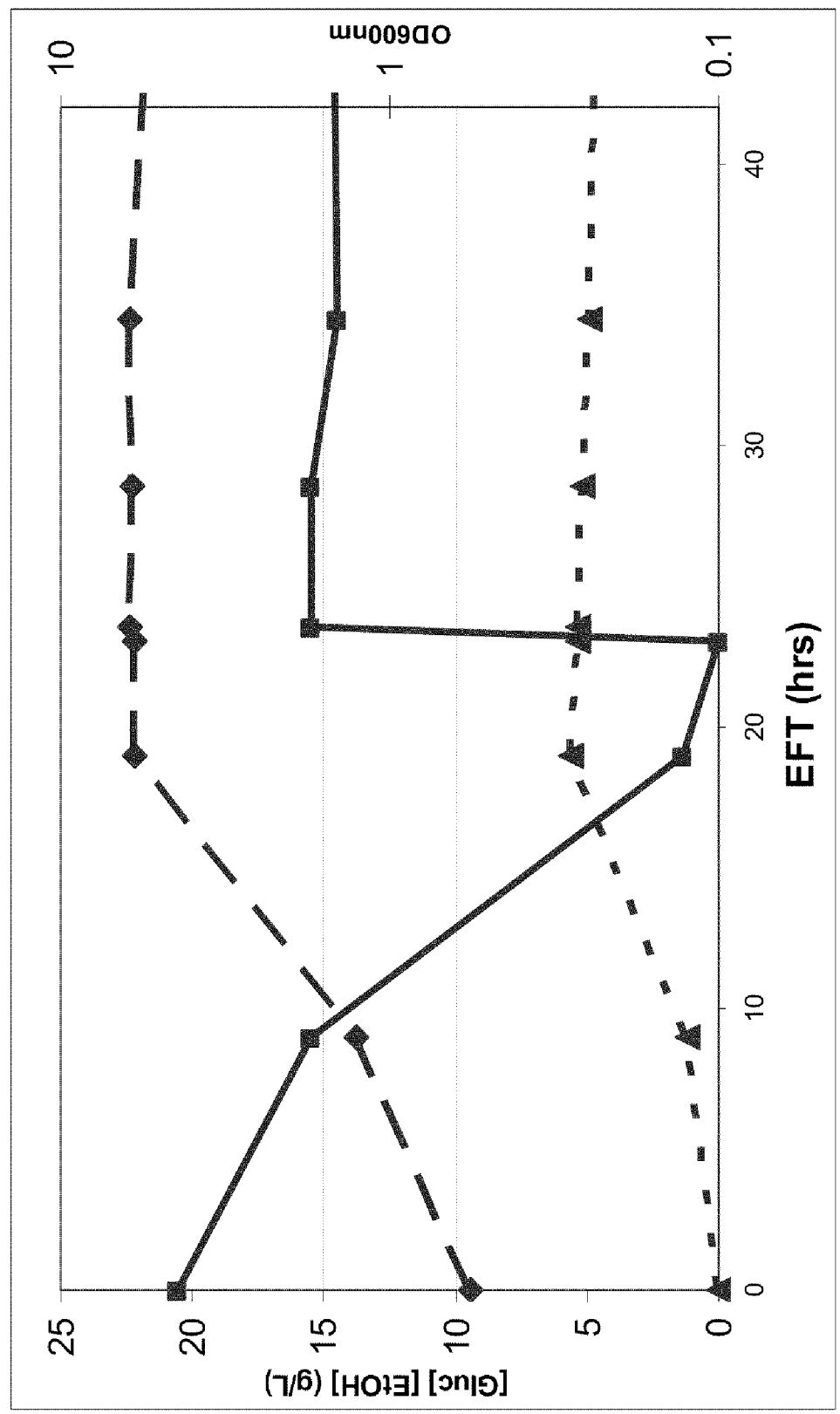
FIGS. 13A and 13B graphically illustrate fermentation data for engineered yeast strains as described herein.
Figure 13B:
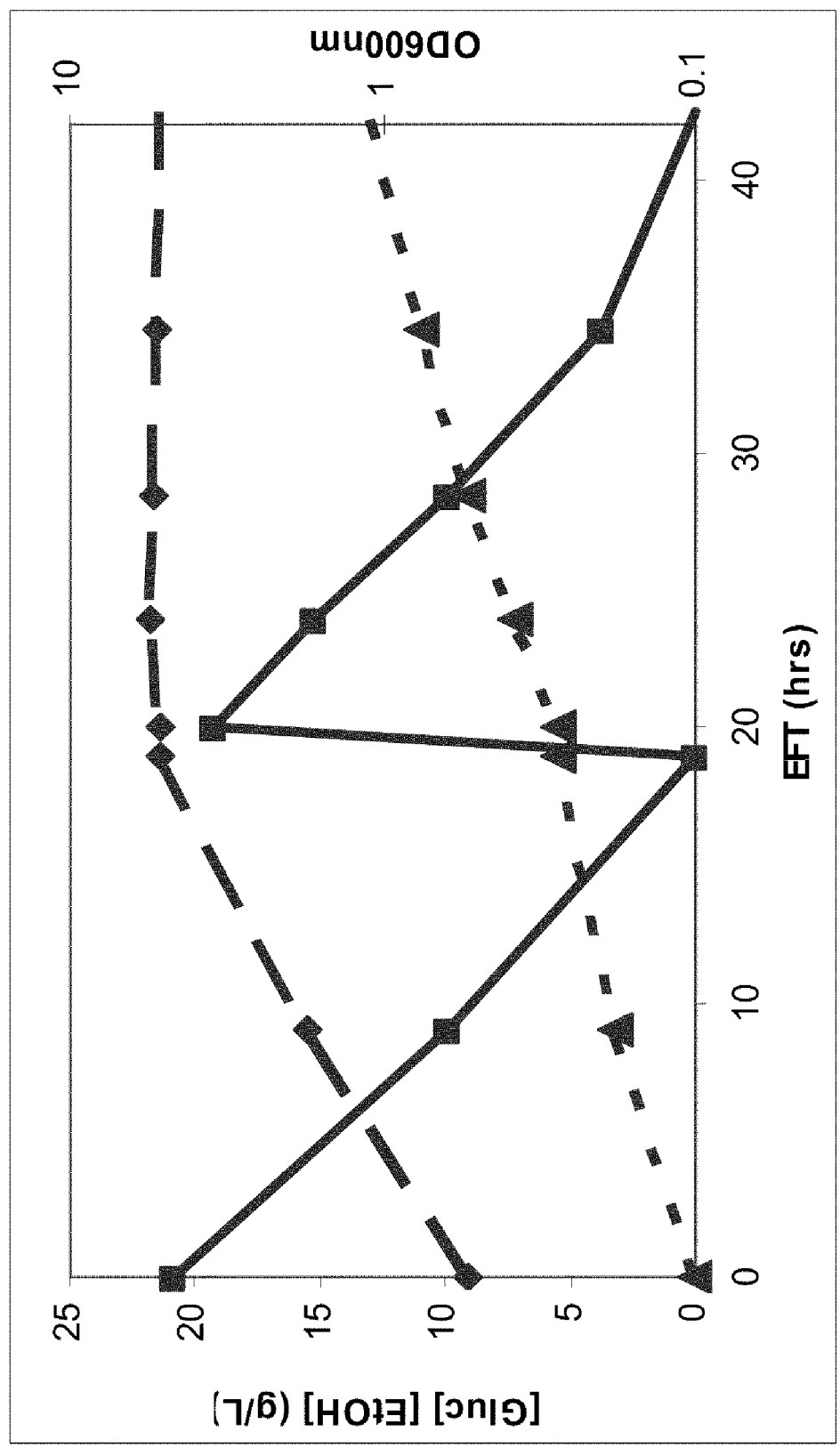

The results also are present graphically in FIGS. 13A and 13B. The results presented in FIG. 13A illustrate the fermentation data for strain BF740 grown on 2% dextrose and the results presented in FIG. 13B illustrate the fermentation data for strain BF743 grown on 2% dextrose. The results indicate that the BY4742 pfk1 mutant strain, BF740 cannot utilize glucose nor produce ethanol under anaerobic conditions. However, the engineered strain BF743 is capable of both utilizing glucose and producing ethanol under anaerobic conditions. Strain BF743 has a yield of about 0.39 g ethanol per gram of glucose consumed versus no yield in the control strain BF740. The fermentation profile for strains BF740 and BF743 are presented in the table below.

| Strain | Yx/s | Yp/s | Yp/x | Qp | qp |
|---|---|---|---|---|---|
| BF740 | 2.133 | −0.700 | −0.328 | −0.022 | −0.003 |
| BF743 | 0.264 | 0.390 | 1.483 | 0.178 | 0.035 |

Yx/s = OD/g glucose, Yp/s = q ethanol/g glucose, Yp/x = g ethanol/OD Qp = g ethanol/Lh$^{-1}$, qp = g ethanol/ODh$^{-1}$ Example 15

EDD and EDA Activities from Other Sources

The EDD and EDA genes also have been isolated from additional sources and tested for the ability to direct fermentation in yeast. The additional EDD and EDA genes have been isolated from *Shewanella oneidensis*, *Gluconobacter oxydans*, and *Ruminococcus flavefaciens*. Genomic DNA was purchased from ATCC for both *S. oneidensis* (Cat. No. 700550D) and *G. oxydans* (621 HD-5). *R. flavefaciens*, strain C94 (NCDO 2213) was also purchased from ATCC (Cat. No. 19208). To prepare genomic DNA, *R. flavefaciens* was grown in cooked meat media (Becton Dickinson, Franklin Lakes, N.J. USA) overnight at 37° C. and genomic DNA was isolated using a Qiagen DNeasy Blood and Tissue kit according to the manufacture's protocol. The eda and edd genes were PCR amplified from the corresponding genomic DNA using the following sets of PCR oligonucleotides. The nucleotide and amino acid sequences of eda and edd genes PCR amplified using the following sets of PCR oligonucleotide primers, also is given below.

The *S. oneidensis* edd gene:

(SEQ. ID. NO: 73)
5'-GTTCACTGCactagtaaaaaaATGCACTCAGTCGTTCAATCT G-3'

(SEQ. ID. NO: 74)
5'-CTTCGAGATCTCGAGTTAGTAAAGTTCATCGATGGC-3'

The *S. oneidensis* eda gene:

(SEQ. ID. NO: 75)
5'-GTTCACTGCactagtaaaaaaATGCTTGAGAATAACTGGTC-3'

(SEQ. ID. NO: 76)
5'-CTTCGAGATCTCGAGTTAAAGTCCGCCAATCGCCTC-3'

The *G. oxydans* edd gene:

(SEQ. ID. NO: 77)
5'-GTTCACTGCactagtaaaaaaATGTCTCTGAATCCCGTCGT C-3'

(SEQ. ID. NO: 78)
5'-CTTCGAGATCTCGAGTTAGTGAATGTCGTCGCCAAC-3'

The *G. oxydans* eda gene:

(SEQ. ID. NO: 79)
5'-GTTCACTGCactagtaaaaaaATGATCGATACTGCCAAACT C-3'

(SEQ. ID. NO: 80)
5'-CTTCGAGATCTCGAGTCAGACCGTGAAGAGTGCCGC-3'

The *R. flavefaciens* edd gene:

(SEQ. ID. NO: 81)
5'-GTTCACTGCactagtaaaaaaATGAGCGATAATTTTTTCT GCG-3'

-continued (SEQ. ID. NO: 82)
5'-CTTCGAGATCTCGAGCTATTTCCTGTTGATGATAGC-3'

*S. oneidensis* 6-phosphogluconate dehydratase (edd)

(SEQ. ID. NO: 83)
ATGCACTCAGTCGTTCAATCTGTTACTGACAGAATTATTGCCCGT
AGCAAAGCATCTCGTGAAGCATACCTTGCTGCGTTAAACGATGCC
CGTAACCATGGTGTACACCGAAGTTCTTAAGTTGCGGTAACTTA
GCCCACGGTTTTGCGGCTTGTAATCCCGATGACAAAAATGCATTG
CGTCAATTGACGAAGGCCAATATTGGGATTATCACCGCATTCAAC
GATATGTTATCTGCACACCAACCCTATGAAACCTATCCTGATTTG
CTGAAAAAAGCCTGTCAGGAAGTCGGTAGTGTTGCGCAGGTGGCT
GGCGGTGTTCCCGCCATGTGTGACGGCGTGACTCAAGGTCAGCCC
GGTATGGAATTGAGCTTACTGAGCCGTGAAGTGATTGCGATGGCA
ACCGCGGTTGGCTTATCACACAATATGTTTGATGGAGCCTTACTC
CTCGGTATTTGCGATAAAATTGTACCGGGTTTACTGATTGGTGCC
TTAAGTTTTTGGCCATTTACCTATGTTGTTTGTGCCGTGCAGGCCCA
ATGAAATCGGGTATTCCTAATAAGGAAAAAGCTCGCATTCGTCAG
CAATTTGCTCAAGGTAAGGTCGATAGAGCACAACTGCTCGAAGCG
GAAGCCCAGTCTTACCACAGTGCGGGTACTTGTACCTTCTATGGT
ACCGCTAACTCGAACCAACTGATGCTCGAAGTGATGGAGCTTGCA
TTGCCGGGTTCATCTTTTGTGAATCCAGACGATCCACTGCGCGAA
GCCTTAAACAAAATGGCGGCCAAGCAGGTTTGTCGTTTAACTGAA
CTAGGCACTCAATACAGTCCGATTGGTGAAGTCGTTAACGAAAAA
TCGATAGTGAATGGTATTGTTGCATTGCTCGCGACGGCTGGTTCA
ACAAACTTAACCATGCACATTGTGGCGGCGGCCCGTGCTGCAGGT
ATTATCGTCAACTGGGATGACTTTTCGGAATTATCCGATGCGGTG
CCTTTGCTGGCACGTGTTTATCCAAACGGTCATGCGGATATTAAC
CATTTCCACGCTGCGGGTGGTATGGCTTTCCTTATCAAAGAATTA
CTCGATGCAGGTTTGCTGCATGAGGATGTCAATACTGTCGCGGGT
TATGGTCTGCGCCGTTACACCCAAGAGCCTAAACTGCTTGATGGC
GAGCTGCGCTGGGTCGATGGCCCAACAGTGAGTTTAGATACCGAA
GTATTAACCTCTGTGGCACCATTCCAAAACAACGGTCTGAAA
AGCTGCTGAAGGGTAACTTAGGCCGCGTGATTAAAGTGTCT
GCCGTTCAGCCACAGCACCGTGTGGTGGAAGCGCCCGCAGTGGTG
ATTGACGATCAAAACAAACTCGATGCGTTATTTAAATCCGGCGCA
TTAGACAGGGATTGTGGTGGTGGTGAAAGGCCAAGGGCCGAAA
GCCAACGGTATGCCAGAGCTGCATAAACTAACGCCCGCTGTTAGGT
TCATTGCAGGACAAAGGCTTTAAAGTGGCACTGATGACTGATGGT
CGTATGTCGGGCGCATCGGCAAAGTACCTGCGGCGATTCATTTA
ACCCCTGAAGCGATTGATGGCGGGTTAATTGCAAAGGTACAAGAC
GGCGATTTAATCCGAGTTGATGCACTGGACCGGCGAGCTGAGTTA
TTAGTCTCTGACACCGAGCTTGCCACCAGAACTGCCACTGAAATT
GATTTACGCCATTCTCGTTATGGCATGGGGCGTGAGTTATTGGA
GTACTGCGTTCAAACTTAAGCAGTCCTGAAACCGGTGCGCGTAGT
ACTAGCGCCATCGATGAACTTTACTAA

*S. oneidensis* 6-phosphogluconate dehydratase (edd)-Amino Acid sequence (SEQ. ID. NO: 84)
MHSVVQSVTDRIIARSKASREAYLAALNDARNHGVHRSSLSCGNL
AHGFAACNPDDKNALRQLTKANIGIITAFNDMLSAHQPYETYPDL
LKKACQEVGSVAQVAGGVPAMCDGVTQGQPGMELSLLSREVIAMA
TAVGLSHNMFDGALLLGICDKIVPGLLIGALSFGHLPMLFVPAGP
MKSGIPNKEKARIRQQFAQGKVDRAQLLEAEAQSYHSAGTCTFYG
TANSNQLMLEVMGLQLPGSSFVNPDDPLREALNKMAAKQVCRLTE
LGTQYSPIGEVVNEKSIVNGIVALLATGGSTNLTMHIVAAARAAG
IIVNWDDFSELSDAVPLLARVYPNGHADINHFHAAGGMAFLIKEL
LDAGLLHEDVNTVAGYGLRRYTQEPKLLDGELRWVDGPTVSLDTE
VLTSVATPFQNNGGLKLLKGNLGRAVIKVSAVQPQHRVVEAPAVV
IDDQNKLDALFKSGALDRDCVVVVKGQGPKANGMPELHKLTPLLG
SLQDKGFKVALMTDGRMSGASGKVPAAIHLTPEAIDGGLIAKVQD
GDLIRVDALTGELSLLVSDTELATRTATEIDLRHSRYGMGRELFG
VLRSNLSSPETGARSTSAIDELY

*G. oxydans* 6-phosphogluconate dehydratase (edd)

(SEQ. ID. NO: 85)
ATGTCTCTGAATCCCGTCGTCGAGAGCGTGACTGCCCGTATCATC
GAGCGTTCGAAAGTCTCCCGTCGCCGGTATCTCGCCCTGATGGAG
CGCAACCGCGCCAAGGGTGTGCTCCGGCCCAAGCTGGCCTGCGGT
AATCTGGCGCATGCCATCGCAGCGTCCAGCCCCGACAAGCCGGAT
CTGATGCGTCCCACCGGGACCAATATCGGCGTGATCACGACCTAT
AACGACATGCTCTCGGCGCATCAGCCGTATGGCCGCTATCCCGAG
CAGATCAAGCTGTTCGCCCGTGAAGTGGGCACCGCGCAGGTTGCC
GCAGGCGGCGCACCAGCAATGTGTGATGGTGACAGGGCAG
GAGGGCATGGAACTCTCCCTGTTCTCCCGTGACGTGATCGCCATG
TCCACGGCGGTCGGGCTGAGCCACGGCATGTTTGAGGGCGTGGCG
CTGCTGGGCATCTGTGACAAGATTGTGCCGGGCCTTTCTGATGGGC
GCGCTGCGCTTCGGTCATCTCCCGGCCATGCTGATCCCGGCAGGG

-continued

CCAATGCCGTCCGGTCTTCCCAAACAAGGAAAAGCAGCGCATCCGC
CAGCTCTATGTGCAGGGCAAGGTCGGGCAGGACGAGCTGATGGAA
GCGGAAAACGCCTCCTATCACAGCCCGGGCACCTGCACGTTCTAT
GGCACGGCCAATACGAACCAGATGATGGTCGAAATCATGGGTCTG
ATGATGCCGGACTCGGCTTTCATCAATCCCAACACGAAGCTGCGT
CAGGCAATGACCCGCTCGGGTATTCACCGTCTGGCCGAAATCGGC
CTGAACGGCGAGGATGTGCGCCCGCTCGCTCATTGCGTAGACGAA
AAGGCCATCGTGAATGCGGCGGTCGGGTTGCTGGCGACGGGTGGT
TCGACCAACCATTCGATCCATCTTCCTGCTATCGCCCGTCGCCGCT
GGTATCCTCGATCGACTGGGAAGACATCAGCCGCCTCGTCGTCCGC
GTTCCGCTGATCACCCGTGTTTATCCGAGCGGTTCCGAGGACGTG
AACGCGTTCAACCGCGTGGGTGGTATGCCGACCGTGATCGCCGAA
CTGACGCGCGCCGGGATGCTGCACAAGGACATTCTGACGGTCTCT
CGTGGCGGTTTCTCCGATTATGCCCGTCGCGCATCGCTGGAAGGC
GATGAGATCGTCTACACCCACGCGAAGCCGTCCACGGACACCGAT
ATCCTGCGCGATGTGGCTACGCCTTTCCGGCCCGATGGCGGTATG
CGCCTGATGACTGGTAATCTGGGCCGCGCGATCTACAAGAGCAGC
GCTATTGCGCCCGAGCACCTGACCGTTGAAGCGCCGGCACGGGTC
TTCCAGGACCAGCATGACGTCCTCACGGCCTATCAGAATGGTGAG
CTTGAGCGTGATGTTGTCGTGGTCGTCCGGTTCCAGGGACCGGAA
GCCAACGGCATGCCGGAGCTTCACAAGCTGACCCCGACTCTGGGC
GTGCTTCAGGATCGCGGCTTCAAGGTGGCCCTGCTGACGGATGGA
CGCATGTCCGGTGCGAGCGGCAAGGTGCCGGCCGCCATTCATGTC
GGTCCCGAAGCGCAGGTTGGCGGTCCGATCGCCCGCGTGCGGGAC
GGCGACATGATCCGTGTCTGCGCGGTGACGGGACAGATCGAGGCT
CTGGTGGATCGCGCAGTGGAGGCCGCCAAGCCGGTCCCGCCG
CCGCTCCCGGCATTGGGAACGGGCCGGAACTGTTCGCGCTGATG
CGTTCGGTGCATGATCCGGCCGAGGCTGGCGGATCCGCGATGCTG
GCCCAGATGGATCGCGTGATCGAAGCCGTTGGCGACGACATTCAC
TAA

*G. oxydans* 6-phosphogluconate dehydratase (edd)-Amino Acid sequence (SEQ. ID. NO: 86)
MSLNPVVESVTARIIERSKVSRRRYLALMERNRAKGVLRPKLACG
NLAHAIAASSPDKPDLMRPTGTNIGVITTYNDMLSAHQPYGRYPE
QIKLFAREVGATAQVAGGAPAMCDGVTQGQEGMELSLFSRDVIAM
STAVGLSHGMFEGVALLGICDKIVPGLLMGALRFGHLPAMLIPAG
PMPSGLPNKEKQRIRQLYVQGKVGQDELMEAENASYHSPGTCTFY
GTANTNQMMVEIMGLMMPDSAFINPNTKLRQAMTRSGIHRLAEIG
LNGEDVRPLAHCVDEKAIVNAAVGLLATGGSTNHSIHLPAIARAA
GILIDWEDISRLSSAVPLITRVYPSGSEDVNAFNRVGGMPTVIAE
LTRAGMLHKDILTVSRGGFSDYARRASLEGDEIVYTHAKPSTDTD
ILRDVATPFRPDGGMRLMTGNLGRAIYKSSAIAPEHLTVEAPARV
FQDQHDVLTAYQNGELERDVVVVVRFQGPEANGMPELHKLTPTLG
VLQDRGFKVALLTDGRMSGASGKVPAAIHVGPEAQVGGPIARVRD
GDMIRVCAVTGQIEALVDAAEWESRKPVPPPLPALGTGRELFALM
RSVHDPAEAGGSAMLAQMDRVIEAVGDDIH

*R. flavefaciens* phosphogluconate dehydratase/DHAD (SEQ. ID. NO: 87)
ATGAGCGATAATTTTTTCTGCGAGGGTGCGGATAAAGCCCCTCAG
CGTTCACTTTTCAATGCACTGGGCATGACTAAAGAGGAAATGAAG
CGTCCCCTCGTTGGTATCCGTTTCTTCCTACAATGAGATCGTTCCC
GGCCATATGAACATCGACAAGCTGGTCGAAGCCGTTAAGCTGGGT
GTAGCTATGGGCGGCGGCACTCCTGTTGTTTTCCCTGCTATCGCT
GTATGCGACGGTATCGCTATGGGTCACACAGGCATGAAGTACAGC
CTTGTTACCCGTGACCTTATTGCCGATTCTACAGAGTGTATGGCT
CTTGCTCATCACTTCTGACGCACTGGTAATGATAACCTAACTGCGAC
AAGAACGTTCCCGGCCTGCTTATGGCGGCTGCACGTATCAATGTT
CCTACTGTATTCGTAAGCGGCGGCCCTATGCTTGCAGGCCATGTA
AAGGGTAAGAAGACCTCTCTTTCATCCATGTTCGAGGCTGTAGGC
GCTTACACAGCAGGCAAGATAGACGAGGCTGAACTTGACGAATTC
GAGAACAAGACCTGCCCTACCTGCGGTTCATGTTCGGGTATGTAT
ACCGCTAACTCCATGAACTGCCTCACTGAGGTACTGGGTATGGGT
CTCAGAGGCAACGGCACTATCCCTGCTGTTTACTCCGAGCGTATC
AAGCTTGCAAAGCAGGCAGGTATGCAGGTTATGGAACTCTACAGA
AAGAATATCCGCCCTCTCGATATCATGACAGAGAGGCTTTCCAG
AACGCTCTCACAGCTGATATGGCTCTTGGATGTTCCACAAACAGT
ATGTCCATCTCCCTGCTATCGCCAACGAATGCGGCATAAATATC
AACCTTGACATGGCTAACGAGATAAGCGCCAAGCTCCTAACCTC
TGCCATCTTGCACCGGCAGGCCACACCTACATGGAAGACCTCAAC
GAAGCAGGCGGAGTTTATGCAGTTCTCAACGAGCTGAGCAAAAAG
GGACTTATCAACACCGACTGCATGACTGTTACAGGCAAGACCGTA
GGCGAAGATATCAAGGCTGCTGTCAACCGTGACCCTGAGACTGTA
CGTCCTATCGACAACCCATACAGTGAAACAGGCGGAATCGCCGTA
CTCAAGGGCAATCTTGCTCCCGACAGATGTGTTGTAAGAGAAGC
GCAGTTGCTCCCGAAATGCTGGTACACAAAGGCCCTGCAAGAGTA
TTCGACAGCGAGGAAGAAGCTATCAAGGTCATCTATGAGGGCGGT
ATCAAGGCAGGCGACGTTGTTGTTATCCGTTACGAAGGCCCTGCA -continued
```
GGCGGCCCCGGCATGAGAGAAATGCTCTCTCCTACATCAGCTATA
CAGGGTGCAGGTCTCGGCTCAACTGTTGCTCTAATCACTGACGGA
CGTTTCAGCGGCGCTACCCGTGGTGCGGCTATCGGACACGTATCC
CCCGAAGCTGTAAACGGCGGTACTATCGCATATGTCAAGGACGGC
GATATTATCTCCATCGACATACCGAATTACTCCATCACTCTTGAA
GTATCCGACGAGGAGCTTGCAGAGCGCAAAAAGGCAATGCCTATC
AAGCGCAAGGAGAACATCACAGGCTATCTGAAGCGCTATGCACAG
CAGGTATCATCCGCAGACAAGGGCGCTATCATCAACAGGAAATAG
```

R. flavefaciens phosphogluconate
dehydratase/DHAD-Amino Acid sequence
(SEQ. ID. NO: 88)
```
MSDNFFCEGADKAPQRSLFNALGMTKEEMKRPLVGIVSSYNEIVPG
HMNIDKLVEAVKLGVAMGGGTPVVFPAIAVCDGIAMGHTGMKYSLV
TRDLIADSTECMALAHHFDALVMIPNCDKNVPGLLMAAARINVPTV
FVSGGPMLAGHVKGKKTSLSSMFEAVGAYTAGKIDEAELDEFENKT
CPTCGSCSGMYTANSMNCLTEVLGMGLRGNGTIPAVYSERIKLAKQ
AGMQVMELYRKNIRPLDIMTEKAFQNALTADMALGCSTNSMLHLPA
IANECGININLDMANEISAKTPNLCHLAPAGHTYMEDLNEAGGVYA
VLNELSKKGLINTDCMTVTGKTVGENIKGCINRDPETIRPIDNPYS
ETGGIAVLKGNLAPDRCVVKRSAVAPEMLVHKGPARVFDSEEEAIK
VIYEGGIKAGDVVVIRYEGPAGGPGMREMLSPTSAIQGAGLGSTVA
LITDGRFSGATRGAAIGHVSPEAVNGGTIAYVKDGDIISIDIPNYS
ITLEVSDEELAERKKAMPIKRKENITGYLKRYAQQVSSADKGAIIN
RK
```

Pair wise homology comparisons for various edd proteins are presented in the table below. The comparisons were made using ClustalW software (ClustalW and ClustalX version 2; Larkin M. A., Blackshields G., Brown N. P., Chema R., McGettigan P. A., McWilliam H., Valentin F., Wallace I. M., Wilm A., Lopez R., Thompson J. D., Gibson T. J. and Higgins D. G., Bioinformatics 2007 23(21): 2947-2948). ClustalW is a free alignment tool available at the European Bioinformatics Institute website (e.g., world wide web uniform resource locator ebi.ac.uk, specific ClustalW location is ebi.ac.uk/Tools/clustalw2/index.html). PAO1=*Pseudomonas aeruginosa* PAO1, E.C.=*Eschericia coli*, S.O.=*S. oneidensis*, G.O.=*G. oxydans*, R.F.=*Ruminococcus flavefaciens*.

|       | PAO1 | E.C. | S.O. | G.O. | R.F. |
|-------|------|------|------|------|------|
| PAO1  | 100  | 62   | 62   | 55   | 29   |
| E.C.  | 62   | 100  | 66   | 56   | 30   |
| S.O.  | 62   | 66   | 100  | 56   | 28   |
| G.O.  | 55   | 56   | 56   | 100  | 28   |
| R.F.  | 29   | 30   | 28   | 28   | 100  |

S. oneidensis keto-hydroxyglutarate-aldolase/
keto-deoxy-phosphogluconate aldolase (eda)
(SEQ/ ID. NO: 89)
```
ATGCTTGAGAATAACTGGTCATTACAACCACAAGATATTTTTAAAC
GCAGCCCTATTGTTCCTGTTATGGTGATTAACAAGATTGAACATGC
GGTGCCCTTAGCTAAAGCGCTGGTTGCCGGAGGGATAAGCGTGTTG
GAAGTGACATTACGCACGCCATGCGCCCTTGAAGCTATCACCAAAA
TCGCCAAGGAAGTGCCTGAGGCGCTGGTTGGCGCGGGGACTATTTT
AAATGAAGCCCAGCTTGGACAGGCTATCGCCGCTGGTGCGCAATTT
ATTATCACTCCAGGTGCGACAGTTGAGCTGCTCAAAGCGGGCATGC
AAGGACCGGTGCCGTTAATTCCGGGCGTTGCCAGTATTTCCGAGGT
GATGACGGGCATGGCGCTGGGCTACACTCACTTTAAATTCTTCCCT
GCTGAAGCGTCAGGTGGCGTTGATGCGCTTAAGGCTTTCTCTGGGC
CGTTAGCAGATATCCGCTTCTGCCCAACAGGTGGAATTACCCCGAG
CAGCTATAAAGATTACTTAGCGCTGAAGAATGTCGATTGTATTGGT
GGCAGCTGGATTGCTCCTACCGATGCGATGGAGCAGGGCGATTGGG
ATCGTATCACTCAGCTGTGTAAAGAGGCGATTGGCGGACTTTAA
```

S. oneidensis keto-hydroxyglutarate-aldolase/
keto-deoxy-phosphogluconate aldolase
(eda)-Amino Acid sequence
(SEQ. ID. NO: 90)
```
MLENNWSLQPQDIFKRSPIVPVMVINKIEHAVPLAKALVAGGISVL
EVTLRTPCALEAITKIAKEVPEALVGAGTILNEAQLGQAIAAGAQF
IITPGATVELLKAGMQGPVPLIPGVASISEVMTGMALGYTHFKFFP
AEASGGVDALKAFSGPLADIRFCPTGGITPSSYKDYLALKNVDCIG
GSWIAPTDAMEQGDWDRITQLCKEAIGGL
```

G. oxydans keto-hydroxyglutarate-aldolase/keto-
deoxy-phosphogluconate aldolase (eda)
(SEQ. ID. NO: 91)
```
ATGATCGATACTGCCAAACTCGACGCCGTCATGAGCCGTTGTCCGG
TCATGCCGGTGCTGGTGGTCAATGATGTGGCTCTGGCCCGCCCGAT
GGCCGAGGCTCTGGTGGCGGGTGGACTGTCCACGCTGGAAGTCACG
CTGCGCACGCCCTGCGCCCTTGAAGCTATTGAGGAAATGTCGAAAG
TACCAGGCGCGCTGGTCGGTGCCGGTACGGTGCTGAATCCGTCCGA
CATGGACCCGTGCCGTGAAGGCGGGTGCGCGCTTCATCGTCAGCCCC
GGCCTGACCGAGGCGCTGGCAAAGGCGTCGGTTGAGCATGACGTCC
CCTTCCTGCCAGGCGTTGCCAATGCGGGTGACATCATGCGGGGTCT
GGATCTGGGTCTGTCACGCTTCAAGTTCTTCCCGGCTGTGACGAAT
GGCGGCATTCCCGCGCTCAAGAGCTTGGCCAGTGTTTTTGGCAGCA
ATGTCCGTTTCTGCCCCACGGGCGGCATTACGGAGAGAGCGCACC
GGACTGGCTGGCGCTTCCCTCCGTGGCCTGCGTCGGCGGATCCTGG
GTGACGGCCGGCACGTTCGATGCGGACAAGGTCCGTCAGCGCGCCA
CGGCTGCGGCACTCTTCACGGTCTGA
```

G. oxydans keto-hydroxyglutarate-aldolase/
keto-deoxy-phosphogluconate aldolase
(eda)-Amino) Acid
(SEQ. ID. NO: 92)
```
MIDTAKLDAVMSRCPVMPVLVVNDVALARPMAEALVAGGLSTLEVT
LRTPCALEAIEEMSKVPGALVGAGTVLNPSDMDRAVKAGARFIVSP
GLTEALAKASVEHDVPFLPGVANAGDIMRGLDLGLSRFKFFPAVTN
GGIPALKSLASVFGSNVRFCPTGGITEESAPDWLALPSVACVGGSW
VTAGTFDADKVRQRATAAALFTV
```

Pair wise homology comparisons for various eda proteins are presented in the table below. The comparisons were made using ClustalW software (ClustalW and ClustalX version 2; Larkin M. A., Blackshields G., Brown N. P., Chema R., McGettigan P. A., McWilliam H., Valentin F., Wallace I. M., Wilm A., Lopez R., Thompson J. D., Gibson T. J. and Higgins D. G., Bioinformatics 2007 23(21): 2947-2948). PAO1=*Pseudomonas aeruginosa* PAO1, E.C.=*Eschericia coli*, S.O.=*S. oneidensis*, G.O.=*G. oxydans*, R.F.=*Ruminococcus flavefaciens*.

|       | PAO1 | E.C. | S.O. | G.O. |
|-------|------|------|------|------|
| PAO1  | 100  | 41   | 44   | 40   |
| E.C.  | 41   | 100  | 60   | 46   |
| S.O.  | 44   | 60   | 100  | 45   |
| G.O.  | 40   | 46   | 45   | 100  |

All oligonucleotides set forth above were purchased from Integrated technologies ("IDT", Coralville, Iowa). These oligonucleotides were designed to incorporate a SpeI restriction endonuclease cleavage site upstream and an XhoI restriction endonuclease cleavage site downstream of the edd and eda gene constructs, such that the sites could be used to clone the genes into yeast expression vectors p426GPD (ATCC accession number 87361) and p425GPD (ATCC accession number 87359). In addition to incorporating restriction endonuclease cleavage sites, the forward oligonucleotides were designed to incorporate six consecutive A nucleotides immediately upstream of the ATG initiation codon.

PCR amplification of the genes were performed as follows: about 100 ng of the genomic DNA was added to 1×Pfu Ultra II buffer, 0.3 mM dNTPs, 0.3 µmol gene-specific primers and 1 U Pfu Ultra II polymerase (Agilent, La Jolla, Calif.) in a 50 µl reaction mix. The reaction mixture was cycled as follows: 95° C. 10 minutes followed by 30 rounds of 95° C. for 20 seconds, 50° C. (eda amplifications) or 53° C. (edd amplifications) for 30 seconds, and 72° C. for 15 seconds (eda amplifications) or 30 seconds (edd amplifications). A final 5 minute extension reaction at 72° C. was also included. Each amplified product was TOPO cloned into the pCR Blunt II TOPO vector (Life Technologies, Carlsbad, Calif.) according to the manufacturer's recommendations and the sequences verified (GeneWiz, La Jolla, Calif.).

Cloning of New edd and eda Genes into Yeast Expression Vectors

Each of the sequence-verified eda and edd fragments were subcloned into the corresponding restriction sites in plasmids p425GPD and p426GPD vectors (ATCC #87361; PubMed: 7737504). Briefly, about 50 ng of SpeI-XhoI-digested p425GPD vector was ligated to about 50 ng of SpeI/XhoI-restricted eda or edd fragment in a 10 µl reaction with 1×T4 DNA ligase buffer and 1 U T4 DNA ligase (Fermentas) overnight at 16° C. About 3 µl of this reaction was used to transform DH5α competent cells (Zymo Research) and plated onto LB agar media containing 100 µg/ml ampicillin. Final constructs were confirmed by restriction endonuclease digests and sequence verification (GeneWiz, La Jolla, Calif.).

In Vivo Assay to Determine Optimal EDD/EDA Combination

To determine the optimal EDD/EDA gene combinations, a yeast strain was developed to enable in vivo gene combination evaluation. Growth on glucose was impaired in this strain by disrupting both copies of phosphofructokinase (PFK), however, the strain could grow normally on galactose due to the presence of a single plasmid copy of the PFK2 gene under the control of a GAL1 promoter. The strain can only grow on glucose if a functional EDD/EDA is present in the cell. The strain was generated using strain BF205 (YGR240C/ BY4742, ATCC Cat. No. 4015893; Winzeler E A, et al. Science 285: 901-906, 1999, PubMed: 10436161) as the starting strain.

PFK2 Expressing Plasmid

The plasmid expressing the PFK2 gene under the control of the GAL1 promoter, for use in the in vivo edd/eda gene combination evaluations, was constructed by first isolating the PFK2 gene. Primers JML/89 and JML/95 were used to amplify the PFK2 gene from BY4742 in a PCR reaction containing about 100 ng of the genomic DNA, 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reactions were cycled as follows: 95° C. for 10 minutes followed by 10 rounds of 95° C. for 20 seconds, 55° C. for 20 seconds, and 72° C. for 90 seconds and 25 rounds of 95° C. for 20 seconds, 62° C. for 20 seconds, and 72° C. for 90 seconds. A final 5 minute extension reaction at 72° C. was also included. Each amplified product was TOPO cloned into the pCR Blunt II TOPO vector (Life Technologies, Carlsbad, Calif.) according to the manufacturer's recommendations and sequence verified (GeneWiz, San Diego, Calif.). The sequences of JML/89 and JML/95 are given below.

```
                                      (SEQ ID NO: 282)
JML/89  ACTAGTATGACTGTTACTACTCCTTTTGTGAATGGTAC (SEQ ID NO: 283)
JML/95  CTCGAGTTAATCAACTCTCTTTCTTCCAACCAAATGGTC
```

The primers used were designed to include a unique SpeI restriction site at the 5' end of the gene and a unique XhoI restriction site at the 3' end of the gene. This SpeI-XhoI fragment (approximately 2900 bp) was cloned into the SpeI-XhoI sites of the yeast vector p416GAL (ATCC Cat. No. 87332; Mumberg D, et al., Nucleic Acids Res. 22: 5767-5768, 1994. PubMed: 7838736) in a 10 µl ligation reaction containing about 50 ng of the p416GAL plasmid and about 100 ng of the PFK2 fragment with 1× ligation buffer and 1 U T4 DNA ligase (Fermentas). This ligation reaction was allowed to incubate at room temperature for about one hour and was transformed into competent DH5α (Zymo Research, Orange, Calif.) and plated onto LB plates containing 100 µg/ml ampicillin. The final plasmid was verified by restriction digests and sequence confirmed (GeneWiz, San Diego, Calif.) and was called pBF744. Plasmid pBF744 was transformed in yeast strain BF205 (BY4742 pfk1) using the procedure outlined below. This resulting strain was called BF1477.

1. Inoculate 5 mLs YPD with a single yeast colony. Grow O/N at 30° C.
2. Next day: add 50 µl culture to 450 µl fresh YPD, check A660. Add suitable amount of cells to 60 mLs fresh YPD to give an A660=0.2 ($2 \times 10^6$ cells/mL). Grow to A660=1.0 ($2 \times 10^7$ cells/mL), approximately 5 hours.
3. Boil a solution of 10 mg/ml salmon sperm DNA for 5 min, then quick chill on ice.
4. Spin down 50 mL cells at 3000 rpm for 5 min, wash in 10 mL sterile water, recentrifuge.
5. Resuspend in 1 mL sterile water. Transfer to 1.5 mL sterile microfuge tube, spin down.
6. Resuspend in 1 mL sterile TE/LiOAC solution. Spin down, resuspend in 0.25 mLs TE/LiOAc ($4 \times 10^9$ cells).
7. In a 1.5 mL microfuge tube, mix 50 µl yeast cells with 1-5 µg transforming DNA and 5 µl single stranded carrier DNA (boiled salmon sperm DNA).
8. Add 300 µl sterile PEG solution. Mix thoroughly. Incubate at 30° C. for 60 min with gentle mixing every 15 min.
9. Add 40 µl DMSO, mix thoroughly. Heat shock at 42° C. for 15 min.
10. Microfuge cells at 13000 rpm for 30 seconds, remove supernatant. Resuspend in 1 mL 1×TE, microfuge 30 sec. Resuspend in 1 mL 1×TE. Plate 100-200 µl on selective media (SCD-ura).

pfk2 Knockout Cassette

A knockout cassette for the PFK2 gene was constructed by first PCR amplifying about 300 bp of the 5' and 3' flanking regions of the PFK2 gene from S. cerevisiae, strain BY4742 using primers JML/85 and JML/87 and primers JML/86 and JML/88, respectively. These flanking regions were designed such that the 5' flanking region had a HindIII site at its 5' edge and a BamHI site at its 3' end. The 3' flanking region had a BamHI site at its 5' edge and a EcoRI site at its 3' edge. The nucleotide sequence of the PFK2 gene and the primers used for amplification of the PFK2 gene are given below.

```
S. cerevisiae PFK2 (from genomic sequence)
                             SEQ. ID. NO: 121
ATGACTGTTACTACTCCTTTTGTGAATGGTACTTCTTATTGTACCG
TCACTGCATATTCCGTTCAATCTTATAAAGCTGCCATAGATTTTTA
CACCAAGTTTTTGTCATTAGAAAACCGCTCTTCTCCAGATGAAAAC
TCCACTTTATTGTCTAACGATTCCATCTCTTTGAAGATCCTTCTAC
GTCCTGATGAAAAAATCAATAAAAATGTTGAGGCTCATTTGAAGGA
ATTGAACAGTATTACCAAGACTCAAGACTGGAGATCACATGCCACC
CAATCCTTGGTATTTAACACTTCCGACATCTTGGCAGTCAAGGACA
CTCTAAATGCTATGAACGCTCCTCTTCAAGGCTACCCAACAGAACT
ATTTCCAATGCAGTTGTACACTTTGGACCCATTAGGTAACGTTGTT
GGTGTTACTTCTACTAAGAACGCAGTTTCAACCAAGCCAACTCCAC
CACCAGCACCAGAAGCTTCTGCTGAGTCTGGTCTTTCCTCTAAAGT
TCACTCTTACACTGATTTGGCTTACCGTATGAAAACCACCGACACC
TATCCATCTCTGCCAAAGCCATTGAACAGGCCTCAAAAGGCAATTG
CCGTCATGACTTCCGGTGGTGATGCTCCAGGTATGAACTCTAACGT
TAGAGCCATCGTGCGTTCCGCTATCTTCAAAGGTTGTCGTGCCTTT
GTTGTCATGGAAGGTTATGAAGGTTTGGTTCGTGGTGGTCCAGAAT
ACATCAAGGAATTCCACTGGGAAGACGTCCGTGGTTGGTCTGCTGA
AGGTGGTACCAACATTGGTACTGCCCGTTGTATGGAATTCAAGAAG
```

-continued

```
CGCGAAGGTAGATTATTGGGTGCCCAACATTTGATTGAGGCCGGTG
TCGATGCTTTGATCGTTTGTGGTGGTGACGGTTCTTTGACTGGTGC
TGATCTGTTTAGATCAGAATGGCCTTCTTTGATCGAGGAATTGTTG
AAAACAAACAGAATTTCCAACGAACAATACGAAAGAATGAAGCATT
TGAATATTTGCGGTACTGTCGGTTCTATTGATAACGATATGTCCAC
CACGGATGCTACTATTGGTGCTTACTCTGCCTTGGACAGAATCTGT
AAGGCCATCGATTACGTTGAAGCCACTGCCAACTCTCACTCAAGAG
CTTTCGTTGTTGAAGTTATGGGTAGAAACTGTGGTTGGTTAGCTTT
ATTAGCTGGTATCGCCACTTCCGCTGACTATATCTTTATTCCAGAG
AAGCCAGCCACTTCCAGCGAATGGCAAGATCAAATGTGTGACATTG
TCTCCAAGCACAGATCAAGGGGTAAGAGAACCACCATTGTTGTTGT
TGCAGAAGGTGCTATCGCTGCTGACTTGACCCCAATTTCTCCAAGC
GACGTCCACAAAGTTCTAGTTGACAGATTAGGTTTGGATACAAGAA
TTACTACCTTAGGTCACGTTCAAAGAGGTGGTACTGCTGTTGCTTA
CGACCGTATCTTGGCTACTTTACAAGGTCTTGAGGCCGTTAATGCC
GTTTTGGAATCCACTCCAGACACCCCATCACCATTGATTGCTGTTA
ACGAAAACAAAATTGTTCGTAAACCATTAATGGAATCCGTCAAGTT
GACCAAAGCAGTTGCAGAAGCCATTCAAGCTAAGGATTTCAAGAGA
GCTATGTCTTTAAGAGACACTGAGTTCATTGAACATTTAAACAATT
TCATGGCTATCAACTCTGCTGACCACAACGAACCAAAGCTACCAAA
GGACAAGAGACTGAAGATTGCCATTGTTAATGTCGGTGCTCCAGCT
GGTGGTATCAACTCTGCCGTCTACTCGATGGCTACTTACTGTATGT
CCCAAGGTCACAGACCATACGCTATCTACAATGGTTGGTCTGGTTT
GGCAAGACATGAAAGTGTTCGTTCTTTGAACTGGAAGGATATGTTG
GGTTGGCAATCCCGTGGTGGTTCTGAAATCGGTACTAACAGAGTCA
CTCCAGAAGAAGCAGATCTAGGTATGATTGCTTACTATTTCCAAAA
GTACGAATTTGATGGTTTGATCATCGTTGGTGGTTTCGAAGCTTTT
GAATCTTTACATCAATTAGAGAGAGCAAGAGAAAGTTATCCAGCTT
TCAGAATCCCAATGGTCTTGATACCAGCTACTTTGTCTAACAATGT
TCCAGGTACTGAATACTCTTTGGGTTCTGATACCGCTTTGAATGCT
CTAATGGAATACTGTGATGTTGTTAAACAATCCGCTTCTTCAACCA
GAGGTAGAGCCTTCGTTGTCGATTGTCAAGGTGGTAACTCAGGCTA
TTTGGCCACTTACGCTTCTTTGGCTGTTGGTGCTCAAGTCTCTTAT
GTCCCAGAAGAAGGTATTTCTTTGGAGCAATTGTCCGAGGATTTG
AATACTTAGCTCAATCTTTTGAAAAGGCAGAAGGTAGAGGTAGATT
TGGTAAATTGATTTTGAAGAGTACAAACGCTTCTAAGGCTTTATCA
GCCACTAAATTGGCTGAAGTTATTACTGCTGAAGCCGATGGCAGAT
TTGACGCTAAGCCAGCTTATCCAGGTCATGTACAACAAGGTGGTTT
GCCATCTCCAATTGATAGAACAAGAGCCACTAGAATGGCCATTAAA
GCTGTCGGCTTCATCAAAGACAACCAAGCTGCCATTGCTGAAGCTC
GTGCTGCCGAAGAAACTTCAACGCTGATGACAAGACCATTTCTGA
CACTGCTGCTGTCGTTGGTGTTAAGGGTTCACATGTCGTTTACAAC
TCCATTAGACAATTGTATGACTATGAAACTGAAGTTTCCATGAGAA
TGCCAAAGGTCATTCACTGGCAAGCTACCAGACTCATTGCTGACCA
TTTGGTTGGAAGAAAGAGAGTTGATTAA
```

JML/85
(SEQ ID NO: 284)
AAGCTTTTAATTAATATAACGCTATGACGGTAGTTGAATGTTAAAA
AC

JML/86
(SEQ ID NO: 285)
GAATTCTTAATTAAAGAGAACAAAGTATTTAACGCACATGTATAAA
TATTG

JML/87
(SEQ ID NO: 286)
GGATCCGCATGCGGCCGGCCAGCTTTTAATCAAGGAAGTAATAAAT
AAAGGAC

JML/88
(SEQ ID NO: 287)
GGATCCGAGCTCGCGGCCGCAGCTTTTGAACAATGAATTTTTTGTT
CCTTTC

The nucleic acid fragments were amplified using the following conditions; about 100 ng of the BY4742 genomic DNA was added to 1× Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 58° C. for 30 seconds, and 72° C. for 20 seconds. A final 5 minute extension reaction at 72° C. was also included. Each amplified product was TOPO cloned into the pCR Blunt II TOPO vector (Life Technologies, Carlsbad, Calif.) according to the manufacturer's recommendations and the sequence of the construct was verified (GeneWiz, San Diego, Calif.). The resulting plasmids were named pBF648 (5' flanking region) and pBF649 (3' flanking region). A three fragment ligation was performed using about 100 ng of the 5' flanking region HindIII-BamHI fragment, about 100 ng of the 3' flanking region BamHI-EcoRI fragment and about 50 ng of pUC19 digested with HindIII and EcoRI in a 5 µl ligation reaction containing 1× ligation buffer and 1 U T4 DNA ligase (Fermentas). This reaction was incubated at room temperature for about one hour. About 2 µl of this reaction mix was used to transform competent DH5α cells (Zymo Research, Orange, Calif.) and plated onto LB agar media containing 100 µg/ml ampicillin. The final construct was confirmed by restriction endonuclease digests and sequence verification (GeneWiz, San Diego, Calif.), resulting in plasmid pBF653.

Lys 2 Gene Cloning

The Lys2 gene was isolated by PCR amplification from pRS317 (ATCC Cat. No. 77157; Sikorski R S, Boeke J D. Methods Enzymol. 194: 302-318, 1991. PubMed: 2005795) using primers JML/93 and JML/94. PCR amplification was performed as follows: about 25 ng of the pRS317 plasmid DNA was added to 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reactions were cycled at: 95° C. 10 minutes followed by 10 rounds of 95° C. for 20 seconds, 55° C. for 30 seconds, and 72° C. for 2 minutes, followed by 25 more rounds of 95° C. for 20 seconds, 62° C. for 30 seconds, and 72° C. for 2 minutes. A final 5 minute extension reaction at 72° C. was also included. The amplified product was TOPO cloned into the pCR Blunt II TOPO vector as described herein, resulting in plasmid pBF656. The nucleotide sequence of Lys2 gene and the primers used for amplification of the Lys2 gene are given below.

JML/93
(SEQ ID NO: 288)
GCGGCCGCAGCTTCGCAAGTATTCATTTTAGACCCATG

JML/94
(SEQ ID NO: 289)
GGCCGGCCGGTACCAATTCCACTTGCAATTACATAAAAAATTCC

Lys 2 (from genomic sequence database),
SEQ. ID. NO: 122
```
ATGACTAACGAAAAGGTCTGGATAGAGAAGTTGGATAATCCAACT
CTTTCAGTGTTACCACATGACTTTTTACGCCCACAACAAGAACCT
TATACGAAACAAGCTACATATTCGTTACAGCTACCTCAGCTCGAT
GTGCCTCATGATAGTTTTTCTAACAAATACGCTGTCGCTTTGAGT
GTATGGGCTGCATTGATATATAGAGTAACCGGTGACGATGATATT
GTTCTTTATATTGCGAATAACAAAATCTTAAGATTCAATATTCAA
CCAACGTGGTCATTTAATGAGCTGTATTCTACAATTAACAATGAG
TTGAACAAGCTCAATTCTATTGAGGCCAATTTTTCCTTTGACGAG
CTAGCTGAAAAAATTCAAAGTTGCCAAGATCTGGAAAGGACCCCT
CAGTTGTTCCGTTTGGCCTTTTTGGAAAACCAAGATTTCAAATTA
GACGAGTTCAAGCATCATTTAGTGGACTTTGCTTTGAATTTGGAT
ACCAGTAATAATGCGCATGTTTTGAACTTAATTTATAACAGCTTA
CTGTATTCGAATGAAAGAGTAACCATTGTTGCGGACCAATTTACT
CAATATTTGACTGCTGCGCTAAGCGATCCATCCAATTGCATAACT
AAAATCTCTCTGATCACCGCATCATCCAAGGATAGTTTACCTGAT
CCAACTAAGAACTTGGGCTGGTGCGATTTCGTGGGGTGTATTCAC
GACATTTTCCAGGACAATGCTGAAGCCTTCCCAGAGAGAACCTGT
GTTGTGGAGACTCCAACACTAAATTCCGACAAGTCCCGTTCTTTC
ACTTATCGCGACATCAACCGCACTTCTAACATAGTTGCCCATTAT
TTGATTAAAACAGGTATCAAAAGAGGTGATGTAGTGATGATCTAT
TCTTCTAGGGGTGTGGATTTGATGGTATGTGTGATGGGTGTCTTG
AAAGCCGGCGCAACCTTTTCAGTTATCGACCCTGCATATCCCCCA
GCCAGACAAACCATTTACTTAGGTGTTGCTAAACCACGTGGGTTG
ATTGTTATTAGAGCTGCTGGACAATTGGATCAACTAGTAGAAGAT
TACATCAATGATGAATTGGAGATTGTTTCAAGAATCAATTCCATC
GCTATTCAAGAAAATGGTACCATTGAAGGTGGCAAATTGGACAAT
GGCGAGGATGTTTTGGCTCCATATGATCACTACAAAGACACCAGA
ACAGGTGTTGTAGTTGGACCAGATTCCAACCCAACCCTATCTTTC
ACATCTGGTTCCGAAGGTATTCCTAAGGGTGTTCTTGGTAGACAT
TTTTCCTTGGCTTATTATTTCAATTGGATGTCCAAAAGGTTCAAC
TTAACAGAAAATGATAAATTCACAATGCTGAGCGGTATTGCACAT
```

-continued
```
GATCCAATTCAAAGAGATATGTTTACACCATTATTTTTAGGTGCC
CAATTGTATGTCCCTACTCAAGATGATATTGGTACACCGGGCCGT
TTAGCGGAATGGATGAGTAAGTATGGTTGCACAGTTACCCATTTA
ACACCTGCCATGGGTCAATTACTTACTGCCCAAGCTACTACACCA
TTCCCTAAGTTACATCATGCGTTCTTTGTGGGTGACATTTTAACA
AAACGTGATTGTCTGAGGTTACAAACCTTGGCAGAAAATTGCCGT
ATTGTTAATATGTACGGTACCACTGAAACACAGCGTGCAGTTTCT
TATTTCGAAGTTAAATCAAAAAATGACGATCCAAACTTTTTGAAA
AAATTGAAAGATGTCATGCCTGCTGGTAAAGGTATGTTGAACGTT
CAGCTACTAGTTGTTAACAGGAACGATCGTACTCAAATATGTGGT
ATTGGCGAAATAGGTGAGATTTATGTTCGTGCAGGTGGTTTGGCC
GAAGGTTATAGAGGATTACCAGAATTGAATAAAGAAAAATTTGTG
AACAACTGGTTTGTTGAAAAAGATCACTGGAATTATTTGGATAAG
GATAATGGTGAACCTTGGAGACAATTCTGGTTAGGTCCAAGAGAT
AGATTGTACAGAACGGGTGATTTAGGTCGTTATCTACCAAACGGT
GACTGTGAATGTTGCGGTAGGGCTGATGATCAAGTTAAAATTCGT
GGGGTTCAGAATCGAATTAGGAGAAATAGATACGCACATTTCCCAA
CATCCATTGGTAAGAGAAAACATTACTTTAGTTCGCAAAAATGCC
GACAATGAGCCAACATTGATCACATTTATGGTCCCAAGATTTGAC
AAGCCAGATGACTTGTCTAAGTTCCAAAGTGATGTTCCAAAGGAG
GTTGAAACTGACCCTATAGTTAAGGGCTTAATCGGTTACCATCTT
TTATCCAAGGACATCAGGACTTTCTTAAAGAAAAGATTGGCTAGC
TATGCTATGCCTTCCTTGATTGTGGTTATGGATAAACTACCATTG
AATCCAAATGGTAAAGTTGATAAGCCTAAACTTCAATTCCCAACT
CCCAAGCAATTAAATTTGGTAGCTGAAAATACAGTTTCTGAAACT
GACGACTCTCAGTTTACCAATGTTGAGCGCGAGGTTAGAGACTTA
TGGTTAAGTATATTACCTACCAAGCCAGCATCTGTATCACCAGAT
GATTCGTTTTTCGATTTAGGTGGTCATTCTATCTTGGCTACCAAA
ATGATTTTTACCTTAAAGAAAAAGCTGCAAGTTGATTTACCATTG
GGCACAATTTTCAAGTATCCAACGATAAAGGCCTTTGCCGCGGAA
ATTGACAGAATTAAATCATCGGGTGGATCATCTCAAGGTGAGGTC
GTCGAAAATGTCACTGCAAATTATGCGGAAGACGCCAAGAAATTG
GTTGAGACGCTACCAAGTTCGTACCCCTCTCGAGAATATTTTGTT
GAACCTAATAGTGCCGAAGGAAAAACAACAATTAATGTGTTTGTT
ACCGGTGTCACAGGATTTCTGGGCTCCTACATCCTTGCAGATTTG
TTAGGACGTTCTCCAAAGAACTACAGTTTCAAAGTGTTTGCCCAC
GTCAGGGCCAAGGATGAAGAAGCTGCATTTGCAAGATTACAAAAG
GCAGGTATCACCTATGGTACTTGGAACGAAAAATTTGCCTCAAAT
ATTAAAGTTGTATTAGGCGATTTATCTAAAAGCCAATTTGGTCTT
TCAGATGAGAAGTGGATGGATTTGGCAAACACAGTTGATATAATT
ATCCATAATGGTGCGTTAGTTCACTGGGTTTATCCATATGCCAAA
TTGAGGGATCCAAATGTTATTTCAACTATCAATGTTATGAGCTTA
GCCGCCGTCGGCAAGCCAAAGTTCTTTGACTTTGTTTCCTCCACT
TCTACTCTTGACACTGAATACTACTTTAATTTGTCAGATAAACTT
GTTAGCGAAGGGAAGCCAGGCATTTTAGAATGACGATTTAATG
AACTCTGCAAGCGGGCTCACTGGTGGATATGGTCAGTCCAAATGG
GCTGCTGAGTACATCATTAGACGTGCAGGTGAAAGGGGCCTACGT
GGGTGTATTGTCAGACCAGGTTACGTAACAGGTGCCTCTGCCAAT
GGTTCTTCAAACACAGATGATTTCTTATTGAGATTTTTGAAAGGT
TCAGTCCAATTAGGTAAGATTCCAGATATCGAAAATTCCGTGAAT
ATGGTTCCAGTAGATCATGTTGCTCGTGTTGTTGTTGCTACGTCT
TTGAATCCTCCCAAAGAAAATGAATTGGCCGTTGCTCAAGTAACG
GGTCACCCAAGAATATTATTCAAAGACTACTTGTATACTTTACAC
GATTATGGTTACGATGTCGAAATCGAAAGCTATTCTAAATGGAAG
AAATCATTGGAGGCGTCTGTTATTGACAGGAATGAAGAAAATGCG
TTGTATCCTTTGCTACACATGGTCTTAGACAACTTACCTGAAAGT
ACCAAAGCTCCGGAACTAGACGATAGGAACGCCGTGGCATCTTTA
AAGAAAGACACCGCATGGACAGGTGTTGATTGGTCTAATGGAATA
GGTGTTACTCCAGAAGAGGTTGGTATATATATTGCATTTTTAAAC
AAGGTTGGATTTTTACCTCCACCAACTCATAATGACAAACTTCCA
CTGCCAAGTATAGAACTAACTCAAGCGCAAATAAGTCTAGTTGCT
TCAGGTGCTGGTGCTCGTGGAAGCTCCGCAGCAGCTTAA
```

The knockout cassette was fully assembled by cloning the NotI-FseI LYS2 fragment from plasmid pBF656 into the NotI-FseI sites located between the 5' and 3' flanking PFK2 regions in plasmid pBF653. About 50 ng of plasmid pBF653 digested with NotI and FseI was ligated to about 100 ng of the NotI-FseI LYS2 fragment from plasmid pBF656 in a 5 µl reaction containing 1× ligation buffer and 1 U T4 DNA ligase (Fermentas) for about 1 hour at room temperature. About 2 µl of this reaction was used to transform competent DH5α (Zymo Research, Orange, Calif.) and plated on 100 µg/ml ampicillin. The structure of the final plasmid, pBF745, was confirmed by restriction enzyme digests. The approximately 5 kbp PacI fragment containing the LYS2 cassette and PFK2 flanking regions was gel extracted using the Zymoclean Gel DNA Recovery Kit (Zymo Research, Orange, Calif.) according to the manufacturer's conditions.

Strain BF1477 was transformed with the about 5 kbp PacI fragment using the method described above (LiOAc/PEG method) generating strain BF1411. Strain BF1411 has the ability to grow on galactose as a carbon source, but cannot grow on glucose. Various combinations of the EDD and EDA constructs can be expressed in this strain and monitored for growth on glucose. Strains which show growth on glucose (or the highest growth rate on glucose) can be further characterized to determine which combination of EDD and EDA genes is present. Using the strain and method described herein, libraries of EDD and EDA genes can be screened for improved activities and activity combinations in a host organism.

Example 16

Single Plasmid System for Industrial Yeast

A single plasmid system expressing EDD and EDA for industrial yeast was constructed as follows: The approximately 2800 bp fragment containing the GPD1 promoter, EDD-PAO1 gene and CYC1 terminator from plasmid pBF291 (p426GPD with EDD-PAO1) was PCR amplified using primers KAS/5'-BamHI-Pgpd and KAS/3'-NdeI-CYCt, described below. About 25 ng of the plasmid DNA was added to 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 55° C. for 30 seconds, and 72° C. for 45 seconds. A final 5 minute extension reaction at 72° C. was also included. The amplified product was TOPO cloned into the pCR Blunt II TOPO vector, as described herein, and the final plasmid was sequence verified and designated, pBF475.

```
KAS/5'-BamHI-Pgpd
                                      (SEQ ID NO: 290)
    GGATCCgtttatcattatcaatactcgccatttcaaag KAS/3'-NdeI-CYCt
                                      (SEQ ID NO: 291)
    CATATGttgggtaccggccgcaaattaaagccttcgagcg
```

An approximately 1500 bp KANMX4 cassette was PCR amplified from plasmid pBF413 HO-poly-KanMX4-HO (ATCC Cat. No. 87804) using primers KAS/5'-Bam_NdeI-KANMX4 and KAS/3'-Sal_NheI-KANMX4, described below.

```
KAS/5'-Bam_NdeI-KANMX4
                                      (SEQ ID NO: 292)
    GGATTCagtcagatCATATGggtaccccgggttaattaaggcgcg
    ccagatctg KAS/3'-Sal_NheI-KANMX4
                                      (SEQ ID NO: 293)
    GTCGACaggcctactgtacgGCTAGCgaattcgagctcgttttcga
    cactggatggcggc
```

About 25 ng of plasmid pBF413 HO-poly-KanMX4-HO DNA was added to 1×Pfu Ultra II buffer, 0.3 mM dNTPs, 0.3 µmol gene-specific primers and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 55° C. for 30 seconds, and 72° C. for 30 seconds. A final 5 minute extension reaction at 72° C. was also included. The amplified product was TOPO cloned into the pCR Blunt II TOPO vector, as described herein. The resulting plasmid was sequence verified and designated, pBF465.

An approximately 225 bp ADH1 terminator was PCR amplified from the genome of BY4742 using primers KAS/ 5'-Xba-XhoI-ADHt and KAS/3'-StuI-ADH5. The sequence of primers KAS/5'-Xba-XhoI-ADHt and KAS/3'-StuI-ADH5 is given below.

```
KAS/5'-Xba-XhoI-ADHt
                                        (SEQ ID NO: 294)
tctagaCTCGAGtaataagcgaatttcttatgatttatg KAS/3'-StuI-ADH5
                                        (SEQ ID NO: 295)
aagcttAGGCCTggagcgatttgcaggcatttgc
```

About 100 ng of genomic DNA from BY4742 was added to 1×Pfu Ultra II buffer, 0.3 mM dNTPs, 0.3 μmol gene-specific primers and 1 U Pfu Ultra II polymerase (Agilent, La Jolla, Calif.) in a 50 μl reaction mix. The reaction was cycled at 95° C. for 10 minutes, followed by 30 rounds of 95° C. for 20 seconds, 55° C. for 30 seconds, and 72° C. for 15 seconds. A final 5 minute extension reaction at 72° C. was also included. The amplified product was TOPO cloned into the pCR Blunt II TOPO vector according to the manufacturer's recommendations and sequence verified. The resulting plasmid was designated pBF437.

The TEF2 promoter was PCR amplified from the genome of BY4742 using primers KAS/5'-Xba-XhoI-ADHt and KAS/3'-StuI-ADH5, described below.

```
KAS/5'-Bam-NheI-Ptef
                                        (SEQ ID NO: 296)
GGATCCgctagcACCGCGAATCCTTACATCACACCC KAS/3'-XbaI-SpeI-Ptef
                                        (SEQ ID NO: 297)
tctagaCTCGAGtaataagcgaatttcttatgatttatg
```

About 100 ng of genomic DNA from BY4742 was added to 1×Pfu Ultra II buffer, 0.3 mM dNTPs, 0.3 μmol gene-specific primers, and 1 U Pfu Ultra II polymerase (Agilent, La Jolla, Calif.) in a 50 μl reaction mix. This was cycled at 95° C. for 10 minutes, followed by 30 rounds of 95° C. for 20 seconds, 55° C. for 30 seconds, and 72° C. for 15 seconds. A final 5 minute extension reaction at 72° C. was also included. The amplified product was TOPO cloned into the pCR Blunt II TOPO vector (Life Technologies, Carlsbad, Calif.) according to the manufacturer's recommendations and sequence verified (GeneWiz, San Diego, Calif.). The resulting plasmid was called pBF440.

The EDA gene cassettes were constructed as follows: First the TEF2 promoter from the plasmid pBF440 was digested with BamHI and XbaI and was cloned into the BamHI and XbaI sites of pUC19 creating plasmid pBF480. Plasmid pBF480 was then digested with XbaI and HindIII and was ligated to the XbaI-HindIII fragment from plasmid pBF437 containing the ADH1 terminator, creating plasmid pBF521. Plasmid pBF521 was then digested with SpeI and XhoI and then ligated to either SpeI-XhoI fragment containing either the PAO1 eda gene from plasmid pBF292 or the *E. coli* eda gene from plasmid pBF268. The 2 plasmids generated, depending on the eda gene chosen, were designated pBF523 (e.g., containing the PAO1-eda) and pBF568 (e.g., containing the *E. coli*-eda), respectively. The approximately 1386 bp TEF-EDA-ADHt cassette from either plasmid pBF 523 or pBF568 was then gel extracted using the NheI-StuI sites.

The final vector was generated by first altering the NdeI site in pUC19 using the mutagenesis primers described below.

```
KAS/SDM-NdeI-pUC18-5
                                        (SEQ ID NO: 298)
gattgtactgagagtgcacaatatgcggtgtgaaatacc KAS/SDM-NdeI-pUC18-3
                                        (SEQ ID NO: 299)
ggtatttcacaccgcatattgtgcactctcagtacaatc
```

About 50 ng of pUC19 plasmid DNA was added to 1×Pfu Ultra II buffer, 0.3 mM dNTPs, 0.3 μmol SDM-specific primers and 1 U Pfu Ultra II polymerase (Agilent, La Jolla, Calif.) in a 50 μl reaction mix. The reaction was cycled at 95° C. for 10 minutes, followed by 15 rounds of 95° C. for 15 seconds, 55° C. for 40 seconds, and 72° C. for 3 minutes. A final 10 minute extension reaction at 72° C. was also included. The PCR reaction mixture was then digested with 30 U of DpnI for about 2 hours and 5 μl of the digested PCR reaction mixture was used to transform competent DH5α (Zymo Research, Orange, Calif.) and plated onto LB plates containing 100 μg/ml ampicillin. The structure of the final plasmid, pBF421, was confirmed by restriction digests.

An approximately 1359 bp EcoRI fragment containing the 2μ yeast origin cassette was cloned into the EcoRI site of plasmid pBF421 in a 10 μl ligation reaction mixture containing 1× ligation buffer, 50 ng of EcoRI-digested pBF421 80 ng of EcoRI-digested 2μ cassette, and 1 U T4 DNA ligase (Fermentas). The reaction was incubated at room temperature for about 2 hours and 3 μl of this was used to transform competent DH5α (Zymo Research, Orange, Calif.). The structure of the resultant plasmid, pBF429, was confirmed by restriction enzyme digests.

Plasmid pBF429 was then digested with BamHI and SalI and ligated to the BamHI-SalI KANMX4 cassette described above. The resultant plasmid, designated pBF515, was digested with BamHI and NdeI and ligated to the BamHI-NdeI fragment containing the 2802 bp GPD-EDD-CYCt fragment from pBF475. The resulting plasmid, designated pBF522, was digested with NheI-StuI and was ligated to the 1386 bp NheI-StuI TEF-EDA-ADHt fragment from plasmids pBF523 or pBF568, creating final plasmids pBF524 and pBF612.

Figure 14:
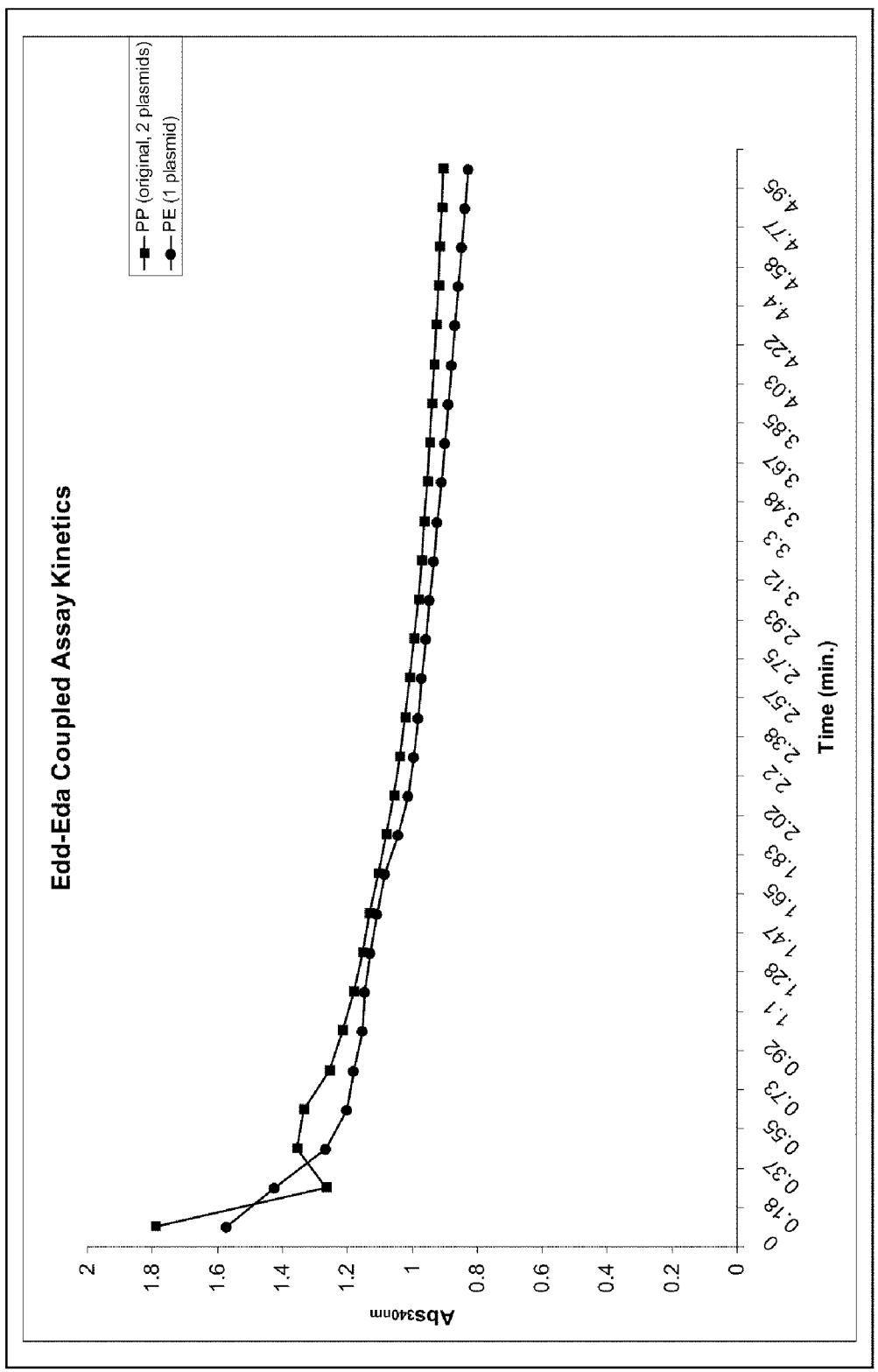
FIG. 14 graphically illustrates the results of coupled assay kinetics for single plasmid and two plasmid edd/eda expression vector systems. Vector construction and experimental conditions are described in Example 16.

Expression levels of each of the single plasmid eda/edd expression system vectors was assayed and compared against the original eda/edd two plasmid expression system vectors. The results, presented in FIG. 14, graphically illustrate edd/eda coupled assay kinetics for the single and two plasmid systems. The kinetics graphs for both expression systems show substantially similar enzyme kinetics over the major of the time course.

Example 17

Nucleotide and Amino Acid Sequences of Over Expressed Activities Useful for Increasing Sugar Transport and/or Sugar Metabolism As noted herein, increased or over expression of certain activities can result in increased ethanol production due to an increase in the utilization of the fermentation substrate, sometimes due to an increase in transport and/or metabolism of a desired sugar. Non-limiting examples of activities that can be over expressed to increase ethanol production by increasing sugar transport and/or metabolism include activities encoded by the genes gxf1, gxs1, hxt7, zwf1, gal2, sol3, sol4, the like, homologs thereof (e.g., *Candida albicans* Sol1p, *Schizosaccharomyces pombe* Sol1p, human PGLS and human H6PD), that can be expressed in a desired host organism, and combinations thereof. Nucleotide and amino acid sequences for some of these additional activities are given below. In some embodiments, 1, 2, 3, 4, 5, 6 or more of the non-limiting additional activities can be increased in expression or over expressed in an engineered host, thereby increasing transport and/or metabolism of a desired carbon source, wherein increased transport and/or metabolism of a desired carbon source results in increased ethanol production.

| Nucleotide Sequences |
|---|
| *Debaryomyces hansenii* gxf1 |
| (SEQ ID NO: 113) |
| ATGTCTCAAGAAGAATATAGTTCTGGGGTACAAACCCCAGTTTCTAACCATTCTGGTTTA |
| GAGAAAGAAGAGCAACACAAGTTAGACGGTTTAGATGAGGATGAAATTGTCGATCAATTA |
| CCTTCTTTACCAGAAAAATCAGCTAAGGATTATTTATTAATTTCTTTCTTCTGTGTATTA |
| GTTGCATTTGGTGGTTTTGTTTTCGGTTTCGATACTGGTACTATCTCAGGTTTCGTTAAC |
| ATGAGTGATTACTTGGAAAGATTCGGTGAGCTTAATGCAGATGGTGAATATTTCTTATCT |
| AATGTTAGAACTGGTTTGATTGTTGCTATTTTTAATGTTGGTTGTGCTGTCGGTGGTATT |
| TTCTTATCTAAGATTGCTGATGTTTATGGTAGAAGAATTGGTCTTATGTTTTCCATGATT |
| ATTTATGTGATTGGTATAATTGTTCAAATCTCAGCTTCTGACAAGTGGTATCAAATCGTT |
| GTTGGTAGAGCTATTGCAGGTTTAGCTGTTGGTACCGTTTCTGTCTTATCCCCATTATTC |
| ATTGGTGAATCAGCACCTAAAACCTTAAGAGGTACTTTAGTGTGTTGTTTCCAATTATGT |
| ATTACCTTAGGTATCTTCTTAGGTTACTGTACTACATATGGTACTAAAACCTACACCGAC |
| TCTAGACAATGGAGAATTCCATTAGGTTTATGTTTTGTTGGGCTATCATGTTGGTTATT |
| GGTATGGTTTGCATGCCAGAATCACCAAGATACTTAGTTGTCAAGAACAAGATTGAAGAA |
| GCTAAGAAATCGATTGGTAGATCCAACAAGGTTTCACCAGAAGATCCTGCTGTTTACACC |
| GAAGTCCAATTGATTCAAGCAGGTATTGAAAGAGAAAGTTTAGCTGGTTCTGCCTCTTGG |
| ACCGAATTGGTTACTGGTAAGCCAAGAATCTTTCGTAGAGTCATTATGGGTATTATGTTA |
| CAATCTTTACAACAATTGACTGGTGACAACTATTTCTTCTACTATGGTACTACTATTTTC |
| CAAGCTGTCGGTATGACTGATTCCTTCCAAACATCTATTGTTTTAGGTGTTGTTAACTTT |
| GCATCTACATTTCTCGGTATCTACACAATTGAAAGATTCGGTAGAAGATTATGTTTGTTA |
| ACTGGTTCTGTCTGTATGTTCGTTTGTTTCATCATTTACTCCATTTTGGGTGTTACAAAC |
| TTATATATTGATGGCTACGATGGTCCAACTTCGGTTCCAACCGGTGATGCGATGATTTTC |
| ATTACTACCTTATACATTTTCTTCTTCGCATCCACCTGGGCTGGTGGTGTCTACTGTATC |
| GTTTCCGAAACATACCCATTGAGAATTAGATCTAAGGCCATGTCCGTTGCCACCGCTGCT |
| AACTGGATTTGGGGTTTCTTGATCTCTTTCTTCACTCCATTCATCACCTCGGCTATCCAC |
| TTCTACTACGGTTTCGTTTTCACAGGATGTTTGTTATTCTCGTTCTTTTACGTTTACTTC |
| TTTGTTGTTGAAACTAAGGGATTAACTTTAGAAGAAGTTGATGAATTGTATGCCCAAGGT |
| GTTGCCCCATGGAAGTCATCGAAATGGGTTCCACCAACCAAGGAAGAAATGGCCCATTCT |
| TCAGGATATGCTGCTGAAGCCAAACCTCACGATCAACAAGTATAA |
| |
| *Saccharomyces cerevisiae* gal2 |
| (SEQ ID NO: 114) |
| ATGGCAGTTGAGGAGAACAATATGCCTGTTGTTTCACAGCAACCCCAAGCTGGTGAAGAC |
| GTGATCTCTTCACTCAGTAAAGATTCCCATTTAAGCGCACAATCTCAAAAGTATTCTAAT |
| GATGAATTGAAAGCCGGTGAGTCAGGGTCTGAAGGCTCCCAAAGTGTTCCTATAGAGATA |
| CCCAAGAAGCCCATGTCTGAATATGTTACCGTTTCCTTGCTTTGTTTGTGTGTTGCCTTC |
| GGCGGCTTCATGTTTGGCTGGGATACCGGTACTATTTCTGGGTTTGTTGTCCAAACAGAC |
| TTTTTGAGAAGGTTTGGTATGAAACATAAGGATGGTACCCACTATTTGTCAAACGTCAGA |
| ACAGGTTTAATCGTCGCCATTTTCAATATTGGCTGTGCCTTTGGTGGTATTATACTTTCC |
| AAAGGTGGAGATATGTATGGCCGTAAAAAGGGTCTTTCGATTGTCGTCTCGGTTTATATA |
| GTTGGTATTATCATTCAAATTGCCTCTATCAACAAGTGGTACCAATATTTCATTGGTAGA |
| ATCATATCTGGTTTGGGTGTCGGCGGCATCGCCGTCTTATGTCCTATGTTGATCTCTGAA |
| ATTGCTCCAAAGCACTTGAGAGGCACACTAGTTTCTTGTTATCAGCTGATGATTACTGCA |
| GGTATCTTTTTGGGCTACTGTACTAATTACGGTACAAAGAGCTATTCGAACTCAGTTCAA |
| TGGAGAGTTCCATTAGGGCTATGTTTCGCTTGGTCATTATTTATGATTGGCGCTTTGACG |
| TTAGTTCCTGAATCCCCACGTTATTTATGTGAGGTGAATAAGGTAGAAGACGCCAAGCGT |
| TCCATTGCTAAGTCTAACAAGGTGTCACCAGAGGATCCTGCCGTCCAGGCAGAGTTAGAT |
| CTGATCATGGCCGGTATAGAAGCTGAAAACTGGCTGGCAATGCGTCCTGGGGGGAATTA |
| TTTTCCACCAAGACCAAAGTATTTCAACGTTTGTTGATGGGTGTGTTTGTTCAAATGTTC |
| CAACAATTAACCGGTAACAATTATTTTTTCTACTACGGTACCGTTATTTTCAAGTCAGTT |
| GGCCTGGATGATTCCTTTGAAACATCCATTGTCATTGGTGTAGTCAACTTTGCCTCCACT |
| TTCTTTAGTTTGTGGACTGTCGAAAACTTGGGACATCGTAAATGTTTACTTTTGGGCGCT |
| GCCACTATGATGGCTTGTATGGTCATCTACGCCTCTGTTGGTGTTACTAGATTATATCCT |
| CACGGTAAAAGCCAGCCATCTTCTAAAGGTGCCGGTAACTGTATGATTGTCTTTACCTGT |
| TTTTATATTTTCTGTTATGCCACAACCTGGGCGCCAGTTGCCTGGGTCATCACAGCAGAA |
| TCATTCCCACTGAGAGTCAAGTCGAAATGTATGGCGTTGGCCTCTGCTTCCAATTGGGTA |
| TGGGGGTTCTTGATTGCATTTTTCACCCCATTCATCACATCTGCCATTAACTTCTACTAC |
| GGTTATGTCTTCATGGGCTGTTTGGTTGCCATGTTTTTTATGTCTTTTTCTTTGTTCCA |
| GAAACTAAAGGCCTATCGTTAGAAGAAATTCAAGAATTATGGGAAGAAGGTGTTTTACCT |
| TGGAAATCTGAAGGCTGGATTCCTTCATCCAGAAGAGGTAATAATTACGATTTAGAGGAT |
| TTACAACATGACGACAAACCGTGGTACAAGGCCATGCTAGAATAA |
| |
| *Saccharomyces cerevisiae* sol3 |
| (SEQ ID NO: 115) |
| ATGGTGACAGTCGGTGTGTTTCTGAGAGGGCTAGTTTGACCCATCAATTGGGGGAATTC |
| ATCGTCAAGAAACAAGATGAGGCGCTGCAAAAGAAGTCAGACTTTAAAGTTTCCGTTAGC |
| GGTGGCTCTTTGATCGATGCTCTGTATGAAAGTTTAGTAGCGGACGAATCACTATCTTCT |

| Nucleotide Sequences |
|---|
| CGAGTGCAATGGTCTAAATGGCAAATCTACTTCTCTGATGAAAGAATTGTGCCACTGACG<br>GACGCTGACAGCAATTATGGTGCCTTCAAGAGAGCTGTTCTAGATAAATTACCCTCGACT<br>AGTCAGCCAAACGTTTATCCCATGGACGAGTCCTTGATTGGCAGCGATGCTGAATCTAAC<br>AACAAAATTGCTGCAGAGTACGAGCGTATCGTACCTCAAGTGCTTGATTTGGTACTGTTG<br>GGCTGTGGTCCTGATGGACACACTTGTTCCTTATTCCCTGGAGAAACACATAGGTACTTG<br>CTGAACGAAACAACCAAAAGAGTTGCTTGGTGCCACGATTCTCCCAAGCCTCCAAGTGAC<br>AGAATCACCTTCACTCTGCCTGTGTTGAAAGACGCCAAAGCCCTGTGTTTTGTGGCTGAG<br>GGCAGTTCCAAACAAAATATAATGCATGAGATCTTTGACTTGAAAAACGATCAATTGCCA<br>ACCGCATTGGTTAACAAATTATTTGGTGAAAAAACATCCTGGTTCGTTAATGAGGAAGCT<br>TTTGGAAAAGTTCAAACGAAAACTTTTTAG |

*Saccharomyces cerevisiae* zwf1

(SEQ ID NO: 116)

```
ATGAGTGAAGGCCCCGTCAAATTCGAAAAAAATACCGTCATATCTGTCTTTGGTGCGTCA
GGTGATCTGGCAAAGAAGAAGACTTTTCCCGCCTTATTTGGGCTTTTCAGAGAAGGTTAC
CTTGATCCATCTACCAAGATCTTCGGTTATGCCCGGTCCAAATTGTCCATGGAGGAGGAC
CTGAAGTCCCGTGTCCTACCCCACTTGAAAAAACCTCACGGTGAAGCCGATGACTCTAAG
GTCGAACAGTTCTTCAAGATGGTCAGCTACATTTCGGGAAATTACGACACAGATGAAGGC
TTCGACGAATTAAGAACGCAGATCGAGAAATTCGAGAAAAGTGCCAACGTCGATGTCCCA
CACCGTCTCTTCTATCTGGCCTTGCCGCCAAGCGTTTTTTTGACGGTGGCCAAGCAGATC
AAGAGTCGTGTGTACGCAGAGAATGGCATCACCCGTGTAATCGTAGAGAAACCTTTCGGC
CACGACCTGGCCTCTGCCAGGGAGCTGCAAAAAAACCTGGGGCCCCTCTTTAAAGAAGAA
GAGTTGTACAGAATTGACCATTACTTGGGTAAAGAGTTGGTCAAGAATCTTTTAGTCTTG
AGGTTCGGTAACCAGTTTTTGAATGCCTCGTGGAATAGAGACAACATTCAAAGCGTTCAG
ATTTCGTTTAAAGAGAGGTTCGGCACCGAAGGCCGTGGCGGCTATTTCGACTCTATAGGC
ATAATCAGAGACGTGATGCAGAACCATCTGTTACAAATCATGACTCTCTTGACTATGGAA
AGACCGGTGTCTTTTGACCCGGAATCTATTCGTGACGAAAAGGTTAAGGTTCTAAAGGCC
GTGGCCCCCATCGACACGGACGACGTCCTCTTGGGCCAGTACGGTAAATCTGAGGACGGG
TCTAAGCCCGCCTACGTGGATGATGACACTGTAGACAAGGACTCTAAATGTGTCACTTTT
GCAGCAATGACTTTCAACATCGAAAACGAGCGTTGGGAGGGCGTCCCCATCATGATGCGT
GCCGGTAAGGCTTTGAATGAGTCCAAGGTGGAGATCAGACTGCAGTACAAAGCGGTCGCA
TCGGGTGTCTTCAAAGACATTCCAAATAACGAACTGGTCATCAGAGTGCAGCCGATGCC
GCTGTGTACCTAAAGTTTAATGCTAAGACCCCTGGTCTGTCAAATGCTACCCAAGTCACA
GATCTGAATCTAACTTACGCAAGCAGGTACCAAGACTTTTGGATTCCAGAGGCTTACGAG
GTGTTGATAAGAGACGCCCTACTGGGTGACCATTCCAACTTTGTCAGAGATGACGAATTG
GATATCAGTTGGGGCATATTCACCCCATTACTGAAGCACATAGAGCGTCCGGACGGTCA
ACACCGGAAATTTACCCCTACGGATCAAGAGGTCCAAAGGGATTGAAGGAATATATGCAA
AAACACAAGTATGTTATGCCCGAAAAAGCACCCTTACGCTTGGCCCGTGACTAAGCCAGAA
GATACGAAGGATAATTAG
```

Amino Acid Sequences

*Debaryomyces hansenii* gxf1

(SEQ ID NO: 117)

```
  1 MSQEEYSSGV QTPVSNHSGL EKEEQHKLDG LDEDEIVDQL PSLPEKSAKD YLLISFFCVL
 61 VAFGGFVFGF DTGTISGFVN MSDYLERFGE LNADGEYFLS NVRTGLIVAI FNVGCAVGGI
121 FLSKIADVYG RRIGLMFSMI IYVIGIIVQI SASDKWYQIV VGRAIAGLAV GTVSVLSPLF
181 IGESAPKTLR GTLVCCFQLC ITLGIFLGYC TTYGTKTYTD SRQWRIPLGL CFVWAIMLVI
241 GMVCMPESPR YLVVKNKIEE AKKSIGRSNK VSPEDPAVYT EVQLIQAGIE RESLAGSASW
301 TELVTGKPRI FRRVIMGIML QSLQQLTGDN YFFYYGTTIF QAVGMTDSFQ TSIVLGVVNF
361 ASTFLGIYTI ERFGRRLCLL TGSVCMFVCF IIYSILGVTN LYIDGYDGPT SVPTGDAMIF
421 ITTLYIFFFA STWAGGVYCI VSETYPLRIR SKAMSVATAA NWIWGFLISF FTPFITSAIH
481 FYYGFVFTGC LLFSFFYVYF FVVETKGLTL EEVDELYAQG VAPWKSSKWV PPTKEEMAHS
541 SGYAAEAKPH DQQV
```

*Saccharomyces cerevisiae* gal2

(SEQ ID NO: 118)

```
  1 MAVEENNMPV VSQQPQAGED VISSLSKDSH LSAQSQKYSN DELKAGESGS
 51 EGSQSVPIEI PKKPMSEYVT VSLLCLCVAF GGFMFGWDTG TISGFVVQTD
101 FLRRFGMKHK DGTHYLSNVR TGLIVAIFNI GCAFGGIILS KGGDMYGRKK
151 GLSIVVSVYI VGIIIQIASI NKWYQYFIGR IISGLGVGGI AVLCPMLISE
201 IAPKHLRGTL VSCYQLMITA GIFLGYCTNY GTKSYSNSVQ WRVPLGLCFA
251 WSLFMIGALT LVPESPRYLC EVNKVEDAKR SIAKSNKVSP EDPAVQAELD
301 LIMAGIEABK LAGNASWGEL FSTKTKVFQR LLMGVFVQMF QQLTGNNYFF
351 YYGTVIFKSV GLDDSFETSI VIGVVNFAST FFSLWTVENL GHRKCLLLGA
401 ATMMACMVIY ASVGVTRLYP HGKSQPSSKG AGNCMIVFTC FYIFCYATTW
451 APVAWVITAE SFPLRVKSKC MALASASNWV WGFLIAFFTP FITSAINFYY
501 GYVFMGCLVA MFFYVFFFVP ETKGLSLEEI QELWEEGVLP WKSEGWIPSS
551 RRGNNYDLED LQHDDKPWYK AMLE
```

*Saccharomyces cerevisiae* zwf1

(SEQ ID NO: 119)

```
  1 MSEGPVKFEK NTVISVFGAS GDLAKKKTFP ALFGLFREGY LDPSTKIFGY
 51 ARSKLSMEED LKSRVLPHLK KPHGEADDSK VEQFFKMVSY ISGNYDTDEG
101 FDELRTQIEK FEKSANVDVP HRLFYALPPS VFLTVAKQI KSRVYAENGI
151 TRVIVEKPFG HDLASARELQ KNLGPLFKEE ELYRIDHYLG KELVKNLLVL
201 RFGNQFLNAS WNRDNIQSVQ ISFKERFGTE GRGGYFDSIG IIRDVMQNHL
251 LQIMTLLTME RPVSFDPESI RDEKVKVLKA VAPIDTDDVL LGQYGKSEDG
301 SKPAYVDDDT VDKDSKCVTF AAMTFNIENE RWEGVPIMMR AGKALNESKV
```

-continued

Nucleotide Sequences

```
351 EIRLQYKAVA SGVFKDIPNN ELVIRVQPDA AVYLKFNAKT PGLSNATQVT
401 DLNLTYASRY QDFWIPEAYE VLIRDALLGD HSNFVRDDEL DISWGIFTPL
451 LKHIERPDGP TPEIYPYGSR GPKGLKEYMQ KHKYVMPEKH PYAWPVTKPE
501 DTKDN
```

Saccharomyces cerevisiae sol3
(SEQ ID NO: 120)
```
  1 MVTVGVFSER ASLTHQLGEF IVKKQDEALQ KKSDFKVSVS GGSLIDALYE
 51 SLVADESLSS RVQWSKWQIY FSDERIVPLT DADSNYGAFK RAVLDKLPST
101 SQPNVYPMDE SLIGSDAESN NKIAAEYERI VPQVLDLVLL GCGPDGHTCS
151 LFPGETHRYL LNETTKRVAW CHDSPKPPSD RITFTLPVLK DAKALCFVAE
201 GSSKQNIMHE IFDLKNDQLP TALVNKLFGE KTSWFVNEEA FGKVQTKTF
```

Example 18

Cloning of Additional ZWF1 Candidate Genes

A variety of ZWF1 genes were cloned from *S. cerevisiae, Zymomonas mobilis, Pseudomonas fluorescens* (zwf1 and zwf2), and *P. aeruginosa* strain PAO1. The sequences of these additional ZWF1 genes are given below.

zwf1 from *P. fluorescens*
Amino Acid Sequence
(SEQ. ID. NO: 123)
```
MTTTRKKSKALPAPPTTLFLFGARGDLVKRLLMPALYNLSRDGLLD
EGLRIVGVDHNAVSDAEFATLLEDFLRDEVLNKQGQGAAVDAAVWA
RLTRGINYVQGDFLDDSTYAELAARIAASGTGNAVFYLATAPRFFS
EVVRRLGSAGLLEEGPQAFRRVVIEKPFGSDLQTAEALNGCLLKVM
SEKQIYRIDHYLGKETVQNILVSRFSNSLFEAFWNNHYIDHVQITA
AETVGVETRGSFYEHTGALRDMVPNHLFQLLAMVAMEPPAAFGADA
VRGEKAKVVGAIRPWSVEEARANSVRGQYSAGEVAGKALAGYREEA
NVAPDSSTETYVALKVMIDNWRVVVGVPFYLRTGKRMSVRDTEIVI
CFKPAPYAQFRDTEVERLLPTYLRIQIQPNEGMWFDLLAKKPGPSL
DMANIELGFAYRDFFEMQPSTGYETLIYDCLIGDQTLFQRADNIEN
GWRAVQPFLDAWQQDASLQNYPAGVDGPAAGDELLARDGRVWRPLG
```

Nucleotide Sequence
(SEQ. ID. NO: 124)
```
ATGACCACCACGCGAAAGAAGTCCAAGGCGTTGCCGGCGCCGCCGA
CCACGCTGTTCCTGTTCGGCGCCCGCGGTGATCTGGTCAAGCGCCT
GCTGATGCCGGCGCTGTACAACCTCAGCCGCGACGGTTTGCTGGAT
GAGGGGCTGCGGATTGTCGGCGTCGACCACAACGCGGTGAGCGACG
CCGAGTTCGCCACGCTGCTGGAAGACTTCCTTCGCGATGAAGTGCT
CAACAAGCAAGGCCAGGGGGCGGCGGTGGATGCCGCCGTCTGGGCC
CGCCTGACCCGGGGCATCAACTATGTCCAGGGCGATTTTCTCGACG
ACTCCACCTATGCCGAACTGGCGGCGCGGATTGCCGCCAGCGGCAC
CGGCAACGCGGTGTTCTACCTGGCCACCGCACCGCGCTTCTTCAGT
GAAGTGGTGCGCCGCCTGGGCAGCGCCGGGTTGCTGGAGGAGGGGC
CGCAGGCTTTTCGCCGGGTGGTGATCGAAAAACCCTTCGGCTCCGA
CCTGCAGACCGCCGAAGCCCTCAACGGCTGCCTGCTCAAGGTCATG
AGCGAGAAGCAGATCTATCGCATCGACCATTACCTGGGCAAGGAAA
CGGTCCAGAACATCCTGGTCAGCCGTTTTTCCAACAGCCTGTTCGA
GGCATTCTGGAACAACCATTACATCGACCACGTGCAGATCACCGCG
GCGGAAACCGTCGGCGTGGAAACCCGTGGCAGCTTTTATGAACACA
CCGGTGCCCTGCGGGACATGGTGCCCAACCACCTGTTCCAGTTGCT
GGCGATGGTGGCCATGGAGCCGCCCGCTGCCTTTGGCGCCGATGCG
GTACGTGGCGAAAAGGCCAAGGTGGTGGGGGCTATCCGCCCCTGGT
CCGTGGAAGAGGCCCGGGCCAACTCGGTGCGGGCCCAGTACAGCGC
CGGTGAAGTGGCCGGCAAGGCCTGGCGGGCTACCGCGAGGAAGCC
AACGTGGCGCCGGACAGCAGCACCGAAACCTACGTTGCGCTGAAGG
TGATGATCGACAACTGGCGCTGGGTCGGGGTGCCGTTCTACCTGCG
CACCGGCAAGCGCATGAGTGTGCGCGACACCGAGATCGTCATCTGC
TTCAAGCCGGCGCCCTATGCACAGTTCCGCGATACCGAGGTCGAGC
GCCTGTTGCCGACCTACCTGCGGATCCAGATCCAGCCCAACGAAGG
CATGTGGTTCGACCTGCTGGCGAAAAAGCCCGGGCCGAGCCTGGAC
ATGGCCAACATCGAACTGGGTTTTGCCTACCGCGACTTTTTCGAGA
TGCAGCCCTCCACCGGCTACGAAACCCTGATCTACGACTGCCTGAT
CGGCGACCAGACCCTGTTCCAGCGCGCCGACAACATCGAGAACGGC
TGGCGCGCGGTGCAACCCTTCCTCGATGCCTGGCAACAGGACGCCA
GCTTGCAGAACTACCCGGCGGGCGTGGATGGCCCGGCAGCCGGGA
TGAACTGCTGGCCCGGGATGGCCGCGTATGGCGACCCCTGGGGTGA
``` zwf2 from *P. fluorescens*
Amino Acid Sequence
(SEQ. ID. NO: 125)
```
MPSITVEPCTFALFGALGDLALRKLFPALYQLDAAGLLHDDTRILA
LAREPGSEQEHLANIETELHKYVGDKDIDSQVLQRFLVRLSYLHVD
FLKAEDYVALAERVGSEQRLIAYFATPAAVYGAICENLSRVGLNQH
TRVVLEKPIGSDLDSSRKVNDAVAQFFPETRIYRIDHYLGKETVQN
LIALRFANSLFETQWNQNYISHVEITVAEKVGIEGRWGYFDKAGQL
RDMIQNHLLQLLCLIAMDPPADLSADSIRDEKVKVLKALAPISPEG
LTTQWRGQYIAGHSEGQSVPGYLEEENSNTQSDTETFVALRADIRN
WRWAGVPFYLRTGKRMPQKLSQIVIHFKEPSHYIFAPEQRLQISNK
LIIRLQPDEGISLRVMTKEQGLDKGMQLRSGPLQLNFSDTYRSARI
PDAYERLLLEVMRGNQNLFVRKDEIEAAWKWCDQLIAGWKKSGDAP
KPYAAGSWGPMSSIALITRDGRSWYGDI
```

Nucleotide Sequence
(SEQ. ID. NO: 126)
```
ATGCCTTCGATAACGGTTGAACCCTGCACCTTTGCCTTGTTTGGCG
CGCTGGGCGATCTGGCGCTGCGTAAGCTGTTTCCTGCCCTGTACCA
ACTCGATGCCGCCGGTTTGCTGCATGACGACACGCGCATCCTGGCC
CTGGCCCGCGAGCCTGGCAGCGAGCAGGAACACCTGGCGAATATCG
AAACCGAGCTGCACAAGTATGTCGGCGACAAGGATATCGATAGCCA
GGTCCTGCAGCGTTTTCTCGTCCGCCTGAGCTACCTGCATGTGGAC
TTCCTCAAGGCCGAGGACTACGTCGCCCTGGCCGAACGTGTCGGCA
GCGAGCAGCGCCTGATTGCCTACTTCGCCACGCCGGCGGCGGTGTA
TGGCGCGATCTGCGAAAACCTCTCCCGGGTCGGGCTCAACCAGCAC
ACCCGTGTGGTCCTGGAAAAACCCATCGGCTCGGACCTGGATTCAT
CACGCAAGGTCAACGACGCGGTGGCGCAGTTCTTCCCGGAAACCCG
CATCTACCGGATCGACCACTACCTGGGCAAGGAAACGGTGCAGAAC
CTGATTGCCCTGCGTTTCGCCAACAGCCTGTTCGAAACCCAGTGGA
ACCAGAACTACATCTCCCACGTGGAAATCACCGTGGCCGAGAAGGT
CGGCATCGAAGGTCGCTGGGGCTATTTCGACAAGGCCGGCCAACTG
CGGGACATGATCCAGAACCACTTGCTGCAACTGCTCTGCCTGATCG
CGATGGACCCGCCGGCCGACCTTTCGGCCGACAGCATCCGCGACGA
GAAGGTCAAGGTGCTCAAGGCCCTGGCGCCCATCAGCCCGGAAGGC
CTGACCACCCAGGTGGTGCCGCAGTACATCGCCGGCCACAGCG
AAGGCCAGTCGGTGCCGGGCTACCTGGAGGAAGAAAATCCAACAC
CCAGAGCGACACCGAGACCTTCGTCGCCCTGCGCGCCGATATCCGC
AACTGGCGCTGGGCCGGTGTGCCTTCTACCTGCGCACCGGCAAGC
GCATGCCACAGAAGCTGTCGCAGATCGTCATCCACTTCAAGGAACC
CTCGCACTACATCTTCGCCCCCGAGCAGCGCCTGCAGATCAGCAAC
AAGCTGATCATCCGCCTGCAGCCGGACGAAGGTATCTCGTTGCGGG
TGATGACCAAGGAGCAGGGCCTGGACAAGGGCATGCAACTGCGCAG
CGGTCCGTTGCAGCTGAATTTTTCCGATACCTATCGCAGTGCACGG
ATCCCCGATGCCTACGAGCGGTTGTTGCTGGAAGTGATGCGCGGCA
ATCAGAACCTGTTTGTGCGCAAAGATGAAATCGAAGCCGCGTGGAA
GTGGTGTGACCAGTTGATTGCCGGGTGGAAGAAATCCGGCGATGCG
CCCAAGCCGTACGCGGCCGGGTCCTGGGGGCCGATGAGCTCCATTG
CACTGATCACGCGGGATGGGAGGTCTTGGTATGGCGATATCTaA
``` zwf1 from *P. aeruginosa, PAO1*
Amino Acid Sequence
(SEQ. ID. NO: 127)
```
MPDVRVLPCTLALFGALGDLALRKLFPALYQLDRENLLHRDTRVLA
LARDEGAPAEHLATLEQRLRLAVPAKEWDDVVWQRFRERLDYLSMD
FLDPQAYVGLREAVDDELPLVAYFATPASVFGGICENLAAAGLAER
TRVVLEKPIGHDLESSREVNEAVARFFPESRIYRIDHYLGKETVQN
LIALRFANSLFETQWNQNHISHVEITVAEKVGIEGRWGYFDQAGQL
RDMVQNHLLQLLCLIAMDPPSDLSADSIRDEKVKVLRALEPIPAEQ
LASRVVRGQYTAGFSDGKAVPGYLEEEHANRDSDAETFVALRVDIR
```

-continued
NWRWSGVPFYLRTGKRMPQKLSQIVIHFKEPPHYIFAPEQRSLISN
RLIIRLQPDEGISLQVMTKDQGLGKGMQLRTGPLQLSFSETYHAAR
IPDAYERLLLEVTQGNQYLFVRKDEVEFAWKWCDQLIAGWERLSEA
PKPYPAGSWGPVASVALVARDGRSWYGDF Nucleotide Sequence
(SEQ. ID. NO: 128)
ATGCCTGATGTCCGCGTTCTGCCTTGCACGTTAGCGCTGTTCGGTG
CGCTGGGCGATCTCGCCTTGCGCAAGCTGTTCCCGGCGCTCTACCA
ACTCGATCGTGAGAACCTGCTGCACCGCGATACCCGCGTCCTGCC
CTGGCCCGTGACGAAGGCGCTCCCGCCAACACCTGGCGACGCTGG
AGCAGCGCCTGCGCCTGGCAGTGCCGGCGAAGGAGTGGGACGACGT
GGTCTGGCAGCGTTTCCGCGAACGCCTCGACTACCTGAGCATGGAC
TTCCTCGACCCGCAGGCCTATGTCGGCTTGCGCGAGGCGGTGGATG
ACGAACTGCCGCTGGTCGCCTACTTCGCCACGCCGGCCTCGGTGTT
CGGCGGCATCTGCGAGAACCTCGCCGCCGCCGGTCTCGCCGAGCGC
ACCCGGGTGGTGCTGGAGAAGCCCATCGGTCATGACCTGGAGTCGT
CCCGCGAGGTCAACGAGGCAGTCGCCCGGTTCTTCCCGGAAAGCCG
CATCTACCGGATCGACCATTACCTGGGCAAGGAGACGGTGCAGAAC
CTGATCGCCCTGCGCTTCGCCAACAGCCTCTTCGAGACCCAGTGGA
ACCAGAACCACATCTCCCACGTGGAGATCACCGTGGCCGAGAAGGT
CGGCATCGAAGGCCGCTGGGGCTACTTCGACCAGGCCGGCAACTG
CGCGACATGGTGCAGAACCACCTGCTGCAACTGCTCTGCCTGATCG
CCATGGATCCGCCCAGCGACCTTTCGGCGGACAGCATTCGCGACGA
GAAGGTCAAGGTCCTCCGCGCCCTCGAGCCGATTCCCGCAGAACAA
CTGGCTTCGCGCGTGGTGCGTGGGCAGTACACCGCCGGTTTCAGCG
ACGGCAAGGCAGTGCCGGGCTACCTGGAGGAGGAACATGCGAATCG
CGACAGCGACGCGGAAACCTTCGTCGCCCTGCGCGTGGACATCCGC
AACTGGCGCTGGTCGGGCGTGCCGTTCTACCTGCGCACCGGCAAGC
GCATGCCGCAGAAGCTGTCGCAGATCGTCATCCACTTCAAGGAGCC
GCCGCACTACATCTTCGCTCCCGAGCAGCGTTCGCTGATCAGCAAC
CGGCTGATCATCCGCCTGCAGCCGGACGAAGGTATCTCCCTGCAAG
TGATGACCAAGGACCAGGGCCTGGGCAAGGGCATGCAATTGCGTAC
CGGCCCGCTGCAACTGAGTTTTTCCGAGACCTACCACGCGGCGCGG
ATTCCCGATGCCTACGAGCGTCTGCTGCTGGAGGTCACCCAGGGCA
ACCAGTACCTGTTCGTGCGCAAGGACGAGGTGGAGTTCGCCTGGAA
GTGGTGCGACCAGCTGATCGCTGGCTGGGAACGCCTGAGCGAAGCG
CCCAAGCCGTATCCGGCGGGGAGTTGGGGGCCGGTGGCCTCGGTGG
CCCTGGTGGCCCGCGATGGGAGGAGTTGGTATGCGATTTCTGA zwf1 from Z. mobilis
Amino Acid Sequence
(SEQ. ID. NO: 129)
MTNTVSTMILFGSTGDLSQRMLLPSLYGLDADGLLADDLRIVCTSR
SEYDTDGFRDFAEKALDRFVASDRLNDDAKAKFLNKLFYATVDITD
PTQFGKLADLCGPVEKGIAIYLSTAPSLFEGAIAGLKQAGLAGPTS
RLALEKPLGQDLASSDHINDAVLKVFSEKQVYRIDHYLGKETVQNL
LTLRFGNALFEPLWNSKGIDHVQISVAETVGLEGRIGYFDGSGSLR
DMVQSHILQLVALVAMEPPAHMEANAVRDEKVKVFRALRPINNDTV
FTHTVTGQYGAGVSGGKEVAGYIDELGQPSDTETFVAIKAHVDNWR
WQGVPFYIRTGKRLPARRSEIVVQFKPVPHSIFSSSGGILQPNKLR
IVLQPDETIQISMMVKEPGLDRNGAHMREVWLDLSLTDVFKDRKRR
IAYERLMLDLIEGDATLFVRRDEVEAQWVWIDGIREGWKANSMKPK
TYVSGTWGPSTAIALAERDGVTWYD Nucleotide Sequence
(SEQ. ID. NO: 130)
ATGACAAATACCGTTTCGACGATGATATTGTTTGGCTCGACTGGCG
ACCTTTCACAGCGTATGCTGTTGCCGTCGCTTTATGGTCTTGATGC
CGATGGTTTGCTTGCAGATGATCTGCGTATCGTCTGCACCTCTCGT
AGCGAATACGACACAGATGGTTTCCGTGATTTTGCAGAAAAAGCTT
TAGATCGCTTTGTCGCTTCTGACCGGTTAAATGATGACGCTAAAGC
TAAATTCCTTAACAAGCTTTTCTACGCGACGGTCGATATTACGGAT
CCGACCCAATTCGGAAAATTAGCTGACCTTTGTGGCCCGGTCAGAA
AAGGTATCGCCATTTATCTTTCGACTGCGCCTTCTTTGTTTGAAGG
GGCAATCGCTGGCCTGAAACAGGCTGGTCTGGCTGGTCAACTTCT
CGCCTGGCGCTTGAAAAACCTTTAGGTCAAGATCTTGCTTCTTCCG
ATCATATTAATGATGCGGTTTTGAAAGTTTTCTCTGAAAAGCAAGT
TTATCGTATTGACCATTATCTGGGTAAAGAAACGGTTCAGAATCTT
CTGACCCTGCGTTTTGGTAATGCTTTGTTTGAACCGCTTTGGAATT
CAAAAGGCATTGACCACGTTCAGATCAGCGTTGCTGAAACGGTTGG
TCTTGAAGGTCGTATCGGTTATTTCGACGGTTCTGGCAGCTTGCGC
GATATGGTTCAAAGCCATATCCTTCAGTTGGTCGCTTTGGTTGCAA
TGGAACCACCGGCTCATATGGAAGCCAACGCTGTTCGTGACGAAAA
GGTAAAAGTTTTCCGCGCTCTGCGTCCGATCAATAACGACACCGTC
TTTACGCATACCGTTACCGGTCAATATGGTGCCGGTGTTTCTGGTG
GTAAAGAAGTTGCCGGTTACATTGACGAACTGGGTCAGCCTTCCGA
TACCGAAACCTTTGTTGCTATCAAAGCGCATGTTGATAACTGGCGT
TGGCAGGGTGTTCCGTTCTATATCCGCACTGGTAAGCGTTTACCTG
CACGTCGTTCTGAAATCGTGGTTCAGTTTAAACCTGTTCCGCATTC
GATTTTCTCTTCTTCAGGTGGTATCTTGCAGCCGAACAAGCTGCGT -continued
ATTGTCTTACAGCCTGATGAAACCATCCAGATTTCTATGATGGTGA
AAGAACCGGGTCTTGACCGTAACGGTGCGCATATGCGTGAAGTTTG
GCTGGATCTTTCCCTCACGGATGTGTTTAAAGACCGTAAACGTCGT
ATCGCTTATGAACGCCTGATGCTTGATCTTATCGAAGGCGATGCTA
CTTTATTTGTGCGTCGTGACGAAGTTGAGGCGCAGTGGGTTTGGAT
TGACGGAATTCGTGAAGGCTGGAAAGCCAACAGTATGAAGCCAAAA
ACCTATGTCTCTGGTACATGGGGGCCTTCAACTGCTATAGCTCTGG
CCGAACGTGATGGAGTAACTTGGTATGACTGA All the above genes were PCR amplified from their genomic DNA sources with and without c-terminal 6-HIS tags (SEQ ID NO: 35) and cloned into the yeast expression vector p426GPD for testing.

Assays of Candidate ZWF1 Genes

Strain BY4742 zwf1 (ATCC Cat. No. 4011971; Winzeler E A, et al. Science 285: 901-906, 1999. PubMed: 10436161) was used as the base strain for all ZWF1 assays. The assays were performed as follows: A 5 ml overnight of the strain expressing the ZWF1 gene was grown in SCD-ura. A 50 ml culture of the strain was then grown for about 18 hours from an initial $OD_{600}$ of about 0.2 until it had reached about $OD_{600}$ of about 4. The cells were centrifuged at 1046×g washed twice with 25 ml cold sterile water, and resuspended in 2 ml/g Yper Plus (Thermo Scientific) plus 1× protease inhibitors (EDTA-free). The cells were allowed to lyse at room temperature for about 30 minutes with constant rotation of the tubes. The lysate was centrifuged at 16,100×g for 10 minutes at 4° C. and the supernatants were transferred to a new 1.5 ml microcentrifuge tube. Quantification of the lysates was performed using the Coomassie-Plus kit (Thermo Scientific, San Diego, Calif.) as directed by the manufacturer.

Each kinetic assay was done using approximately 50 to 60 µg of crude extract in a reaction mixture containing 50 mM Tris-HCl, pH 8.9, and 1 mM NADP+ or NAD+. The reaction was started with 20 mM glucose-6-phosphate and the reaction was monitored at A340. The specific activity was measured as the µmol substrate/min/mg protein. The results of the assays are presented in the table below.

| Zwf1 | Cofactors | Vmax (µmol min$^{-1}$) | Km (M$^{-1}$) | Specific Activity (µmol min$^{-1}$ mg$^{-1}$) |
|---|---|---|---|---|
| S. cerevisiae | NAD+ | NA | NA | NA |
|  | NADP+ | 0.9523 | 0.4546 | 224.07 |
| S. cerevisiae + His | NAD+ | NA | NA | NA |
|  | NADP+ | 0.7267 | 0.4109 | 164.79 |
| ZM4 | NAD+ | NA | NA | NA |
|  | NADP+ | NA | NA | NA |
| ZM4 + His | NAD+ | 0.0213 | 0.0156 | 0.1267 |
|  | NADP+ | 0.0027 | 0.0140 | 0.0160 |
| P. fluorescens 1 | NAD+ | 0.0158 | 0.6201 | 0.3132 |
|  | NADP+ | 0.0213 | 0.8171 | 0.4208 |
| P. fluorescens 1 + His | NAD+ | 0.0126 | 4.9630 | 0.2473 |
|  | NADP+ | 0.0139 | 0.9653 | 0.2739 |
| P. fluorescens 2 | NAD+ | ND | ND | ND |
|  | NADP+ | NA | NA | NA |
| P. fluorescens 2 + His | NAD+ | NA | NA | NA |
|  | NADP+ | ND | ND | ND |
| PAO1 | NAD+ | NA | NA | NA |
|  | NADP+ | 0.0104 | 0.6466 | 0.1564 |
| PAO1 + His | NAD+ | 0.0074 | 0.0071 | 0.1098 |
|  | NADP+ | 0.0123 | 3.9050 | 0.1823 |

NA = cannot be calculated (substrate not used by enzyme)
ND = was not determined (either not enough crude available or cells did not grow)

Altering Cofactor Preference of S. cerevisiae ZWF1

ZWF1 from S. cerevisiae is an NADP+-only utilizing enzyme. Site-directed mutagenesis was used to alter of ZWF1 so that the altered ZWF1 could also utilize NAD+, thereby improving the REDOX balance within the cell. Site directed mutagenesis reactions were performed in the same manner for all mutations, and for mutants which include more than one mutation, each mutation was performed sequentially. About 50 ng of plasmid DNA was added to 1×Pfu Ultra II buffer, 0.3 mM dNTPs, 0.3 μmol site directed mutagenesis specific primers, and 1 U Pfu Ultra II polymerase (Agilent, La Jolla, Calif.) in a 50 μl reaction mix. The reaction was cycled at 95° C. for 10 minutes, followed by 15 rounds of 95° C. for 15 seconds, 55° C. for 40 seconds, and 72° C. for 3 minutes. A final 10 minute extension reaction at 72° C. was also included. The PCR reaction mixture was then digested with 30 U of DpnI for about 2 hours and 5 μl of the digested PCR reaction mixture was used to transform competent DH5α (Zymo Research, Orange, Calif.) and plated onto LB plates containing the appropriate antibiotics. The table below lists mutants generated in a first round of mutagenesis.

| Mutant # | zwf1_sc | Codon changes |
|---|---|---|
| 1 | A24G | GCA -> GGT |
| 2 | A24G/T28G | GCA -> GGT, ACT -> GGT |
| 3 | A51N | GCC -> AAT |
| 4 | A51D | GCC -> GAT |
| 5 | T28F | ACT -> TTT |
| 6 | K46R | AAG -> AGA |
| 7 | Y40L | TAC -> TTG |
| 8 | F33Y | TTT -> TAC |
| 9 | T28L | ACT -> TTG |
| 10 | V16L | GTC -> TTG |
| 11 | V13T | GTC -> ACT |
| 12 | L66E | CTA -> GAA |
| 13 | A24G/A51D | GCA -> GGT, GCC -> GAT |
| 14 | A24G/T28G/A51D | GCA -> GGT, ACT -> GGT, GCC -> GAT |
| 15 | R52D | CGG -> GAT |
| 16 | A51D/R52A | GCC -> GAT, CGG -> GCT |
| 17 | A24G/A51D/R52A | GCA -> GGT, GCC -> GAT, CGG -> GCT |
| 18 | A24G/T28G/A51D/R52A | GCA -> GGT, ACT -> GGT, GCC -> GAT, CGG -> GCT |
| 19 | A51D/R52H | GCC -> GAT, CGG -> CAT |
| 20 | R52H | CGG -> CAT |
| 21 | D22R | GAT -> AGA |

The oligonucleotides, utilized to generate the mutants listed in the table above, are listed in the table below. All oligonucleotides were purchased from Integrated DNA Technologies (IDT).

| Base Mutation | plasmid | Oligo Name | Nucleotide sequence | SEQ ID NO: |
|---|---|---|---|---|
| 1 | pBF300 | ka/zwf1sc_A24Gfor | gtgcgtcaggtgatctgggtaagaagaagacttttccc | 300 |
| 1 | pBF300 | ka/zwf1sc_A24Grev | gggaaaagtcttcttcttacccagatcacctgacgcac | 301 |
| 2 | pBF300 | ka/zwf1sc_T28Gfor | gtgatctgggtaagaagaagggttttcccgccttatttgg | 302 |
| 2 | pBF300 | ka/zwf1sc_T28Grev | CCAAATAAGGCGGGAAAACCCTTCTTCTTACCCAGATCAC | 303 |
| 3 | pBF300 | ka/zwf1sc_A51Nfor | ccttgatccatctaccaagatcttcggttataatcggtccaaattgtccat | 304 |
| 3 | pBF300 | ka/zwf1sc_A51Nrev | atggacaatttggaccgattataaccgaagatcttggtagatggatcaagg | 305 |
| 4 | pBF300 | ka/zwf1sc_A51Dfor | atctaccaagatcttcggttatgatcggtccaaattgtccatg | 306 |
| 4 | pBF300 | ka/zwf1sc_A51Drev | catggacaatttggaccgatcataaccgaagatcttggtagat | 307 |
| 5 | pBF300 | ka/zwf1sc_T28Ffor | ggtgatctggcaaagaagaagttttttcccgccttatttggg | 308 |
| 5 | pBF300 | ka/zwf1sc_T28Frev | cccaaataaggcgggaaaaaacttcttctttgccagatcacc | 309 |
| 6 | pBF300 | ka/zwf1sc_K46Rfor | taccttgatccatctaccagaatcttcggttatgcccggt | 310 |
| 6 | pBF300 | ka/zwf1sc_K46Rrev | accgggcataaccgaagattctggtagatggatcaaggta | 311 |
| 7 | pBF300 | ka/zwf1sc_Y39Lfor | gggcttttcagagaaggtttgcttgatccatctaccaaga | 312 |
| 7 | pBF300 | ka/zwf1sc_Y39Lrev | tcttggtagatggatcaagcaaaccttctctgaaaagccc | 313 |
| 8 | pBF300 | ka/zwf1sc_F33Yfor | gaagaagacttttcccgccttatacgggcttttcagagaag | 314 |
| 8 | pBF300 | ka/zwf1sc_F33Yrev | cttctctgaaaagcccgtataaggcgggaaaagtcttcttc | 315 |
| 9 | pBF300 | ka/zwf1sc_T28Lfor | gtcaggtgatctggcaaagaagaagttgtttcccgccttatttgg | 316 |
| 9 | pBF300 | ka/zwf1sc_T28Lrev | ccaaataaggcgggaaacaacttcttctttgccagatcacctgac | 317 |

-continued

| Mutation | Base plasmid | Oligo Name | Nucleotide sequence | SEQ ID NO: |
|---|---|---|---|---|
| 10 | pBF300 | ka/zwf1sc_V16Lfor | cgaaaaaataccgtcatatctttgtttggtgcgtcaggtgatctg | 318 |
| 10 | pBF300 | ka/zwf1sc_V16rev | cagatcacctgacgcaccaaacaaagatatgacggtattttttcg | 319 |
| 12 | pBF300 | ka/zwf1sc_L66Efor | gacctgaagtcccgtgtcgaacccacttgaaaaaacc | 320 |
| 12 | pBF300 | ka/zwf1sc_L66Erev | ggttttttcaagtgggttcgacacgggacttcaggtc | 321 |
| 13 | pBF374 | ka/zwf1sc_A24Gfor | gtgcgtcaggtgatctgggtaagaagaagacttttccc | 322 |
| 13 | pBF374 | ka/zwf1sc_A24Grev | gggaaaagtcttcttcttacccagatcacctgacgcac | 323 |
| 14 | pBF374 | ka/zwf1sc_A24Gfor | gtgcgtcaggtgatctgggtaagaagaagacttttccc | 324 |
| 14 | pBF374 | ka/zwf1sc_A24Grev | gggaaaagtcttcttcttacccagatcacctgacgcac | 325 |
| 15 | pBF300 | KA/zwf1mut15for | accaagatcttcggttatgccgattccaaattgtccatggaggag | 326 |
| 15 | pBF300 | KA/zwf1mut15rev | ctcctccatggacaatttggaatcggcataaccgaagatcttggt | 327 |
| 16 | pBF374 | KA/zwf1mut16for | tccatctaccaagatcttcggttatgatgcttccaaattgtccatggaggaggac | 328 |
| 16 | pBF374 | KA/zwf1mut16rev | gtcctcctccatggacaatttggaagcatcataaccgaagatcttggtagatgga | 329 |
| 17 | pBF441 | KA/zwf1mut16for | tccatctaccaagatcttcggttatgatgcttccaaattgtccatggaggaggac | 330 |
| 17 | pBF441 | KA/zwf1mut16rev | gtcctcctccatggacaatttggaagcatcataaccgaagatcttggtagatgga | 331 |
| 18 | pBF442 | KA/zwf1mut16for | tccatctaccaagatcttcggttatgatgcttccaaattgtccatggaggaggac | 332 |
| 18 | pBF442 | KA/zwf1mut16rev | gtcctcctccatggacaatttggaagcatcataaccgaagatcttggtagatgga | 333 |
| 19 | pBF374 | KA/zwf1sc_mut19for | aagatcttcggttatgatcattccaaattgtccatggagg | 334 |
| 19 | pBF374 | KA/zwf1sc_mut19rev | cctccatggacaatttggaatgatcataaccgaagatctt | 335 |
| 20 | pBF300 | KA/zwf1sc_mut20for | aagatcttcggttatgcccattccaaattgtccatggagg | 336 |
| 20 | pBF300 | KA/zwf1sc_mut20rev | cctccatggacaatttggaatgggcataaccgaagatctt | 337 |

Initial kinetic screening of the ZWF1 mutants generated as described above, identified the following altered ZWF1 genes and preliminary cofactor phenotype.

| Mutant # | zwf1_sc | NAD+ usage | NADP+ usage |
|---|---|---|---|
| 1 | A24G | No | Yes |
| 2 | A24G/T28G | No | No |
| 3 | A51N | No | Yes |
| 4 | A51D | Yes | No |
| 5 | T28F | No | Yes |
| 6 | K46R | No | Yes |
| 7 | Y40L | No | Yes |
| 8 | F33Y | No | Yes |
| 9 | T28L | No | Yes |
| 10 | V16L | No | Yes |
| 11 | V13T | ND | ND |
| 12 | L66E | No | Yes |
| 13 | A24G/A51D | Yes | No |
| 14 | A24G/T28G/A51D | No | No |
| 15 | R52D | No | No |
| 16 | A51D/R52A | No | No |
| 17 | A24G/A51D/R52A | No | No |
| 18 | A24G/T28G/A51D/R52A | ND | ND |
| 19 | A51D/R52H | ND | ND |
| 20 | R52H | ND | ND |
| 21 | D22R | ND | ND |

ND = not determined

Mutants 4 (A51D) and 13 (A24G/A51D) were identified as mutants which enabled NAD+ utilization with concomitant loss of NADP+ utilization.

Cloning of SOL3

The SOL3 gene from *S. cerevisiae* was cloned as follows. The approximately 750 bp SOL3 gene was PCR amplified from the BY4742 genome using primers KAS/5-SOL3-NheI and KAS/3'-SOL3-SalI, shown below.

```
KAS/5-SOL3-NheI
                                       (SEQ ID NO: 338)
gctagcatggtgacagtcggtgtgttttctgag KAS/3'-SOL3-SalI
                                       (SEQ ID NO: 339)
gtcgacctaaaaagttttcgtttgaacttttcc
```

About 100 ng of genomic DNA from *S. cerevisiae* strain BY4742 was added to 1×Pfu Ultra II buffer, 0.3 mM dNTPs, 0.3 μmol gene-specific primers, and 1 U Pfu Ultra II polymerase (Agilent, La Jolla, Calif.) in a 50 μl reaction mix. The reaction was cycled at 95° C. for 10 minutes, followed by 30 rounds of 95° C. for 20 seconds, 55° C. for 30 seconds, and 72° C. for 15 seconds. A final 5 minute extension reaction at 72° C. was also included. The amplified product was TOPO cloned into the pCR Blunt II TOPO vector (Life Technologies, Carlsbad, Calif.) according to the manufacturer's recommendations and sequence verified (GeneWiz, San Diego, Calif.). The resultant plasmid was designated pBF301. The sequence of the *S. cerevisiae* SOL3 gene is given below.

```
JML/237:
                                       (SEQ ID NO: 340)
CCAACACTAAGAAATAATTTCGCCATTTCTTG

JML/238:
                                       (SEQ ID NO: 341)
GCCAACAATTAAATCCAAGTTCACCTATTCTG
```

The PCR amplification was performed as follows: 10 ng of yeast genomic DNA with 0.1 μmol gene specific primers, 1×Pfu Ultra II buffer, 0.2 mmol dNTPs, and 0.2 U Taq DNA polymerase. The PCR mixture was cycled at 95° C. for 2 minutes, followed by 30 cycles of 95° C. for 20 seconds, 55° C. for 30 seconds and 72° C. for 45 seconds. A final step of 72° C. for 5 minutes was also included. The resultant strain was designated BF1618.

Strain BF1618 is undergoing transformation with the following plasmid combinations. Additionally, the affect of the ZWF1 mutant constructs will also be evaluated with and without SOL3 constructs. The table below shows the plasmid combinations being transformed into strain BF1618.

```
S. cerevisiae SOL3
                                                    (SEQ. ID. NO: 131)
ATGGTGACAGTCGGTGTGTTTTCTGAGAGGGCTAGTTTGACCCATCAATTGGGGGAATTCATCGTCAAGAAAC

AAGATGAGGCGCTGCAAAAGAAGTCAGACTTTAAAGTTTCCGTTAGCGGTGGCTCTTTGATCGATGCTCTGTA

TGAAAGTTTAGTAGCGGACGAATCACTATCTTCTCGAGTGCAATGGTCTAAATGGCAAATCTACTTCTCTGAT

GAAAGAATTGTGCCACTGACGGACGCTGACAGCAATTATGGTGCCTTCAAGAGAGCTGTTCTAGATAAATTAC

CCTCGACTAGTCAGCCAAACGTTTATCCCATGGACGAGTCCTTGATTGGCAGCGATGCTGAATCTAACAACAA

AATTGCTGCAGAGTACGAGCGTATCGTACCTCAAGTGCTTGATTTGGTACTGTTGGGCTGTGGTCCTGATGGA

CACACTTGTTCCTTATTCCCTGGAGAAACACATAGGTACTTGCTGAACGAAACAACCAAAAGAGTTGCTTGGT

GCCACGATTCTCCCAAGCCTCCAAGTGACAGAATCACCTTCACTCTGCCTGTGTTGAAAGACGCCAAAGCCCT

GTGTTTTGTGGCTGAGGGCAGTTCCAAACAAAATATAATGCATGAGATCTTTGACTTGAAAAACGATCAATTG

CCAACCGCATTGGTTAACAAATTATTTGGTGAAAAAACATCCTGGTTCGTTAATGAGGAAGCTTTTGGAAAAG

TTCAAACGAAAACTTTTTAG
```

The NheI-SalI SOL3 gene fragment from plasmid pBF301 will be cloned into the SpeI-XhoI site in plasmids p413GPD and p423GPD (HIS3 marker-based plasmids; ATCC 87354 and ATCC 87355).

Testing of ZWF1/SOL3 Combinations in BY4742

A URA blaster cassette was digested with NotI and ligated into the MET17 integration cassette plasmid pBF691 to generate the Met17 knockout plasmid pBF772. Plasmid pBF772 was digested with PacI and linear fragments were purified by Zymo PCR purification kit (Zymo Research, Orange, Calif.) and concentrated in 10 μl ddH2O. LiCl2 high efficiency transformation was performed as shown described. About 1 μg linear MET17 knockout fragment was transformed into 50 μl fresh made BY4742 competent cells and cells were plated onto SCD-Ura plates at 30° C. for about 2-3 days. A single URA+ colony was streaked out on a SCD-Ura plate and grown at 30° C. for about 2-3 days. A single colony was inoculated overnight in YPD medium at 30° C. 50 μl of the overnight culture was then plated onto SCD complete-5FOA plates and incubated at 30° C. for about 3 days.

A single colony which grew on SCD complete-5FOA plates was then picked and inoculated in YPD medium and grown at 30° C. overnight. Yeast genomic DNA was extracted by YeaStar genomic extraction kit (Zymo Research, Orange, Calif.) and confirmation of the strain was confirmed by PCR using primers JML/237 and JML/238, shown below.

| Test Strain | EDD | EDA | ZWF1 | SOL3 |
|---|---|---|---|---|
| 1 | 2μ | 2μ | cen/ars | NONE |
| 2 | 2μ | 2μ | 2μ | NONE |
| 3 | 2μ | 2μ | cen/ars | cen/ars |
| 4 | 2μ | 2μ | 2μ | 2μ |
| 5 | 2μ | 2μ | NONE | cen/ars |
| 6 | 2μ | 2μ | NONE | 2μ |

Strains with improved ethanol production may benefit from two or more copies of the ZWF1 gene due to increased flux of the carbon towards the alternative pathway. A strain embodiment currently under construction has the phenotype; pfk1, ZWF1, SOL3, tal1, EDD-PAO1*, EDA-*E. coli**, where the "*" represents additional copies of the gene. It is believed that multiple copies of the EDD and EDA genes may provide additional increases in ethanol production.

Example 19

Construction of the KanMX-ATO1-L75Q Cassette

A unique disruption cassette suitable for use when auxotrophic markers are unavailable, such as in diploid industrial strains or haploids derived from such strains, was constructed to allow homologous recombination or integration of sequences in the absence of traditional auxotrophic marker selection. The primers used for amplification of nucleic acids utilized to generate the disruption cassette are described in the table below.

| | | |
|---|---|---|
| JML/51 | ACTAGTATGTCTGACAAGGAACAAACGAGC (SEQ ID NO: 342) | 5'ScAto1SpeI |
| JML/52 | CTCGAGTTAAAAGATTACCCTTTCAGTAGATGGTAATG (SEQ ID NO: 343) | 3'ScAto1XhoI |
| JML/55 | caagcctttggtggtacccagaatccagggttagctcc (SEQ ID NO: 344) | ScATO(L75Q)_For |
| JML/56 | ggagctaaccctggattctgggtaccaccaaaggcttg (SEQ ID NO: 345) | ScATO(L75Q)_Rev |
| JML/57 | ggtacaacgcatatgcagatgttgctacaaagcagaa (SEQ ID NO: 346) | ScATO1G259D_For |
| JML/58 | ttctgctttgtagcaacatctgcatatgcgttgtacc (SEQ ID NO: 347) | ScATO1G259D_Rev |
| JML/59 | GACGACGTCTAGAAAAGAATACTGGAGAAATGAAAAGAAAAC (SEQ ID NO: 348) | ReplacesJML/30 |
| JML/63 | GCATGCTTAATTAATGCGAGGCATATTTATGGTGAAGG (SEQ ID NO: 349) | F' of 5' Flanking Region of ScURA3 |
| JML/64 | GGCCGGCCAGATCTGCGGCCGCGGCCAGCAAAACTAAAAAAC TGTATTATAAG (SEQ ID NO: 350) | F' of 3' Flanking Region of ScURA3 |
| JML/65 | GCGGCCGCAGATCTGGCCGGCCGATTTATCTTCGTTTCCTGC AGGTTTTTG (SEQ ID NO: 351) | R' of 5' Flanking Region of ScURA3 |
| JML/66 | GAATTCTTAATTAACTTTTGTTCCACTACTTTTTGGAACTCT TG (SEQ ID NO: 352) | R' of 3 Flanking Region of ScURA3 |
| JML/67 | GCATGCGCGGCCGCACGTCGGCAGGCCCG (SEQ ID NO: 353) | F'200mer-R |
| JML/68 | CGAAGGACGCGCGACCAAGTTTATCATTATCAATACTCGCCA TTTC (SEQ ID NO: 354) | F'200mer-R-pGPD-ATO1-CYC |
| JML/69 | GAAATGGCGAGTATTGATAATGATAAACTTGGTCGCGCGTCC TTCG (SEQ ID NO: 355) | R'pGPD-ATO1-CYC-200mer-R |
| JML/70 | GTCGACCCGCAAATTAAAGCCTTCGAGC (SEQ ID NO: 356) | R-pGPD-ATO1-CYC |
| JML/71 | GTCGACGTACCCCCGGGTTAATTAAGGCG (SEQ ID NO: 357) | F-KanMX |
| JML/72 | GTCGAAAACGAGCTCGAATTCGACGTCGGCAGGCCCG (SEQ ID NO: 358) | F-KanMX-200mer-R |
| JML/73 | CGGGCCTGCCGACGTCGAATTCGAGCTCGTTTTCGAC (SEQ ID NO: 359) | R-200mer-R-KanMX |
| JML/74 | GGATCCGCGGCCGCTGGTCGCGCGTCCTTCG (SEQ ID NO: 360) | R-200mer-R |

ScATO1 was amplified from genomic DNA (gDNA) isolated from BY4742 with primers oJML51 and oJML52 and cloned into pCR Blunt II-TOPO (Invitrogen, Carlsbad, Calif.). Site Directed Mutagenesis (SDM) was performed on that plasmid with oJML55 and oJML56, as described herein. The mutagenized clone was re-amplified with primers oJML51 and oJML52 and cloned into pCR Blunt II-TOPO (Invitrogen, Carlsbad, Calif.), and designated ATO1-L75Q. ATO1-L75Q was subcloned into p416GPD using SpeI/XhoI restriction enzyme sites. The resulting plasmid was designated pJLV048.

The 5' and 3' flanking regions of URA3 were amplified via PCR of the 5' regions with primers oJML63 and oJML65, the 3' region with primers oJML64 and oJML66. The amplified nucleic acids were annealed and re-amplified with oligonucleotides oJML63 and oJML66. The template used was TURBO gDNA. The PCR product was Topo cloned into pCR-Blunt II. The desired sequence was moved as an EcoR1-Sph1 fragment into vector pUC19 and designated pJLV63.

The R-KanMX fragment was made as follows: The KANMX fragment was first amplified from pBF524 with primers oJML71 and oJML73. The R-200-mer from plasmid pBF32 was then amplified using primers oJML72 and oJML74. The two fragments were annealed together and PCR amplified using primers oJML67 and oJML70 and topo cloned using pCR-Blunt II. The final plasmid construct was designated pJLV062. The R-P$_{TDH3}$-ATO1-L75Q construct was generated by amplifying a mixture of PCR oJML67-oJM L69 (pBF32)+PCR oJML68-oJML70 (pJLV048). The resulting plasmid was designated pJLV065. The R-PT$_{DH3}$-ATO1-L75Q (SalI/SphI) fragment from pJLV065 was ligated in a 3 piece ligation to the SalI/BamHI (R-KanMX) fragment from pJLV063 into the BamHI/SphI site of pUC19. The entire R-KanMX-P$_{TDH3}$-ATO1-L75Q-R fragment was ligated as a NotI piece into the NotI site of pJLV63 and designated pJLV74. The letter "R" with reference to nucleic acid fragments, primers, plasmids and unique 200-mer sequence tags, refers to a unique 200-mer tag identification number. The unique sequence tags are described in Example 28. A table describing the intermediate and final plasmids is presented below.

200-mer sequence was verified by PCR with primers complementary to the 200-mer in combination with primers complementary to a region outside of the flanking region used for the disruption. The absence of the URA3 loci was verified by PCR that amplifies a 500 bp region of the Actin gene open reading frame and a 300 bp region of the URA3 open reading frame. The primers utilized for amplification and verification are presented, respectively, in the tables below.

Primers Used for Amplification of URA and Actin

```
JML/211   GAGGGCACAGTTAAGCCGCTAAAGG              URA3
          (SEQ ID NO: 361)
```

| | | | |
|---|---|---|---|
| pJLV0035 | pBF493 | pCR-Topo BluntII - ScATO1 L75Q | PCR oJML51, oJML52 (SDM oJML55, oJML56 (Clone of ScATO1 Not Kept) |
| pJLV0048 | pBF506 | pRS416-ProGPD-ScATO1 L75Q | XhoI-SpeI (pRAS416-GPD) + XhoI-SpeI(pJLV035) |
| pJLV0061 | pBF604 | pCR-Topo BluntII-5' + 3' ScURA3 | PCR oJML63, oJML66 (PCR oJML63, oJML65 gDNA ScTURBO + PCR oJML64, oJML66 gDNA ScTURBO) |
| pJLV0062 | pBF605 | pCR-Topo BluntII-KanMX-200m-448 | PCR oJML71-oJML74 (PCR oJML71, oJML73 pBF524 + PCR oJML72, oJML74 pBF32) |
| pJLV0063 | pBF606 | pUC19-5 + 3' ScURA3 | EcoR1-SphI(pJLV0061) + EcoR1-SphI(pUC19) |
| pJLV0065 | pBF608 | pCR-Topo BluntII - 200m448 - ProGDP-ScATO1 L75Q | PCR oJML67-oJML70 (PCR oJML67-oJML59 (pBF32) + PCR oJML68-oJML70 (pJLV048)) |
| pJLV0070 | pBF650 | pUC19-200m448-ProGDP-ScATO1 L75Q - KanMX-200m448 | SalI/SphI (pJLV0065) + BamHI /SalI (pJLV0062) + SphI/BamHI (pUC19) |
| pJLV0074 | pBF654 | PUC19-5' URA3-200m448-ProGDP-ScATO1 L75Q - KanMX-200m448-3' URA3 | NotI(pJLV070) + NotI(pJLV063) |

Example 20

Construction of the ura3 Disruptions in each Haploid

Haploid yeast strains were transformed with 2 to 3 μg of a PvuII, SphI digested ura3::R-KanMX-ATO1-L75Q-R disruption cassette using the high-efficiency Li-PEG procedure with a heat shock time of 8 minutes. Transformants were plated on YPD plus G418 (200 μg/ml) plates. Colonies were re-streaked onto ScD FOA plates. Single colonies were replica plated on ScD-ura, ScD+FOA, YPD, and YPD G418 200 μg/ml plates. Ura-FOA$^R$ G418$^R$ colonies were grown overnight in YPD. Genomic DNA was extracted and the presence of the KanMX-ATO1-L75Q gene in the URA3 loci was verified by PCR. 50 μl of each overnight culture was plated on ScD Acetate (2 g/L), pH 4.0, plates. Colonies were restreaked on ScD Acetate plates and single colonies grown overnight in YPD. Disruptions of the URA3 loci were verified by PCR with primers complementary to a region outside of the flanking region used for the disruption. The presence of the unique

```
JML/212   GTCAACAGTACCCTTAGTATATTCTCCAGTAGCTAGG   URA3
          GAG (SEQ ID NO: 362)

JML/213   CGTTACCCAATTGAACACGGTATTGTCAC           ACT1
          (SEQ ID NO: 363)

JML/214   GAAGATTGAGCAGCGGTTTGCATTTC              ACT1
          (SEQ ID NO: 364)
```

Primers Used to Verify the Presence or Absence of URA3

```
JML/67    GCATGCgcggccgcACGTCGGCAGGCCCG (SEQ ID NO: F'200mer-R
          365)

JML/74    GGATCCgcggccgcTGGTCGCGCGTCCTTCG (SEQ ID    R-200mer-R
          NO: 366)

JML/102   gagtcaaacgacgttgaaattgaggctactgc (SEQ ID   PCR to verify
          NO: 367)                                   disruption
                                                     of URA3

JML/103   GATTACTGCTGCTGTTCCAGCCCATATCCAAC (SEQ ID   PCR to verify
          NO: 368)                                   disruption
                                                     of URA3
```

Example 21

EDA Gene Integration Method and Constructs

Plasmid DNA was digested with PacI using manufacturers suggestions. The digestions were purified using the GeneJET™ Gel Extraction Kit I (Fermentas). Each column was eluted with 20 μl of Elution buffer and multiple digests were combined. S. cerevisiae was transformed using the high-efficiency Li-PEG procedure with 2 to 3 μg of DNA and transformants were selected on ScD-ura solid media. Correct integrations were confirmed by PCR analysis with primers outside the flanking regions used as the disruption cassette and primers complementary to either the open reading frame of EDA or the 200-mer repeat. Oligonucleotide primers utilized for verification are described in the tables below.

Primers—Outside

```
YBR110.5 5' GGCAATCAAATTGGGAACGAACAATG      JML/187
            (SEQ ID NO: 369)
         3' CTCAAGGTATCCTCATGGCCAAGCAATAC   JML/188
            (SEQ ID NO: 370)

YDL075.5 5' GGGTCTACAAACTGTTGTTGTCGAAGAAGA  JML/189
            TG (SEQ ID NO: 371)
         3' CATTCAGTTCCAATGATTTATTGACAGTGC  JML/190
            AC (SEQ ID NO: 372)
```

Primers—Repeat and EDA Going Out

```
JML/276    CCTACCCGCCTCGGATCCCAGCTACC  R-repeat
           (SEQ ID NO: 373)

JML/277    GGTAGCTGGGATCCGAGGCGGGTAGG  R-repeat
           (SEQ ID NO: 374)

JML/278    CCTCCCGGCACAGCGTGTCGATGC    R at the 5'EDA
           (SEQ ID NO: 375)
```

PaEDA Going Out and Similar Primers for EcEDA

```
JML/  CGAAGCCCTGGAGCGCTTCGC   PCR for PaEDA going
297   (SEQ ID NO: 376)        out at the 3' of
                              the ORF JML/  GTGGTCAGGATTGATTCTGCACT PCR for EcEDA
298   TGTTTTCCAG (SEQ ID      Reverse at the 5' end
      NO: 377)

JML/  CGCGTGAAGCTGTAGAAGGCGC  PCR for EcEDA
299   TAAG (SEQ ID NO: 378)   Forward at the 3' end
```

The PCR reactions were performed in a final reaction volume of 25 μl using the following amplification profile; 1 cycle at 94 degrees C. for 2 minutes, followed by 35 cycles of 94 degrees C. for 30 seconds, 52 degrees C. for 30 second and 72 degrees C. for 2 minutes.

Construction of EDA Disruption Cassettes $P_{TDH3}$-PaEDA was amplified from pBF292 using primers oJML225 and oJML226, shown in the table below and Topo cloned in pCR Blunt II to make pJLV95.

```
JML/225  GAGCTCGGCCGCAAATTAAA       3'cyCTERMINATOR
         GCCTTCGAG (SEQ ID NO: 379)

JML/226  GGCCGGCCGTTTATCATTATCAATA  5'PROMOTERgpd
         CTCGCCATTTCAAAGAATACG (SEQ ID NO: 380)
```

The desired fragment was moved as a FseI-SacI piece into pBF730 or pBF731 (the integration cassette of either YBR110.5 or YDL075.5, respectively) to make plasmids pJLV114 and pJLV115, respectively. YBR110.5 is located in between loci YBR110 and YBR111, and YDL075.5 is located in between loci YDL075 and YDL076. The R-URA3-R sequence was moved into these plasmids as a NotI fragment to make pJLV119 and pJLV120. The resultant plasmids are described in the table below.

| | | | |
|---|---|---|---|
| pJLV0095 | pBF777 | pCR-Topo BluntII - PaEDA | PCR oJML225-oJML226 (pBF292) |
| pJLV0114 | pBF862 | pUC19-5'-YBR110.5-PGDP1-PaEDA-TCYC-3'YBR110.5 | FseI-SacI(pBF730) + FseI-SacI(pJLV95) |
| pJLV0115 | pBF863 | pUC19-5'-YDL075.5-PGDP1-PaEDA-TCYC-3'YDL075.5 | FseI-SacI(pBF731) + FseI-SacI(pJLV95) |
| pJLV0119 | pBF867 | pUC19-5'-YBR110.5-PGDP1-PaEDA-TCYC-R-URA3-R-3'YBR110.5 | NotI(pBF742) + NotI(pJLV114) |
| pJLV0120 | pBF868 | pUC19-5'-YDL075.5-PGDP1-PaEDA-TCYC-R-URA3-R-3'YDL075.5 | NotI(pBF742) + NotI(pJLV115) |

Example 22

Isolation and Evaluation of Additional EDA Genes

EDA genes isolated from a variety of sources were expressed in yeast and evaluated independently of EDA activity, to identify EDA activities suitable of inclusion in an engineered yeast strain. The EDA activities were was independently assessed by adding saturating amounts of over expressed E. coli EDD extracts to S. cerevisiae EDA extracts lacking EDD (Cheriyan et al., Protein Science 16:2368-2377, 2007). The relative activities of EDAs, expressed in S. cerevisiae, were compared and ranked in this way. The activity of integrated EDAs in Thermosacc-Gold haploids, were also evaluated in this manner. The table below describes oligonucleotide primers used to isolate the various EDA genes.

| Name | Description | Sequence | SEQ ID NO: |
|---|---|---|---|
| KA/EDA-SoFor | Cloning primer for *Shewanella oneidensis* EDA | GTTCACTGCACTAGTAAAAAAATG CTTGAGAATAACTGGTC | 381 |
| KA/EDA-SoRev | Cloning primer for *Shewanella oneidensis* EDA | CTTCGAGATCTCGAGTTAAAGTCC GCCAATCGCCTC | 382 |
| KA/EDA-GoFor | Cloning primer for *Gluconobacter oxydans* EDA | GTTCACTGCACTAGTAAAAAAATG ATCGATACTGCCAAACTC | 383 |
| KA/EDA-GoRev | Cloning primer for *Gluconobacter oxydans* EDA | CTTCGAGATCTCGAGTCAGACCGT GAAGAGTGCCGC | 384 |
| KA/EDA-BLFor | Cloning primer for *Bacilluis licheniformis* EDA | GTTCACTGCACTAGTAAAAAAATG GTATTGTCACACATCGAAG | 385 |
| KA/EDA-BLRev | Cloning primer for *Bacilluis licheniformis* EDA | CTTCGAGATCTCGAGTTACTGTTT TGCTGCTTCAACAAATTG | 386 |
| KA/EDA-BsFor | Cloning primer for *Bacillus subtilis* EDA | GTTCACTGCACTAGTAAAAAAATG GAGTCCAAAGTCGTTGAAAACC | 387 |
| KA/EDA-BsRev | Cloning primer for *Bacillus subtilis* EDA | CTTCGAGATCTCGAGTTACACTTG GAAAACAGCCTGCAAATCC | 388 |
| KA/EDA-PfFor | Cloning primer for *Pseudomonas fluorescens* EDA | GTTCACTGCACTAGTAAAAAAATG ACAAACCTCGCCCCGACC | 389 |
| KA/EDA-PfRev | Cloning primer for *Pseudomonas fluorescens* EDA | CTTCGAGATCTCGAGTCAGTCCAG CAGGGCCAGG | 390 |
| KA/EDA-PsFor | Cloning primer for *Pseudomonas syringae* EDA | GTTCACTGCACTAGTAAAAAAATG ACACAGAACGAAAATAATCAGCCGC | 391 |
| KA/EDA-PsRev | Cloning primer for *Pseudomonas syringae* EDA | CTTCGAGATCTCGAGTCAGTCAAA CAGCGCCAGCGC | 392 |
| KA/EDA-SdFor | Cloning primer for *Saccharaophagus degradans* EDA | GTTCACTGCACTAGTAAAAAAATG GCTATTACAAAAGAATTTTTAGCT CCAG | 393 |
| KA/EDA-SdRev | Cloning primer for *Saccharaophagus degradans* EDA | CTTCGAGATCTCGAGTTAGCTAGA AATTTTAGCGGTAGTTGCC | 394 |
| KA/EDA-XaFor | Cloning primer for *Xanthamonas axonopodis* EDA | GTTCACTGCACTAGTAAAAAAATG ACGATTGCCCAGACCCAG | 395 |
| KA/EDA-XaRev | Cloning primer for *Xanthamonas axonopodis* EDA | CTTCGAGATCTCGAGTCAGCCCGC CCGCACC | 396 |
| KA/NdeI EDDfor | Cloning primer for *E. coli* EDD | GTTCACTGCCATATGAATCCACAA TTGTTACGCGTAACAAATCGAATC ATTG | 397 |
| KA/XhoI EDDrev | Cloning primer for *E. coli* EDD | CTTCGAGATCTCGAGTTAAAAAGT GATACAGGTTGCGCCCTGTTCGGC | 398 |

Listed below are the amino acid sequences, nucleotide sequences and accession numbers of the EDA genes evaluated as described in this Example.

| Accession Number | Species | Strain Number | Nucleotide Sequence | Amino Acid Sequence |
|---|---|---|---|---|
| YP_526856.1 | *Saccharophagus degradans* | 2-40 | ATGGCTATTACAAAAGAATTTTTAGCTCCAGTTGGCGTAATGCCTGT TGTGGTTGTGGATCGTGTAGAAGATGCGGTGCCTATTACAAACGCAT TAAAAGCCGGCGGTATTAAAGCAGTTGAGATTACTTTACGTACTCCT GCGGCACTGGATGCTATTCGCGCTATTAAAGCTGAGTGTGAAGACAT CCTGGTGGGGGTAGGTACGGTTATTAACCATCAAAACCTTAAAGATA TTGCTGCAATTGGTGTTGATTTCGCCGTATCTCCTGGTTACACCCCA ACATTGCTGAAGCAAGCGCAAGATTTGGGCGTAGAAATGTTGCCTGG TGTAACTTCGCCTTCTGAAGTTATGCTTGGTATGGAGCTAGGTTTGT | MAITKEFLAPVGVMPVV VVDRVEDAVPITNALKA GGIKAVEITLRTPAALD AIRAIKAECEDILVGVG TVINHQNLKDIAAIGVD FAVSPGYTPTLLKQAQD LGVEMLPGVTSPSEVML GMELGLSCFKLFPAVAV |

| Accession Number | Species | Strain Number | Nucleotide Sequence | Amino Acid Sequence |
|---|---|---|---|---|
| | | | CTTGCTTCAAGCTATTCCCTGCGGTTGCAGTAGGTGGTTTGCCATTA<br>CTTAAGTCTATTGGTGGCCCATTACCACAGGTTTCCTTCTGTCCAAC<br>AGGCGGTTTGACTATCGATACTTTCACCGACTTCTTGGCATTGCCTA<br>ACGTTGCTTGTGTGGGTGGTACTTGGTTGGTGCCTGCAGATGCTGTT<br>GCAGCTAAAAACTGGCAAGCTATTACTGATATTGCGGCGGCAACTAC<br>CGCTAAAATTTCTAGCTAA (SEQ ID NO: 399) | GGLPLLKSIGGPLPQVS<br>FCPTGGLTIDTFTDFLA<br>LPNVACVGGTWLVPADA<br>VAAKNWQAITDIAAATT<br>AKISS (SEQ ID NO: 400) |
| | Xanthomonas axonopodis pv. Vasculorum | ATCC 13902 | ATGACGATTGCCCAGACCCAGAACACCGCCGAACAGT -continued

| Accession Number | Species | Strain Number | Nucleotide Sequence | Amino Acid Sequence |
|---|---|---|---|---|
| | | | GCTGATCTTGCTGAACATCTATCTTTTGTAAAGACACATTATATCCC<br>CGGCGTCTTGACTCCGAGCGAAATTATGGAAGCGCTGACATTCGGTT<br>TTACGACATTAAAGCTGTTCCCAAGCGGTGTGTTTGGCATTCCGTTT<br>ATGAAAAATTTAGCGGGTCCTTTCCCGCAGGTGACCTTTATTCCGAC<br>AGGCGGGATACATCCGTCTGAAGTCGTGATTGGCTTAGAGCCGGAG<br>CTGGCGCCGTCGGAGTCGGCAGCCAGTTGGGCAGCTGTTCAAAAGAG<br>GATTTGCAGGCTGTTTTCCAAGTGTAA (SEQ ID NO: 409) | FVKTHYIPGVLTPSEIM<br>EALTFGFTTLKLFPSGV<br>FGIPFMKNLAGPFPQVT<br>FIPTGGIHPSEVPDWLR<br>AGAGAVGVGSQLGSCSK<br>EDLQAVFQV (SEQ ID NO: 410) |
| YP_081150.2 | Bacillus licheniformis | ATCC 14580 | ATGGTATTGTCACACATCGAAGAACAAAAACTGATTGCGATCATCCG<br>CGGATACAATCCGGAGGAGGCAGTGAGCATTGCCGGCGCCTTAAAAG<br>CGGGCGGCATCAGGCTTGTGGAGATTACGCTTAATTCCCCTCAAGCG<br>ATCAAAGCGATTGAAGCGGTTTCAGAGCATTTTGGGGACGAAATGCT<br>TGTCGGAGCGGGAACCGTACTTGATCCCGAATCTGCGAGAGCGGCGC<br>TTTTAGCCGGCGCGGTTTATCCTGTCTCCGACCGTCAATGAAGAG<br>ACGATCAAGCTGACAAAACGGTATGGAGCGGTCAGCATTCCAGGCGC<br>TTTTACCCCGACTGAAATATTGACGGCGTATGAAAGCGGGGGAGACA<br>TCATCAAGGTATTTCCCGGAACAATGGGGCCTGGCTATATCAAGGAT<br>ATCCACGGACCGCTTCCGCATATTCCGCTGCTTCCGACTGGGAGGAGT<br>CGGATTGGAAAACCTTCACGAGTTTCTGCAGGCCGGTGCGGTCGGAG<br>CGGGAATCGGCGGTTCGCTTGTTCGGGCTAATAAAGATGTTAATGAC<br>GCGTTTTTAGAAGAGCTGTCCAAAAAGCAAAGCAATTTGTTGAAGC<br>AGCAAAACAGTAA (SEQ ID NO: 411) | MVLSHIEEQKLIAIIRG<br>YNPEEAVSIAGALKAGG<br>IRLVEITLNSPQAIKAI<br>EAVSEHFGDEMLVGAGT<br>VLDPESARAALLAGARF<br>ILSPTVNEETIKLTKRY<br>GAVSIPGAFTPTEILTA<br>YESGGDIIKVFPGTMGP<br>GYIKDIHGPLPHIPLLP<br>TGGVGLENLHEFLQAGA<br>VGAGIGGSLVRANKDVN<br>DAFLEELSKKAKQFVEA<br>AKQ (SEQ ID NO: 412) |
| YP_190869.1 | Gluconobacter oxydans | 62IH | ATGATCGATACTGCCAAACTCGACGCCGTCATGAGCCGTTGTCCGGT<br>CATGCCGGTGCTGGTGGTCAATGATGTGGCTCTGGCCCGCCCGATGG<br>CCGAGGCTCTGGTGGCGGGTGGACTGTCCACGCTGGAAGTCACGCTG<br>CGCACGCCCTGCGCCCTTGAAGCTATTGAGGAAATGTCGAAAGTACC<br>AGGCGCGCTGGTCGGTGCCGGTACGGTGCTGAATCCGTCCGACATGG<br>ACCGTGCCGTGAAGGCGGGTGCGCGCTTCATCGTCAGCCCCGGCCTG<br>ACCGAGGCGCTGGCAAAGGCGTCGGTTGAGCATGACGTCCCCTTCCT<br>GCCAGGCGTTGCCAATGCGGGTGACATCATGCGGGGTCTGGATCTGG<br>GTCTGTCACGCTTCAAGTTCTTCCCGGCTGTGACGAATGGCGGCATT<br>CCCGCGCTCAAGAGCTTGGCCAGTGTTTTTGGCAGCAATGTCCGTTT<br>CTGCCCCACGGGCGGCATTACGGAAGAGAGCGCACCGGACTGGCTGG<br>CGCTTCCCTCCGTGGCCTGCGTCGGCGGATCCTGGGTGACGGCCTGG<br>ACGTTCGATGCGGACAAGGTCCGTCAGCGCGCCACGGCTGCCGCACT<br>CTTCACGGTCTGA (SEQ ID NO: 413) | MIDTAKLDAVMSRCPVM<br>PVLVVNDVALARPMAEA<br>LVAGGLSTLEVTLRTPC<br>ALEAIEEMSKVPGALVG<br>AGTVLNPSDMDRAVKAG<br>ARFIVSPGLTEALAKAS<br>VEHDVPFLPGVANAGDI<br>MRGLDLGLSRFKFFPAV<br>TNGGIPALKSLASVFGS<br>NVRFCPTGGITEESAPD<br>WLALPSVACVGGSWVTA<br>GTFDADKVRQRATAAAL<br>FTV (SEQ ID NO: 414) |
| NP_251871.1 | P. aeruginosa | PAO1 Codon Optimized | ATGAAAAACTGGAAAACAAGTGCAGAATCAATCCTGACCACCGGCCC<br>GGTTGTACCGGTTATCGTGGTAAAAAAACTGGAACACGCGGTGCCGA<br>TGGCAAAAGCGTTGGTTGCTGGTGGGGTGCGCGTTCTGGAAGTGACT<br>CTGCGTACCGAGTGTGCAGTTGACGCTATCCGTGCTATCGCCAAAGA<br>AGTGCCTGAAGCGATTGTGGGTGCCGGTACGGTGCTGAATCCACAGC<br>AGCTGGCAGAAGTCACTGAAGCGGGTGCACAGTTCGCAATTAGCCCG<br>GGTCTGACCGAGCCGCTGCTGAAAGCTGCTACCGAAGGGACTATTCC<br>TCTGATTCCGGGGATCAGCACTGTTTCCGAACTGATGCTGGGTATGG<br>ACTACGGTTTGAAAGAGTTCAAATTCTTCCCGGCTGAAGCTAACGGC<br>GGCGTGAAAGCCCTGCAGGCGATCGCGGGTCCGTTCTCCCAGGTCCG<br>TTTCTGCCCGACGGGTGGTATTTCTCCGGCTAACTACCGTGACTACC<br>TGGCGCTGAAAAGCGTGCTGTGCATCGGTGGTTCCTGGCTGGTTCCG<br>GCAGATGCGCTGGAAGCGGGCGATTACGACCGCATTACTAAGCTGGC<br>GCGTGAAGCTGTAGAAGGCGCTAAGCTGTAA (SEQ ID NO: 415) | MKNWKTSAESILTTGPV<br>VPVIVVKKLEHAVPMAK<br>ALVAGGVRVLEVTLRTE<br>CAVDAIRAIAKEVPEAI<br>VGAGTVLNPQQLAEVTE<br>AGAQFAISPGLTEPLLK<br>AATEGTIPLIPGISTVS<br>ELMLGMDYGLKEFKFFP<br>AEANGGVKALQAIAGPF<br>SQVRFCPTGGISPANYR<br>DYLALKSVLCIGGSWLV<br>PADALEAGDYDRITKLA<br>REAVEGAKL (SEQ ID NO: 416) |
| | | PAO1-Ec5 | ATGAAAAACTGGAAACAGAAGACCGCCCGCATCGACACGCTGTGCCG<br>GGAGGCGCGCATCCTCCCGGTGATCACCATCGACCGCGAGGCGGACA<br>TCCTGCCGATGGCCGATGCCCTCGCCGCCGGCGGCCTGACCGCCCTG<br>GAGATCACCCTGCGCACGGCCACGGGCTGACCGCCATCCGGCCGCCT<br>CAGCGAGGAGCGCCCGCACCTGCGCATCGGCGCCGGCACCGTGCTCG<br>ACCCGCGGACCTTCGCCGCCGCGGAAAAGGCCGGGGCGAGCTTCGTG<br>GTCACCCCGGGTTGCACCGACGAGTTGCTGCGCTTCGCCCTGGACAG<br>CGAAGTCCCGCTGTTGCCCGGCGTGGCCAGCGCTTCCGAGATCATGC<br>TCGCCTACCGCCATGGCTACCGCCGCTTCAAGCTGTTTCCCGCCGAA<br>GTCAGCGGCGGCCCGGCCGCGCTGAAGGCGTTCTCGGGACCATTCCC<br>CGATATCCGCTTCTGCCCCACCGGAGCGTCAGCCTGAACAATCTCG<br>CCGACTACCTGGCCGTACCCAACGTGATGTGCGTCGGCGGCACCTGG<br>ATGCTGCCCAAGGCCGTGGTCGACCGCGGCGACTGGGCCCAGGTCGA<br>GCGCCTCAGCCGCGAAGCCCTGGAGCGCTTCGCCGAGCACCGCCGAC<br>ACTAATAGCTCGAGTTACTTTACT (SEQ ID NO: 417) | MKNWKQKTARIDTLCRE<br>ARILPVITIDREADILP<br>MADALAAGGLTALEITL<br>RTAHGLTAIRRLSEERP<br>HLRIGAGTVLDPRTFAA<br>AEKAGASFVVTPGCTDE<br>LLRFALDSEVPLLPGVA<br>SASEIMLAYRHGYRRFK<br>LFPAEVSGGPAALKAFS<br>GPPPDIRFCPTGGVSLN<br>NLADYLAVPNVMCVGGT<br>WMLPKAVVDRGDWAQVE<br>RLSREALERFAEHRRH (SEQ ID NO: 418) |
| | | PAO1-Ec10 | ATGAAAAACTGGAAACAAGTGCAGAATCAATCGACACGCTGTGCCG<br>GGAGGCGCGCATCCTCCCGGTGATCACCATCGACCGCGAGGCGGACA<br>TCCTGCCGATGGCCGATGCCCTCGCCGCCGGCGGCCTGACCGCCCTG<br>GAGATCACCCTGCGCACGGCCACGGGCTGACCGCCATCCGGCCGCCT<br>CAGCGAGGAGCGCCCGCACCTGCGCATCGGCGCCGGCACCGTGCTCG<br>ACCCGCGGACCTTCGCCGCCGCGGAAAAGGCCGGGGCGAGCTTCGTG<br>GTCACCCCGGGTTGCACCGACGAGTTGCTGCGCTTCGCCCTGGACAG | MKNWKTSAESIDTLCRE<br>ARILPVITIDREADILP<br>MADALAAGGLTALEITL<br>RTAHGLTAIRRLSEERP<br>HLRIGAGTVLDPRTFAA<br>AEKAGASFVVTPGCTDE<br>LLRFALDSEVPLLPGVA |

-continued

| Accession Number | Species | Strain Number | Nucleotide Sequence | Amino Acid Sequence |
|---|---|---|---|---|
| | | | CGAAGTCCCGCTGTTGCCCGGCGTGGCCAGCGCTTCCGAGATCATGC<br>TCGCCTACCGCCATGGCTACCGCCGCTTCAAGCTGTTTCCCGCCGAA<br>GTCAGCGGCGGCCCGGCGGCGCTGAAGGCGTTCTCGGGACCATTCCC<br>CGATATCCGCTTCTGCCCCACCGGAGGCGTCAGCCTGAACAATCTCG<br>CCGACTACCTGGCGGTACCCAACGTGATGTGCGTCGGCGGCACCTGG<br>ATGCTGCCCAAGGCCGTGGTCGACCGCGGCGACTGGGCCCAGGTCGA<br>GCGCCTCAGCCGCGAAGCCCTGGAGCGCTTCGCCGAGCACCGCAGAC<br>ACTAATAGCTCGAGTTACTTTACT (SEQ ID NO: 419) | SASEIMLAYRHGYRRFK<br>LFPAEVSGGPAALKAFS<br>GPFPDIRFCPTGGVSLN<br>NLADYLAVPNVMCVGGT<br>WMLPKAVVDRGDWAQVE<br>RLSREALERFAEHRRH<br>(SEQ ID NO: 420) |
| | | PAO1-Ec15 | ATGAAAAACTGGAAAACAAGTGCAGAATCAATCCTGACCACCGGCCG<br>GGAGGCGCGCATCCTCCCGGTGATCACCATCGACCGCGAGGCGGACA<br>TCCTGCCGATGGCCGATGCCCTCGCCGCCGGCGGCCTGACCGCCCTG<br>GAGATCACCCTGCGCACGGCGCACGGGCTGACCGCCATCCGGCGCCT<br>CAGCGAGGAGCGCCCCGCACCTGCGCATCGGCGCCGGCACCGTGCTCG<br>ACCCGCGGACCTTCGCCGCCGCGGAAAAGGCCGGGGCGAGCTTCGTG<br>GTCACCCCGGGTTGCACCGACGAGTTGCTGCGCTTCGCCCTGGACAG<br>CGAAGTCCCGCTGTTGCCCGGCGTGGCCAGCGCTTCCGAGATCATGC<br>TCGCCTACCGCCATGGCTACCGCCGCTTCAAGCTGTTTCCCGCCGAA<br>GTCAGCGGCGGCCCGGCGGCGCTGAAGGCGTTCTCGGGACCATTCCC<br>CGATATCCGCTTCTGCCCCACCGGAGGCGTCAGCCTGAACAATCTCG<br>CCGACTACCTGGCGGTACCCAACGTGATGTGCGTCGGCGGCACCTGG<br>ATGCTGCCCAAGGCCGTGGTCGACCGCGGCGACTGGGCCCAGGTCGA<br>GCGCCTCAGCCGCGAAGCCCTGGAGCGCTTCGCCGAGCACCGCAGAC<br>ACTAATAGCTCGAGTTACTTTACT (SEQ ID NO: 421) | MKNWKTSAESILTTGRE<br>ARILPVITIDREADILP<br>MADALAAGGLTALEITL<br>RTAHGLTAIRRLSEERP<br>HLRIGAGTVLDPRTFAA<br>AEKAGASFVVTPGCTDE<br>LLRFALDSEVPLLPGVA<br>SASEIMLAYRHGYRRFK<br>LFPAEVSGGPAALKAFS<br>GPFPDIRFCPTGGVSLN<br>NLADYLAVPNVMCVGGT<br>WMLPKAVVDRGDWAQVE<br>RLSREALERFAEHRRH<br>(SEQ ID NO: 422) |

EDA extracts were prepared using the following protocol.

Day 1

Grow 5 ml LB-Kan preps of BF1055 (BL21/DE3 with pET26b empty vector) and BF1706 (BL21DE3 with pET26b+*E. coli* EDD).

Grow 5 ml preps of each EDA construct expressed in *S. cerevisiae* in appropriate selective media (e.g. ScD-leu).

Day 2

Grow 50 ml LB-Kan prep of BF1055, 2% (v/v) inoculate.

Grow 50 ml prep of BF1706 using Novagen's Overnight Express (46.45 ml LB-Kan, 1 ml solution 1, 2.5 ml solution 2, 50 µl solution 3, 5 µl of 1M MnCl$_2$, 50 µl of 0.5 M FeCl$_2$), 2% (v/v) inoculate.

Grow 50 ml prep of each EDA construct expressed in *S. cerevisiae* in appropriate selective media+10 mM MnCl$_2$. Inoculate to OD$_{600}$ of 0.2.

Day 3

EDD extractions (adapted from Cheriyan et al, Protein Science 16:2368-2377, 2007):

1) Pellet cells in 50 ml conical tubes, 4° C., 3,000 rpm, 10 mins, discard supernatant.
2) Resuspend in 2 ml degassed PDGH buffer (20 mM MES pH 6.5, 30 mM NaCl, 5 mM MnCl$_2$, 0.5 mM FeCl$_2$, 10 mM 2-mercaptoethanol, 10 mM cysteine, sparged with nitrogen gas). Move to hungate tube.
3) Add 0.1% Triton X-100, 10 ng/ml DNase, 10 µg/ml PMSF, 10 µg/ml TAME (Nα-(p-toluene sulfonyl)-L-arginine methyl ester), 100 µg/ml lysozyme.
4) Sparge hungate tube with nitrogen gas, cap and seal. Incubate 2 hours at 37° C., swirl occasionally.
5) Clarify by centrifugation in 2-ml tube, 4° C., 10 mins, 14,000 rpm. Keep supernatant.
6) Treat with 150 mM pyruvate and 10 mM sodium cyanoborohydride (work in hood) to inactivate aldolase activity. Incubate 30 mins at room temperature.
7) During incubation, pre-equilibrate PD-10 column from GE
   a. Remove top cap, pour off storage buffer.
   b. Cut off bottom tip, fit in 50 ml conical with adapter.
   c. Pour 5 ml of 20 mM MES buffer, pH 6.5 (total of 5 times). Discard flow-through.
8) Run sample through column, then add MES buffer to a total of 2.5 ml volume added. Discard flow-through.
9) Run 3.5 ml 20 mM MES pH 6.5 buffer to elute protein. Discard column in appropriate waste receptacle.
10) Perform Bradford assay (1:10 or 1:20 dilution).

EDA Extractions:

1) Spin down in 50 ml conicals, 4° C., 3,400 rpm, 5 mins. Wash 2× with 25 ml water.
2) Resuspend in 1 ml lysis buffer (50 mM Tris-HCl, pH 7, 10 mM MgCl$_2$, 1× protease inhibitor.
3) Add 1 cap of zirconia beads, vortex 4-6 times, 15 sec bursts, ice in between.
4) Spin down cell debris, 4° C., 14,000 rpm, 10 mins. Save supernatant.
5) Perform Bradford assay (1:2 dilution).

Activity Assays:

Each reaction contains 50 mM Tris-HCl, pH 7, 10 mM MgCl$_2$, 0.15 mM NADH, 15 µg LDH, saturating amounts of EDD determined empirically (usually ~100 µg), 1-50 µg EDA (depending on level of activity), and 1 mM 6-phosphogluconate. Reactions are started by the addition of 6-phosphogluconate and monitored for 5 mins at 30° C.

Results

The *S. cerevisiae* strains tested for EDA activity are described in the table below. yCH strains are Thermosacc-based (Lallemand). BF strains are based on BY4742.

| Strain | Vector | Construct |
|---|---|---|
| BF542 | pBF150 | *Zymomonas mobilis* EDA |
| BF1689 | pBF892 | PAO1 + 5aa *E. coli* EDA |
| BF1691 | pBF894 | PAO1 + 10aa *E. coli* EDA |
| BF1693 | pBF896 | PAO1 + 15aa *E. coli* EDA |
| BF1721 | pBF909 | *Bacilluis licheniformis* EDA |
| BF1722 | pBF910 | *Bacillus subtilis* EDA |
| BF1723 | pBF911 | *Pseudomonas fluorescens* EDA |
| BF1724 | pBF912 | *Pseudomonas syringae* EDA |
| BF1725 | pBF913 | *Saccharaophagus degradans* EDA |
| BF1726 | pBF914 | *Xanthamonas axonopodis* EDA |
| BF1727 | pBF766 | *Escherichia coli* EDA |
| BF1728 | pBF764 | *Pseudomonas aeruginosa* EDA |

-continued

| Strain | Vector | Construct |
|---|---|---|
| BF1729 | pBF729 | *Gluconobacter oxydans* EDA |
| BF1730 | pBF727 | *Shewanella oneidensis* EDA |
| BF1775 | pBF87 | p425GPD (empty vector) |
| BF1776 | pBF928 | PAO1 EDA codon optimized for *S. cerevisiae* |

Figure 15:
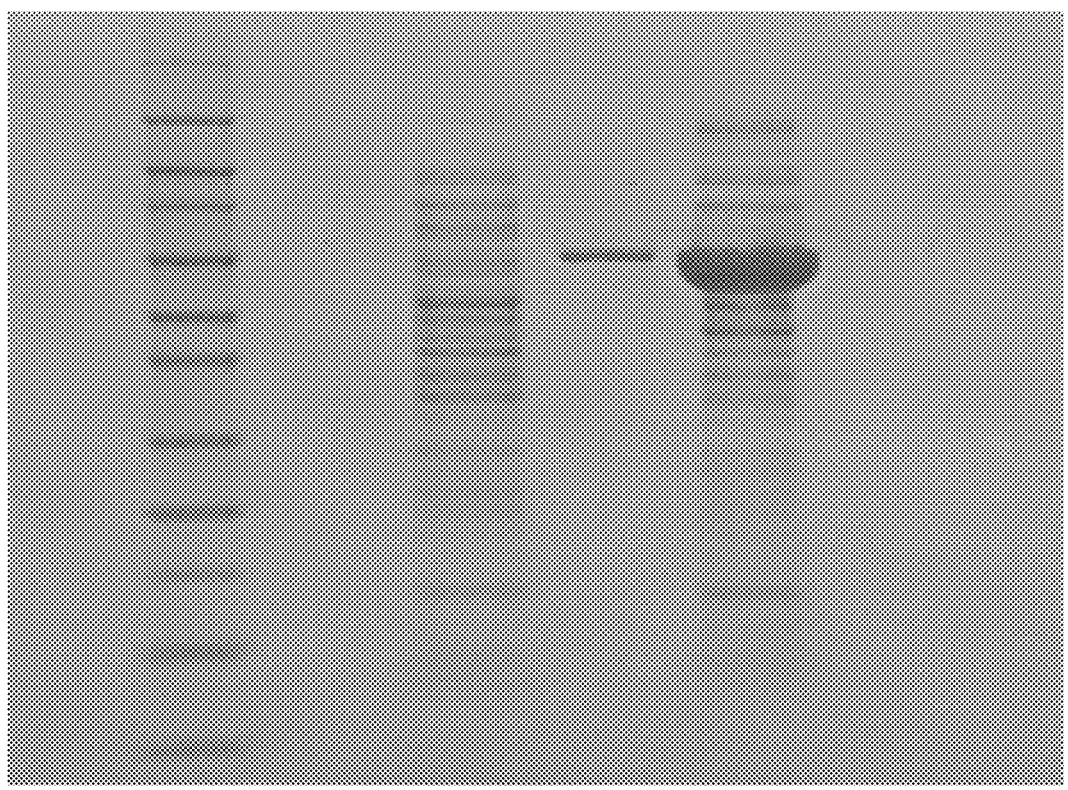
FIG. 15 shows a western blot of *E. coli* crude extract illustrated the presence of the EDD protein at the expected size. Lane 1 is a standard size ladder (Novex Sharp standard), Lane 2 is 1 µg BF1055 cell lysate, Lane 3 is 10 µg BF1055 cell lysate, Lane 4 is 1.5 µg BF1706 cell lysate, Lane 5 is 15 µg BF1706 cell lysate. Experimental methods and results are described in Example 22.

*E. coli* expressed EDD was prepared and confirmed by western blot analysis as shown in FIG. 15. The expected size of EDD is approximately 66 kilodaltons (kDa). A band of approximately that size (e.g., as determined by the nearest sized protein standard of approximately 60 kDa) was identified by western blot. The *E. coli* expressed EDD was used with *S. cerevisiae* expressed EDA's to evaluate the EDA activities. The results of EDA kinetic assays are presented in the table below.

| EDD/EDA | slope | % max |
|---|---|---|
| EC/EC | 0.3467 | 100.00 |
| EC/SO | 0.1907 | 55.00 |
| EC/BS | 0.0897 | 25.87 |
| EC/GO | 0.0848 | 24.46 |
| EC/PCO | 0.084 | 24.23 |
| EC/PA | 0.0533 | 15.37 |
| EC/PE5 | 0.0223 | 6.43 |
| EC/PE10 | 0.0218 | 6.29 |
| EC/SD | 0.015 | 4.33 |
| EC/PS | 0.0135 | 3.89 |
| EC/BL | 0.0112 | 3.23 |
| EC/ZM | 0.0109 | 3.14 |
| EC/PF | 0.0082 | 2.37 |
| EC/V | 0.0074 | 2.13 |
| EC/XA | 0.0065 | 1.87 |
| EC/PE15 | 0.005 | 1.44 |

Figure 16:
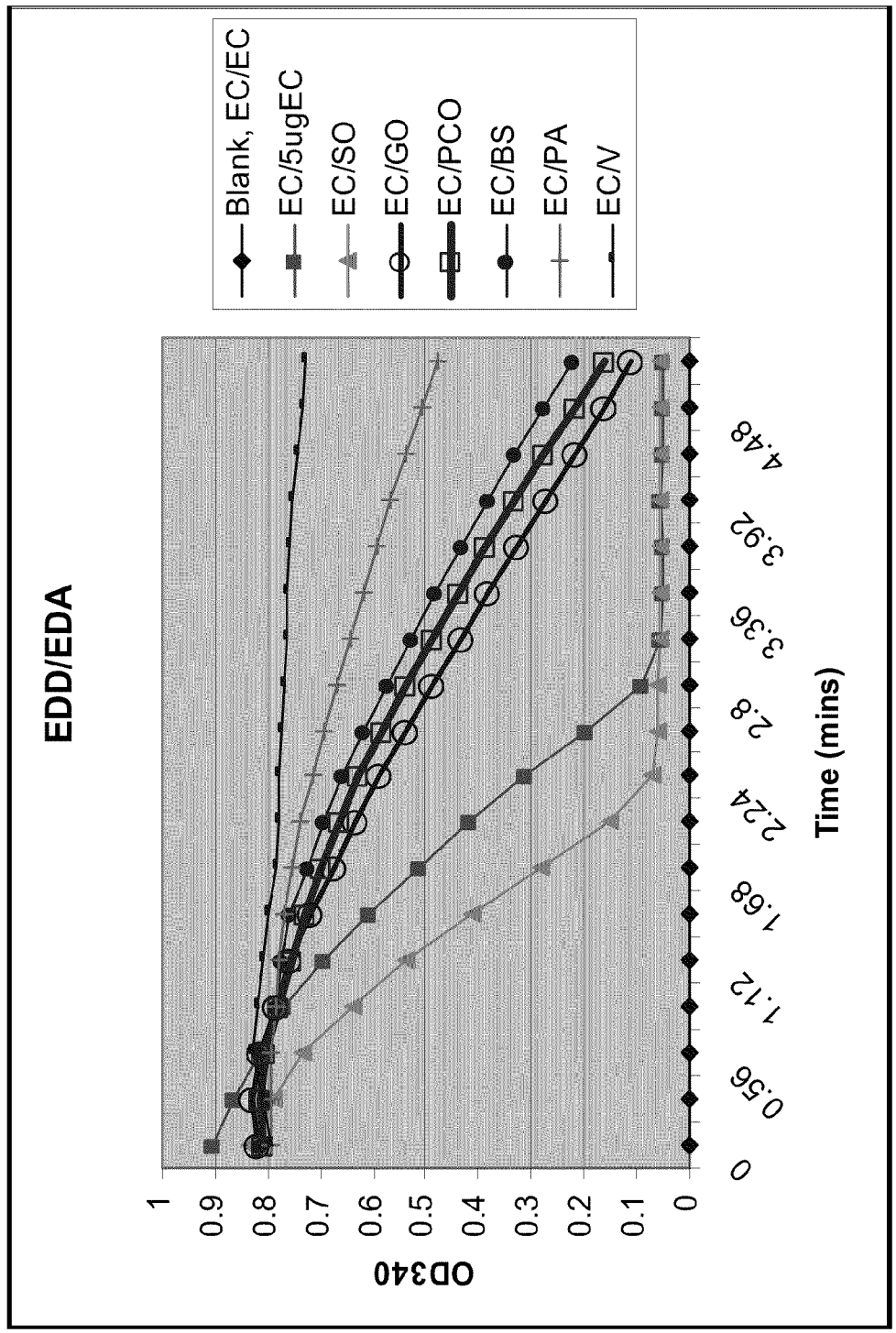
FIG. 16 graphically illustrates the results of activity evaluations of EDA genes expressed in yeast. Experimental methods and results are described in Example 22.

In the results presented above, the slope of the *E. coli* (EC) EDA is outside the linear range for accurate detection, and is therefore underestimated. For the other EDA's, when compared to the *E. coli* EDA, the calculated percentage of maximum activity (e.g., % max) is overestimated, however the slopes are accurate. The results of this experiment indicate that the *E. coli* EDA has higher activity as compared to the other EDA activities evaluated herein, and is approximately 16-fold more active than the EDA from *P. aeruginosa*. EDA's from *X. anoxopodis* and a chimera between *E. coli* EDA and *P. aeruginosa* (e.g., PE15) show less activity than the vector control. Codon-optimized EDA from *P. aeruginosa* showed a slight improvement over the native sequence, however chimeric versions (e.g., PE5, PE10, PE15) showed less activity than native. The experiments were repeated using 100 µg of EDD and 25 µg of EDA cell lysates in each reaction (unless otherwise noted, such as 5 µg of *E. coli* EDA). The reactions in the repeated experiment all were in the linear range of detection and the results of these additional kinetic assays are shown graphically in FIG. 16, and in the table below. *E. coli* EDA was again found to be the most active of those EDA's tested.

| EDA | slope | % max |
|---|---|---|
| EC | 0.462 | 100.00 |
| SO | 0.128 | 27.71 |
| GO | 0.0544 | 11.77 |
| PCO | 0.0539 | 11.67 |
| BS | 0.0505 | 10.93 |
| PA | 0.0273 | 5.91 |
| V | 0.0006 | 0.13 |

Example 23

Nucleotide and Amino Acid Sequence of *S. cerevisiae* Phosphoglucose Isomerase

Phosphoglucose isomerase (PGI1) activity was decreased or disrupted, in some embodiments, to favor the conversion of glucose-6-phosphate to gluconolactone-6-phosphate by the activity of ZWF1 (e.g., glucose-6-phosphate dehydrogenase). The nucleotide sequence of the *S. cerevisiae* PGI1 gene altered to decrease or disrupt phosphoglucose isomerase activity is shown below.

```
PGI1 nucleotide sequence
                                           (SEQ ID NO: 423)
ATGTCCAATAACTCATTCACTAACTTCAAACTGGCCACTGAATTGCCAGCCTGGTCTAAG

TTGCAAAAAATTTATGAATCTCAAGGTAAGACTTTGTCTGTCAAGCAAGAATTCCAAAAA

GATGCCAAGCGTTTTGAAAAATTGAACAAGACTTTCACCAACTATGATGGTTCCAAAATC

TTGTTCGACTACTCAAAGAACTTGGTCAACGATGAAATCATTGCTGCATTGATTGAACTG

GCCAAGGAGGCTAACGTCACCGGTTTGAGAGATGCTATGTTCAAAGGTGAACACATCAAC

TCCACTGAAGATCGTGCTGTCTACCACGTCGCATTGAGAAACAGAGCTAACAAGCCAATG

TACGTTGATGGTGTCAACGTTGCTCCAGAAGTCGACTCTGTCTTGAAGCACATGAAGGAG

TTCTCTGAACAAGTTCGTTCTGGTGAATGGAAGGGTTATACCGGTAAGAAGATCACCGAT

GTTGTTAACATCGGTATTGGTGGTTCCGATTTGGGTCCAGTCATGGTCACTGAGGCTTTG

AAGCACTACGCTGGTGTCTTGGATGTCCACTTCGTTTCCAACATTGACGGTACTCACATT

GCTGAAACCTTGAAGGTTGTTGACCCAGAAACTACTTTGTTTTTGATTGCTTCCAAGACT

TTCACTACCGCTGAAACTATCACTAACGCTAACACTGCCAAGAACTGGTTCTTGTCGAAG

ACAGGTAATGATCCATCTCACATTGCTAAGCATTTCGCTGCTTTGTCCACTAACGAAACC
```

-continued

```
GAAGTTGCCAAGTTCGGTATTGACACCAAAAACATGTTTGGTTTCGAAAGTTGGGTCGGT
GGTCGTTACTCTGTCTGGTCGGCTATTGGTTTGTCTGTTGCCTTGTACATTGGCTATGAC
AACTTTGAGGCTTTCTTGAAGGGTGCTGAAGCCGTCGACAACCACTTCACCCAAACCCCA
TTGGAAGACAACATTCCATTGTTGGGTGGTTTGTTGTCTGTCTGGTACAACAACTTCTTT
GGTGCTCAAACCCATTTGGTTGCTCCATTCGACCAATACTTGCACAGATTCCCAGCCTAC
TTGCAACAATTGTCAATGGAATCTAACGGTAAGTCTGTTACCAGAGGTAACGTGTTTACT
GACTACTCTACTGGTTCTATCTTGTTTGGTGAACCAGCTACCAACGCTCAACACTCTTTC
TTCCAATTGGTTCACCAAGGTACCAAGTTGATTCCATCTGATTTCATCTTAGCTGCTCAA
TCTCATAACCCAATTGAGAACAAATTACATCAAAAGATGTTGGCTTCAAACTTCTTTGCT
CAAGCTGAAGCTTTAATGGTTGGTAAGGATGAAGAACAAGTTAAGGCTGAAGGTGCCACT
GGTGGTTTGGTCCCACACAAGGTCTTCTCAGGTAACAGACCAACTACCTCTATCTTGGCT
CAAAAGATTACTCCAGCTACTTTGGGTGCTTTGATTGCCTACTACGAACATGTTACTTTC
ACTGAAGGTGCCATTTGGAATATCAACTCTTTCGACCAATGGGGTGTTGAATTGGGTAAA
GTCTTGGCTAAAGTCATCGGCAAGGAATTGGACAACTCCTCCACCATTTCTACCCACGAT
GCTTCTACCAACGGTTTAATCAATCAATTCAAGGAATGGATGTGA
```

Example 24

Nucleotide and Amino Acid Sequence of *S. cerevisiae* 6-Phosphogluconate Dehydrogenase (Decarboxylating)

6-phosphogluconate dehydrogenase (decarboxylating) (GND1) activity was decreased or disrupted, in some embodiments, to minimize or eliminate the conversion of gluconate-6-phosphate to ribulose-5-phosphate. The nucleotide sequence of the *S. cerevisiae* GND1 and GND2 genes altered to decrease or disrupt 6-phosphogluconate dehydrogenase (decarboxylating) activity is shown below.

GND1/YHR183W (SEQ ID NO: 424)
```
ATGTCTGCTGATTTCGGTTTGATTGGTTTGGCCGTCATGGGTCAAAATTTGATCTTGAAC
GCTGCTGACCACGGTTTCACTGTTTGTGCTTACAACAGAACTCAATCCAAGGTCGACCAT
TTCTTGGCCAATGAAGCTAAGGGCAAATCTATCATCGGTGCTACTTCCATTGAAGATTTC
ATCTCCAAATTGAAGAGACCTAGAAAGGTCATGCTTTTGGTTAAAGCTGGTGCTCCAGTT
GACGCTTTGATCAACCAAATCGTCCCACTTTTGGAAAAGGGTGATATTATCATCGATGGT
GGTAACTCTCACTTCCCAGATTCTAATAGACGTTACGAAGAATTGAAGAAGAAGGGTATT
CTTTTCGTTGGTTCTGGTGTCTCCGGTGGTGAGGAAGGTGCCCGTTACGGTCCATCTTTG
ATGCCAGGTGGTTCTGAAGAAGCTTGGCCACATATTAAGAACATCTTCCAATCCATCTCT
GCTAAATCCGACGGTGAACCATGTTGCGAATGGGTTGGCCCAGCCGGTGCTGGTCACTAC
GTCAAGATGGTTCACAACGGTATTGAATACGGTGATATGCAATTGATTTGTGAAGCTTAT
GACATCATGAAGAGATTGGGTGGGTTACCGATAAGGAAATCAGTGACGTTTTTGCCAAA
TGGAACAATGGTGTCTTGGATTCCTTCTTGGTCGAAATTACCAGAGATATTTTGAAATTC
GACGACGTCGACGGTAAGCCATTAGTTGAAAAAATCATGGATACTGCTGGTCAAAAGGGT
ACTGGTAAGTGGACTGCCATCAACGCCTTGGATTTGGGTATGCCAGTTACTTTGATTGGT
GAAGCTGTCTTTGCCCGTTGTCTATCTGCTTTGAAGAACGAGAGAATTAGAGCCTCCAAG
GTCTTACCAGGCCCAGAAGTTCCAAAAGACGCCGTCAAGGACAGAGAACAATTTGTCGAT
GATTTGGAACAAGCTTTGTATGCTTCCAAGATTATTTCTTACGCTCAAGGTTTCATGTTG
ATCCGTGAAGCTGCTGCTACTTATGGCTGGAAACTAAACAACCCTGCCATCGCTTTGATG
```

-continued

```
TGGAGAGGTGGTTGTATCATTAGATCTGTTTTCTTGGGTCAAATCACAAAGGCCTACAGA

GAAGAACCAGATTTGGAAAACTTGTTGTTCAACAAGTTCTTCGCTGATGCCGTCACCAAG

GCTCAATCTGGTTGGAGAAAGTCAATTGCGTTGGCTACCACCTACGGTATCCCAACACCA

GCCTTTTCCACCGCTTTGTCTTTCTACGATGGGTACAGATCTGAAAGATTGCCAGCCAAC

TTACTACAAGCTCAACGTGACTACTTTGGTGCTCACACTTTCAGAGTGTTGCCAGAATGT

GCTTCTGACAACTTGCCAGTAGACAAGGATATCCATATCAACTGGACTGGCCACGGTGGT

AATGTTTCTTCCTCTACATACCAAGCTTAA
```

GND2/YGR256W (SEQ ID NO: 425)
```
ATGTCAAAGGCAGTAGGTGATTTAGGCTTAGTTGGTTTAGCCGTGATGGGTCAAAATTTG

ATCTTAAACGCAGCGGATCACGGATTTACCGTGGTTGCTTATAATAGGACGCAATCAAAG

GTAGATAGGTTTCTAGCTAATGAGGCAAAAGGAAAATCAATAATTGGTGCAACTTCAATT

GAGGACTTGGTTGCGAAACTAAAGAAACCTAGAAAGATTATGCTTTTAATCAAAGCCGGT

GCTCCGGTCGACACTTTAATAAAGGAACTTGTACCACATCTTGATAAAGGCGACATTATT

ATCGACGGTGGTAACTCACATTTCCCGGACACTAACAGACGCTACGAAGAGCTAACAAAG

CAAGGAATTCTTTTTGTGGGCTCTGGTGTCTCAGGCGGTGAAGATGGTGCACGTTTTGGT

CCATCTTTAATGCCTGGTGGGTCAGCAGAAGCATGGCCGCACATCAAGAACATCTTTCAA

TCTATTGCCGCCAAATCAAACGGTGAGCCATGCTGCGAATGGGTGGGCCTGCCGGTTCT

GGTCACTATGTGAAGATGGTACACAACGGTATCGAGTACGGTGATATGCAGTTGATTTGC

GAGGCTTACGATATCATGAAACGAATTGGCCGGTTTACGGATAAAGAGATCAGTGAAGTA

TTTGACAAGTGGAACACTGGAGTTTTGGATTCTTTCTTGATTGAAATCACGAGGGACATT

TTAAAATTCGATGACGTCGACGGTAAGCCATTGGTGGAAAAAATTATGGATACTGCCGGT

CAAAAGGGTACTGGTAAATGGACTGCAATCAACGCCTTGGATTTAGGAATGCCAGTCACT

TTAATTGGGGAGGCTGTTTTCGCTCGTTGTTTGTCAGCCATAAAGGACGAACGTAAAAGA

GCTTCGAAACTTCTGGCAGGACCAACAGTACCAAAGGATGCAATACATGATAGAGAACAA

TTTGTGTATGATTTGGAACAAGCATTATACGCTTCAAAGATTATTTCATATGCTCAAGGT

TTCATGCTGATCCGCGAAGCTGCCAGATCATACGGCTGGAAATTAAACAACCCAGCTATT

GCTCTAATGTGGAGAGGTGGCTGTATAATCAGATCTGTGTTCTTAGCTGAGATTACGAAG

GCTTATAGGGACGATCCAGATTTGGAAAATTTATTATTCAACGAGTTCTTCGCTTCTGCA

GTTACTAAGGCCCAATCCGGTTGGAGAAGAACTATTGCCCTTGCTGCTACTTACGGTATT

CCAACTCCAGCTTTCTCTACTGCTTTAGCGTTTTACGACGGCTATAGATCTGAGAGGCTA

CCAGCAAACTTGTTACAAGCGCAACGTGATTATTTTGGCGCTCATACATTTAGAATTTTA

CCTGAATGTGCTTCTGCCCATTTGCCAGTAGACAAGGATATTCATATCAATTGGACTGGG

CACGGAGGTAATATATCTTCCTCAACCTACCAAGCTTAA
```

Example 25

Nucleotide and Amino Acid Sequence of S. cerevisiae Transaldolase

Transaldolase (TAL1) activity was increased in some embodiments, and in certain embodiments transaldolase activity was decreased or disrupted. Transaldolase converts sedoheptulose 7-phosphate and glyceraldehyde 3-phosphate to erythrose 4-phosphate and fructose 6-phosphate. The rationale for increasing or decreasing transaldolase activity is described herein with respect to various embodiments. The nucleotide sequence of the S. cerevisiae TAL1 gene altered to increase or decrease transaldolase activity, and the encoded amino acid sequence are shown below.

```
TAL1 nucleotide sequence
                                                  (SEQ ID NO: 426)
ATGTCTGAACCAGCTCAAAAGAAACAAAAGGTTGCTAACAACTCTCTAGAACAATTGAAA

GCCTCCGGCACTGTCGTTGTTGCCGACACTGGTGATTTCGGCTCTATTGCCAAGTTTCAA

CCTCAAGACTCCACAACTAACCCATCATTGATCTTGGCTGCTGCCAAGCAACCAACTTAC

GCCAAGTTGATCGATGTTGCCGTGGAATACGGTAAGAAGCATGGTAAGACCACCGAAGAA

CAAGTCGAAAATGCTGTGGACAGATTGTTAGTCGAATTCGGTAAGGAGATCTTAAAGATT

GTTCCAGGCAGAGTCTCCACCGAAGTTGATGCTAGATTGTCTTTTGACACTCAAGCTACC

ATTGAAAAGGCTAGACATATCATTAAATTGTTTGAACAAGAAGGTGTCTCCAAGGAAAGA

GTCCTTATTAAAATTGCTTCCACTTGGGAAGGTATTCAAGCTGCCAAAGAATTGGAAGAA

AAGGACGGTATCCACTGTAATTTGACTCTATTATTCTCCTTCGTTCAAGCAGTTGCCTGT

GCCGAGGCCCAAGTTACTTTGATTTCCCCATTTGTTGGTAGAATTCTAGACTGGTACAAA

TCCAGCACTGGTAAAGATTACAAGGGTGAAGCCGACCCAGGTGTTATTTCCGTCAAGAAA

ATCTACAACTACTACAAGAAGTACGGTTACAAGACTATTGTTATGGGTGCTTCTTTCAGA

AGCACTGACGAAATCAAAAACTTGGCTGGTGTTGACTATCTAACAATTTCTCCAGCTTTA

TTGGACAAGTTGATGAACAGTACTGAACCTTTCCCAAGAGTTTTGGACCCTGTCTCCGCT

AAGAAGGAAGCCGGCGACAAGATTTCTTACATCAGCGACGAATCTAAATTCAGATTCGAC

TTGAATGAAGACGCTATGGCCACTGAAAAATTGTCCGAAGGTATCAGAAAATTCTCTGCC

GATATTGTTACTCTATTCGACTTGATTGAAAAGAAAGTTACCGCTTAA

TAL1 amino acid sequence
                                                  (SEQ ID NO: 427)
MSEPAQKKQKVANNSLEQLKASGTVVVADTGDFGSIAKFQPQDSTTNPSLILAAAKQPTY

AKLIDVAVEYGKKHGKTTEEQVENAVDRLLVEFGKEILKIVPGRVSTEVDARLSFDTQAT

IEKARHIIKLFEQEGVSKERVLIKIASTWEGIQAAKELEEKDGIHCNLTLLFSFVQAVAC

AEAQVTLISPFVGRILDWYKSSTGKDYKGEADPGVISVKKIYNYYKKYGYKTIVMGASFR

STDEIKNLAGVDYLTISPALLDKLMNSTEPFPRVLDPVSAKKEAGDKISYISDESKFRFD

LNEDAMATEKLSEGIRKFSADIVTLFDLIEKKVTA
```

Example 26

Nucleotide and Amino Acid Sequence of S. cerevisiae Transketolase

Transketolase (TKL1 and TKL2) activity was increased in some embodiments, and in certain embodiments transaldolase activity was decreased or disrupted. Transketolase converts xylulose-5-phosphate and ribose-5-phosphate to sedoheptulose-7-phosphate and glyceraldehyde-3-phosphate. The rationale for increasing or decreasing transketolase activity is described herein with respect to various embodiments. The nucleotide sequence of the S. cerevisiae TKL1 gene altered to increase or decrease transketolase activity, and the encoded amino acid sequence are shown below.

```
TKL1 nucleotide sequence
                                                  (SEQ ID NO: 428)
ATGACTCAATTCACTGACATTGATAAGCTAGCCGTCTCCACCATAAGAATTTTGGCTGTG

GACACCGTATCCAAGGCCAACTCAGGTCACCCAGGTGCTCCATTGGGTATGGCACCAGCT

GCACACGTTCTATGGAGTCAAATGCGCATGAACCCAACCAACCCAGACTGGATCAACAGA

GATAGATTTGTCTTGTCTAACGGTCACGCGGTCGCTTTGTTGTATTCTATGCTACATTTG

ACTGGTTACGATCTGTCTATTGAAGACTTGAAACAGTTCAGACAGTTGGGTTCCAGAACA

CCAGGTCATCCTGAATTTGAGTTGCCAGGTGTTGAAGTTACTACCGGTCCATTAGGTCAA

GGTATCTCCAACGCTGTTGGTATGGCCATGGCTCAAGCTAACCTGGCTGCCACTTACAAC

AAGCCGGGCTTTACCTTGTCTGACAACTACACCTATGTTTTCTTGGGTGACGGTTGTTTG
```

-continued

```
CAAGAAGGTATTTCTTCAGAAGCTTCCTCCTTGGCTGGTCATTTGAAATTGGGTAACTTG

ATTGCCATCTACGATGACAACAAGATCACTATCGATGGTGCTACCAGTATCTCATTCGAT

GAAGATGTTGCTAAGAGATACGAAGCCTACGGTTGGGAAGTTTTGTACGTAGAAAATGGT

AACGAAGATCTAGCCGGTATTGCCAAGGCTATTGCTCAAGCTAAGTTATCCAAGGACAAA

CCAACTTTGATCAAAATGACCACAACCATTGGTTACGGTTCCTTGCATGCCGGCTCTCAC

TCTGTGCACGGTGCCCCATTGAAAGCAGATGATGTTAAACAACTAAAGAGCAAATTCGGT

TTCAACCCAGACAAGTCCTTTGTTGTTCCACAAGAAGTTTACGACCACTACCAAAGACA

ATTTTAAAGCCAGGTGTCGAAGCCAACAACAAGTGGAACAAGTTGTTCAGCGAATACCAA

AAGAAATTCCCAGAATTAGGTGCTGAATTGGCTAGAAGATTGAGCGGCCAACTACCCGCA

AATTGGGAATCTAAGTTGCCAACTTACACCGCCAAGGACTCTGCCGTGGCCACTAGAAAA

TTATCAGAAACTGTTCTTGAGGATGTTTACAATCAATTGCCAGAGTTGATTGGTGGTTCT

GCCGATTTAACACCTTCTAACTTGACCAGATGGAAGGAAGCCCTTGACTTCCAACCTCCT

TCTTCCGGTTCAGGTAACTACTCTGGTAGATACATTAGGTACGGTATTAGAGAACACGCT

ATGGGTGCCATAATGAACGGTATTTCAGCTTTCGGTGCCAACTACAAACCATACGGTGGT

ACTTTCTTGAACTTCGTTTCTTATGCTGCTGGTGCCGTTAGATTGTCCGCTTTGTCTGGC

CACCCAGTTATTTGGGTTGCTACACATGACTCTATCGGTGTCGGTGAAGATGGTCCAACA

CATCAACCTATTGAAACTTTAGCACACTTCAGATCCCTACCAAACATTCAAGTTTGGAGA

CCAGCTGATGGTAACGAAGTTTCTGCCGCCTACAAGAACTCTTTAGAATCCAAGCATACT

CCAAGTATCATTGCTTTGTCCAGACAAAACTTGCCACAATTGGAAGGTAGCTCTATTGAA

AGCGCTTCTAAGGGTGGTTACGTACTACAAGATGTTGCTAACCCAGATATTATTTTAGTG

GCTACTGGTTCCGAAGTGTCTTTGAGTGTTGAAGCTGCTAAGACTTTGGCCGCAAAGAAC

ATCAAGGCTCGTGTTGTTTCTCTACCAGATTTCTTCACTTTTGACAAACAACCCCTAGAA

TACAGACTATCAGTCTTACCAGACAACGTTCCAATCATGTCTGTTGAAGTTTTGGCTACC

ACATGTTGGGGCAAATACGCTCATCAATCCTTCGGTATTGACAGATTTGGTGCCTCCGGT

AAGGCACCAGAAGTCTTCAAGTTCTTCGGTTTCACCCCAGAAGGTGTTGCTGAAAGAGCT

CAAAAGACCATTGCATTCTATAAGGGTGACAAGCTAATTTCTCCTTTGAAAAAGCTTTC

TAA
```

TKL1 amino acid sequence
(SEQ ID NO: 429)

MTQFTDIDKLAVSTIRILAVDTVSKANSGHPGAPLGMAPAAHVLWSQMRMNPTNPDWINR

DRFVLSNGHAVALLYSMLHLTGYDLSIEDLKQFRQLGSRTPGHPEFELPGVEVTTGPLGQ

GISNAVGMAMAQANLAATYNKPGFTLSDNYTYVFLGDGCLQEGISSEASSLAGHLKLGNL

IAIYDDNKITIDGATSISFDEDVAKRYEAYGWEVLYVENGNEDLAGIAKAIAQAKLSKDK

PTLIKMTTTIGYGSLHAGSHSVHGAPLKADDVKQLKSKFGFNPDKSFVVPQEVYDHYQKT

ILKPGVEANNKWNKLFSEYQKKFPELGAELARRLSGQLPANWESKLPTYTAKDSAVATRK

LSETVLEDVYNQLPELIGGSADLTPSNLTRWKEALDFQPPSSGSGNYSGRYIRYGIREHA

MGAIMNGISAFGANYKPYGGTFLNFVSYAAGAVRLSALSGHPVIWVATHDSIGVGEDGPT

HQPIETLAHFRSLPNIQVWRPADGNEVSAAYKNSLESKHTPSIIALSRQNLPQLEGSSIE

SASKGGYVLQDVANPDIILVATGSEVSLSVEAAKTLAAKNIKARVVSLPDFFTFDKQPLE

YRLSVLPDNVPIMSVEVLATTCWGKYAHQSFGIDRFGASGKAPEVFKFFGFTPEGVAERA

QKTIAFYKGDKLISPLKKAF

Example 27

Nucleotide and Amino Acid Sequences of Additional
EDD Genes Evaluated for Activity

| Accession Number | Species | Strain Number | NUCLEOTIDE SEQUENCE | Amino Acid Sequence |
|---|---|---|---|---|
| YP_526855.1 | Saccharophagus degradans | 2-40 | ATGAATAGCGTAATCGAAGCTGTAACTCAGCGAATTATTGAGCGCAGT CGACATTCTCGTCAGGCGTATTTGAATTTAATGCGCAACACCATGGAG CAGCATCCTCCTAAAAAGCGTCTATCTTGCGGCAATTTGGCTCATGCCT ATGCAGCATGTGGTCAATCCGATAAGCAAACAATTCGTTTAATGCAAA GTGCAAACATAAGTATTACTACGGCATTTAACGATATGCTTTCGGCGC ATCAGCCTTTAGAAACATACCCTCAAATAATCAAAGAAACTGCGCGTG CAATGGGTTCAACTGCTCAAGTTGCAGGCGGCGTGCCGGCAATGTGTG ATGGTGTAACTCAAGGCCAGCCCGGTATGGAGCTGAGTTTGTTTAGCC GCGAAGTTGTAGCAATGGCTACAGCAGTAGGCCTTTCGCACAATATGT TTGATGGCAATATGTTTTTGGGTGTATGCGATAAAATTGTTCCTGGCAT GCTAATTGGCGCGTTGCAGTTTGGTCATATTCCTGGGGTGTTTGTGCCT GCCGGACCAATGCCTTCTGGTATTCCCAACAAAGAAAAGCAAAAGTT CGTCAGCAATATGCGGCGGGCATTGTGGGGAAGATAAGCTTTTAGAA ACCGAGTCGGCTTCCTATCACAGTGCAGGCACGTGTACTTTTTACGGTA CAGCGAATACAAACCAAATGATGGTTGAAATGTTGGGTGTTCAGTTGC CTGGCTCGTCGTTTGTTTACCCCGGTACTGAGTTGCGTGATGCCTTAAC GAGAGCTGCTGTTGAAAAGTTGGTAAAAATCACAGATTCAGCCGGTAA CTACCGTCCGCTCTACGAAGTCATTACGGAAAAATCCATCGTCAATTC AATAATTGGTTTGTTGGCTACCGGCGGTTCTACTAACCACACGCTACAC ATTGTTGCTGTGGCTCGCGCTGCGGGTATAGAGGTTACGTGGGCAGAT ATGGACGAGCTTTCGCGTGCTGTGCCATTACTTGCACGTGTTTACCCTA ACGGCGAAGCTGATGTTAACCAATTCCAGCAGGCTGGCGGCATGGCTT ATTTAGTAAGAGAGCTGCGCAGCGGCGGTTTGCTAAATGAAGATGTGG TTACTATTATGGGTGAGGGCCTCGAGGCCTACGAAAAAGAGCCCATGC TTAACGATAAGGGGCAGGCTGAATGGGTAAATGATGTACCTGTTAGCC GCGACGATACCGTTGTGCGTCCAGTTACCTCGCCTTTCGATAAAGAGG GTGGGTTGCGTCTACTCAAGGGTAACTTAGGGCAGGGCGTAATCAAAA TTTCTGCGGTAGCGCCAGAAAATCGCGTTGTTGAGGCCCCATGTATTGT ATTCGAGGCCCAAGAAGAGCTAATAGCTGCGTTTAAGCGTGGTGAGCT CGAAAAAGACTTTGTTGCGGTAGTGCGCTTCCAAGGGCCTTCTGCCAA TGGCATGCCAGAACTTCATAAAATGACCCCGCCTTTAGGTGTGCTTCA AGATAAGGGTTTCAAGGTAGCGTTAGTTACCGATGGCAGAATGTCTGG TGCATCTGGTAAAGTGCCGGCCGGTATACACTTGTCGCCAGAAGCGAG TAAGGGTGGCCTGTTGAATAAGCTGCGCACGGGTGATGTGATTCGCTT CGATGCCGAAGCGGGCGTTATTCAAGCGCTTGTTAGTGATGAAGAGTT AGCTGCGCGTGAGCCAGCTGTGCAACCGGTCGTGGAGCAGAACCTCGG ACGCTCTCTGTTTGGTGGTTTGCGCGATTTGGCTGGTGTATCGCTACAA GGCGGAACAGTTTTCGATTTTGAAAGAGAGTTTGGCGAAAAATAG (SEQ ID NO: 430) | MNSVIEAVTQRIIERSR HSRQAYLNLMRNTME QHPPKKRLSCGNLAHA YAACGQSDKQTIRLMQ SANISITTAFNDMLSAH QPLETYPQIIKETARAM GSTAQVAGGVPAMCD GVTQGQPGMELSLFSR EVVAMATAVGLSHNM FDGNMFLGVCDKIVPG MLIGALQFGHIPGVFVP AGPMPSGIPNKEKAKV RQQYAAGIVGEDKLLE TESASYHSAGTCTFYGT ANTNQMMVEMLGVQL PGSSFVYPGTELRDALT RAAVEKLVKITDSAGN YRPLYEVITEKSIVNSII GLLATGGSTNHTLHIVA VARAAGIEVTWADMD ELSRAVPLLARVYPNGE ADVNQFQQAGGMAYL VRELRSGGLLNEDVVTI MGEGLEAYEKEPMLND KGQAEWVNDVPVSRD DTVVRPVTSPFDKEGGL RLLKGNLGQGVIKISAV APENRVVEAPCIVFEAQ EELIAAFKRGELEKDFV AVVRFQGPSANGMPEL HKMTPPLGVLQDKGFK VALVTDGRMSGASGKV PAGIHLSPEASKGGLLN KLRTGDVIRFDAEAGVI QALVSDEELAAREPAV QPVVEQNLGRSLFGGL RDLAGVSLQGGTVFDF EREFGEK (SEQ ID NO: 431) |
| NP_642389.1 | Xanthomonas axonopodis | Pv. citri str. 306 | ATGAGCCTGCATCCGAATATCCAAGCCGTCACCGACCGTATCCGCAAG CGCAGTGCTCCCTCGCGCGCGGCGTATCTGGCCGGCCTCGATGCCGCC CTGCGTGAGGGCCCGTTCCGTAGCCGGTTGAGCTGCGGCAATCTCGCG CATGGCTTCGCTGCGTCCGAGCCGGGCGACAAATCGCGCCTGCGCGGT GCGGCCACGCCGAACCTGGGCATCATCACTGCCTATAACGACATGTTG TCGGCACATCAGCCGTTCGAGCACTACCCGCAGCTGATCCGCGAAACC GCGCGCTCACTTGGCGCCACTGCGCAGGTGGCCGGCGGCGTGCCGGCG ATGTGTGACGGCGTGACCCAGGGCCGCGCCGGCATGGAGCTGTCGCTG TTCTCGCGCGACAACATCGCTCAGGCTGCGGCCATTGGCCTGAGCCAT GACATGTTCGACAGCGTGGTGTACCTGGGGGTGTGCGACAAGATCGTG CCGGGTCTGCTGATCGGTGCGGTGGCGTTTGCCTTTGCCGGCGATCT TCATGCCGGCTGGTCCGATGACCCCGGGCATCCCGAACAAGCAGAAAG CCGAAGTCCGCGAACGCTACGCCGCTGGCGAAGCCACCCGCGCCGAAT TGCTGGAGGCCGAATCCTCGTCTTATCACTCGCCCGGCACCTGCACCTT TTACGGCACGGCGAACTCCAACCAGGTGTTGCTCGAAGCGATGGGCGT GCAGTTGCCCGGCGCCTCGTTCGTCAATCCGGAGCTGCCGCTGCGCGA TGCACTGACCCGCGAAGGCACCGCACGCGCATTGGCGATCTCCGCGCT GGGCGATGACTTCCGCCCGTTCGGTCGTTTGATCGACGAACGGGCCAT CGTCAATGCCGTGGTCGCGCTGATGGCGACCGGCGGTTCGACCAACCA CACCATCCACTGGATCGCGGTGGCGCGTGCGGCCGGCATCGTGTTGAC CTGGGACGACATGGATCTGATCTCGCAGACCGTGCCGCTGTTGACACG CATCTACCCGAACGGCGAAGCCGACGTGAACCGCTTCCAGGCCGCAGG CGGCACGGCGTTCGTGTTCCGCGAATTGATGGACGCCGGCTACATGCA CGACGACCTGCCGACCATCGTCGAAGGCGGCATGCGCGCGTACGTCAA CGAACGCGCCTGCAGGACGGCAAGGTGACCTACGTGCCCGGCACCG CGACCACTGCCGACGACAGCGTCGCGCGTCCGGTCAGCGATGCATTCG AATCACAAGGCGCCTGCGCCTGCTGCGCGGCAACCTCGGCCGCTCGT TGATCAAGCTGTCGGCGGTCAAGCCGCAGCACCGCAGCATCCAAGCGC CAGCGGTGGTGATCGACACCCCGCAAGTGCTCAACAAACTGCATGCGG CGGGCGTACTGCCGCACGATTTCGTGGTGGTACTGCGCTATCAGGGCC | MSLHPNIQAVTDRIRKR SAPSRAAYLAGIDAALR EGPFRSRLSCGNLAHGF AASEPTDKSRLRGAATP NLGIITAYNDMLSAHQP FEHYPQLIRETARSLGA TAQVAGGVPAMCDGV TQGRAGMELSLFSRDNI AQAAAIGLSHDMFDSV VYLGVCDKIVPGLLIGA LAFGHLPAIFMPAGPMT PGIPNKQKAEVRERYA AGEATRAELLEAESSSY HSPGTCTFYGTANSNQ VLLEAMGVQLPGASFV NPELPLRDALTREGTAR ALAISALGDDFRPFGRLI DERAIVNAVVALMATG GSTNHTIHWIAVARAA GIVLTWDDMDLISQTVP LLTRIYPNGEADVNRFQ AAGTAFVFRELMDAG YMHDDLPTIVEGGMRA YVNEPRLQDGKVTYVP GTATTADDSVARPVSD AFESQGGLRLLRGNLG RSLIKLSAVKPQHRSIQ APAVVIDTPQVLNKLH AAGVLPHDFVVVLRYQ GPRANGMPELHSMAPL |

-continued

| Accession Number | Species | Strain Number | NUCLEOTIDE SEQUENCE | Amino Acid Sequence |
|---|---|---|---|---|
| | | | CACGCGCAAACGGCATGCCGGAGCTGCATTCGATGGCGCCGCTACTGG<br>GCCTGCTGCAGAACCAGGGCCGGCGCGTGGCGTTGGTCACCGACGGCC<br>GTCTGTCCGGCGCCTCGGGCAAGTTCCCGGCGGCGATCCACATGACCC<br>CGGAAGCCGCACGCGGCGGCCCGATCGGGCGCGTACGCGAAGGCGAC<br>ATCGTGCGACTGGACGGCGAAGCCGGCACCTTGGAAGTGCTGGTTTCG<br>GCCGAAGAATGGGCATCGCGCGAGGTCGCACCGAACACTGCCGTTGGC<br>CGGCAACGACCTGGGCCGCAACCTGTTCGCCATCAACCGCCAGGTGGT<br>TGGCCCGGCCGACCAGGGCGCGATTTCCATTTCCTGCGGCCCGACCCA<br>TCCGGACGGTGCGCTGTGGAGCTACGACGCCGAGTACGAACTCGGTGC<br>CGATGCAGCTGCAGCCGCCGCGCCGCACGAGTCCAAGGACGCCTGA<br>(SEQ ID NO: 432) | LGLLQNQGRRVALVTD<br>GRLSGASGKFPAAIHMT<br>PEAARGGPIGRVREGDI<br>VRLDGEAGTLEVLVSA<br>EEWASREVAPNTALAG<br>NDLGRNLFAINRQVVG<br>PADQGAISISCGPTHPD<br>GALWSYDAEYELGAD<br>AAAAAAPHESKDA<br>(SEQ ID NO: 433) |
| NP_791117.1 | Pseudomonas syringae | Pv. tomato str. DC3000 | ATGCATCCCCGCGTCCTTGAAGTAACCGAGCGGCTCATTGCTCGCAGT<br>CGCGATACCCGTCAGCGCTACCTTCAATTGATTCGAGGCGCAGCAGC<br>GATGGCCCGATGCGCGGCAAGCTTCAATGTGCCAACTTTGCTCACGGC<br>GTCGCCGCCTGCGGACCGGAGGACAAGCAAAGCCTGCGTTTGATGAAC<br>GCCGCCAACGTGGCAATCGTCTCTTCCTACAATGAAATGCTCTCGGCG<br>CATCAGCCCTACGAGCACTTTCCTGCACAGATCAAACAGGCGTTACGT<br>GACATTGGTTCGGTCGGTCAGTTTGCCGGCGGCGTGCCTGCCATGTGC<br>GATGGCGTGACTCAGGGTGAGCCGGGCATGGAACTGGCCATTGCCAGC<br>CGCGAAGTGATTGCCATGTCCACGGCAATTGCCTTGTCACACAATATG<br>TTCGACGCCGCCATGATGCTGGGTATCTGCGACAAGATCGTCCCCGGC<br>CTGATGATGGGGCGTTGCGTTTCGGTCATCGTGCCGACCATCTTCGTG<br>CCGGGCGGGCCGATGGTGTCAGGTATCTCCAACAAGGAAAAAGCCGAC<br>GTACGGCAGCGTTACGCTGAAGGCAAGGCCAGCCGTGAAGAGCTGCT<br>GGACTCGGAAATGAAGTCCTATCACGGGCCCGGGAACCTGCACGTTCTA<br>CGGCACCGCCAACACCAATCAGTTGGTGATGGAAGTCATGGGCATGCA<br>CCTTCCCGGTGCCTCGTTCGTCAATCCCTACACCACTGCGTGATGCG<br>CTGACAGCTGAAGCGGCTCGTCAGGTCACGCGTCTGACCATGCAAAGC<br>GGCAGTTTCATGCCGATTGGTGAAATCGTCGACGAGCGCTCGCTGGTC<br>AATTCCATCGTTGCGCTGCACGCCACCGGCGGCTCGACCAACCACACG<br>CTGCACATGCCGGCGATTGCTCAGGCTGCGGGTATTCAGCTGACCTGG<br>CAGGACATGGCCGACCTCTCCGAAGTGGTGCCGACCCTCAGTCACGTC<br>TACCCCAACGGCAAGGCCGACATCAACCATTTCCAGGCCGCAGGCGGC<br>ATGTCTTCCTGATTCGCGAGCTGCTGGCAGCCGGTCTGCTGCACGAA<br>AACGTTAACACCGTGGCCGGTTATGGCGTGAGCCGCTACACCAAAGAG<br>CCATTCCTGGAGGATGGCAAACTGGTCTGGCGTGAAGGCCCGCTGGAC<br>AGCCTGGATGAAAACATCCTGCGCCCGGTGGCGCGTCCGTTCTCCCCT<br>GAAGGCGGTTTGCGGGTCATGGAAGGCAACCTGGGTCGCGGTGTCATG<br>AAAGTATCGGCCGTTGCGCTGGAGCATCAGATTGTCGAAGCGCCAGCC<br>CGAGTGTTTCAGGATCAGAAGGAGCTGGCCGATGCGTTCAAGGCCGGC<br>GAGCTGGAATGTGATTTCGTCGCCGTCATGCGTTTTCAGGGCCCGCGCT<br>GCAACGGCATGCCCGAACTGCACAAGATGACCCCGTTTCTGGGCGTGC<br>TGCAGGATCGTGGTTTCAAAGTGGCGCTGGTCACCGATGGACGGATGT<br>CGGGCGCCTCAGGCAAGATTCCGGCGGCGATTCACGTCTGCCCGGAAG<br>CGTTCGATGGTGGCCCGTTGGCACTGGTACGCGACGGCGATGTGATCC<br>GCGTGGATGGCGTAAAAGGCACGTTACAAGTGCTGGTCGAAGCGTCA<br>GAATTGGCCGCCCGAGAACCGGCCATCAACCAGATCGACAACAGTGTC<br>GGCTGCGGTCGCGAGCTTTTTGGATTCATGCGCATGGCCTTCAGCTCCG<br>CAGAGCAAGGCGCCAGCGCCTTTACCTCTAGTCTGGAGACGCTCAAGT<br>GA (SEQ ID NO: 434) | MHPRVLEVTERLIARSR<br>DTRQRYLQLIRGAASD<br>GPMRGKLQCANFAHG<br>VAACGPEDKQSLRLMN<br>AANVAIVSSYNEMLSA<br>HQPYEHFPAQIKQALRD<br>IGSVGQFAGGVPAMCD<br>GVTQGEPGMELAIASRE<br>VIAMSTAIALSHNMFDA<br>AMMLGICDKIVPGLMM<br>GALRFGHLPTIFVPGGP<br>MVSGISNKEKADVRQR<br>YAEGKASREELLDSEM<br>KSYHGPGTCTFYGTAN<br>TNQLVMEVMGMHLPG<br>ASFVNPYTPLRDALTAE<br>AARQVTRLTMQSGSFM<br>PIGEIVDERSLVNSIVAL<br>HATGGSTNHTLHMPAI<br>AQAAGIQLTWQDMAD<br>LSEVVPTLSHVYPNGK<br>ADINHFQAAGGMSFLIR<br>ELLAAGLLHENVNTVA<br>GYGLSRYTKEPFLEDG<br>KLVWREGPLDSLDENIL<br>RPVARPFSPEGGLRVME<br>GNLGRGVMKVSAVAL<br>EHQIVEAPARVFQDQK<br>ELADAFKAGELECDFV<br>AVMRFQGPRCNGMPEL<br>HKMTPFLGVLQDRGFK<br>VALVTDGRMSGASGKI<br>PAAIHVCPEAFDGGPLA<br>LVRDGDVIRVDGVKGT<br>LQVLVEASELAAREPAI<br>NQIDNSVGCGRELFGF<br>MRMAFSSAEQGASAFT<br>SSLETLK (SEQ ID NO: 435) |
| YP_261706.1 | Pseudomonas fluorescens | Pf-5 | ATGCATCCCCGCGTTCTTGAGGTCACCGAACGGCTTATCGCCCGTAGTC<br>GCGCCACTCGCCAGGCCTATCTCGCGCTGATCCGCGATGCCGCCAGCG<br>ACGGCCCGCAGCGGGGCAAGCTGCAATGTGCGAACTTCGCCACGGC<br>GTGGCCGGTTGCGGCACCGACGACAAGCACAACCTGCGGATGATGAA<br>TGCGGCCAACGTGGCAATTGTTTCGTCATATAACGACATGTTGTCGGC<br>GCACCAGCCTTACGAGGTGTTCCCCGAGCAGATCAAGCGCGCCCTGCG<br>CGAGATCGGCTCGGTGGGCCAGTTCGCCGGCGGCACCCCGGCCATGTG<br>CGATGGCGTGACCCAGGGCGAGGCCGGTATGGAACTGAGCCTGCCGA<br>GCCGTGAAGTGATCGCCCTGTCTACGGCGGTGGCCCTCTCTCACAACA<br>TGTTCGATGCCGCGCTGATGCTGGGGATCTGCGACAAGATTGTCCCG<br>GGTTGATGATGGGCGCTCTGCGCTTCGGTCACCTGCCGACCATCTTCGT<br>TCCGGGCGGGCCCATGGTCTCGGGCATTTCCAACAAGCAGAAAGCCGA<br>CGTGCGCCAGCGTTACGCCGAAGGCAAGGCCAGCCGCGAGGAACTGC<br>TGGAGTCGGAAATGAAGTCCTACCACAGCCCCGGCACCTGCACTTTCT<br>ACGGCACCGCCAACACCAACCAGTTGCTGATGGAAGTGATGGGCCTGC<br>ACCTGCCGGGCGCCTCTTGTCAACCCCAATACGCCGCTGCGCGACG<br>CCCTGACCCATGAGGCGGCGCAGCAGGTCACGCGCCTGACCAAGCAG<br>AGCGGGGCCTTCATGCCGATTGGCGAGATCGTCGACGAGCGCGTGCTG<br>GTCAACTCCATCGTTGCCCTGCACGCCACGGGCGGCTCCACCAACCAC<br>ACCCTGCACATGCCGGCGATTGCCCAGGCGGCAGGCATCCAGCTGACC<br>TGGCAGGACATGGCCGACCTCTCCGAGGTGGTGCCGACCCTGTCCCAC<br>GTCTATCCCAACGGCAAGGCCGATATCAACCACTTCCAGGCGGCGGGC<br>GGCATGTCTTTCCTGATCCGCGAGCTGCTGGAAGCCGGCCTGCTCCAC<br>GAAGACGTCAATACCGTGGCCGGCCGCGGCCTGAGCCGCTATACCCAG<br>GAACCCTTCCTGGACAACGGCAAGCTGGTGTGGCGCGACGGCCCGATT | MHPRVLEVTERLIARSR<br>ATRQAYLALIRDAASD<br>GPQRGKLQCANFAHGV<br>AGCGTDDKHNLRMMN<br>AANVAIVSSYNDMLSA<br>HQPYEVFPEQIKRALRE<br>IGSVGQFAGGTPAMCD<br>GVTQGEAGMELSLPSR<br>EVIALSTAVALSHNMFD<br>AALMLGICDKIVPGLM<br>MGALRFGHLPTIFVPGG<br>PMVSGISNKQKADVRQ<br>RYAEGKASREELLESE<br>MKSYHSPGTCTFYGTA<br>NTNQLLMEVMGLHLPG<br>ASFVNPNTPLRDALTHE<br>AAQQVTRLTKQSGAFM<br>PIGEIVDERVLNSIVAL<br>HATGGSTNHTLHMPAI<br>AQAAGIQLTWQDMAD<br>LSEVVPTLSHVYPNGK<br>ADINHFQAAGGMSFLIR<br>ELLEAGLLHEDVNTVA<br>GRGLSRYTQEPFLDNG<br>KLVWRDGPIESLDENIL |

| Accession Number | Species | Strain Number | NUCLEOTIDE SEQUENCE | Amino Acid Sequence |
|---|---|---|---|---|
| | | | GAAAGCCTGGACGAAAACATCCTGCGCCCGGTGGCCCGGGCGTTCTCT GCGGAGGGCGGCTTGCGGGTCATGAAGGCAACCTCGGTCGCGGCGT GATGAAGGTTTCCGCCGTGGCCCCGGAGCACCAGATCGTCGAGGCCCC GGCCGTGGTGTTCCAGGACCAGCAGGACCTGGCCGATGCCTTCAAGGC CGGCCTGCTGGAGAAGGACTTCGTCGCGGTGATGCGCTTCCAGGGCCC GCGCTCCAACGGCATGCCCGAGCTGCACAAGATGACCCCCTTCCTCGG GGTGCTGCAGGACCGCGGCTTCAAGGTGGCGCTGGTCACCGACGGGGC CATGTCCGGCGCTTCGGGCAAGATTCCGGCAGCGATCCATGTCAGCCC CGAAGCCCAGGTGGGTGGCGCGCTGGCCCGGGTGCTGGACGGCGATA TCATCCGAGTGGATGGCGTCAAGGGCACCCTGGAGCTTAAGGTAGACG CCGCAGAATTCGCCGCCCGGGAGCCGGCCAAGGGCCTGCTGGGCAAC AACGTTGGCACCGGCCGCGAACTCTTCGCCTTCATGCGCATGGCCTTC AGCTCGGCAGAGCAGGGCGCCAGCGCCTTTACCTCTGCCCTGGAGACG CTCAAGTGA (SEQ ID NO: 436) | RPVARAFSAEGGLRVM EGNLGRGVMKVSAVAP EHQIVEAPAVVFQDQQ DLADAFKAGLLEKDFV AVMRFQGPRSNGMPEL HKMTPFLGVLQDRGFK VALVTDGRMSGASGKI PAAIHVSPEAQVGGAL ARVLDGDIIRVDGVKG TLELKVDAAEFAAREP AKGLLGNNVGTGRELF AFMRMAFSSAEQGASA FTSALETLK (SEQ ID NO: 437) |
| ZP_0359148.1 | Bacillus subtilis | subtilis str. 168 | ATGGCAGAATTACGCAGTAATATGATCACACAAGGAATCGATAGAGCT CCGCACCGCAGTTTGCTTCGTGCAGCAGGGGTAAAAGAAGAGGATTTC GGCGAAGCCGTTTTATTCGTGTGTAATTCATACATTGATATCGTTCCCG GTCATGTTCACTTGCAGGAGTTTGGGAAAATCGTAAAAGAAGCAATCA GAGAAGCAGGGGGCGTTCCGTTTGAATTTAATACCATTGGGGTAGATG ATGGCATCGCAATGGGGCATATCGGTATGAGATATTCGCTGCCAAGCC GTGAAATTATCGCAGACTCTGTGGAAACGGTTGTATCCGCACACTGGT TTGACGGAATGGTCTGTATTCCGAACTGCGACAAAATCACACCGGGAA TGCTTATGGCGGCAATGCGCATCAACATTCCGACGATTTTTGTCAGCG GCGGACCGATGGCGGCAGGAAGAACAAGTTACGGGCGAAAAATCTCC CTTTCCTCAGTATTCGAAGGGTAGGCGCCTACCAAGCAGGGAAAATC AACGAAAACGAGCTTCAAGAACTAGAGCAGTTCGGATGCCCAACGTG CGGGTCTTGCTCAGGCATGTTTACGGCGAACTCAATGAACTGTCTGTC AGAAGCACTTGGTCTTGCTTTGCCGGGTAATGGAACCATTCTGGCAAC ATCTCCGGAACGCAAAGAGTTTGTGAGAAAATCGGCTGCGCAATTAAT GGAAACGATTCGCAAAGATATCAAACCGCGTGATATTGTTACAGTAAA AGCGATTGATAACGCGTTTGCACTCGATATGGCGCTCGGAGGTTCTAC AAATACCGTTCTTCATACCCTTGCCCTTGCAAACGAAGCCGGCGTTGA ATACTCTTTAGAACGCATTAACGAAGTCGCTGAGCGCGTGCCGCACTT GGCTAAGCTGGCGCCTGCATCGGATGTTTATTGAAGATCTTCACGA AGCGGCGGCGTTTCAGCGGCTCTGAATGAGCTTTCGAAGAAAGAAG GAGCGCTTCATTTAGATGCGCTGACTGTTACAGGAAAAACTCTTGGAG AAACCATTGCCGGACATGAAGTAAAGGATTATGACGTCATTCACCCGC TGGATCAACCATTCACTGAAAAGGGAGGCCTTGCTGTTTTATTCGGTA ATCTAGCTCCGGACGGCGCTATCATTAAAACAGGCGGCGTACAGAATG GGATTACAAGACACGAAGGGCCGGCTGTCGTATTCGATTCTCAGGACG AGGCGCTTGACGGCATTATCAACCGAAAAGTAAAAGAAGGCGACGTT GTCATCATCAGATACGAAGGCCCAAAAGGCGGACCTGGCATGCCGGA AATGCTGGCGCCAACATCCCAAATCGTTGGAATGGGACTCGGGCCAAA AGTGGCATTGATTACGGACGGACGTTTTTCCGGAGCCTCCCGTGGCCT CTCAATCGGCCACGTATCACCTGAGGCCGCTGAGGGCGGGCCGCTTGC CTTTGTTGAAAACGGAGACCATATTATCGTTGATATTGAAAAACGCAT CTTGGATGTACAAGTGCCAGAAGAAGAGTGGGAAAAACGAAAAGCGA ACTGGAAAGGTTTTGAACCGAAAGTGAAAACCGGCTACCTGGCACGTT ATTCTAAACTTGTGACAAGTGCCAACACCGGCGGTATTATGAAAATCT AG (SEQ ID NO: 438) | MAELRSNMITQGIDRAP HRSLLRAAGVKEEDFG KPPIAVCNSYIDIVPGHV HLQEFGKIVKEAIREAG GVPFEFNTIGVDDGIAM GHIGMRYSLPSREIIADS VETVVSAHWFDGMVCI PNCDKITPGMLMAAMR INIPTIFVSGGPMAAGRT SYGRKISLSSVFEGVGA YQAGKINENELQELEQF GCPTCGSCSGMFTANS MNCLSEALGLALPGNG TILATSPERKEFVRKSA AQLMETIRKDIKPRDIV TVKAIDNAFALDMALG GSTNTVLHTLALANEA GVEYSLERINEVAERVP HLAKLAPASDVFIEDLH EAGGVSAALNELSKKE GALHLDALTVTGKTLG ETIAGHEVKDYDVIHPL DQPFTEKGGLAVLFGN LAPDGAIIKTGGVQNGI TRHEGPAVVFDSQDEA LDGIINRKVKEGDVVIIR YEGPKGGPGMPEMLAP TSQIVGMGLGPKVALIT DGRFSGASRGLSIGHVS PEAAEGGPLAFVENGD HIIVDIEKRILDVQVPEE EWEKRKANWKGFEPK VKTGYLARYSKLVTSA NTGGIMKI (SEQ ID NO: 439) |
| YP_091897.1 | Bacillus licheniformis | ATCC 14580 | ATGACAGGTTTACGCAGTGACATGATTACAAAAGGGATCGACAGAGC GCCGCACCGCAGTTTGCTGCGCGCGGCTGGGGTAAAAGAAGAGGACTT CGGCGAAGCCGTTTTATTGCGTGTTGCAACTCATACATCGATATCGTACCG GGTCATGTCCATTTGCAGGAGTTTGGAAAAATCGTCAAAGAGGCGATC AGAGAGGCCGGCGTGTTCCGTTTGAATTTAATACAATCGGGGTCGAC GACGGAATTGCGATGGGGCACATCGGAATGAGGTATTCTCTCCCGAGC CGCGAAATCATCGCAGATTCAGTGGAAACGGTTGTATCGGCGCACTGG TTTGACGGAATGGTATGTATTCCAAACTGTGATAAAATCACACCGGGC ATGATCATGGCGGCAATGCGGATCAACATTCCGACCGTGTTTGTCAGC GGGGGGCCGATGGAAGCGGGAAGAACGAGCGACGGACGAAAAATCTC GCTTTCCTCTGTATTTGAAGGCGTTGGCGCTTATCAATCAGGCAAAATC GATGAGAAAGGACTTGAGGAGCTTGAACAGTTCGGCTGTCCGACTTGC GGATCATGCTCGGGCATGTTTACGGCGAACTCGATGAACTGTCTTTCTG AAGCTCTTGGCATCGCCATGCCGGGCAACGGCACCATTTTGGCGACAT CGCCCGACCGCAGGGAATTTGCCAAACAGTCGGCCCGCCAGCTGATGG AGCTGATCAAGTCGGATATCAAACCGCGCGACATCGTGACCGAAAAA GCGATCGACAACGCGTTCGCTTTAGACATGGCGCTCGGCGGATCAACG AATACGATCCTTCATACGCTTGCGATCGCCAATGAAGCGGGTGTAGAC TATTCGCTTGAACGGATCAATGAGGTAGCGGCAAGGGTTCCGCATTTA TCGAAGCTTGCACCGGCTTCCGATGTGTTTATTGAAGATTTGCATGAAG GGGGTTCTGCCGTGCTTAACGAGCTGTCGAAAAAGAAGGC AGGAGGCGTATCGGCAGTCTTAAACGAGCTGTCGAAAAAGAAGGC GCGCTTCACTTGGATACGCTGACTGTAACGGGGAAAACGCTTGGCGAA AATATTGCCGGACGCGAAGTGAAAGATTACGAGGTCATTCATCCGATC GATCAGCCGTTTTCAGAGCAAGGCGGACTCGCCGTCCTGTTCGGCAAC CTGGCTCCTGACGGTGCGATCATTAAAACGGGCGGCGTCCAAGACGGG | MTGLRSDMITKGIDRAP HRSLLRAAGVKEEDFG KPPIAVCNSYIDIVPGHV HLQEFGKIVKEAIREAG GVPFEFNTIGVDDGIAM GHIGMRYSLPSREIIADS VETVVSAHWFDGMVCI PNCDKITPGMIMAAMRI NIPTVFVSGGPMEAGRT SDGRKISLSSVFEGVGA YQSGKIDEKGLEELEQF GCPTCGSCSGMFTANS MNCLSEALGIAMPGNG TILATSPDRREFAKQSA RQLMELIKSDIKPRDIVT EKAIDNAFALDMALGG STNTILHTLAIANEAGV DYSLERINEVAARVPHL SKLAPASDVFIEDLHEA GGVSAVLNELSKKEGA LHLDTLTVTGKTLGENI AGREVKDYEVIHPIDQP FSEQGGLAVLFGNLAP DGAIIKTGGVQDGITRH EGPAVVFDSQEEALDGI |

-continued

| Accession Number | Species | Strain Number | NUCLEOTIDE SEQUENCE | Amino Acid Sequence |
|---|---|---|---|---|
| | | | ATTACCCGCCATGAAGGACCTGCGGTTGTCTTTGATTCACAGGAAGAA GCGCTTGACGGCATCATCAACCGTAAAGTAAAAGCGGGAGATGTCGTC ATCATCCGCTATGAAGGCCCTAAAGGCGGACCGGGAATGCCTGAAATG CTTGCGCCGACTTCACAGATCGTCGGAATGGGCCTCGGCCCGAAAGTC GCCTTGATTACCGACGGCCGTTTTCAGGAGCCGTCTCCCGCGGTCTTTGA TCGGCCACGTTTCACCGGAAGCAGCCGAAGGCGGCCCGCTTGCTTTCG TAGAAAACGGCGACCATATCGTTGTCGATATCGAAAGCGGATTTTAA ACATCGAAATCTCCGATGAGGAATGGGAAAAAAGAAAAGCAAACTGG CCCGGCTTTGAACCGAAAGTGAAAACGGGCTATCTCGCCAGGTATTCA AAGCTTGTGACATCTGCCAATACCGGCGGCATTATGAAAATCTAG (SEQ ID NO: 440) | INRKVKAGDVVIIRYEG PKGGPGMPEMLAPTSQI VGMGLGPKVALITDGR FSGASRGLSIGHVSPEA AEGGPLAFVENGDHIV VDIEKRILNIEISDEEWE KRKANWPGFEPKVKTG YLARYSKLVTSANTGGI MKI (SEQ ID NO: 441) |
| NP_0718074.1 | Sewanella oneidensis | MR-1 | ATGCACTCAGTCGTTCAATCTGTTACTGACAGAATTATTGCCCGTAGCA AAGCATCTCGTGAAGCATACCTTGCTGCGTTAAACGATGCCCGTAACC ATGGTGTACACCGAAGTTCCTTAAGTTGCGGTAACTTAGCCCACGGTTT TGCCGGCTTGTAATCCCGATGACAAAAATGCATTGCGTCAATTGACGAA GGCCAATATTGGGATTATCACCGCATTCAACGATATGTTATCTGCACA CCAACCCTATGAAACCTATCCTGATTTTGCTGAAAAAAGCCTGTCAGGA AGTCGGTAGTGTTGCGCAGGTGGCTGGCGGTGTTCCCGCCATGTGTGA CGGCGTGACTCAAGGTCAGCCCGGTATGGAATTGAGCTTACTGAGCCG TGAAGTGATTGCGATGGCAACCGCGGTTGGCTTATCACACAATATGTT TGATGGAGCCTTACTCCTCGGTATTTGCGATAAAATTGTACCGGGTTTA CTGATTGGTGCCTTAAGTTTTGGCCATTTACCTATGTTGTTTGTGCCCG CAGGCCCAATGAAATCGGGTATTCCTAATAAGGAAAAAGCTCGCATTC GTCAGCAATTTGCTCAAGGTAAGGTCGATAGAGCACAACTGCTCGAAG CGGAAGCCCAGTCTTACCACAGTGCGGGTACTTGTACCTTCTATGGTA CCGCTAACTCGAACCAACTGATGCTCGAAGTGATGGGGCTGCAATTGC CGGGTTCATCTTTTGTGAATCCAGACGATCCACTGCGCGAAGCCTTAA ACAAAATGGCGGCCAAGCAGGTTTGTCGTTTAACTGAACTAGGCACTC AATACAGTCCGATTGGTGAAGTCGTTAACGAAAAATCGATAGTGAATG GTATTGTTGCATTGCTCGCGACGGGTGGTTCAACAAACTTAACCATGC ACATTGTGGCGGCGGCCCGTGCTGCAGGTATTATCGTCAACTGGGATG ACTTTTCGGAATTATCCGATGCGGTGCCTTTGCTGGCACGTGTTTATCC AAACGGTCATGCGGATATTAACCATTTCCACGCTGCGGGTGGTATGGC TTTCCTTATCAAAGAATTACTCGATGCAGGTTTGCTGCATGAGGATGTC AATACTGTCGCGGGTTATGGTCTGCGCCGTTACACCAAGAGCCTAAA CTGCTTGATGGCGAGCTGCGCTGGGTCGATGGCCCAACAGTGAGTTTA GATACCGAAGTATTAACCTCTGTGGCAACACCATTCCAAAACAACGGT GGTTTAAAGCTGCTGAAGGGTAACTTAGGCCGCGCTGTGATTAAAGTG TCTGCCGTTCAGCCACAGCACCGTGTGGAAGCGCCCGCAGTGGTG ATTGACGATCAAAACAAACTCGATGCGTTATTTAAATCCGGCGCATTA GACAGGGATTGTGTGGTGGTGGTGAAAGGCCAAGGGCCGAAAGCCAA CGGTATGCCAGAGCTGCATAAACTAACGCCGCTGTTAGGTTCATTGCA GGACAAAGGCTTTAAAGTGGCACTGATGACTGATGGTCGTATGTCGGG CGCATCGGGCAAAGTACCTGCGGCGATTCATTTAACCCCTGAAGCGAT TGATGGCGGGTTAATTGCAAAGGTACAAGACGGCGATTTAATCCGAGT TGATGCACTGACCGGCGAGCTGAGTTTATTAGTCTCTGACACCGAGCT TGCCACCAGAACTGCCACTGAAATTGATTTACGCCATTCTCGTTATGGC ATGGGGCGTGAGTTATTGGAGTACTGCGTTCAAACTTAAGCAGTCCT GAAACCGGTGCGCGTAGTACTAGCGCCATCGATGAACTTTACTAA (SEQ ID NO: 442) | MHSVVQSVTDRIIARSK ASREAYLAALNDARNH GVHRSSLSCGNLAHGF AACNPDDKNALRQLTK ANIGIITAFNDMLSAHQ PYETYPDLLKKACQEV GSVAQVAGGVPAMCD GVTQGQPGMELSLLSR EVIAMATAVGLSHNMF DGALLLGICDKIVPGLLI GALSFGHLPMLFVPAGP MKSGIPNKEKARIRQQF AQGKVDRAQLLEAEAQ SYHSAGTCTFYGTANS NQLMLEVMGLQLPGSS FVNPDDPLREALNKMA AKQVCRLTELGTQYSPI GEVVNEKSIVNGIVALL ATGGSTNLTMHIVAAA RAAGIIVNWDDFSELSD AVPLLARVYPNGHADI NHFHAAGGMAFLIKEL LDAGLLHEDVNTVAGY GLRRYTQEPKLLDGEL RWVDGPTVSLDTEVLT SVATPFQNNGGLKLLK GNLGRAVIKVSAVQPQ HRVVEAPAVVIDDQNK LDALFKSGALDRDCVV VVKGQGPKANGMPEL HKLTPLLGSLQDKGFK VALMTDGRMSGASGK VPAAIHLTPEAIDGGLIA KVQDGDLIRVDALTGE LSLLVSDTELATRTATEI DLRHSRYGMRELFGV LRSNLSSPETGARSTSAI DELY (SEQ ID NO: 443) |
| YP_190870.1 | Gluconobacter oxydans | 621H | ATGTCTCTGAATCCCGTCGTCGAGAGCGTGACTGCCCGTATCATCGAG CGTTCGAAAGTCTCCCGTCGCCGGTATCTCGCCCTGATGGAGCGCAAC CGCGCCAAGGGTGTGCTCCGGCCCAAGCTGGCCTGCGGTAATCTGGCG CATGCCATCGCAGCGTCCAGCCCCGACAAGCCGGATCTGATGCGTCCC ACCGGGACCAATATCGGCGTGATCACGACCTATAACGACATGCTCTCG GCGCATCAGCCGTATGGCCGCTATCCCGAGCAGATCAAGCTGTTCGCC CGTGAAGTCGGTGCGCAGGTCGCCCAGGTTGCAGGCGGCGCACCAGCGT GTGTGATGGTGTGACGCAGGGGCAGGAGGGCATGGAACTCTCCCTGTT CTCCCGTGACGTGATCGCCATGTCCACGGCGGTCGGGCTGAGCCACGG CATGTTTGAGGGCGTGGCGCTGCTGGGCATCTGTGACAAGATTGTGCC GGGCCTTCTGATGGGCGCGCTGCGCTTCGGTCATCTCCCGGCCATGCTG ATCCCGGCCGGGCCAATGCCGTCGGGCCTTCCCAACAAGGAAAAGCA GCGCATCCGCCAGCTCTATGTGCAGGGCAAGGTCGGGCAGGACGAGCT GATGGAAGCGGAAAACGCCTCCTATCACAGCCCGGGCACCTGCACGTT CTATGGCACGGCCAATACGAACCAGATGATGGTCGAAATCATGGGTCT GATGATGCCGGACTCGGCTTTCATCAATCCCAACACGAAGCTGCGTCA GGCAATGACCCGCTCGGGTATTCACCGTCTGGCCGAAATCGGCCTGAA CGGCGAGGATGTGCGCCCGCTCGCTCATTGCGTAGACGAAAAGGCCAT AGCCGTGAATGCGGCGGTCGGTTGCTGGCGACGGGTGGTTCGACCAACCA TTCCATCCATCTTCCTGCTATCGCGGCCAGGGCTATCTGATCGAC TGGGAAGACATCAGCCGCCTGTCGTCCGGCGGTTCCGCTGATCACCCGT GTTTATCCGAGCGGTTCCGAGGACGTGAACGCGTTCAACCGCGTGGGT GGTATGCCGACCGTGATCGCCGAACTGACGCGCGCCGGGATGCTGCAC AAGGACATTCTGACGGTCTCTCGTGGCCGTTTCTCCGATTATGCCCGTC GCGCATCGCTGGAAGGCGATGAGATCGTCTACACCCACGCGAAGCCGT (continues) | MSLNPVVESVTARIIER SKVSRRRYLALMERNR AKGVLRPKLACGNLAH AIAASSPDKPDLMRPTG TNIGVITTYNDMLSAHQ PYGRYPEQIKLFAREVG ATAQVAGGAPAMCDG VTQGQEGMELSLFSRD VIAMSTAVGLSHGMFE GVALLGICDKIVPGLLM GALRFGHLPAMLIPAGP MPSGLPNKEKQRIRQLY VQGKVGQDELMEAEN ASYHSPGTCTFYGTANT NQMMVEIMGLMMPDS AFINPNTKLRQAMTRSG IHRLAEIGLNGEDVRPL AHCVDEKAIVNAAVGL LATGGSTNHSIHLPAIA RAAGILIDWEDISRLSSA VPLITRVYPSGSEDVNA FNRVGGMPTVIAELTR AGMLHKDILTVSRGGF SDYARRASLEGDEIVYT HAKPSTDTDILRDVATP |

| Accession Number | Species | Strain Number | NUCLEOTIDE SEQUENCE | Amino Acid Sequence |
|---|---|---|---|---|
| | | | CCACGGACACCGATATCCTGCGCGATGTGGCTACGCCTTTCCGGCCCG ATGGCGGTATGCGCCTGATGACTGGTAATCTGGGCCGCGCGATCTACA AGAGCAGCGCTATTGCGCCCGAGCACCTGACCGTTGAAGCGCCGGCAC GGGTCTTCCAGGACCAGCATGACGTCCTCACGGCCTATCAGAATGGTG AGCTTGAGCGTGATGTTGTCGTGGTCGTCCGGTTCCAGGGACCGGAAG CCAACGGCATGCCGGAGCTTCACAAGCTGACCCCGACTCTGGGCGTGC TTCAGGATCGCGGCTTCAAGGTGGCCCTGCTGACGGATGGACGCATGT CCGGTGCGAGCGGCAAGGTGCCGGCCGCCATTCATGTCGGTCCCGAAG CGCAGGTTGGCGGTCCGATCGCCCGCGTGCGGGACGGCGACATGATCC GTGTCTGCGCGGTGACGGGACAGATCGAGGCTCTGGTGGATGCCGCCG AGTGGGAGAGCCGCAAGCCGGTCCCGCCGCCGCTCCCGGCATTGGGA ACGGGCCGCGAACTGTTCGCGCTGATGCGTTCGGTGCATGATCCGGCC GAGGCTGGCGGATCCGCGATGCTGGCCCAGATGGATCGCGTGATCGAA GCCGTTGGCGACGACATTCACTAA (SEQ ID NO: 444) | FRPDGGMRLMTGNLGR AIYKSSAIAPEHLTVEAP ARVFQDQHDVLTAYQN GELERDVVVVRFQGP EANGMPELHKLTPTLG VLQDRGFKVALLTDGR MSGASGKVPAAIHVGP EAQVGGPIARVRDGDM IRVCAVTGQIEALVDAA EWESRKPVPPPLPALGT GRELFALMRSVHDPAE AGGSAMLAQMDRVIEA VGDDIH (SEQ ID NO: 445) |
| ZP_06145432.1 | Ruminococcus flavefaciens | FD-1 | ATGAGCGATAATTTTTTCTGCGAGGGTGCGGATAAAGCCCCTCAGCGT TCACTTTTCAATGCACTGGGCATGACTAAAGAGGAAATGAAGCGTCCC CTCGTTGGTATCGTTTCTTCCTACAATGAGATCGTTCCCGGCCATATGA ACATCGACAAGCTGGTCGAAGCCGTTAAGCTGGGTGTAGCTATGGGCG GCGGCACTCCTGTTGTTTTCCCTGCTATCGCTGTATGCGACGGTATCGC TATGGGTCACACAGGCATGAAGTACAGCCTTGTTACCCGTGACCTTAT TGCCGATTCTACAGAGTGTATGGCTCTTGCTCATCACTTCGACGCACTG GTAATGATACCTAACTGCGACAAGAACGTTCCCGGCCTGCTTATGGCG GCTGCACGTATCAATGTTCCTACTGTATTCGTAAGCGGCGGCCCTATGC TTGCAGGCCATGTAAAGGGTAAGAAGACCTCTCTTTCATCCATGTTCG AGGCTGTAGGCGCTTACACAGCAGGCAAGATAGACGAGGCTGAACTT GACGAATTCGAGAACAAGACCTGCCCTACCTGCGGTTCATGTTCGGGT ATGTATACCGCTAACTCCATGAACTGCCTCACTGAGGTACTGGGTATG GGTCTCAGAGGCAACGGCACTATCCCTGCTGTTTACTCCGAGCGTATC AAGCTTGCAAAGCAGGCAGGTATGCAGGTTATGGAACTCTACAGAAA GAATATCCGCCCTCTCGATATCATGACAGAGAAGGCTTTCCAGAACGC TCTCACAGCTGATATGGCTCTTGGATGTTCCACAAACAGTATGCTCCAT CTCCCTGCTATCGCCAACGAATGCGGCATAAATATCAACCTTGACATG GCTAACGAGATAAGCGCCAAGACTCCTAACCTCTGCCATCTTGCACCG GCAGGCCACACCTACATGGAAGACCTCAACGAAGCAGGCGGAGTTTA TGCAGTTCTCAACGAGCTGAGCAAAAAGGGACTTATCAACACCGACTG CATGACTGTTACAGGCAAGACCGTAGGCGAGAATATCAAGGGCTGCAT CAACCGTGACCCTGAGACTATCCGTCCTATCGACAACCCATACAGTGA AACAGGCGGAATCGCCGTACTCAAGGGCAATCTTGCTCCCGACAGATG TGTTGTGAAGAGAAGCGCAGTTGCTCCCGAAATGCTGGTACACAAAGG CCCTGCAAGAGTATTCGACAGCGAGGAAGAAGCTATCAAGGTCATCTA TGAGGGCGGTATCAAGGCAGGCGACGTTGTTGTTATCCGTTACGAAGG CCCTGCAGGCGGCCCCGGCATGAGAGAAATGCTCTCTCCTACATCAGC TATACAGGGTGCAGGTCTCGGCTCAACTGTTGCTCTAATCACTGACGG ACGTTTCAGCGGCGCTACCCGTGGTGCGGCTATCGGACACGTATCCCC CGAAGCTGTAAACGGCGGTACTATCGCATATGTCAAGGACGGCGATAT TATCTCCATCGACATACCGAATTACTCCATCACTCTTGAAGTATCCGAC GAGGAGCTTGCAGAGCGCAAAAAGGCAATGCCTATCAAGCGCAAGGA GAACATCACAGGCTATCTGAAGCGCTATGCACAGCAGGTATCATCCGC AGACAAGGGCGCTATCATCAACAGGAAATAG (SEQ ID NO: 446) | MSDNFFCEGADKAPQR SLFNALGMTKEEMKRP LVGIVSSYNEIVPGHMN IDKLVEAVKLGVAMGG GTPVVFPAIAVCDGIAM GHTGMKYSLVTRDLIA DSTECMALAHHFDALV MIPNCDKNVPGLLMAA ARINVPTVFVSGGPMLA GHVKGKKTSLSSMFEA VGAYTAGKIDEAELDE FENKTCPTCGSCSGMY TANSMNCLTEVLGMGL RGNGTIPAVYSERIKLA KQAGMQVMELYRKNI RPLDIMTEKAFQNALTA DMALGCSTNSMLHLPA IANECGININLDMANEIS AKTPNLCHLAPAGHTY MEDLNEAGGVYAVLN ELSKKGLINTDCMTVT GKTVGENIKGCINRDPE TIRPIDNPYSETGGIAVL KGNLAPDRCVVKRSAV APEMLVHKGPARVFDS EEEAIKVIYEGGIKAGD VVVIRYEGPAGGPGMR EMLSPTSAIQGAGLGST VALITDGRFSGATRGAA IGHVSPEAVNGGTIAYV KDGDIISIDIPNYSITLE VSDEELAERKKAMPIKR KENITGYLKRYAQQVS SADKGAIINRK (SEQ ID NO: 447) |

Example 28

Unique 200-mer Nucleotide Sequences Used for Integration Constructs

50

| 200-mer number | Sequence |
|---|---|
| 11 | GCGTCCATACCGGACCGTCCATCCGTCCCGGCGGGCTATCGTTAGTCCCC GCGAGCGGATTCCGAGGTGTCGATGACGCGCTCGGTCCCCGCATCTCGGG GTGGCCCGCACCTAGCTTAAGCGGACTACGAAGCGCGGGGCGAGCGGCG ACGATCGCGTACTCACACTCGGACCCTCGCGGGTCGGCTCGGAGCCCTGGT CA (SEQ ID NO: 448) |
| 17 | AGCGGTCAGTGCACGGGACGCGATCGGGCACCCTCGACGCAGCGATGGG CCGTGCGTCGTGTAGTCCGATAGTGCCGGCGTCGCTCGGTAAGCCCCTTAT ACCTGCGCGCTGGCGAGAGATGGGTTCGCGAGTCTAGCGCGATCGCTCTA GAGGGTCCAGGAGTACCTACACGGCGCGAGGCGCGGACATCCTAGGGCG CA (SEQ ID NO: 449) |

-continued

| 200-mer number | Sequence |
|---|---|
| 21 | CCCCTGCGTTTGCCGAGCGACGAGTCCTACACCCTGTCCGCGCCCGAGCAGGGTCGTCCCCGCGAACCGACGGATGCGCGGCCCGAATCGCCTAGACCCCTACGGGGCGGCTCGCTCGGCCCCGCCTGACCGGTCGATCCCACGAGACCCCGCCCTATAGGGAGAGCACCGACCCGCCTCCTCGGGCCTTACGGCGTGCGA (SEQ ID NO: 450) |
| 24 | GCCAGTGTAGAGATCCGGGGATCCCCAGCGCCTGGAGCTAGGCCCACGGCGTCTGACCGGGTGTACCGGGCCCCTAGGACGGGTGCGCCCGTAGTCCGTCTGCGAGGGGGCCGTCCGGTCGGGGGCATCCGGCGCTCCGCGGGGAGGCGCTACGTGCCCGACCGGGGGAGTCGAGTCTCTATGCTCGCGACCGCGTGCGA (SEQ ID NO: 451) |
| 25 | AAGCGCGCACTACGTCAGGCATAGCGTACTGGGCTTGCGGAGCCACGCGGGCGCGGAGCGGGCCGGTTGAGTGCGGGATAGACGGACCGTACGCATGCCTCAAGTCGACGGTACGGGGGGCAGGGTAGCTGGGATCCGAGGCGGGTAGGCGTCGGCCGCGACTGTGCCCGTACGACGGGAGAACCCCCCGCGCGAGTTGGA (SEQ ID NO: 452) |
| 448 | ACGTCGGCAGGCCCGCTCGGTTCCGAGCACCGGATCGACGCTACACGAGGCCCGACACTAGGCGCGTACTCCGGGGGGTCCGCCTCCGTCCCGTGAGTATCGCGGGCGGGAACAGGGCGGGCTGCCGGGGCCGACCGGTGTGGGCGTGACTCCGACCGACTCGGGCGAGGGCCGCCTAGTCGCGAAGGACGCGCGACCA (SEQ ID NO: 453) |

Example 29

Examples of Embodiments

Provided hereafter are certain non-limiting embodiments of the technology.

A1. A composition comprising a nucleic acid that includes heterologous polynucleotides that encode a phosphogluconate dehydratase enzyme, a 2-keto-3-deoxygluconate-6-phosphate aldolase enzyme and a nucleotide sequence identification tag selected from the group of six (6) nucleotide sequences consisting of (SEQ ID NO: 448)
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA (SEQ ID NO: 449)
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA (SEQ ID NO: 450)
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

CCCGCCTGACCGGTCGATCCCACGAGACCCCGCCCTATAGGGAGAGCACCGACCCGCCTC

CTCGGGCCTTACGGCGTGCGA (SEQ ID NO: 451)
GCCAGTGTAGAGATCCGGGGATCCCCAGCGCCTGGAGCTAGGCCCACGGCGTCTGACCGG

GTGTACCGGGCCCCTAGGACGGGTGCGCCCGTAGTCCGTCTGCGAGGGGCCGTCCGGT

CGGGGGCATCCGGCGCTCCGCGGGAGGCGCTACGTGCCCGACCGGGGAGTCGAGTCTC

TATGCTCGCGACCGCGTGCGA (SEQ ID NO: 452)
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

```
                          -continued
CAGGGTAGCTGGGATCCGAGGCGGGTAGGCGTCGGCCGCGACTGTGCCCGTACGACGGGA

GAACCCCCGCGCGAGTTGGA (SEQ ID NO: 453)
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA
```

A2. The composition of embodiment A1, wherein the yeast is a *Saccharomyces* spp. yeast.

A3. The composition of embodiment A2, wherein the yeast is a *Saccharomyces cerevisiae* yeast strain.

A3.1. The composition of any one of embodiments A1 to A3, wherein the polynucleotides encoding the phosphogluconate dehydratase enzyme and the 3-deoxygluconate-6-phosphate aldolase enzyme independently are from an *Escherichia* spp. microbe or *Psuedomonas* spp. microbe.

A4. The composition of embodiment A3, wherein the *Escherichia* spp. microbe is an *Escherichia coli* strain.

A5. The composition of embodiment A3 or A4, wherein the *Pseudomonas* spp. microbe is a *Pseudomonas aeruginosa* strain.

A6. The composition of any one of embodiments A1 to A5, wherein the polynucleotide that encodes the phosphogluconate dehydratase enzyme is an EDD gene.

A7. The composition of any one of embodiments A1 to A5, wherein the polynucleotide that encodes the 2-keto-3-deoxygluconate-6-phosphate aldolase enzyme is an EDA gene.

A8. The composition of any one of embodiments A1 to A7, wherein the nucleic acid includes a polynucleotide that encodes a 6-phosphogluconolactonase enzyme.

A8.1. The composition of embodiment A8, wherein the 6-phosphogluconolactonase enzyme is expressed from a SOL gene.

A9. The composition of embodiment A8, wherein the SOL gene is a SOL3 gene.

A10. The composition of any one of embodiments A1 to A9, wherein the nucleic acid includes a polynucleotide that encodes a glucose-6-phosphate dehydrogenase enzyme.

A11. The composition of embodiment A10, wherein the polynucleotide that encodes the glucose-6-phosphate dehydrogenase enzyme is from a yeast.

A12. The composition of embodiment A11, wherein the yeast is *Saccharomyces* spp. yeast.

A13. The composition of embodiment A12, wherein the yeast is a *Saccharomyces cerevisiae* strain.

A14. The composition of any one of embodiments A10 to A13, wherein the nucleic acid includes a polynucleotide that encode an endogenous glucose-6-phosphate dehydrogenase enzyme.

A15. The composition of any one of embodiments A10 to A14, wherein the glucose-6-phosphate dehydrogenase enzyme is expressed from a ZWF gene.

A16. The composition of embodiment A15, wherein the ZWF gene is a ZWF1 gene.

A17. The composition of any one of embodiments A1 to A16, wherein the nucleic acid includes one or more promoters operable in a yeast, wherein the promoter is in operable connection with one or more of the polynucleotides.

A18. The composition of embodiment A17, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

A19. The composition of any one of embodiments A1 to A18, wherein the nucleic acid includes one or more polynucleotides that homologously combine in a gene of a host that encodes a phosphofructokinase (PFK) enzyme, phosphoglucoisomerase (PGI) enzyme, 6-phosphogluconate dehydrogenase (decarboxylating) enzyme, transketolase enzyme, transaldolase enzyme, or combination thereof.

A20. The composition of embodiment A19, wherein the transketolase enzyme is encoded by a TKL-1 coding sequence or a TKL-2 coding sequence.

A21. The composition of embodiment A19, wherein the transaldolase is encoded by a TAL-1 coding sequence.

A22. The composition of embodiment A19, wherein the phosphofructokinase (PFK) enzyme is a PFK-2 enzyme or PFK-1 enzyme.

A23. The composition of embodiment A19, wherein the 6-phosphogluconate dehydrogenase (decarboxylating) enzyme is encoded by a GND-1 gene or a GND-2 gene.

A24. The composition of embodiment A19, wherein the PGI is encoded by a PGI-1 gene.

A25. The composition of any one of embodiments A1 to A24, wherein the nucleic acid is one or two separate nucleic acid molecules.

A26. The composition of embodiment A25, wherein each nucleic acid molecule includes one or two or more of the polynucleotide subsequences, one or two or more of the promoters, or one or two or more of the polynucleotide subsequences and one or two or more of the promoters.

A27. The composition of embodiment A25 or A26, wherein each of the one or two nucleic acid molecules are in circular form.

A28. The composition of embodiment A25 or A26, wherein each of the one or two nucleic acid molecules are in linear form.

A29. The composition of any one of embodiments A25 to A28, wherein each of the one or two nucleic acid molecules functions as an expression vector.

A30. The composition of any one of embodiments A25 to A29, wherein each of the one or two nucleic acid molecules includes flanking sequences for integrating the polynucleotides, the promoter sequences, or the polynucleotides and the promoter sequences in the nucleic acid into genomic DNA of a host organism.

B1. A composition comprising an engineered yeast that includes an alteration that adds or increases a phosphogluconate dehydratase activity and a 2-keto-3-deoxygluconate-6-phosphate aldolase activity, and a nucleotide sequence identification tag having a nucleotide sequence selected from the group of six (6) nucleotide sequences consisting of

```
                                                (SEQ ID NO: 448)
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA (SEQ ID NO: 449)
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA (SEQ ID NO: 450)
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

CCCGCCTGACCGGTCGATCCCACGAGACCCCGCCCTATAGGGAGAGCACCGACCCGCCTC

CTCGGGCCTTACGGCGTGCGA (SEQ ID NO: 451)
GCCAGTGTAGAGATCCGGGGATCCCCAGCGCCTGGAGCTAGGCCCACGGCGTCTGACCGG

GTGTACCGGGCCCCCTAGGACGGGTGCGCCCGTAGTCCGTCTGCGAGGGGGCCGTCCGGT

CGGGGGCATCCGGCGCTCCGCGGGGAGGCGCTACGTGCCCGACCGGGGAGTCGAGTCTC

TATGCTCGCGACCGCGTGCGA (SEQ ID NO: 452)
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

CAGGGTAGCTGGGATCCGAGGCGGGTAGGCGTCGGCCGCGACTGTGCCCGTACGACGGGA

GAACCCCCCGCGCGAGTTGGA (SEQ ID NO: 453)
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA
```

B2. The composition of embodiment B1, wherein the yeast is a *Saccharomyces* spp. yeast.

B3. The composition of embodiment B2, wherein the yeast is a *Saccharomyces cerevisiae* yeast strain.

B4. The composition of any one of embodiments B1 to B3 that includes heterologous polynucleotides that encode independently a phosphogluconate dehydratase enzyme and a 2-keto-3-deoxygluconate-6-phosphate aldolase enzyme.

B5. The composition of embodiment B4, wherein the polynucleotides encoding the phosphogluconate dehydratase enzyme and the 3-deoxygluconate-6-phosphate aldolase enzyme independently are from an *Escherichia* spp. microbe or *Psuedomonas* spp. microbe.

B6. The composition of embodiment B5, wherein the *Escherichia* spp. microbe is an *Escherichia coli* strain.

B7. The composition of embodiment B5, wherein the *Pseudomonas* spp. microbe is a *Pseudomonas aeruginosa* strain.

B8. The composition of any one of embodiments B4 to B7, wherein the polynucleotide that encodes the phosphogluconate dehydratase enzyme is an EDD gene.

B9. The composition of any one of embodiments B4 to B7, wherein the polynucleotide that encodes the 2-keto-3-deoxygluconate-6-phosphate aldolase enzyme is an EDA gene.

B10. The composition of any one of embodiments B1 to B9, wherein the yeast includes an alteration that adds or increases a 6-phosphogluconolactonase activity.

B10.1. The composition of embodiment B10, wherein the yeast includes a heterologous polynucleotide, or multiple copies of an endogenous polynucleotide, that encodes a 6-phosphogluconolactonase enzyme.

B10.2. The composition of embodiment B10.1, wherein the 6-phosphogluconolactonase enzyme is expressed from a SOL gene.

B11. The composition of embodiment B10.2, wherein the SOL gene is a SOL3 gene.

B12. The composition of any one of embodiments B1 to B11, wherein a glucose-6-phosphate dehydrogenase activity is added or increased.

B13. The composition of embodiment B12, wherein the yeast comprises a heterologous polynucleotide that encodes a glucose-6-phosphate dehydrogenase enzyme, or wherein the yeast comprises multiple copies of an endogenous polynucleotide that encodes a glucose-6-phosphate dehydrogenase enzyme.

B14. The composition of embodiment B13, wherein the polynucleotide that encodes the glucose-6-phosphate dehydrogenase enzyme is from a yeast.

B15. The composition of embodiment B14, wherein the yeast is a *Saccharomyces* spp. yeast.

B16. The composition of embodiment B15, wherein the yeast is a *Saccharomyces cerevisiae* strain.

B17. The composition of any one of embodiments B13 to B17, wherein the glucose-6-phosphate dehydrogenase enzyme is expressed from a ZWF gene.

B18. The composition of embodiment B17, wherein the ZWF gene is a ZWF1 gene.

B19. The composition of any one of embodiments B1 to B18, wherein the nucleic acid includes one or more promoters operable in a yeast, wherein the promoter is in operable connection with one or more of the polynucleotides.

B20. The composition of embodiment B19, wherein the promoter is selected from promoters that regulate glucose phosphate dehydrogenase (GBD), translation elongation factor (TEF-1), phosphoglucokinase (BGK-1) and triose phosphate dehydrogenase (TDH-1).

B21. The composition of any one of embodiments B1 to B20, wherein the yeast includes a reduction in one or more of the following activities: phosphofructokinase (PFK) activity, phosphoglucoisomerase (PGI) activity, 6-phosphogluconate dehydrogenase (decarboxylating) activity, transketolase activity, transaldolase activity, or combination thereof.

B22. The composition of embodiment B21, wherein the yeast includes an alteration in one or more polynucleotides that inhibits production of one or more enzymes selected from the group consisting of phosphofructokinase (PFK) enzyme, phosphoglucoisomerase (PGI) enzyme, 6-phosphogluconate dehydrogenase (decarboxylating) enzyme, transketolase enzyme, transaldolase enzyme, or combination thereof.

B23. The composition of embodiment B22, wherein the transketolase enzyme is encoded by a TKL-1 coding sequence or a TKL-2 coding sequence.

B24. The composition of embodiment B22, wherein the transaldolase is encoded by a TAL-1 coding sequence.

B25. The composition of embodiment B22, wherein the phosphofructokinase (PFK) enzyme is a PFK-2 enzyme or PFK-1 enzyme.

B26. The composition of embodiment B22, wherein the 6-phosphogluconate dehydrogenase (decarboxylating) enzyme is encoded by a GND-1 gene or GND-2 gene.

B27. The composition of embodiment B22, wherein the PGI is encoded by a PGI-1 gene.

B28. The composition of any one of embodiments B1 to B27, wherein the polynucleotides, the promoters, or the polynucleotides and the promoters are not integrated in the yeast nucleic acid.

B29. The composition of embodiment B28, wherein the polynucleotides, the promoters, or the polynucleotides and the promoters are in one or more plasmids.

B30. The composition of any one of embodiments B1 to B29, wherein the polynucleotide subsequences, the promoters, or the polynucleotide subsequences and the promoters are integrated in genomic DNA of the yeast.

B31. The composition of embodiment B30, wherein the polynucleotides, the promoters, or the polynucleotides and the promoters are integrated in a transposition integration event, in a homologous recombination integration event, or in a transposition integration event and a homologous recombination integration event.

B32. The composition of embodiment B31, wherein the transposition integration event includes transposition of an operon comprising two or more of the polynucleotide subsequences, the promoters, or the polynucleotide subsequences and the promoters.

B33. The composition of embodiment B31, wherein the homologous recombination integration event includes homologous recombination of an operon comprising two or more of the polynucleotide subsequences, the promoters, or the polynucleotide subsequences and the promoters.

C1. A method, comprising contacting an engineered yeast of any one of embodiments B1 to B33 with a feedstock that contains one or more hexose sugars under conditions in which the microbe synthesizes ethanol.

C2. The method of embodiment C1, wherein the engineered yeast synthesizes ethanol to about 85% to about 99% of theoretical yield.

C3. The method of embodiment C1 or C2, comprising recovering ethanol synthesized by the engineered yeast.

C4. The method of any one of embodiments C1 to C3, wherein the conditions are fermentation conditions.

D1. A composition comprising a synthetic nucleic acid that includes a polynucleotide sequence selected from the group consisting of (SEQ ID NO: 448)
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA (SEQ ID NO: 449)
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA (SEQ ID NO: 450)
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

-continued

```
CCCGCCTGACCGGTCGATCCCACGAGACCCCGCCCTATAGGGAGAGCACCGACCCGCCTC

CTCGGGCCTTACGGCGTGCGA
```

(SEQ ID NO: 451)
```
GCCAGTGTAGAGATCCGGGGATCCCCAGCGCCTGGAGCTAGGCCCACGGCGTCTGACCGG

GTGTACCGGGCCCCTAGGACGGGTGCGCCCGTAGTCCGTCTGCGAGGGGGCCGTCCGGT

CGGGGGCATCCGGCGCTCCGCGGGGAGGCGCTACGTGCCCGACCGGGGGAGTCGAGTCTC

TATGCTCGCGACCGCGTGCGA
```

(SEQ ID NO: 452)
```
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

CAGGGTAGCTGGGATCCGAGGCGGGTAGGCGTCGGCCGCGACTGTGCCCGTACGACGGGA

GAACCCCCCGCGCGAGTTGGA
```

(SEQ ID NO: 453)
```
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA
```

D2. A microorganism comprising a polynucleotide that includes a sequence selected from the group consisting of (SEQ ID NO: 448)
```
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA
```

(SEQ ID NO: 449)
```
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA
```

(SEQ ID NO: 450)
```
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

CCCGCCTGACCGGTCGATCCCACGAGACCCCGCCCTATAGGGAGAGCACCGACCCGCCTC

CTCGGGCCTTACGGCGTGCGA
```

(SEQ ID NO: 451)
```
GCCAGTGTAGAGATCCGGGGATCCCCAGCGCCTGGAGCTAGGCCCACGGCGTCTGACCGG

GTGTACCGGGCCCCTAGGACGGGTGCGCCCGTAGTCCGTCTGCGAGGGGGCCGTCCGGT

CGGGGGCATCCGGCGCTCCGCGGGGAGGCGCTACGTGCCCGACCGGGGGAGTCGAGTCTC

TATGCTCGCGACCGCGTGCGA
```

(SEQ ID NO: 452)
```
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

CAGGGTAGCTGGGATCCGAGGCGGGTAGGCGTCGGCCGCGACTGTGCCCGTACGACGGGA

GAACCCCCCGCGCGAGTTGGA
```

```
                                                         (SEQ ID NO: 453)
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA
```

D3. A method comprising detecting the presence or absence of a nucleotide sequence identification tag in a microorganism, wherein the nucleotide sequence is selected from the group consisting of

```
                                                         (SEQ ID NO: 448)
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA (SEQ ID NO: 449)
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA (SEQ ID NO: 450)
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

CCCGCCTGACCGGTCGATCCCACGAGACCCCGCCCTATAGGGAGAGCACCGACCCGCCTC

CTCGGGCCTTACGGCGTGCGA (SEQ ID NO: 451)
GCCAGTGTAGAGATCCGGGGATCCCCAGCGCCTGGAGCTAGGCCCACGGCGTCTGACCGG

GTGTACCGGGCCCCCTAGGACGGGTGCGCCCGTAGTCCGTCTGCGAGGGGGCCGTCCGGT

CGGGGGCATCCGGCGCTCCGCGGGGAGGCGCTACGTGCCCGACCGGGGAGTCGAGTCTC

TATGCTCGCGACCGCGTGCGA (SEQ ID NO: 452)
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

CAGGGTAGCTGGGATCCGAGGCGGGTAGGCGTCGGCCGCGACTGTGCCCGTACGACGGGA

GAACCCCCGCGCGAGTTGGA (SEQ ID NO: 453)
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA
```

D4. The method of embodiment D3, wherein the microorganism includes two or more different identification tags.

D5. The method of embodiment D3, wherein the microorganism includes multiple copies of one or more of the identification tags.

E1. A composition comprising a nucleic acid comprising (i) heterologous polynucleotides that encode a phosphogluconate dehydratase enzyme and a 2-keto-3-deoxygluconate-6-phosphate aldolase enzyme, (ii) one or more polynucleotides that homologously combine in a gene of a host that encodes a 6-phosphogluconate dehydrogenase (decarboxylating) enzyme, and (iii) a nucleotide sequence identification tag selected from the group consisting

```
                                              (SEQ ID NO: 448)
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA
                                              (SEQ ID NO: 449)
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA
                                              (SEQ ID NO: 450)
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

CCCGCCTGACCGGTCGATCCCACGAGACCCCGCCCTATAGGGAGAGCACCGACCCGCCTC

CTCGGGCCTTACGGCGTGCGA
                                              (SEQ ID NO: 451)
GCCAGTGTAGAGATCCGGGGATCCCCAGCGCCTGGAGCTAGGCCCACGGCGTCTGACCGG

GTGTACCGGGCCCCCTAGGACGGGTGCGCCCGTAGTCCGTCTGCGAGGGGGCCGTCCGGT

CGGGGGCATCCGGCGCTCCGCGGGGAGGCGCTACGTGCCCGACCGGGGGAGTCGAGTCTC

TATGCTCGCGACCGCGTGCGA
                                              (SEQ ID NO: 452)
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

CAGGGTAGCTGGGATCCGAGGCGGGTAGGCGTCGGCCGCGACTGTGCCCGTACGACGGGA

GAACCCCCGCGCGAGTTGGA
                                              (SEQ ID NO: 453)
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA
```

E2. The composition of embodiment E1, wherein the yeast is a *Saccharomyces* spp. yeast.

E3. The composition of embodiment E2, wherein the yeast is a *Saccharomyces cerevisiae* yeast strain.

E3.1. The composition of any one of embodiments E1 to E3, wherein the polynucleotides encoding the phosphogluconate dehydratase enzyme and the 3-deoxygluconate-6-phosphate aldolase enzyme independently are from an *Escherichia* spp. microbe or *Psuedomonas* spp. microbe.

E4. The composition of embodiment E3, wherein the *Escherichia* spp. microbe is an *Escherichia coli* strain.

E5. The composition of embodiment E3 or E4, wherein the *Pseudomonas* spp. microbe is a *Pseudomonas aeruginosa* strain.

E6. The composition of any one of embodiments E1 to E5, wherein the polynucleotide that encodes the phosphogluconate dehydratase enzyme is an EDD gene.

E7. The composition of any one of embodiments E1 to E5, wherein the polynucleotide that encodes the 2-keto-3-deoxygluconate-6-phosphate aldolase enzyme is an EDA gene.

E8. The composition of any one of embodiments E1 to E7, wherein the nucleic acid includes a polynucleotide that encodes a 6-phosphogluconolactonase enzyme.

E8.1. The composition of embodiment E8, wherein the polynucleotide that encodes the 6-phosphogluconolactonase enzyme is from a yeast.

E8.2. The composition of embodiment E8.1, wherein the yeast is a *Saccharomyces* spp. yeast.

E8.3. The composition of embodiment E8.2, wherein the yeast is a *Saccharomyces cerevisiae* strain.

E8.4. The composition of any one of embodiments E8 to E8.3, wherein the 6-phosphogluconolactonase enzyme is expressed from a SOL gene.

E9. The composition of embodiment E8.4, wherein the SOL gene is a SOL3 gene.

E10. The composition of any one of embodiments E1 to E9, wherein the nucleic acid includes a polynucleotide that encodes a glucose-6-phosphate dehydrogenase enzyme.

E11. The composition of embodiment E10, wherein the polynucleotide that encodes the glucose-6-phosphate dehydrogenase enzyme is from a yeast.

E12. The composition of embodiment E11, wherein the yeast is a *Saccharomyces* spp. yeast.

E13. The composition of embodiment E12, wherein the yeast is a *Saccharomyces cerevisiae* strain.

E14. The composition of any one of embodiments E10 to E13, wherein the nucleic acid includes a polynucleotide that encode an endogenous glucose-6-phosphate dehydrogenase enzyme.

E15. The composition of any one of embodiments E10 to E14, wherein the glucose-6-phosphate dehydrogenase enzyme is expressed from a ZWF gene.

E16. The composition of embodiment E15, wherein the ZWF gene is a ZWF1 gene.

E17. The composition of any one of embodiments E1 to E16, wherein the nucleic acid includes one or more promoters operable in a yeast, wherein the promoter is in operable connection with one or more of the polynucleotides.

E18. The composition of embodiment E17, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

E19. The composition of any one of embodiments E1 to E18, wherein the nucleic acid includes one or more polynucleotides that homologously combine in a gene of a host that encodes a phosphofructokinase (PFK) enzyme, phosphoglucoisomerase (PGI) enzyme, transketolase enzyme, transaldolase enzyme, or combination thereof.

E20. The composition of embodiment E19, wherein the transketolase enzyme is encoded by a TKL-1 coding sequence or a TKL-2 coding sequence.

E21. The composition of embodiment E19, wherein the transaldolase is encoded by a TAL-1 coding sequence.

E22. The composition of embodiment E19, wherein the phosphofructokinase (PFK) enzyme is a PFK-2 enzyme or PFK-1 enzyme.

E23. The composition of any one of embodiments E1 to E22, wherein the 6-phosphogluconate dehydrogenase (decarboxylating) enzyme is encoded by a GND-1 gene or a GND-2 gene.

E24. The composition of embodiment E19, wherein the PGI is encoded by a PGI-1 gene.

E25. The composition of any one of embodiments E1 to E24, wherein the nucleic acid is one or two separate nucleic acid molecules.

E26. The composition of embodiment E25, wherein each nucleic acid molecule includes one or two or more of the polynucleotide subsequences, one or two or more of the promoters, or one or two or more of the polynucleotide subsequences and one or two or more of the promoters.

E27. The composition of embodiment E25 or E26, wherein each of the one or two nucleic acid molecules are in circular form.

E28. The composition of embodiment E25 or E26, wherein each of the one or two nucleic acid molecules are in linear form.

E29. The composition of any one of embodiments E25 to E28, wherein each of the one or two nucleic acid molecules functions as an expression vector.

E30. The composition of any one of embodiments E25 to E29, wherein each of the one or two nucleic acid molecules includes flanking sequences for integrating the polynucleotides, the promoter sequences, or the polynucleotides and the promoter sequences in the nucleic acid into genomic DNA of a host organism.

F1. A composition comprising an engineered yeast that includes (i) an alteration that adds or increases a phosphogluconate dehydratase activity and a 2-keto-3-deoxygluconate-6-phosphate aldolase activity, (ii) an alteration that reduces a 6-phosphogluconate dehydrogenase (decarboxylating) activity, and (iii) a nucleotide sequence identification tag selected from the group consisting of

```
                                                  (SEQ ID NO: 448)
GCGTCCATACCGGACCGTCCATCCGTCCCGGCGGGCTATCGTTAGTCCCCGCGAGCGGAT

TCCGAGGTGTCGATGACGCGCTCGGTCCCCGCATCTCGGGGTGGCCCGCACCTAGCTTAA

GCGGACTACGAAGCGCGGGGCGAGCGGCGACGATCGCGTACTCACACTCGGACCTCGCGG

GTCGGCTCGGAGCCCTGGTCA (SEQ ID NO: 449)
AGCGGTCAGTGCACGGGACGCGATCGGGCACCCTCGACGCAGCGATGGGCCGTGCGTCGT

GTAGTCCGATAGTGCCGGCGTCGCTCGGTAAGCCCCTTATACCTGCGCGCTGGCGAGAGA

TGGGTTCGCGAGTCTAGCGCGATCGCTCTAGAGGGTCCAGGAGTACCTACACGGCGCGAG

GCGCGGACATCCTAGGGCGCA (SEQ ID NO: 450)
CCCCTGCGTTTGCCGAGCGACGAGTCCTACACCCTGTCCGCGCCCGAGCAGGGTCGTCCC

CGCGAACCGACGGATGCGCGGCCCGAATCGCCTAGACCCCTACGGGGCGGCTCGCTCGGC

CCCGCCTGACCGGTCGATCCCACGAGACCCCGCCCTATAGGGAGAGCACCGACCCGCCTC

CTCGGGCCTTACGGCGTGCGA
```

-continued (SEQ ID NO: 451)
GCCAGTGTAGAGATCCGGGGATCCCCAGCGCCTGGAGCTAGGCCCACGGCGTCTGACCGG

GTGTACCGGGCCCCCTAGGACGGGTGCGCCCGTAGTCCGTCTGCGAGGGGGCCGTCCGGT

CGGGGGCATCCGGCGCTCCGCGGGGAGGCGCTACGTGCCCGACCGGGGGAGTCGAGTCTC

TATGCTCGCGACCGCGTGCGA (SEQ ID NO: 452)
AAGCGCGCACTACGTCAGGCATAGCGTACTGGGCTTGCGGAGCCACGCGGGCGCGGAGCG

GGCCGGTTGAGTGCGGGATAGACGGACCGTACGCATGCCTCAAGTCGACGGTACGGGGGG

CAGGGTAGCTGGGATCCGAGGCGGGTAGGCGTCGGCCGCGACTGTGCCCGTACGACGGGA

GAACCCCCCGCGCGAGTTGGA (SEQ ID NO: 453)
ACGTCGGCAGGCCCGCTCGGTTCCGAGCACCGGATCGACGCTACACGAGGCCCGACACTA

GGCGCGTACTCCGGGGGGGTCCGCCTCCGTCCCGTGAGTATCGCGGGCGGGAACAGGGCG

GGCTGCCGGGGCCGACCGGTGTGGGGCGTGACTCCGACCGACTCGGGCGAGGGCCGCCTA

GTCGCGAAGGACGCGCGACCA

F2. The composition of embodiment F1, wherein the yeast is a *Saccharomyces* spp. yeast.
F3. The composition of embodiment F2, wherein the yeast is a *Saccharomyces cerevisiae* yeast strain.
F4. The composition of any one of embodiments F1 to F3, wherein the yeast includes an altered gene that encodes a 6-phosphogluconate dehydrogenase (decarboxylating) enzyme.
F4.1. The composition of any one of embodiments F1 to F4 where the yeast includes heterologous polynucleotides, or multiple copies of endogenous polynucleotides, that encode a phosphogluconate dehydratase enzyme and a 2-keto-3-deoxygluconate-6-phosphate aldolase enzyme.
F5. The composition of embodiment F4, wherein the polynucleotides encoding the phosphogluconate dehydratase enzyme and the 3-deoxygluconate-6-phosphate aldolase enzyme independently are from an *Escherichia* spp. microbe or *Psuedomonas* spp. microbe.
F6. The composition of embodiment F5, wherein the *Escherichia* spp. microbe is an *Escherichia coli* strain.
F7. The composition of embodiment F5, wherein the *Pseudomonas* spp. microbe is a *Pseudomonas aeruginosa* strain.
F8. The composition of any one of embodiments F4 to F7, wherein the polynucleotide that encodes the phosphogluconate dehydratase enzyme is an EDD gene.
F9. The composition of any one of embodiments F4 to F7, wherein the polynucleotide that encodes the 2-keto-3-deoxygluconate-6-phosphate aldolase enzyme is an EDA gene.
F10. The composition of any one of embodiments F1 to F11, wherein a glucose-6-phosphate dehydrogenase activity is added or increased.
F10.1. The composition of embodiment F10, wherein the yeast comprises a heterologous polynucleotide that encodes a 6-phosphogluconolactonase enzyme, or wherein the yeast comprises multiple copies of an endogenous polynucleotide that encodes a 6-phosphogluconolactonase enzyme.
F10.2. The composition of embodiment F10.1, wherein the polynucleotide that encodes the 6-phosphogluconolactonase enzyme is from a yeast.
F10.3. The composition of embodiment F10.2, wherein the yeast is a *Saccharomyces* spp. yeast.
F10.4. The composition of embodiment F10.3, wherein the yeast is a *Saccharomyces cerevisiae* strain.
F10.5. The composition of any one of embodiments F10 to F10.4, wherein the 6-phosphogluconolactonase enzyme is expressed from a SOL gene.
F11. The composition of embodiment F10.4, wherein the SOL gene is a SOL3 gene.
F12. The composition of any one of embodiments F4 to F11, wherein a glucose-6-phosphate dehydrogenase activity is added or increased.
F13. The composition of embodiment F12, wherein the yeast comprises a heterologous polynucleotide that encodes a glucose-6-phosphate dehydrogenase enzyme, or wherein the yeast comprises multiple copies of an endogenous polynucleotide that encodes a glucose-6-phosphate dehydrogenase enzyme.
F14. The composition of embodiment F13, wherein the polynucleotide that encodes the glucose-6-phosphate dehydrogenase enzyme is from a yeast.
F15. The composition of embodiment F14, wherein the yeast is a *Faccharomyces* spp. yeast.
F16. The composition of embodiment F15, wherein the yeast is a *Faccharomyces cerevisiae* strain.
F17. The composition of any one of embodiments F13 to F17, wherein the glucose-6-phosphate dehydrogenase enzyme is expressed from a ZWF gene.
F18. The composition of embodiment F17, wherein the ZWF gene is a ZWF1 gene.
F19. The composition of any one of embodiments F1 to F18, wherein the nucleic acid includes one or more promoters operable in a yeast, wherein the promoter is in operable connection with one or more of the polynucleotides.
F20. The composition of embodiment F19, wherein the promoter is selected from promoters that regulate glucose phosphate dehydrogenase (GFD), translation elongation factor (TEF-1), phosphoglucokinase (FGK-1) and triose phosphate dehydrogenase (TDH-1).
F21. The composition of any one of embodiments F1 to F20, wherein the yeast includes a reduction in one or more of the following activities: phosphofructokinase (PFK) activity, phosphoglucoisomerase (PGI) activity, transketolase activity, transaldolase activity, or combination thereof.

F22. The composition of embodiment F21, wherein the yeast includes an alteration in one or more polynucleotides that inhibits production of one or more enzymes selected from the group consisting of phosphofructokinase (PFK) enzyme, phosphoglucoisomerase (PGI) enzyme, 6-phosphogluconate dehydrogenase (decarboxylating) enzyme, transketolase enzyme, transaldolase enzyme, or combination thereof.

F23. The composition of embodiment F22, wherein the transketolase enzyme is encoded by a TKL-1 coding sequence or a TKL-2 coding sequence.

F24. The composition of embodiment F22, wherein the transaldolase is encoded by a TAL-1 coding sequence.

F25. The composition of embodiment F22, wherein the phosphofructokinase (PFK) enzyme is a PFK-2 enzyme or PFK-1 enzyme.

F26. The composition of any one of embodiments F4 to F25, wherein the 6-phosphogluconate dehydrogenase (decarboxylating) enzyme is encoded by a GND-1 gene or GND-2 gene.

F27. The composition of embodiment F22, wherein the PGI is encoded by a PGI-1 gene.

F28. The composition of any one of embodiments F1 to F27, wherein the polynucleotides, the promoters, or the polynucleotides and the promoters are not integrated in the yeast nucleic acid.

F29. The composition of embodiment F28, wherein the polynucleotides, the promoters, or the polynucleotides and the promoters are in one or more plasmids.

F30. The composition of any one of embodiments F1 to F29, wherein the polynucleotide subsequences, the promoters, or the polynucleotide subsequences and the promoters are integrated in genomic DNA of the yeast.

F31. The composition of embodiment F30, wherein the polynucleotides, the promoters, or the polynucleotides and the promoters are integrated in a transposition integration event, in a homologous recombination integration event, or in a transposition integration event and a homologous recombination integration event.

F32. The composition of embodiment F31, wherein the transposition integration event includes transposition of an operon comprising two or more of the polynucleotide subsequences, the promoters, or the polynucleotide subsequences and the promoters.

F33. The composition of embodiment F31, wherein the homologous recombination integration event includes homologous recombination of an operon comprising two or more of the polynucleotide subsequences, the promoters, or the polynucleotide subsequences and the promoters.

G1. A method, comprising contacting an engineered yeast of any one of embodiments F1 to F33 with a feedstock that contains one or more hexose sugars under conditions in which the microbe synthesizes ethanol.

G2. The method of embodiment G1, wherein the engineered yeast synthesizes ethanol to about 85% to about 99% of theoretical yield.

G3. The method of embodiment G1 or G2, comprising recovering ethanol synthesized by the engineered yeast.

G4. The method of any one of embodiments G1 to G3, wherein the conditions are fermentation conditions.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A composition comprising an engineered *Saccharomyces* spp. yeast that comprises:
   (i) a heterologous polynucleotide that encodes a phosphogluconate dehydratase from *Pseudomonas aeruginosa;*
   (ii) a heterologous polynucleotide that encodes a 2-keto-3-deoxygluconate-6-phosphate aldolase from *Escherichia coli;* and
   (iii) a nucleotide sequence identification tag having the nucleotide sequence of SEQ ID NO: 452.

2. The composition of claim 1, wherein the polynucleotide that encodes the phosphogluconate dehydratase comprises nucleotide sequences independently complementary to the full-length sequences of SEQ ID NO: 63 and SEQ ID NO: 64.

3. The composition of claim 2, wherein the polynucleotide that encodes the phosphogluconate dehydratase comprises the nucleotide sequence of SEQ ID NO:69.

4. The composition of claim 3, wherein the phosphogluconate dehydratase comprises the amino acid sequence of SEQ ID NO:70.

5. The composition of claim 1, wherein the polynucleotide that encodes the 2-keto-3-deoxygluconate-6-phosphate aldolase comprises nucleotide sequences independently complementary to the full-length sequences of SEQ ID NO: 5 and SEQ ID NO: 6.

6. The composition of claim 5, wherein the polynucleotide that encodes the 2-keto-3-deoxygluconate-6-phosphate aldolase comprises the nucleotide sequence of SEQ ID NO:269.

7. The composition of claim 6, wherein the 2-keto-3-deoxygluconate-6-phosphate aldolase comprises the amino acid sequence of SEQ ID NO:273.

8. The composition of claim 1, wherein the *Saccharomyces* spp. yeast comprises a heterologous polynucleotide, or multiple copies of an endogenous polynucleotide, that encodes one or more additional copies of a glucose-6-phosphate dehydrogenase.

9. The composition of claim 8, wherein the glucose-6-phosphate dehydrogenase comprises the amino acid sequence of SEQ ID NO:119.

10. The composition of claim 1, wherein the *Saccharomyces* spp. yeast comprises a heterologous polynucleotide, or multiple copies of an endogenous polynucleotide, that encodes one or more additional copies of a 6-phosphogluconolactonase.

11. The composition of claim 10, wherein the 6-phosphogluconolactonase comprises the amino acid sequence of SEQ ID NO:120.

12. The composition of claim 1, wherein the yeast comprises one or more promoters in operable connection with one or more of the polynucleotides.

13. The composition of claim 12, wherein the promoter is selected from promoters that regulate glucose phosphate dehydrogenase (GBD), translation elongation factor (TEF-1), phosphoglucokinase (PGK-1), and triose phosphate dehydrogenase (TDH-1).

14. The composition of claim 1, wherein the yeast includes a genetic modification in one or more polynucleotides that inhibits production of one or more enzymes chosen from a phosphoglucoisomerase (PGI) enzyme, 6-phosphogluconate dehydrogenase (decarboxylating) enzyme, transketolase enzyme, transaldolase enzyme, or combination thereof.

15. The composition of claim 14, wherein the yeast includes a genetic modification in one or more polynucleotides that inhibits production of 6-phosphogluconate dehydrogenase (decarboxylating) enzyme.

16. The composition of claim 1, wherein the yeast is a *Saccharomyces cerevisiae* yeast strain.

* * * * *